US011014935B2

(12) United States Patent
Wang et al.

(10) Patent No.: US 11,014,935 B2
(45) Date of Patent: *May 25, 2021

(54) COMPOUNDS FOR THE TREATMENT OF PARAMYXOVIRUS VIRAL INFECTIONS

(71) Applicant: JANSSEN BIOPHARMA, INC., South San Francisco, CA (US)

(72) Inventors: Guangyi Wang, Carlsbad, CA (US); Leonid Beigelman, San Mateo, CA (US); Anh Truong, Burlingame, CA (US); Carmela Napolitano, Verona (IT); Daniele Andreotti, Verona (IT); Haiying He, Shanghai (CN)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,757

(22) Filed: Jun. 20, 2017

(65) Prior Publication Data

US 2017/0283429 A1 Oct. 5, 2017

Related U.S. Application Data

(62) Division of application No. 14/422,920, filed as application No. PCT/US2013/056052 on Aug. 21, 2013, now Pat. No. 9,724,351.

(Continued)

(51) Int. Cl.
*C07D 409/04* (2006.01)
*C07D 495/04* (2006.01)
(Continued)

(52) U.S. Cl.
CPC .......... *C07D 495/04* (2013.01); *A61K 31/165* (2013.01); *A61K 31/277* (2013.01); *A61K 31/341* (2013.01); *A61K 31/343* (2013.01); *A61K 31/352* (2013.01); *A61K 31/381* (2013.01); *A61K 31/382* (2013.01); *A61K 31/40* (2013.01); *A61K 31/404* (2013.01); *A61K 31/407* (2013.01); *A61K 31/4025* (2013.01); *A61K 31/4155* (2013.01); *A61K 31/4164* (2013.01); *A61K 31/4196* (2013.01); *A61K 31/423* (2013.01); *A61K 31/426* (2013.01); *A61K 31/427* (2013.01); *A61K 31/428* (2013.01); *A61K 31/4365* (2013.01); *A61K 31/4375* (2013.01); *A61K 31/444* (2013.01); *A61K 31/4418* (2013.01); *A61K 31/4427* (2013.01); *A61K 31/4436* (2013.01); *A61K 31/4439* (2013.01); *A61K 31/4545* (2013.01); *A61K 31/47* (2013.01); *A61K 31/4704* (2013.01); *A61K 31/4709* (2013.01); *A61K 31/4725* (2013.01); *A61K 31/496* (2013.01); *A61K 31/497* (2013.01); *A61K 31/501* (2013.01); *A61K 31/506* (2013.01); *A61K 31/538* (2013.01); *A61K 31/5377* (2013.01); *A61K 45/06* (2013.01); *C07C 243/18* (2013.01); *C07C 243/34* (2013.01); *C07C 251/80* (2013.01); *C07C 251/84* (2013.01); *C07C 255/34* (2013.01); *C07C 255/66* (2013.01); *C07D 207/335* (2013.01); *C07D 209/08* (2013.01); *C07D 209/14* (2013.01); *C07D 209/20* (2013.01); *C07D 209/86* (2013.01); *C07D 213/42* (2013.01); *C07D 213/50* (2013.01); *C07D 213/65* (2013.01); *C07D 213/68* (2013.01); *C07D 215/12* (2013.01); *C07D 215/14* (2013.01); *C07D 215/38* (2013.01); *C07D 215/42* (2013.01); *C07D 217/24* (2013.01); *C07D 233/38* (2013.01); *C07D 233/60* (2013.01); *C07D 233/61* (2013.01); *C07D 233/64* (2013.01); *C07D 233/88* (2013.01); *C07D 261/20* (2013.01); *C07D 277/56* (2013.01); *C07D 277/64* (2013.01); *C07D 307/40* (2013.01); *C07D 307/52* (2013.01); *C07D 307/81* (2013.01); *C07D 307/91* (2013.01); *C07D 311/68* (2013.01); *C07D 333/16* (2013.01);
(Continued)

(58) Field of Classification Search
CPC .................................................. C07D 409/04
USPC ....................................... 546/281.1; 514/337
See application file for complete search history.

(56) References Cited

U.S. PATENT DOCUMENTS 2,516,098 A 7/1950 Louis
4,876,346 A 10/1989 Musser et al.
(Continued)

FOREIGN PATENT DOCUMENTS

CN 1261276 A 7/2000
CN 1358182 A 7/2002
(Continued)

OTHER PUBLICATIONS

Indian Office Action dated Sep. 26, 2018 for IN Application No. 1556/DELNP/2015 filed Aug. 21, 2013.
(Continued)

*Primary Examiner* — Patricia L Morris
(74) *Attorney, Agent, or Firm* — Morrison & Foerster LLP

(57) ABSTRACT

Disclosed herein are new antiviral compounds, together with pharmaceutical compositions that include one or more antiviral compounds, and methods of synthesizing the same. Also disclosed herein are methods of ameliorating and/or treating a paramyxovirus viral infection with one or more small molecule compounds. Examples of paramyxovirus infection include an infection caused by human respiratory syncytial virus (RSV).

8 Claims, No Drawings

Related U.S. Application Data

(60) Provisional application No. 61/702,646, filed on Sep. 18, 2012, provisional application No. 61/692,595, filed on Aug. 23, 2012.

(51) Int. Cl.

| | |
|---|---|
| C07D 333/58 | (2006.01) |
| C07D 215/12 | (2006.01) |
| C07D 215/14 | (2006.01) |
| C07D 311/68 | (2006.01) |
| C07D 215/42 | (2006.01) |
| C07D 217/24 | (2006.01) |
| C07D 333/16 | (2006.01) |
| C07D 333/20 | (2006.01) |
| C07D 233/38 | (2006.01) |
| C07D 333/50 | (2006.01) |
| C07D 333/54 | (2006.01) |
| C07D 233/61 | (2006.01) |
| C07D 333/62 | (2006.01) |
| C07D 333/66 | (2006.01) |
| C07D 333/68 | (2006.01) |
| C07D 335/06 | (2006.01) |
| C07D 233/88 | (2006.01) |
| C07D 401/04 | (2006.01) |
| C07D 401/10 | (2006.01) |
| C07D 401/12 | (2006.01) |
| C07D 405/04 | (2006.01) |
| C07D 405/12 | (2006.01) |
| C07D 409/14 | (2006.01) |
| C07D 413/04 | (2006.01) |
| C07D 413/12 | (2006.01) |
| C07D 417/04 | (2006.01) |
| C07D 417/12 | (2006.01) |
| C07D 471/04 | (2006.01) |
| C07D 261/20 | (2006.01) |
| C07D 207/335 | (2006.01) |
| C07D 209/08 | (2006.01) |
| C07D 209/14 | (2006.01) |
| C07D 277/64 | (2006.01) |
| C07D 209/86 | (2006.01) |
| C07D 213/42 | (2006.01) |
| C07D 213/50 | (2006.01) |
| C07D 213/65 | (2006.01) |
| C07D 213/68 | (2006.01) |
| C07D 307/52 | (2006.01) |
| C07D 307/81 | (2006.01) |
| C07D 233/60 | (2006.01) |
| C07D 495/14 | (2006.01) |
| C07C 251/84 | (2006.01) |
| A61K 45/06 | (2006.01) |
| A61K 31/381 | (2006.01) |
| A61K 31/404 | (2006.01) |
| A61K 31/407 | (2006.01) |
| A61K 31/4155 | (2006.01) |
| A61K 31/4418 | (2006.01) |
| A61K 31/4439 | (2006.01) |
| A61K 31/444 | (2006.01) |
| A61K 31/506 | (2006.01) |
| C07C 243/34 | (2006.01) |
| C07C 251/80 | (2006.01) |
| C07C 255/34 | (2006.01) |
| A61K 31/4164 | (2006.01) |
| A61K 31/426 | (2006.01) |
| A61K 31/4436 | (2006.01) |
| A61K 31/496 | (2006.01) |
| A61K 31/497 | (2006.01) |
| A61K 31/501 | (2006.01) |
| A61K 31/5377 | (2006.01) |
| C07D 209/20 | (2006.01) |
| C07D 233/64 | (2006.01) |
| C07D 277/56 | (2006.01) |
| C07D 409/06 | (2006.01) |
| C07D 409/12 | (2006.01) |
| A61K 31/165 | (2006.01) |
| A61K 31/277 | (2006.01) |
| A61K 31/341 | (2006.01) |
| A61K 31/343 | (2006.01) |
| A61K 31/352 | (2006.01) |
| A61K 31/382 | (2006.01) |
| A61K 31/40 | (2006.01) |
| A61K 31/4025 | (2006.01) |
| A61K 31/4196 | (2006.01) |
| A61K 31/423 | (2006.01) |
| A61K 31/427 | (2006.01) |
| A61K 31/428 | (2006.01) |
| A61K 31/4365 | (2006.01) |
| A61K 31/4375 | (2006.01) |
| A61K 31/4427 | (2006.01) |
| A61K 31/4545 | (2006.01) |
| A61K 31/47 | (2006.01) |
| A61K 31/4704 | (2006.01) |
| A61K 31/4709 | (2006.01) |
| A61K 31/4725 | (2006.01) |
| A61K 31/538 | (2006.01) |
| C07C 243/18 | (2006.01) |
| C07C 255/66 | (2006.01) |
| C07D 215/38 | (2006.01) |
| C07D 307/40 | (2006.01) |
| C07D 307/91 | (2006.01) |
| C07D 333/76 | (2006.01) |
| C07D 405/10 | (2006.01) |
| C07D 413/14 | (2006.01) |

(52) U.S. Cl.
CPC ......... *C07D 333/20* (2013.01); *C07D 333/50* (2013.01); *C07D 333/54* (2013.01); *C07D 333/58* (2013.01); *C07D 333/62* (2013.01); *C07D 333/66* (2013.01); *C07D 333/68* (2013.01); *C07D 333/76* (2013.01); *C07D 335/06* (2013.01); *C07D 401/04* (2013.01); *C07D 401/10* (2013.01); *C07D 401/12* (2013.01); *C07D 405/04* (2013.01); *C07D 405/10* (2013.01); *C07D 405/12* (2013.01); *C07D 409/04* (2013.01); *C07D 409/06* (2013.01); *C07D 409/12* (2013.01); *C07D 409/14* (2013.01); *C07D 413/04* (2013.01); *C07D 413/12* (2013.01); *C07D 413/14* (2013.01); *C07D 417/04* (2013.01); *C07D 417/12* (2013.01); *C07D 471/04* (2013.01); *C07D 495/14* (2013.01); *C07C 2602/08* (2017.05)

(56) References Cited

U.S. PATENT DOCUMENTS

| | | | |
|---|---|---|---|
| 5,618,938 A | 4/1997 | Emonds-Alt et al. | |
| 5,688,960 A | 11/1997 | Shankar | |
| 5,696,267 A | 12/1997 | Reichard et al. | |
| 7,407,969 B2 | 8/2008 | Janssens et al. | |
| 7,482,448 B2 | 1/2009 | Thurairatnam et al. | |
| 9,724,351 B2 * | 8/2017 | Wang | A61K 45/06 |
| 10,358,453 B2 | 7/2019 | Wang et al. | |

(56) References Cited

U.S. PATENT DOCUMENTS

| | | |
|---|---|---|
| 2003/0232986 A1 | 12/2003 | Wannamaker et al. |
| 2004/0024024 A1 | 2/2004 | Freskos et al. |
| 2004/0054186 A1 | 3/2004 | Das et al. |
| 2004/0127574 A1 | 7/2004 | Kori et al. |
| 2005/0176714 A1 | 8/2005 | Eggenweiler et al. |
| 2007/0037752 A1 | 2/2007 | Ansorge et al. |
| 2007/0276002 A1 | 11/2007 | Tully et al. |
| 2010/0045558 A1 | 2/2010 | Rossetto |
| 2010/0048558 A1 | 2/2010 | Eggenweiler et al. |
| 2010/0160311 A1 | 6/2010 | Dietz et al. |
| 2011/0136831 A1 | 6/2011 | Oda et al. |
| 2012/0225867 A1 | 9/2012 | Wohlfahrt |
| 2015/0065504 A1 | 3/2015 | Wang et al. |
| 2015/0238498 A1 | 8/2015 | Wang et al. |
| 2016/0244460 A1 | 8/2016 | Wang et al. |
| 2018/0065932 A1 | 3/2018 | Wang et al. |

FOREIGN PATENT DOCUMENTS

| | | |
|---|---|---|
| EP | 2508513 A1 | 10/2012 |
| JP | S60-500669 A | 5/1985 |
| JP | 2002-504097 | 2/2002 |
| JP | 2002-506878 | 3/2002 |
| JP | 2002-518444 | 6/2002 |
| JP | 2002-293764 | 10/2002 |
| JP | 2002-539115 A | 11/2002 |
| JP | 2003-505008 A | 2/2003 |
| JP | 2006-504725 | 2/2006 |
| JP | 2007-501788 A | 2/2007 |
| JP | 2007-501803 A | 2/2007 |
| JP | 2007-508349 | 4/2007 |
| JP | 2007-509175 A | 4/2007 |
| JP | 2008-521787 A | 6/2008 |
| JP | 2009209090 | 9/2009 |
| JP | 2009-538326 | 11/2009 |
| JP | 2009-539791 A | 11/2009 |
| JP | 2010-518097 | 5/2010 |
| JP | 2013-517278 A | 5/2013 |
| WO | WO-1984/02907 A1 | 8/1984 |
| WO | WO 1995/035308 | 12/1995 |
| WO | WO 1996/034857 | 11/1996 |
| WO | WO 1998/048799 | 11/1998 |
| WO | WO 1999/047545 | 9/1999 |
| WO | WO 1999/061437 | 12/1999 |
| WO | WO 1999/066925 | 12/1999 |
| WO | WO-2000/09542 A1 | 2/2000 |
| WO | WO 2000/052034 | 9/2000 |
| WO | WO-2000/053583 A1 | 9/2000 |
| WO | WO 2000/062778 | 10/2000 |
| WO | WO 2002/092588 | 11/2002 |
| WO | WO 2003/024955 | 3/2003 |
| WO | WO 2003/029245 | 4/2003 |
| WO | WO 2003/037877 | 5/2003 |
| WO | WO-2003/045381 A1 | 6/2003 |
| WO | WO 2003/104204 | 12/2003 |
| WO | WO-2004/026843 A1 | 4/2004 |
| WO | WO 2004/033434 | 4/2004 |
| WO | WO-2005/014540 A1 | 2/2005 |
| WO | WO-2005/016876 A2 | 2/2005 |
| WO | WO-2005/016876 A3 | 2/2005 |
| WO | WO-2005/035514 A2 | 4/2005 |
| WO | WO-2005/035514 A3 | 4/2005 |
| WO | WO 2005/074513 | 8/2005 |
| WO | WO-2005/089770 A1 | 9/2005 |
| WO | WO-2005/094514 A2 | 10/2005 |
| WO | WO-2005/094514 A3 | 10/2005 |
| WO | WO 2006/044133 | 4/2006 |
| WO | WO 2006/053109 | 5/2006 |
| WO | WO-2006/056815 A1 | 6/2006 |
| WO | WO 2007/030567 | 3/2007 |
| WO | WO 2007/108483 | 9/2007 |
| WO | WO 2007/140117 | 12/2007 |
| WO | WO-2007/141009 A1 | 12/2007 |
| WO | WO 2008/006761 | 1/2008 |
| WO | WO 2008/036843 | 3/2008 |
| WO | WO 2008/057599 | 5/2008 |
| WO | WO 2008/097673 | 8/2008 |
| WO | WO-2008/098239 A2 | 8/2008 |
| WO | WO-2008/098239 A3 | 8/2008 |
| WO | WO-2008/150486 A2 | 12/2008 |
| WO | WO-2008/150486 A3 | 12/2008 |
| WO | WO-2009/045503 A1 | 4/2009 |
| WO | WO 2009/087379 | 7/2009 |
| WO | WO 2009/155362 | 12/2009 |
| WO | WO 2010/018874 | 2/2010 |
| WO | WO 2010/065461 | 6/2010 |
| WO | WO 2010/132992 | 11/2010 |
| WO | WO 2010/150281 | 12/2010 |
| WO | WO-2011/005842 A1 | 1/2011 |
| WO | WO 2011/046954 | 4/2011 |
| WO | WO 2011/050098 | 4/2011 |
| WO | WO 2011/051535 | 5/2011 |
| WO | WO 2011/068211 | 6/2011 |
| WO | WO 2011/088181 | 7/2011 |
| WO | WO 2011/097607 | 8/2011 |
| WO | WO 2011/109261 | 9/2011 |
| WO | WO-2012/040527 A2 | 3/2012 |
| WO | WO 2012/068406 | 5/2012 |
| WO | WO 2013/010380 | 1/2013 |
| WO | WO 2013/055793 | 4/2013 |
| WO | WO 2013/059119 | 4/2013 |
| WO | WO 2013/064518 | 5/2013 |
| WO | WO 2014/031784 | 2/2014 |
| WO | WO 2015/026792 | 2/2015 |

OTHER PUBLICATIONS

Notice of Allowance dated Oct. 17, 2017 for Japanese Application No. 2015-528636, filed Feb. 23, 2015.
Examination Report dated Nov. 1, 2017 for New Zealand Application No. 704666, filed Feb. 9, 2015.
Notice of Eligibility for Grant dated Dec. 15, 2017 for Singapore Application No. 11201501036R, filed Feb. 11, 2015.
Chinese Office Action dated Mar. 23, 2018 for Chinese Application No. 201380054579.3, filed Aug. 21, 2013.
European Communication Under Rule 71(3) EPC—Intention to Grant dated Jun. 20, 2018 in European Patent Application No. 13830584.2, filed on Feb. 15, 2015.
Israeli Office Action dated Feb. 22, 2018 for IL Application No. 237275, filed Aug. 21 2013.
Israeli Office Action dated Jun. 21, 2018 for IL Application No. 237275, filed Aug. 21, 2013.
New Zealand Notice of Acceptance dated May 21, 2018 for New Zealand Application No. 704666, filed Feb. 9, 2015.
Philippines Notice of Allowance dated Jul. 3, 2018 for Philippines Application No. 1/2015/500355, filed Feb. 18, 2015.
Philippines Office Action dated Mar. 22, 2018 for Philippines Application No. 1/2015/500355, filed Feb. 18, 2015.
Examination Report dated Aug. 1, 2017 for Philippines Application No. 1/2015/500355, filed Feb. 18, 2015.
Office Action dated Jun. 21, 2017 for Chinese Application No. 201380054579.3, filed Aug. 21, 2013.
Notice of Acceptance dated Sep. 13, 2017 for Australian Application No. 2013305759, filed Mar. 6, 2015.
Al-Afaleq et al., "L-Amino Acid Esters Studies: Part II: Synthesis of N-(Dimethoxy/3,5-Diacetoxybenzoyl)-L-Amino Acid Hydrazides and their Reactions with Aldehydes and Ketons" Synthetic Communications (1999) 29(8):1317-1331.
Bhattacherjee et al., "Discovery of non-oxime reactivators using an in silico pharmacophore model of oxime reactivators of OP-inhibited acetylcholinesterase" European Journal of Medicinal Chemistry (2012) 49:229-238.
CAS Registry No. 1276363-72-4, Entered Apr. 7, 2011.
CAS Registry No. 1235682-49-1, Entered Aug. 10, 2010.
CAS Registry No. 817189-89-2, Entered Jan. 20, 2005.
CAS Registry No. 817189-87-0, Entered Jan. 20, 2005.
CAS Registry No. 476430-91-8, Entered Dec. 17, 2002.
CAS Registry No. 476430-75-8, Entered Dec. 17, 2002.
CAS Registry No. 391891-52-4, Entered Feb. 13, 2002.

(56) References Cited

OTHER PUBLICATIONS

CAS Registry No. 391891-51-3, Entered Feb. 13, 2002.
CAS Registry No. 374606-62-9, Entered Dec. 10, 2001.
CAS Registry No. 373613-54-8, Entered Dec. 5, 2001.
CAS Registry No. 373373-41-2, Entered Dec. 4, 2001.
CAS Registry No. 349568-79-2, Entered Jul. 31, 2001.
CAS Registry No. 339005-10-6, Entered May 30, 2001.
CAS Registry No. 328126-15-4, Entered Mar. 20, 2001.
CAS Registry No. 1386825-26-8, Entered Aug. 6, 2012, Retrieved on Oct. 21, 2013.
CAS Registry No. 1371789-14-8, Entered May 6, 2012, Retrieved on Oct. 21, 2013.
CAS Registry No. 1321793-72-9, Entered Aug. 23, 2011, Retrieved on Oct. 21, 2013.
CAS Registry No. 1321772-62-6, Entered Aug. 23, 2011, Retrieved on Oct. 21, 2013.
CAS Registry No. 1299457-43-4, Entered May 24, 2011, Retrieved on Oct. 21, 2013.
CAS Registry No. 1294568-99-2, Entered May 15, 2011, Retrieved on Oct. 21, 2013.
CAS Registry No. 1235686-10-8, Entered Aug. 10, 2010, Retrieved on Oct. 21, 2013.
CAS Registry No. 1025828-66-3, Entered Jun. 5, 2008, Retrieved on Oct. 21, 2013.
CAS Registry No. 847596-86-5, Entered Mar. 30, 2005, Retrieved on Oct. 21, 2013.
CAS Registry No. 383168-68-1, Entered Jan. 16, 2002, Retrieved on Oct. 21, 2013.
CAS Registry No. 382157-09-7, Entered Jan. 11, 2002, Retrieved on Oct. 21, 2013.
CAS Registry No. 327988-51-2, Entered Mar. 19, 2001, Retrieved on Oct. 21, 2013.
Greene, et al., Protective Groups in Organic Synthesis, 3. Ed., John Wiley & Sons, (1999) Cover & Contents pages.
Hansen, et al., "Efficient microwave-assisted synthesis of 1,2,4-triazole-based peptidomimetics using benzotriazole methodology," Heterocycles (2012), vol. 84(1), p. 515-526.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5):942-944.
Kametani et al., "9,10-Dimethoxy-3-safryl-5,6-dihydrobenzoglyoxaolcoline" Yakuguku Zasshi (1950) 70:261-263.
Mcomie, J. F. W., Protective Groups in Organic Chemistry, Plenum Press, 1973. Cover & Contents pages only.
Murty et al., "Synthesis of New S-alkylated-3-mercapto-1,2,4-triazole Derivatives Bearing Cyclic Amine Moiety as Potent Anticancer Agents" Letters in Drug Design & Discovery (2012) 9(3):276-281.
Palmer et al., "Keto-1, 3, 4-oxadiazoles as cathepsin K inhibitors," Bioorganic & Medicinal Chemistry Letters, vol. 16, p. 2909-2914, 2006.
Perni, R.T., et al., "Inhibitors of hepatitis C virus NS3-4A protease 2. Warhead SAR and optimization" Bioorg. & Med. Chem. Letters (2004) 14:1441-1446.
Prieto, et al., "Application of linear discriminant analysis in the virtual screening of antichagasic drugs through trypanothione reductase inhibition," Molecular Diversity (2006), vol. 10(3), p. 361-375.
Rusinov et al., Pharm. Chem. Journal 2012, vol. 45, 655-659.
Seo et al., "Chemoselective and Microwave-Assisted Synthesis of Glycopeptoids" Org. Lett. (2009) 11(22):5210-5213.
Shao et al., "Synthesis and evaluation of tacrine-E2020 hybrids as acetylcholinesterase inhibitors for the treatment of Alzheimer's disease" Bioorganic & Medicinal Chemistry Letters (2004) 14:4639-4642.
Shinozuka et al., "A Practical Method for the Preparation of 4-Nitrogen-substituted Benzoic Acids" Chemistry Letters (2006) 35(10):1090-1091.
Sidwell et al., "Use of disposable micro tissue culture plates for antiviral and interferon induction studies" Appl. Microbiol. (1971) 22(5):797-801.
Steert et al., "α-Ketoheterocycles as inhibitors of Leishmania Mexicana cysteine protease CPB," ChemMedChem, Oct. 4, 2010, vol. 5(10), p. 1734-1748.
Examination Report dated May 19, 2017 for New Zealand Patent Application No. 704666, filed on Feb. 9, 2015.
Examination Report dated Jun. 23, 2017 for Australian Application No. 2013305759, filed Aug. 23, 2012.
Extended European Search Report dated Mar. 29, 2016 in European Application No. 13830584.2, filed Aug. 21, 2013.
International Preliminary Report on Patentability dated Feb. 24, 2015 for International Application No. PCT/US2013/056052, filed Aug. 21, 2013.
International Search Report and Written Opinion dated Oct. 9, 2013 for International Application No. PCT/US2013/056052, filed Aug. 21, 2013.
Invitation to Respond to Written Opinion dated May 30, 2017 for Singapore Patent Application No. 11201501036R.
Office Action dated Jan. 6, 2016 for Chinese Application No. 201380054579.3, filed Aug. 21, 2013.
Office Action dated Jan. 11, 2016 for Eurasian Application No. 201590197, filed Aug. 21, 2013.
Office Action dated Aug. 18, 2016 for Philippines Application No. 1/2015/500355, filed Feb. 18, 2015.
Office Action dated Nov. 28, 2016 for Chinese Application No. 201380054579.3, filed Aug. 21, 2013.
Office Action dated Dec. 1, 2016 for European Application No. 13 830 584.2, filed Feb. 15, 2015.
Office Action dated Feb. 17, 2017 for Australian Application No. 2013305759.
Office Action dated Apr. 21, 2017 in European Patent Application No. 13830584.2, filed on Feb. 15, 2015.
Office Action dated Jun. 27, 2017 for Japanese Application No. 2015-528636, filed Aug. 23, 2012.
Search Report and Written Opinion dated Mar. 3, 2016 for Singapore Application No. 11201501036R, filed Aug. 21, 2013.
European Communication Under Rule 71(3) EPC—Intention to Grant dated Aug. 16, 2019 in European Patent Application No. 13830584.2, filed on Feb. 15, 2015.
CAS Reg. No. 1276808-00-4, Entered Apr. 8, 2011, Copyright 2017 ACS on STN, 1 page.
Federal Register. (Feb. 9, 2011). "Federal Register, Notices," *Federal Register* 76(27):7166.
Kuzuhara, H. (1963). "Studies on the D-xylose series. Part I. Syntheses of 3-acetamido-3,5-dideoxy-D-xylofuranose and its derivatives," *Agricultural and Biological Chemistry* 27(10):689-694.
Mina, J.G. (2011). "Exploring *Leishmania major* Inositol Phosphorylceramide Synthase (LmjIPCS): Insights Into the Ceramide Binding Domain," *Organic & Biomolecular Chemistry* 9(6):1823-1830.
Rydzewski, R. (2008). "The Drug Discovery Business to Date," Chapter 1 in *Real World Drug Discovery. A Chemist's Guide to Biotech and Pharmaceutical Research*, Elsevier, Oxford, United Kingdom, pp. 42-43.
Eurasian Office Action dated Dec. 26, 2018 for Eurasian Application No. 201590197, filed Aug. 21, 2013.
European Communication Under Rule 71(3) EPC—Intention to Grant dated Mar. 4, 2019 in European Patent Application No. 13830584.2, filed on Feb. 15, 2015.
European Office Action dated Nov. 26, 2018 in European Patent Application No. 13830584.2, filed on Feb. 15, 2015.
Mexican Office Action dated Aug. 29, 2018 for Mexican Application No. MX/a/2015/002231 filed Aug. 21, 2013.
U.S. Appl. No. 16/165,865, filed Oct. 19, 2018 by Wang et al. U.S. Patent Application is not submitted herewith pursuant to the waiver of 37 C.F.R. § 1.98(a)(2)(iii) issued by the Office on Sep. 21, 2004.
European Communication Under Rule 97(1) EPC—Decision to Grant dated Dec. 19, 2019 in European Patent Application No. 13830584.2, filed on Feb. 16, 2015.
Canadian Office Action dated Oct. 17, 2019, for Canadian Patent Application No. 2,882,088, filed on Feb. 12, 2015.

(56) References Cited

OTHER PUBLICATIONS

CAS Registry No. 1290350-29-6, created May 5, 2011, Copyright 2020, 2 pages.

* cited by examiner

COMPOUNDS FOR THE TREATMENT OF PARAMYXOVIRUS VIRAL INFECTIONS

This application is a divisional of U.S. application Ser. No. 14/422,920, filed Feb. 20, 2015; which is a 371 of international application number PCT/US2013/056052, filed Aug. 21, 2013; which claims the benefit of U.S. Provisional Application Nos. 61/702,646, filed Sep. 18, 2012, and 61/692,595, filed Aug. 23, 2012; all of which are incorporated herein by reference in their entireties.

BACKGROUND

Field

The present application relates to the fields of chemistry, biochemistry and medicine. More particularly, disclosed herein are new antiviral compounds, together with pharmaceutical compositions, and methods of synthesizing the same. Also disclosed herein are methods of ameliorating and/or treating a paramyxovirus viral infection with one or more small molecule compounds.

Description

Respiratory viral infections, including upper and lower respiratory tract viral infections, are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs. Human respiratory syncytial virus (RSV) is a common cause of respiratory tract infections. Up to 60% of human infants are infected with RSV within their first year of life. Children and adults are also infected with RSV, where it is often manifesting as a lower respiratory tract infection with possible complications of bronchiolitis. RSV infections can be particularly severe in infants and elderly patients. RSV is a negative-sense, single-stranded RNA virus classified within the Paramyxoviridae family, which also includes viruses that cause Newcastle disease, parainfluenza, mumps, measles, and canine distemper.

SUMMARY

Some embodiments disclosed herein relate to a compound of Formula (I), or a pharmaceutically acceptable salt thereof. Other embodiments disclosed herein relate to a compound of Formula (II), or a pharmaceutically acceptable salt thereof.

Some embodiments disclosed herein relate to a method of ameliorating and/or treating a paramyxovirus viral infection that can include administering to a subject suffering from the paramyxovirus viral infection an effective amount of one or more compounds of Formula (I) and/or Formula (II), or a pharmaceutically acceptable salt of the foregoing, or a pharmaceutical composition that includes one or more compounds of Formula (I) and/or Formula (II), or a pharmaceutically acceptable salt of the foregoing. Other embodiments described herein relate to using one or more compounds of Formula (I) and/or Formula (II), or a pharmaceutically acceptable salt of the foregoing, in the manufacture of a medicament for ameliorating and/or treating a paramyxovirus viral infection. Still other embodiments described herein relate to compounds of Formula (I) and/or Formula (II), or a pharmaceutically acceptable salt of the foregoing, that can be used for ameliorating and/or treating a paramyxovirus viral infection. Yet still other embodiments disclosed herein relate to a method of ameliorating and/or treating a paramyxovirus viral infection that can include contacting a cell infected with the paramyxovirus with an effective amount of one or more compounds of Formula (I) and/or Formula (II), or a pharmaceutically acceptable salt of the foregoing, or a pharmaceutical composition that includes one or more compounds of Formula (I) and/or Formula (II), or a pharmaceutically acceptable salt of the foregoing. Some embodiments disclosed herein relate to a method of inhibiting the replication of a paramyxovirus that can include contacting a cell infected with the paramyxovirus with an effective amount of one or more compounds of Formula (I) and/or Formula (II), or a pharmaceutically acceptable salt of the foregoing, or a pharmaceutical composition that includes one or more compounds of Formula (I), and/or Formula (II), or a pharmaceutically acceptable salt of the foregoing. For example, the paramyxovirus viral infection can be caused by a henipavirus, a morbillivirus, a respirovirus, a rubulavirus, a pneumovirus (including a respiratory syncytial viral infection), a metapneumovirus, hendravirus, nipahvirus, measles, sendai virus, mumps, a human parainfluenza virus (HPIV-1, HPIV-2, HPIV-3 and HPIV-4) and/or a metapneumovirus.

Some embodiments disclosed herein relate to a method of ameliorating and/or treating a paramyxovirus viral infection that can include administering to a subject suffering from the viral infection an effective amount of a compound described herein or a pharmaceutically acceptable salt thereof (for example, one or more compounds of Formulae (I) and/or (II), or a pharmaceutically acceptable salt of the foregoing), or a pharmaceutical composition that includes one or more compounds described herein, in combination with one or more agents described herein. Some embodiments disclosed herein relate to a method of ameliorating and/or treating a paramyxovirus viral infection that can include contacting a cell infected with the paramyxovirus with an effective amount of a compound described herein or a pharmaceutically acceptable salt thereof (for example, one or more compounds of Formulae (I) and/or (II), or a pharmaceutically acceptable salt of the foregoing), or a pharmaceutical composition that includes one or more compounds described herein, in combination with one or more agents described herein.

DETAILED DESCRIPTION

Paramyxoviridae family is a family of single stranded RNA viruses. Several genera of the paramyxoviridae family include henipavirus, morbillivirus, respirovirus, rubulavirus, pneumovirus and metapneumovirus. These viruses can be transmitted person to person via direct or close contact with contaminated respiratory droplets or fomites. Species of henipavirus include hendravirus and nipahvirus. A species of morbillivirus is measles. Species of respirovirus include sendai virus and human parainfluenza viruses 1 and 3; and species of rubulavirus include mumps virus and human parainfluenza viruses 2 and 4. A species of metapneumovirus is human metapneumovirus.

Human Respiratory Syncytial Virus (RSV), a species of pneumovirus, can cause respiratory infections, and can be associated with bronchiolitis and pneumonia. Symptoms of an RSV infection include coughing, sneezing, runny nose, fever, decrease in appetite, and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV. In severe cases, a nebulized bronchodilator, such as albuterol, may be prescribed to relieve some of the symptoms, such as wheezing. Respi-Gram® (RSV-IGIV, MedImmune, approved for high risk children younger than 24 months of age), Synagis® (palivizumab, MedImmune, approved for high risk children younger than 24 months of age), and Virzole® (ribavirin by aerosol, ICN pharmaceuticals) have been approved for treatment of RSV.

Symptoms of the measles include fever, cough, runny nose, red eyes and a generalized rash. Some individuals with measles can develop pneumonia, ear infections and bronchitis. Mumps leads to swelling of the salivary glands. Symptoms of mumps include fever, loss of appetite and fatigue. Individuals are often immunized against measles and mumps via a three-part MMR vaccine (measles, mumps, and rubella). Human parainfluenza virus includes four serotypes types, and can cause upper and lower respiratory tract infections. Human parainfluenza virus 1 (HPIV-1) can be associated with croup; human parainfluenza virus 3 (HPIV-3) can be associated with bronchiolitis and pneumonia. According to the Centers of Disease Control and Prevention (CDC), there are no vaccines against human parainfluenza virus.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, and $R^A$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

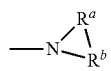

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, alkoxyalkyl, aminoalkyl, amino acid, aryl, heteroaryl, heterocyclyl, aryl(alkyl0, heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl, and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl, and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "acylalkyl" refers to an acyl connected, as a substituent, via a lower alkylene group. Examples include aryl-C(=O)—$(CH_2)_n$— and heteroaryl-C(=O)—$(CH_2)_n$—, where n is an integer in the range of 1 to 6.

As used herein, "alkoxyalkyl" refers to an alkoxy group connected, as a substituent, via a lower alkylene group.

Examples include $C_{1-4}$ alkyl-O—$(CH_2)_n$—, wherein n is an integer in the range of 1 to 6.

As used herein, "aminoalkyl" refers to an optionally substituted amino group connected, as a substituent, via a lower alkylene group. Examples include $H_2N(CH_2)_n$—, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chlorofluoroalkyl, chloro-difluoroalkyl, and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—$SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, ===== indicates a single or double bond, unless stated otherwise.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. As used herein, "amino acid" also includes amino acids wherein the main-chain carboxylic acid group has been converted to an ester group.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead are merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds
Formula (I)

Some embodiments disclosed herein relate to a compound of Formula (I), or a pharmaceutically acceptable salt thereof, having the structure:

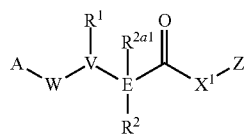

(I)

wherein: A can be selected from an optionally substituted cycloalkyl, an optionally substituted cycloalkenyl, an optionally substituted aryl, an optionally substituted aryl($C_{1-2}$ alkyl), an optionally substituted heteroaryl and an optionally substituted heterocyclyl; W can be O, S, C=O, C=S, $NR^{3a3}$, S=O, $S(=O)_2$ or $—C(R^{1a1})(R^{1a2})—$; V can be N or CH; E can be C or N; provided that when E is N, then $R^{2a1}$ is absent; Z can be selected from

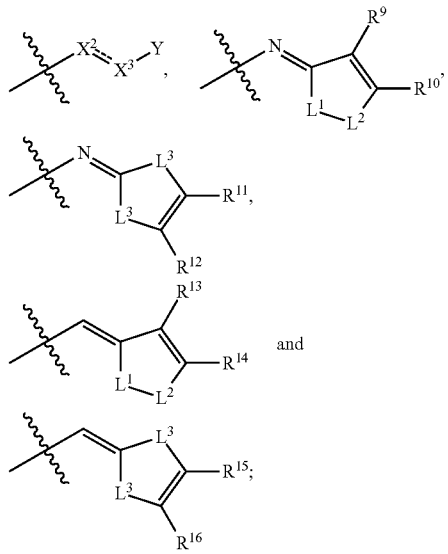

Y can be selected from an optionally substituted acylalkyl, an optionally substituted cycloalkyl, an optionally substituted cycloalkenyl, an optionally substituted aryl, an optionally substituted heteroaryl and an optionally substituted heterocyclyl; ----- between $X^2$ and $X^3$ represents a single or double bond between $X^2$ and $X^3$; wherein when ----- is a double bond, then $X^1$ can be $NR^{3a1}$ or $CR^{3a2}R^6$, $X^2$ can be N (nitrogen) or $CR^{7a1}$, and $X^3$ can be N (nitrogen) or $CR^4$; and when ----- is a single bond, then $X^1$ can be $NR^{3a1}$ or $CR^{3a2}R^6$, $X^2$ can be O, $NR^7$, C(=O) or $C(R^{7a2})(R^{7a3})$, and $X^3$ can be $NR^4$, C(=O), $CR^4R^8$ or $CH_2CH_2C(=O)$; or $X^1$, $X^2$ and $X^3$ can be each independently C (carbon), N (nitrogen), O (oxygen) or C(=O), and form a mono-cyclic ring selected from an optionally substituted mono-cyclic heteroaryl and an optionally substituted mono-cyclic heterocyclyl by joining $X^1$ and $X^3$ together; and provided that at least one of $X^1$, $X^2$ and $X^3$ comprises a nitrogen atom, with the proviso that the valencies of $X^1$, $X^2$ and $X^3$ can be each independently satisfied with a substituent selected from hydrogen and an optionally substituted $C_{1-4}$ alkyl; and $X^1$, $X^2$ and $X^3$ are uncharged; $L^1$ can be $—C(R^{17})_2—$, $—C(R^{18})_2C(R^{18a1})_2—$, $C(R^{18a2})=C(R^{18a3})—$ or $—C(R^{19})_2N(R^{19a1})—$; $L^2$ can be $—C(R^{20})_2—$, $—N(R^{21})—$, S, or O; each $L^3$ can be independently $—C(R^{22})_2—$, $—C(R^{23})_2C(R^{23a1})_2—$ or $—C(R^{23a2})=C(R^{23a3})—$; provided that when $L^1$ is $—C(R^{19})_2N(R^{19a1})—$, then $L^2$ is $—C(R^{20})_2—$; $R^1$ can be hydrogen or an unsubstituted $C_{1-4}$ alkyl; $R^{1a1}$ and $R^{1a2}$ can be each independently hydrogen, hydroxy or an unsubstituted $C_{1-4}$ alkyl; $R^2$ and $R^{2a1}$ can be each independently selected from hydrogen, an optionally substituted $C_{1-4}$ alkyl, alkoxyalkyl, aminoalkyl, hydroxyalkyl, hydroxy, an optionally substituted aryl($C_{1-6}$ alkyl), an optionally substituted heteroaryl($C_{1-6}$ alkyl) and an optionally substituted heterocyclyl($C_{1-6}$ alkyl); or $R^1$ and $R^2$, together with the atoms to which they are attached, can be joined to form an optionally substituted 5-membered heterocyclic ring or an optionally substituted 6-membered heterocyclic ring; and $R^{2a1}$ can be selected from hydrogen, an optionally substituted $C_{1-4}$ alkyl, alkoxyalkyl, aminoalkyl, hydroxyalkyl, hydroxy, an optionally substituted aryl($C_{1-6}$ alkyl), an optionally substituted heteroaryl($C_{1-6}$ alkyl) and an optionally substituted heterocyclyl($C_{1-6}$ alkyl); $R^{3a1}$, $R^{3a2}$ and $R^{3a3}$ can be each independently hydrogen or an unsubstituted $C_{1-4}$ alkyl; $R^4$ can be selected from hydrogen, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted $C_{3-6}$ cycloalkyl($C_{1-6}$ alkyl), an optionally substituted aryl($C_{1-6}$ alkyl), an optionally substituted heteroaryl($C_{1-6}$ alkyl), an optionally substituted heterocyclyl ($C_{1-6}$ alkyl), halo($C_{1-8}$ alkyl), an optionally substituted hydroxyalkyl, an optionally substituted alkoxyalkyl and cyano; $R^6$, $R^7$ and $R^{7a1}$ can be each independently hydrogen or an unsubstituted $C_{1-4}$ alkyl; $R^{7a2}$ and $R^{7a3}$ can be each independently hydrogen or an unsubstituted $C_{1-4}$ alkyl; $R^8$ can be hydrogen or optionally substituted $C_{1-4}$ alkyl; $R^9$, $R^{10}$, $R^{11}$, $R^{12}$, $R^{13}$, $R^{14}$, $R^{15}$, and $R^{16}$ can be each independently hydrogen or an unsubstituted $C_{1-4}$ alkyl; or $R^9$ and $R^{10}$, $R^{11}$ and $R^{12}$, $R^{13}$ and $R^{14}$, and $R^{15}$ and $R^{16}$, can be each independently taken together form an optionally substituted cycloalkyl, an optionally substituted aryl, an optionally substituted heteroaryl or an optionally substituted heterocyclyl; and each $R^{17}$, each $R^{18}$, each $R^{18a1}$, $R^{18a2}$, $R^{18a3}$, each $R^{19}$, $R^{19a1}$, each $R^{20}$, $R^{21}$, each $R^{22}$, each $R^{23}$, each $R^{23a1}$, $R^{23a2}$ and $R^{23a3}$ can be each independently hydrogen or an unsubstituted $C_{1-4}$ alkyl.

In some embodiments, ----- between $X^2$ and $X^3$ can be a double bond, $X^2$ can be N (nitrogen) or $CR^{7a1}$, and $X^3$ can be N (nitrogen) or $CR^4$. In other embodiments, ----- between $X^2$ and $X^3$ can be a single bond, $X^2$ can be O, $NR^7$, C(=O) or $C(R^{7a2})(R^{7a3})$, and $X^3$ can be $NR^4$, C(=O), $CR^4R^8$ or $CH_2CH_2C(=O)$. In still other embodiments, $X^1$, $X^2$ and $X^3$ can be each independently C (carbon), N (nitrogen), O (oxygen) or C(=O), and form a mono-cyclic ring selected from an optionally substituted mono-cyclic heteroaryl and an optionally substituted mono-cyclic heterocyclyl by joining $X^1$ and $X^3$ together; and provided that at least one of $X^1$, $X^2$ and $X^3$ comprises a nitrogen atom; with the proviso that the valencies of $X^1$, $X^2$ and $X^3$ can be each independently satisfied with a substituent selected from hydrogen and an optionally substituted $C_{1-4}$ alkyl; and $X^1$, $X^2$ and $X^3$ are uncharged. In some embodiments, the valencies of $X^1$, $X^2$ and $X^3$ can be each independently satisfied with a substituent selected from hydrogen and an unsubstituted $C_{1-4}$ alkyl (such as $CH_3$).

In some embodiments, W can be O (oxygen). In other embodiments, W can be S (sulfur). In still other embodiments, W can be C=O. In yet still other embodiments, W can be C=S. In some embodiments, W can be S=O. In other embodiments, W can be $S(=O)_2$. In still other embodiments, W can be —$C(R^{1a1})(R^{1a2})$—. In yet still other embodiments, W can be $NR^{3a3}$. In some embodiments, both $R^{1a1}$ and $R^{1a2}$ can be hydrogen. In other embodiments, at least one of $R^{1a1}$ and $R^{1a2}$ can be hydrogen and the other of $R^{1a1}$ and $R^{1a2}$ can be hydroxy or an unsubstituted $C_{1-4}$ alkyl. In some embodiments, W can be —$CH_2$—. In other embodiments, W can be NH. In still other embodiments, W can be $NR^{3a3}$, wherein $R^{3a3}$ can be an unsubstituted $C_{1-4}$ alkyl.

In some embodiments, V can be N (nitrogen). In some embodiments, V—$R^1$ can be NH. In other embodiments, V—$R^1$ can be $NR^1$, wherein $R^1$ can be an unsubstituted $C_{1-4}$ alkyl. In some embodiments, V can be CH. In some embodiments, V—$R^1$ can be $CH_2$. In other embodiments, V—$R^1$ can be $CHR^1$, wherein $R^1$ can be unsubstituted $C_{1-4}$ alkyl.

In some embodiments, E can be C. In some embodiments, when E is C, at least one of $R^{2a1}$ and $R^2$ can be hydrogen and the other of $R^{2a1}$ and $R^2$ can be hydroxy, an optionally substituted $C_{1-4}$ alkyl or an optionally substituted aryl($C_{1-6}$ alkyl). In some embodiments, when E is C, at least one of $R^{2a1}$ and $R^2$ can be hydrogen and the other of $R^{2a1}$ and $R^2$ can be an unsubstituted $C_{1-4}$ alkyl or an optionally substituted benzyl. In some embodiments, $ER^2R^{2a1}$ can be $CH_2$. In some embodiments, E can be N, provided that $R^{2a1}$ is absent. In some embodiments, E-$R^2$ can be NH. In other embodiments, E-$R^2$ can be $NR^2$, wherein $R^2$ can be hydroxy, an optionally substituted $C_{1-4}$ alkyl or an optionally substituted aryl($C_{1-6}$ alkyl). For example, E can be $NCH_3$, $NCH_2CH_3$, $NCH_2CH_2CH_3$, $NCHCH_3CH_3$.

In some embodiments,

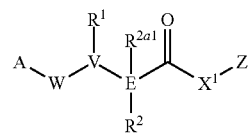

can be selected from

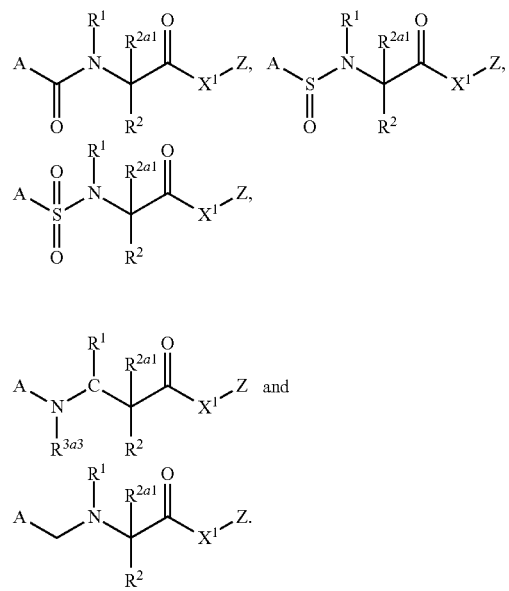

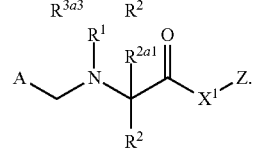

In any of embodiments of this paragraph, $R^1$ can be hydrogen. In any of the embodiments of this paragraph, $R^1$ can be an unsubstituted $C_{1-4}$ alkyl. In any of the embodiments of this paragraph, both $R^2$ and $R^{2a1}$ can be hydrogen. In any of the embodiments of this paragraph, $R^2$ can be hydrogen and $R^{2a1}$ can be an unsubstituted $C_{1-4}$ alkyl, a substituted $C_{1-4}$ alkyl, hydroxy or an optionally substituted benzyl. In any of the embodiments of this paragraph, $R^{2a1}$ can be hydrogen, and $R^1$ and $R^2$ can be joined together with the atoms to which they are attached to form an optionally substituted 5 membered heterocyclyl or an optionally substituted 6 membered heterocyclyl.

Formula (Ia)

In some embodiments, a compound of Formula (I), or pharmaceutically acceptable salt thereof, can be represented by Formula (Ia):

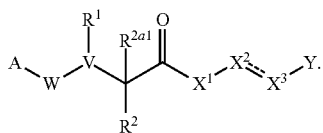

(Ia)

In some embodiments of Formula (Ia), ===== between $X^2$ and $X^3$ represents a double bond and

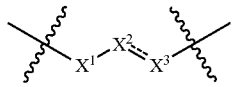

can be

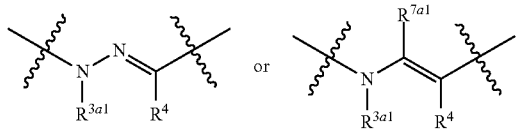

In some embodiments, $X^1$, $X^2$ and $X^3$ can be each independently C (carbon), N (nitrogen), O (oxygen) or C(=O), and form a mono-cyclic ring having the structure

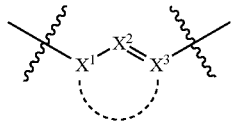

and selected from an optionally substituted mono-cyclic heteroaryl and an optionally substituted mono-cyclic heterocyclyl by joining $X^1$ and $X^3$ together; provided that at least one of $X^1$, $X^2$ and $X^3$ comprises a nitrogen atom; with the proviso that the valencies of $X^1$, $X^2$ and $X^3$ can be each independently satisfied with a substituent selected from hydrogen and an optionally substituted $C_{1-4}$ alkyl; and $X^1$, $X^2$ and $X^3$ are uncharged. In any of embodiments of this paragraph, W can be C(=O) and V can be N (nitrogen). In any of embodiments of this paragraph, W can be C(=S) and V can be N (nitrogen).

In some embodiments, ===== between $X^2$ and $X^3$ can be a double bond, $X^1$ can be $NR^{3a1}$, $X^2$ can be N (nitrogen) and $X^3$ can be $CR^4$. In some embodiments, ===== between $X^2$ and $X^3$ can be a double bond, $X^1$ can be NH, $X^2$ can be N, and $X^3$ can be CH. In other embodiments, ===== between $X^2$ and $X^3$ can be a double bond, $X^1$ can be $NR^{3a1}$, $X^2$ can be N, and $X^3$ can be $CR^4$, wherein $R^{3a1}$ can be hydrogen or an unsubstituted $C_{1-6}$ alkyl, and $R^4$ can be an unsubstituted $C_{1-6}$ alkyl. In still other embodiments, ===== between $X^2$ and $X^3$ can be a double bond, $X^1$ can be $NR^{3a1}$, $X^2$ can be N, and $X^3$ can be $CR^4$, wherein $R^{3a1}$ can be hydrogen or an unsubstituted $C_{1-6}$ alkyl, and $R^4$ can be cyano, an optionally substituted $C_{1-6}$ alkyl (for example, a cyano substituted $C_{1-6}$ alkyl), an unsubstituted $C_{2-4}$ alkenyl, an optionally substituted $C_{2-4}$ alkynyl, an unsubstituted $C_{3-6}$ cycloalkyl, an unsubstituted $C_{3-6}$ cycloalkyl($C_{1-4}$ alkyl), a hydroxy ($C_{1-4}$ alkyl), an unsubstituted $C_{1-4}$ alkoxyalkyl a halo($C_{1-4}$ alkyl), an optionally substituted phenyl or an optionally substituted heteroaryl. In yet still other embodiments, ===== between $X^2$ and $X^3$ can be a double bond, $X^1$ can be $NR^{3a1}$, $X^2$ can be N, and $X^3$ can be $CR^4$, wherein $R^4$ can be an hydrogen or an unsubstituted $C_{1-6}$ alkyl. In some embodiments, ===== between $X^2$ and $X^3$ can be a double bond, $X^1$ can be $NR^{3a1}$, $X^2$ can be $CR^{7a1}$, and $X^3$ can be $CR^4$, such as $X^1$ can be NH, $X^2$ can be CH, and $X^3$ can be CH.

In some embodiments of Formula (Ia), ===== between $X^2$ and $X^3$ represents a single bond and

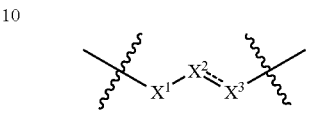

can be

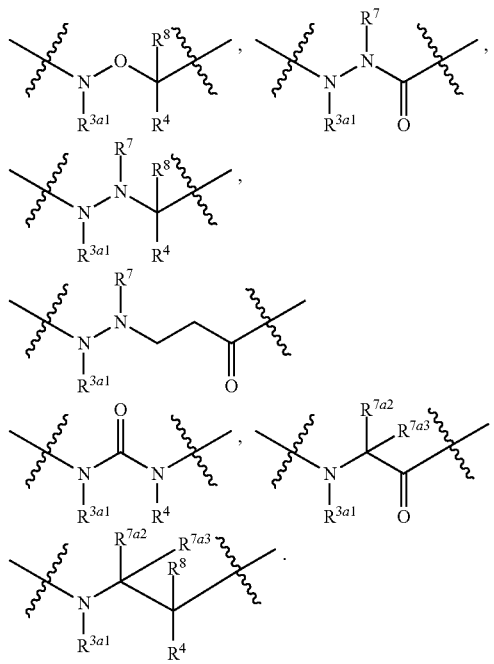

In some embodiments, $X^1$, $X^2$ and $X^3$ can be each independently C (carbon), N (nitrogen), O (oxygen) or C(=O), and form a mono-cyclic ring having the structure

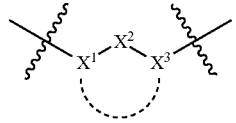

and selected from an optionally substituted mono-cyclic heteroaryl and an optionally substituted mono-cyclic heterocyclyl by joining $X^1$ and $X^3$ together; provided that at least one of $X^1$, $X^2$ and $X^3$ comprises a nitrogen atom; with the proviso that the valencies of $X^1$, $X^2$ and $X^3$ can be each independently satisfied with a substituent selected from hydrogen and an optionally substituted $C_{1-4}$ alkyl; and $X^1$, $X^2$ and $X^3$ are uncharged. In any of the embodiments of this paragraph, W can be C(=O), V can be N (nitrogen) and E can be C (carbon).

In some embodiments, ===== between $X^2$ and $X^3$ can be a single bond, $X^1$ can be NH, $X^2$ can be NH, and $X^3$ can be CH$_2$. In other embodiments, ----- between X$^2$ and X$^3$ can be a single bond, X$^1$ can be NH, X$^2$ can be CH$_2$, and X$^3$ can be CHR$^4$, wherein R$^4$ can be H, an optionally substituted C$_{1-4}$ alkyl or C$_{1-4}$ alkoxyalkyl. In still other embodiments, ----- between X$^2$ and X$^3$ can be a single bond, X$^1$ can be NR$^{3a1}$, X$^2$ can be O, and X$^3$ can be CH$_2$, wherein R$^{3a1}$ can be an unsubstituted C$_{1-4}$ alkyl. In yet still embodiments, ----- between X$^2$ and X$^3$ can be a single bond, X$^1$ can be NH, X$^2$ can be NR$^7$, and X$^3$ can be C(=O), wherein R$^7$ can be hydrogen or an unsubstituted C$_{1-4}$ alkyl. In some embodiments, ----- between X$^2$ and X$^3$ can be a single bond, X$^1$ can be NR$^{3a1}$, X$^2$ can be C(=O), and X$^3$ can be NR$^4$, wherein R$^{3a1}$ can be an unsubstituted C$_{1-4}$ alkyl and R$^4$ can be an unsubstituted C$_{1-4}$ alkyl or alkoxyalkyl. In other embodiments, ----- between X$^2$ and X$^3$ can be a single bond, X$^1$ can be NH, X$^2$ can be CH$_2$, and X$^3$ can be C(=O).

Formula (Ib)

In some embodiments, a compound of Formula (I) can be represented by Formula (Ib):

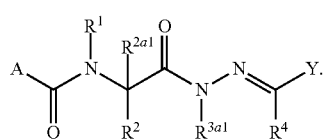

(Ib)

In some embodiments of Formula (Ib), R$^{3a1}$ can be hydrogen. In other embodiments of Formula (Ib), R$^{3a1}$ can be an unsubstituted C$_{1-4}$ alkyl.

In some embodiments of Formula (Ib), R$^4$ can be selected from hydrogen, an optionally substituted C$_{1-8}$ alkyl, an optionally substituted C$_{2-8}$ alkenyl, an optionally substituted C$_{2-8}$ alkynyl, an optionally substituted C$_{3-6}$ cycloalkyl, an optionally substituted aryl (for example, phenyl), an optionally substituted heteroaryl (for example, thiophenyl or pyridinyl), an optionally substituted heterocyclyl, an optionally substituted C$_{3-6}$ cycloalkyl(C$_{1-6}$ alkyl), an optionally substituted aryl(C$_{1-6}$ alkyl) (for example, benzyl), an optionally substituted heteroaryl(C$_{1-6}$ alkyl), an optionally substituted heterocyclyl(C$_{1-6}$ alkyl), halo(C$_{1-8}$ alkyl), an optionally substituted hydroxyalkyl, an optionally substituted alkoxyalkyl and cyano.

Formula (Ic)

In some embodiments, a compound of Formula (I) can be represented by Formula (Ic):

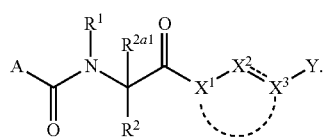

(Ic)

wherein the dotted curved line between X$^1$ and X$^3$ indicates a mono-cyclic ring selected from an optionally substituted mono-cyclic heteroaryl and an optionally substituted mono-cyclic heterocyclyl by joining X$^1$ and X$^3$ together; wherein X$^1$, X$^2$ and X$^3$ can be each independently C (carbon), N (nitrogen), O (oxygen) or C(=O); and provided that at least one of X$^1$, X$^2$ and X$^3$ comprises a nitrogen atom; with the proviso that the valencies of X$^1$, X$^2$ and X$^3$ can be each independently satisfied with a substituent selected from hydrogen and an optionally substituted C$_{1-4}$ alkyl; and X$^1$, X$^2$ and X$^3$ are uncharged. In some embodiments, the valencies of X$^1$, X$^2$ and X$^3$ can be each independently satisfied with a substituent selected from hydrogen and an unsubstituted C$_{1-4}$ alkyl. In some embodiments, the valencies of X$^1$, X$^2$ and X$^3$ can be each independently satisfied with hydrogen or methyl.

In some embodiments of Formula (Ic), the mono-cyclic ring can be an optionally substituted 5 membered heteroaryl. In other embodiments of Formula (Ic), the mono-cyclic ring can be an optionally substituted 5 membered heterocyclyl. In still other embodiments of Formula (Ic), the mono-cyclic ring can be an optionally substituted 6 membered heteroaryl. In yet still other embodiments of Formula (Ic), the mono-cyclic ring can be an optionally substituted 6 membered heterocyclyl.

In some embodiments of Formula (Ic), X$^1$ can be C, X$^2$ can be N and X$^3$ can be C. In some embodiments of Formula (Ic), when X$^1$ can be C, X$^2$ can be N and X$^3$ can be C, the mono-cyclic ring can be an optionally substituted mono-cyclic heteroaryl ring. In other embodiments of Formula (Ic), when X$^1$ can be C, X$^2$ can be N and X$^3$ can be C, the mono-cyclic ring can be an optionally substituted mono-cyclic heterocyclyl.

In some embodiments of Formula (Ic), when X$^1$ can be C, X$^2$ can be N and X$^3$ can be C, the mono-cyclic ring can be selected from an optionally substituted

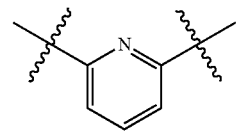

, an optionally substituted

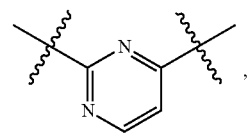

, an optionally substituted

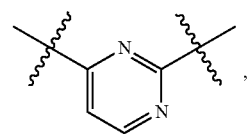

, an optionally substituted

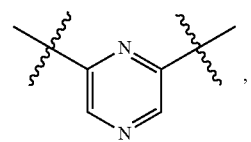 [SMILES: *c1cncc(*)n1]

, an optionally substituted

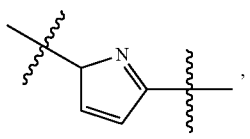 [SMILES: *C1=NC(*)C=C1]

an optionally substituted

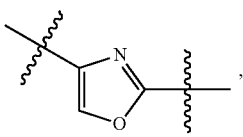 [SMILES: *c1coc(*)n1]

an optionally substituted

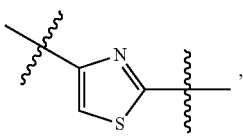 [SMILES: *c1csc(*)n1]

an optionally substituted

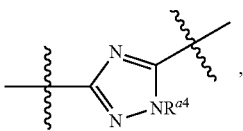

and an optionally substituted

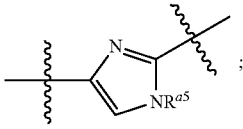

wherein $R^{a4}$ and $R^{a5}$ can be each independently hydrogen or an unsubstituted $C_{1-6}$ alkyl.

In some embodiments of Formula (Ic), when $X^1$ can be C, $X^2$ can be N and $X^3$ can be C, the mono-cyclic ring can be selected from an optionally substituted

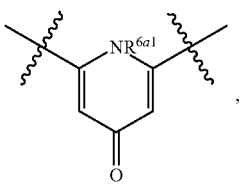

an optionally substituted

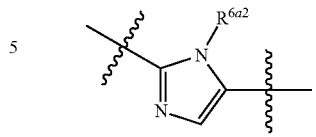

and an optionally substituted

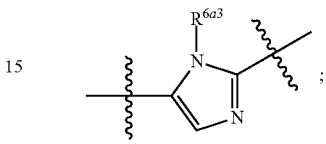

wherein $R^{6a1}$, $R^{6a2}$ and $R^{6a3}$ can be each independently hydrogen or an unsubstituted $C_{1-6}$ alkyl In some embodiments of Formula (Ic), $X^1$ can be N, $X^2$ can be N and $X^3$ can be C. In some embodiments of Formula (Ic), when $X^1$ can be N, $X^2$ can be N and $X^3$ can be C, the mono-cyclic ring or can be an optionally substituted mono-cyclic heteroaryl ring. In other embodiments of Formula (Ic), when $X^1$ can be N, $X^2$ can be N and $X^3$ can be C, the mono-cyclic ring can be an optionally substituted mono-cyclic heterocyclyl ring.

In some embodiments of Formula (Ic), when $X^1$ can be N, $X^2$ can be N and $X^3$ can be C, the mono-cyclic ring can be selected from an optionally substituted

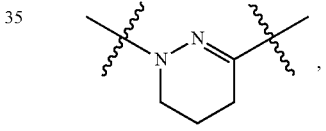

an optionally substituted

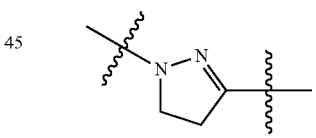

and an optionally substituted

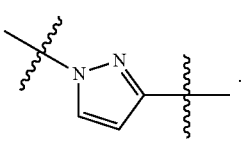 [SMILES: *c1ccn(*)n1]

In some embodiments of Formula (Ic), $X^1$ can be N, $X^2$ can be C(=O) and $X^3$ can be N. In some embodiments of Formula (Ic), when $X^1$ can be N, $X^2$ can be C(=O) and $X^3$ can be N, the mono-cyclic ring can be an optionally substituted mono-cyclic heteroaryl ring. In other embodiments of Formula (Ic), when $X^1$ can be N, $X^2$ can be C(=O) and $X^3$ can be N, the mono-cyclic ring can be an optionally substituted mono-cyclic heterocyclyl.

In some embodiments of Formula (Ic), when $X^1$ can be N, $X^2$ can be C(=O) and $X^3$ can be N, the mono-cyclic ring can be selected from an optionally substituted

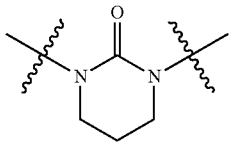 [SMILES: *N1CCCN(*)C1=O]

or an optionally substituted

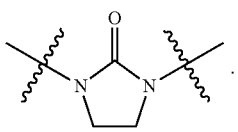 [SMILES: *N1CCN(*)C1=O]

Formula (Id)

In some embodiments, a compound of Formula (I) can be represented by Formula (Id):

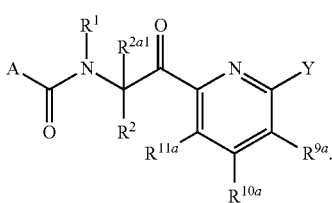

wherein $R^{9a}$, $R^{10a}$ and $R^{11a}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy. In some embodiments, at least one of $R^{9a}$, $R^{10a}$ and $R^{11a}$ can be a $C_{1-4}$ alkoxy. In some embodiments, $R^{9a}$ can be a $C_{1-4}$ alkoxy, and $R^{10a}$ and $R^{11a}$ can be both hydrogen.

Formula (Ie)

In some embodiments, a compound of Formula (I) can be represented by Formula (Ie):

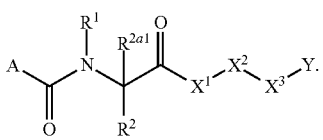

In some embodiments of Formula (Ie), $X^1$ can be $NR^{3a1}$, $X^2$ can be $NR^7$, and $X^3$ can be $CR^4R^8$. In other embodiments of Formula (Ie), $X^1$ can be $NR^{3a1}$, $X^2$ can be $CR^{7a2}R^{7a3}$, and $X^3$ can be $CR^4R^8$. In still other embodiments of Formula (Ie), $X^1$ can be $NR^{3a1}$, $X^2$ can be O, and $X^3$ can be $CR^4R^8$.

In some embodiments, including those of this paragraph, $R^8$ can be hydrogen. In other embodiments, including those of this paragraph, $R^8$ can be an optionally substituted $C_{1-4}$ alkyl. In some embodiments, including those of this paragraph, $R^8$ can be an unsubstituted $C_{1-4}$ alkyl.

In some embodiments of Formula (Ie), $X^1$ can be $NR^{3a1}$, $X^2$ can be $NR^7$, and $X^3$ can be C(=O). In other embodiments of Formula (Ie), $X^1$ can be $NR^{3a1}$, $X^2$ can be C(=O), and $X^3$ can be $NR^4$. In still other embodiments of Formula (Ie), $X^1$ can be $NR^{3a1}$, $X^2$ can be $CR^{7a2}R^{7a3}$, and $X^3$ can be C(=O). In yet still other embodiments of Formula (Ie), $X^1$ can be $NR^{3a1}$, $X^2$ can be $NR^7$, and $X^3$ can be $CH_2CH_2C(=O)$.

Formula (If)

In some embodiments, a compound of Formula (I) can be represented by Formula (If):

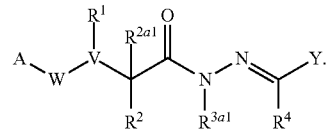

wherein: W can be O (oxygen), S (sulfur), C=S, $NR^{3a3}$, S=O, $S(=O)_2$ or $—C(R^{1a1})(R^{1a2})—$, and V can be N or CH.

In some embodiments of Formula (If), $R^{3a1}$ can be hydrogen. In other embodiments of Formula (If), $R^{3a1}$ can be unsubstituted $C_{1-4}$ alkyl.

In some embodiments of Formula (If), $R^4$ can be selected from hydrogen, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl (for example, phenyl), an optionally substituted heteroaryl (for example, thiophenyl or pyridinyl), an optionally substituted heterocyclyl, an optionally substituted $C_{3-6}$ cycloalkyl($C_{1-6}$ alkyl), an optionally substituted aryl($C_{1-6}$ alkyl) (for example, benzyl), an optionally substituted heteroaryl($C_{1-6}$ alkyl), an optionally substituted heterocyclyl($C_{1-6}$ alkyl), halo($C_{1-8}$ alkyl), an optionally substituted hydroxyalkyl, an optionally substituted alkoxyalkyl and cyano.

Formulae (Ig) and (Ih)

In some embodiments, a compound of Formula (I) can be represented by Formula (Ig) or Formula (Ih):

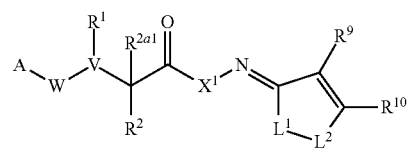

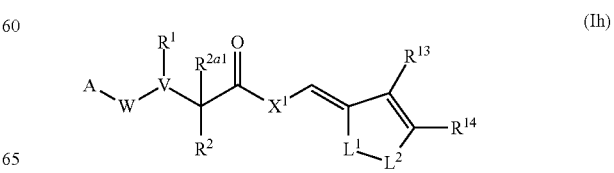

In some embodiments, W of Formula (Ig) or Formula (Ih) can be C(=O).

In some embodiments, V of Formula (Ig) or Formula (Ih) can be N (nitrogen).

In some embodiments, $X^1$ of Formula (Ig) or Formula (Ih) can be $NR^{3a1}$, such as NH.

In some embodiments of Formulae (Ig) and (Ih), $L^1$ can be —$C(R^{18})_2C(R^{18a1})_2$— and $L^2$ can be —$C(R^{20})_2$—. In some embodiments, $L^1$ can be —$CH_2CH_2$— and $L^2$ can be —$CH_2$—. In other embodiments of Formulae (Ig) and (Ih), $L^1$ can be —$C(R^{17})_2$— and $L^2$ can be —$C(R^{20})_2$—, such as $L^1$ can be —$CH_2$— and $L^2$ can be —$CH_2$—. In still other embodiments of Formulae (Ig) and (Ih), $L^1$ can be —$C(R^{18})_2C(R^{18a1})_2$— and $L^2$ can be selected from —$N(R^{21})$—, S and O. In some embodiments, $L^1$ can be —$CH_2CH_2$— and $L^2$ can be —NH—. In other embodiments, $L^1$ can be —$CH_2CH_2$— and $L^2$ can be —O—. In still other embodiments, $L^1$ can be —$CH_2CH_2$— and $L^2$ can be —S—. In yet still other embodiments of Formulae (Ig) and (Ih), $L^1$ can be —$C(R^{19})_2N(R^{19a1})$— and $L^2$ can be —$C(R^{20})_2$— (for example, $L^1$ can be —$CH_2N(CH_2CH_3)$— and $L^2$ can be —$CH_2$—).

In some embodiments of Formula (Ig), $R^9$ and $R^{10}$ can be each joined together with the atoms to which they are attached to form an optionally substituted aryl. For example, the optionally substituted phenyl can be substituted one or more times. In other embodiments of Formula (Ig), the optionally substituted aryl can be an unsubstituted aryl. In some embodiments of Formula (Ig), $R^9$ and $R^{10}$ can be each joined together with the atoms to which they are attached to form an optionally substituted heteroaryl. In some embodiments of Formula (Ig), $R^9$ and $R^{10}$ can be each joined together with the atoms to which they are attached to form an optionally substituted heterocyclyl.

In some embodiments of Formula (Ih), $R^{13}$ and $R^{14}$ can be each joined together with the atoms to which they are attached to form an optionally substituted aryl. For example, the optionally substituted phenyl can be substituted one or more times. In some embodiments of Formula (Ih), the optionally substituted aryl (such as phenyl) can be substituted with one or more substituents selected from halo, alkyl and alkoxy. In other embodiments, the optionally substituted aryl can be an unsubstituted aryl. In some embodiments of Formula (Ih), $R^{13}$ and $R^{14}$ can be each joined together with the atoms to which they are attached to form an optionally substituted heteroaryl. Suitable examples of optionally substituted heteroaryls include, but are not limited to, an optionally substituted thiophene, an optionally substituted benzothiophene, or an optionally substituted indole. In some embodiments, the optionally substituted heteroaryl can be substituted with one or more substituents selected from halo, alkyl and alkoxy. In some embodiments, the heteroaryl can be unsubstituted. In some embodiments of Formula (Ih), $R^{13}$ and $R^{14}$ can be each joined together with the atoms to which they are attached to form an optionally substituted heterocyclyl.

Formulae (Ii) and (Ij)

In some embodiments, a compound of Formula (I) can be represented by Formula (Ii) or Formula (Ij):

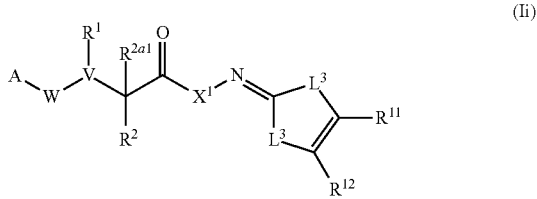

(Ii)

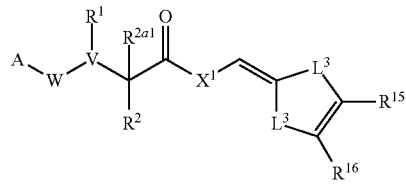

(Ij)

In some embodiments, W of Formula (Ii) or Formula (Ij) can be C(=O).

In some embodiments, V of Formula (Ii) or Formula (Ij) can be N (nitrogen).

In some embodiments, $X^1$ of Formula (Ii) or Formula (Ij) can be $NR^{3a1}$, such as NH.

In some embodiments of Formula (Ii) or Formula (Ij), $L^3$ can be —$C(R^{22})_2$—, for example, —$CH_2$—.

In some embodiments of Formula (Ii), $R^{11}$ and $R^{12}$ can be each joined together with the atoms to which they are attached to form an optionally substituted aryl. For example, the optionally substituted phenyl can be substituted one or more times. In other embodiments, the optionally substituted aryl can be an unsubstituted aryl. In some embodiments of Formula (Ii), $R^{11}$ and $R^{12}$ can be each joined together with the atoms to which they are attached to form an optionally substituted heteroaryl. In some embodiments of Formula (Ii), $R^{11}$ and $R^{12}$ can be each joined together with the atoms to which they are attached to form an optionally substituted heterocyclyl.

In some embodiments of Formula (Ij), $R^{15}$ and $R^{16}$ can be each joined together with the atoms to which they are attached to form an optionally substituted aryl. For example, the optionally substituted phenyl can be substituted one or more times. In some embodiments, the optionally substituted aryl (such as phenyl) can be substituted with one or more substituents selected from halo, alkyl and alkoxy. In other embodiments, the optionally substituted aryl can be an unsubstituted aryl. In some embodiments of Formula (Ij), $R^{15}$ and $R^{16}$ can be each joined together with the atoms to which they are attached to form an optionally substituted heteroaryl. Suitable examples of optionally substituted heteroaryls include, but are not limited to, an optionally substituted thiophene, an optionally substituted benzothiophene, or an optionally substituted indole. In some embodiments, the optionally substituted heteroaryl can be substituted with one or more substituents selected from halo, alkyl and alkoxy. In some embodiments, the heteroaryl can be unsubstituted. In some embodiments of Formula (Ij), $R^{15}$ and $R^{16}$ can be each joined together with the atoms to which they are attached to form an optionally substituted heterocyclyl.

In some embodiments of Formulae (Ia), (Ib), (Ic), (Id), (Ie), (If), (Ig), (Ih), (Ii) and/(Ij), $R^1$ can be hydrogen. In some embodiments of Formulae (Ia), (Ib), (Ic), (Id), (Ie), (If), (Ig), (Ih), (Ii) and/(Ij), $R^1$ can be an unsubstituted $C_{1-4}$ alkyl.

In some embodiments of Formulae (Ia), (Ib), (Ic), (Id), (Ie), (If), (Ig), (Ih), (Ii) and/(Ij), both $R^2$ and $R^{2a1}$ can be hydrogen. In other embodiments of Formulae (Ia), (Ib), (Ic), (Id), (Ie), (If), (Ig), (Ih), (Ii) and/(Ij), $R^2$ can be hydrogen and $R^{2a1}$ can be an unsubstituted $C_{1-4}$ alkyl. In still other embodiments of Formulae (Ia), (Ib), (Ic), (Id), (Ie), (If), (Ig), (Ih), (Ii) and/(Ij), $R^2$ can be hydrogen and $R^{2a1}$ can be a substituted $C_{1-4}$ alkyl. In yet still other embodiments of Formulae (Ia), (Ib), (Ic), (Id), (Ie), (If), (Ig), (Ill), (Ii) and/(Ij), $R^2$ can be hydrogen and $R^{2a1}$ can be an optionally substituted aryl($C_{1-6}$ alkyl) or an optionally substituted heterocyclyl($C_{1-6}$ alkyl). In some embodiments of Formulae (Ia), (Ib), (Ic), (Id), (Ie), (If), (Ig), (Ih), (Ii) and/(Ij), $R^2$ can be hydrogen and $R^{2a1}$ can be an alkoxyalkyl, an aminoalkyl or a hydroxyalkyl. In other embodiments of Formulae (Ia), (Ib), (Ic), (Id), (Ie), (If), (Ig), (Ih), (Ii) and/(Ij), $R^2$ can be hydrogen and $R^{2a1}$ can be hydroxy. In still other embodiments of Formulae (Ia), (Ib), (Ic), (Id), (Ie), (If), (Ig), (Ih), (Ii) and/(Ij), $R^{2a1}$ can be hydrogen, and $R^1$ and $R^2$ can be joined together with the atoms to which they are attached to form an optionally substituted 5 membered heterocyclyl (for example, pyrrolidinyl) or an optionally substituted 6 membered heterocyclyl (for example, piperidinyl).

In some embodiments, A can be substituted. In other embodiments, A can be unsubstituted.

In some embodiments, A can be an optionally substituted aryl. For example, A can be an optionally substituted phenyl. In some embodiments, A can be a para-substituted phenyl, a meta-substituted phenyl or an ortho-substituted phenyl. In some embodiments, A can be a di-substituted phenyl. For example, A can be a 3,4-substituted phenyl, such as

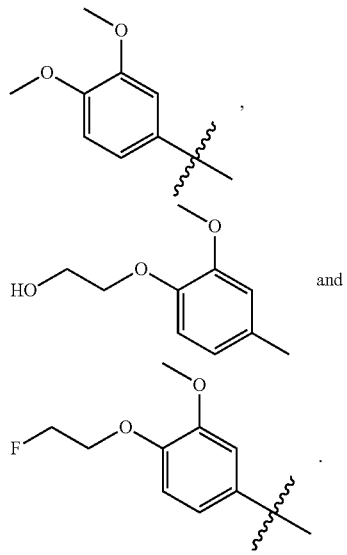

In some embodiments, A can be a substituted phenyl that is substituted with 3 more substituents. In other embodiments, A can be unsubstituted phenyl. In some embodiments, A can be an optionally substituted naphthyl.

In some embodiments and without limitation, A can be a phenyl substituted with one or more substituents selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, sulfenyl, alkyoxyalkyl, aryl, mono-cyclic heteroaryl, mono-cyclic heterocyclyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

Examples of suitable substituents include, but are not limited to, methyl, ethyl, propyl (n-propyl and iso-propyl), butyl (n-butyl, iso-butyl and t-butyl), hydroxy, methoxy, ethoxy, propoxy (n-propoxy and iso-propoxy), butoxy (n-butoxy, iso-butoxy and t-butoxy), phenoxy, bromo, chloro, fluoro, trifluoromethyl, difluoromethoxy, trifluoromethoxy, N,N-di-methyl-amine, N,N-di-ethyl-amine, N-methyl-N-ethyl-amine, N-methyl-amino, N-ethyl-amino, amino, alkylthio (such as $CH_3CH_2S$—), phenyl, imidazole, morpholinyl, pyrazole, pyrrolidinyl, pyridinyl, piperidinyl, pyrrolidinone, pyrimidine, pyrazine, 1,2,4-oxadiazole, —$(CH_2)_{1-2}$—$NH(CH_3)$, —$O(CH_2)_2$—$NH_2$, —$O(CH_2)_2$—$NH(CH_3)$, —$O(CH_2)_2$—$N(CH_3)_2$, —O—$(CH_2)_{2-4}OH$, —$O(CH_2)_2OCH_3$, —$O(CH_2)_{1-2}$-morpholinyl, —$O(CH_2)_{1-2}$-triazole, —$O(CH_2)_{1-2}$-imidazole,

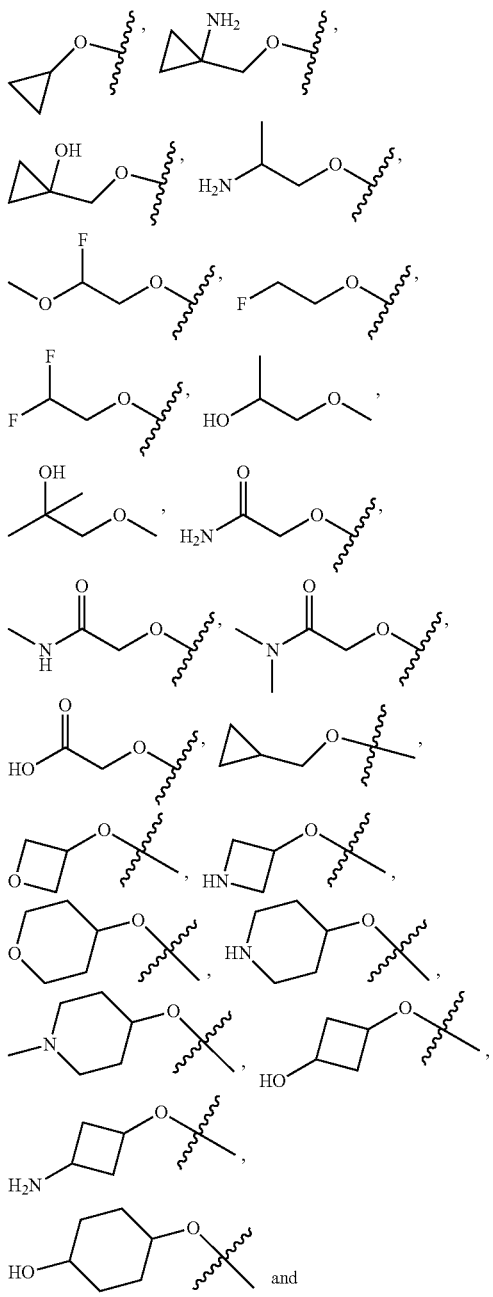

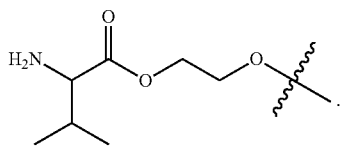

In some embodiments, A can be an optionally substituted cycloalkyl. Suitable examples of optionally substituted cycloalkyls include, but are not limited to, an optionally substituted cyclohexyl and an optionally substituted cycloheptyl. In other embodiments, A can be an optionally substituted cycloalkenyl, for example, an optionally substituted cyclohexenyl. In some embodiments, A can be an optionally substituted bi-cyclic cycloalkenyl, such as

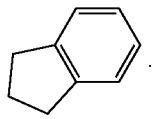

In some embodiments, A can be an optionally substituted aryl($C_{1-2}$ alkyl). In some embodiments, A can be an optionally substituted benzyl.

In some embodiments, A can be an optionally substituted mono-cyclic heteroaryl. In some embodiments, A can be an optionally substituted mono-cyclic 5-membered heteroaryl. In other embodiments, A can be an optionally substituted mono-cyclic 6-membered heteroaryl. In some embodiments, A can be an optionally substituted bi-cyclic heteroaryl.

In some embodiments, the optionally substituted heteroaryl can be selected from an optionally substituted imidazole, an optionally substituted thiazole, an optionally substituted furan, an optionally substituted thiophene, an optionally substituted pyrrole, an optionally substituted pyridine, an optionally substituted pyrimidine, an optionally substituted pyrazine, an optionally substituted quinolone, an optionally substituted imidazole, an optionally substituted oxazole and an optionally substituted isoxazole. In some embodiments, A can be an optionally substituted thiophene. In other embodiments, A can be an optionally substituted thiazole. In still other embodiments, A can be an optionally substituted pyridine. In yet still other embodiments, A can be an optionally substituted pyrimidine. In some embodiments, A can be an optionally substituted pyrazine. In other embodiments, A can be an optionally substituted imidazole.

In some embodiments, A can be an optionally substituted heterocyclyl, for example, an optionally substituted mono-cyclic heterocyclyl or an optionally substituted bi-cyclic heterocyclyl. In some embodiments, A can be an optionally substituted

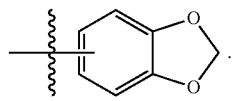

In other embodiments, A can be an optionally substituted

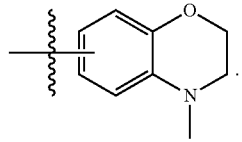

In still other embodiments, A can be an optionally substituted

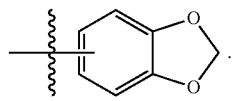

In some embodiments, A can be substituted with one or more $R^{A'}$s. In some embodiments, one $R^A$ can be present. In some embodiments, two $R^{A'}$s can be present. In some embodiments, three $R^{A'}$s can be present. In some embodiments, four or more $R^{A'}$s can be present. When two or more $R^{A'}$s are present, two or more $R^{A'}$s can be the same or two or more $R^{A'}$s can be different. In some embodiments, at least two $R^{A'}$s can be the same. In some embodiments, at least two $R^{A'}$s can be different. In some embodiments, all the $R^{A'}$s can be the same. In other embodiments, all the $R^{A'}$s can be different.

In some embodiments, $R^A$ can be each independently selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, sulfenyl, alkyoxyalkyl, aryl, mono-cyclic heteroaryl, mono-cyclic heterocyclyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

In some embodiments, each $R^A$ can be an alkyl, such as methyl, ethyl, propyl (n-propyl and iso-propyl) and/or butyl (n-butyl, iso-butyl and t-butyl).

In some embodiments, each $R^A$ can be an optionally substituted alkoxy, for example, methoxy, ethoxy, propoxy (n-propoxy and iso-propoxy), butoxy (n-butoxy, iso-butoxy and t-butoxy), phenoxy, —O(CH$_2$)$_2$—NH$_2$, —O(CH$_2$)$_2$—NH(CH$_3$), —O(CH$_2$)$_2$—N(CH$_3$)$_2$, —O—

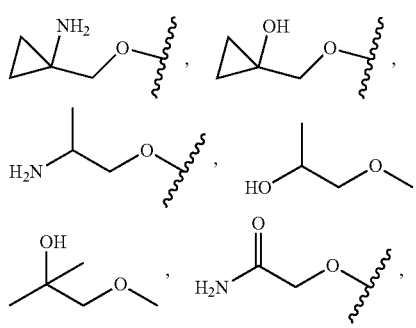

-continued

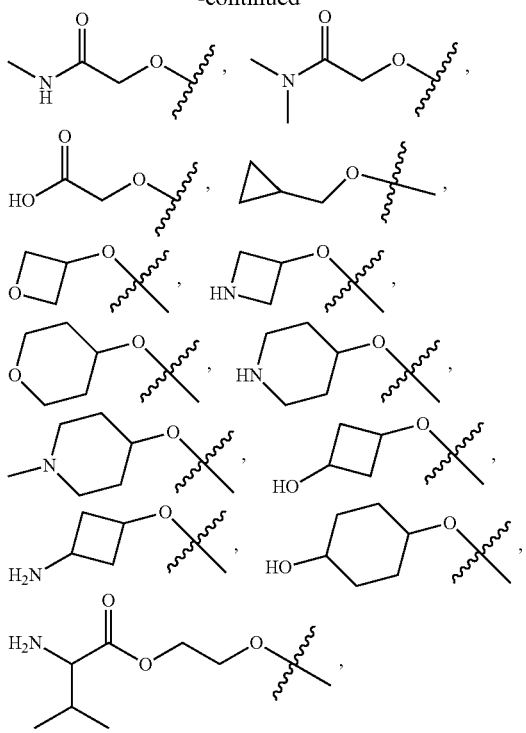

—O(CH$_2$)$_2$OCH$_3$, —O(CH$_2$)$_{1-2}$-morpholinyl, —O(CH$_2$)$_{1-2}$-triazole, —O(CH$_2$)$_{1-2}$-imidazole and/or

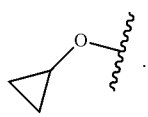 [SMILES: *OC1CC1]

In some embodiments, each R$^A$ can be haloalkyl, for example, trifluoromethyl.

In some embodiments, each R$^A$ can be an optionally substituted haloalkoxy, for example, difluoromethoxy, trifluoromethoxy,

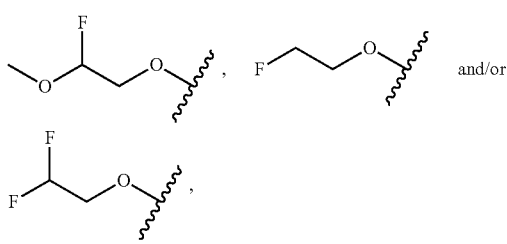

In some embodiments, each R$^A$ can be halogen, for example, chloro, bromo and/or fluoro.

In some embodiments, each R$^A$ can be amino, a mono-substituted amine or a di-substituted amine. For examples, R$^A$ can be N,N-di-methyl-amine, N,N-di-ethyl-amine, N-methyl-N-ethyl-amine, N-methyl-amino, N-ethyl-amino and/or amino.

In some embodiments, each R$^A$ can be hydroxy.

In some embodiments, each R$^A$ can be alkylthio, for example ethylthio.

In some embodiments, each R$^A$ can be aminoalkyl, such as —(CH$_2$)$_{1-2}$—NH(CH$_3$).

In some embodiments, each R$^A$ can be alkoxyalkyl, for example, —CH$_2$—O—CH$_3$.

In some embodiments, each R$^A$ can be aminoalkyl, for example, —CH$_2$—NH$_2$ and/or —CH$_2$—N(CH$_3$)H.

In some embodiments, each R$^A$ can be an optionally substituted aryl, for example, an optionally substituted phenyl.

In some embodiments, each R$^A$ can be an optionally substituted mono-cyclic heteroaryl, such as an optionally substituted imidazole, an optionally substituted pyrazole, an optionally substituted pyridinyl, an optionally substituted pyrimidine, an optionally substituted pyrazine and/or an optionally substituted 1,2,4-oxadiazole.

In some embodiments, each R$^A$ can be an optionally substituted mono-cyclic heterocyclyl, for example, an optionally substituted pyrrolidinyl, an optionally substituted piperidinyl, an optionally substituted morpholinyl and/or an optionally substituted pyrrolidinone.

In some embodiments, Y can be an optionally substituted aryl. In some embodiments, Y can be a para-substituted phenyl, a meta-substituted phenyl or an ortho-substituted phenyl. In some embodiments, Y can be a di-substituted phenyl, for example a di-halo substituted phenyl. For example, di-halo substituted phenyls include, but are not limited to,

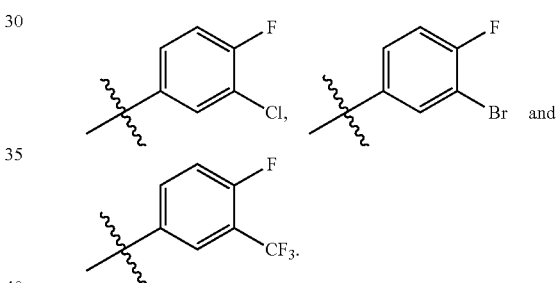

In some embodiments, Y can be a substituted phenyl that is substituted with 3 more substituents. In other embodiments, Y can be unsubstituted phenyl. In some embodiments, Y can be a substituted naphthyl. In other embodiments, Y can be an unsubstituted naphthyl.

In some embodiments, Y can be an optionally substituted acylalkyl, such as an optionally substituted acyl(C$_{1-3}$ alkyl). In other embodiments, Y can be an optionally substituted cycloalkyl (e.g., an optionally substituted cyclohexyl and an optionally substituted cycloheptyl). In still other embodiments, Y can be an optionally substituted cycloalkenyl, for example, an optionally substituted cyclohexenyl. In other embodiments. Y can be an optionally substituted bi-cyclic cycloalkenyl, such as

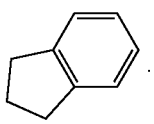

In some embodiments, Y can be an optionally substituted mono-cyclic heteroaryl. In some embodiments, Y can be selected from an optionally substituted imidazole, an optionally substituted furan, an optionally substituted thiophene, an optionally substituted pyrrole, an optionally substituted pyrimidine, an optionally substituted pyrazine, an optionally substituted pyridine, an optionally substituted pyrazole, an optionally substituted oxazole and an optionally substituted isoxazole. In some embodiments, Y can be a substituted mono-cyclic heteroaryl, including those described herein. In some embodiments, Y can be an unsubstituted mono-cyclic heteroaryl, including those described herein.

In some embodiments, Y can be an optionally substituted bi-cyclic heteroaryl. In some embodiments, Y can be selected from an optionally substituted benzothiophene, an optionally substituted benzofuran, an optionally substituted indole, an optionally substituted quinoline, an optionally substituted isoquinoline, an optionally substituted benzo-oxazole, an optionally substituted benzoisoxazole, an optionally substituted benzoisothiazole, an optionally substituted benzothiazole, an optionally substituted benzoimidazole, an optionally substituted benzotriazole, an optionally substituted 1H-indazole and an optionally substituted 2H-indazole. In some embodiments, Y can be selected from an optionally substituted

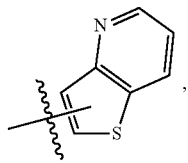

an optionally substituted

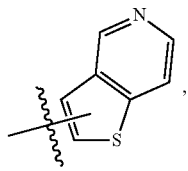

an optionally substituted

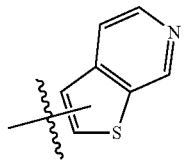

an optionally substituted

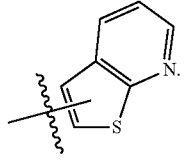

an optionally substituted an optionally substituted an optionally substituted and an optionally substituted

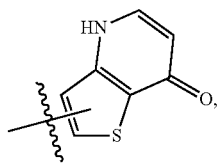

In some embodiments, Y can be a substituted bi-cyclic heteroaryl, including those described herein. In some embodiments, Y can be an unsubstituted bi-cyclic heteroaryl, including those described herein.

In some embodiments, Y can be an optionally substituted heterocyclyl. In some embodiments, Y can be an optionally substituted mono-cyclic heterocyclyl. In other embodiment, Y can be an optionally substituted bi-cyclic heterocyclyl. For example, Y can be an optionally substituted an optionally substituted

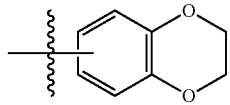

or an optionally substituted

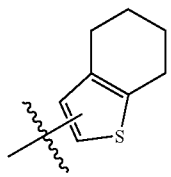

When Y is substituted, Y can be substituted with one or more $R^B$'s. In some embodiments, each $R^B$ can be independently selected from cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

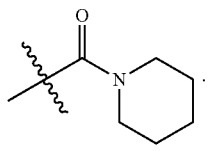

In some embodiments, when Y is an optionally substituted phenyl, the phenyl can be substituted 1, 2, 3 or more times with cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, $C_{1-4}$ haloalkyl (such as $CF_3$, $CHF_2$), haloalkoxy (such as $OCF_3$), an unsubstituted acyl, an optionally substituted —C-carboxy, an optionally substituted —C-amido, sulfonyl, amino, mono-$C_{1-4}$ alkyl amine, di-$C_{1-4}$ alkyl amine and/or

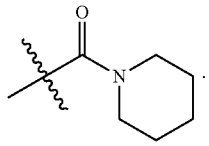

In other embodiments, when Y is an optionally substituted mono-cyclic heteroaryl, the mono-cyclic heteroaryl can be substituted 1, 2, 3 or more times with halo, an optionally substituted $C_{1-4}$ alkyl, an optionally substituted phenyl and/or an unsubstituted acyl. In still other embodiments, when Y is an optionally substituted bi-cyclic heteroaryl, the bi-cyclic heteroaryl can be substituted 1, 2, 3 or more times with halo, an optionally substituted $C_{1-4}$ alkyl, an optionally substituted phenyl, hydroxy, $C_{1-4}$ alkoxy, an unsubstituted acyl, carbonyl, cyano, amino, mono-$C_{1-4}$ alkyl amine and/or di-$C_{1-4}$ alkyl amine.

In some embodiments, Y can be an optionally substituted benzothiophene. In some embodiments, Y can be a substituted benzothiophene. In other embodiments, Y can be an unsubstituted benzothiophene. In some embodiments, the benzothiophene can be substituted with one or more of the following: halogen (such as fluoro, chloro and/or bromo), carbonyl, $C_{1-4}$ alkyl, hydroxy, $C_{1-4}$ alkoxy, $NH_2$ and/or mono-substituted amine. For example, the benzothiophene can be an optionally substituted

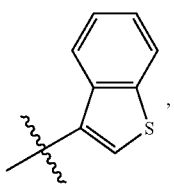 [SMILES: *c1csc2ccccc12]

such as an optionally substituted

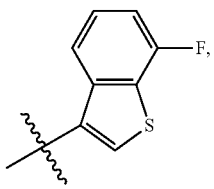 [SMILES: *c1csc2c(F)cccc12]

an optionally substituted

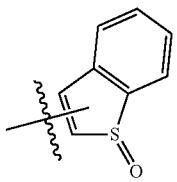

and an optionally substituted

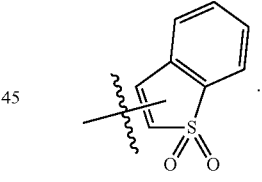

In some embodiments, Y can be an optionally substituted benzofuran.

In some embodiments, Y can be an optionally substituted indole. In some embodiments, Y can be a substituted indole. In some embodiments, the indole can be substituted 1, 2, 3 or more time with phenyl (substituted or unsubstituted), $C_{1-4}$ alkyl and/or halo. In other embodiments, Y can be an unsubstituted indole.

In some embodiments, Y can be substituted with one or more halogen. In some embodiments, Y can be substituted with one or more unsubstituted $C_{1-4}$ alkyl. In some embodiments, Y can be substituted with more or more hydroxy. In some embodiments, Y can be substituted with one or more optionally substituted phenyl. In some embodiments, Y can be substituted with one or more alkoxy. In some embodiments, Y can be substituted with one or more acyl. In some embodiments, Y can be substituted with one or more amino, mono-substituted amino, or di-substituted amino. In some embodiments, Y can be substituted with one or more haloalkyl. In some embodiments, Y can be substituted with one or more haloalkoxy. In some embodiments, Y can be substituted with one or more C-carboxy. In some embodiments, Y can be substituted with one or more C-amido.

In some embodiments, when $X^1$ is $NR^{3a1}$, $X^2$ ---- $X^3$ is $N=CR^4$, Y is an optionally substituted indolyl, then $R^4$ is selected from hydrogen, cyano, an optionally substituted $C_{2-6}$ alkyl, an optionally substituted acylalkyl, an optionally substituted hydroxyalkyl, an optionally substituted alkoxy(alkyl), an optionally substituted $C_{2-6}$ alkenyl, an optionally substituted $C_{2-6}$ alkynyl, haloalkyl, an optionally substituted $C_{3-6}$ cycloalkyl, an optionally substituted $C_{3-6}$ cycloalkyl($C_{1-6}$ alkyl), an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, when $X^1$ is $NR^{3a1}$, $X^2$ ---- $X^3$ is $N=CR^4$, Y is

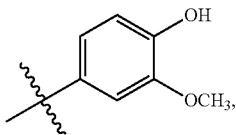

then $R^4$ is selected from cyano, halo($C_{1-8}$alkyl), an optionally substituted acylalkyl, an optionally substituted $C_{1-8}$ alkyl, an optionally substituted hydroxyalkyl, an optionally substituted alkoxy(alkyl), an optionally substituted $C_{2-8}$ alkenyl, an optionally substituted $C_{2-8}$ alkynyl, an optionally substituted $C_{3-6}$ cycloalkyl, an optionally substituted $C_{3-6}$ cycloalkyl($C_{1-6}$ alkyl), an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, Y cannot be an optionally substituted indolyl. In other embodiments, Y cannot be

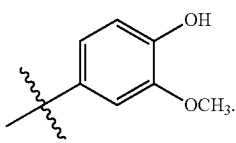 [SMILES: *c1ccc(O)c(OC)c1]

In some embodiments, $R^4$ cannot be methyl. In other embodiments, $R^4$ cannot be hydrogen.

In some embodiments, the compound of Formula (I) can be selected from the following compounds: 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 242, 244, 245, 246A, 246B, 247, 300, 400, 401, 402, 403, 404, 405, 406, 407, 408, 409, 410, 411, 412, 413, 415, 416, 417, 419, 422, 423, 426, 427, 428, 429, 430, 431, 432, 433, 434, 435, 437, 438, 439, 440, 441, 442, 443, 444, 445, 448A, 448B, 449, 450, 453, 454, 455A, 455B, 456, 457, 458A, 458B, 459, 460, 461, 462A, 462B, 463A, 463B, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 400-1, 400-2, 400-3, 400-4, 400-5, 400-6, 400-7, 400-8, 400-9, 400-10, 400-11, 400-12, 400-13, 400-14, 400-15, 400-16, 400-17, 400-18, 400-19, 400-20, 400-21, 400-22, 400-24, 400-25, 400-26, 400-27, 400-28, 500, 501, 502, 503, 504, 505, 506, 507, 508, 509, 510, 511, 512, 513, 514A, 514B, 600, 601, 602, 603A, 603B, 604, 605, 606, 650, 651, 700, 701, 702, 703, 704, 705, 706, 707, 708, 709, 901, 1206, 1352, 2300, 2301, 2302, 2303, 2304, 2400, 2401, 4105, 4304, 4305, 4306, 4307, 4308, 4309, 4310, 4311, 4312, 4313 and 4314.

In some embodiments, the compound of Formula (I) can be selected from the following compounds: 1200, 1202, 1204, 1209, 1211, 1213, 1214, 1216, 1217, 1220, 1221, 1223, 1224, 1225, 1226, 1227, 1230, 1231, 1232, 1233, 1234, 1235, 1236, 1237, 1238, 1239, 1242, 1243, 1244, 1245, 1246, 1247, 1248, 1249, 1250, 1251, 1252, 1253, 1255, 1256, 1257, 1258, 1300, 1301, 1302, 1303, 1304, 1307, 1308, 1309, 1310, 1311, 1312, 1313, 1314, 1315, 1316, 1317, 1318, 1319, 1320, 1321, 1322, 1323, 1325, 1326, 1327, 1328, 1329, 1330, 1331, 1332, 1333, 1334, 1335, 1336, 1340, 1341, 1343, 1344, 1345, 1346, 1359, 1360, 1401, 1402, 1403, 1404, 1405, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1800, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1829, 1830, 1831, 1832, 1833, 1834, 1835, 1836, 1837, 1838, 1839, 1900, 1901, 1902, 1903, 2000, 2100, 2101, 2103, 2104, 2105, 2106, 2107, 2108, 2109, 2111, 2112, 2113, 2114, 2115, 2504, 2506, 2507, 2508, 2601, 2602, 2603, 2604, 2605, 2613, 2615, 2617, 2618, 2619, 2620, 2621, 2622, 2624, 2626, 2627, 2638, 2641, 2642, 2643, 2644, 2645, 2646, 2647, 2648, 2649, 2650, 2651, 2652, 2654, 3302, 3800, 3903, 4002, 4201, 4202, 4203, 4204, 4205, 4206, 4207, 4208, 4209, 4210, 4212 and 4216.

In some embodiments, the compound of Formula (I) can be selected from the following compounds: 840, 1100, 1101, 1201, 1205, 1210, 1215, 1219, 1222, 1228, 1240, 1241, 2204, 2205, 2800, 2801, 3200, 3401, 3500, 3501, 3900 and 4303.

In some embodiments, the compound of Formula (I) can be selected from the following compounds: 900, 902, 903, 904, 908, 910, 917, 1000, 2803, 3300 and 4302.

In some embodiments, the compound of Formula (I) can be selected from the following compounds: 239, 240, 241, 2305, 2306 and 2802.

Formula (II)

Some embodiments disclosed herein relate to a compound of Formula (II), or a pharmaceutically acceptable salt thereof, having the structure:

$$A^b\text{-}L^b\text{-}Y^b \quad (II)$$

wherein: $L^b$ can be selected from:

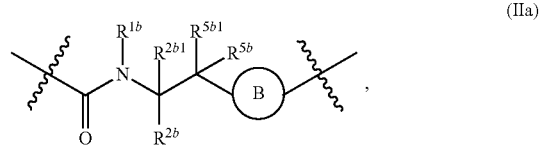

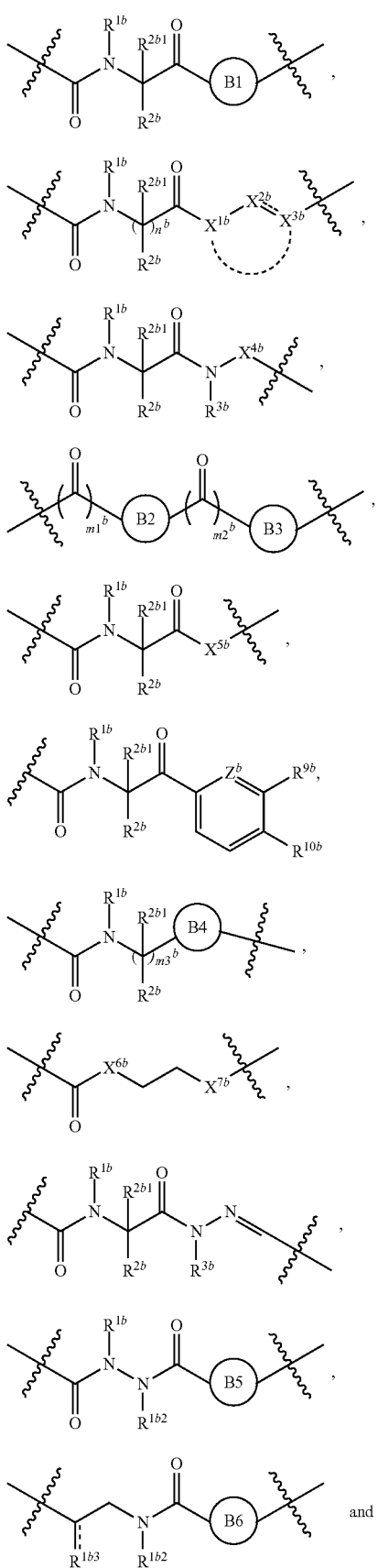

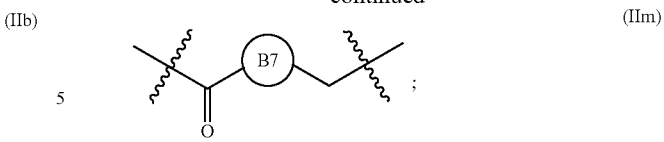

A$^b$ can be an optionally substituted cycloalkyl, an optionally substituted cycloalkenyl, an optionally substituted aryl, an optionally substituted aryl(C$_{1-2}$ alkyl), an optionally substituted heteroaryl or an optionally substituted heterocyclyl. Y$^b$ can be an optionally substituted cycloalkyl, an optionally substituted cycloalkenyl, an optionally substituted aryl, an optionally substituted heteroaryl or an optionally substituted heterocyclyl; when L$^b$ is Formula (IIc), ═══ between X$^{2b}$ and X$^{3b}$ represents a single or double bond between X$^{2b}$ and X$^{3b}$, when ═══ between X$^{2b}$ and X$^{3b}$ is a double bond, then X$^{1b}$ can be independently NR$^{3b}$ or CR$^{3b1}$R$^{3b2}$, X$^{2b}$ can be N (nitrogen) or CR$^{7b1}$, and X$^{3b}$ can be N (nitrogen) or CR$^{4b}$; when ═══ between X$^{2b}$ and X$^{3b}$ is a single bond, then X$^{1b}$ can be independently NR$^{3b}$ or CR$^{3b1}$R$^{3b2}$, X$^{2b}$ can be O (oxygen), NR$^{7b}$ or C(R$^{7b2}$)(R$^{7b3}$), and X$^{3b}$ can be NR$^{4b}$, C(═O) or CR$^{4b}$R$^{8b}$; or X$^{1b}$, X$^{2b}$ and X$^{3b}$ can be each independently C (carbon), N (nitrogen), O (oxygen) or C(═O), and form a ring or ring system selected from an optionally substituted aryl, an optionally substituted heteroaryl and an optionally substituted heterocyclyl by joining X$^{1b}$ and X$^{3b}$ together; with the proviso that the valencies of X$^{1b}$, X$^{2b}$ and X$^{3b}$ are satisfied with a substituent selected from hydrogen and an optionally substituted C$_{1-4}$ alkyl, and X$^{1b}$, X$^{2b}$ and X$^{3b}$ are uncharged; X$^{4b}$ can be NR$^{6b1}$ or C(R$^{6b2}$)$_2$; X$^{5b}$ can be NR$^{6b3}$ or C(R$^{6b4}$)$_2$; X$^{6b}$ can be NR$^{6b5}$ or C(═O); X$^{7b}$ can be NR$^{6b6}$CH$_2$ or —C(═O)— an optionally substituted pyridinyl-; Z$^b$ can be N or CH; R$^{1b}$ can be hydrogen or an unsubstituted C$_{1-4}$ alkyl; R$^{1b2}$ can be hydrogen or an unsubstituted C$_{1-4}$ alkyl; when L$^b$ is Formula (IIg), then Y$^b$ is absent; when ═══ of Formula (III) is a single bond, then R$^{1b3}$ can be hydroxy; when ═══ of Formula (III) is a double bond, then R$^{1b3}$ can be O (oxygen); R$^{2b}$ and R$^{2b1}$ can be each independently hydrogen or an optionally substituted C$_{1-4}$ alkyl, and when more than one R$^{2b}$ and/or more than one R$^{2b1}$ are present, each R$^{2b}$ and each R$^{2b1}$ can be the same or different; R$^{3b}$, R$^{3b1}$ and R$^{3b2}$ can be hydrogen or an unsubstituted C$_{1-4}$ alkyl; R$^{4b}$ can be hydrogen, an optionally substituted C$_{1-4}$ alkyl or an optionally substituted alkoxyalkyl; R$^{5b}$ and R$^{5b1}$ can be each independently hydrogen or hydroxy; R$^{6b1}$, each R$^{6b2}$, R$^{6b3}$, each R$^{6b4}$, R$^{6b5}$ and R$^{6b6}$ can be each independently hydrogen or an unsubstituted C$_{1-4}$ alkyl; R$^{7b}$ and R$^{7b1}$ can be each independently hydrogen or an unsubstituted C$_{1-4}$ alkyl; R$^{7b2}$ and R$^{7b3}$ can be each independently hydrogen or an unsubstituted C$_{1-4}$ alkyl; or R$^{7b2}$ and R$^{7b3}$ together form ═O; R$^{8b}$ can be hydrogen or an unsubstituted C$_{1-4}$ alkyl; R$^{9b}$ and R$^{10b}$ can be each independently an unsubstituted C$_{1-4}$ alkyl, an unsubstituted C$_{1-4}$ alkenyl or an unsubstituted C$_{1-4}$ alkoxy; or R$^{9b}$ and R$^{10b}$ can be taken together to form an unsubstituted aryl, an unsubstituted heteroaryl or an optionally substituted heterocyclyl; ring B is an optionally substituted

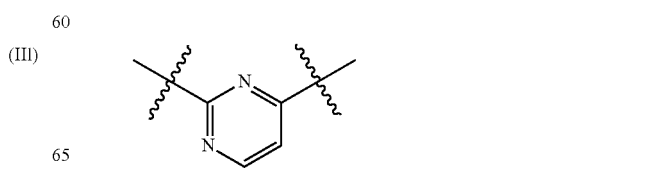

or an optionally substituted

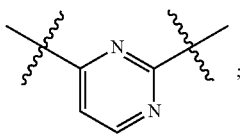;

ring B1 can be an optionally substituted mono-cyclic cycloalkyl, an optionally substituted phenyl, an optionally substituted mono-cyclic heteroaryl or an optionally substituted mono-cyclic heterocyclyl; ring B2 can be an optionally substituted heteroaryl; ring B3 can be an optionally substituted pyridinyl; ring B4 can be an optionally substituted heteroaryl or an optionally substituted heterocyclyl; ring B5 can be an optionally substituted pyridinyl; ring B6 can be an optionally substituted pyridinyl; ring B7 can be an optionally substituted heterocyclyl; $m1^b$ and $m2^b$ can be each independently 0 or 1; provided that at least one of $m1^b$ and $m2^b$ is 1; $m3^b$ can be 0 or 1; and $n^b$ can be 2 or 3.

Formula (IIa)

In some embodiments, $L^b$ can be Formula (IIa):

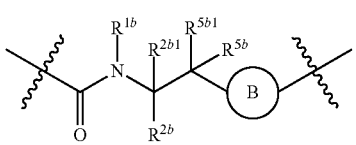 (IIa)

In some embodiments of Formula (IIa), $R^{1b}$ can be hydrogen. In other embodiments of Formula (IIa), $R^{1b}$ can be an unsubstituted $C_{1-4}$ alkyl.

In some embodiments of Formula (IIa), $R^{2b}$ and $R^{2b1}$ both can be hydrogen. In other embodiments of Formula (IIa), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIa), $R^{2b}$ and $R^{2b1}$ both can be an optionally substituted $C_{1-4}$ alkyl.

In some embodiments of Formula (IIa), both $R^{5b}$ and $R^{5b1}$ can be hydrogen. In other embodiments, $R^{5b}$ can be hydrogen, and $R^{5b1}$ can be hydroxy.

In some embodiments of Formula (IIa), ring B can be an optionally substituted

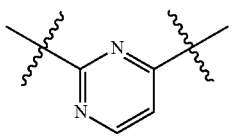 [SMILES: *c1ccnc(*)n1]

In other embodiments, ring B can be an optionally substituted

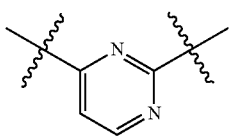

In some embodiments of Formula (IIa), ring B can be an unsubstituted

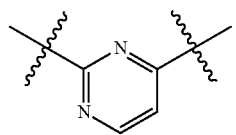

In other embodiments, ring B can be an unsubstituted

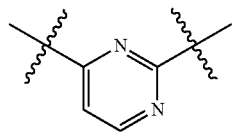

In some embodiments, a compound of Formula (II) with $L^b$ being (IIa) can be selected from the following compounds: 839, 1207 and 1208.

Formula (IIb)

In some embodiments, $L^b$ can be Formula (IIb):

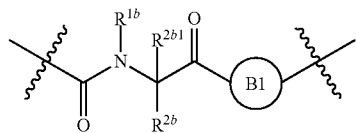 (IIb)

In some embodiments of Formula (IIb), $R^{1b}$ can be hydrogen. In other embodiments of Formula (IIb), $R^{1b}$ can be an unsubstituted $C_{1-4}$ alkyl.

In some embodiments of Formula (IIb), $R^{2b}$ and $R^{2b1}$ both can be hydrogen. In other embodiments of Formula (IIb), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIb), $R^{2b}$ and $R^{2b1}$ both can be an optionally substituted $C_{1-4}$ alkyl.

In some embodiments of Formula (IIb), ring B1 can be an optionally substituted mono-cyclic cycloalkyl. In other embodiments of Formula (IIb), ring B1 can be an optionally substituted phenyl. In still other embodiments of Formula (IIb), ring B1 can be an optionally substituted mono-cyclic heteroaryl. In yet still other embodiments of Formula (IIb), ring B1 can be or an optionally substituted mono-cyclic heterocyclyl.

Examples of suitable ring B1 include, but are not limited to, the following: an optionally substituted

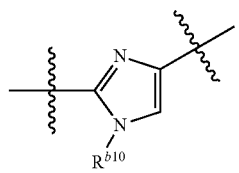, an optionally substituted

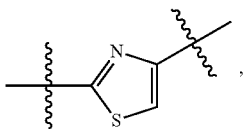 [SMILES: *c1csc(*)n1]

an optionally substituted

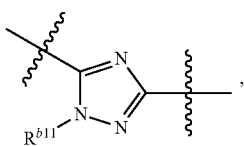

an optionally substituted

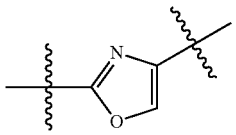 [SMILES: *c1coc(*)n1]

and an optionally substituted

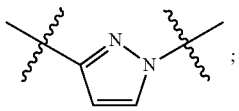

wherein $R^{b10}$ and $R^{b11}$ can be each independently hydrogen or unsubstituted $C_{1-6}$ alkyl. Additional examples of suitable ring B1 include, but are not limited to, the following: an optionally substituted

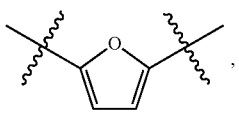 [SMILES: *c1ccc(*)o1]

an optionally substituted

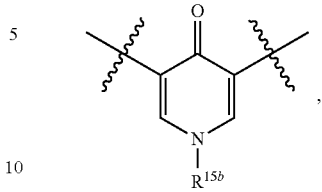

an optionally substituted

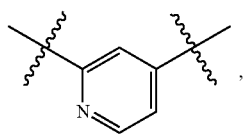 [SMILES: *c1ccnc(*)c1]

an optionally substituted

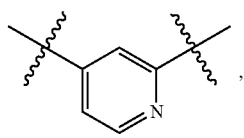 [SMILES: *c1ccnc(*)c1]

an optionally substituted

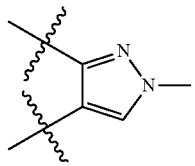 [SMILES: *c1cn(C)nc1*]

and an optionally substituted

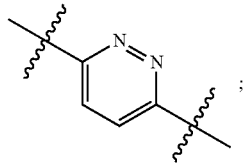 [SMILES: *c1ccc(*)nn1]

wherein $R^{15b}$ can be hydrogen or an unsubstituted $C_{1-4}$ alkyl.

In some embodiment, a compound of Formula (II) with $L^b$ being (IIb) can be selected from the following compounds: 860, 1206, 1352, 1353, 1354, 1355, 1356, 1358, 2203, 2500, 2502, 2607 and 3201.

In other embodiment, a compound of Formula (II) with $L^b$ being (IIb) can be selected from the following compounds: 1218, 1337, 1338, 1351, 2102, 2200, 2606, 2623, 2653 and 3901.

Formula (IIc)

In some embodiments, $L^b$ can be Formula (IIc):

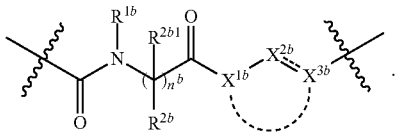

(IIc)

In some embodiments of Formula (IIc), $R^{1b}$ can be hydrogen. In other embodiments of Formula (IIc), $R^{1b}$ can be an unsubstituted $C_{1-4}$ alkyl.

In some embodiments of Formula (IIc), $n^b$ can be 2. In other embodiments of Formula (IIc), $n^b$ can be 3.

In some embodiments of Formula (IIc), each $R^{2b}$ and each $R^{2b1}$ can be hydrogen. In other embodiments of Formula (IIc), one or more $R^{2b}$'s can be hydrogen and one or more $R^{2b1}$'s can be an optionally substituted $C_{1-4}$ alkyl. In some embodiments of Formula (IIc), each $R^{2b}$ and each $R^{2b1}$ can be an optionally substituted $C_{1-4}$ alkyl.

In some embodiments of Formula (IIc), $X^{1b}$ can be $NR^{3b}$ or $CR^{3b1}R^{3b2}$; ==== ==== between $X^{2b}$ and $X^{3b}$ can be a double bond, $X^{2b}$ can be N (nitrogen) or $CR^{7b1}$, and $X^{3b}$ can be N (nitrogen) or $CR^{4b}$. In other embodiments of Formula (IIc), $X^{1b}$ can be $NR^{3b}$ or $CR^{3b1}R^{3b2}$; ------ between $X^{2b}$ and $X^{3b}$ can be a single bond, $X^{2b}$ can be O (oxygen), $NR^{7b}$ or $C(R^{7b2})(R^{7b3})$, and $X^{3b}$ can be $NR^{4b}$, C(=O) or $CR^{4b}R^{8b}$. In still other embodiments of Formula (IIc), $X^{1b}$, $X^{2b}$ and $X^{3b}$ can be each independently C (carbon), N (nitrogen), O (oxygen) or C(=O), and form a ring or ring system selected from an optionally substituted aryl, an optionally substituted heteroaryl and an optionally substituted heterocyclyl by joining $X^{1b}$ and $X^{3b}$ together; with the proviso that the valencies of $X^{1b}$, $X^{2b}$ and $X^{3b}$ can be each independently satisfied with a substituent selected from hydrogen and an optionally substituted $C_{1-4}$ alkyl; and such that $X^{1b}$, $X^{2b}$ and $X^{3b}$ are uncharged. In some embodiments of Formula (IIc), $X^{1b}$ can be $NR^{3b}$, ------ between $X^{2b}$ and $X^{3b}$ can be a double bond, $X^{2b}$ can be N (nitrogen), and $X^{3b}$ can be $CR^{4b}$ (such as CH or $C(CH_3)$). In other embodiments of Formula (IIc), $X^{1b}$ and $X^{3b}$ can be each C (carbon) and $X^{2b}$ can be N (nitrogen). In some embodiments, $X^{1b}$, $X^{2b}$ and $X^{3b}$ can form an optionally substituted heteroaryl, for example, an optionally substituted

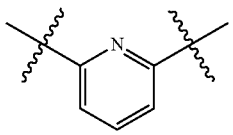

In some embodiments, the optionally substituted pyridinyl can have the structure

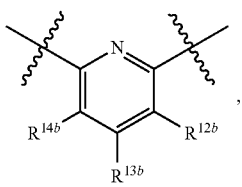

wherein $R^{12b}$, $R^{13b}$ and $R^{14b}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy; or $R^{12b}$ and $R^{13b}$ along with the atoms to which they are connected can be taken together to form an optionally substituted cycloalkyl an optionally substituted aryl, an optionally substituted heteroaryl or an optionally substituted heterocyclyl; and $R^{14b}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy. In some embodiments, the valencies of $X^{1b}$, $X^{2b}$ and $X^{3b}$ can be each independently satisfied with a substituent selected from hydrogen and an unsubstituted $C_{1-4}$ alkyl. In some embodiments, the valencies of $X^{1b}$, $X^{2b}$ and $X^{3b}$ can be each independently satisfied hydrogen or methyl.

In some embodiment, a compound of Formula (II) with $L^b$ being (IIc) can be selected from the following compounds: 243 and 1801.

Formula (IId)

In some embodiments, $L^b$ can be Formula (IId):

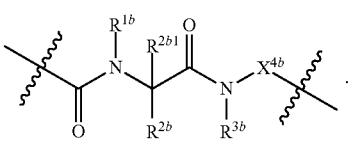

(IId)

In some embodiments of Formula (IId), $R^{1b}$ can be hydrogen. In other embodiments of Formula (IId), $R^{1b}$ can be an unsubstituted $C_{1-4}$ alkyl.

In some embodiments of Formula (IId), $R^{2b}$ and $R^{2b1}$ both can be hydrogen. In other embodiments of Formula (IId), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IId), $R^{2b}$ and $R^{2b1}$ both can be an optionally substituted $C_{1-4}$ alkyl.

In some embodiments of Formula (IId), $R^{3b}$ can be hydrogen. In other embodiments, $R^{3b}$ can be an unsubstituted $C_{1-4}$ alkyl.

In some embodiments of Formula (IId), $X^{4b}$ can be $NR^{6b1}$, for example, NH. In some of Formula (IId), $X^{4b}$ can be $C(R^{6b2})_2$, such as $CH_2$.

In some embodiment, a compound of Formula (II) with $L^b$ being (IId) can be compound 4301.

Formula (IIe)

In some embodiments, $L^b$ can be Formula (IIe):

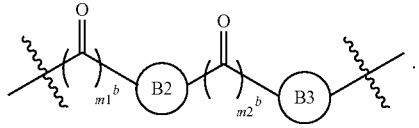

(IIe)

In some embodiments of Formula (IIe), $m1^b$ can be 0, and $m2^b$ can be 1. In other embodiments of Formula (IIe), $m1^b$ can be 1, and $m2^b$ can be 0. In still other embodiments of Formula (IIe), $m1^b$ can be 1, and $m2^b$ can be 1.

In some embodiments of Formula (IIe), ring B2 can be an optionally substituted

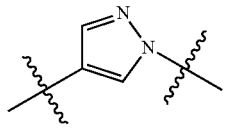

In other embodiments of Formula (IIe), ring B2 can be an optionally substituted

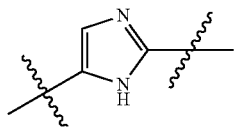

In still other embodiments of Formula (IIe), ring B2 can be an optionally substituted

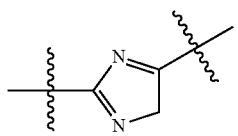

In some embodiments of Formula (IIe), ring B3 can be an optionally substituted

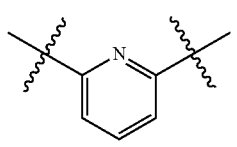

In some embodiments, the optionally substituted pyridinyl can have the structure

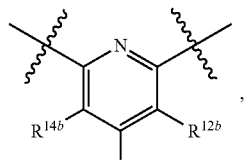

wherein $R^{12b}$, $R^{13b}$ and $R^{14b}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy; or $R^{12b}$ and $R^{13b}$ along with the atoms to which they are connected can be taken together to form an optionally substituted cycloalkyl an optionally substituted aryl, an optionally substituted heteroaryl or an optionally substituted heterocyclyl; and $R^{14b}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments, a compound of Formula (II) with $L^b$ being (IIe) can be selected from the following compounds: 1702, 1703 and 2612.

Formula (IIf)

In some embodiments, $L^b$ can be Formula (IIf):

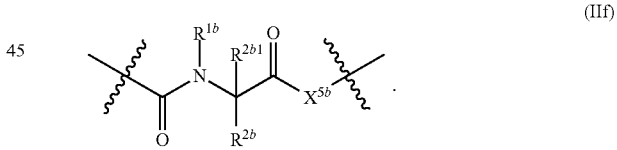

(IIf)

In some embodiments of Formula (IIf), $R^{1b}$ can be hydrogen. In other embodiments of Formula (IIf), $R^{1b}$ can be an unsubstituted $C_{1-4}$ alkyl.

In some embodiments of Formula (IIf), $R^{2b}$ and $R^{2b1}$ both can be hydrogen. In other embodiments of Formula (IIf), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIf), $R^{2b}$ and $R^{2b1}$ both can be an optionally substituted $C_{1-4}$ alkyl.

In some embodiments of Formula (IIf), $X^{5b}$ can be $NR^{6b3}$, such as NH or $N(CH_3)$. In other embodiments of Formula (IIf), $X^{5b}$ can be $C(R^{6b4})_2$, for example, $CH_2$ or $C(CH_3)_2$.

In some embodiment, a compound of Formula (II) with $L^b$ being (IIf) can be selected from the following compounds: 905, 906, 907, 909, 911, 912, 913, 914, 915, 916, 4100 and 4104.

Formula (IIg)

In some embodiments, $L^b$ can be Formula (IIg):

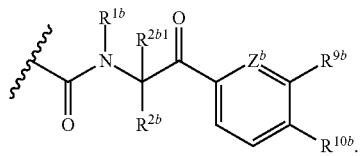

(IIg)

In some embodiments of Formula (IIg), $R^{1b}$ can be hydrogen. In other embodiments of Formula (IIg), $R^{1b}$ can be an unsubstituted $C_{1-4}$ alkyl.

In some embodiments of Formula (IIg), $R^{2b}$ and $R^{2b1}$ both can be hydrogen. In other embodiments of Formula (IIg), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIg), $R^{2b}$ and $R^{2b1}$ both can be an optionally substituted $C_{1-4}$ alkyl.

In some embodiments of Formula (IIg), $Z^b$ can be N (nitrogen). In some embodiments of Formula (IIg), $Z^b$ can be CH.

In some embodiments of Formula (IIg), one of $R^{9b}$ and $R^{10b}$ can be an unsubstituted $C_{1-4}$ alkyl and the other of $R^{9b}$ and $R^{10b}$ can be an unsubstituted $C_{1-4}$ alkoxy. In other embodiments of Formula (IIg), one of $R^{9b}$ and $R^{10b}$ can be an unsubstituted $C_{1-4}$ alkenyl and the other of $R^{9b}$ and $R^{10b}$ can be an unsubstituted $C_{1-4}$ alkoxy. In still other embodiments of Formula (IIg), $R^{9b}$ and $R^{10b}$ can be taken together to form an unsubstituted aryl (for example, phenyl). In some embodiments of Formula (IIg), $R^{9b}$ and $R^{10b}$ can be taken together to form an unsubstituted heteroaryl, such as piperidinyl. In other embodiments of Formula (IIg), $R^{9b}$ and $R^{10b}$ can be taken together to form an optionally substituted heterocyclyl, for example, an optionally substituted,

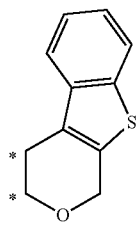

wherein * each indicate a point of attachment to the 6-membered ring.

In some embodiments, a compound of Formula (II) with $L^b$ being (IIg) can be selected from the following compounds: 1700, 1701, 2614, 2616, 2701 and 2703.

Formula (IIh)

In some embodiments, $L^b$ can be Formula (IIh):

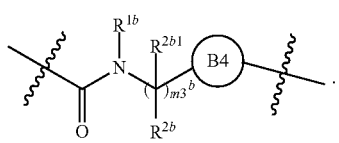

(IIh)

In some embodiments of Formula (IIh), $R^{1b}$ can be hydrogen. In other embodiments of Formula (IIh), $R^{1b}$ can be an unsubstituted $C_{1-4}$ alkyl.

In some embodiments of Formula (IIh), $R^{2b}$ and $R^{2b1}$ both can be hydrogen. In other embodiments of Formula (IIh), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIh), $R^{2b}$ and $R^{2b1}$ both can be an optionally substituted $C_{1-4}$ alkyl.

In some embodiments of Formula (IIh), $m3^b$ can be 0. In other embodiments of Formula (IIh), $m3^b$ can be 1.

In some embodiments of Formula (IIh), ring B4 can be an optionally substituted heteroaryl. In other embodiments of Formula (IIh), ring B4 can be an optionally substituted heterocyclyl.

In some embodiments, ring B4 can be an optionally substituted

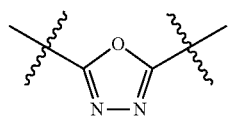 [SMILES: *c1nnc(*)o1]

or an optionally substituted

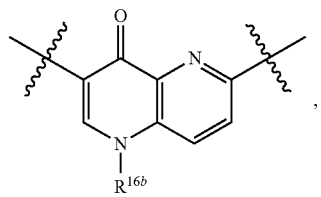

wherein $R^{16b}$ can be hydrogen or an unsubstituted $C_{1-4}$ alkyl.

In some embodiments, a compound of Formula (II) with $L^b$ being (IIh) can be selected from the following compounds: 2900, 2901 and 4103.

Formula (IIi)

In some embodiments, $L^b$ can be Formula (IIi):

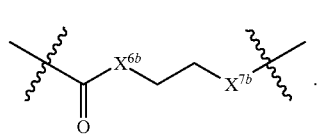

(IIi)

In some embodiments of Formula (IIi), $X^{6b}$ can be $NR^{6b5}$ and $X^{7b}$ can be $NR^{6b6}CH_2$. In some embodiments, $R^{6b5}$ and $R^{6b6}$ can be both hydrogen. In other embodiments of Formula (IIi), $R^{6b5}$ can be an unsubstituted $C_{1-4}$ alkyl, and $R^{6b6}$ can be hydrogen. In still other embodiments of Formula (IIi), $R^{6b5}$ can be an unsubstituted $C_{1-4}$ alkyl, and $R^{6b6}$ can be hydrogen. In yet still other embodiments of Formula (IIi), $R^{6b5}$ and $R^{6b6}$ can be both an unsubstituted $C_{1-4}$ alkyl.

In some embodiments of Formula (IIi), $X^{6b}$ can be C(=O) and $X^{7b}$ can be —C(=O)— an optionally substituted pyridinyl-. In some embodiments of Formula (IIi), the optionally substituted pyridinyl of $X^{7b}$ can be an optionally substituted

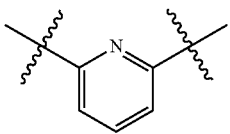

In some embodiments, the optionally substituted pyridinyl can have the structure

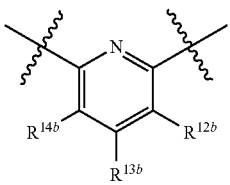

wherein $R^{12b}$, $R^{13b}$ and $R^{14b}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy; or $R^{12b}$ and $R^{13b}$ along with the atoms to which they are connected can be taken together to form an optionally substituted cycloalkyl an optionally substituted aryl, an optionally substituted heteroaryl or an optionally substituted heterocyclyl; and $R^{14b}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments, a compound of Formula (II) with $L^b$ being (IIi) can be selected from the following compounds: 1339 and 4101.

Formula (IIj)

In some embodiments, $L^b$ can be Formula (IIj):

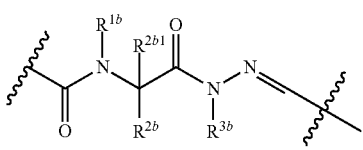

(IIj)

In some embodiments of Formula (IIj), $R^{1b}$ can be hydrogen. In other embodiments of Formula (IIj), $R^{1b}$ can be an unsubstituted $C_{1-4}$ alkyl.

In some embodiments of Formula (IIj), $R^{2b}$ and $R^{2b1}$ both can be hydrogen. In other embodiments of Formula (IIj), one of $R^{2b}$ and $R^{2b1}$ can be hydrogen and the other of $R^{2b}$ and $R^{2b1}$ can be an optionally substituted $C_{1-4}$ alkyl. In still other embodiments of Formula (IIj), $R^{2b}$ and $R^{2b1}$ both can be an optionally substituted $C_{1-4}$ alkyl.

In some embodiments of Formula (IIj), $R^{3b}$ can be hydrogen. In other embodiments of Formula (IIk), $R^{3b}$ can be an unsubstituted $C_{1-4}$ alkyl.

In some embodiments, a compound of Formula (II) with $L^b$ being (IIj) can be selected from the following compounds: 414, 418, 420, 421, 424, 425, 426, 446, 447, 451, 452, 464 and 400-23.

Formula (IIk)

In some embodiments, $L^b$ can be Formula (IIk):

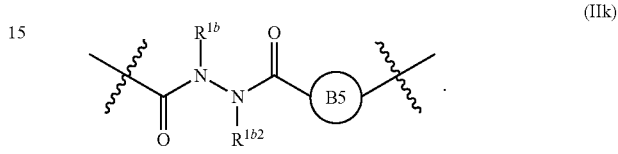

(IIk)

In some embodiments of Formula (IIk), $R^{1b}$ and $R^{1b2}$ can be both hydrogen. In other embodiments of Formula (IIk), $R^{1b}$ can be an unsubstituted $C_{1-4}$ alkyl, and $R^{1b2}$ can be hydrogen. In still other embodiments of Formula (IIk), $R^{1b}$ can be an unsubstituted $C_{1-4}$ alkyl, and $R^{1b2}$ can be hydrogen. In yet still other embodiments of Formula (IIk), $R^{1b}$ and $R^{1b2}$ can be both an unsubstituted $C_{1-4}$ alkyl.

In some embodiments of Formula (IIk), ring B5 can be an optionally substituted optionally substituted

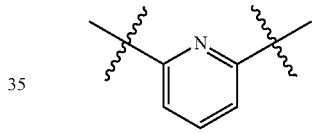

In some embodiments, the optionally substituted pyridinyl can have the structure

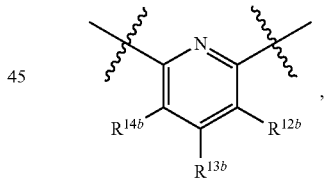

wherein $R^{12b}$, $R^{13b}$ and $R^{14b}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy; or $R^{12b}$ and $R^{13b}$ along with the atoms to which they are connected can be taken together to form an optionally substituted cycloalkyl an optionally substituted aryl, an optionally substituted heteroaryl or an optionally substituted heterocyclyl; and $R^{14b}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments, a compound of Formula (II) with $L^b$ being (IIk) can be selected from the following compounds: 3100, 3101, 3102 and 3103.

Formula (III)

In some embodiments, $L^b$ can be Formula (III):

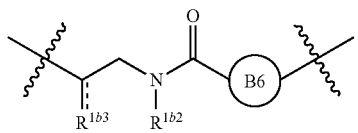

(III)

In some embodiments of Formula (III), $R^{1b2}$ can be hydrogen. In other embodiments of Formula (III), $R^{1b2}$ can be an unsubstituted $C_{1-4}$ alkyl.

In some embodiments of Formula (III), ----- is a single bond, and $R^{1b3}$ can be hydroxy. In other embodiments of Formula (III), ----- is a double bond, and $R^{1b3}$ can be O (oxygen).

In some embodiments of Formula (III), ring B6 can be an optionally substituted optionally substituted

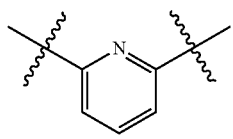

In some embodiments, the optionally substituted pyridinyl can have the structure

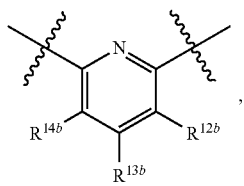

wherein $R^{12b}$, $R^{13b}$ and $R^{14b}$ can be each independently selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy; or $R^{12b}$ and $R^{13b}$ along with the atoms to which they are connected can be taken together to form an optionally substituted cycloalkyl an optionally substituted aryl, an optionally substituted heteroaryl or an optionally substituted heterocyclyl; and $R^{14b}$ can be selected from hydrogen, halogen, hydroxy, an optionally substituted $C_{1-8}$ alkyl, an optionally substituted $C_{2-8}$ alkenyl, an optionally substituted $C_{2-8}$ alkynyl, an optionally substituted $C_{3-6}$ cycloalkyl, an optionally substituted aryl, an optionally substituted heteroaryl, an optionally substituted heterocyclyl, an optionally substituted hydroxyalkyl, an optionally substituted $C_{1-8}$ alkoxy, an optionally substituted alkoxyalkyl, amino, mono-substituted amino, di-substituted amino, halo($C_{1-8}$ alkyl), haloalkyl and an optionally substituted C-carboxy.

In some embodiments, a compound of Formula (II) with $L^b$ being (III) can be selected from the following compounds: 3000 and 3001.

Formula (IIm)

In some embodiments, $L^b$ can be Formula (IIm):

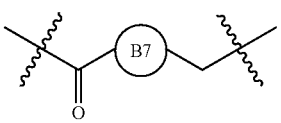

(IIm)

In some embodiments of Formula (IIm), ring B7 can be an optionally substituted heterocyclyl, such as an optionally substituted piperazinyl. In some embodiments, the optionally substituted piperazinyl can have the structure:

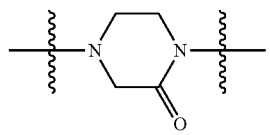

In some embodiments, a compound of Formula (II) with $L^b$ being (IIm) can be compound 800.

In some embodiments, $A^b$ can be substituted. In other embodiments, $A^b$ can be unsubstituted.

In some embodiments, $A^b$ can be an optionally substituted aryl. For example, $A^b$ can be an optionally substituted phenyl. In some embodiments, $A^b$ can be a para-substituted phenyl, a meta-substituted phenyl or an ortho-substituted phenyl. In some embodiments, $A^b$ can be a di-substituted phenyl. For example, $A^b$ can be a 3,4-substituted phenyl, such as

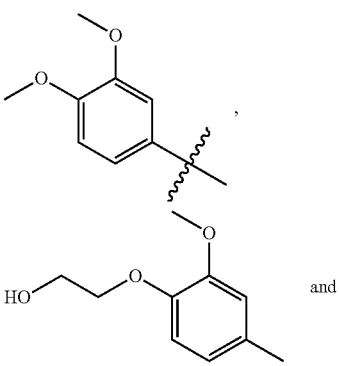

and

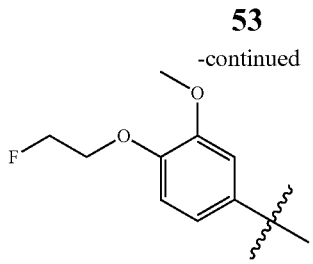

In some embodiments, $A^b$ can be a substituted phenyl that is substituted with 3 more substituents. In other embodiments, $A^b$ can be unsubstituted phenyl. In some embodiments, $A^b$ can be an optionally substituted naphthyl.

In some embodiments and without limitation, $A^b$ can be a phenyl substituted with one or more substituents selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, sulfenyl, alkyoxyalkyl, aryl, mono-cyclic heteroaryl, mono-cyclic heterocyclyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

Examples of suitable substituents include, but are not limited to, methyl, ethyl, propyl (n-propyl and iso-propyl), butyl (n-butyl, iso-butyl and t-butyl), hydroxy, methoxy, ethoxy, propoxy (n-propoxy and iso-propoxy), butoxy (n-butoxy, iso-butoxy and t-butoxy), phenoxy, bromo, chloro, fluoro, trifluoromethyl, difluoromethoxy, trifluoromethoxy, N,N-di-methyl-amine, N,N-di-ethyl-amine, N-methyl-N-ethyl-amine, N-methyl-amino, N-ethyl-amino, amino, alkylthio (such as $CH_3CH_2S—$), phenyl, imidazole, morpholinyl, pyrazole, pyrrolidinyl, pyridinyl, piperidinyl, pyrrolidinone, pyrimidine, pyrazine, 1,2,4-oxadiazole, $—(CH_2)_{1-2}—NH(CH_3)$, $—O(CH_2)_2—NH_2$, $—O(CH_2)—NH(CH_3)$, $—O(CH_2)_2—N(CH_3)_2$, $—O—(CH_2)_{2-4}OH$, $—O(CH_2)_2OCH_3$, $—O(CH_2)_{1-2}$-morpholinyl, $—O(CH_2)_{1-2}$-triazole, $—O(CH_2)_{1-2}$-imidazole,

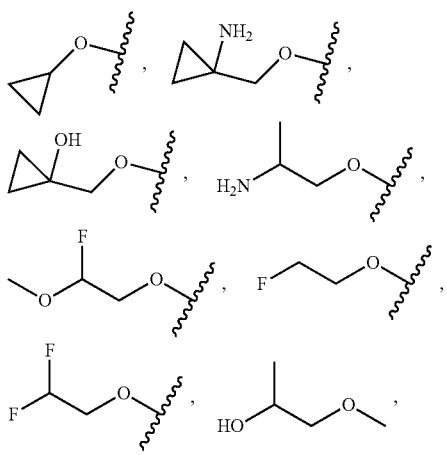

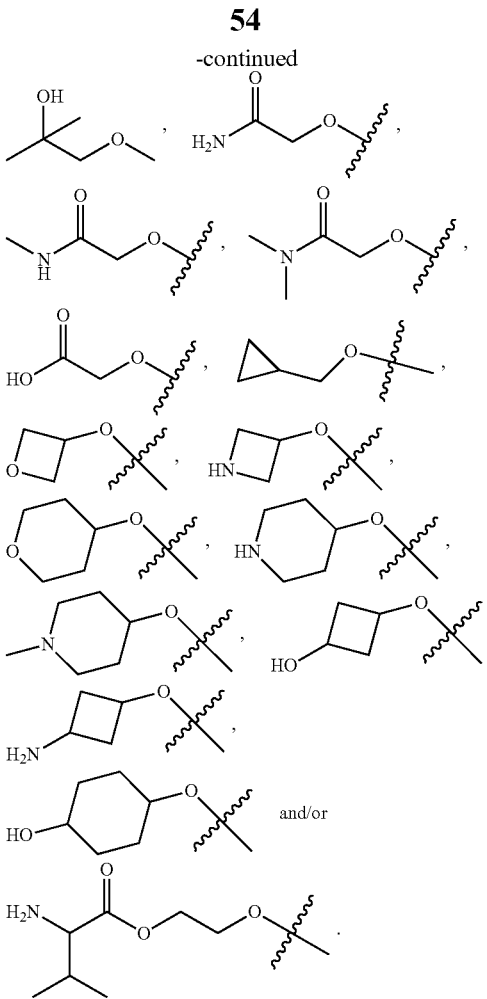

In some embodiments, $A^b$ can be an optionally substituted cycloalkyl. Suitable examples of optionally substituted cycloalkyls include, but are not limited to, an optionally substituted cyclohexyl and an optionally substituted cycloheptyl. In other embodiments, $A^b$ can be an optionally substituted cycloalkenyl, for example, an optionally substituted cyclohexenyl. In some embodiments, $A^b$ can be an optionally substituted bi-cyclic cycloalkenyl, such as

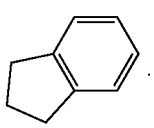

In some embodiments, $A^b$ can be an optionally substituted aryl($C_{1-2}$ alkyl). In some embodiments, $A^b$ can be an optionally substituted benzyl.

In some embodiments, $A^b$ can be an optionally substituted mono-cyclic heteroaryl. In some embodiments, $A^b$ can be an optionally substituted mono-cyclic 5-membered heteroaryl. In other embodiments, $A^b$ can be an optionally substituted mono-cyclic 6-membered heteroaryl. In some embodiments, $A^b$ can be an optionally substituted bi-cyclic heteroaryl.

In some embodiments, the optionally substituted heteroaryl can be selected from an optionally substituted imidazole, an optionally substituted thiazole, an optionally substituted furan, an optionally substituted thiophene, an optionally substituted pyrrole, an optionally substituted pyridine, an optionally substituted pyrimidine, an optionally substituted pyrazine, an optionally substituted quinolone, an optionally substituted imidazole, an optionally substituted oxazole and an optionally substituted isoxazole. In some embodiments, $A^b$ can be an optionally substituted thiophene. In other embodiments, $A^b$ can be an optionally substituted thiazole. In still other embodiments, $A^b$ can be an optionally substituted pyridine. In yet still other embodiments, $A^b$ can be an optionally substituted pyrimidine. In some embodiments, $A^b$ can be an optionally substituted pyrazine. In other embodiments, $A^b$ can be an optionally substituted imidazole.

In some embodiments, $A^b$ can be an optionally substituted heterocyclyl, for example, an optionally substituted monocyclic heterocyclyl or an optionally substituted bi-cyclic heterocyclyl. In some embodiments, $A^b$ can be an optionally substituted

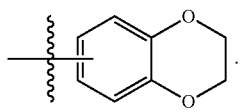

In other embodiments, $A^b$ can be an optionally substituted

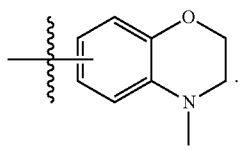

In still other embodiments, $A^b$ can be an optionally substituted

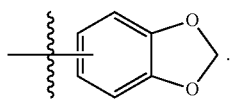

In some embodiments, $A^b$ can be substituted with one or more $R^C$'s. In some embodiments, one $R^C$ can be present. In some embodiments, two $R^C$'s can be present. In some embodiments, three $R^C$'s can be present. In some embodiments, four or more $R^C$'s can be present. When two or more $R^C$'s are present, two or more $R^C$'s can be the same or two or more $R^C$'s can be different. In some embodiments, at least two $R^C$'s can be the same. In some embodiments, at least two $R^C$'s can be different. In some embodiments, all the $R^C$'s can be the same. In other embodiments, all the $R^C$'s can be different.

In some embodiments, $R^C$ can be each independently selected from an unsubstituted $C_{1-4}$ alkyl, an optionally substituted $C_{1-4}$ alkyl, cycloalkyl, hydroxy, an optionally substituted $C_{1-4}$ alkoxy, $C_{1-4}$ alkoxy, halogen, haloalkyl, an optionally substituted haloalkoxy, nitro, amino, mono-substituted amino, di-substituted amine, sulfenyl, alkyoxyalkyl, aryl, mono-cyclic heteroaryl, mono-cyclic heterocyclyl and aminoalkyl. In some embodiments, the optionally substituted $C_{1-4}$ alkoxy can be further substituted, for example, further substituted with a substituent selected from $C_{1-4}$ alkyl, halo, hydroxy, C-carboxy, C-amido, amino, mono-alkyl amine, di-alkyl amine and an amino acid. In some embodiments, the optionally substituted haloalkoxy can be further substituted, for example, further substituted with an $C_{1-4}$ alkoxy. In some embodiments, the optionally substituted heteroaryl can be further substituted, for example, further substituted with an $C_{1-4}$ alkyl.

In some embodiments, each $R^C$ can be an alkyl, such as methyl, ethyl, propyl (n-propyl and iso-propyl) and/or butyl (n-butyl, iso-butyl and t-butyl).

In some embodiments, each $R^C$ can be an optionally substituted alkoxy, for example, methoxy, ethoxy, propoxy (n-propoxy and iso-propoxy), butoxy (n-butoxy, iso-butoxy and t-butoxy), phenoxy, —O(CH$_2$)$_2$—NH$_2$, —O(CH$_2$)$_2$—NH(CH$_3$), —O(CH$_2$)$_2$—N(CH$_3$)$_2$, —O—(CH$_2$)$_{2-4}$OH,

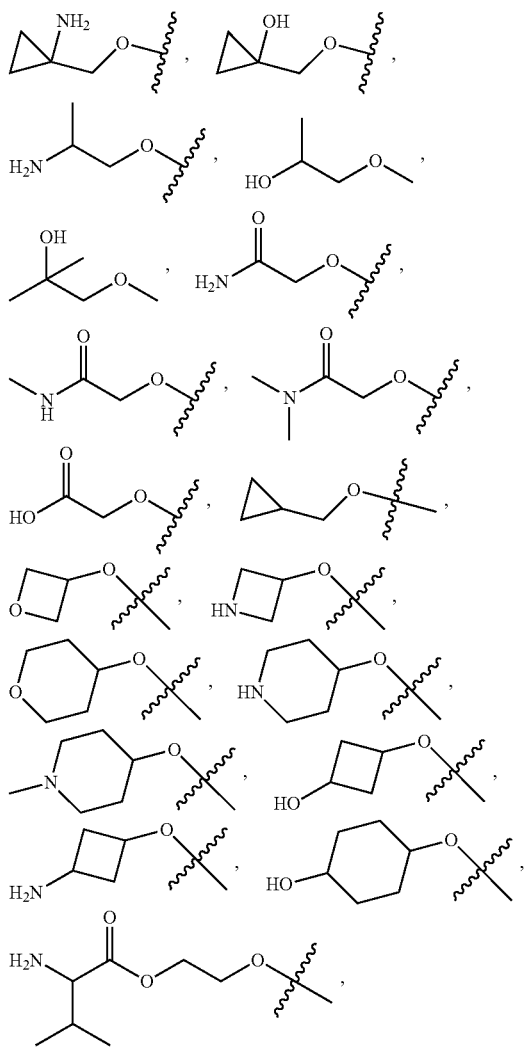

—O(CH$_2$)$_2$OCH$_3$, —O(CH$_2$)$_{1-2}$-morpholinyl, —O(CH$_2$)$_{1-2}$-triazole, —O(CH$_2$)$_{1-2}$-imidazole and/or

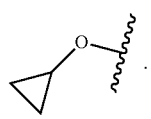

In some embodiments, each $R^C$ can be haloalkyl, for example, trifluoromethyl.

In some embodiments, each $R^C$ can be an optionally substituted haloalkoxy, for example, difluoromethoxy, trifluoromethoxy,

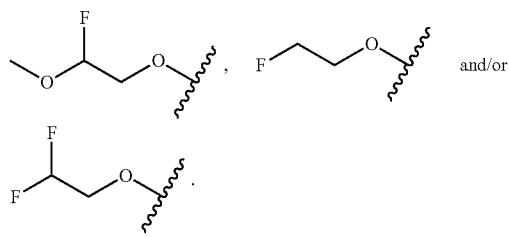

In some embodiments, each $R^C$ can be halogen, for example, chloro, bromo and/or fluoro.

In some embodiments, each $R^C$ can be amino, a mono-substituted amine or a di-substituted amine. For examples, $R^C$ can be N,N-di-methyl-amine, N,N-di-ethyl-amine, N-methyl-N-ethyl-amine, N-methyl-amino, N-ethyl-amino and/or amino.

In some embodiments, each $R^C$ can be hydroxy.

In some embodiments, each $R^C$ can be alkylthio, for example ethylthio.

In some embodiments, each $R^C$ can be aminoalkyl, such as $-(CH_2)_{1-2}-NH(CH_3)$.

In some embodiments, each $R^C$ can be alkoxyalkyl, for example, $-CH_2-O-CH_3$.

In some embodiments, each $R^C$ can be aminoalkyl, for example, $-CH_2-NH_2$ or $-CH_2-N(CH_3)H$.

In some embodiments, each $R^C$ can be an optionally substituted aryl, for example, an optionally substituted phenyl.

In some embodiments, each $R^C$ can be an optionally substituted mono-cyclic heteroaryl, such as an optionally substituted imidazole, an optionally substituted pyrazole, an optionally substituted pyridinyl, an optionally substituted pyrimidine, an optionally substituted pyrazine and/or an optionally substituted 1,2,4-oxadiazole.

In some embodiments, each $R^C$ can be an optionally substituted mono-cyclic heterocyclyl, for example, an optionally substituted pyrrolidinyl, an optionally substituted piperidinyl, an optionally substituted morpholinyl and/or an optionally substituted pyrrolidinone.

In some embodiments, $Y^b$ can be an optionally substituted aryl. In some embodiments, $Y^b$ can be a para-substituted phenyl, a meta-substituted phenyl or an ortho-substituted phenyl. In some embodiments, $Y^b$ can be a di-substituted phenyl, for example a di-halo substituted phenyl. For example, di-halo substituted phenyls include, but are not limited to,

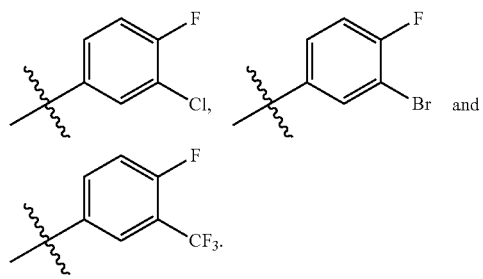

In some embodiments, $Y^b$ can be a substituted phenyl that is substituted with 3 more substituents. In other embodiments, $Y^b$ can be unsubstituted phenyl. In some embodiments, $Y^b$ can be a substituted naphthyl. In other embodiments, $Y^b$ can be an unsubstituted naphthyl.

In some embodiments, $Y^b$ can be an optionally substituted cycloalkyl (e.g., an optionally substituted cyclohexyl and an optionally substituted cycloheptyl). In some embodiments, $Y^b$ can be an optionally substituted cycloalkenyl, for example, an optionally substituted cyclohexenyl. In some embodiments, $Y^b$ can be an optionally substituted bi-cyclic cycloalkenyl, such as

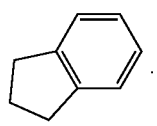

In some embodiments, $Y^b$ can be an optionally substituted mono-cyclic heteroaryl. In some embodiments, $Y^b$ can be selected from an optionally substituted imidazole, an optionally substituted furan, an optionally substituted thiophene, an optionally substituted pyrrole, an optionally substituted pyrimidine, an optionally substituted pyrazine, an optionally substituted pyridine, an optionally substituted pyrazole, an optionally substituted oxazole and an optionally substituted isoxazole. In some embodiments, $Y^b$ can be a substituted mono-cyclic heteroaryl, including those described herein. In some embodiments, $Y^b$ can be an unsubstituted mono-cyclic heteroaryl, including those described herein.

In some embodiments, $Y^b$ can be an optionally substituted bi-cyclic heteroaryl. In some embodiments, $Y^b$ can be selected from an optionally substituted benzothiophene, an optionally substituted benzofuran, an optionally substituted indole, an optionally substituted quinoline, an optionally substituted isoquinoline, an optionally substituted benzoxazole, an optionally substituted benzoisoxazole, an optionally substituted benzoisothiazole, an optionally substituted benzothiazole, an optionally substituted benzoimidazole, an optionally substituted benzotriazole, an optionally substituted 1H-indazole and an optionally substituted 2H-indazole. In some embodiments, $Y^b$ can be selected from an optionally substituted

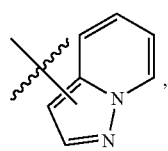

an optionally substituted

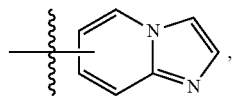

an optionally substituted

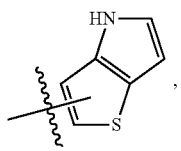, an optionally substituted

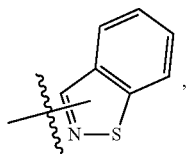, an optionally substituted

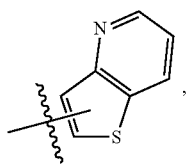, an optionally substituted

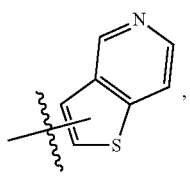, an optionally substituted

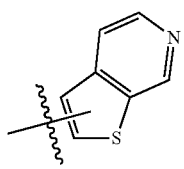, and an optionally substituted

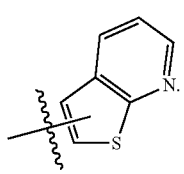.

In some embodiments, $Y^b$ can be a substituted bi-cyclic heteroaryl, including those described herein. In some embodiments, $Y^b$ can be an unsubstituted bi-cyclic heteroaryl, including those described herein.

In some embodiments, $Y^b$ can be an optionally substituted heterocyclyl. In some embodiments, $Y^b$ can be an optionally substituted mono-cyclic heterocyclyl. In other embodiment, $Y^b$ can be an optionally substituted bi-cyclic heterocyclyl. For example, $Y^b$ can be an optionally substituted

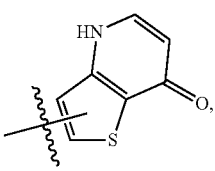, an optionally substituted

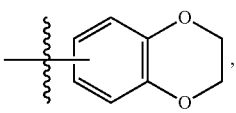, an optionally substituted

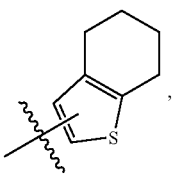, an optionally substitute

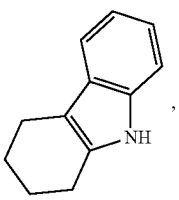 [SMILES: c1ccc2c3c([nH]c2c1)CCCC3], an optionally substituted

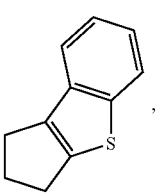 [SMILES: c1ccc2c3c(sc2c1)CCC3], an optionally substituted

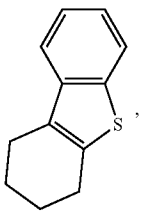 [SMILES: c1ccc2c3c(sc2c1)CCCC3]

an optionally substituted

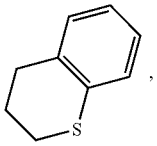

an optionally substituted

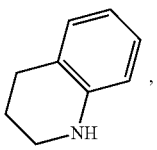

an optionally substituted

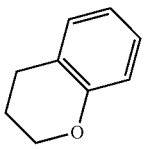

and/or an optionally substituted

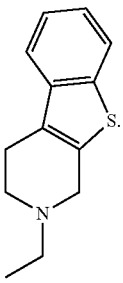

When $Y^b$ is substituted, $Y^b$ can be substituted with one or more $R^D$'s. In some embodiments, each $R^D$ can be independently selected from cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, alkoxyalkyl, $C_{1-4}$ haloalkyl, haloalkoxy, an unsubstituted acyl, an optionally substituted —C-carboxy, an optionally substituted —C-amido, sulfonyl, carbonyl, amino, mono-substituted amine, di-substituted amine and

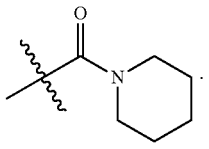 [SMILES: *C(=O)N1CCCCC1]

In some embodiments, when $Y^b$ is an optionally substituted phenyl, the phenyl can be substituted 1, 2, 3 or more times with cyano, halogen, an optionally substituted $C_{1-4}$ alkyl, an unsubstituted $C_{2-4}$ alkenyl, an unsubstituted $C_{2-4}$ alkynyl, an optionally substituted aryl, an optionally substituted 5 or 6 membered heteroaryl, an optionally substituted 5 or 6 membered heterocyclyl, hydroxy, $C_{1-4}$ alkoxy, $C_{1-4}$ haloalkyl (such as $CF_3$, $CHF_2$), haloalkoxy (such as $OCF_3$), an unsubstituted acyl, an optionally substituted —C-carboxy, an optionally substituted —C-amido, sulfonyl, amino, mono-$C_{1-4}$ alkyl amine, di-$C_{1-4}$ alkyl amine and/or

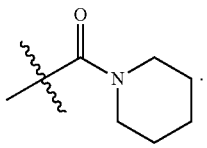 [SMILES: *C(=O)N1CCCCC1]

In other embodiments, when $Y^b$ is an optionally substituted mono-cyclic heteroaryl, the mono-cyclic heteroaryl can be substituted 1, 2, 3 or more times with halo, an optionally substituted $C_{1-4}$ alkyl, an optionally substituted phenyl and/or an unsubstituted acyl. In still other embodiments, when $Y^b$ is an optionally substituted bi-cyclic heteroaryl, the bi-cyclic heteroaryl can be substituted 1, 2, 3 or more times with halo, an optionally substituted $C_{1-4}$ alkyl, an optionally substituted phenyl, hydroxy, $C_{1-4}$ alkoxy, an unsubstituted acyl, carbonyl, cyano, amino, mono-$C_{1-4}$ alkyl amine and/or di-$C_{1-4}$ alkyl amine.

In some embodiments, $Y^b$ can be an optionally substituted benzothiophene. In some embodiments, $Y^b$ can be a substituted benzothiophene. In other embodiments, $Y^b$ can be an unsubstituted benzothiophene. In some embodiments, the benzothiophene can be substituted with one or more of the following: halogen (such as fluoro, chloro and/or bromo), carbonyl, $C_{1-4}$ alkyl, hydroxy, $C_{1-4}$ alkoxy, $NH_2$ and/or mono-substituted amine. For example, the benzothiophene can be an optionally substituted

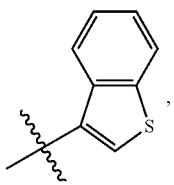 [SMILES: *c1csc2ccccc12]

such as an optionally substituted

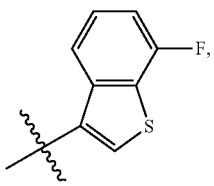 [SMILES: *c1csc2c(F)cccc12]

an optionally substituted

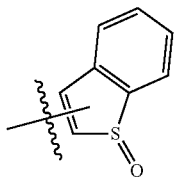

and an optionally substituted

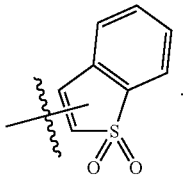

In some embodiments, $Y^b$ can be an optionally substituted benzofuran.

In some embodiments, $Y^b$ can be an optionally substituted indole. In some embodiments, $Y^b$ can be a substituted indole. In some embodiments, the indole can be substituted 1, 2, 3 or more time with phenyl (substituted or unsubstituted), $C_{1-4}$ alkyl and/or halo. In other embodiments, $Y^b$ can be an unsubstituted indole.

In some embodiments, $Y^b$ can be substituted with one or more halogen. In some embodiments, $Y^b$ can be substituted with one or more unsubstituted $C_{1-4}$ alkyl. In some embodiments, $Y^b$ can be substituted with more or more hydroxy. In some embodiments, $Y^b$ can be substituted with one or more optionally substituted phenyl. In some embodiments, $Y^b$ can be substituted with one or more alkoxy. In some embodiments, $Y^b$ can be substituted with one or more acyl. In some embodiments, $Y^b$ can be substituted with one or more amino, mono-substituted amino, or di-substituted amino. In some embodiments, $Y^b$ can be substituted with one or more haloalkyl. In some embodiments, $Y^b$ can be substituted with one or more haloalkoxy. In some embodiments, $Y^b$ can be substituted with one or more C-carboxy. In some embodiments, $Y^b$ can be substituted with one or more C-amido.

Pharmaceutical Compositions

Some embodiments described herein relate to a pharmaceutical composition, that can include an effective amount of one or more compounds described herein (e.g., a compound of Formula (I) and/or a compound of Formula (II), or a pharmaceutically acceptable salt of the foregoing) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal, and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating, treating and/or preventing a paramyxovirus viral infection, which can comprise administering an effective amount of one or more compounds described herein, or a pharmaceutical composition that includes one or more compounds described herein (e.g., a compound of Formula (I) and/or a compound of Formula (II), or a pharmaceutically acceptable salt of the foregoing).

Some embodiments described herein relate to a method for inhibiting viral replication of a paramyxovirus, which can comprise contacting a cell infected with the virus with an effective amount of a compound of Formula (I), or a pharmaceutically acceptable salt thereof, an effective amount of a compound of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing).

Some embodiments described herein relate to a method for contacting a cell infected with a paramyxovirus, which can comprise contacting a cell infected with the virus with an effective amount of a compound of Formula (I), or a pharmaceutically acceptable salt thereof, an effective amount of a compound of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing).

In some embodiments, the paramyxovirus infection is a human respiratory syncytial virus infection.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a respiratory syncytial viral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a respiratory syncytial viral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication a respiratory syncytial virus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the RSV polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a hendraviral infection and/or nipahviral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a hendraviral infection and/or nipahviral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication a hendravirus and/or nipahvirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the hendravirus polymerase complex and/or nipahvirus polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a measles. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a measles. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication a measles virus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the measles polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate mumps. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent mumps. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication a mumps virus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the mumps polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a sendai viral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a sendai viral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication a sendai virus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the sendai virus polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a HPIV-1 infection and/or HPIV-3 infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a HPIV-1 infection and/or HPIV-3 infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication of a HPIV-1 and/or HPIV-3. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the HPIV-1 polymerase complex and/or HPIV-3 polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a HPIV-2 infection and/or HPIV-4 infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a HPIV-2 infection and/or HPIV-4 infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication of a HPIV-2 and/or HPIV-4. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the HPIV-2 polymerase complex and/or HPIV-4 polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to treat and/or ameliorate a human metapneumoviral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a human metapneumoviral infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the replication of a human metapneumovirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to inhibit the human metapneumovirus polymerase complex.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate an upper respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate a lower respiratory viral infection caused by a virus selected from a henipavirus, a morbillivirus, a respirovirus, a rubulavirus, a pneumovirus, and a metapneumovirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate one or more symptoms of an infection caused by a virus selected from a henipavirus, a morbillivirus, a respirovirus, a rubulavirus, a pneumovirus, and a metapneumovirus (such as those described herein).

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate an upper respiratory viral infection caused by RSV infection, measles, mumps, parainfluenza infection, and/or metapneumovirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate a lower respiratory viral infection caused by RSV infection, measles, mumps, parainfluenza infection, and/or metapneumovirus. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate one or more symptoms of an infection caused by RSV infection, measles, mumps, parainfluenza infection, and/or metapneumovirus (such as those described herein).

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate bronchiolitis and/or tracheobronchitis due to a RSV infection and/or human parainfluenza virus 3 (HPIV-3) infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate pneumonia due to a RSV infection and/or human parainfluenza virus 3 (HPIV-3) infection. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate croup due to a RSV infection and/or human parainfluenza virus 1 (HPIV-1) infection.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate due to fever, cough, runny nose, red eyes, a generalized rash, pneumonia, an ear infection and/or bronchitis due to measles. In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used treat and/or ameliorate due to swelling of the salivary glands, fever, loss of appetite and/or fatigue due to mumps.

In some embodiments, an effective amount of one or more compounds of Formula (I), or a pharmaceutically acceptable salt thereof, one or more compounds of Formula (II), or a pharmaceutically acceptable salt thereof, and/or a pharmaceutical composition that includes one or more compounds described herein (e.g., a compound of Formula (I) and/or a compound of Formula (II), or a pharmaceutically acceptable salt of the foregoing) can be used to prevent a human parainfluenza viral infection. In some embodiments, the human parainfluenza viral infection can be a human parainfluenza virus 1 (HPIV-1). In other embodiments, the human parainfluenza viral infection can be a human parainfluenza virus 2 (HPIV-2). In other embodiments, the human parainfluenza viral infection can be a human parainfluenza virus 3 (HPIV-3). In other embodiments, the human parainfluenza viral infection can be a human parainfluenza virus 4 (HPIV-4). In some embodiments, one or more compounds of Formula (I), or a pharmaceutically acceptable salt thereof, and/or one or more compounds of Formula (II), or a pharmaceutically acceptable salt thereof, can be used to treat and/or ameliorate one or more subtypes of human parainfluenza virus. For example, one or more compounds of Formula (I), or a pharmaceutically acceptable salt thereof, and/or one or more compounds of Formula (II), or a pharmaceutically acceptable salt thereof, can be used to treat HPIV-1 and/or HPIV-3.

The one or more compounds of Formula (I) or a pharmaceutically acceptable salt thereof, and/or one or more compounds of Formula (II), or a pharmaceutically acceptable salt thereof, that can be used to treat, ameliorate and/or prevent a paramyxovirus viral infection can be a compound of Formula (I), or pharmaceutically acceptable salt thereof, and/or a compound of Formula (II), or a pharmaceutically acceptable salt thereof, provided in any of the embodiments described in the section under the "Compounds" heading above.

As used herein, the terms "prevent" and "preventing," mean lowering the efficiency of viral replication and/or inhibiting viral replication to a greater degree in a subject who receives the compound compared to a subject who does not receive the compound. Examples of forms of prevention include prophylactic administration to a subject who has been or may be exposed to an infectious agent, such as a paramyxovirus (e.g., RSV).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesirable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a viral infection, such as a paramyxovirus, are known to those skilled in the art. Example of suitable indicators include, but are not limited to, a reduction in viral load, a reduction in viral replication, a reduction in viral RNA, a reduction in time to seroconversion (virus undetectable in patient serum), a reduction of morbidity or mortality in clinical outcomes, and/or other indicator of disease response.

In some embodiments, an effective amount of a compound of Formulae (I) and/or (II), or a pharmaceutically acceptable salt of the foregoing, is an amount that is effective to reduce viral titers to essentially undetectable or very low levels, for example, to about 1000 to about 5000, to about 500 to about 1000, or to about 100 to about 500 genome copies/mL serum. In some embodiments, an effective amount of a compound of Formulae (I) and/or (II), or a pharmaceutically acceptable salt of the foregoing, is an amount that is effective to reduce viral load compared to the viral load before administration of the compound of Formulae (I) and/or (II), or a pharmaceutically acceptable salt of the foregoing. For example, wherein the viral load is measured before administration of the compound of Formulae (I) and/or (II), or a pharmaceutically acceptable salt of the foregoing, and again after completion of the treatment regime with the compound of Formulae (I) and/or (II), or a pharmaceutically acceptable salt of the foregoing (for example, 1 week after completion). In some embodiments, an effective amount of a compound of Formulae (I) and/or (II), or a pharmaceutically acceptable salt of the foregoing, can be an amount that is effective to reduce viral load by 2×, 5×, 10×, 100×, 1000×, or more, or to lower than about 100 genome copies/mL serum. In some embodiments, an effective amount of a compound of Formulae (I) and/or (II), or a pharmaceutically acceptable salt of the foregoing, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formulae (I) and/or (II), or a pharmaceutically acceptable salt of the foregoing. For example, wherein the viral load is measure before administration of the compound of Formulae (I) and/or (II), or a pharmaceutically acceptable salt of the foregoing, and again after completion of the treatment regime with the compound of Formulae (I) and/or (II), or a pharmaceutically acceptable salt of the foregoing (for example, 1 week after completion).

In some embodiments, a compound of Formulae (I) and/or (II), or a pharmaceutically acceptable salt of the foregoing, can result in at least a 1, 2, 3, 4, 5, 10, 15, 20, 25, 50, 75, 100-fold or more reduction in the replication of a paramyxovirus relative to pre-treatment levels in a subject, as determined after completion of the treatment regime (for example, 1 week after completion). In some embodiments, a compound of Formulae (I) and/or (II), or a pharmaceutically acceptable salt of the foregoing, can result in a reduction of the replication of a paramyxovirus relative to pre-treatment levels in the range of about 2 to about 5 fold, about 10 to about 20 fold, about 15 to about 40 fold, or about 50 to about 100 fold. In some embodiments, a compound of Formulae (I) and/or (II), or a pharmaceutically acceptable salt of the foregoing, can result in a reduction of paramyxovirus replication in the range of 1 to 1.5 log, 1.5 log to 2 log, 2 log to 2.5 log, 2.5 to 3 log, 3 log to 3.5 log or 3.5 to 4 log more reduction of paramyxovirus replication compared to the reduction of paramyxovirus reduction achieved by ribavirin (Virazole®), or may achieve the same reduction as that of ribavirin (Virazole®) therapy in a shorter period of time, for example, in one week, two weeks, one month, two months, or three months, as compared to the reduction achieved after six months of ribavirin (Virazole®) therapy.

In some embodiments, an effective amount of a compound of Formula (I) and/or a compound of Formula (II), or a pharmaceutically acceptable salt of the foregoing, is an amount that is effective to achieve a sustained viral response, for example, non-detectable or substantially non-detectable paramyxovirus (e.g., less than about 500, less than about 400, less than about 200, or less than about 100 genome copies per milliliter serum) is found in the subject's serum for a period of at least about one week, two weeks, one month, at least about two months, at least about three months, at least about four months, at least about five months, or at least about six months following cessation of therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I) and/or a compound of Formula (II), or a pharmaceutically acceptable salt of the foregoing, can be administered to a subject infected with RSV that is resistant to one or more different anti-RSV agents (for example, ribavirin). In some embodiments, development of resistant RSV strains is delayed when subjects are treated with a compound of Formula (I) and/or a compound of Formula (II), or a pharmaceutically acceptable salt of the foregoing, compared to the development of RSV strains resistant to other RSV drugs.

In some embodiments, a compound of Formula (I) and/or a compound of Formula (II), or a pharmaceutically acceptable salt of the foregoing, can decrease the percentage of subjects that experience complications from a RSV viral infection compared to the percentage of subjects that experience complication being treated with ribavirin. For example, the percentage of subjects being treated with a compound of Formula (I) and/or a compound of Formula (II), or a pharmaceutically acceptable salt of the foregoing, that experience complications can be 10%, 25%, 40%, 50%, 60%, 70%, 80% and 90% less compared to subjects being treated with ribavirin.

In some embodiments, a compound of Formula (I) and/or a compound of Formula (II), or a pharmaceutically acceptable salt of the foregoing, or a pharmaceutical composition that includes a compound described herein, can be used in combination with one or more additional agent(s). In some embodiments, a compound of Formula (I) and/or a compound of Formula (II), or a pharmaceutically acceptable salt of the foregoing, can be used in combination with one or more agents currently used in a conventional standard of care for treating RSV. For example, the additional agent can be ribavirin, palivizumab, and RSV-IGIV. For the treatment of RSV, additional agents include but are not limited to ALN-RSV01 (Alnylam Pharmaceuticals), ALN-RSV01 second generation (Alnylam Pharmaceuticals), CG-100 (Clarassance), STP-92 (Sirnaomics), iKT-041 (Inhibikase), BMS-433771 (1-cyclopropyl-3-[[1-(4-hydroxybutyl)benzimidazol-2-yl]methyl]imidazo[4,5-c]pyridin-2-one), RFI-641 ((4,4"-bis-{4,6-bis-[3-(bis-carbamoylmethyl-sulfamoyl)-phenylamino]-(1,3,5)triazin-2-ylamino}-biphenyl-2, 2"-disulfonic-acid)), RSV604 ((S)-1-(2-fluorophenyl)-3-(2-oxo-5-phenyl-2,3-dihydro-1H-benzo[e][1,4]di-azepin-3-yl)-urea), MDT-637 ((4Z)-2-methylsulfanyl-4-[(E)-3-thiophen-2-ylprop-2-enylidene]-1,3-thiazol-5-one), BTA9881, TMC-353121 (Tibotec), MBX-300, YM-53403 (N-cyclopropyl-6-[4-[(2-phenylbenzoyl)amino]benzoyl]-4, 5-dihydrothieno[3,2-d][1]benzazepine-2-carboxamide), motavizumab (Medi-524, MedImmune), Medi-559, Medi-534 and Medi-557.

In combination therapy, the additional agents can be administered in amounts that have been shown to be effective for those additional agents. Such amounts are known in the art; alternatively, they can be derived from viral load or replication studies using the parameters for "effective amount" set forth above. Alternatively, the amount used can be less than the effective monotherapy amount for such additional agents. For example, the amount used could be between 90% and 5% of such amount, e.g., 90%, 80%, 70%, 60%, 50%, 40%, 30%, 20%, 10%, or 5%, or intermediate values between those points.

In some embodiments, a compound of Formula (I) and/or a compound of Formula (II), or a pharmaceutically acceptable salt of the foregoing, can be administered with one or more additional agent(s) together in a single pharmaceutical composition. In some embodiments, a compound of Formula (I) and/or a compound of Formula (II), or a pharmaceutically acceptable salt of the foregoing, can be administered with one or more additional agent(s) as two or more separate pharmaceutical compositions. For example, a compound of Formula (I) and/or a compound of Formula (II), or a pharmaceutically acceptable salt of the foregoing, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I) and/or a compound of Formula (II), or a pharmaceutically acceptable salt of the foregoing, and at least one of the other additional agent(s) can be in a second pharmaceutical composition.

The order of administration of a compound of Formula (I) and/or a compound of Formula (II), or a pharmaceutically acceptable salt of the foregoing, with one or more additional agent(s) can vary. In some embodiments, a compound of Formula (I) and/or a compound of Formula (II), or a pharmaceutically acceptable salt of the foregoing, can be administered prior to all additional agents. In other embodiments, a compound of Formula (I) and/or a compound of Formula (II), or a pharmaceutically acceptable salt of the foregoing, can be administered prior to at least one additional agent. In still other embodiments, a compound of Formula (I) and/or a compound of Formula (II), or a pharmaceutically acceptable salt of the foregoing, can be administered concomitantly with one or more additional agent(s). In yet still other embodiments, a compound of Formula (I) and/or a compound of Formula (II), or a pharmaceutically acceptable salt of the foregoing, can be administered subsequent to the administration of at least one additional agent. In some embodiments, a compound of Formula (I) and/or a compound of Formula (II), or a pharmaceutically acceptable salt of the foregoing, can be administered subsequent to the administration of all additional agents.

A potential advantage of utilizing a compound of Formula (I) and/or a compound of Formula (II), or a pharmaceutically acceptable salt of the foregoing, in combination with one or more additional agent(s) described above, including pharmaceutically acceptable salts and prodrugs thereof, may be a reduction in the required amount(s) of one or more additional agent(s) described above (including pharmaceutically acceptable salts and prodrugs thereof) that is effective in treating a disease condition disclosed herein (for example, RSV), as compared to the amount required to achieve same therapeutic result when one or more additional agent(s) described above, including pharmaceutically acceptable salts thereof, are administered without a compound of Formula (I) and/or a compound of Formula (II), or a pharmaceutically acceptable salt of the foregoing. For example, the amount of one or more additional agent(s) described above, including a pharmaceutically acceptable salt and prodrug thereof, can be less compared to the amount of the one or more additional agent(s) described above, including a pharmaceutically acceptable salt and prodrug thereof, needed to achieve the same viral load reduction when administered as a monotherapy. Another potential advantage of utilizing a compound of Formula (I) and/or a compound of Formula (II), or a pharmaceutically acceptable salt of the foregoing, in combination with one or more additional agent(s) described above, including pharmaceutically acceptable salts and prodrugs thereof, is that the use of two or more compounds having different mechanism of actions can create a higher barrier to the development of resistant viral strains compared to the barrier when a compound is administered as monotherapy.

Additional advantages of utilizing a compound of Formula (I) and/or a compound of Formula (II), or a pharmaceutically acceptable salt the foregoing, in combination with one or more additional agent(s) described above, including pharmaceutically acceptable salts and prodrugs thereof, may include little to no cross resistance between a compound of Formula (I) and/or a compound of Formula (II), or a pharmaceutically acceptable salt the foregoing, and one or more additional agent(s) described above (including pharmaceutically acceptable salts and prodrugs thereof); different routes for elimination of a compound of Formula (I) and/or a compound of Formula (II), or a pharmaceutically acceptable salt the foregoing, and one or more additional agent(s) described above (including pharmaceutically acceptable salts and prodrugs thereof); little to no overlapping toxicities between a compound of Formula (I) and/or a compound of Formula (II), or a pharmaceutically acceptable salt the foregoing, and one or more additional agent(s) described above (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described above (including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Synthesis

Compounds of Formulae (I) and Formula (II), and those described herein may be prepared in various ways. Some compounds of Formulae (I) and (II) can be obtained commercially and/or prepared utilizing known synthetic procedures. General synthetic routes to the compounds of Formulae (I) and (II), and some examples of starting materials used to synthesize the compounds of Formulae (I) and (II) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

EXAMPLES

Additional embodiments are disclosed in further detail in the following examples, which are not in any way intended to limit the scope of the claims.

Example 1

Preparation of Compound 100

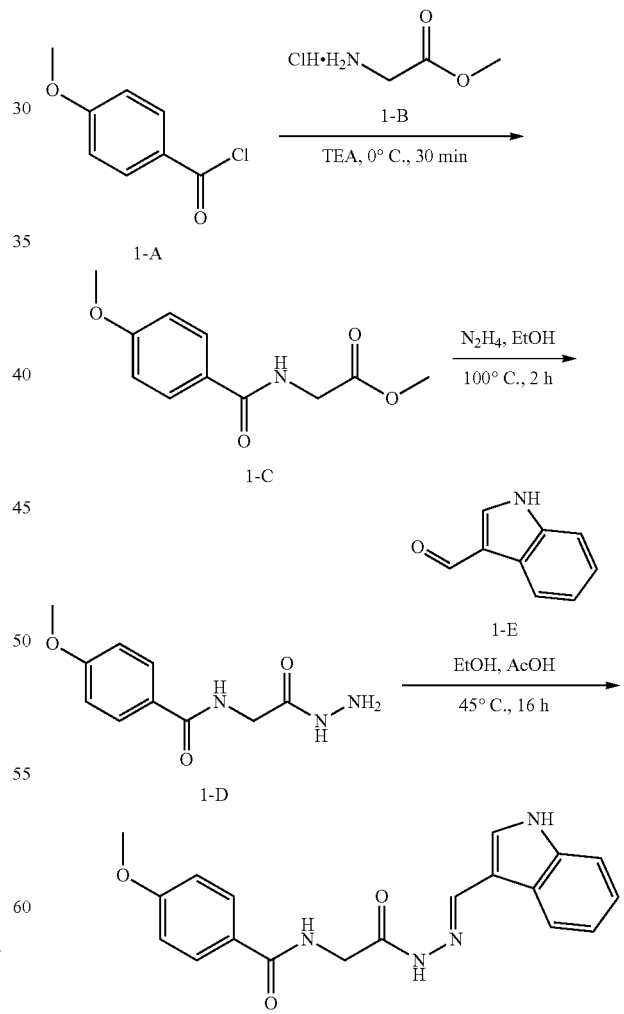

To a stirred solution of glycine methyl ester hydrochloride (1-B) (5.1 g, 40 mmol) in water and TEA (1:1, 40 mL) was added 4-methoxybenzoyl chloride (1-A) (4.0 g, 20 mmol) dropwise at 0° C. The mixture was stirred at 0° C. for 30 mins. The mixture was poured into saturated NaHCO$_3$ aq. cooled by ice bath, and then extracted with EA (ethyl acetate) and washed by brine, dried and concentrated to afford 1-C (6.4 g, yield: 63%) as a white solid.

To a solution of 1-C (6.40 g, 25.30 mmol) in anhydrous ethanol (50 mL) was added N$_2$H$_4$—H$_2$O (9.59 g, 191.80 mmol), the mixture was stirred at 100° C. for 2 hours (h). Then the mixture was allowed to cool to room temperature (rt) and a white precipitate was formed in the solution. The precipitate was filtered and washed with EtOH (20 mL) to give 1-D (5.8 g, 91.6%) as a white solid.

To a solution of 1-D (115 mg, 0.5 mmol) in anhydrous ethanol (3 mL) was added 1-E (80 mg, 0.5 mmol) and AcOH (0.1 mL), the mixture was stirred at 45° C. for 16 h. Then the mixture was allowed to cool to rt and a white precipitate was formed in the solution. The precipitate was filtered and washed with EtOAc to afford compound 100 as a white solid (155 mg, 87.9%). +ESI-MS: m/z 351.0 [M+H]$^+$.

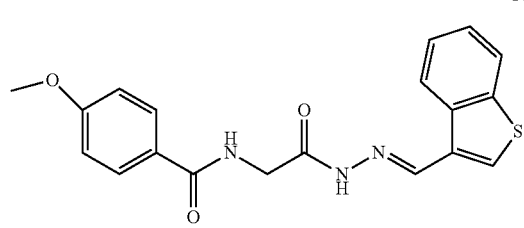

101

Compound 101 was obtained following the procedure for obtaining Compound 100 using the appropriate aldehyde in place of 1-E. Compound 101 was obtained as a white solid (151 mg, 76.8%). +ESI-MS: m/z 368.0 [M+H]$^+$.

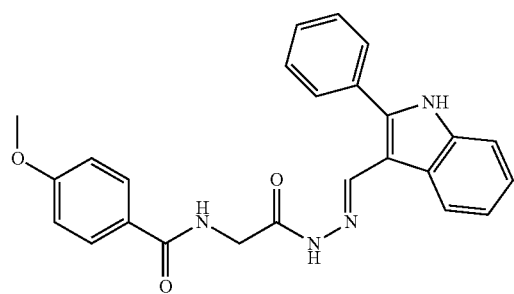

102

Compound 102 was obtained following the procedure for obtaining Compound 100 using the appropriate aldehyde in place of 1-E. Compound 102 was obtained as a white solid (166 mg, 79.8%). +ESI-MS: m/z 427.0 [M+H]$^+$.

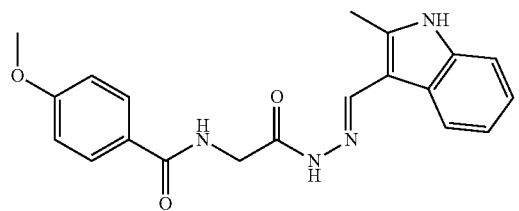

103

Compound 103 was obtained following the procedure for obtaining Compound 100 using the appropriate aldehyde in place of 1-E. Compound 103 was obtained as a white solid (112 mg, 59.8%). +ESI-MS: m/z 365.0 [M+H]$^+$.

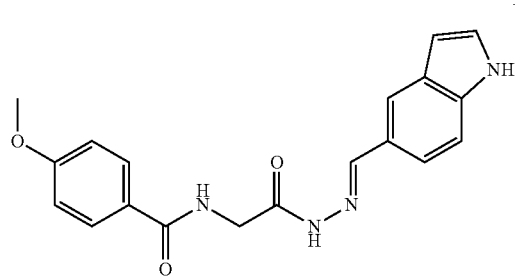

104

Compound 104 was obtained following the procedure for obtaining Compound 100 using the appropriate aldehyde in place of 1-E. Compound 104 was obtained as a white solid (118 mg, 60.2%). +ESI-MS: m/z 351.0 [M+H]$^+$.

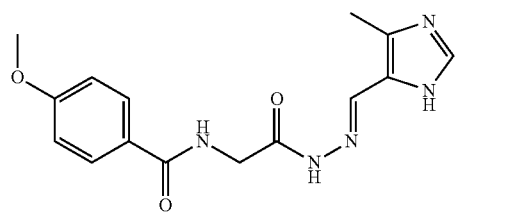

105

Compound 105 was obtained following the procedure for obtaining Compound 100 using the appropriate aldehyde in place of 1-E. Compound 105 was obtained as a white solid (118 mg, 60.2%). +ESI-MS: m/z 316.0 [M+H]$^+$.

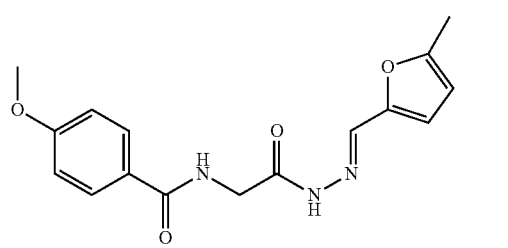

106

Compound 106 was obtained following the procedure for obtaining Compound 100 using the appropriate aldehyde in place of 1-E. Compound 106 was obtained as a white solid (111 mg, 59.8%). +ESI-MS: m/z 316.0 [M+H]$^+$.

107

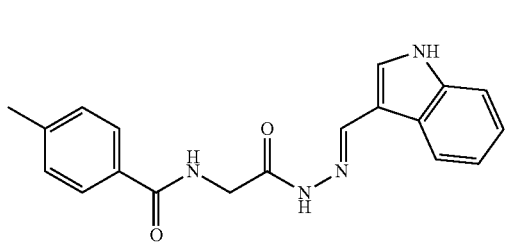

Compound 107 was obtained following the procedure for obtaining Compound 100 using the appropriate acid chloride in place of 1-A. Compound 107 was obtained as a white solid (108 mg, 59.2%). +ESI-MS: m/z 335.0 [M+H]$^+$.

108

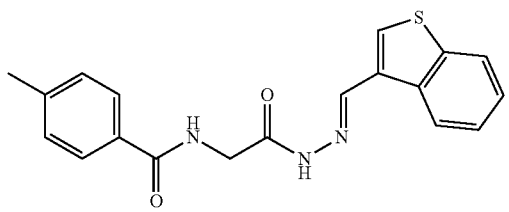

Compound 108 was obtained following the procedure for obtaining Compound 100 using the appropriate acid chloride in place of 1-A and using the appropriate aldehyde in place of 1-E. Compound 108 was obtained as a white solid (108 mg, 59.2%). +ESI-MS: m/z 352.0 [M+H]$^+$.

109

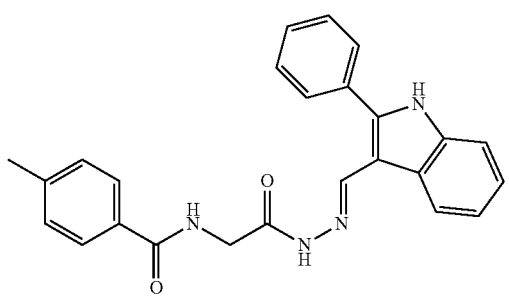

Compound 109 was obtained following the procedure for obtaining Compound 100 using the appropriate acid chloride in place of 1-A and using the appropriate aldehyde in place of 1-E. Compound 109 was obtained as a white solid (105 mg, 58.5%). +ESI-MS: m/z 411.0 [M+H]$^+$.

110

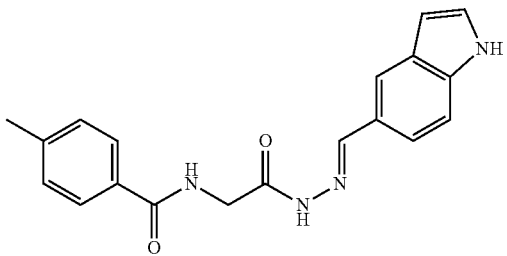

Compound 110 was obtained following the procedure for obtaining Compound 100 using the appropriate acid chloride in place of 1-A and using the appropriate aldehyde in place of 1-E. Compound 110 was obtained as a white solid (114 mg, 61.2%). +ESI-MS: m/z 349.0 [M+H]$^+$.

111

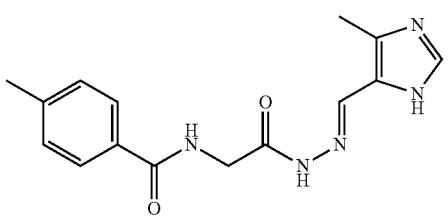

Compound 111 was obtained following the procedure for obtaining Compound 100 using the appropriate acid chloride in place of 1-A and using the appropriate aldehyde in place of 1-E. Compound 111 was obtained as a white solid (121 mg, 67.2%). +ESI-MS: m/z 335.0 [M+H]$^+$.

112

Compound 112 was obtained following the procedure for obtaining Compound 100 using the appropriate acid chloride in place of 1-A and using the appropriate aldehyde in place of 1-E. Compound 112 was obtained as a white solid (122 mg, 67.5%). +ESI-MS: m/z 300.0 [M+H]$^+$.

113

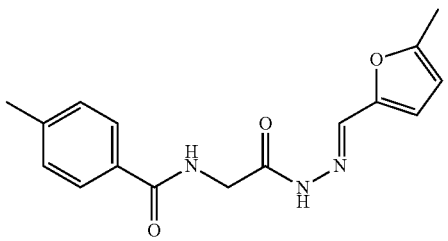

Compound 113 was obtained following the procedure for obtaining Compound 100 using the appropriate acid chloride in place of 1-A and using the appropriate aldehyde in place of 1-E. Compound 113 was obtained as a white solid (128 mg, 69.5%). +ESI-MS: m/z 300.0 [M+H]$^+$.

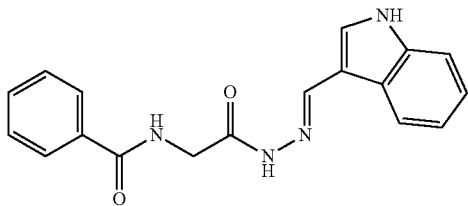

114

Compound 114 was obtained following the procedure for obtaining Compound 100 using the appropriate acid chloride in place of 1-A. Compound 114 was obtained as a white solid (101 mg, 57.5%). +ESI-MS: m/z 321.0 [M+H]$^+$.

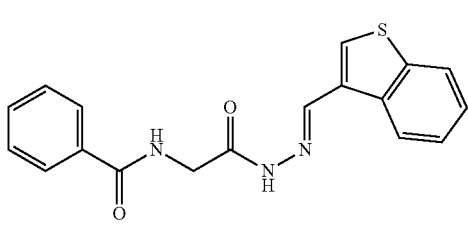

115

Compound 115 was obtained following the procedure for obtaining Compound 100 using the appropriate acid chloride in place of 1-A and using the appropriate aldehyde in place of 1-E. Compound 115 was obtained as a white solid (108 mg, 59.8%). +ESI-MS: m/z 338.0 [M+H]$^+$.

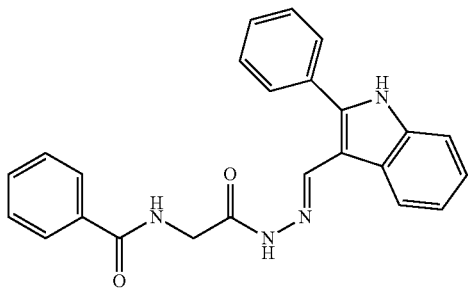

116

Compound 116 was obtained following the procedure for obtaining Compound 100 using the appropriate acid chloride in place of 1-A and using the appropriate aldehyde in place of 1-E. Compound 116 was obtained as a white solid (125 mg, 64.8%). +ESI-MS: m/z 397.0 [M+H]$^+$.

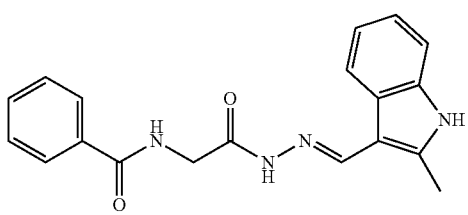

117

Compound 117 was obtained following the procedure for obtaining Compound 100 using the appropriate acid chloride in place of 1-A and using the appropriate aldehyde in place of 1-E. Compound 117 was obtained as a white solid (122 mg, 63.8%). +ESI-MS: m/z 335.0 [M+H]$^+$.

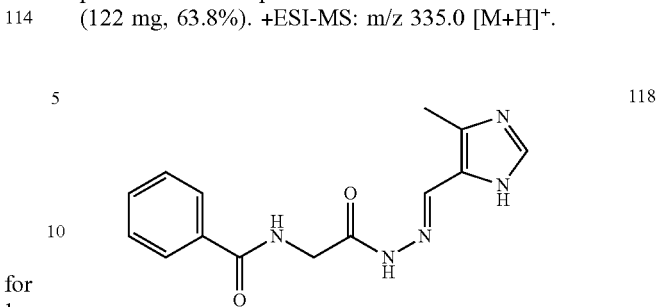

118

Compound 118 was obtained following the procedure for obtaining Compound 100 using the appropriate acid chloride in place of 1-A and using the appropriate aldehyde in place of 1-E. Compound 118 was obtained as a white solid (121 mg, 62.7%). +ESI-MS: m/z 286.0 [M+H]$^+$.


119

Compound 119 was obtained following the procedure for obtaining Compound 100 using the appropriate acid chloride in place of 1-A and using the appropriate aldehyde in place of 1-E. Compound 119 was obtained as a white solid (128 mg, 64.8%). +ESI-MS: m/z 286.0 [M+H]$^+$.


120

Compound 120 was obtained following the procedure for obtaining Compound 100 using the appropriate acid chloride in place of 1-A. Compound 120 was obtained as a white solid (124 mg, 52.8%). +ESI-MS: m/z 423.0 [M+H]$^+$.

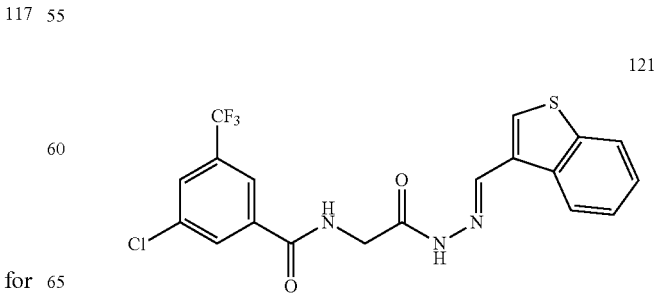

121

Compound 121 was obtained following the procedure for obtaining Compound 100 using the appropriate acid chloride in place of 1-A and using the appropriate aldehyde in place of 1-E. Compound 121 was obtained as a white solid (121 mg, 51.2%). +ESI-MS: m/z 440.0 [M+H]+.

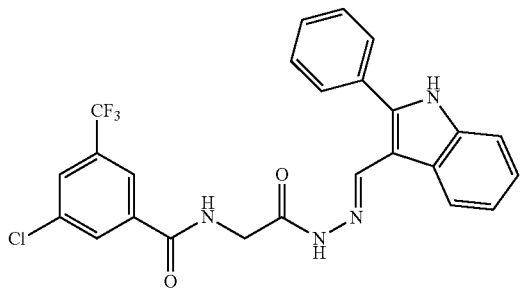

Compound 122 was obtained following the procedure for obtaining Compound 100 using the appropriate acid chloride in place of 1-A and using the appropriate aldehyde in place of 1-E. Compound 122 was obtained as a white solid (113 mg, 48.2%). +ESI-MS: m/z 499.0 [M+H]+.

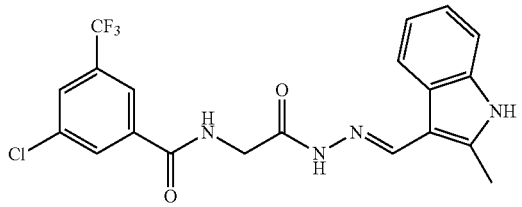

Compound 123 was obtained following the procedure for obtaining Compound 100 using the appropriate acid chloride in place of 1-A and using the appropriate aldehyde in place of 1-E. Compound 123 was obtained as a white solid (131 mg, 56.2%). +ESI-MS: m/z 437.0 [M+H]+.

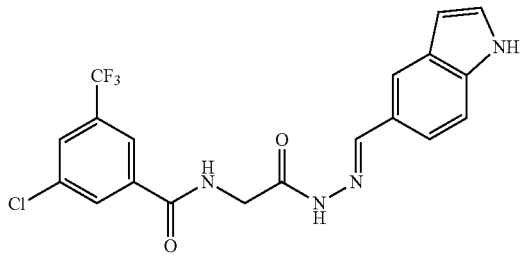

Compound 124 was obtained following the procedure for obtaining Compound 100 using the appropriate acid chloride in place of 1-A and using the appropriate aldehyde in place of 1-E. Compound 124 was obtained as a white solid (133 mg, 58.1%). +ESI-MS: m/z 423.0 [M+H]+.

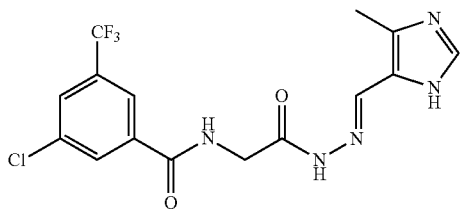

Compound 125 was obtained following the procedure for obtaining Compound 100 using the appropriate acid chloride in place of 1-A and using the appropriate aldehyde in place of 1-E. Compound 125 was obtained as a white solid (131 mg, 57.8%). +ESI-MS: m/z 388.0 [M+H]+.

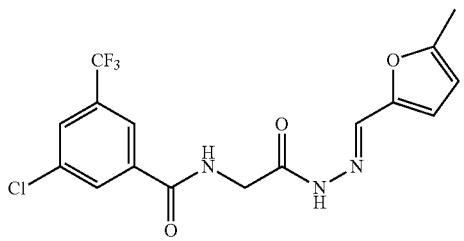

Compound 126 was obtained following the procedure for obtaining Compound 100 using the appropriate acid chloride in place of 1-A and using the appropriate aldehyde in place of 1-E. Compound 126 was obtained as a white solid (134 mg, 59.2%). +ESI-MS: m/z 388.0 [M+H]+.

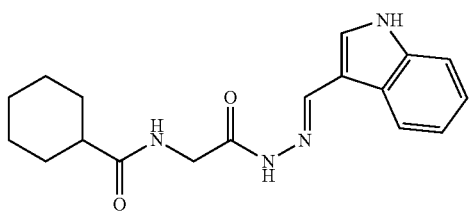

Compound 127 was obtained following the procedure for obtaining Compound 100 using the appropriate acid chloride in place of 1-A. Compound 127 was obtained as a white solid (81 mg, 39.2%). +ESI-MS: m/z 327.0 [M+H]+.

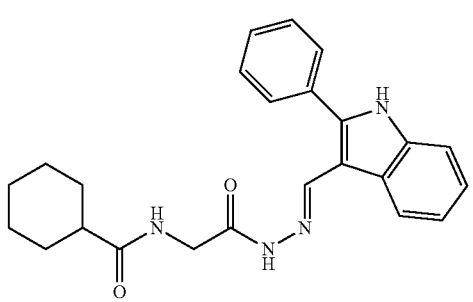

Compound 128 was obtained following the procedure for obtaining Compound 100 using the appropriate acid chloride in place of 1-A and using the appropriate aldehyde in place of 1-E. Compound 128 was obtained as a white solid (87 mg, 42.1%). +ESI-MS: m/z 403.0 [M+H]+.

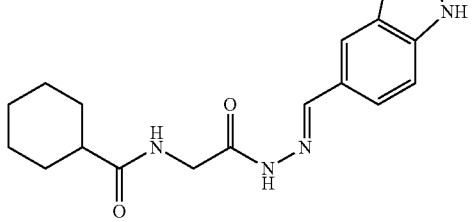

129

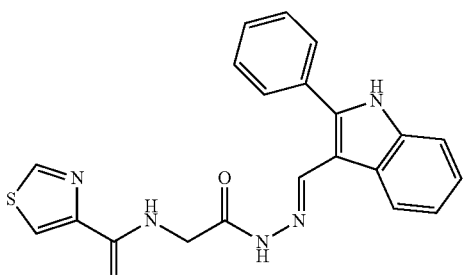

132

Compound 132 was obtained following the procedure for obtaining Compound 100 using the appropriate acid chloride in place of 1-A. Compound 132 was obtained as a white solid (89 mg, 43.3%). +ESI-MS: m/z 328.0 [M+H]+.

Compound 129 was obtained following the procedure for obtaining Compound 100 using the appropriate acid chloride in place of 1-A and using the appropriate aldehyde in place of 1-E. Compound 129 was obtained as a white solid (67 mg, 33.1%). +ESI-MS: m/z 327.0 [M+H]+.

133

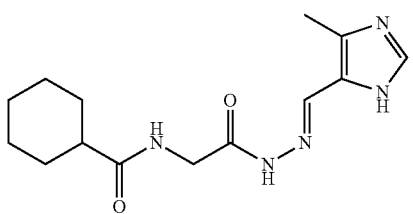

130

Compound 130 was obtained following the procedure for obtaining Compound 100 using the appropriate acid chloride in place of 1-A and using the appropriate aldehyde in place of 1-E. Compound 130 was obtained as a white solid (66 mg, 32.6%). +ESI-MS: m/z 292.0 [M+H]+.

Compound 133 was obtained following the procedure for obtaining Compound 100 using the appropriate acid chloride in place of 1-A and using the appropriate aldehyde in place of 1-E. Compound 133 was obtained as a white solid (87 mg, 42.3%). +ESI-MS: m/z 404.0 [M+H]+.

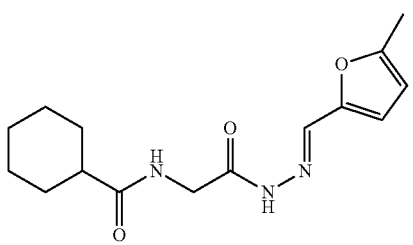

131

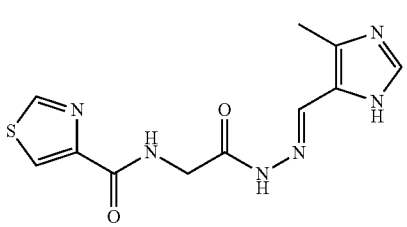

134

Compound 131 was obtained following the procedure for obtaining Compound 100 using the appropriate acid chloride in place of 1-A and using the appropriate aldehyde in place of 1-E. Compound 131 was obtained as a white solid (58 mg, 30.6%). +ESI-MS: m/z 292.0 [M+H]+.

Compound 134 was obtained following the procedure for obtaining Compound 100 using the appropriate acid chloride in place of 1-A and using the appropriate aldehyde in place of 1-E. Compound 134 was obtained as a white solid (76 mg, 38.3%). +ESI-MS: m/z 293.0 [M+H]+.

Example 2

Preparation of Compound 200

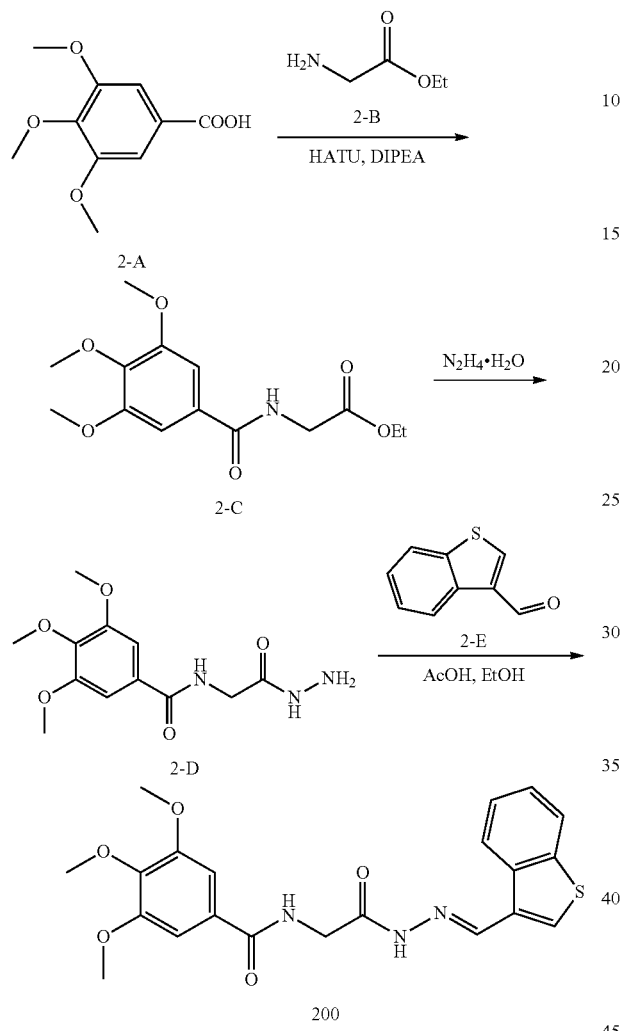

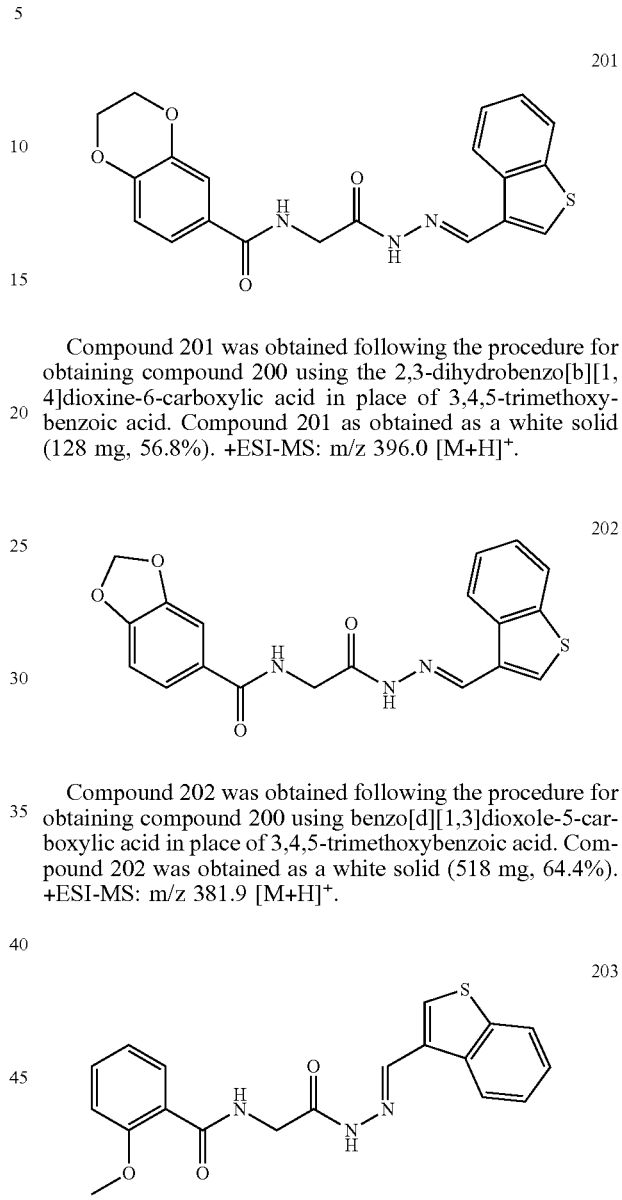

To a solution of 3,4,5-trimethoxybenzoic acid (2-A) (2.0 g, 9.43 mmol) in DCM (60 mL) was added HATU (5.4 g, 14.2 mmol) and DIPEA (5.0 g, 38.76 mmol), the mixture was stirred at room temperature for 30 mins, then was added glycine ethyl ester (2-B) (19.7 g, 14.2 mmol). The mixture was stirred at rt for another 15 h. The mixture was washed with water and the organic layer was collected. The solvent was removed and the residue was purified by silica gel column (PE/EA=20/1 to 5/1) to afford 2-C as a white solid (1.5 g, 53.6%). +ESI-MS: m/z 297.9 [M+H]$^+$.

To a solution of 2-C (1.54 g, 5.20 mmol) in anhydrous ethanol (50 mL) was added N$_2$H$_4$—H$_2$O (2.59 g, 80.9 mmol), the mixture was stirred at 80° C. for 15 h. Then the mixture was allowed to cool to rt and a white precipitate was formed in the solution. The precipitate was filtered and washed with EtOH (20 mL) to afford 2-D as a white product (1.2 g, 81.6%). +ESI-MS: m/z 283.9 [M+H]$^+$.

To a solution of 2-D (200 mg, 0.71 mmol) in anhydrous ethanol (30 mL) was added benzo[b]thiophene-3-carbaldehyde (2-E) (150 mg, 0.92 mmol) and AcOH (0.1 mL), the mixture was stirred at 50° C. for 15 h. Then the mixture was allowed to cool to rt and a white precipitate was formed in the solution. The precipitate was filtered and washed with EtOAc to afford compound 200 as a white solid (118 mg, 38.9%). +ESI-MS: m/z 428.0 [M+H]$^+$.

Compound 201 was obtained following the procedure for obtaining compound 200 using the 2,3-dihydrobenzo[b][1,4]dioxine-6-carboxylic acid in place of 3,4,5-trimethoxybenzoic acid. Compound 201 as obtained as a white solid (128 mg, 56.8%). +ESI-MS: m/z 396.0 [M+H]$^+$.

Compound 202 was obtained following the procedure for obtaining compound 200 using benzo[d][1,3]dioxole-5-carboxylic acid in place of 3,4,5-trimethoxybenzoic acid. Compound 202 was obtained as a white solid (518 mg, 64.4%). +ESI-MS: m/z 381.9 [M+H]$^+$.

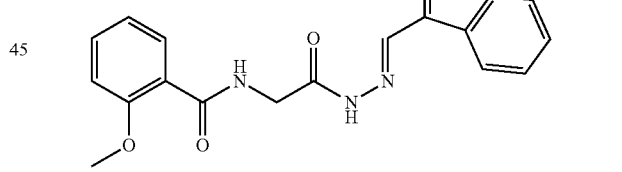

Compound 203 was obtained following the procedure for obtaining compound 200 using 2-methoxybenzoic acid in place of 3,4,5-trimethoxybenzoic acid. +ESI-MS: m/z 368.0 [M+H]$^+$.

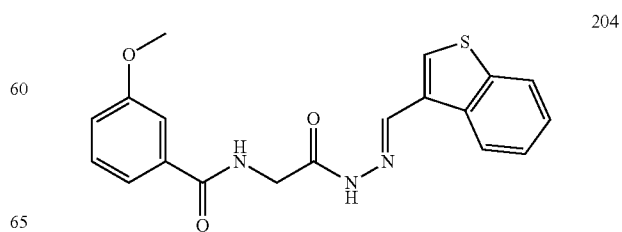

Compound 204 was obtained following the procedure for obtaining compound 200 using 3-methoxybenzoic acid in place of 3,4,5-trimethoxybenzoic acid. Compound 204 was obtained as a white solid (179 mg, 68.2%). +ESI-MS: m/z 368.0 [M+H]+.

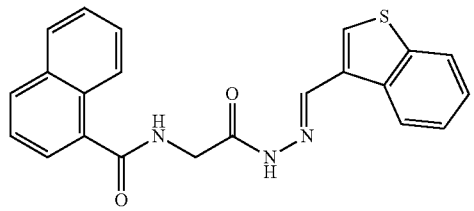
205

Compound 205 was obtained following the procedure for obtaining compound 200 using 1-naphthoic acid in place of 3,4,5-trimethoxybenzoic acid. Compound 205 was obtained as a white solid (672 mg, 81.3%). +ESI-MS: m/z 387.9 [M+H]+.

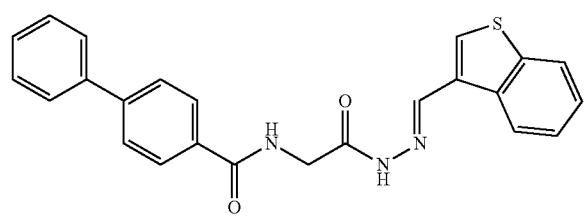
206

Compound 206 was obtained following the procedure for obtaining compound 200 using 4-phenyl benzoic acid in place of 3,4,5-trimethoxybenzoic acid. Compound 206 was obtained as a white solid (167 mg, 90.8%). +ESI-MS: m/z 414.0 [M+H]+.

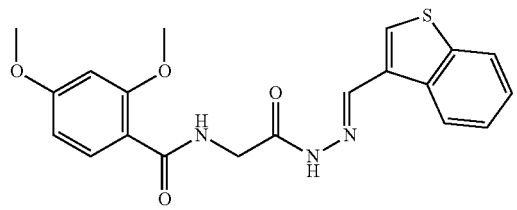
207

Compound 207 was obtained following the procedure for obtaining compound 200 using 2,4-dimethoxybenzoic acid in place of 3,4,5-trimethoxybenzoic acid. Compound 206 was obtained as a white solid (130 mg, 57.8%). +ESI-MS: m/z 398.0 [M+H]+.

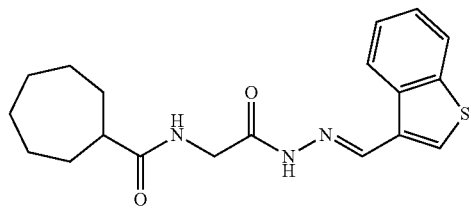
208

Compound 208 was obtained following the procedure for obtaining compound 200 using cycloheptanecarboxylic acid in place of 3,4,5-trimethoxybenzoic acid. Compound 208 was obtained as a white solid (50 mg, 30.0%). +ESI-MS: m/z 358.0 [M+H]+

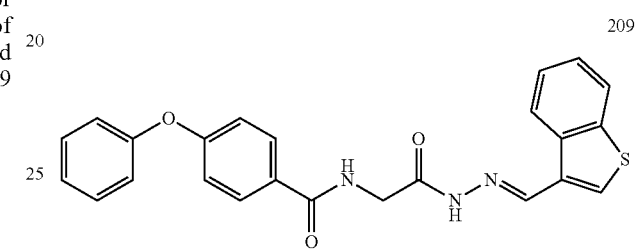
209

Compound 209 was obtained following the procedure for obtaining compound 200 using 4-phenoxybenzoic acid in place of 2-A. Compound 209 was obtained as a white solid (60 mg, 40.0%). +ESI-MS: m/z 430.0 [M+H]+.

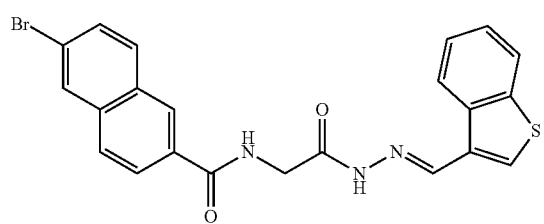
210

Compound 210 was obtained following the procedure for obtaining compound 200 using 6-bromo-2-naphthoic acid in place of 3,4,5-trimethoxybenzoic acid. Compound 210 was obtained as a white solid (50 mg, 35.0%). +ESI-MS: m/z 489.9 [M+Na]+

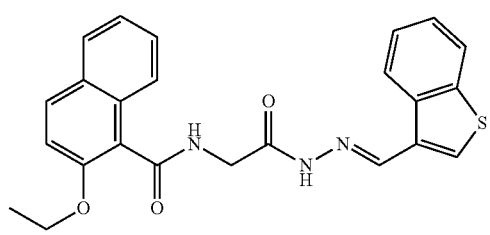
211

Compound 211 was obtained following the procedure for obtaining compound 200 using 2-ethoxy-1-naphthoic acid in place of 3,4,5-trimethoxybenzoic acid. Compound 211 was obtained as a white solid (60 mg, 40.0%). +ESI-MS: m/z 431.9 [M+H]+

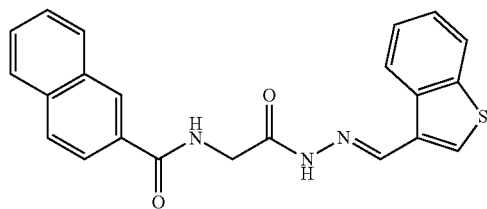

212

Compound 212 was obtained following the procedure for obtaining compound 200 using 2-naphthoic acid in place of 3,4,5-trimethoxybenzoic acid. Compound 212 was obtained as a white solid (70 mg, 43.7%). +ESI-MS: m/z 387.4 [M+H]+

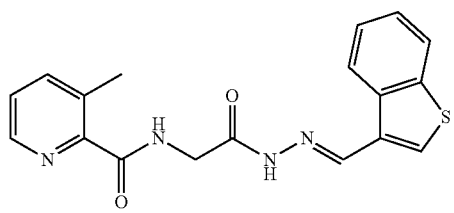

213

Compound 213 was obtained following the procedure for obtaining compound 200 using 3-methylpicolinic acid in place of 3,4,5-trimethoxybenzoic acid. Compound 213 was obtained as a white solid (130.4 mg, 88.5%). +ESI-MS: m/z 352.9 [M+H]+.

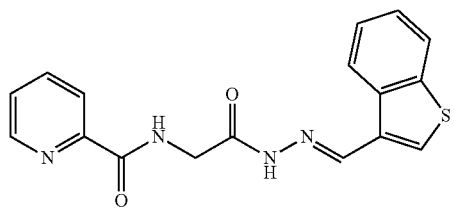

214

Compound 214 was obtained following the procedure for obtaining compound 200 using picolinic acid in place of 3,4,5-trimethoxybenzoic acid. Compound 214 was obtained as a white solid (204.1 mg, 91.5%). +ESI-MS: m/z 338.9 [M+H]+.

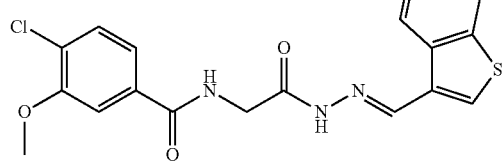

215

Compound 215 was obtained following the procedure for obtaining compound 200 using 4-chloro-3-methoxybenzoic acid in place of 3,4,5-trimethoxybenzoic acid. Compound 215 was obtained as a white solid (46.3 mg, 65.8%). +ESI-MS: m/z 401.9 [M+H]+.

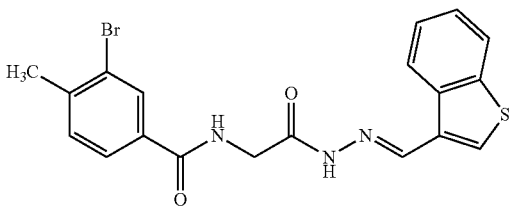

216

Compound 216 was obtained following the procedure for obtaining compound 200 using 3-bromo-4-methylbenzoic acid in place of 3,4,5-trimethoxybenzoic acid. Compound 216 was obtained as a white solid (68 mg, 22.7%). +ESI-MS: m/z 431.8 [M+H]+.

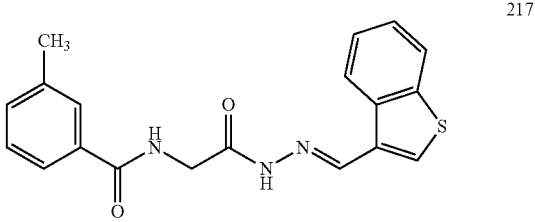 [SMILES: Cc1cccc(C(=O)NCC(=O)N/N=C/c2csc3ccccc23)c1]

217

Compound 217 was obtained following the procedure for obtaining compound 200 using 3-methylbenzoic acid in place of 3,4,5-trimethoxybenzoic acid. Compound 217 was obtained as a white solid (92 mg, 36.5%). +ESI-MS: m/z 351.9 [M+H]+.

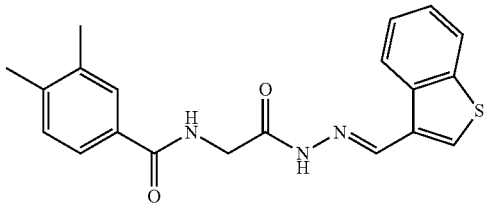

218

Compound 218 was obtained following the procedure for obtaining compound 200 using 3,4-dimethylbenzoic acid in place of 3,4,5-trimethoxybenzoic acid. Compound 218 was obtained as a white solid (40 mg, 42.4%). +ESI-MS: m/z 365.9 [M+H]+.

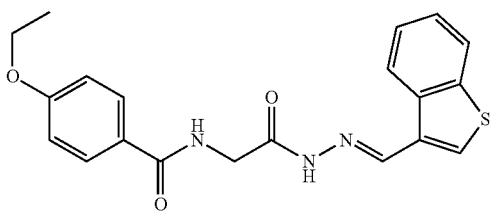

219

Compound 219 was obtained following the procedure for obtaining compound 200 using 4-ethoxybenzoic acid in place of 3,4,5-trimethoxybenzoic acid. Compound 219 was obtained as a white solid (100 mg, 46.8%). +ESI-MS: m/z 381.9 [M+H]+.

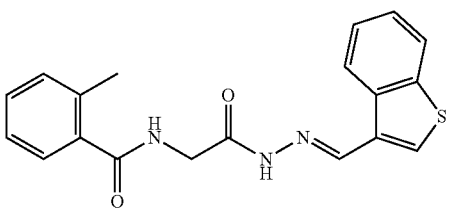

220

Compound 220 was obtained following the procedure for obtaining compound 200 using 2-methylbenzoic acid in place of 3,4,5-trimethoxybenzoic acid. Compound 220 was obtained as a white solid (40 mg, 23.7%). +ESI-MS: m/z 351.9 [M+H]+.

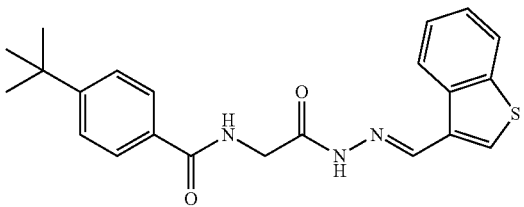

221

Compound 221 was obtained following the procedure for obtaining compound 200 using 4-(tert-butyl)benzoic acid in place of 3,4,5-trimethoxybenzoic acid. Compound 221 was obtained as a white solid (57 mg, 53.2%). +ESI-MS: m/z 394.1 [M+H]+.

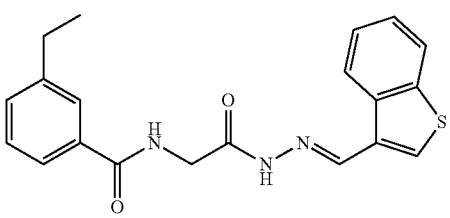

222

Compound 222 was obtained following the procedure for obtaining compound 200 using 4-(tert-butyl)benzoic acid in place of 3,4,5-trimethoxybenzoic acid. Compound 222 was obtained as a white solid (75 mg, 22.8%). +ESI-MS: m/z 366.0 [M+H]+.

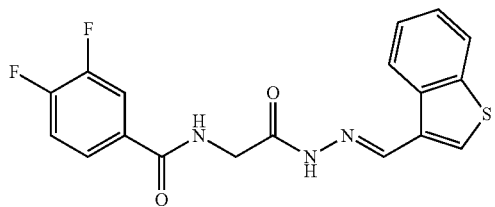

223

Compound 223 was obtained following the procedure for obtaining compound 200 using 3,4-difluorobenzoic acid in place of 3,4,5-trimethoxybenzoic acid. Compound 223 was obtained as a white solid (75 mg, 23.1%). +ESI-MS: m/z 373.9 [M+H]+.

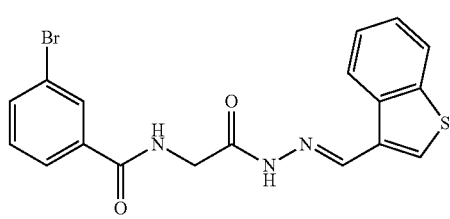

224

Compound 224 was obtained following the procedure for obtaining compound 200 using 3-bromobenzoic acid in place of 3,4,5-trimethoxybenzoic acid. Compound 224 was obtained as a white solid (124 mg, 40.3%). +ESI-MS: m/z 417.7 [M+H]+.

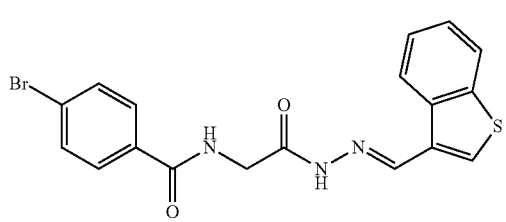

225

Compound 225 was obtained following the procedure for obtaining compound 200 using 4-bromobenzoic acid in place of 3,4,5-trimethoxybenzoic acid. Compound 225 was obtained as a white solid (160 mg, 51.9%). +ESI-MS: m/z 417.9 [M+H]+.

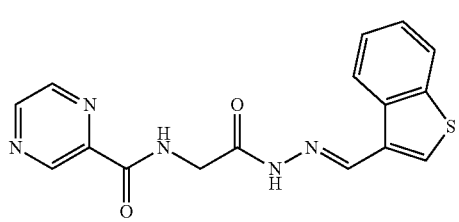

226

Compound 226 was obtained following the procedure for obtaining compound 200 using pyrazine-2-carboxylic acid in place of 3,4,5-trimethoxybenzoic acid. Compound 226 was obtained as a white solid (3 mg, 7.8%). +ESI-MS: m/z 339.9 [M+H]+.

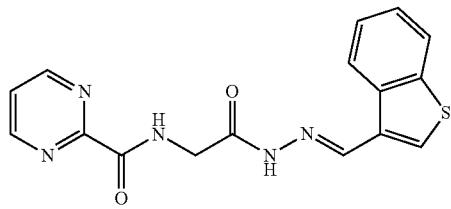

227

Compound 227 was obtained following the procedure for obtaining compound 200 using pyrimidine-2-carboxylic acid in place of 3,4,5-trimethoxybenzoic acid. Compound 227 was obtained as a white solid (5 mg, 16.8%). +ESI-MS: m/z 339.9 [M+H]+.

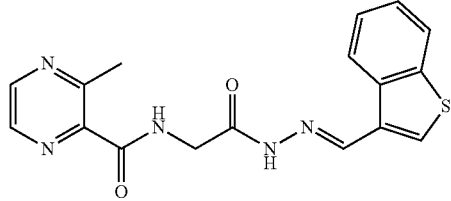

228

Compound 228 was obtained following the procedure for obtaining compound 200 using 3-methylpyrazine-2-carboxylic acid in place of 3,4,5-trimethoxybenzoic acid. Compound 228 was obtained as a white solid (50 mg, 14.1%). +ESI-MS: m/z 353.9 [M+H]+.

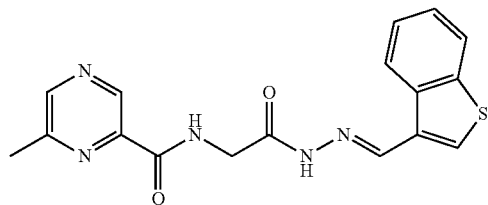

229

Compound 229 was obtained following the procedure for obtaining compound 200 using 4-methylpyrimidine-2-carboxylic acid in place of 3,4,5-trimethoxybenzoic acid. Compound 229 was obtained as a white solid (10 mg, 11.3%). +ESI-MS: m/z 353.9 [M+H]+.

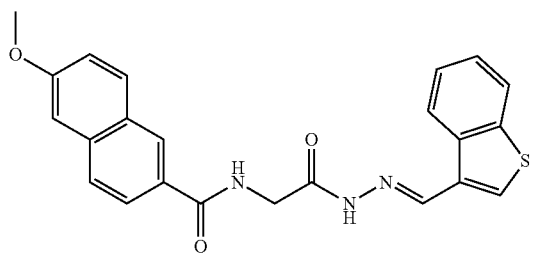

230

Compound 230 was obtained following the procedure for obtaining compound 200 using 6-methoxy-2-naphthoic acid in place of 3,4,5-trimethoxybenzoic acid. Compound 230 was obtained as a white solid (70 mg, 46.05%). +ESI-MS: m/z 418.1 [M+H]+.

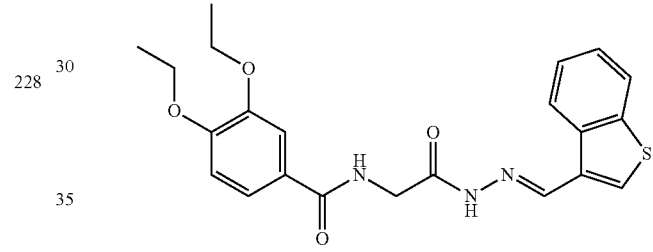

231

Compound 231 was obtained following the procedure for obtaining compound 200 using 3,4-diethoxybenzoic acid in place of 3,4,5-trimethoxybenzoic acid. Compound 231 was obtained as a white solid (150 me, 60%). ESI-LCMS: m/z 426 [M+H]+.

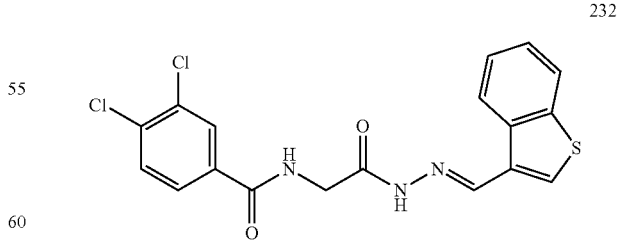

232

Compound 232 was obtained following the procedure for obtaining compound 200 using 3,4-dichlorobenzoic acid in place of 3,4,5-trimethoxybenzoic acid. Compound 232 was obtained as a white solid (154 mg, 62.5%). +ESI-MS: m/z 405.9 [M+H]+.

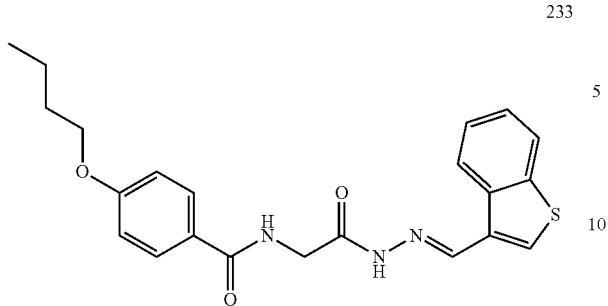

233

Compound 233 was obtained following the procedure for obtaining compound 200 using 4-butoxybenzoic acid in place of 3,4,5-trimethoxybenzoic acid. Compound 233 was obtained as a white solid (60 mg, 20%). ESI-LCMS: m/z 409.9 [M+H]+.

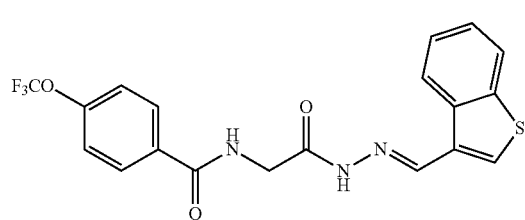

234

Compound 234 was obtained following the procedure for obtaining compound 200 using 4-(trifluoromethoxy)benzoic acid in place of 3,4,5-trimethoxybenzoic acid. Compound 234 was obtained as a white solid (90 mg, 59.2%). +ESI-MS: m/z 443.8 [M+Na]+.

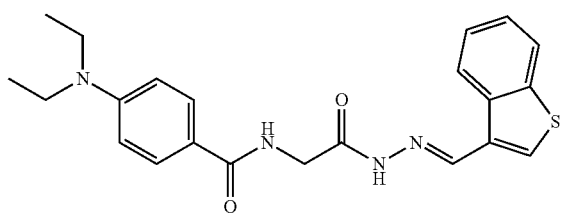

235

Compound 235 was obtained following the procedure for obtaining compound 200 using 4-(diethylamino)benzoic acid in place of 3,4,5-trimethoxybenzoic acid. Compound 235 was obtained as a white solid (115 mg, 74.2%). +ESI-MS: m/z 409.1 [M+H]+.

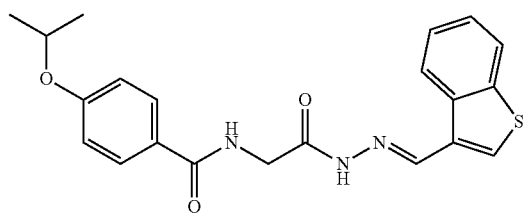

236

Compound 236 was obtained following the procedure for obtaining compound 200 using 4-isopropoxybenzoic acid in place of 3,4,5-trimethoxybenzoic acid. Compound 236 was obtained as a white solid (15 mg, 25.8%). +ESI-MS: m/z 396.0 [M+H]+.

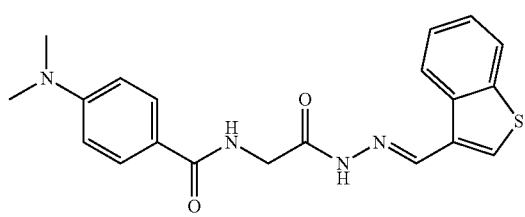

237

Compound 237 was obtained following the procedure for obtaining compound 200 using 4-(dimethylamino)benzoic acid in place of 3,4,5-trimethoxybenzoic acid. Compound 237 was obtained as a white solid (80 mg, 20%). ESI-LCMS: m/z 381 [M+H]+.

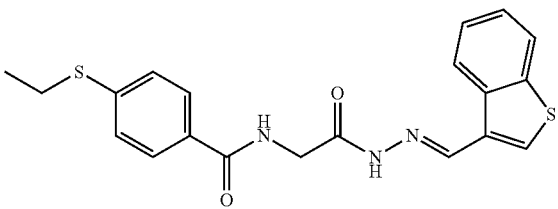

238

Compound 238 was obtained following the procedure for obtaining compound 200 using 4-(ethylthio)benzoic acid in place of 3,4,5-trimethoxybenzoic acid. Compound 238 was obtained as a white solid (80 mg, 34.1%). +ESI-MS: m/z 398.0 [M+H]+.

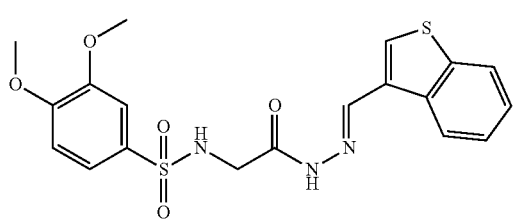

239

Compound 239 was obtained following the procedure for obtaining compound 200. Compound 239 was obtained as a white solid (100 mg, 25.1%). ESI-LCMS: m/z 434.0 [M+H]+.

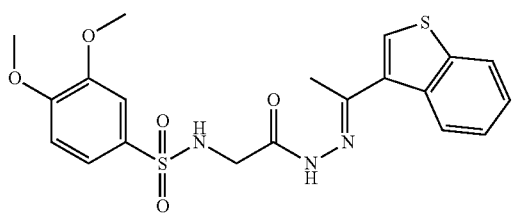

240

Compound 240 was obtained following the procedure for obtaining compound 239 using 1-(benzo[b]thiophen-3-yl)ethanone in place of benzo[b]thiophene-3-carbaldehyde. Compound 240 was obtained as a white solid (50 mg, 16.0%). ESI-LCMS: m/z 447.9 [M+H]+.

241

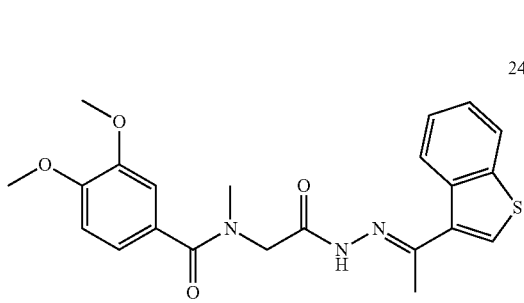

Compound 241 was obtained following the procedure for obtaining compound 200 using the appropriate acylhydrazine in place of 2-D. Compound 241 was obtained as a white solid (22 mg, 18.3%). +ESI-MS: m/z 383.9 [M+H]+.

242

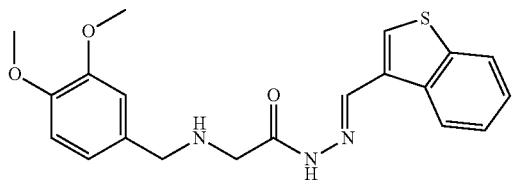

Compound 242 was obtained following the procedure for obtaining compound 200 using N-(2-hydrazinyl-2-oxoethyl)-3,4-dimethoxy-N-methylbenzamide in place of 2-D and using 1-(benzo[b]thiophen-3-yl)ethanone in place of benzo[b]thiophene-3-carbaldehyde. Compound 242 was obtained as a white solid (8 mg, 11.2%). ESI-LCMS: m/z 426.2 [M+H]+.

243

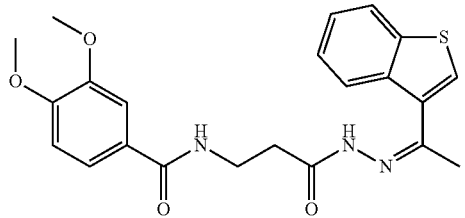

Compound 243 was obtained following the procedure for obtaining compound 200 using 3,4-dimethoxybenzoic acid in place of 3,4,5-trimethoxybenzoic acid and using 1-(benzo[b]thiophen-3-yl)ethanone in place of benzo[b]thiophene-3-carbaldehyde. Compound 243 was obtained as a white solid (120 mg, 52.2%). +ESI-MS: m/z 426.0 [M+H]+.

244

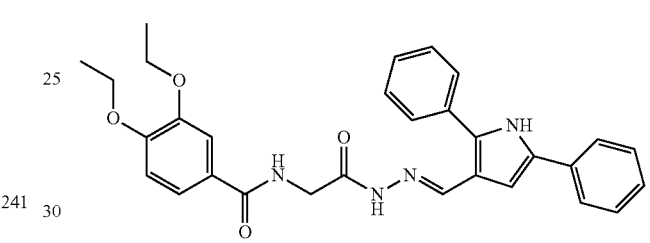

Compound 244 was obtained following the procedure for obtaining compound 200 using 3,4-diethoxybenzoic acid in place of 3,4,5-trimethoxybenzoic acid and using 2,5-diphenyl-1H-pyrrole-3-carboxaldehyde in place of benzo[b]thiophene-3-carbaldehyde. Compound 244 was obtained as a white solid (10 mg, 10.6%). ESI-LCMS: m/z 511.2 [M+H]+.

245

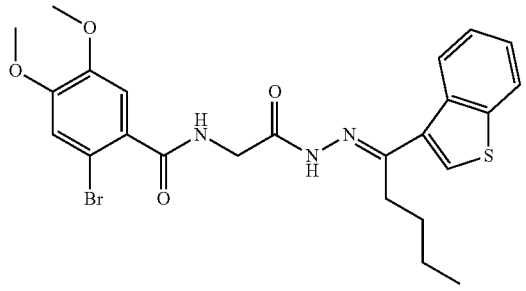

Compound 245 was obtained following the procedure for obtaining compound 200 using 2-bromo-4,5-dimethoxybenzoic acid in place of 3,4,5-trimethoxybenzoic acid and using 1-(benzo[b]thiophen-3-yl)pentan-1-one in place of benzo[b]thiophene-3-carbaldehyde. Compound 245 was obtained as a white solid (128 mg, 56.8%). +ESI-MS: m/z 396.0 [M+H]+.

246A

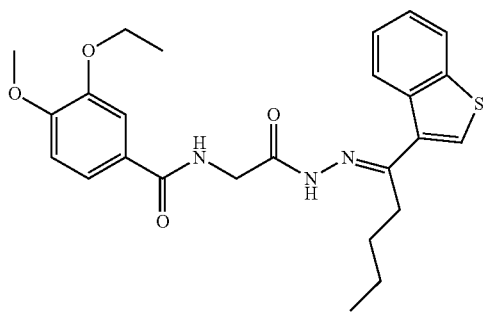

246B

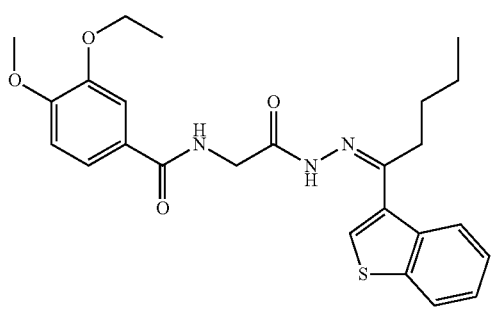

Compounds 246A and 246B were obtained following the procedure for obtaining compound 200 using 3-ethoxy-4-methoxy-benzoic acid in place of 3,4,5-trimethoxybenzoic acid and using 1-(benzo[b]thiophen-3-yl)pentan-1-one in place of benzo[b]thiophene-3-carbaldehyde. Compound 246A (25 mg, yield: 10.6%) and compound 246B (5 mg, yield: 2.1%) were obtained as a white solid. Compound 246A: +ESI-MS: m/z 467.89 [M+H]+. Compound 246B: +ESI-MS: m/z 467.90 [M+H]+.

247

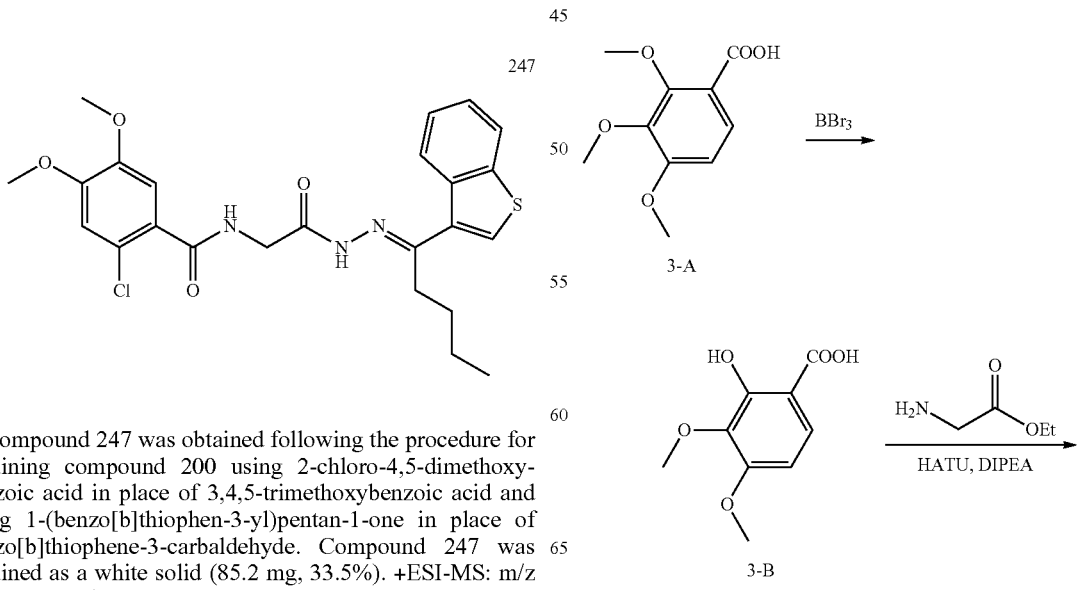

Compound 247 was obtained following the procedure for obtaining compound 200 using 2-chloro-4,5-dimethoxy-benzoic acid in place of 3,4,5-trimethoxybenzoic acid and using 1-(benzo[b]thiophen-3-yl)pentan-1-one in place of benzo[b]thiophene-3-carbaldehyde. Compound 247 was obtained as a white solid (85.2 mg, 33.5%). +ESI-MS: m/z 488.1 [M+H]+.

Example 2-1

Preparation of Compound 2-F

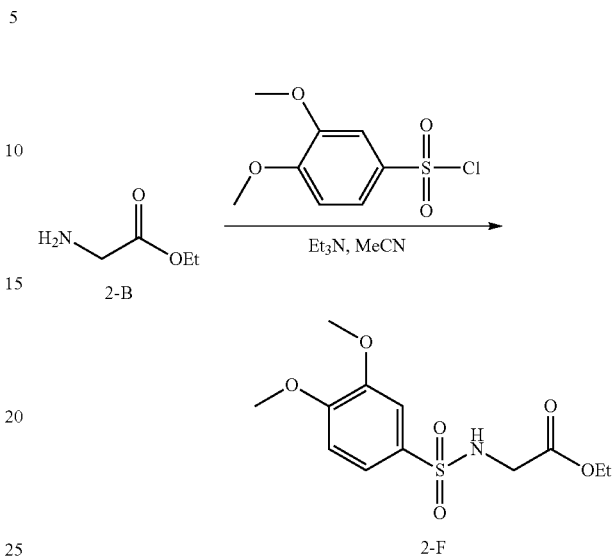

2-F

To a solution of 3,4-dimethoxy-benzenesulfonyl chloride (1 g, 4.3 mmol) and glycine ethyl ester (2-B) (0.6 g, 4.3 mmol) in anhydrous MeCN (7.0 mL) was added triethylamine (2.0 mL) dropwise at 10° C. The solution was stirred at 50° C. for 4 h and then cooled to rt. The precipitate was removed by filtration and the solid was washed with MeCN. The combined filtrate was concentrated in vacuo. The residue was crystallized from EtOH to afford 2-F (0.8 g, 61%) used in next step directly without purification. +ESI-LCMS: m/z 303 [M+H]+.

Example 3

Preparation of Compound 300

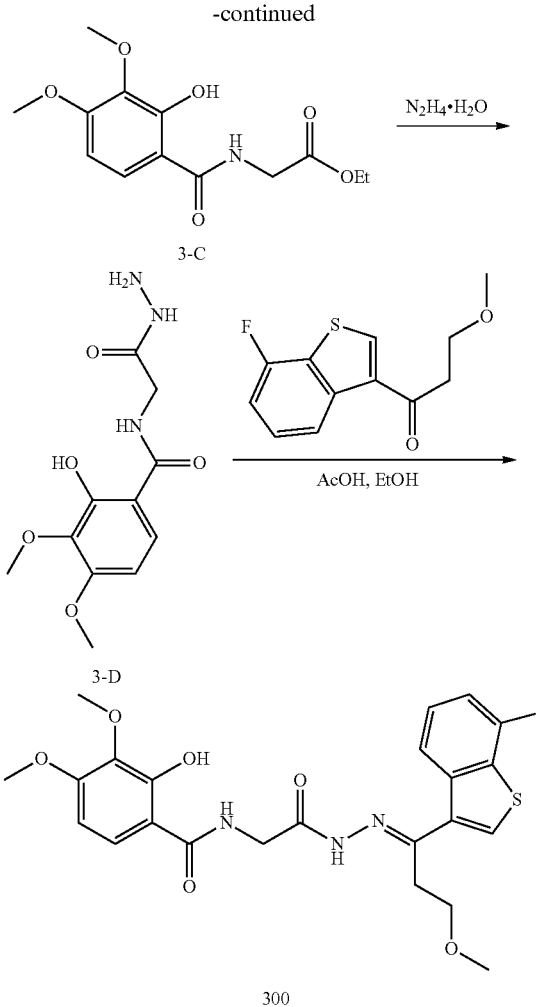

3-C

3-D

300

(0.1 mL), the mixture was stirred at 50° C. for 15 h. Then the mixture was allowed to cool to rt and a white precipitate was formed. The precipitate was filtered and washed with EtOAc to afford compound 300 as a white solid (15 mg, 15.2%). $^1$H NMR (DMSO-$d_6$, 400 MHz) δ 10.80 (m, 0.5H), 8.90-8.89 (m, 1H), 8.44-8.42 (m, 0.5H), 8.33 (s, 1H), 7.68-7.63 (m, 1H), 7.55-7.49 (m, 1H), 7.46-7.31 (m, 1H), 6.68-6.61 (m, 1H), 4.53-4.49 (m, 1H) 4.14 (d, J=5.2 Hz, 1H), 3.83 (s, 3H), 3.67 (s, 3H), 3.57-3.54 (m, 2H), 3.21-3.20 (m, 4H), 2.32-2.30 (m, 3H).

Example 4

Preparation of Compound 400

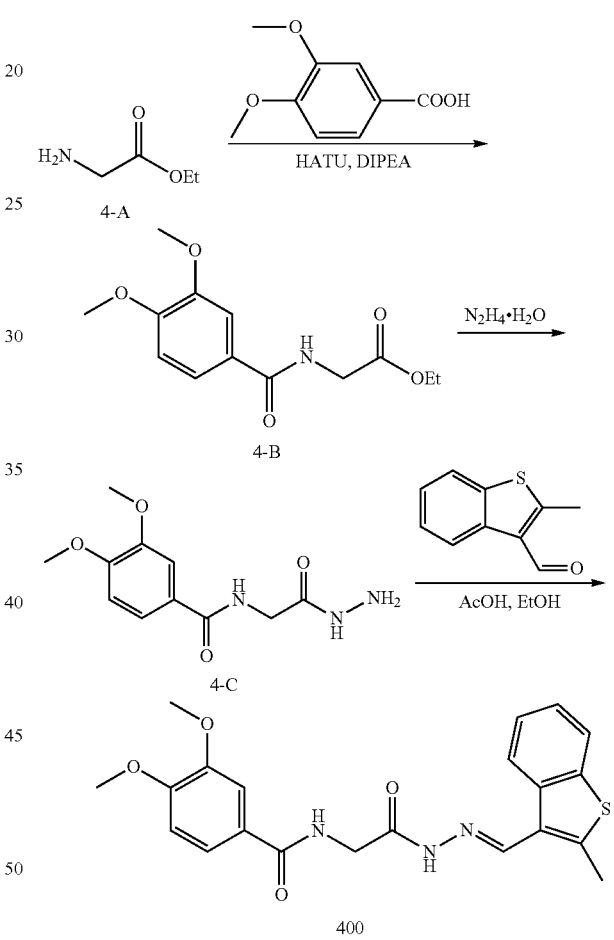

4-A

4-B

4-C

400

To a solution of 2,3,4-trimethoxybenzoic acid (3-A) (1.06 g, 5 mmol) in DCM (30 mL) was added BBr$_3$ (0.5 mL, 5.5 mmol) at −20° C., the mixture was stirred at −20° C. for 30 mins. Then NaHCO$_3$ was added to quench the reaction. 2N HCl (50 mL) was added and the mixture was extracted with DCM to afford 2-hydroxy-3,4-dimethoxybenzoic acid (3-B) (705 mg, 62.2%).

To a solution of 2-hydroxy-3,4-dimethoxybenzoic acid (3-B) (2.0 g, 9.43 mmol) in DCM (60 mL) was added HATU (5.4 g, 14.2 mmol) and DIPEA (5.0 g, 38.76 mmol), the mixture was stirred at rt for 30 mins, then was added glycine ethyl ester (19.7 g, 14.2 mmol). The mixture was stirred at rt for another 15 h. The mixture was washed with water and partitioned, the organic layer was collected. The solvent was removed and the residue was purified by silica gel column (PE/EA=20/1 to 5/1) to afford 3-C as a white solid (1.5 g, 53.6%).

To a solution of 3-C (1.54 g, 5.20 mmol) in anhydrous ethanol (50 mL) was added N$_2$H$_4$—H$_2$O (2.59 g, 80.9 mmol), the mixture was stirred at 80° C. for 15 h. Then the mixture was allowed to cool to rt and the white precipitate was formed in the solution. The precipitate was filtered and washed with EtOH (20 mL) to afford 3-D as a white product (1.2 g, 81.6%).

To a solution of 3-D (93 mg, 0.31 mmol) in anhydrous ethanol (3 mL) was added 1-(7-fluorobenzo[b]thiophen-3-yl)-3-methoxypropan-1-one (50 mg, 0.21 mmol) and AcOH To a solution of 3,4-dimethoxy-benzoic acid (30 g, 0.19 mol) and HATU (80 g, 0.19 mol) in anhydrous DCM (600 mL) was added glycine ethyl ester (4-A) (26.7 g, 0.21 mol) and DIPEA (62 g, 0.48 mol) at 25° C. The solution was stirred for 10 h at this temperature and then diluted with 1.0 N aqueous NaHCO$_3$ solution (600 mL×2), extracted with EA (500 mL×2). The combined organic phase dried over anhydrous Na$_2$SO$_4$, and concentrated under reduced pressure to afford 4-B (40 g, 78.5%). $^1$H NMR (DMSO, 400 MHz) δ 8.81 (t, J=6.0 Hz, 1H), 7.51-7.45 (dd, J$_1$=8.4 Hz, J$_2$=2.0 Hz, 1H), 7.45 (d, J=2.0 Hz, 1H), 7.03 (d, J=8.4 Hz, 1H), 4.14-4.08 (m, 2H), 3.97 (d, J=5.6 Hz, 2H), 3.81 (s, 3H), 3.80 (s, 3H), 1.20 (t, J=7.2 Hz, 3H).

To a solution of 4-B (40 g, 0.15 mol) in anhydrous EtOH (600 mL) was added NH$_2$NH$_2$.xH$_2$O (48 g, 1.5 mol). The solution was stirred for 10 h at 70° C. and then cooled to rt, A precipitate was formed in the solution and was collected by filtration to afford 4-C (37.5 g, 98.9%). $^1$H NMR (DMSO-d$_6$, 400 MHz) δ 9.11 (s, 1H), 8.59 (t, J=6.0 Hz, 1H), 7.50-7.48 (dd, J$_1$=8.0 Hz, J$_2$=2.0 Hz, 1H), 7.46 (d, J=2.0 Hz, 1H), 7.02 (d, J=8.4 Hz, 1H), 4.21 (s, 2H), 3.82 (s, 1H), 3.80 (s, 3H), 3.79 (s, 3H).

To a solution of 4-C (200 mg, 0.79 mmol) in anhydrous EtOH (5 mL) and AcOH (0.3 mL) was added 2-methylbenzo[b]thiophene-3-carboxaldehyde (140 mg, 0.79 mmol). The solution was stirred at 70° C. for 10 h and then cooled to rt. A precipitate was formed in the solution and was collected by filtration. The solid was washed with EA and EtOH to give the compound 400 as a white solid (100 mg, 30%). ESI-LCMS: m/z 412 [M+H]$^+$.

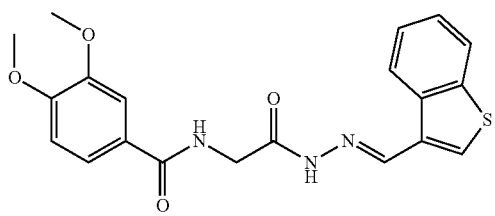

401

Compound 401 was obtained following the procedure for obtaining compound 400 using benzo[b]thiophene-3-carboxaldehyde in place of 2-methylbenzo[b]thiophene-3-carboxaldehyde. Compound 401 was obtained as a white solid (177 mg, 56.4%). +ESI-MS: m/z 397.9 [M+H]$^+$.

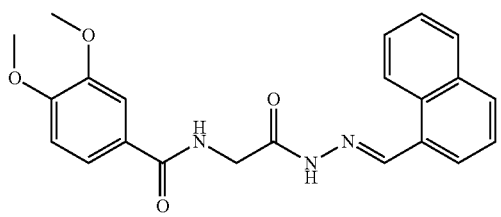

402

Compound 402 was obtained following the procedure for obtaining compound 400 using naphthalene-1-carboxaldehyde in place of 2-methylbenzo[b]thiophene-3-carboxaldehyde. Compound 402 was obtained as a white solid (198.6 mg, 86.5%). ESI-MS: m/z 391.9 [M+H]$^+$.

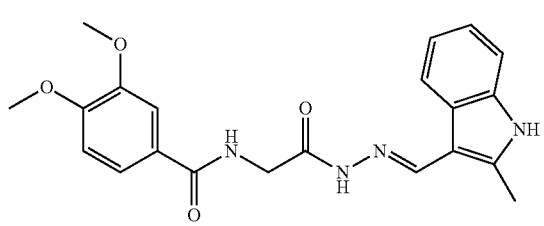

403

Compound 403 was obtained following the procedure for obtaining compound 400 using 2-methyl-1H-indole-3-carboxaldehyde in place of 2-methylbenzo[b]thiophene-3-carboxaldehyde. Compound 403 was obtained as a white solid (50 mg, 30.2%). ESI-MS: m/z 394 [M+H]$^+$.

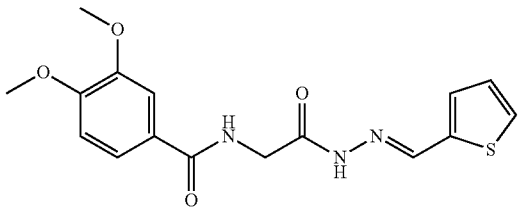

404

Compound 404 was obtained following the procedure for obtaining compound 400 using thiophene-2-carboxaldehyde in place of 2-methylbenzo[b]thiophene-3-carboxaldehyde. Compound 404 was obtained as a white solid (60 mg, 20%). ESI-MS: m/z 347.9 [M+H]$^+$.

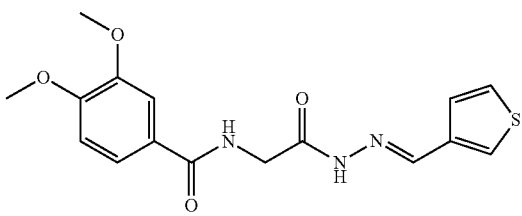

405

Compound 405 was obtained following the procedure for obtaining compound 400 using thiophene-3-carboxaldehyde in place of 2-methylbenzo[b]thiophene-3-carboxaldehyde. Compound 405 was obtained as a white solid (100 mg, 40%). ESI-MS: m/z 347.9 [M+H]$^+$.

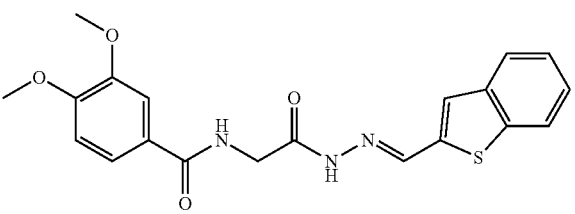

406

Compound 406 was obtained following the procedure for obtaining compound 400 using benzo[b]thiophene-2-carboxaldehyde in place of 2-methylbenzo[b]thiophene-3-carboxaldehyde. Compound 406 was obtained as a white solid (120 mg, 42%). ESI-MS: m/z 398 [M+H]$^+$.

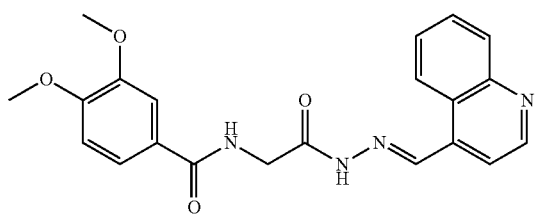

407

Compound 407 was obtained following the procedure for obtaining compound 400 using quinoline-4-carboxaldehyde in place of 2-methylbenzo[b]thiophene-3-carboxaldehyde. Compound 407 was obtained as a white solid (70 mg, 50%). ESI-LCMS: m/z 393 [M+H]+.

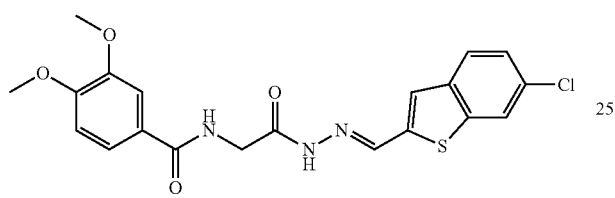

408

Compound 408 was obtained following the procedure for obtaining compound 400 using 6-chlorobenzo[b]thiophene-2-carboxaldehyde in place of 2-methylbenzo[b]thiophene-3-carboxaldehyde. Compound 408 was obtained as a white solid (30 mg, 20%). ESI-LCMS: m/z 432[M+H]+.

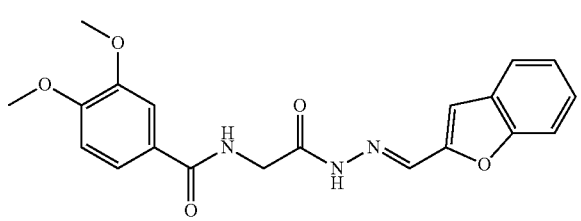

409

Compound 409 was obtained following the procedure for obtaining compound 400 using benzo[b]furan-2-carboxaldehyde in place of 2-methylbenzo[b]thiophene-3-carboxaldehyde. Compound 409 was obtained as a white solid (50 mg, 20%). ESI-LCMS: m/z 392 [M+H]+.

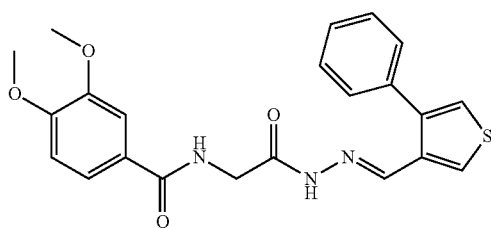

410

Compound 410 was obtained following the procedure for obtaining compound 400 using 3-phenyl-thiophene-2-carboxaldehyde in place of 2-methylbenzo[b]thiophene-3-carboxaldehyde. Compound 410 was obtained as a white solid (63 mg, 55.7%). +ESI-MS: m/z 424.0 [M+H]+.

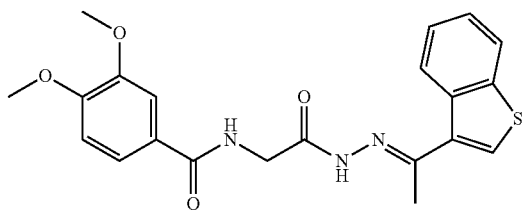

411

Compound 411 was obtained following the procedure for obtaining compound 400 using 1-(benzo[b]thiophen-3-yl)ethanone in place of 2-methylbenzo[b]thiophene-3-carboxaldehyde. Compound 411 was obtained as a white solid (80 mg, 25%). ESI-LCMS: m/z 412 [M+H]+.

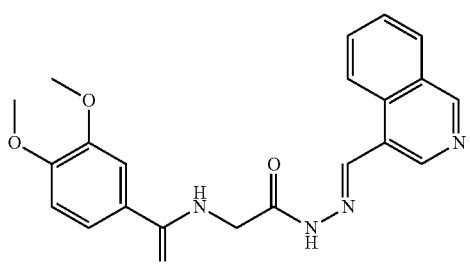

412

Compound 412 was obtained following the procedure for obtaining compound 400 using quinoline-4-carboxaldehyde in place of 2-methylbenzo[b]thiophene-3-carboxaldehyde. Compound 412 was obtained as a white solid (50 mg, 15%). ESI-LCMS: m/z 393 [M+H]+.

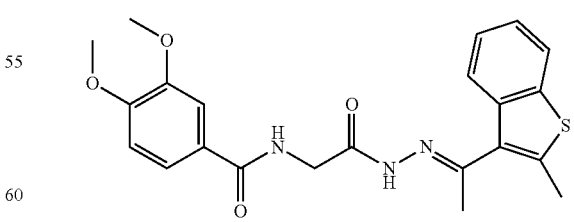

413

Compound 413 was obtained following the procedure for obtaining compound 400 using 1-(2-methylbenzo[b]thiophen-3-yl)ethanone in place of 2-methylbenzo[b]thiophene-3-carboxaldehyde. Compound 413 was obtained as a white solid (180 mg, 55%). +ESI-MS: m/z 425.9 [M+H]+.

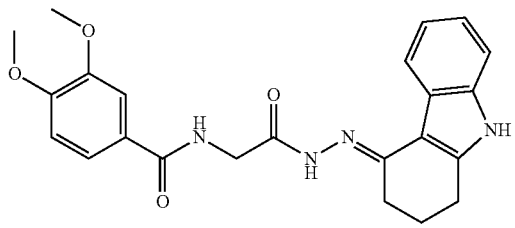

414

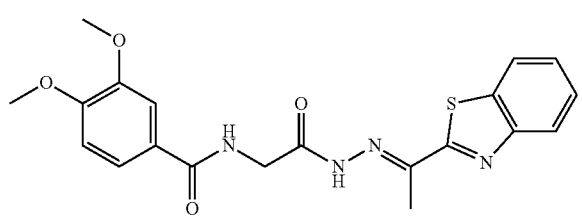

417

Compound 414 was obtained following the procedure for obtaining compound 400 using 2,3-dihydro-1H-carbazol-4(9H)-one in place of 2-methylbenzo[b]thiophene-3-carboxaldehyde. Compound 414 was obtained as a white solid (55 mg, 25%). +ESI-MS: m/z 421.1 [M+H]$^+$.

Compound 417 was obtained following the procedure for obtaining compound 400 using 1-(benzo[d]thiazol-2-yl)ethanone in place of 2-methylbenzo[b]thiophene-3-carboxaldehyde. Compound 417 was obtained as a white solid (200 mg, 86%). +ESI-MS: m/z 413.0 [M+H]$^+$.

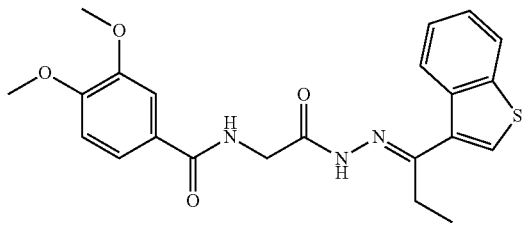

415

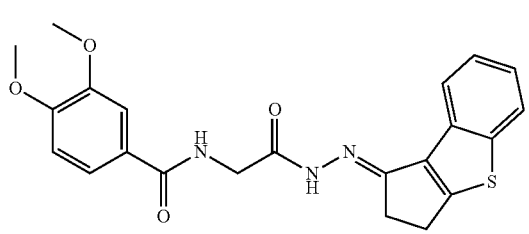

418

Compound 415 was obtained following the procedure for obtaining compound 400 using 1-(benzo[b]thiophen-3-yl)propan-1-one in place of 2-methylbenzo[b]thiophene-3-carboxaldehyde. Compound 415 was obtained as a white solid (50 mg, 15%). $^1$H NMR (DMSO-d$_6$, 400 MHz) δ 10.86-10.70 (br, 1H), 9.13-8.75 (m, 1H), 8.69-8.62 (m, 1H), 8.26 (d, J$_1$=8.8 Hz, 1H), 8.05-7.80 (m, 1H), 7.56-7.39 (m, 4H), 7.06 (d, J$_1$=8.4 Hz, 1H), 4.51 (d, J=5.6 Hz, 1H), 4.15 (d, J=5.6 Hz, 1H), 3.81 (s, 6H), 2.91 (t, 2H), 1.16-1.09 (m, 3H). ESI-LCMS: m/z 426 [M+H]$^+$.

Compound 418 was obtained following the procedure for obtaining compound 400 using 2,3-dihydro-benzo[b]cyclopenta[d]thiophen-1-one in place of 2-methylbenzo[b]thiophene-3-carboxaldehyde. Compound 418 was obtained as a white solid (80 mg, 36%). +ESI-MS: m/z 424.0 [M+H]$^+$.

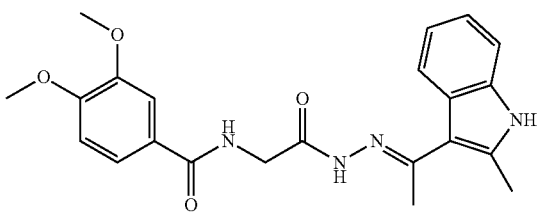

416

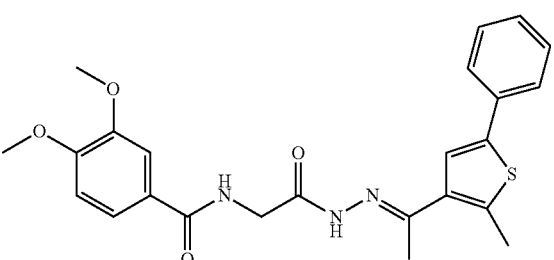

419

Compound 416 was obtained following the procedure for obtaining compound 400 using 1-(2-methyl-1H-indol-3-yl)propan-1-one in place of 2-methylbenzo[b]thiophene-3-carboxaldehyde. Compound 416 was obtained as a white solid (20 mg, 12%). ESI-LCMS: m/z 409 [M+H]$^+$.

Compound 419 was obtained following the procedure for obtaining compound 400 using 1-(2-methyl-5-phenylthiophen-3-yl)ethanone in place of 2-methylbenzo[b]thiophene-3-carboxaldehyde. Compound 419 was obtained as a white solid (60 mg, 20%). ESI-LCMS: m/z 452 [M+H]$^+$.

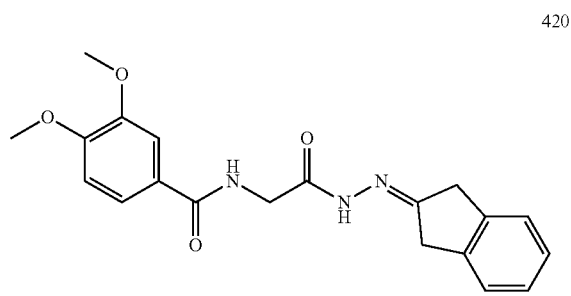 [SMILES: COc1ccc(C(=O)NCC(=O)NN=C2Cc3ccccc3C2)cc1OC]

420

Compound 420 was obtained following the procedure for obtaining compound 400 using 1H-inden-2(3H)-one in place of 2-methylbenzo[b]thiophene-3-carboxaldehyde. Compound 420 was obtained as a white solid (101 mg, 55%). +ESI-MS: m/z 368.0 [M+H]$^+$.

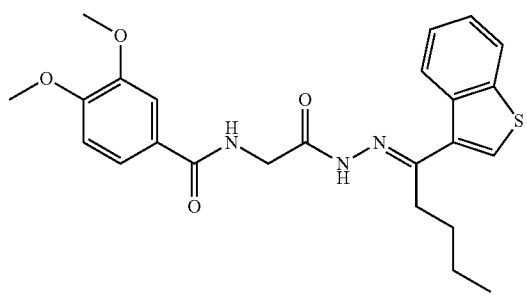

423

Compound 423 was obtained following the procedure for obtaining compound 400 using 1-(benzo[b]thiophen-3-yl)pentan-1-one in place of 2-methylbenzo[b]thiophene-3-carboxaldehyde. Compound 423 was obtained as a white solid (700 mg, 67%). ESI-LCMS: m/z 454 [M+H]$^+$.

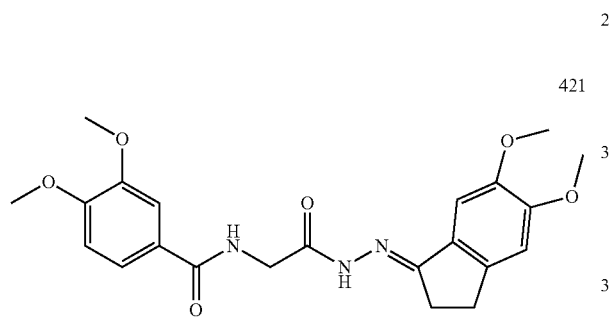

421

Compound 421 was obtained following the procedure for obtaining compound 400 using 2,3-dihydro-5,6-dimethoxy-inden-1-one in place of 2-methylbenzo[b]thiophene-3-carboxaldehyde. Compound 421 was obtained as a white solid (98 mg, 45.8%). +ESI-MS: m/z 428.1 [M+H]$^+$.

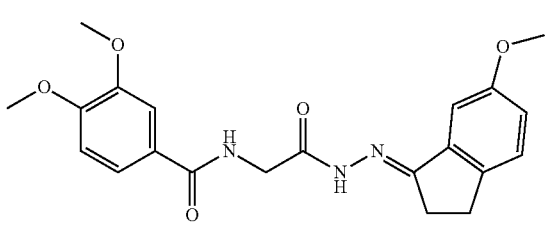

424

Compound 424 was obtained following the procedure for obtaining compound 400 using 2,3-dihydro-6-methoxyinden-1-one in place of 2-methylbenzo[b]thiophene-3-carboxaldehyde. Compound 424 was obtained as a white solid (80 mg, 15%). ESI-LCMS: m/z 398 [M+H]$^+$.

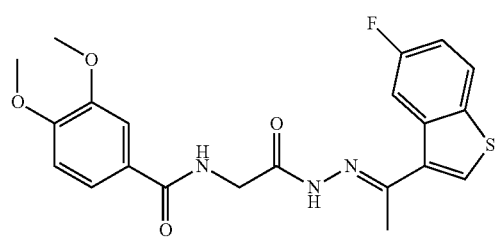

422

Compound 422 was obtained following the procedure for obtaining compound 400 using 1-(5-fluorobenzo[b]thiophen-3-yl)ethanone in place of 2-methylbenzo[b]thiophene-3-carboxaldehyde. Compound 422 was obtained as a white solid (76 mg, 56.6%). +ESI-MS: m/z 429.8 [M+H]$^+$.

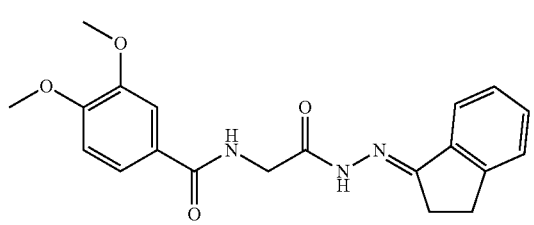

425

Compound 425 was obtained following the procedure for obtaining compound 400 using 2,3-dihydroinden-1-one in place of 2-methylbenzo[b]thiophene-3-carboxaldehyde. Compound 425 was obtained as a white solid (80 mg, 15%). ESI-LCMS: m/z 368 [M+H]$^+$.

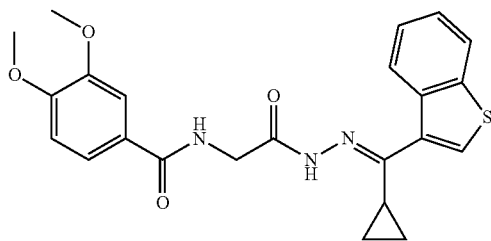

426

Compound 426 was obtained following the procedure for obtaining compound 400 using benzo[b]thiophen-3-yl(cyclopropyl)methanone in place of 2-methylbenzo[b]thiophene-3-carboxaldehyde. Compound 426 was obtained as a white solid (20 mg, 30.0%). +ESI-MS: m/z 438.1 [M+H]+.

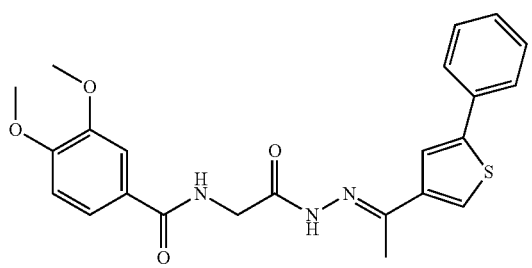

429

Compound 429 was obtained following the procedure for obtaining compound 400 using 1-(5-phenylthiophen-3-yl)ethanone in place of 2-methylbenzo[b]thiophene-3-carboxaldehyde. Compound 429 was obtained as a white solid (7 mg, 38.4%). +ESI-MS: m/z 438.1 [M+H]+.

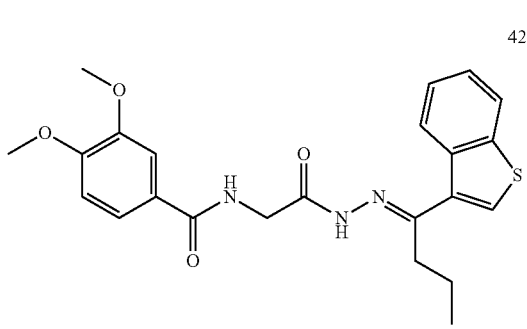

427

Compound 427 was obtained following the procedure for obtaining compound 400 using 1-(benzo[b]thiophen-3-yl)butan-1-one in place of 2-methylbenzo[b]thiophene-3-carboxaldehyde. Compound 427 was obtained as a white solid (30 mg, 6%). ESI-LCMS: m/z 440 [M+H]+.

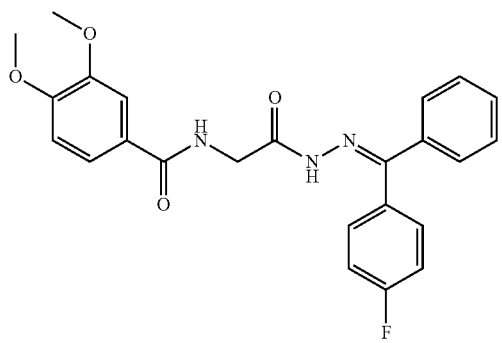

430

Compound 430 was obtained following the procedure for obtaining compound 400 using 4-fluorobenzophenone in place of 2-methylbenzo[b]thiophene-3-carboxaldehyde. Compound 430 was obtained as a white solid (120 mg, 55%). +ESI-MS: m/z 436.1 [M+H]+.

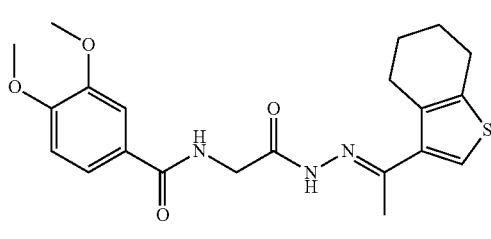

428

Compound 428 was obtained following the procedure for obtaining compound 400 using 1-(4,5,6,7-tetrahydrobenzo[b]thiophen-3-yl)ethanone in place of 2-methylbenzo[b]thiophene-3-carboxaldehyde. Compound 428 was obtained as a white solid (7 mg, 38.42%). +ESI-MS: m/z 425.9 [M+H]+.

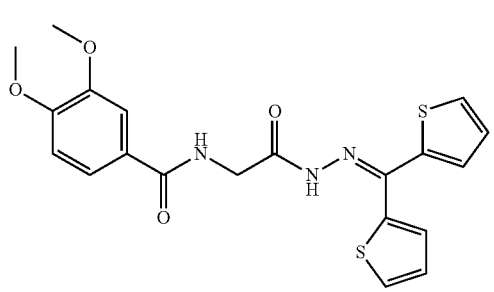

431

Compound 431 was obtained following the procedure for obtaining compound 400 using di-2-thienyl ketone in place of 2-methylbenzo[b]thiophene-3-carboxaldehyde. Compound 431 was obtained as a white solid (76 mg, 75%). +ESI-MS: m/z 430.0 [M+H]+.

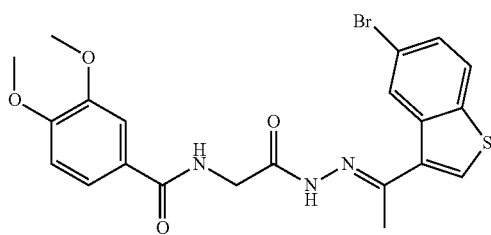

432

Compound 432 was obtained following the procedure for obtaining compound 400 using 1-(5-bromobenzo[b]thiophen-3-yl)ethanone in place of 2-methylbenzo[b]thiophene-3-carboxaldehyde. Compound 432 was obtained as a white solid (80 mg, 37%). +ESI-MS: m/z 491.6 [M+H]+.

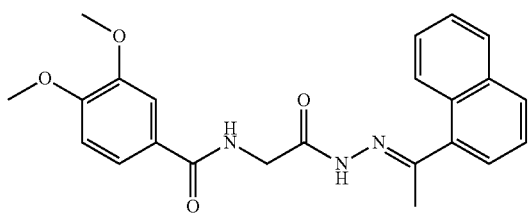

433

Compound 433 was obtained following the procedure for obtaining compound 400 using 1-(naphthalen-1-yl)ethanone in place of 2-methylbenzo[b]thiophene-3-carboxaldehyde. Compound 433 was obtained as a white solid (30 mg, 10%). ESI-LCMS: m/z 406 [M+H]+.

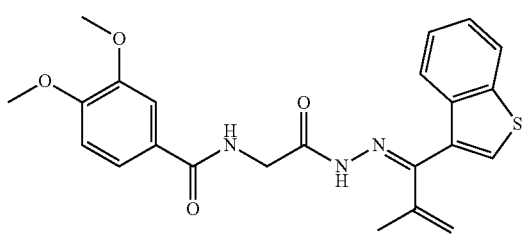

434

Compound 434 was obtained following the procedure for obtaining compound 400 using 1-(benzo[b]thiophen-3-yl)-2-methylprop-2-en-1-one in place of 2-methylbenzo[b]thiophene-3-carboxaldehyde. Compound 434 was obtained as a white solid (3 mg). ESI-LCMS: m/z 438 [M+H]+.

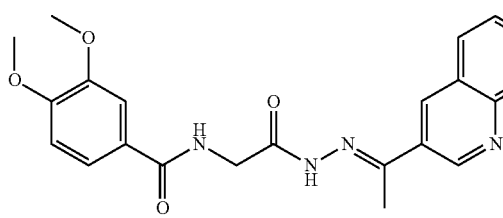

435

Compound 435 was obtained following the procedure for obtaining compound 400 using 1-(quinolin-3-yl)ethanone in place of 2-methylbenzo[b]thiophene-3-carboxaldehyde. Compound 435 was obtained as a white solid (85 mg, 50%). +ESI-MS: m/z 407.0 [M+H]+.

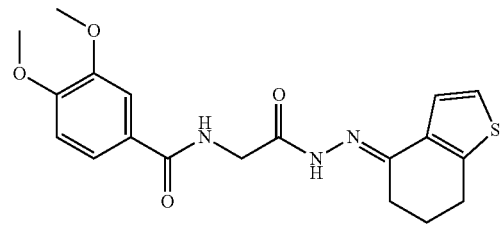

436

Compound 436 was obtained following the procedure for obtaining compound 400 using 6,7-dihydrobenzo[b]thiophen-4(5H)-one in place of 2-methylbenzo[b]thiophene-3-carboxaldehyde. Compound 436 was obtained as a white solid (146 mg, 57.48%). +ESI-MS: m/z 388.0 [M+H]+.

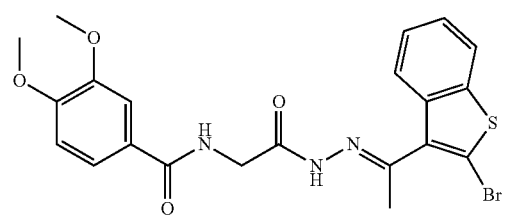

437

Compound 437 was obtained following the procedure for obtaining compound 400 using 1-(2-bromobenzo[b]thiophen-3-yl)ethanone in place of 2-methylbenzo[b]thiophene-3-carboxaldehyde. Compound 437 was obtained as a white solid (50 mg, 12%). +ESI-MS: m/z 490.1 [M+H]+.

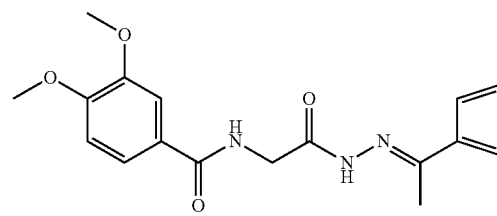

438

Compound 438 was obtained following the procedure for obtaining compound 400 using 1-(2,5-dimethylthiophen-3-yl)ethanone in place of 2-methylbenzo[b]thiophene-3-carboxaldehyde. Compound 438 was obtained as a white solid (50 mg, 13%). ESI-LCMS: m/z 390 [M+H]+.

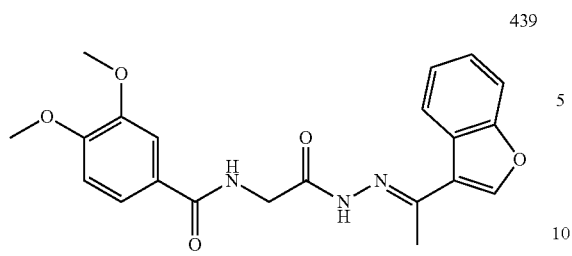

439

Compound 439 was obtained following the procedure for obtaining compound 400 using 1-(benzofuran-3-yl)ethanone in place of 2-methylbenzo[b]thiophene-3-carboxaldehyde. Compound 439 was obtained as a white solid (50 mg, 40%). ESI-LCMS: m/z 396 [M+H]+.

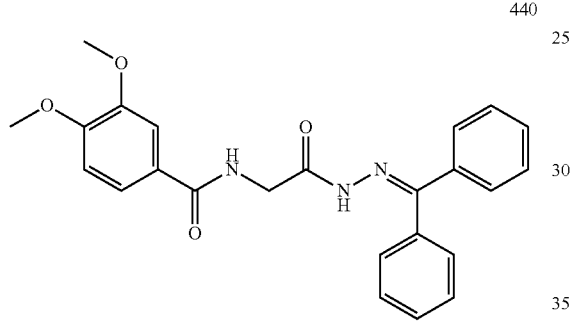

440

Compound 440 was obtained following the procedure for obtaining compound 400 using benzophenone in place of 2-methylbenzo[b]thiophene-3-carboxaldehyde. Compound 440 was obtained as a white solid (10 mg). ESI-LCMS: m/z 418 [M+H]+.

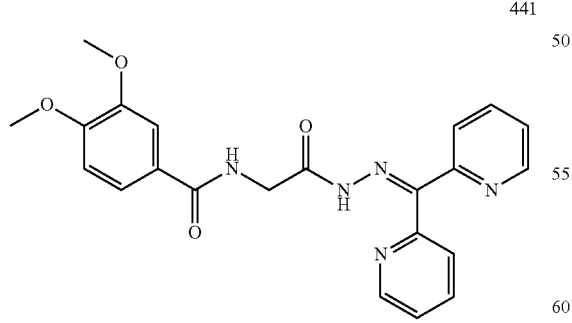

441

Compound 441 was obtained following the procedure for obtaining compound 400 using di(2-pyridyl) ketone in place of 2-methylbenzo[b]thiophene-3-carboxaldehyde. Compound 441 was obtained as a white solid (100 mg, 20%). ESI-LCMS: m/z 420 [M+H]+.

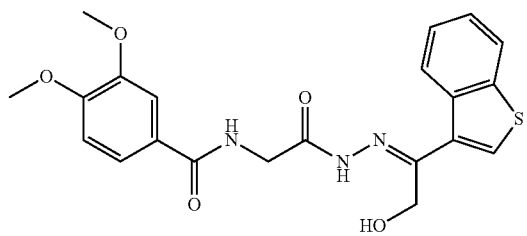

442

Compound 442 was obtained following the procedure for obtaining compound 400 using 1-(benzo[b]thiophen-3-yl)-2-hydroxyethanone in place of 2-methylbenzo[b]thiophene-3-carboxaldehyde. Compound 442 was obtained as a white solid (62 mg, 14.5%). +ESI-MS: m/z 428.0 [M+H]+.

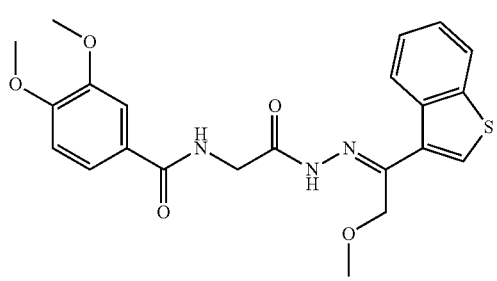

443

Compound 443 was obtained following the procedure for obtaining compound 400 using 1-(benzo[b]thiophen-3-yl)-2-methoxyethanone in place of 2-methylbenzo[b]thiophene-3-carboxaldehyde. Compound 443 was obtained as a white solid (30 mg, 29.2%). +ESI-MS: m/z 442.0 [M+H]+.

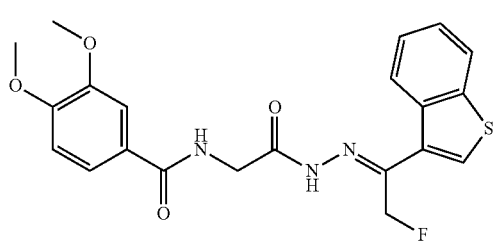

444

Compound 444 was obtained following the procedure for obtaining compound 400 using 1-(benzo[b]thiophen-3-yl)-2-fluoroethanone in place of 2-methylbenzo[b]thiophene-3-carboxaldehyde. Compound 444 was obtained as a white solid (40 mg, 22.73%). +ESI-MS: m/z 430.8 [M+H]+.

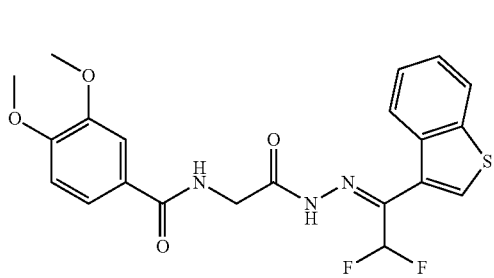

445

Compound 445 was obtained following the procedure for obtaining compound 400 using 1-(benzo[b]thiophen-3-yl)-2-difluoroethanone in place of 2-methylbenzo[b]thiophene-3-carboxaldehyde. Compound 445 was obtained as a white solid (10 mg, 20.0%). ESI-MS: m/z 448.0 [M+H]+.

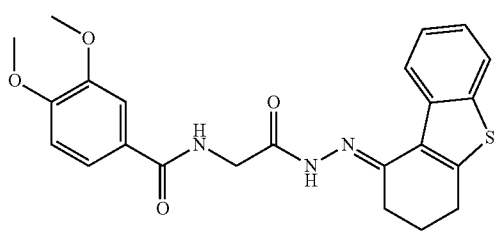

446

Compound 446 was obtained following the procedure for obtaining compound 400 using 3,4-dihydro-2H-dibenzothiophen-1-one in place of 2-methylbenzo[b]thiophene-3-carboxaldehyde. Compound 446 was obtained as a white solid (54 mg, 52%). +ESI-MS: m/z 438.0 [M+H]+.

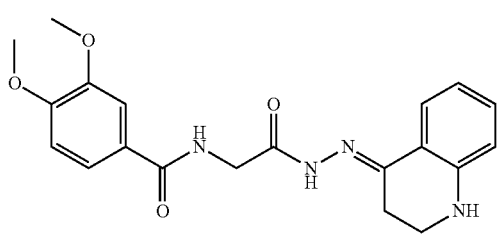

447

Compound 447 was obtained following the procedure for obtaining compound 400 using 2,3-dihydroquinolin-4(1H)-one in place of 2-methylbenzo[b]thiophene-3-carboxaldehyde. Compound 447 was obtained as a white solid (76 mg, 38%). +ESI-MS: m/z 383.0 [M+H]+.

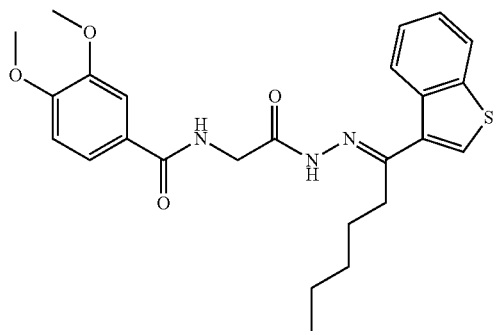

448A

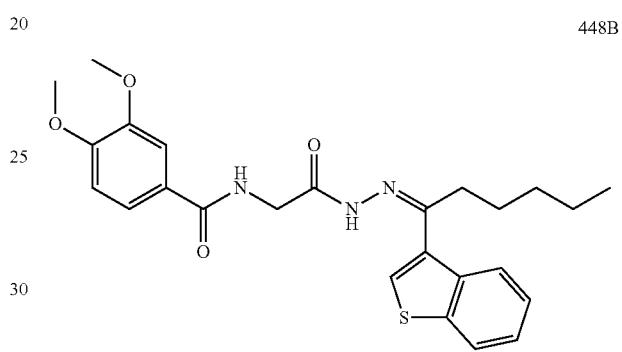

448B

Compounds 448A and 448B were obtained following the procedure for obtaining compound 400 using 1-(benzo[b]thiophen-3-yl)hexan-1-one in place of 2-methylbenzo[b]thiophene-3-carboxaldehyde. Compounds 448A (70 mg, 10.0%) and 448B (10 mg, 1.7%) were obtained as a white solid. Compound 448A: +ESI-MS: m/z 467.9 [M+H]+. Compound 448B: +ESI-MS: m/z 467.9 [M+H]+.

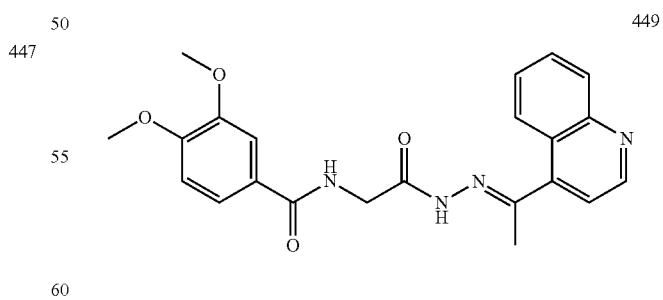

449

Compound 449 was obtained following the procedure for obtaining compound 400 using 4-acetylquinoline in place of 2-methylbenzo[b]thiophene-3-carboxaldehyde. Compound 449 was obtained as a white solid (50 mg, 30%). ESI-LCMS: m/z 407 [M+H]+.

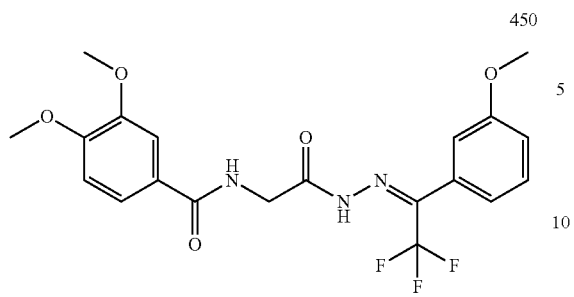

450

Compound 450 was obtained following the procedure for obtaining compound 400 using 3'-methoxy-2,2,2-trifluoroacetophenone in place of 2-methylbenzo[b]thiophene-3-carboxaldehyde. Compound 450 was obtained as a white solid (8 mg). ESI-LCMS: m/z 440 [M+H]+.

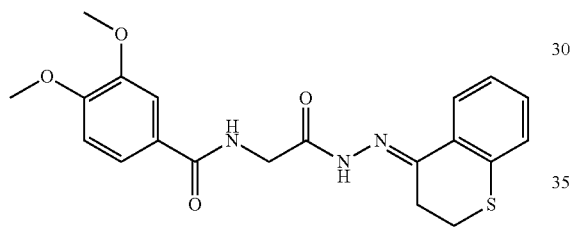

451

Compound 451 was obtained following the procedure for obtaining compound 400 using thiochroman-4-one in place of 2-methylbenzo[b]thiophene-3-carboxaldehyde. Compound 451 was obtained as a white solid (80 mg, 40%). ESI-LCMS: m/z 400 [M+H]+.

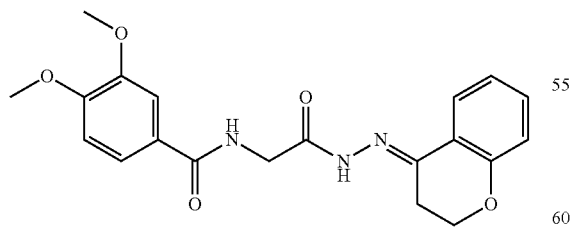

452

Compound 452 was obtained following the procedure for obtaining compound 400 using chroman-4-one in place of 2-methylbenzo[b]thiophene-3-carboxaldehyde. Compound 452 was obtained as a white solid (100 mg, 45%). ESI-LCMS: m/z 384 [M+H]+.

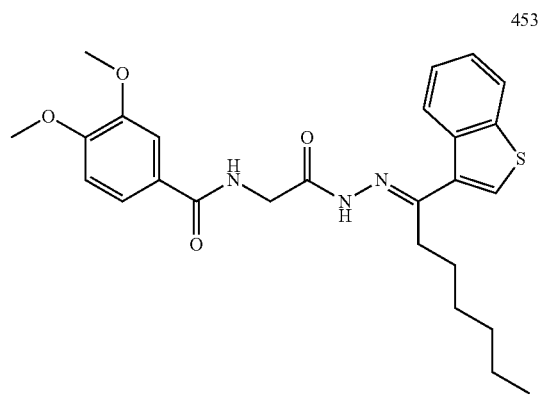 [SMILES: CCCCCC/C(=N\NC(=O)CNC(=O)c1ccc(OC)c(OC)c1)c1csc2ccccc12]

453

Compound 453 was obtained following the procedure for obtaining compound 400 using 1-(benzo[b]thiophen-3-yl)heptan-1-one in place of 2-methylbenzo[b]thiophene-3-carboxaldehyde. Compound 453 was obtained as a white solid (100 mg, 35%). ESI-LCMS: m/z 482 [M+H]+.

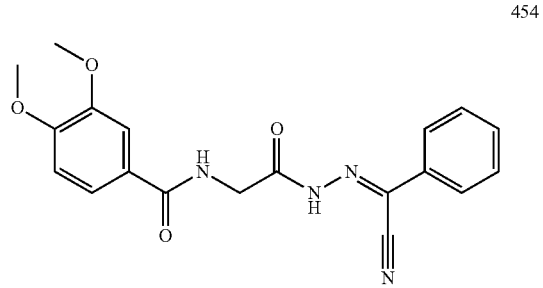 [SMILES: COc1ccc(C(=O)NCC(=O)N/N=C(\C#N)c2ccccc2)cc1OC]

454

Compound 454 was obtained following the procedure for obtaining compound 400 using benzoyl cyanide in place of 2-methylbenzo[b]thiophene-3-carboxaldehyde. Compound 454 was obtained as a white solid (20 mg, 35%). ESI-LCMS: m/z 367 [M+H]+.

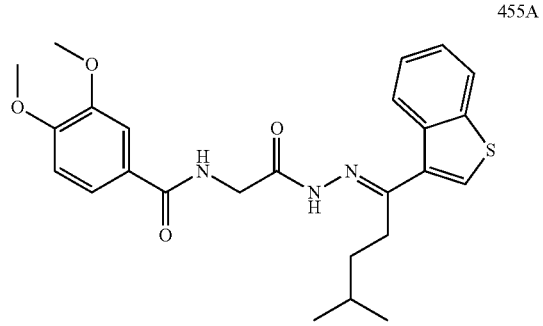

455A

455B

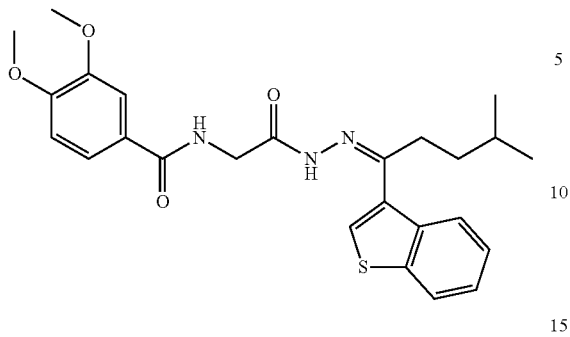

Compounds 455A and 455B were obtained following the procedure for obtaining compound 400 using 1-(benzo[b]thiophen-3-yl)-4-methylpentan-1-one in place of 2-methylbenzo[b]thiophene-3-carboxaldehyde. Compound 455A (64 mg, 20.0%) and Compound 455B (42 mg, 16.0%) were obtained as a white solid. Compound 455A: +ESI-MS: m/z 468.0 [M+H]$^+$. Compound 455B: +ESI-MS: m/z 468.0 [M+H]$^+$.

456

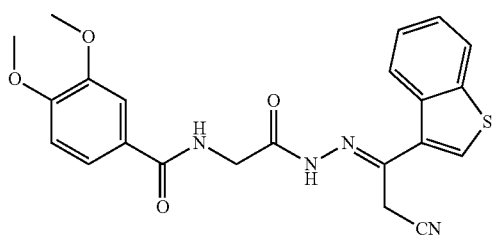

Compound 456 was obtained following the procedure for obtaining compound 400 using 3-(benzo[b]thiophen-3-yl)-3-oxopropanenitrile in place of 2-methylbenzo[b]thiophene-3-carboxaldehyde. Compound 456 was obtained as a white solid (120 mg, 37.25%). +ESI-MS: m/z 458.9 [M+Na]$^+$.

457

Compound 457 was obtained following the procedure for obtaining compound 400 using 3,4-diethoxybenzoic acid in place of 3,4-dimethoxy-benzoic acid and 1-(1H-inden-3-yl)ethanone in place of 2-methylbenzo[b]thiophene-3-carboxaldehyde. Compound 457 was obtained as a white solid (300 mg, 68.3%). +ESI-MS: m/z 439.9 [M+H]$^+$.

458A

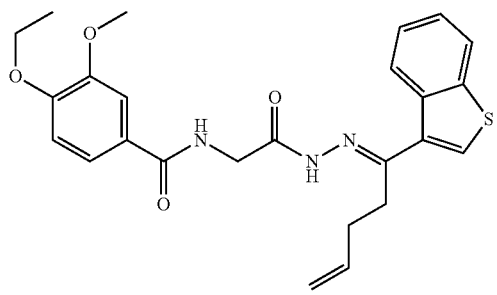

458B

Compounds 458A and 458B were obtained following the procedure for obtaining compound 400 using 4-ethoxy-3-methoxybenzoic acid in place of 3,4-dimethoxy-benzoic acid and 1-benzo[b]thiophen-3-yl-pent-4-en-1-one in place of 2-methylbenzo[b]thiophene-3-carboxaldehyde. Compound 458A (20 mg, 10%) and Compound 458B (2 mg, 1%) were obtained as a white solid. Compound 458A: +ESI-MS: m/z 465.89 [M+Na]$^+$. Compound 458B: +ESI-MS: m/z 465.87 [M+Na]$^+$.

459

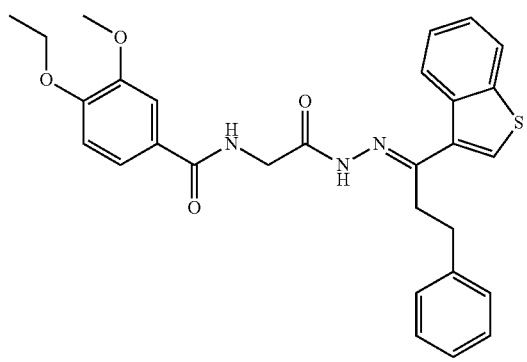

Compound 459 was obtained following the procedure for obtaining compound 400 using 4-ethoxy-3-methoxybenzoic acid in place of 3,4-dimethoxy-benzoic acid and 1-benzo[b]thiophen-3-yl-3-phenyl-propan-1-one in place of 2-methyl-benzo[b]thiophene-3-carboxaldehyde. Compound 459 was obtained as a white solid (85 mg, 22%). +ESI-MS: m/z 516.1[M+H]$^+$.

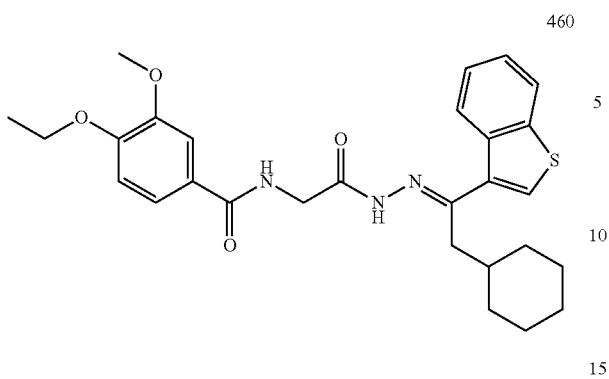

460

Compound 460 was obtained following the procedure for obtaining compound 400 using 4-ethoxy-3-methoxybenzoic acid in place of 3,4-dimethoxy-benzoic acid and 1-benzo[b]thiophen-3-yl-2-cyclohexyl-ethanone in place of 2-methylbenzo[b]thiophene-3-carboxaldehyde. Compound 460 was obtained as a white solid (65 mg, 33%). +ESI-MS: m/z 508.1 [M+H]+.

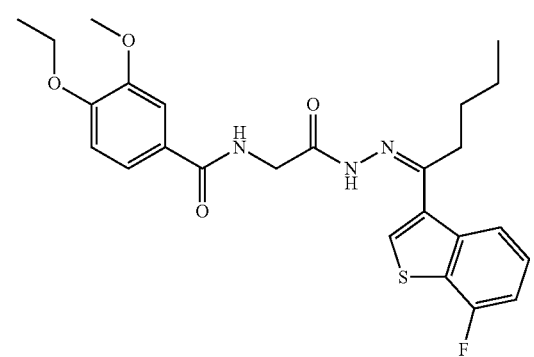

462B

Compound 462A and Compound 462B were obtained following the procedure for obtaining compound 400 using 4-ethoxy-3-methoxybenzoic acid in place of 3,4-dimethoxy-benzoic acid and 1-(7-fluoro-benzo[b]thiophen-3-yl)-pentan-1-one in place of 2-methylbenzo[b]thiophene-3-carboxaldehyde. Compound 462A (50 mg, yield: 30.3%) and Compound 462B (10 mg, yield: 5.9%) were obtained as a white solid. Compound 462A: +ESI-MS: m/z 485.92 [M+H]+. Compound 462B: +ESI-MS: m/z 485.91 [M+H]+.

461

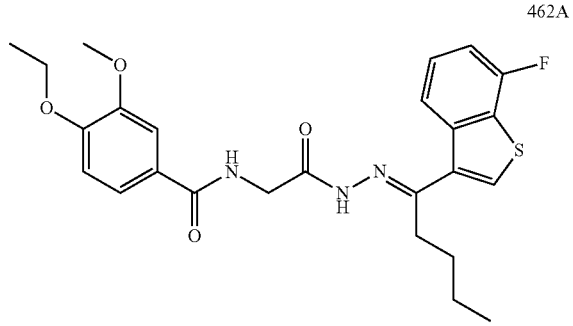

Compound 461 was obtained following the procedure for obtaining compound 400 using 4-ethoxy-3-methoxybenzoic acid in place of 3,4-dimethoxy-benzoic acid and 1-(7-fluoro-benzo[b]thiophen-3-yl)-ethanone in place of 2-methylbenzo[b]thiophene-3-carboxaldehyde. Compound 461 was obtained as a white solid (6 mg, yield: 15%). +ESI-MS: m/z 443.81 [M+H]+.

463A

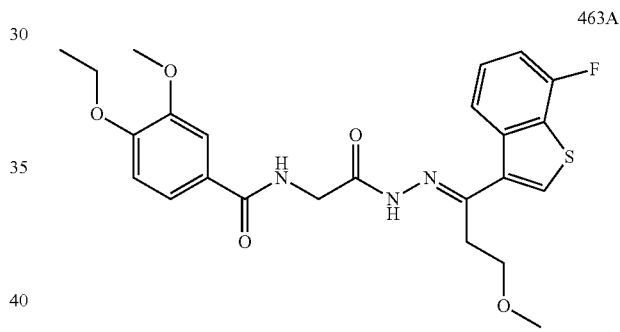

463B

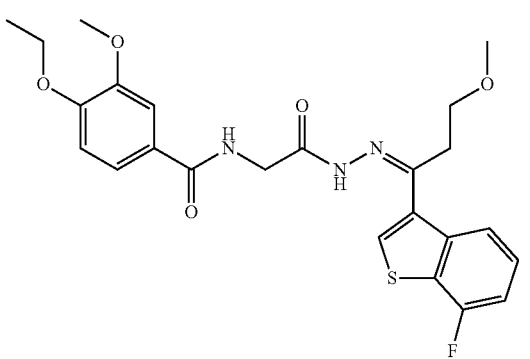

462A

Compound 463A and Compound 463B were obtained following the procedure for obtaining compound 400 using 4-ethoxy-3-methoxybenzoic acid in place of 3,4-dimethoxy-benzoic acid and 1-(7-fluoro-benzo[b]thiophen-3-yl)-3-methoxy-propan-1-one in place of 2-methylbenzo[b]thiophene-3-carboxaldehyde. Compound 463A (200 mg, yield: 24.5%) and Compound 463B (30 mg, yield: 7.6%) were obtained as a white solid. Compound 463A: +ESI-MS: m/z 487.85 [M+H]+. Compound 463B: +ESI-MS: m/z 487.87 [M+H]+.

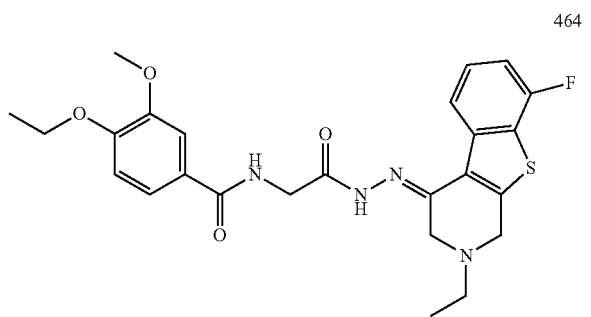 [SMILES: CCOc1ccc(C(=O)NCC(=O)N/N=C2\CN(CC)Cc3sc4c(F)cccc4c32)cc1OC]

464

467

Compound 464 was obtained following the procedure for obtaining compound 400 using 4-ethoxy-3-methoxybenzoic acid in place of 3,4-dimethoxy-benzoic acid and 2-ethyl-6-fluoro-1,2,3,4-tetrahydro-[1]benzothieno[3,2-c]pyridin-4-one in place of 2-methylbenzo[b]thiophene-3-carboxaldehyde. Compound 464 was obtained as a white solid (15 mg, 26%). $^1$H NMR (400 MHz, DMSO-d6) δ 1.14-1.49 (m, 6H), 2.13-2.34 (m, 2H), 3.70-3.86 (m, 3H), 4.05 (d, J=7.06 Hz, 3H), 4.51 (br s, 2H), 6.85-7.15 (m, 3H), 7.23-7.76 (m, 5H), 8.40 (d, J=7.72 Hz, 1H), 8.63-8.91 (m, 1H), 11.01-11.30 (m, 1H).

Compound 467 was obtained following the procedure for obtaining compound 400 using 4-(piperidin-1-yl) benzoic acid in place of 3,4-dimethoxy-benzoic acid and 1-(benzo[b]thiophen-3-yl)ethanone in place of 2-methylbenzo[b]thiophene-3-carboxaldehyde. Compound 467 was obtained as a white solid (320 mg, 78.2%). +ESI-MS: m/z 435.1 [M+H]$^+$.

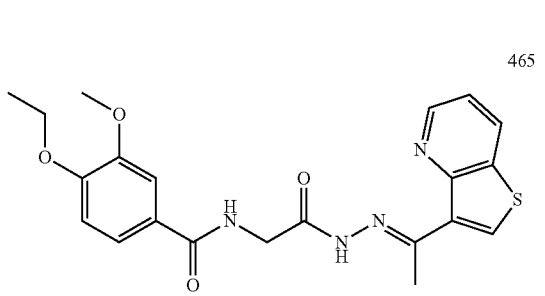 [SMILES: CCOc1ccc(C(=O)NCC(=O)N/N=C(\C)c2csc3cccnc23)cc1OC]

465

468

Compound 465 was obtained following the procedure for obtaining compound 400 using 4-ethoxy-3-methoxybenzoic acid in place of 3,4-dimethoxy-benzoic acid and 1-thieno[3,2-b]pyridin-3-yl-ethanone in place of 2-methylbenzo[b]thiophene-3-carboxaldehyde. Compound 465 was obtained as a white solid (30 mg, yield: 25%). +ESI-MS: m/z 427.1 [M+H]$^+$.

Compound 468 was obtained following the procedure for obtaining compound 400 using 4-(pyrrolidin-1-yl)benzoic acid in place of 3,4-dimethoxy-benzoic acid and 1-(benzo[b]thiophen-3-yl)ethanone in place of 2-methylbenzo[b]thiophene-3-carboxaldehyde. Compound 468 was obtained as a white solid (104 mg, 49.9%). +ESI-MS: m/z 421.1 [M+H]$^+$.

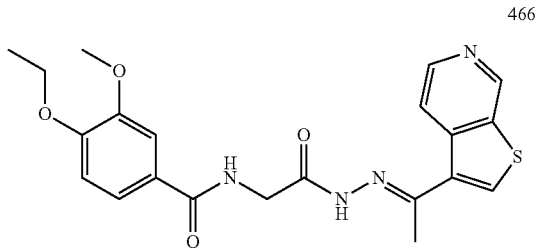 [SMILES: CCOc1ccc(C(=O)NCC(=O)N/N=C(\C)c2csc3cnccc23)cc1OC]

466

469

Compound 466 was obtained following the procedure for obtaining compound 400 using 4-ethoxy-3-methoxybenzoic acid in place of 3,4-dimethoxy-benzoic acid and 1-thieno[2,3-c]pyridin-3-yl-ethanone in place of 2-methylbenzo[b]thiophene-3-carboxaldehyde. Compound 466 was obtained as a white solid (15 mg, yield: 21%). +ESI-MS: m/z 427.0 [M+H]$^+$.

Compound 469 was obtained following the procedure for obtaining compound 400 using 4-(diethylamino)benzoic acid in place of 3,4-dimethoxy-benzoic acid and 1-(benzo[b]thiophen-3-yl)ethanone in place of 2-methylbenzo[b]thiophene-3-carboxaldehyde. Compound 469 was obtained as a white solid (120 mg, 50%). +ESI-MS: m/z 423.1 [M+H]$^+$.

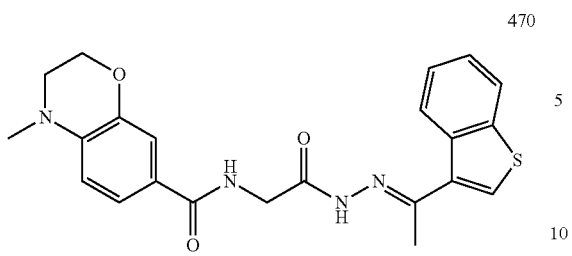

470

Compound 470 was obtained following the procedure for obtaining compound 400 using 4-methyl-3,4-dihydro-2H-benzo[b][1,4]oxazine-7-carboxylic acid in place of 3,4-dimethoxy-benzoic acid and 1-(benzo[b]thiophen-3-yl)ethanone in place of 2-methylbenzo[b]thiophene-3-carboxaldehyde. Compound 470 was obtained as a white solid (10 mg, 10%). ESI-LCMS: m/z 423 [M+H]+.

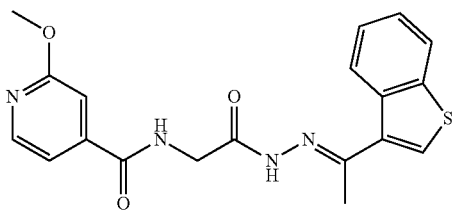

473

Compound 473 was obtained following the procedure for obtaining compound 400 using 2-methoxyisonicotinic acid in place of 3,4-dimethoxy-benzoic acid and 1-(benzo[b]thiophen-3-yl)ethanone in place of 2-methylbenzo[b]thiophene-3-carboxaldehyde. Compound 473 was obtained as a white solid (60 mg, 18%). +ESI-LCMS: m/z 383 [M+H]+.

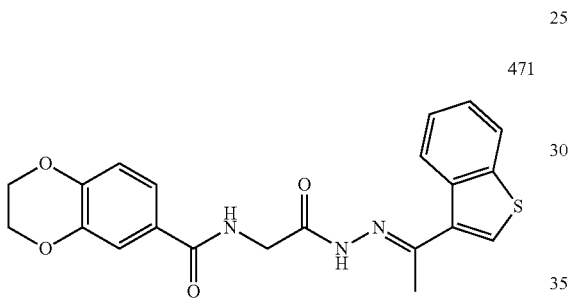

471

Compound 471 was obtained following the procedure for obtaining compound 400 using 2,3-dihydrobenzo[b][1,4]dioxine-6-carboxylic acid in place of 3,4-dimethoxy-benzoic acid and 1-(benzo[b]thiophen-3-yl)ethanone in place of 2-methylbenzo[b]thiophene-3-carboxaldehyde. Compound 471 was obtained as a white solid (50 mg, 43.9%). +ESI-MS: m/z 410.0 [M+H]+.

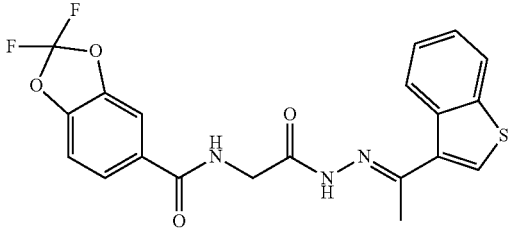

474

Compound 474 was obtained following the procedure for obtaining compound 400 using 2,2-difluorobenzo[d][1,3]dioxole-5-carboxylic acid in place of 3,4-dimethoxy-benzoic acid and 1-(benzo[b]thiophen-3-yl)ethanone in place of 2-methylbenzo[b]thiophene-3-carboxaldehyde. Compound 474 was obtained as a white solid (100 mg, 57.80%). +ESI-MS: m/z 432.0 [M+H]+.

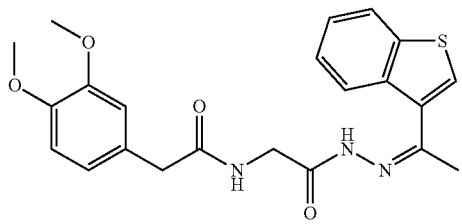

472

Compound 472 was obtained following the procedure for obtaining compound 400 using 2-(3,4-dimethoxyphenyl)acetic acid in place of 3,4-dimethoxy-benzoic acid and 1-(benzo[b]thiophen-3-yl)ethanone in place of 2-methylbenzo[b]thiophene-3-carboxaldehyde. Compound 472 was obtained as a white solid (60 mg, 24.5%). +ESI-LCMS: m/z 426 [M+H]+.

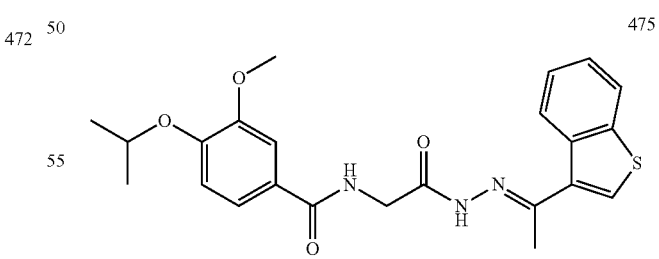

475

Compound 475 was obtained following the procedure for obtaining compound 400 using 4-isopropoxy-3-methoxy-benzoic acid in place of 3,4-dimethoxy-benzoic acid and 1-(benzo[b]thiophen-3-yl)ethanone in place of 2-methylbenzo[b]thiophene-3-carboxaldehyde. Compound 475 was obtained as a white solid (75 mg, 60.0%). +ESI-MS: m/z 440.0 [M+H]+.

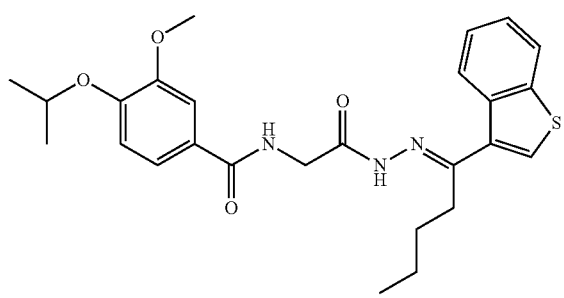

476

Compound 476 was obtained following the procedure for obtaining compound 400 using 4-isopropoxy-3-methoxy-benzoic acid in place of 3,4-dimethoxy-benzoic acid and 1-(benzo[b]thiophen-3-yl)pentan-1-one in place of benzo[b]thiophene-3-carbaldehyde. Compound 476 was obtained as a white solid (142 mg, 57.0%). +ESI-MS: m/z 481.9 [M+H]$^+$.

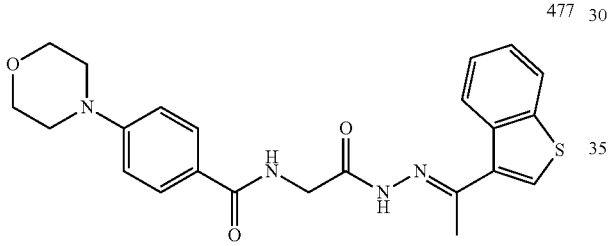

477

Compound 477 was obtained following the procedure for obtaining compound 400 using 4-morpholin-4-ylbenzoic acid in place of 3,4-dimethoxy-benzoic acid and 1-(benzo[b]thiophen-3-yl)ethanone in place of 2-methylbenzo[b]thiophene-3-carboxaldehyde. Compound 477 was obtained as a white solid (60 mg, 13%). ESI-LCMS: m/z 383 [M+H]$^+$.

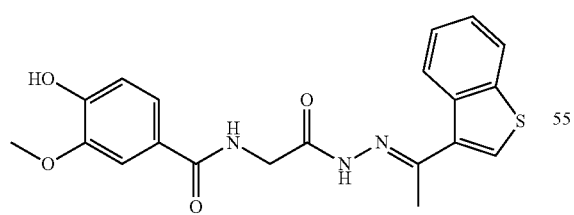

478

Compound 478 was obtained following the procedure for obtaining compound 400 using 4-hydroxy-3-methoxyben-zoic acid in place of 3,4-dimethoxy-benzoic acid and 1-(benzo[b]thiophen-3-yl)ethanone in place of 2-methyl-benzo[b]thiophene-3-carboxaldehyde. Compound 478 was obtained as a white solid (40 mg, 13%). +ESI-LCMS: m/z 398 [M+H]$^+$.

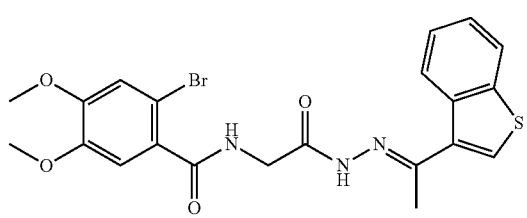

479

Compound 479 was obtained following the procedure for obtaining compound 400 using 2-bromo-4,5-dimethoxyben-zoic acid in place of 3,4-dimethoxy-benzoic acid and 1-(benzo[b]thiophen-3-yl)ethanone in place of 2-methyl-benzo[b]thiophene-3-carboxaldehyde. Compound 479 was obtained as a white solid (80 mg, 13%). +ESI-LCMS: m/z 492 [M+H]$^+$.

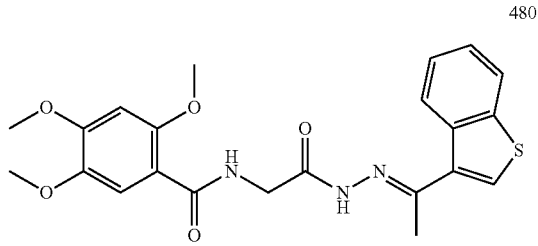 [SMILES: COc1cc(OC)c(C(=O)NCC(=O)N/N=C(\C)c2csc3ccccc23)cc1OC]

480

Compound 480 was obtained following the procedure for obtaining compound 400 using 2,4,5-trimethoxybenzoic acid in place of 3,4-dimethoxy-benzoic acid and 1-(benzo[b]thiophen-3-yl)ethanone in place of 2-methylbenzo[b]thiophene-3-carboxaldehyde. Compound 480 was obtained as a white solid (30 mg, 13%). ESI-LCMS: m/z 442 [M+H]$^+$.

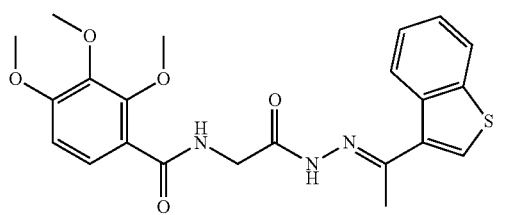

481

Compound 481 was obtained following the procedure for obtaining compound 400 using 2,3,4-trimethoxybenzoic acid in place of 3,4-dimethoxy-benzoic acid and 1-(benzo[b]thiophen-3-yl)ethanone in place of 2-methylbenzo[b]thiophene-3-carboxaldehyde. Compound 481 was obtained as a white solid (180 mg, 57.88%). +ESI-MS: m/z 442.1 [M+H]$^+$.

482

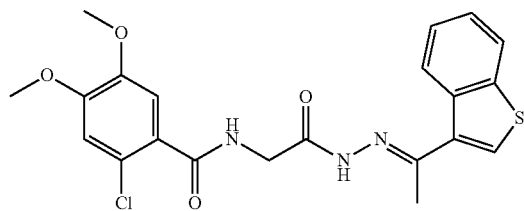

Compound 482 was obtained following the procedure for obtaining compound 400 using 2-chloro-4,5-dimethoxybenzoic acid in place of 3,4-dimethoxy-benzoic acid and 1-(benzo[b]thiophen-3-yl)ethanone in place of 2-methylbenzo[b]thiophene-3-carboxaldehyde. Compound 482 was obtained as a white solid (125 mg, 98.4%). +ESI-MS: m/z 446.0 [M+H]⁺.

483

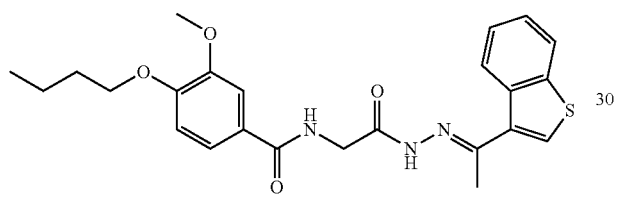

Compound 483 was obtained following the procedure for obtaining compound 400 using 4-butoxy-3-methoxybenzoic acid in place of 3,4-dimethoxy-benzoic acid and 1-(benzo[b]thiophen-3-yl)ethanone in place of 2-methylbenzo[b]thiophene-3-carboxaldehyde. Compound 483 was obtained as a white solid (120 mg, 35.60%). +ESI-MS: m/z 454.3 [M+H]⁺.

484

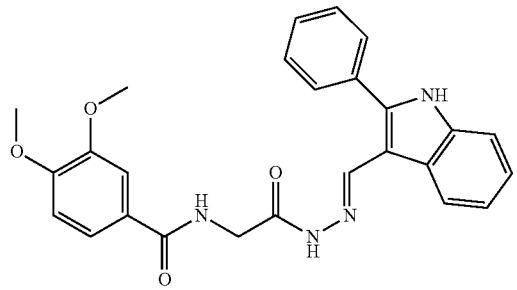

Compound 484 was obtained essentially following the procedure for obtaining compound 400 using N-(2-hydrazinyl-2-oxoethyl)-3,4-dimethoxybenzamide and 2-phenyl-1H-indole-3-carbaldehyde as the starting materials. Compound 484 was obtained as a white solid. +ESI-MS: m/z 457.0 [M+H]⁺.

485

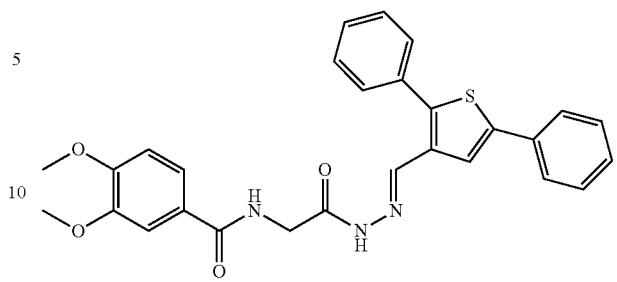

Compound 485 was obtained essentially following the procedure for obtaining compound 400 using N-(2-hydrazinyl-2-oxoethyl)-3,4-dimethoxybenzamide and 2,5-diphenylthiophene-3-carbaldehyde as the starting materials. Compound 485 was obtained as a white solid. +ESI-MS: m/z 500.1 [M+H]⁺.

486

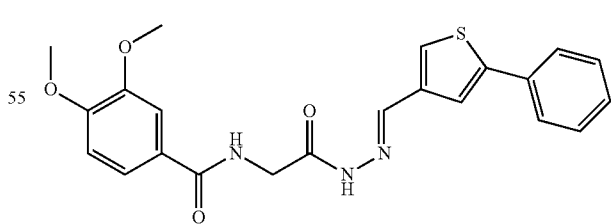

Compound 486 was obtained essentially following the procedure for obtaining compound 400 using 1,2-dimethyl-1H-indole-3-carbaldehyde as the starting material. Compound 486 was obtained as a white solid. +ESI-MS: m/z 409.1 [M+H]⁺.

487

Compound 487 was obtained essentially following the procedure for obtaining compound 400 using N-(2-hydrazinyl-2-oxoethyl)-3,4-dimethoxybenzamide and 5-phenylthiophene-3-carbaldehyde as the starting materials. Compound 487 was obtained as a white solid. +ESI-MS: m/z 424.1 [M+H]⁺.

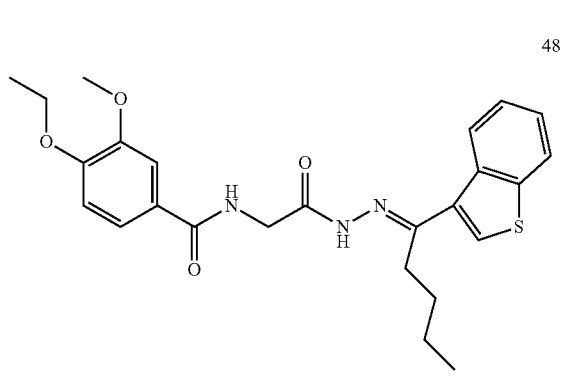

488

Compound 488 was obtained essentially following the procedure for obtaining compound 400 using 4-ethoxy-N-(2-hydrazinyl-2-oxoethyl)-3-methoxybenzamide and 1-(benzo[b]thiophen-3-yl)pentan-1-one as the starting materials. Compound 488 was obtained as a white solid. +ESI-MS: m/z 468.1 [M+H]$^+$.

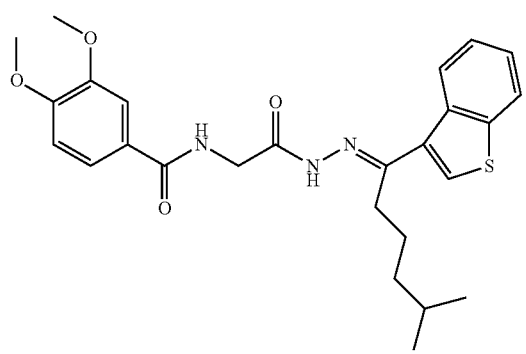

489

Compound 489 was obtained essentially following the procedure for obtaining compound 400. Compound 489 was obtained as a white solid (100 mg, 35%). +ESI-MS: m/z 482.0 [M+H]$^+$.

Example 4-1

Preparation of Compound 4-7

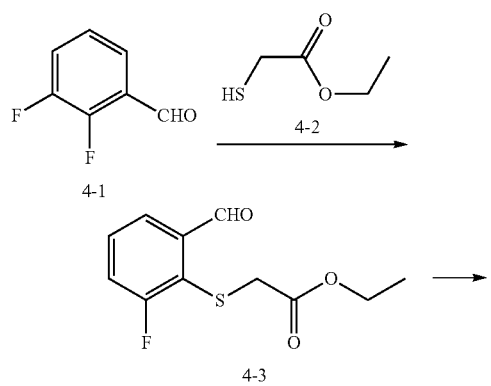

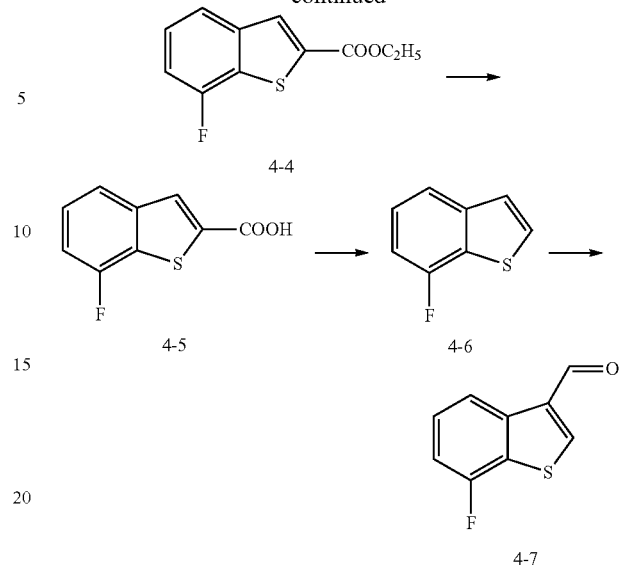

To a solution of 4-1 (48 g, 0.34 mmol) and K$_2$CO$_3$ (60 g, 0.5 mmol) at 0° C. in DMF (200 mL) was added 4-2 (44 g, 0.37 mmol). The mixture was stirred at rt for 12 h, and then heated at 70° C. for 5 h. After cooling to rt, the mixture was poured into water, and extracted with EA. The combined organic layer was washed with brine, dried over anhydrous sodium sulfate and concentrated to give 4-4 (75 g, 80.5%).

A mixture of 4-4 (75 g, 335 mmol), KOH (93 g, 1.66 mol), H$_2$O (500 mL) and EtOH (500 mL) was refluxed for 2 h. The mixture was concentrated, acidified to pH=3 with 2N HCl solution and then extracted with EA. The combined organic layer was dried over sodium sulfate and concentrated to give 4-5 (60 g, 88%).

To a solution of 4-5 (4 g, 20.4 mmol) in quinoline (21 mL) was added Cu powder (440 mg, 6.12 mmol) at rt. The mixture was heated to 185° C. and stirred for 2 h. The solution was cooled to rt, poured into 2N HCl solution and extracted with DCM. The organic phase was concentrated (<40° C.) to give crude 4-6 (3.3 g, 74.2%).

Compound 4-6 (12 g, 79 mmol) and dichloromethyl methyl ether (13.5, 118 mmol) were dissolved in anhydrous DCM (400 mL). To the solution was added titanium tetrachloride (23 g, 122 mmol). After stirring at rt for 1 h, the mixture was poured into a mixture of saturated aqueous NaHCO$_3$ and ice. The mixture was stirred for about 30 mins and then extracted with DCM. The organic layer was dried over sodium sulfate and concentrated. The residue was purified by column chromatograph on silica gel (PE:EA=80:1 to 20:1) to give 4-7 (6.0 g, 40%). $^1$H-NMR (400 MHz, d-DMSO), δ=10.14 (d, J=1.0 Hz, 1H), 9.05 (s, 1H), 8.36-8.34 (m, 1H), 7.60-7.55 (m, 1H), 7.41-7.37 (m, 1H).

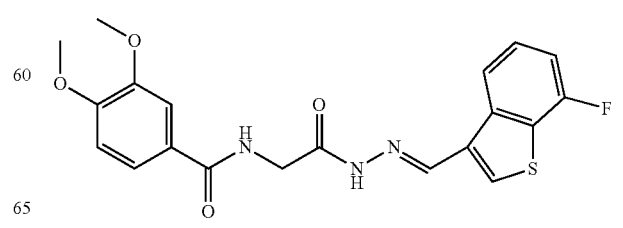

490

Compound 490 was obtained essentially following the procedure for obtaining compound 400 using 4-7 as the starting material. Compound 490 was obtained as a white solid (20 mg, 43.8%). +ESI-MS: m/z 416.2 [M+H]⁺.

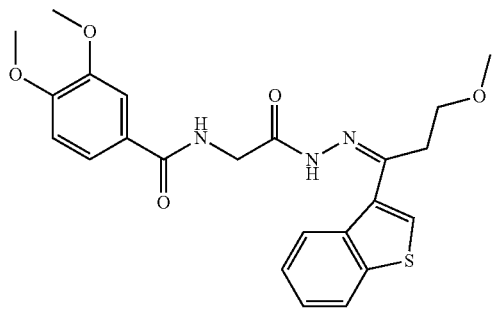

494

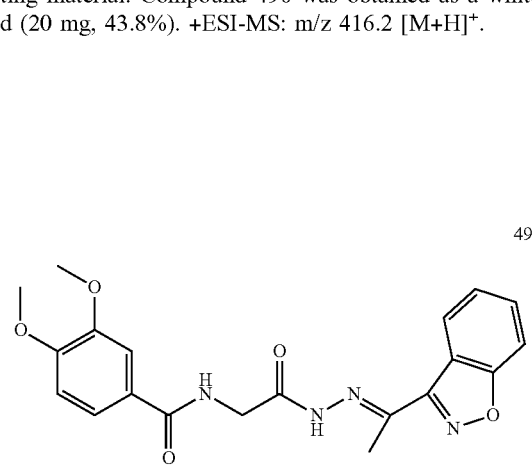

491

Compound 491 was obtained essentially following the procedure for obtaining compound 400. Compound 491 was obtained as a white solid (50 mg, 61.5%). +ESI-MS: m/z 397.0 [M+H]⁺.

Compounds 493 and 494 were obtained essentially following the procedure for obtaining compound 400. Compounds 493 (18 mg, 40.1%) and compound 494 (8 mg, 18.5%) were obtained as a white solid. Compound 493: +ESI-MS: m/z 456.0 [M+H]⁺. Compound 494: +ESI-MS: m/z 456.1 [M+H]⁺.

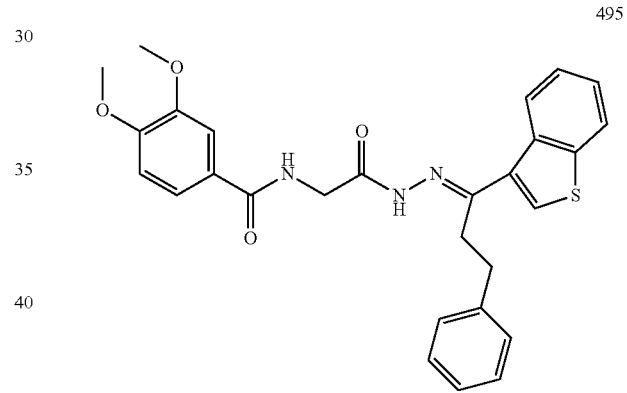

495

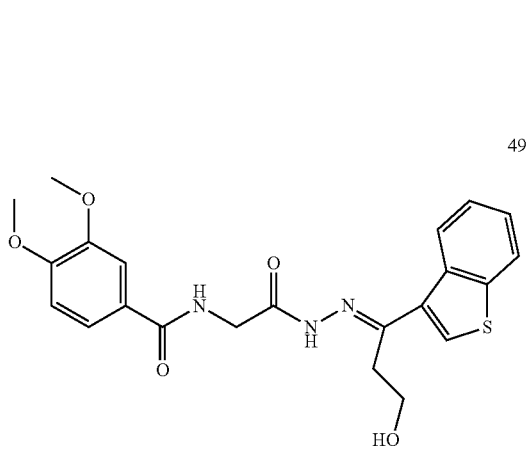

492

Compound 492 was obtained essentially following the procedure for obtaining compound 400. Compound 492 was obtained as a white solid (10 mg, 20%). +ESI-MS: m/z 442.0 [M+H]⁺.

Compound 495 was obtained essentially following the procedure for obtaining compound 400. Compound 495 was obtained as a white solid (95 mg, 25.20%). +ESI-MS: m/z 502.1 [M+H]⁺.

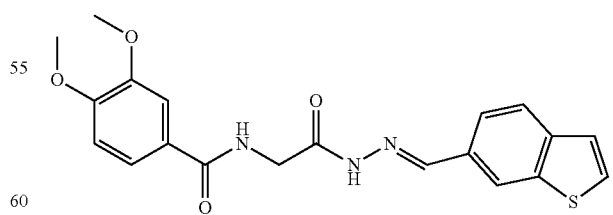

496

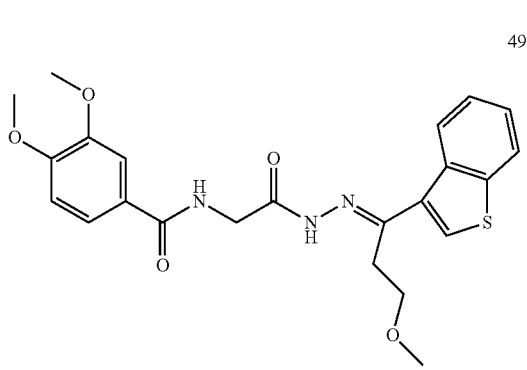

493

Compound 496 was obtained essentially following the procedure for obtaining compound 400. Compound 496 was obtained as a white solid (20 mg, 50%). +ESI-MS: m/z 398.0 [M+H]⁺.

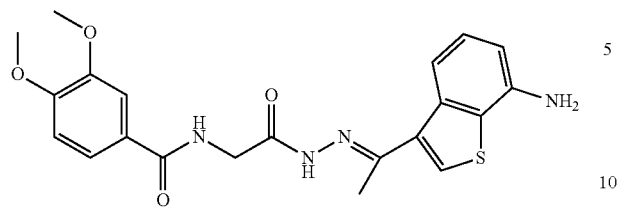

497

Compound 497 was obtained essentially following the procedure for obtaining compound 400. Compound 497 was obtained as a white solid (30 mg, 30%). +ESI-MS: m/z 427.0 [M+H]$^+$.

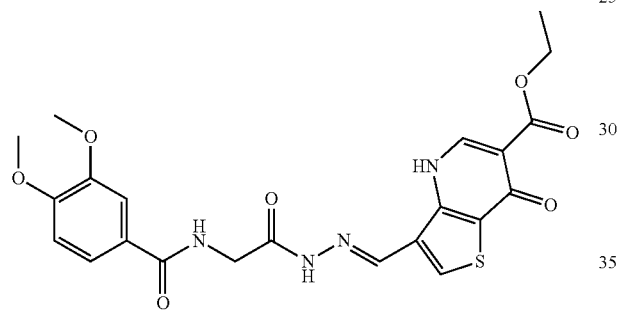

498

Compound 498 was obtained essentially following the procedure for obtaining compound 400. Compound 498 was obtained as a white solid (25 mg, 43.1%). +ESI-MS: m/z 487.0 [M+H]$^+$.

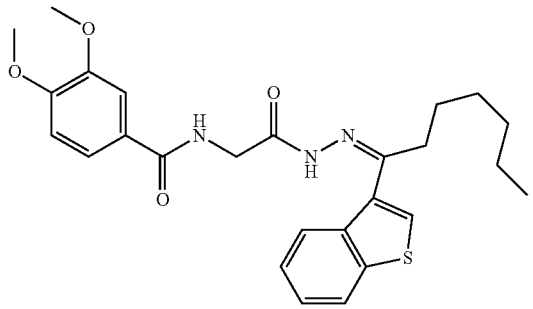

499

Compound 499 was obtained essentially following the procedure for obtaining compound 400. Compound 499 was obtained as a white solid (80 mg, 35.5%). +ESI-MS: m/z 482.1 [M+H]$^+$.

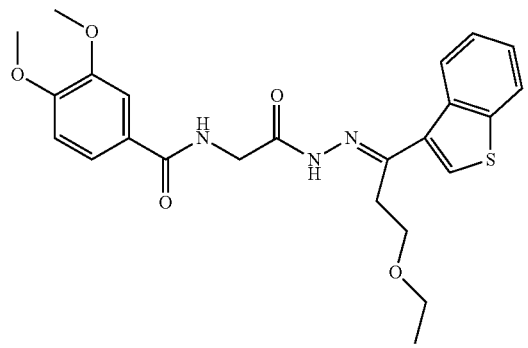

400-1

Compound 400-1 was obtained essentially following the procedure for obtaining compound 400. Compound 400-1 was obtained as a white solid (15 mg, 38.46%). +ESI-MS: m/z 470.0 [M+H]$^+$.

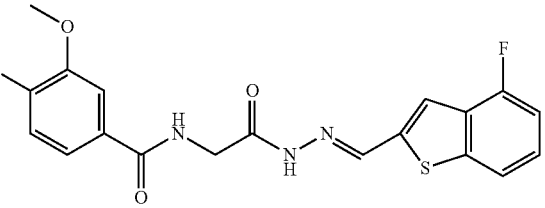

400-2

Compound 400-2 was obtained essentially following the procedure for obtaining compound 400. Compound 400-2 was obtained as a white solid (115 mg, 62.5%). +ESI-MS: m/z 416.0 [M+H]$^+$.

400-3

Compound 400-3 was obtained essentially following the procedure for obtaining compound 400. Compound 400-3 was obtained as a white solid (124 mg, 56.9%). +ESI-MS: m/z 430.0 [M+H]$^+$.

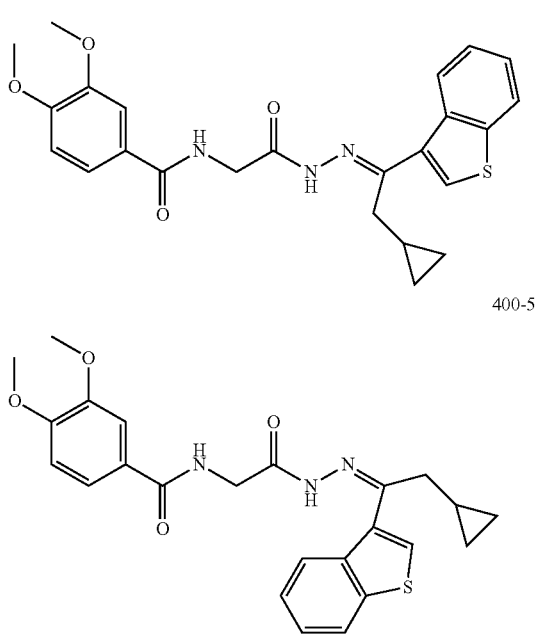

400-4

400-5

Compounds 400-4 and 400-5 were obtained essentially following the procedure for obtaining compound 400. Compounds 400-4 (101 mg, 27.7%) and compound 400-5 (319 mg, 81.8%) were obtained as a white solid. Compound 400-4: +ESI-MS: m/z 452.0 [M+H]$^+$. Compound 400-5: +ESI-MS: m/z 452.1 [M+H]$^+$.

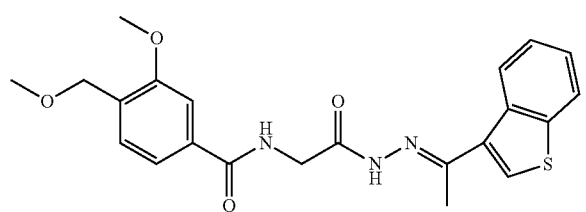

400-6

Compound 400-6 was obtained essentially following the procedure for obtaining compound 400. Compound 400-6 was obtained as a white solid (60 mg, 10.2%). +ESI-MS: m/z 426.1 [M+H]$^+$.

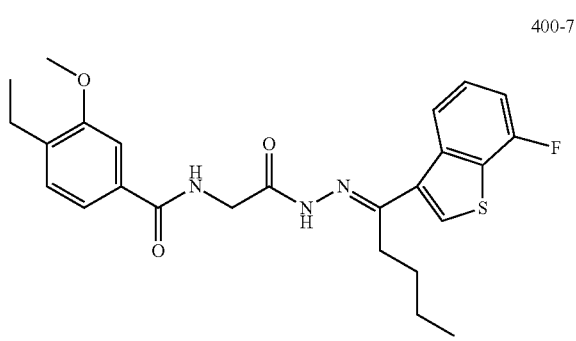 [SMILES: CCCC/C(=N\NC(=O)CNC(=O)c1ccc(CC)c(OC)c1)c1csc2c(F)cccc12]

400-7

Compound 400-7 was obtained essentially following the procedure for obtaining compound 400. Compound 400-7 was obtained as a white solid (20 mg, 20.2%). +ESI-MS: m/z 471.89 [M+H]$^+$.

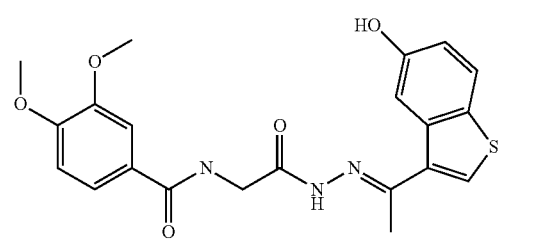

400-8

Compound 400-8 was obtained essentially following the procedure for obtaining compound 400. Compound 400-8 was obtained as a white solid (39 mg, 57.4%). +ESI-MS: m/z 428.0 [M+H]$^+$.

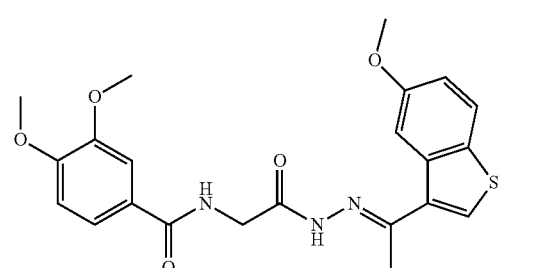

400-9

Compound 400-9 was obtained essentially following the procedure for obtaining compound 400. Compound 400-9 was obtained as a white solid (76 mg, 52.4%). +ESI-MS: m/z 442.0 [M+H]$^+$.

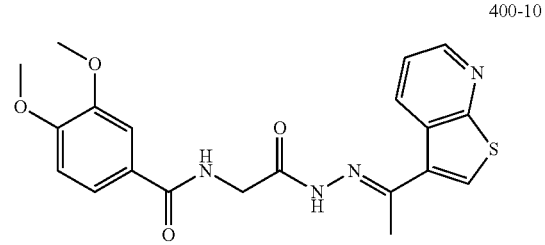 [SMILES: COc1ccc(C(=O)NCC(=O)N/N=C(\C)c2csc3ncccc23)cc1OC]

400-10

Compound 400-10 was obtained essentially following the procedure for obtaining compound 400. Compound 400-10 was obtained as a white solid (40 mg, 21.6%). +ESI-MS: m/z 413.0 [M+H]$^+$.

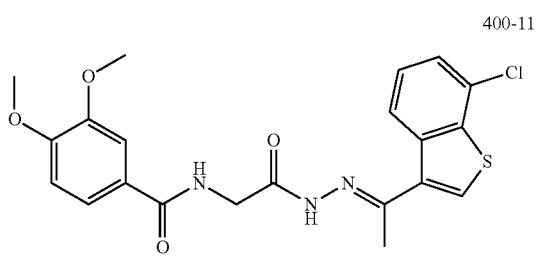 [SMILES: COc1ccc(C(=O)NCC(=O)N/N=C(\C)c2csc3c(Cl)cccc23)cc1OC]

400-11

Compound 400-11 was obtained essentially following the procedure for obtaining compound 400. Compound 400-11 was obtained as a white solid (28 mg, 13.5%). +ESI-MS: m/z 445.8 [M+H]$^+$.

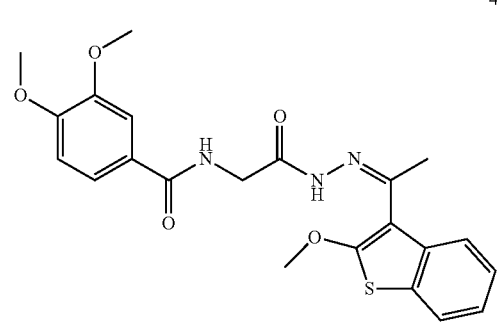

400-14

Compound 400-14 was obtained essentially following the procedure for obtaining compound 400. Compound 400-14 was obtained as a white solid (4 mg, 8.2%). +ESI-MS: m/z 442.0 [M+H]$^+$.

Example 4-2

Preparation of Compound 4-11

400-12

Compound 400-12 was obtained essentially following the procedure for obtaining compound 400. Compound 400-12 was obtained as a white solid (115 mg, 58.1%). +ESI-MS: m/z 432.0 [M+H]$^+$.

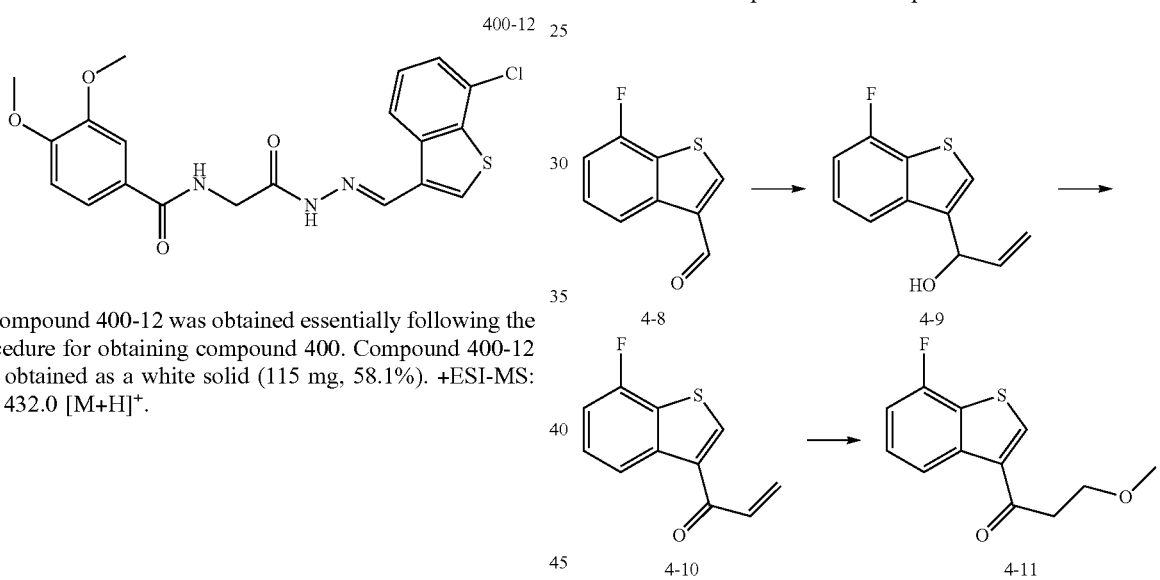

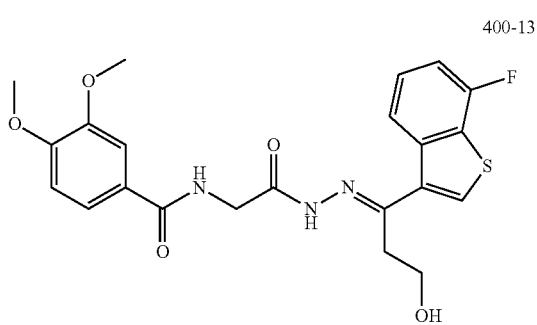 [SMILES: COc1ccc(C(=O)NCC(=O)N/N=C(\CCO)c2csc3c(F)cccc23)cc1OC]

400-13

Compound 400-13 was obtained essentially following the procedure for obtaining compound 400 by using N-(2-hydrazinyl-2-oxoethyl)-3,4-dimethoxybenzamide and 1-(7-fluorobenzo[b]thiophen-3-yl)-3-hydroxypropan-1-one as the starting materials. Compound 400-13 was obtained as a white solid. +ESI-MS: m/z 460.1 [M+H]$^+$.

To a solution of 4-8 (10.0 g, 55.6 mmol) in anhydrous THF (250 mL) was added vinylmagnesium chloride (61 mL, 1.0 M THF) dropwise under a nitrogen atmosphere at 0° C. The mixture was stirred at rt for 2 h with TLC monitoring. The reaction was quenched by addition of aq. NH$_4$Cl and extracted by EA. The organic layer was dried over anhydrous Na$_2$SO$_4$ and concentrated to give crude 4-9 (10.5 g, 80%).

To a solution of 4-9 (10.5 g, 50.5 mmol) in anhydrous DCM (200 mL) was add MnO$_2$ (39 g, 450 mmol). The mixture was stirred at 40° C. for 10 h with TLC monitoring. The mixture was filtered through a 2-cm Celite filter pad and the pad was washed with DCM (100 mL). The clear filtrate was concentrated. The residue was purified by column chromatography on silica gel (PE/EA=20:1-5:1) to give 4-10 (9.0 g, 70%).

To a solution of 4-10 (6.5 g, 31.6 mmol) in anhydrous MeOH (80 mL) was add DBU (0.49 g, 3.2 mmol). The mixture was stirred at 40° C. for 3 h with TLC monitoring. The reaction was quenched with aq. NH$_4$Cl, and extracted by EA. The organic layer was washed with brine, dried over anhydrous Na₂SO₄, and concentrated at low pressure. The residue was purified by column chromatography on silica gel (PE/EA=10:1 to 5:1) to give 4-11 (5.0 g, 60%). ¹H-NMR (d-DMSO, 400 MHz), δ=9.08 (s, 1H), 8.43 (d, J=8.1 Hz, 1H), 7.57-7.52 (m, 1H), 7.38-7.33 (m, 1H), 3.74-3.71 (m, 2H), 3.30-3.27 (m, 2H), 3.25 (s, 3H).

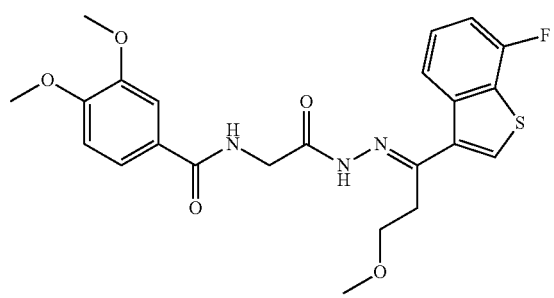

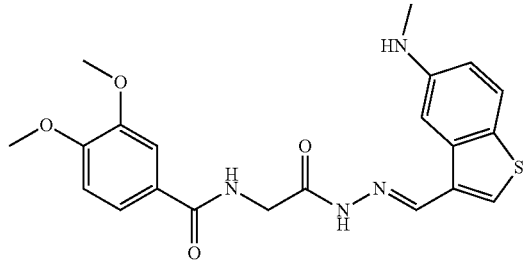

Compound 400-18 was obtained essentially following the procedure for obtaining compound 400. Compound 400-18 was obtained as a white solid (20 mg, 15.0%). +ESI-MS: m/z 427.2 [M+H]⁺.

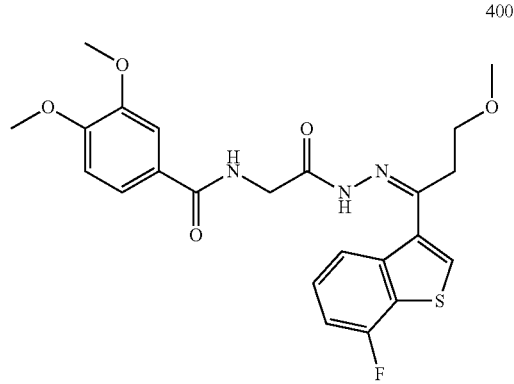

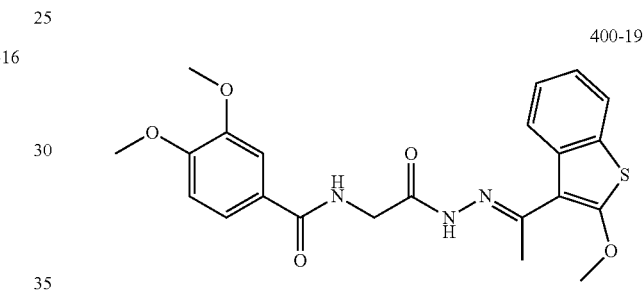

Compound 400-19 was obtained essentially following the procedure for obtaining compound 400. Compound 400-19 was obtained as a white solid (12 mg, 12.4%). +ESI-MS: m/z 442.0 [M+H]⁺.

Compounds 400-15 and 400-16 were obtained essentially following the procedure for obtaining compound 400 using 4-11 as the starting material. Compounds 400-15 (50 mg, 30%) and compound 400-16 (5 mg, 3%) were obtained as a white solid. Compound 400-15: +ESI-MS: m/z 473.8 [M+H]⁺. Compound 400-16: +ESI-MS: m/z 473.9 [M+H]⁺.

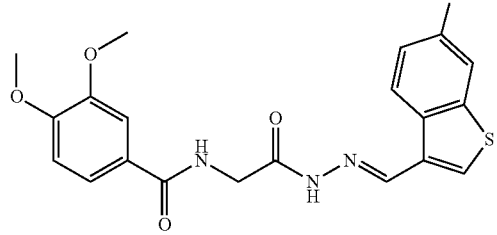

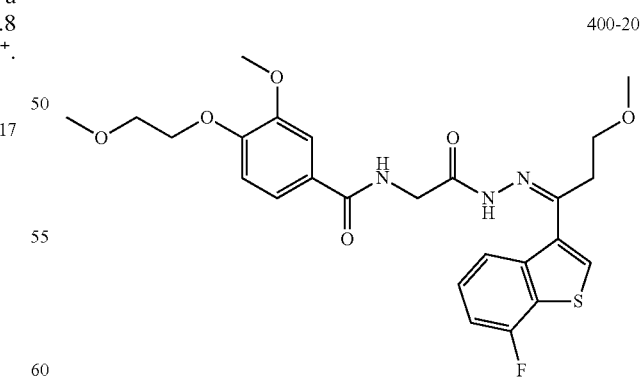

Compound 400-17 was obtained essentially following the procedure for obtaining compound 400. Compound 400-17 was obtained as a white solid (40 mg, 34.8%). +ESI-MS: m/z 415.9 [M+H]⁺.

Compound 400-20 was obtained essentially following the procedure for obtaining compound 400 using 4-hydroxy-3-methoxy-benzoic acid ethyl ester as the starting material. Compound 400-20 was obtained as a white solid (110 mg, 50.8%). +ESI-MS: m/z 518.0 [M+H]⁺.

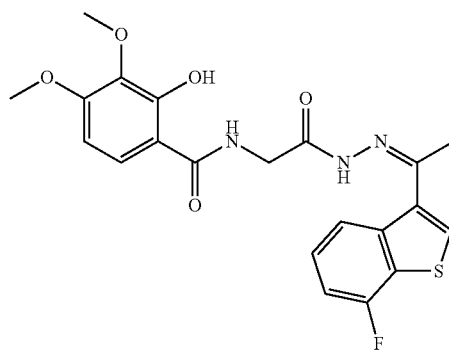

Compound 400-21 was obtained essentially following the procedure for obtaining compound 400 using 4-11 as the starting material. Compound 400-21 was obtained as a white solid (110 mg, 50.8%). +ESI-MS: m/z 490.1 [M+H]+.

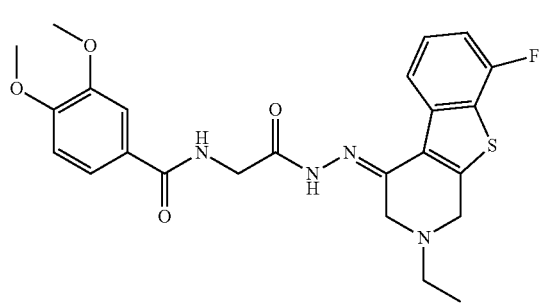

Compound 400-22 was obtained essentially following the procedure for obtaining compound 400. Compound 400-22 was obtained as a white solid (126 mg, 57.3%). +ESI-MS: m/z 430.1 [M+H]+.

Compound 400-23 was obtained essentially following the procedure for obtaining compound 400. Compound 400-23 was obtained as a white solid (15 mg, 35.2%). +ESI-MS: m/z 485.2 [M+H]+.

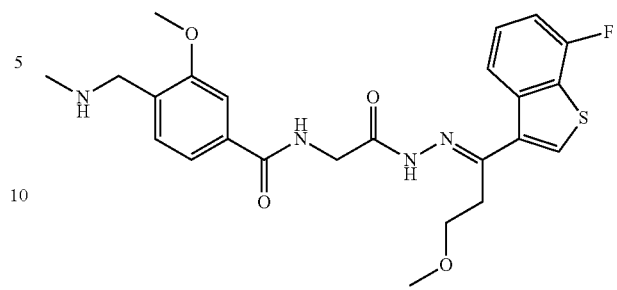

Compound 400-24 was obtained essentially following the procedure for obtaining compound 400. Compound 400-24 was obtained as a white solid (2 mg). +ESI-MS: m/z 487.1 [M+H]+.

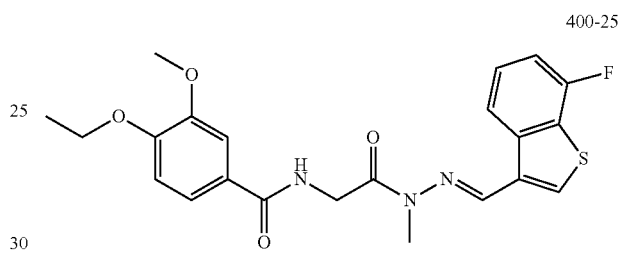

Compound 400-25 was obtained essentially following the procedure for obtaining compound 400. Compound 400-25 was obtained as a white solid. +ESI-MS: m/z 444.0 [M+H]+.

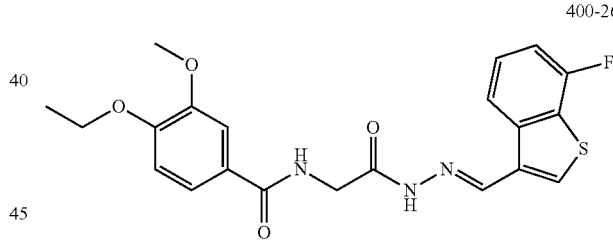

Compound 400-26 was obtained essentially following the procedure for obtaining compound 400 using 7-fluorobenzo[b]thiophene-3-carbaldehyde as starting material. Compound 400-26 was obtained as a white solid (50 mg, 15.0%). +ESI-MS: m/z 430.0 [M+H]+.

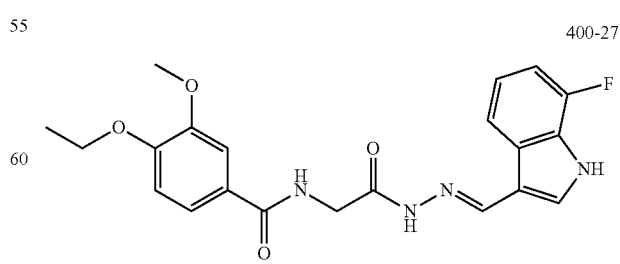

Compound 400-27 was obtained essentially following the procedure for obtaining compound 400 using 7-fluoro-1H- indole-3-carbaldehyde. Compound 400-27 was obtained as a white solid (40 mg, 16.0%). +ESI-MS: m/z 413.0 [M+H]+.

400-28

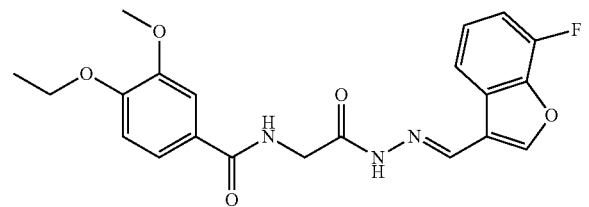

Compound 400-28 was obtained essentially following the procedure for obtaining compound 400 using 7-fluoro-1H-indole-3-carbaldehyde. Compound 400-28 was obtained as a white solid (60 mg, 18.0%). +ESI-MS: m/z 414.0 [M+H]+.

Example 4-3

Preparation of Compound 4-F

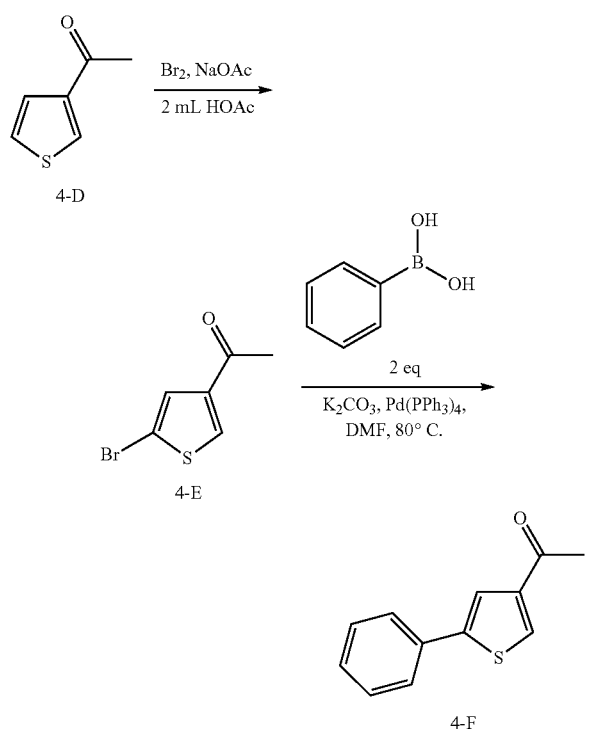

To a solution of 2-acetylthiophene (4-D) (0.4 g, 3.17 mmol) in HOAc (5 mL), NaOAc (0.29 g, 3.5 mmol) was added at rt. The solution was stirred for 10 mins at rt. Then $Br_2$ (0.508 g, 3.17 mmol) was added dropwise at 0° C. The solution was stirred for 2 h. The solution was neutralized with $NaHCO_3$ aqueous and extracted with EA. The organic phase was concentrated to afford crude 4-acetyl-2-bromothiophene (4-E) (0.4 g, 61.5%).

To a solution of 4-acetyl-2-bromothiophene (4-E) (0.4 g, 1.95 mmol) in DMF (10 mL), phenylboronic acid (0.285 g, 2.34 mmol), $Pd(PPh_3)_4$ (0.225 g, 0.195 mmol) and $K_2CO_3$ (0.53 g, 3.9 mmol) were added at rt under $N_2$ atmosphere. The mixture was stirred for 15 h at 80-90° C. The solution was poured into water and extracted with EA. The organic phase was concentrated and the residue was purified by silica gel chromatography with (PE) to afford 1-(5-phenyl-thiophen-3-yl)ethanone (4-F) (100 mg, 25.3%).

Example 4-4

Preparation of Compound 4-J

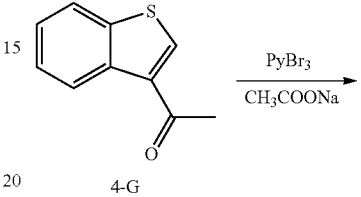

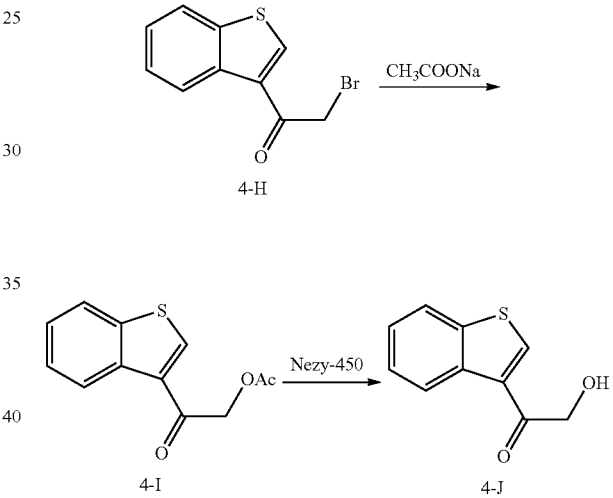

To a solution of 1-(benzo[b]thiophen-3-yl)ethanone (4-G) (1.63 g, 10.0 mmol) in $CH_3CN$ (60 mL) was added $PyBr_3$ (3.19 g, 10 mmol) and $CH_3COONa$ (820 mg, 10.0 mmol), the mixture was stirred at 80° C. overnight. The mixture was washed with water and the organic layer was collected. The solvent was removed and the residue was purified by silica gel column (PE/EA=20/1 to 5/1) to afford 4-H as a white solid (1.3 g, 50.9%).

To a solution of 4-H (1.27 g, 5.0 mmol) in $CH_3CN$ (60 mL) was added $CH_3COONa$ (820 mg, 10.0 mmol), the mixture was stirred at 80° C. overnight. The mixture was washed with water and the organic layer was collected. The solvent was removed and the residue was purified by silica gel column (PE/EA=20/1 to 5/1) to afford 4-I as a white solid (900 mg, 81.4%).

To a solution of 4-I (900 mg, 3.85 mmol) in $CH_3CN$ (60 mL) was added Nezy-450 (200 mg), the mixture was stirred at 80° C. overnight. The mixture was washed with water and the organic layer was collected. The solvent was removed and the residue was purified by silica gel column (PE/EA=20/1 to 5/1) to afford 4-J as a white solid (480 mg, 64.9%).

Example 4-5

Preparation of Compound 4-L

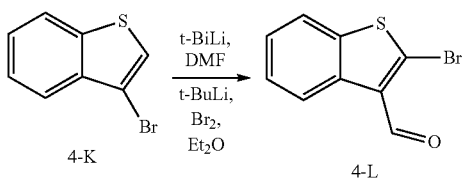 [SMILES: Brc1csc2ccccc12 ; O=Cc1c(Br)sc2ccccc12]

To a solution of 3-bromobenzo[b]thiophene (4-K) (4 g, 18.7 mmol) in Et$_2$O (20 mL), t-BuLi (15.6 mL, 1.3M in hexane) was added at −78° C. The solution was stirred for 30 mins at −78° C. and DMF (1.5 g, 20.6 mmol) was then added. The cooling bath was removed and the mixture was stirred for another 30 mins at rt. The mixture was cooled to −30° C. Another portion of t-BuLi (15.6 mL, 1.3 M in hexane) was added at −30° C. The cooling bath was removed and the mixture was stirred for another 30 mins at rt. The mixture was cooled to −78° C. And a solution of bromine (3.9 g, 24.4 mmol) in hexane was in one portion. The temperature was allowed to gradually rise to 0° C. (2 h). The solution was diluted with 1M HCl and extracted with EA. The organic phase was concentrated and the residue was purified by chromatography with silica gel to afford the 2-bromobenzo[b]thiophene-3-carboxaldehyde (4-L) (0.3 g, 7%).

Example 5

Preparation of Compound 500

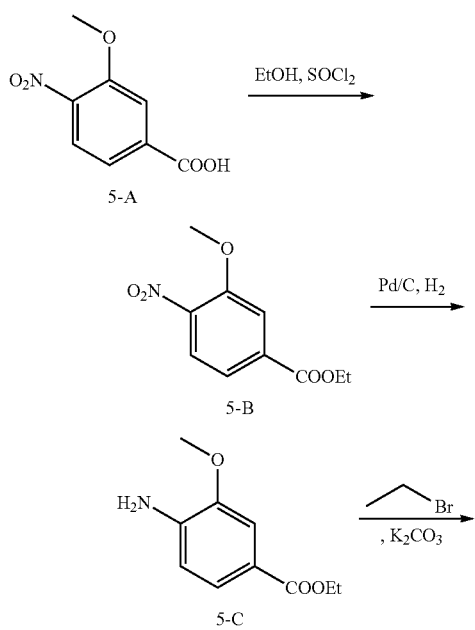

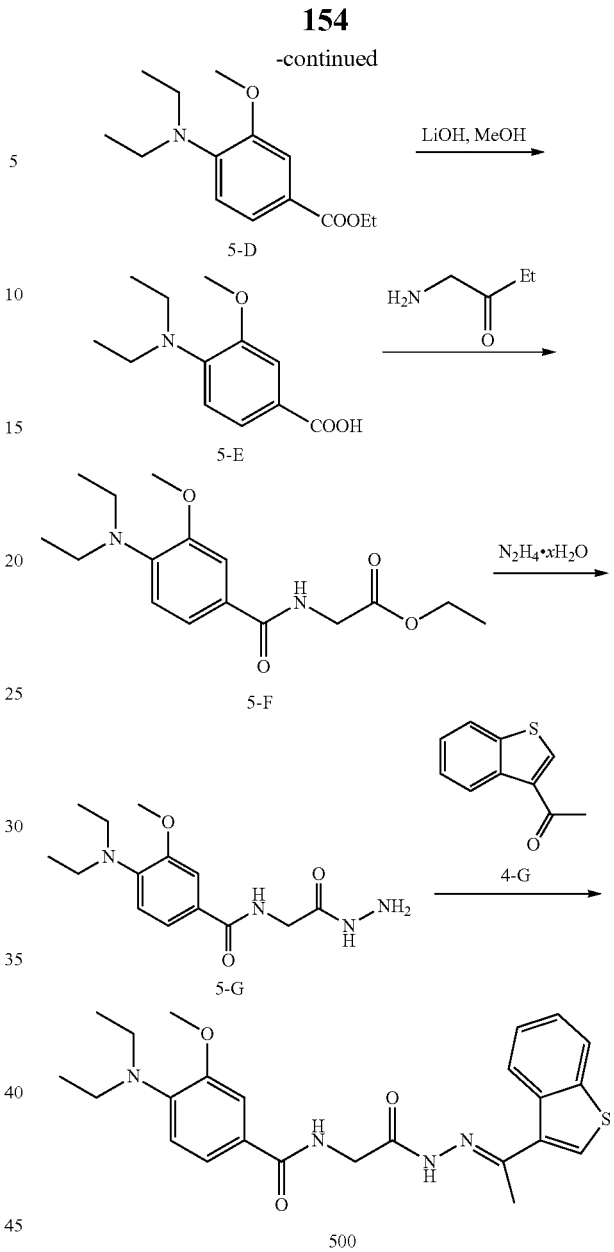

To a solution of 3-methoxy-4-nitrobenzoic acid (5-A) (7.00 g, 35.5 mmol) in EtOH (40 mL) was added SOCl$_2$ (7 mL). The mixture was stirred for 60° C. for 14 h. The mixture was concentrated to afford crude ethyl 3-methoxy-4-nitrobenzoate (5-B) (7.650 g).

To a solution of ethyl 3-methoxy-4-nitrobenzoate (5-B) (7.65 g, 34 mmol) in EtOH (20 mL) was added Pd/C (1.5 g), while stirring at rt under H$_2$ for 12 h. The solid was removed by filtration and the mixture was extracted with EA. The solvent was removed to afford ethyl 4-amino-3-methoxybenzoate (5-C) (7.5 g).

Ethyl 4-amino-3-methoxybenzoate (5-C) (3 g, 15.37 mmol) was dissolved in MeCN (10 mL), K$_2$CO$_3$ (5.310 g, 38.43 mmol) and ethyl bromide (3.350 g, 30.73 mmol) were added. The solution was stirred at 100° C. for 24 h in a 30 mL of autoclave. The mixture was filtered and the filtrate was concentrated to afford ethyl 4-(diethylamino)-3-methoxybenzoate (5-D) (392 mg).

To a solution of ethyl 4-(diethylamino)-3-methoxybenzoate (5-D) (392 mg, 1.56 mmol) in THF (2 mL) and H$_2$O (2 mL) were added LiOH (391.5 mg, 9.33 mmol) and MeOH (2 mL). The mixture was stirred at 40° C. for 2 h. The mixture solution was concentrate and the remaining mixture was dissolved in EA/HCl, then filtered. The filtrate was concentrated to afford 4-(diethylamino)-3-methoxybenzoic acid (5-E) (300 mg, 87%).

To a solution of 4-(diethylamino)-3-methoxybenzoic acid (5-E) (300 mg, 1.34 mmol) in DCM (10 mL) was added HATU (1.02 g, 2.7 mmol) and DIPEA (433 mg, 3.4 mmol), the mixture was stirred at rt for 30 mins, then ethyl 2-aminoacetate (187 g, 1.34 mmol) was added. The mixture was stirred at rt for another 15 h. The mixture was washed with water and the organic layer was collected. The solvent was removed and the residue was purified by silica gel column (PE/EA=20/1 to 5/1) to afford 5-F as a white solid (385 mg, 93%).

To a solution of 5-F (385 mg, 1.25 mmol) in anhydrous ethanol (10 mL) was added $N_2H_4 \cdot xH_2O$ (520 mg, 16.2 mmol), the mixture was stirred at 100° C. for 4 h. Then the mixture was allowed to cool to rt and a white precipitate was formed. The precipitate was filtered and washed with EtOH (20 mL) to afford 5-G as a white product (321 mg, 87%).

Compound 5-G (100 mg, 0.34 mmol) was dissolved in anhydrous EtOH (5 mL). To this solution were added 1-Benzo[b]thiophene-3-yl-ethanone (4-G) (60 mg, 0.34 mmol) and AcOH (0.4 mL). The mixture was stirred at 60° C. for 10 h. The mixture was filtered, and the residue was washed with EtOH (10 mL) and EA (10 mL) to afford compound 500 (40 mg, 26.14%). +ESI-MS: m/z 453.0 [M+H]⁺.

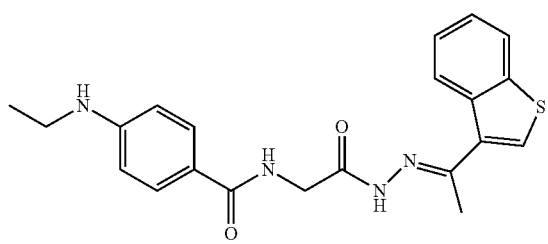

501

Compound 501 was obtained following the procedure for obtaining compound 500 using 4-nitrobenzoic acid in place of 3-methoxy-4-nitrobenzoic acid. Compound 501 was obtained as a white solid (56 mg, 21%). +ESI-MS: m/z 395.0 [M+H]⁺.

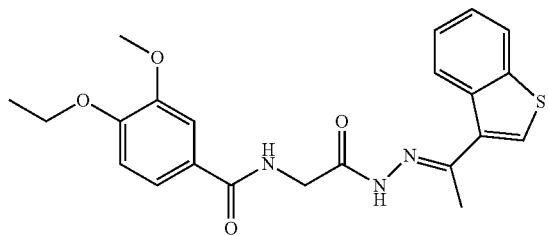

502

Compound 502 was obtained following the procedure for obtaining compound 500 using 4-hydroxy-3-methoxybenzoic acid in place of ethyl 4-amino-3-methoxybenzoate. Compound 502 was obtained as a white solid (75 mg, 62.0%). +ESI-MS: m/z 426.1 [M+H]⁺.

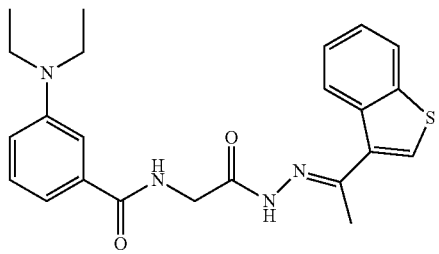

503

Compound 503 was obtained following the procedure for obtaining compound 500 using 3-nitrobenzoic acid in place of 3-methoxy-4-nitrobenzoic acid. Compound 503 was obtained as a white solid (15 mg, 31.25%). +ESI-MS: m/z 423.1.

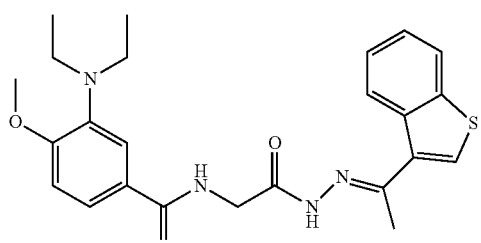

504

Compound 504 was obtained following the procedure for obtaining compound 500 using 4-methoxy-3-nitrobenzoic acid in place of 3-methoxy-4-nitrobenzoic acid. Compound 504 was obtained as a white solid (75 mg, 58%). +ESI-MS: m/z 453.1 [M+H]⁺.

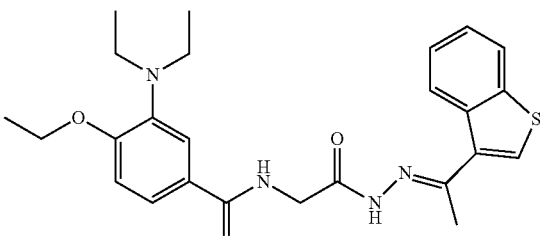

505

Compound 505 was obtained following the procedure for obtaining compound 500 using 4-hydroxy-3-nitrobenzoic acid in place of 3-methoxy-4-nitrobenzoic acid. Compound 505 was obtained as a white solid (68 mg, 52%). +ESI-MS: m/z 467.1 [M+H]⁺.

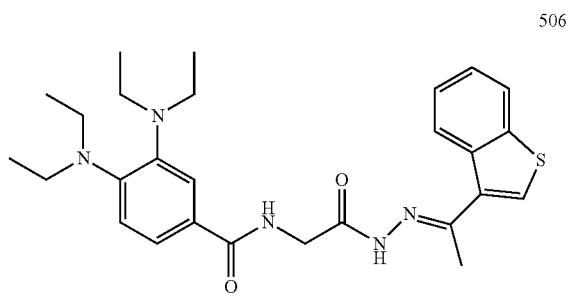 [SMILES: CCN(CC)c1ccc(C(=O)NCC(=O)N/N=C(\C)c2csc3ccccc23)cc1N(CC)CC]

506

Compound 506 was obtained following the procedure for obtaining compound 500 using 3,4-dinitrobenzoic acid in place of 3-methoxy-4-nitrobenzoic acid. Compound 506 was obtained as a white solid (25 mg, 30.9%). +ESI-MS: m/z 494.2 [M+H]$^+$.

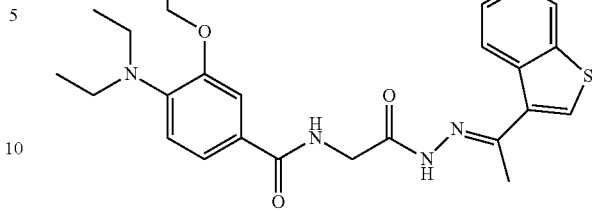

509

Compound 509 was obtained following the procedure for obtaining compound 500 using 3-hydroxy-4-nitrobenzoic acid in place of 3-methoxy-4-nitrobenzoic acid. Compound 509 was obtained as a white solid (50 mg, 37.9%). +ESI-MS: m/z 467.0 [M+H]$^+$.

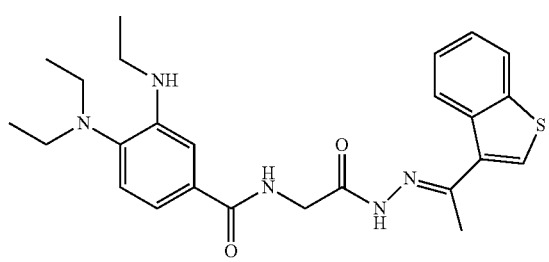

507

Compound 507 was obtained following the procedure for obtaining compound 500 using 3,4-dinitrobenzoic acid in place of 3-methoxy-4-nitrobenzoic acid. Compound 507 was obtained as a white solid (30 mg, yield: 30.0%). +ESI-MS: m/z 469.94 [M+H]$^+$.

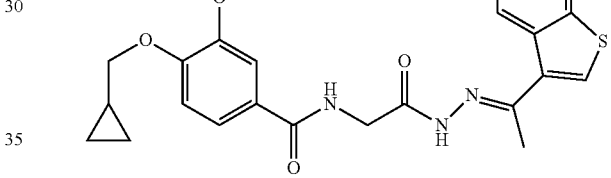

510

Compound 510 was obtained following the procedure for obtaining compound 500 starting from intermediate 3 using 4-hydroxy-3-methoxybenzoic acid in place of ethyl 4-amino-3-methoxybenzoate. Compound 510 was obtained as a white solid (60 mg, yield: 26%). +ESI-MS: m/z 452.1 [M+H]$^+$.

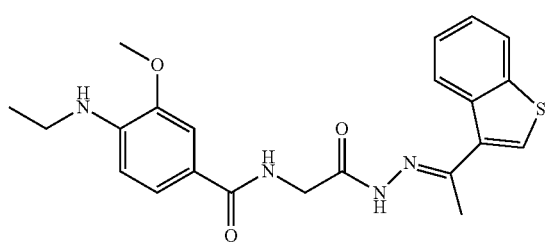

508

Compound 508 was obtained following the procedure for obtaining compound 500 modifying the alkylation step as appropriate. Compound 508 was obtained as a white solid (20 mg, 43%). ESI-LCMS: m/z 425 [M+H]$^+$.

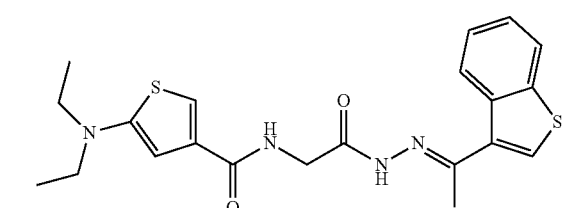

511

Compound 511 was obtained following the procedure for obtaining compound 500 using 5-nitrothiophene-3-carboxylic acid in place of 3-methoxy-4-nitrobenzoic acid. Compound 511 was obtained as a white solid (30 mg, 19%). +ESI-MS: m/z 429.0 [M+H]$^+$.

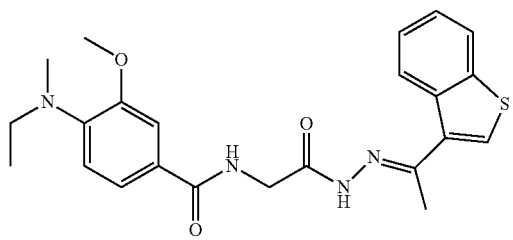

512

Compound 512 was obtained following the procedure for obtaining compound 500 modifying the alkylation step as appropriate. Compound 512 was obtained as a white solid (78 mg, 50.0%). +ESI-MS: m/z 439.0 [M+H]$^+$.

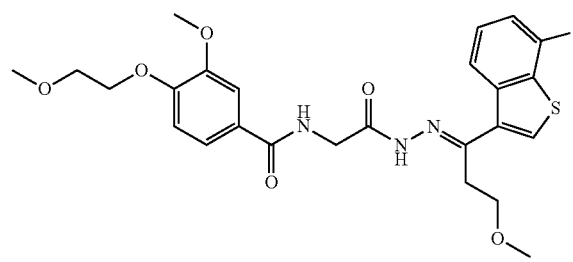

513

Compound 513 was obtained following the procedure for obtaining compound 500. Compound 513 was obtained as a white solid (128 mg, 57%). +ESI-MS: m/z 518.1 [M+H]$^+$.

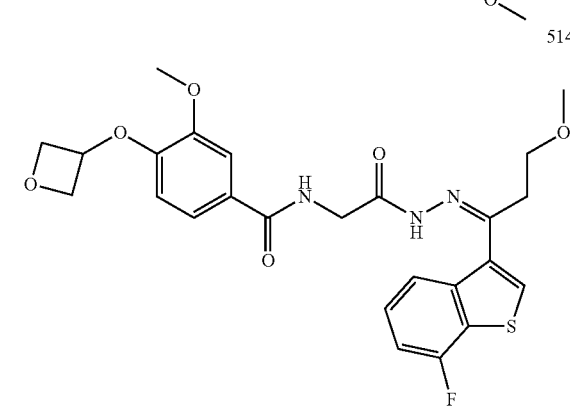

514A

514B

Compound 514A and compound 514B were obtained following the procedure for obtaining compound 500 using 4-hydroxy-3-methoxy-benzoic acid ethyl ester in place of ethyl 4-amino-3-methoxybenzoate. Compound 514A (35 mg, 13.9%) and compound 514B (15 mg, 6.0%) were obtained as a white solid. Compound 514A: +ESI-MS: m/z 516.4 [M+H]$^+$. Compound 514B: +ESI-MS: m/z 516.2 [M+H]$^+$.

Example 6

Preparation of Compound 600

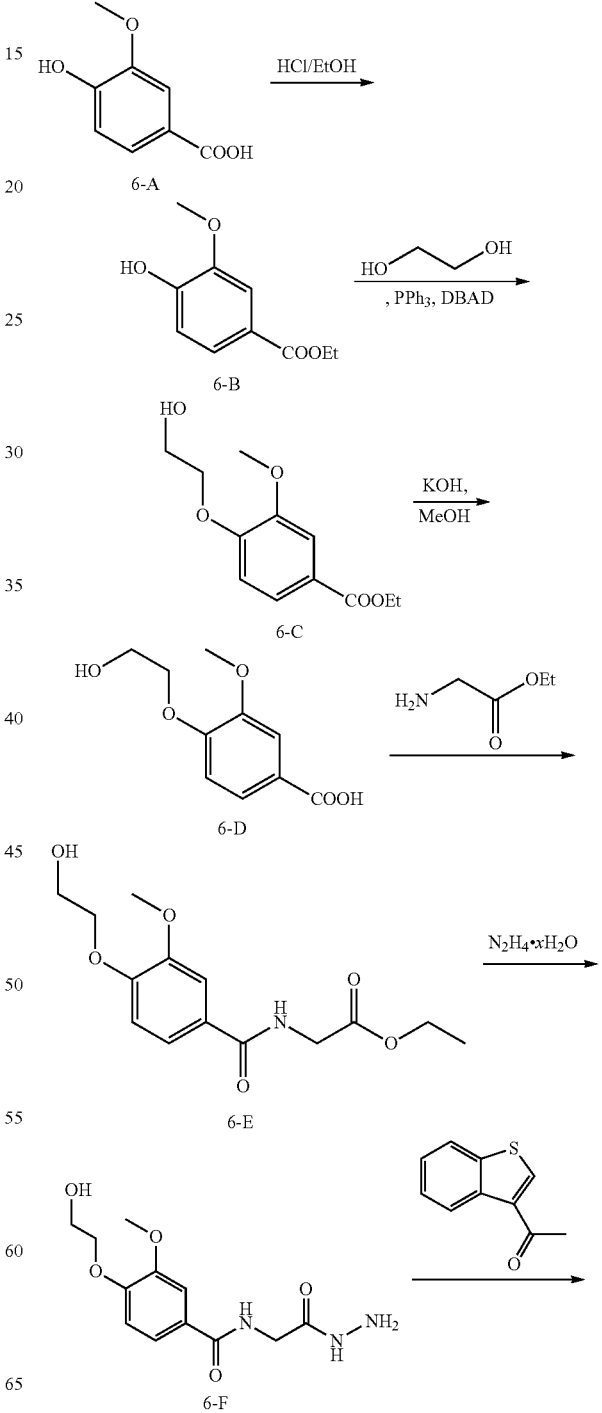

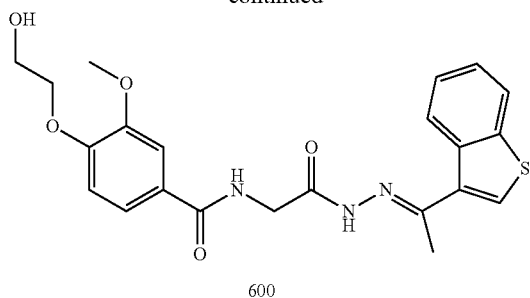

600

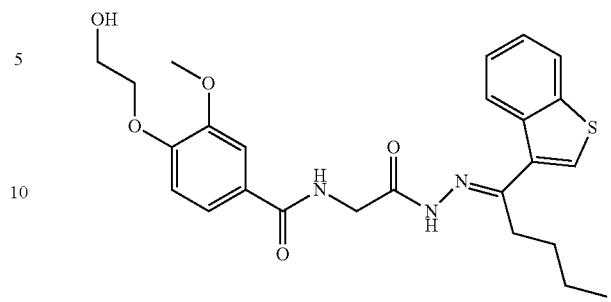

601

To a solution of 4-hydroxy-3-methoxybenzoic acid (6-A) (5 g, 29.7 mmol) in EtOH (20 mL) was added HCl. The mixture was stirred for 60° C. for 14 h. The reaction was concentrated to afford crude ethyl 4-hydroxy-3-methoxybenzoate (6-B) (4.6 g, 79% yield).

To a solution of ethyl 4-hydroxy-3-methoxybenzoate (6-B) (2.3 g, 11.7 mmol) and ethylene glycol (738 mg, 11.89 mmol) in anhydrous THF (20 mL) was added triphenylphosphine (6240 mg, 23.78 mmol) under $N_2$. The mixture was cooled to 0° C., DEAD (3.9 g, 24 mmol) was added in portions. The solution was stirred at rt for 2 h. The crude product was purified by column chromatography on silica gel eluted with PE:EA=20:1 to afford ethyl 4-(2-hydroxyethoxy)-3-methoxybenzoate (6-C) (1500 mg, 53.2%).

To a solution of ethyl 4-(2-hydroxyethoxy)-3-methoxybenzoate (6-C) (1 g, 4.2 mmol) in MeOH (20 mL) was added KOH (1.5 g, 22.7 mmol). The mixture was stirred at 40° C. for 2 h. Solvent was removed and the mixture was dissolved in water. The aqueous mixture was washed three times with tert-butylmethylether and the aqueous phase was maintained. The aqueous phase was treated with HCl to attain pH=6. The precipitate was collected by filtration. The residue was washed by water to afford 4-(2-hydroxyethoxy)-3-methoxybenzoic acid (6-D) (780 mg, 88%).

To a solution of 4-(2-hydroxyethoxy)-3-methoxybenzoic acid (6-D) (300 mg, 1.41 mmol) in DCM (10 mL) was added HATU (1075 mg, 2.82 mmol) and DIPEA (456 mg, 3.53 mmol), the mixture was stirred at rt for 30 mins, then was treated with glycine ethyl ester (197 mg, 1.41 mmol). The mixture was stirred at rt for another 15 h. The mixture was washed with water and the organic layer was collected. The solvent was removed and the residue was purified by silica gel column (PE/EA=20/1 to 5/1) to afford 6-E as a white solid (385 mg, 91.9%).

To a solution of 6-E (297 mg, 1 mmol) in anhydrous ethanol (10 mL) was added $N_2H_4 \cdot xH_2O$ (481 mg, 15 mmol), the mixture was stirred at 80° C. for 15 h. Then the mixture was allowed to cool to rt and a white precipitate was formed. The precipitate was filtered and washed with EtOH (20 mL) to afford 6-F as a white product (198 mg, 70%).

Compound 6-F (100 mg, 0.35 mmol) was dissolved in anhydrous EtOH (5 mL). To this solution was added 1-benzo[b]thiophene-3-yl-ethanone (62 mg, 0.353 mmol) and AcOH (0.4 mL). The mixture was stirred at 60° C. for 10 h. The mixture was filtered, and the solid was washed with EtOH (10 mL) and EA (10 mL) to afford compound 600 (85 mg, 55%). +ESI-MS: m/z 442.0.

Compound 601 was obtained following the procedure for obtaining compound 600 using 1-(7-fluorobenzo[b]thiophen-3-yl)pentan-1-one in place of 1-benzo[b]thiophene-3-yl-ethanone. Compound 601 was obtained as a white solid (30 mg, yield: 28.6%). +ESI-MS: m/z 485.92 [M+H]$^+$.

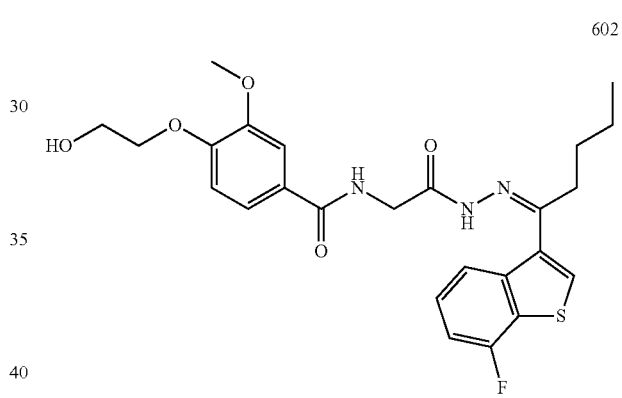

602

Compound 602 was obtained following the procedure for obtaining compound 600 using 1-(7-fluorobenzo[b]thiophen-3-yl)pentan-1-one in place of 1-benzo[b]thiophene-3-yl-ethanone. Compound 602 was obtained as a white solid (45 mg, 10.9%). +ESI-MS: m/z 501.9 [M+H]$^+$.

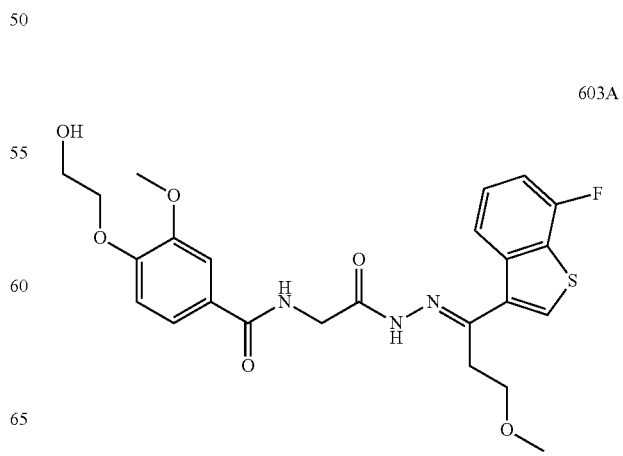

603A

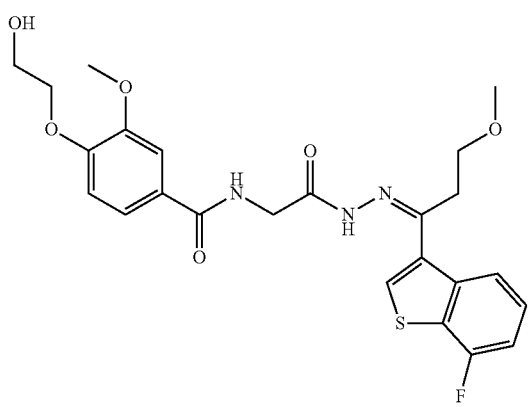

603B

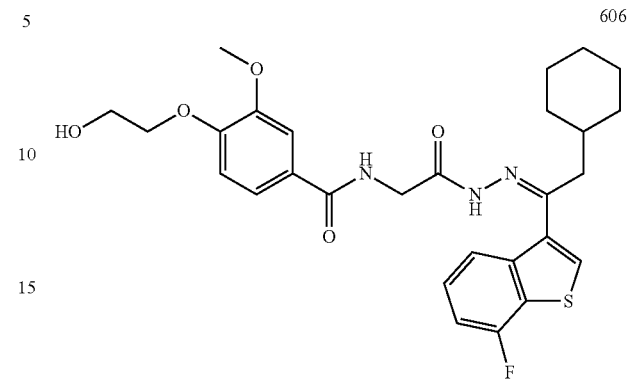

606 thiophene-3-yl-ethanone. Compound 605 was obtained as a white solid (80 mg, 20.5%). +ESI-MS: m/z 542.1 [M+H]⁺.

Compound 603A and compound 603B were obtained following the procedure for obtaining compound 600 using 1-(7-fluorobenzo[b]thiophen-3-yl)-3-methoxypropan-1-one in place of 1-benzo[b]thiophene-3-yl-ethanone. Compound 603A was obtained as a white solid (200 mg, yield: 47.0%) and compound 603B was obtained as a white solid (50 mg, yield: 11.5%). Compound 603A: +ESI-MS: m/z 503.82 [M+H]⁺. Compound 603B: +ESI-MS: m/z 503.87 [M+H]⁺.

Compound 606 was obtained following the procedure for obtaining compound 600 using 2-cyclohexyl-1-(7-fluorobenzo[b]thiophen-3-yl)ethanone in place of 1-benzo[b]thiophene-3-yl-ethanone. Compound 606 was obtained as a white solid (40 mg, 10.2%). +ESI-MS: m/z 542.7 [M+H]⁺.

Example 6-1

Preparation of Compound 650

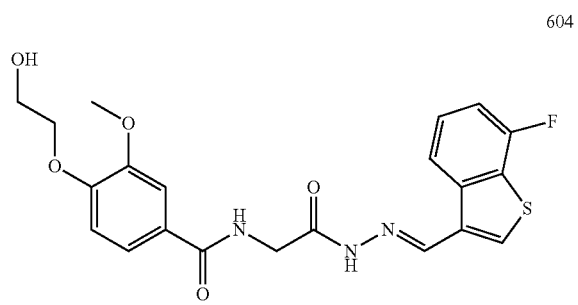 [SMILES: COc1cc(C(=O)NCC(=O)N/N=C/c2csc3c(F)cccc23)ccc1OCCO]

604

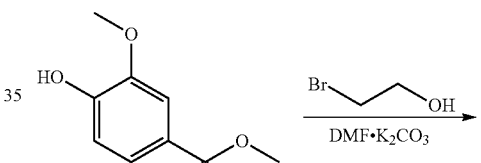

6-G

Compound 604 was obtained following the procedure for obtaining compound 600 using 7-fluorobenzo[b]thiophene-3-carboxaldehyde in place of 1-benzo[b]thiophene-3-yl-ethanone. Compound 604 was obtained as a white solid (40 mg, yield: 85.1%). +ESI-MS: m/z 446.0 [M+H]⁺.

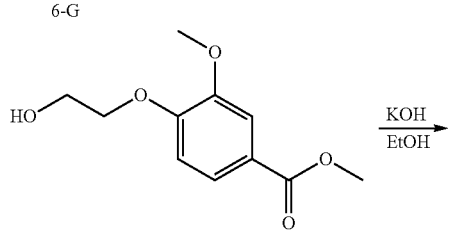

6-H

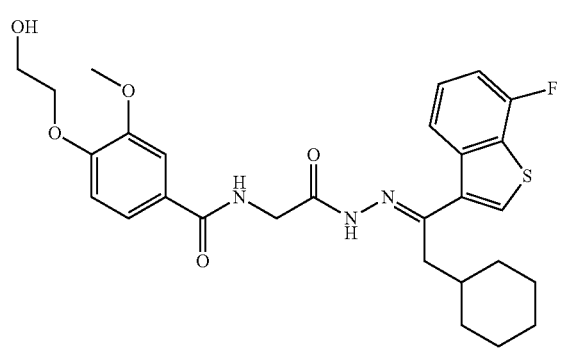

605

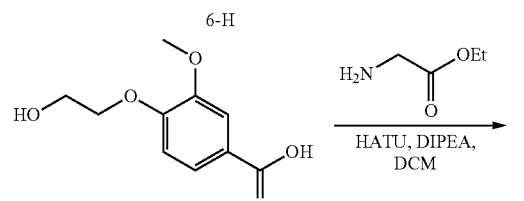

6-D

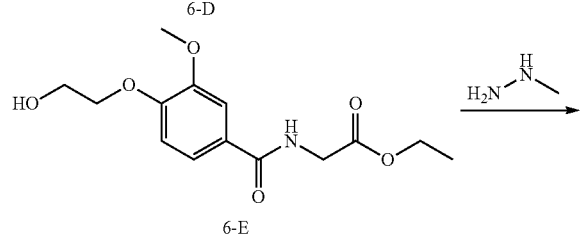

6-E

Compound 605 was obtained following the procedure for obtaining compound 600 using 2-cyclohexyl-1-(7-fluorobenzo[b]thiophen-3-yl)ethanone in place of 1-benzo[b]

165
-continued

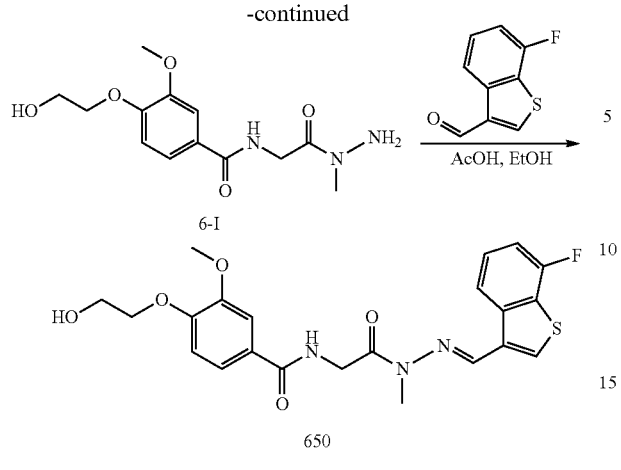

6-I

650

To a solution of methyl 4-hydroxy-3-methoxybenzoate (6-G) (15 g, 83 mmol) and $K_2CO_3$ (34 g, 246 mmol) in DMF (100 mL) was added 2-bromoethanol (30 g, 241 mmol) at 25° C. The mixture was stirred for 15 h at 90° C. The mixture was poured into water and extracted with EA, the combined organic phase was dried over anhydrous $Na_2SO_4$, filtered and the solvent was removed to provide a residue. The residue was purified by chromatography on silica gel (PE:EA=1:1) to afford methyl 4-(2-hydroxyethoxy)-3-methoxybenzoate (6-H) (9.5 g, 60%).

To a solution of methyl 4-(2-hydroxyethoxy)-3-methoxybenzoate (6-H) (9.0 g, 42 mmol) in EtOH (50 mL) was added KOH (15 g, 268 mmol) in $H_2O$ (50 mL). The mixture was stirred for 2 h at 70° C. The mixture was concentrated and a precipitate was formed by addition of 2 N HCl. The precipitate was collected by filtration and washed with $H_2O$ to afford 4-(2-hydroxyethoxy)-3-methoxybenzoic acid (6-D) (6.0 g, 60%). $^1$H NMR (400 MHz, DMSO-$d_6$) δ 12.63 (br, 1H), 7.55-7.52 (dd, J=2.0, 8.4 Hz, 1H), 7.44 (s, 1H), 7.04 (d, J=8.4 Hz, 1H), 4.89 (br, 1H), 4.06-4.03 (m, 2H), 3.80 (s, 3H), 3.75-3.73 (m, 2H).

To a solution of 4-(2-hydroxyethoxy)-3-methoxybenzoic acid (6-D) (6.0 g, 28 mmol), HATU (15 g, 39 mmol) and DIPEA (9 g, 70 mmol) in anhydrous DCM (100 mL) was added ethyl 2-aminoacetate (3.9 g, 28 mmol) at 25° C. The mixture was stirred for 10 h and then diluted with 1.0 N aqueous $NaHCO_3$ solution, extracted with EA. The combined organic phase was dried over anhydrous $Na_2SO_4$, and concentrated to afford a residue. The residue was purified by column chromatography to afford 6-E (4.0 g, 45%). $^1$H NMR (400 MHz, DMSO-$d_6$) δ 8.78-8.75 (br, 1H), 7.45 (m, 1H), 7.43 (s, 1H), 7.01 (d, J=8.4 Hz, 1H), 4.87-4.84 (m, 1H), 4.11-4.06 (m, 2H), 4.02-3.95 (m, 4H), 3.78 (s, 3H), 3.72-3.69 (m, 2H), 1.19-1.15 (m, 3H).

To a solution of 6-E (2.5 g, 8.4 mmol) in anhydrous EtOH (15 mL) was added methylhydrazine (18.3 g, 39 mmol). The mixture was stirred for 10 h at 70° C. and then cooled to rt. The solvent was removed to afford a residue and the residue was purified by prep-HPLC to afford 6-I (300 mg). $^1$H NMR (400 MHz, DMSO-$d_6$) δ 8.26 (br, 1H), 7.47 (m, 1H), 7.45 (s, 1H), 7.02 (d, J=8.4 Hz, 1H), 4.23 (m, 2H), 4.04-4.01 (m, 2H), 3.80 (s, 3H), 3.74-3.72 (m, 2H), 3.12 (m, 3H).

To a solution of 6-I (200 mg, 0.63 mmol) in anhydrous EtOH (6 mL) and AcOH (0.6 mL) was added 7-fluorobenzo[b]thiophene-3-carbaldehyde (121 mg, 0.63 mmol). The mixture was stirred at 70° C. for 10 h and then cooled to rt. A precipitate was formed and was collected by filtration. The solid was washed with EA and EtOH to afford compound 650 (120 mg, 30%). ESI-LCMS: m/z 459.9 [M+H]$^+$.

Example 6-2

Preparation of Compound 651

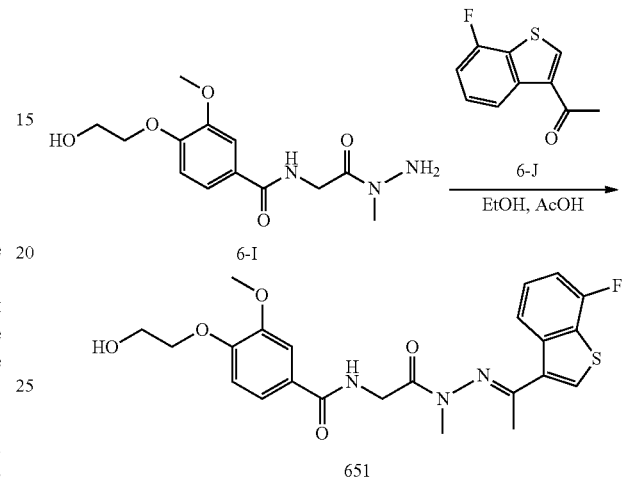

651

To a solution of 6-I (297 mg, 1 mmol) in anhydrous EtOH (6 mL) and AcOH (0.6 mL) was added 1-(7-fluorobenzo[b]thiophen-3-yl)ethanone (6-J) (250 mg, 1.29 mmol). The solution was stirred at 70° C. for 10 h and then cooled to rt. The solution was concentrated and the residue was purified by prep-HPLC to afford compound 651 (60 mg, 20%). ESI-LCMS: m/z 474 [M+H]$^+$.

Example 7

Preparation of Compound 700

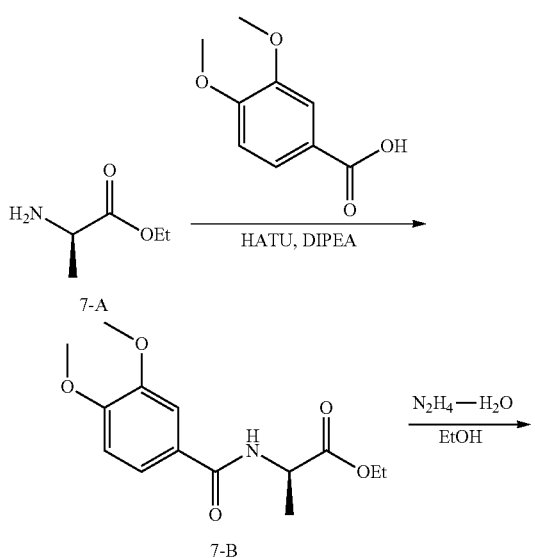

7-B

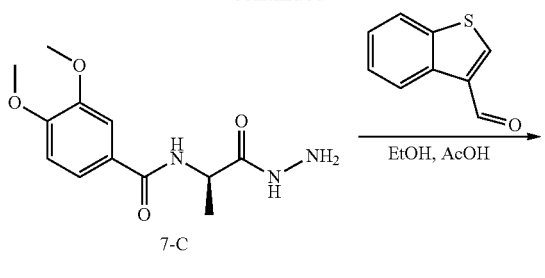

7-C

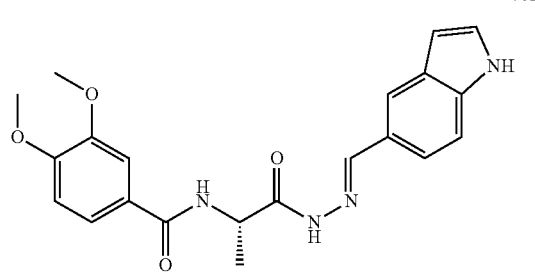

702

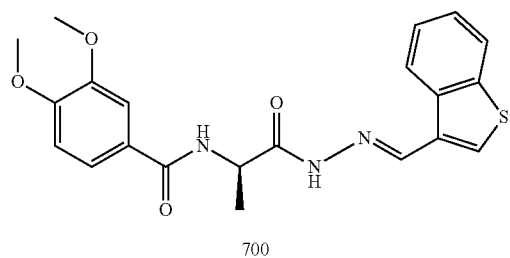

700

Compound 702 was obtained following the procedure for obtaining compound 700 using L-Alanine ethyl ester in place of D-Alanine ethyl ester and using 1H-indole-5-carboxaldehyde in place of benzo[b]thiophene-3-carboxaldehyde. Compound 702 was obtained as a white solid (120 mg, 71.8%). +ESI-MS: m/z 395.0 [M+H]$^+$.

To a solution of 3,4-dimethoxybenzoic acid (3.0 g, 14.3 mmol), HATU (6.5 g, 17.1 mmol) and DIPEA (3.1 g, 24 mmol) in anhydrous DCM (30 mL) was added D-Alanine ethyl ester (7-A) (2.5 g, 16.5 mmol) at 25° C. The mixture was stirred for 10 h and then diluted with 1.0 N aqueous NaHCO$_3$ solution (50 mL×2), extracted with EA (50 mL×2). The combined organic phase dried over anhydrous Na$_2$SO$_4$, and concentrated under reduced pressure to afford 7-B (2.5 g, 40%) used for next step directly without purification To a solution of 7-B (2.5 g, 8.9 mol) in anhydrous EtOH (50 mL) was added NH$_2$NH$_2$.H$_2$O (2.9 g, 90 mmol). The mixture was stirred for 10 h at 70° C. and then cooled to rt, A precipitate was formed and was collected by filtration to afford 7-C (1.8 g, 60%) used in the next step without purification.

To a solution of 7-C (250 mg, 0.94 mmol) in anhydrous EtOH (6 mL) and AcOH (0.2 mL) was added benzo[b]thiophene-3-carboxaldehyde (151 mg, 0.94 mmol). The solution was stirred at 70° C. for 10 h and then cooled to rt. A precipitate was formed and was collected by filtration. The solid was washed with EA and EtOH to afford compound 700 (50 mg, 10%). ESI-LCMS: m/z 412 [M+H]$^+$.

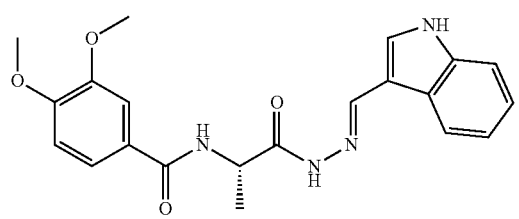

Compound 703 was obtained following the procedure for obtaining compound 700 using L-Alanine ethyl ester in place of D-Alanine ethyl ester and using 1H-indole-3-carboxaldehyde in place of benzo[b]thiophene-3-carboxaldehyde. Compound 703 was obtained as a white solid (134 mg, 78.8%). +ESI-MS: m/z 395.0 [M+H]$^+$.

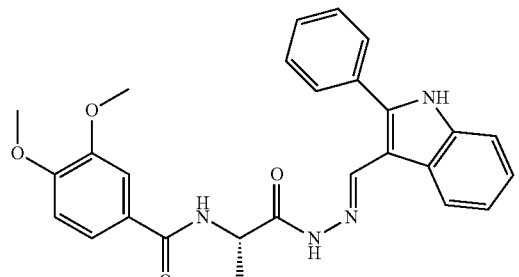

704

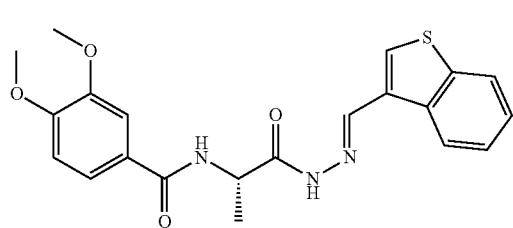

701

Compound 701 was obtained following the procedure for obtaining compound 700 using L-Alanine ethyl ester in place of D-Alanine ethyl ester. Compound 701 was obtained as a white solid (133 mg, 77.8%). +ESI-MS: m/z 368.0 [M+H]$^+$.

Compound 704 was obtained following the procedure for obtaining compound 700 using L-Alanine ethyl ester in place of D-Alanine ethyl ester and using 2-phenyl-1H-indole-3-carboxaldehyde in place of benzo[b]thiophene-3-carboxaldehyde. Compound 704 was obtained as a white solid (135 mg, 79.2%). +ESI-MS: m/z 471.0 [M+H]$^+$.

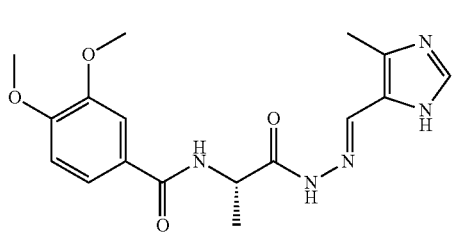

Compound 705 was obtained following the procedure for obtaining compound 700 using L-Alanine ethyl ester in place of D-Alanine ethyl ester and using 4-methyl-1H-imidazole-5-carboxaldehyde in place of benzo[b]thiophene-3-carboxaldehyde. Compound 705 was obtained as a white solid (131 mg, 76.6%). +ESI-MS: m/z 360.0 [M+H]⁺.

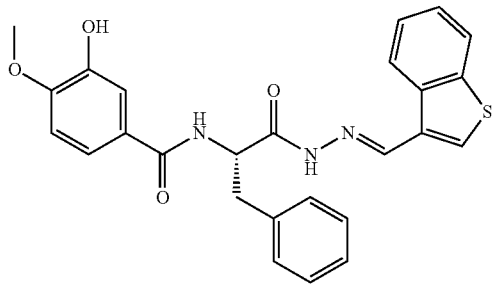

Compound 706 was obtained following the procedure for obtaining compound 700 using 3-hydroxy-4-methoxybenzoic acid in place of 3,4-dimethoxybenzoic acid and using L-Phenylalanine ethyl ester in place of D-Alanine ethyl ester. Compound 706 was obtained as a white solid (32 mg, 24.4%). +ESI-MS: m/z 438.1 [M+H]⁺.

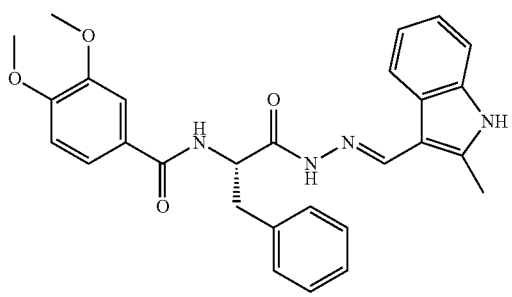

Compound 707 was obtained following the procedure for obtaining compound 700 using L-Phenylalanine ethyl ester in place of D-Alanine ethyl ester and 2-methyl-1H-indole-3-carboxaldehyde in place of benzo[b]thiophene-3-carboxaldehyde. Compound 707 was obtained as a white solid (30 mg, 24.7%). +ESI-MS: m/z 485.2 [M+H]⁺.

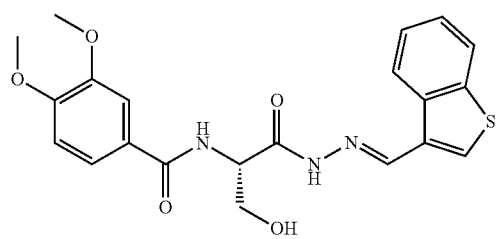

Compound 708 was obtained essentially following the procedure for obtaining compound 700. Compound 708 was obtained as a white solid (3 mg, 7.05%). +ESI-MS: m/z 428.0 [M+H]⁺.

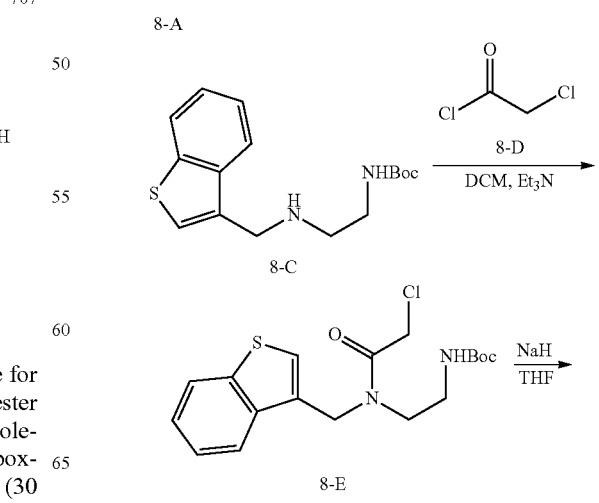

Compound 709 was obtained essentially following the procedure for obtaining compound 700. Compound 709 was obtained as a white solid (13 mg, 22.7%). +ESI-MS: m/z 438.1 [M+H]⁺.

Example 8

Preparation of Compound 800

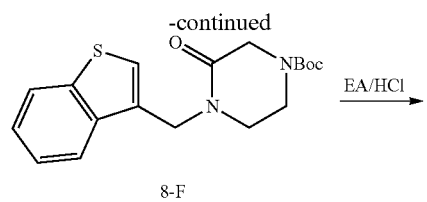

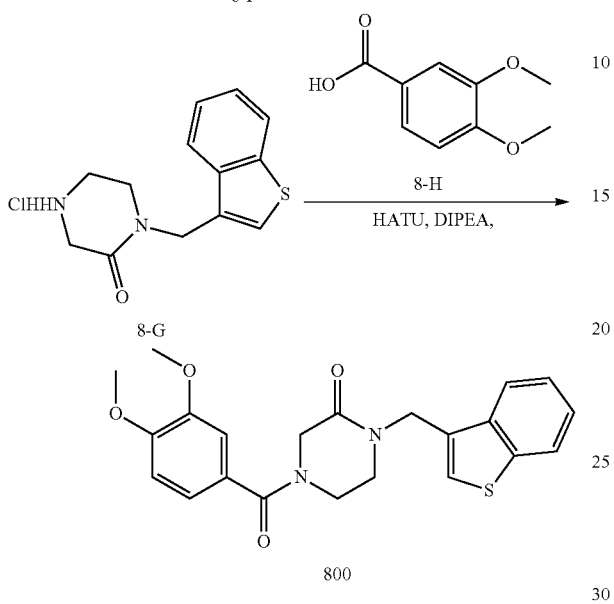

To a solution of benzo[b]thiophene-3-carboxaldehyde (8-a) (10 g, 62 mmol) in THF (100 mL), N-Boc-ethylenediamine (8-B) was added. The mixture was stirred for 1 hour at rt. Then NaBH(OAc)₃ was added. The solution was stirred for 15 h at rt. The mixture was treated with aqueous NaHCO₃ and extracted with EA. The organic phase was concentrated and the residue was purified by chromatography on silica gel (PE:EA=10:1-5:1) to afford 8-C (7 g, yield: 37.4%).

To a solution of 8-C (0.4 g, 1.3 mmol) in DCM (5 mL), was added Et₃N (0.132 g, 1.3 mmol). Then chloroacetyl chloride (8-D) (0.15 g, 1.3 mmol) was added dropwise at 0° C. The solution was stirred for 1 hour and then treated with aqueous NH₄Cl followed by extraction with DCM. The organic phase was removed to afford 8-E as a residue. The residue was dissolved in THF and then NaH was added slowly at 0° C. The solution was stirred for 2 h and then treated with aqueous NH₄Cl followed by extraction with DCM. The organic phase was removed to afford crude 8-F (0.3 g, yield: 65.0%)

To a solution of 8-F (0.3 g, 0.86 mmol) in ethylacetate (5 mL), a solution of HCl in ethylacetate was added. The mixture was stirred for 4 h at rt. The precipitate was collected and washed with EA (EA) to afford crude 8-G (0.18 g, 84.9%)

To a solution of 8-G (90 mg, 0.316 mmol) in DCM (3 mL), 3,4-dimethoxybenzoic acid (8-H) (58 mg, 0.316 mmol), HATU (180 mg, 0.47 mmol) and DIPEA (122 mg, 0.95 mmol) were added. The mixture was stirred for 3 h at rt. The mixture was washed with water and partitioned. The organic phase was dried over Na₂SO₄. Then the solvent was removed and the residue was purified by recrystallization to afford compound 800 (60 mg, 46.0%). +ESI-MS: m/z 411.1 [M+H]⁺.

Example 8-1

Preparation of Compounds 839 and 840

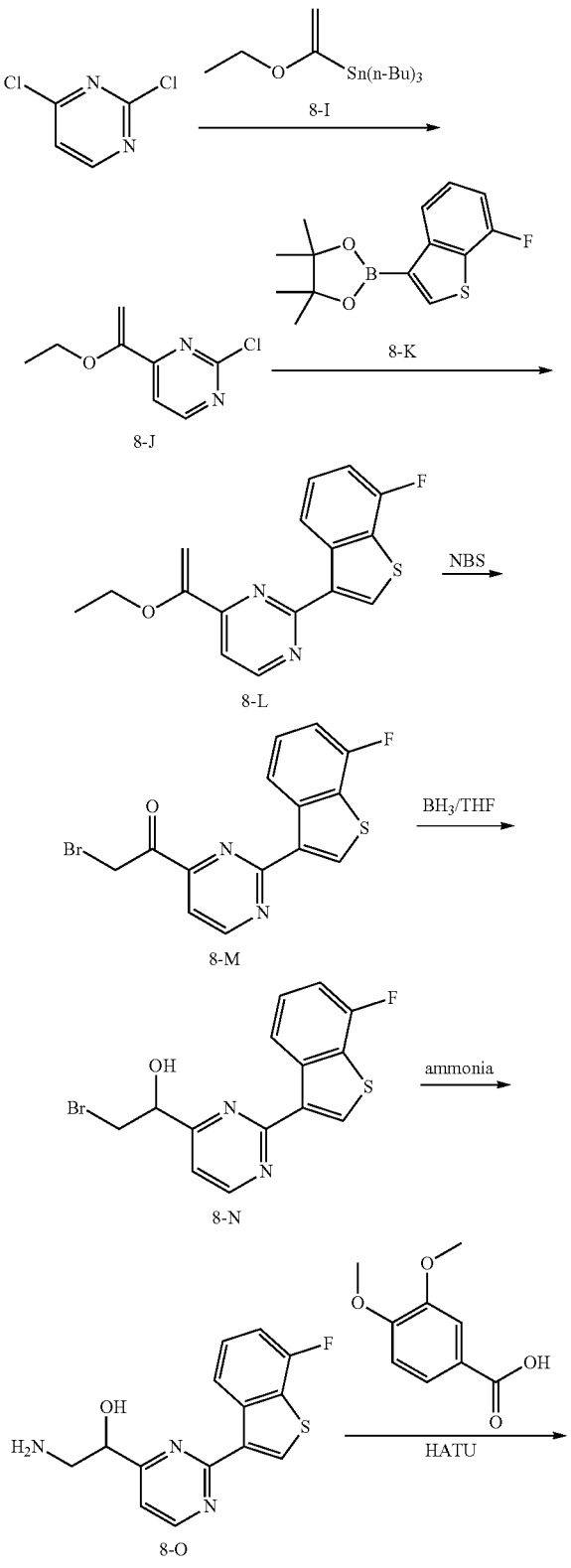

-continued

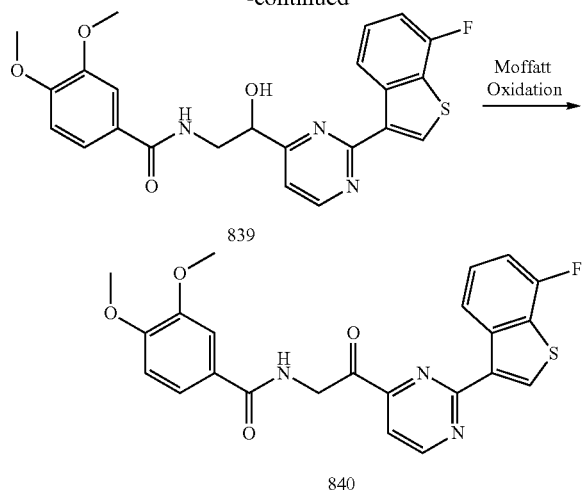

To a stirred solution of 2,4-dichloropyrimidine (10 g, 1.0 eq), KF (12.9 g, 4.0 eq), Pd(dppf)Cl₂ (0.5 g) in dry 100 mL of DMF was added tributyl(1-ethoxyvinyl)stannane (8-I) (25.4 g, 1.05 eq), and the mixture was stirred at 85° C. under N₂ over 4 h. The mixture was cooled to rt, poured into ice-cold water and extracted by MTBE, The combined organic layer was washed with water and brine, concentrated, purified by silica gel (PE/EA: 100/1 to 50/1) to afford 2-chloro-4-(1-ethoxyvinyl)pyrimidine (8-J) (10 g, 80% yield) as a pale yellow solid. ¹H NMR (400 MHz, CDCl₃) δ 8.61-8.60 (s, 1H), 7.57-7.56 (s, 1H), 5.73-5.72 (s, 1H), 4.58-4.57 (s, 1H), 4.00-3.94 (q, 2H), 1.45-1.42 (t, 3H).

To a stirred solution of 2-chloro-4-(1-ethoxyvinyl)pyrimidine (8-J) (2 g, 1.0 eq), KF (2.5 g, 4.0 eq), Pd(dppf)Cl2 (0.2 g) in 20 mL of dry DMF was added 2-(7-fluorobenzo[b]thiophen-3-yl)-4,4,5,5-tetramethyl-1,3,2-dioxaborolane (8-K) (3.3 g, 1.1 eq), and the mixture was stirred at 85° C. under N₂ over 4 h. The mixture was cooled to rt, poured into ice-cold water and extracted by MTBE. The combined organic extract was washed with water and brine, concentrated, purified by silica gel (PE/EA: 100/1 to 50/1) to afford 2.2 g of 4-(1-ethoxyvinyl)-2-(7-fluorobenzo[b]thiophen-3-yl)pyrimidine (8-L) (67% yield) as a pale yellow solid. ¹H NMR (400 MHz, CDCl₃) δ 8.93-8.90 (d, 1H), 8.84-8.83 (d, 1H), 8.64-8.63 (s, 1H), 7.55-7.54 (d, 1H), 7.47-7.46 (t, 1H), 7.15-7.08 (m, 1H), 5.84-5.83 (d, 1H), 4.59-4.58 (d, 1H), 4.03-3.98 (t, 2H), 1.48-1.41 (q, 3H).

To a stirred solution of 4-(1-ethoxyvinyl)-2-(7-fluorobenzo[b]thiophen-3-yl)pyrimidine (8-L) (1.2 g, 1.0 eq) in 8 mL of THF and 3 mL of water was added NBS (0.75 g, 1.05 eq) at 0° C. portionwise, after this addition, the mixture was stirred at 0° C. for 10 mins, then quenched by saturated NaHCO₃, and extracted with EA. The combined organic extracted was purified by silica gel to afford 1.0 g of 2-bromo-1-(2-(7-fluorobenzo[b]thiophen-3-yl) pyrimidin-4-yl)ethanone (8-M) (70% yield) as a pale yellow solid. ¹H NMR (400 MHz, CDCl₃) δ 9.12-9.11 (d, 1H), 8.88-8.87 (d, 1H), 8.74-8.73 (s, 1H), 7.84-7.83 (d, 1H), 7.54-7.48 (m, 1H), 7.18-7.13 (m, 1H), 4.88 (s, 1H).

A mixture of 2-bromo-1-(2-(7-fluorobenzo[b]thiophen-3-yl)pyrimidin-4-yl)ethanone (8-M) (1 g, 1.0 eq) in dry THF at −20° C. under N₂ was added dropwise 1.0M BH₃/THF (2.85 mL, 1.0 eq), after this addition, the mixture was stirred at −20° C. for 30 mins and allowed to warm to 0° C. for 1 hour. The reaction was quenched with MeOH, washed with NaHCO₃, and brine, dried over Na₂SO₄, concentrated to afford crude 2-bromo-1-(2-(7-fluorobenzo[b]thiophen-3-yl)pyrimidin-4-yl)ethanol (8-N) (1 g, 100%) as a pale yellow oil. ¹H NMR (400 MHz, CDCl₃) δ 8.88-8.87 (d, 1H), 8.82-8.79 (d, 1H), 8.65-8.64 (s, 1H), 7.50-7.45 (m, 1H), 7.42-7.40 (d, 1H), 7.16-7.11 (m, 1H), 5.08-5.04 (br, 1H), 4.15-4.10 (q, 1H), 3.97-3.93 (q, 1H), 3.68-3.66 (br, 1H).

A mixture of 2-bromo-1-(2-(7-fluorobenzo[b]thiophen-3-yl)pyrimidin-4-yl)ethanone (8-N) (0.4 g, 1.0 eq) in 8 mL of EtOH and 8 mL of aqueous ammonia in a seal tube was heated to 100° C. for 5 h. The mixture was concentrated to afford a residue. The residue was dissolved in EA, washed with saturated NaHCO₃, and brine, dried over Na₂SO₄, concentrated to afford crude 2-amino-1-(2-(7-fluorobenzo[b] thiophen-3-yl)pyrimidin-4-yl)ethanol (8-O) (0.3 g, 92%) as a pale yellow oil. ¹H NMR (400 MHz, DMSO-d₆) δ 8.98-8.71 (m, 3H), 7.60-7.50 (m, 2H), 7.37-7.33 (br, 1H), 5.78-5.72 (s, 1H), 4.63-4.58 (br, 1H), 3.07-3.01 (m, 1H), 2.82-2.75 (m, 1H).

A mixture of 3,4-dimethoxybenzoic acid (0.189 g, 1.2 eq) and HATU (0.427 g, 1.3 eq), DIPEA (0.199 g, 2.0 eq) in DMF was stirred at rt for 10 mins, then 2-amino-1-(2-(7-fluorobenzo[b]thiophen-3-yl)pyrimidin-4-yl)ethanol (8-0) (0.25 g, 1.0 eq.) was added. The mixture was stirred at rt for an additional 2 h, then treated with NaHCO₃, washed with brine, concentrated, purified by silica gal to afford N-(2-(2-(7-fluorobenzo[b]thiophen-3-yl)pyrimidin-4-yl)-2-hydroxyethyl)-3,4-dimethoxy-benzamide (compound 839) (0.25 g, 51%) as a white solid. ESI-LCMS: m/z 454.1 [M+H]⁺.

A stirred solution of anhydrous pyridine (12.5 mg, 1.2 eq) in anhydrous DMSO (0.2 mL) cooled with a cold water bath (10° C.) under argon was treated with TFA (9 mg, 0.6 eq). After addition, the TFA/pyridine solution was warmed to rt and added (with syringe) very slowly to a stirred solution of N-(2-(2-(7-fluorobenzo[b]thiophen-3-yl)pyrimidin-4-yl)-2-hydroxyethyl)-3,4-dimethoxy-benzamide (839) (60 mg, 1.0 eq) and DCC (81.8 mg, 3.0 eq) in anhydrous DMSO (0.5 mL) cooled with cold water (~10° C.) under argon. The mixture was stirred at rt (22-24° C.) under argon for 18 h and then cooled with cold water (~10° C.). The cooled reaction was quenched slowly with water (1 mL) and stirred at rt for 1 hour. The isolated crude product was purified by prep-HPLC to afford compound 840 (6 mg, 9.9%) as a white solid. ¹H NMR (400 MHz, CDCl₃) δ 9.28-9.26 (d, 1H), 8.08 (s, 1H), 8.95-8.93 (d, 1H), 8.87-8.86 (t, 1H), 7.88-7.86 (d, 1H), 7.68-7.60 (m, 1H), 7.57-7.52 (d, 1H), 7.51-7.50 (s, 1H), 7.42-7.37 (t, 1H), 7.08-7.04 (d, 1H), 5.07-5.05 (d, 1H), 3.83-3.81 (d, 6H).

Example 8-2

Preparation of Compound 860

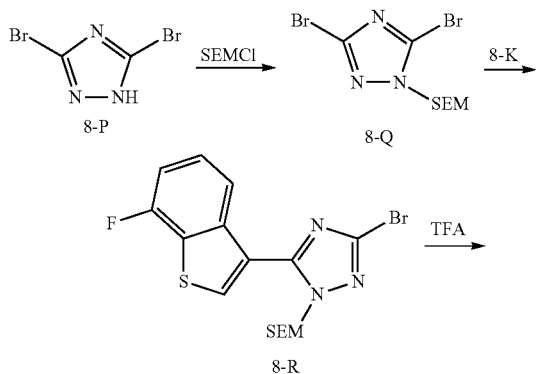

-continued

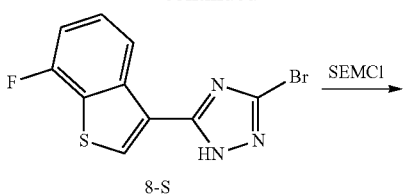

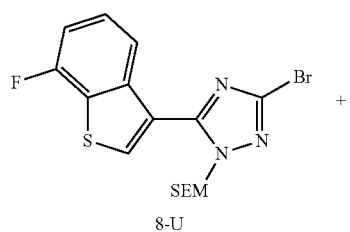

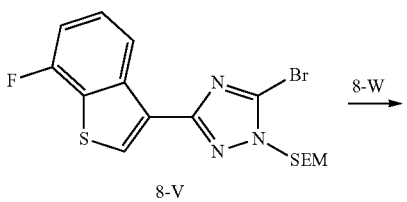

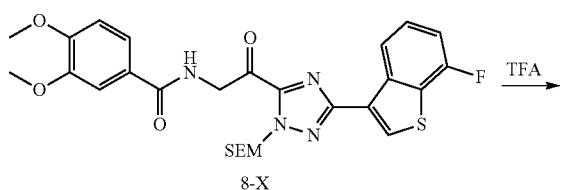

A mixture of 3,5-dibromo-1H-1,2,4-triazole (8-P) (11 g, 50 mmol) and Et₃N (10 mL) in DCM (200 mL) at rt was added 2-(trimethylsilyl)ethoxymethyl chloride (SEMCl) (8.5 g, 50 mmol) in portions. Subsequently, the mixture was stirred for 30 mins at rt, then the volatiles were removed. Purification by column chromatography on silica gel (PE) afforded 8-Q as colorless oil (17 g, 96%). +ESI-MS: m/z 299.7 [M-57]⁺.

A flask with a magnetic stirring bar under a N₂ atmosphere was charged with 8-Q (1.05 g, 3 mmol), 8-K (920 mg, 3.4 mmol), Pd(dppf)Cl₂ (24 mg, 1 mol %), Cs₂CO₃ (3 g, 3 eq), and dry DMF (50 mL). The mixture was stirred for 10 h at 100° C., then 50 mL water and 50 mL EA were added. The organic layer was separated and maintained, and the aqueous phase extracted with EA. The combined organic phases were dried (MgSO₄) and the volatiles were removed. Purification by column chromatography on silica gel (PE) afforded 8-R as an oil (800 mg, 62%). +ESI-MS: m/z 429.7 [M+H]⁺.

Compound 8-R (400 mg, 0.93 mmol) in DCM (10 mL) was treated with TFA (10 mL). The mixture was stirred for 2 h at rt, then the solvent was evaporated to afford the crude product as an oil. The crude product was purified by column chromatography on silica gel (EA) to afford 8-S. (277 mg, 100%). +ESI-MS: m/z 297.7 [M+H]⁺.

To a mixture of 8-S (277 mg, 0.93 mmol) and Et₃N (1 mL) in DCM (50 mL) at rt was added SEMCl (166 mg, 1 mmol) in portions, after that, the mixture was stirred for additional 30 mins at rt, then the volatiles were removed under reduced pressure. Purification by column chromatography on silica gel (PE) provided 8-U and 8-V as colorless oil (328 mg, 100%).

A mixture of 8-U and 8-V (328 mg, 0.93 mmol) and 8-W (282 mg, 1 mmol) in THF (10 mL) at rt under nitrogen atmosphere was treated with i-PrMgCl (0.2 mL, 1.3 M) in portions, after that, the mixture was stirred for additional 10 mins at rt, quenched with NH₄Cl saturated solution, extracted with EA, dried over Na₂SO₄, then the volatiles were removed. Purification by column chromatography on silica gel (PE/EA=2/1) afforded 8-X as colorless oil (200 mg, 36%). +ESI-MS: m/z 571.1 [M+H]⁺

To 8-X (200 mg, 0.38 mmol) in DCM (10 mL) was added TFA (10 mL). The mixture was stirred for 2 h at rt, and then the solvent was removed to afford the crude product as oil. The crude product was purified by Pre-HPLC to afford the compound 860 (50 mg, 100%). +ESI-MS: m/z 440.8 [M+H]⁺.

Example 8-3

Preparation of Compound 8-W

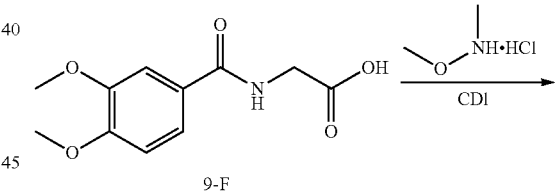

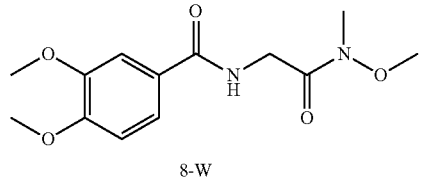

To a solution of 2-(3,4-dimethoxybenzamido)acetic acid (9-F) (4.8 g, 20 mmol) in DCM at rt was added CDI (3.2 g, 20 mmol) in portions, the mixture was stirred for 30 mins at rt, and then N,O-dimethylhydroxylamine hydrochloride was added, and stirring was continued for 4 h. After 4 h, 100 mL water was added to the stirring mixture and the layers were separated. The organic layer was maintained and the aqueous phase extracted with CH₂Cl₂. The combined organic phases were dried (MgSO₄) and the volatiles were removed to afford a residue. Purification by column chromatography on silica gel (EA/PE=1:1) afforded 8-W as a white solid (5.6, 100%). +ESI-MS: m/z 304.8 [M+Na]⁺.

Example 8-4

Preparation of Compound 8-K

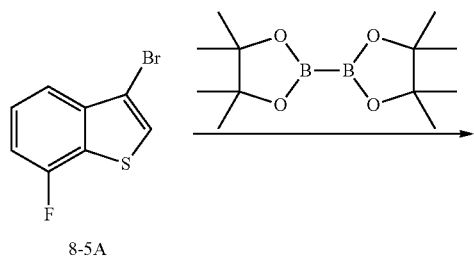

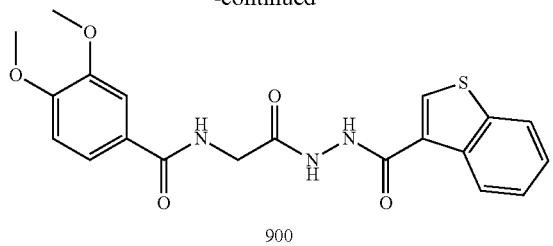

A 250 mL flask with a magnetic stirring bar under a N$_2$ atmosphere was charged with 8-5A (4.6 g, 20 mmol), octamethyl-2,2'-bi(1,3,2-dioxaborolane) (10 g, 40 mmol), Pd(dppf)Cl$_2$ (160 mg, 1 mol %), KOAc (8.0 g, 80 mmol), and dry DMF (50 mL). The mixture was stirred for 10 h at 100° C., and then 50 mL water and 50 mL EA were added. The organic layer was separated and maintained and the aqueous phase was extracted with EA. The combined organic phases were dried (MgSO$_4$) and the volatiles were removed. Purification by column chromatography on silica gel (PE) afforded 8-K as oil (5.6 g). $^1$H NMR (400 MHz, DMSO-d$_6$) δ 8.13 (d, J=8.2 Hz, 1H), 8.07 (s, 1H), 7.34 (dt, J=5.2, 7.9 Hz, 1H), 7.05-6.98 (m, 1H), 1.37 (s, 12H).

Example 9

Preparation of Compound 900

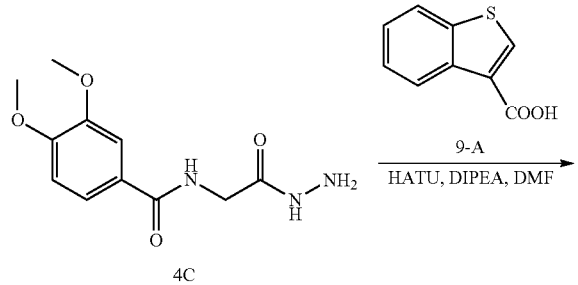

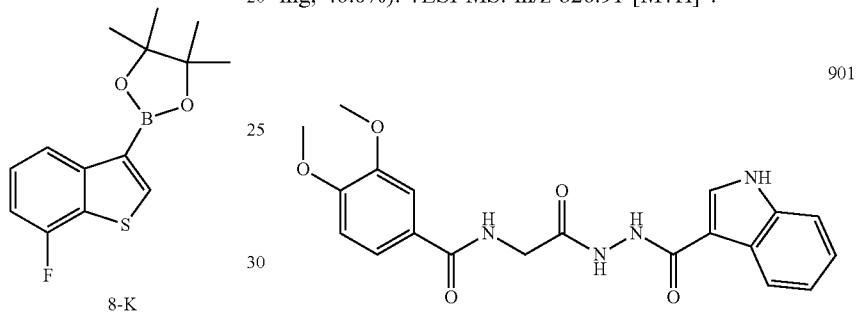

To a solution of N-(2-hydrazinyl-2-oxoethyl)-3,4-dimethoxybenzamide (4-C) (134 mg, 0.564 mmol) in DMF (2 mL), benzo[b]thiophene-3-carboxylic acid (9-A) (100 mg, 0.564 mmol), HATU (322 mg, 0.847 mmol) and DIPEA (218 mg, 1.69 mmol) were added. The mixture was stirred for 15 h at rt. The mixture was treated with water providing a solid. The solid was collected to afford compound 900 (50 mg, 46.0%). +ESI-MS: m/z 826.91 [M+H]$^+$.

Compound 901 was obtained following the procedure for obtaining compound 900 using 1H-indole-3-carboxylic acid in place of benzo[b]thiophene-3-carboxylic acid. Compound 901 was obtained as a white solid (10 mg, 34.8%). +ESI-MS: m/z 396.0 [M+H]$^+$.

Example 9-1

Preparation of Compound 902

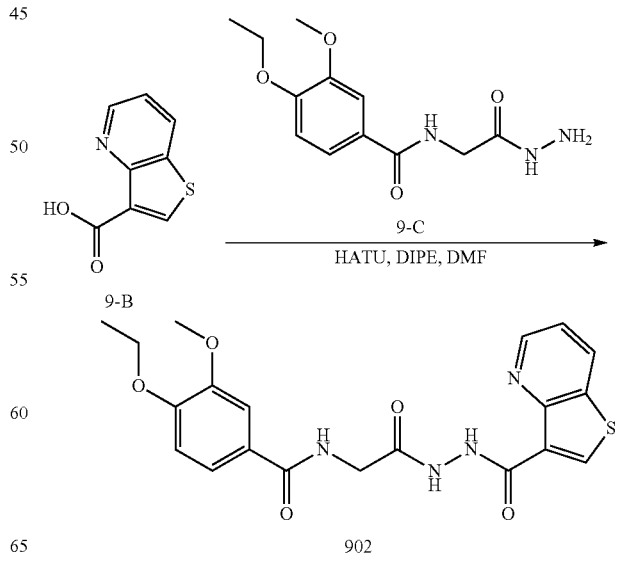

To a solution of thieno[3,2-b]pyridine-3-carboxylic acid (9-B) (50 mg, 0.277 mmol) in DMF (2 mL), 9-C (100 mg, 0.374 mmol), HATU (275 mg, 0.723 mmol) and DIPEA (187 mg, 1.69 mmol) were added. The mixture was stirred for 15 h at rt. The mixture was treated with water and extracted with EA. The organic phase was concentrated and the residue was purified by prep-HPLC to afford compound 902 (30 mg, 25.4%). +ESI-MS: m/z 429.0 [M+H]$^+$.

Example 9-2

Preparation of Compound 903

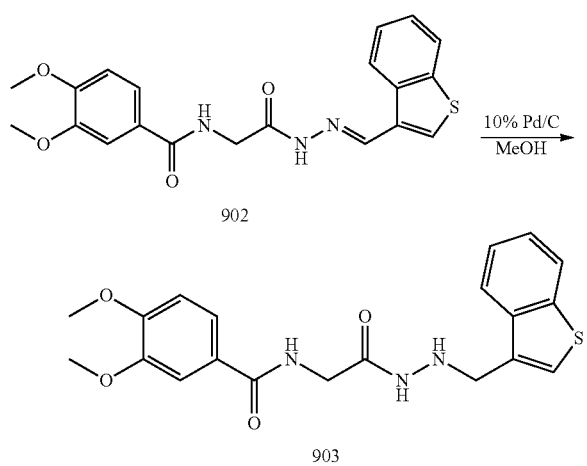

902

903

To a solution of compound 401 (94.2 mg, 0.237 mmol) in anhydrous MeOH (10 mL) was added 10% Pd/C (20 mg) under a nitrogen atmosphere. The nitrogen atmosphere was replaced with a hydrogen atmosphere and then the mixture was stirred at rt for 4 h. The hydrogen atmosphere was replaced with nitrogen and then the mixture was filtered through a pad of celite. The filtrate was concentrated under reduced pressure to afford compound 903 as a white solid (92.4 mg, 97.6%). +ESI-MS: m/z 400.0[M+H]$^+$.

Example 9-3

Preparation of Compound 904

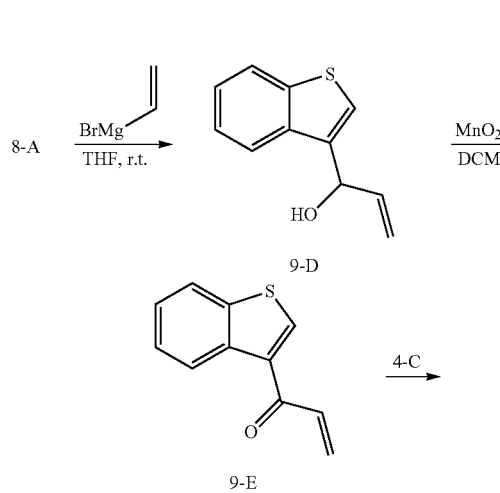

-continued

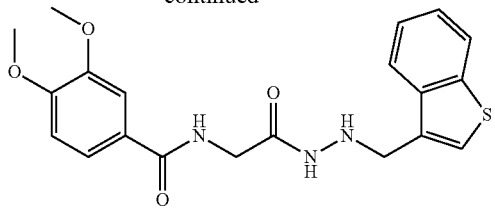

904

To a solution of benzo[b]thiophene-3-carboxaldehyde (8-A) (3.22 g, 20 mmol) in THF (20 mL), vinyl magnesium bromide (20 mmol, 1M in Et$_2$O) was added dropwise at rt. The mixture was stirred for 2 h at rt. The mixture was treated with aqueous NH$_4$Cl and extracted with EA. The organic phase was concentrated and the residue was purified by column chromatography on silica gel (PE:EA=50:1) to afford 9-D (2.50 g, 65.7%).

To a solution of 9-D (1 g, 5.26 mmol) in DCM (10 mL), MnO$_2$ (2.7 g, 31 mmol) was added at rt. The reaction solution was stirred for 15 h at 40° C. The solid was removed by filtration and the organic phase was concentrated. The residue was purified by column chromatography on silica gel (PE:EA=100:1-20:1) to afford 9-E (250 mg, 25.3%).

To a mixture of 9-E (100 mg, 0.532 mmol) in ethanol (5 mL), 4-C (134 mg, 0.532 mmol) was added. The mixture was stirred for 2 h at rt. The mixture was filtrated and the solid was collected and washed with ethanol to afford compound 904 (30 mg, 14%). +ESI-MS: m/z 442.1 [M+H]$^+$.

Example 9-4

Preparation of Compound 905

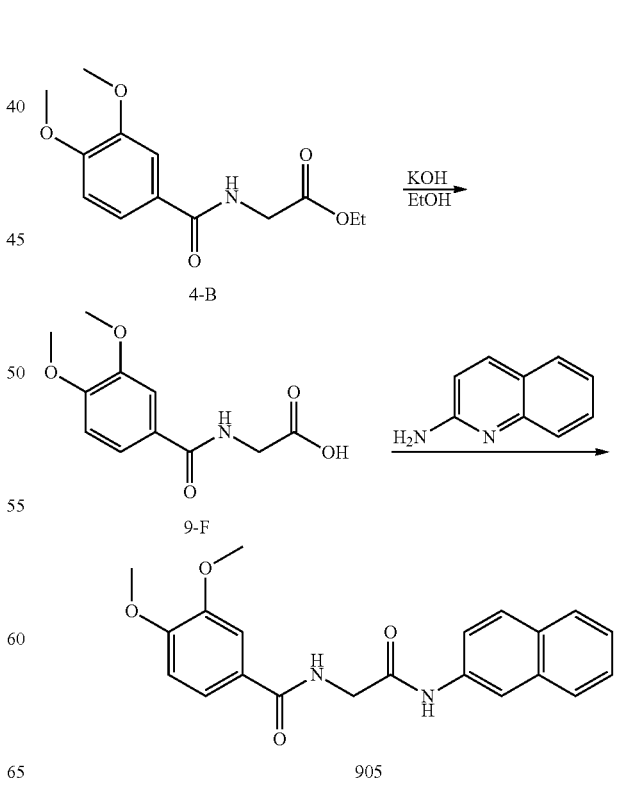

4-B

9-F

905

To a solution of 4-B (16 g, 60 mmol) in EtOH (300 mL) was added KOH (32 g, 570 mmol) in H₂O (300 mL). The mixture was stirred for 2 h at 70° C. The mixture was concentrated, acidified with 2N HCl to form a precipitate. The precipitate was collected by filtration and washed with H₂O to afford 9-F (13 g, 80%). $^1$H NMR (400 MHz, DMSO-d6) δ 12-28-12.43 (br, 1H), 8.71-8.68 (br, 1H), 7.51-7.49 (m, 1H) 7.46 (d, J=2.0 Hz, 1H), 7.02 (d, J=8.4 Hz, 1H), 3.91 (d, J=5.8 Hz, 2H), 3.80 (s, 6H).

A mixture of 9-F (0.8 g, 3.3 mmol) and acetic anhydride (5 mL) was heated 70° C. for 2 h and then the acetic anhydride was removed to afford the mixed anhydride. The anhydride was dissolved in THF and treated with quinolin-2-amine (50 mg, 0.33 mmol). The mixture was stirred for 10 h at 70° C. The solvent was removed to afford a residue and the residue was purified by prep-HPLC to afford compound 905 (10 mg, 10%). +ESI-LCMS: m/z 366.0 [M+H]⁺.

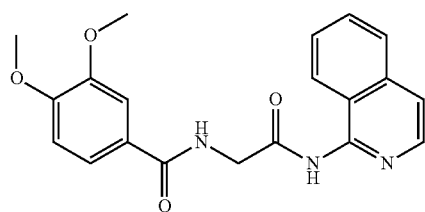

906

Compound 906 was obtained following the procedure for obtaining compound 905 using isoquinolin-1-amine in place of quinolin-2-amine. Compound 906 was obtained as a white solid (12 mg, 36.1%). +ESI-MS: m/z 366.0 [M+H]⁺.

Example 9-5

Preparation of Compound 907

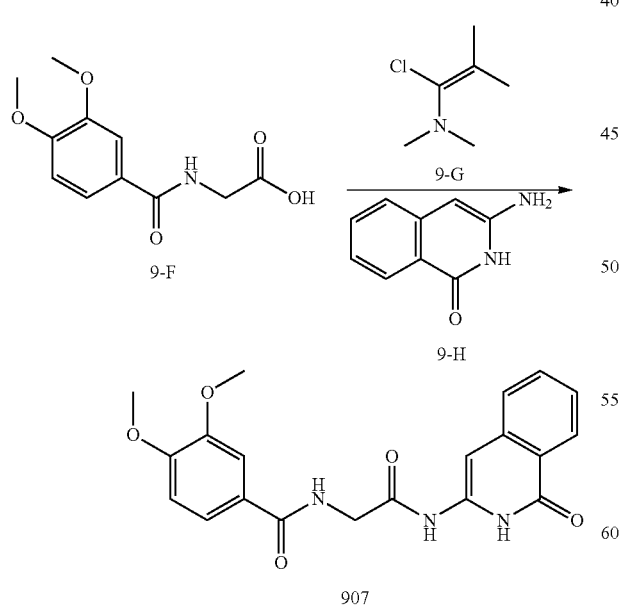

To a solution of 9-F (150 mg, 0.63 mmol) in anhydrous DCM (3 mL) was added 1-chloro-N,N,2-trimethyl-1-propenylamine (9-G) (101 mg, 0.69 mmol) at 0° C. under N₂. The solution was warmed to rt and stirred for 30 mins. Subsequently, 3-aminoisoquinolin-1(2H)-one (9-H) (60 mg, 0.38 mmol) in dry DMF (1 mL) and pyridine (0.5 mL) was added. The mixture was stirred at rt for 10 h. The mixture was concentrated and the crude material was purified by pre-HPLC to afford the compound 907 (15 mg, 10%). ESI-LCMS: m/z 382 [M+H]⁺.

Example 9-6

Preparation of Compound 9-H

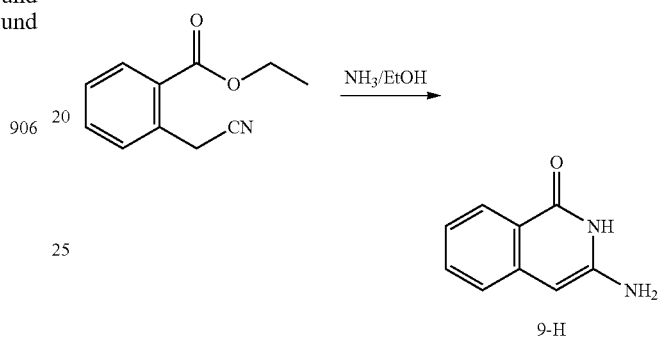

A mixture of ethyl 2-cyanomethylbenzoate (0.8 g, 4 mmol) and NH₃/EtOH (30 mL) in a sealed tube was heated to 50° C. for 3 days and then cooled to rt. A precipitate was formed and was collected to afford 3-aminoisoquinolin-1 (2H)-one (9-H) (100 mg, 15%). $^1$H NMR (DMSO-d₆, 400 MHz) δ 11.66-10.44 (br, 1H), 7.89-7.87 (m, 1H), 7.40-7.36 (m, 1H), 7.19 (d, J=7.9 Hz, 1H), 6.99-6.95 (m, 1H), 5.54 (br, 1H). 5.43 (s, 1H).

Example 9-7

Preparation of Compound 908

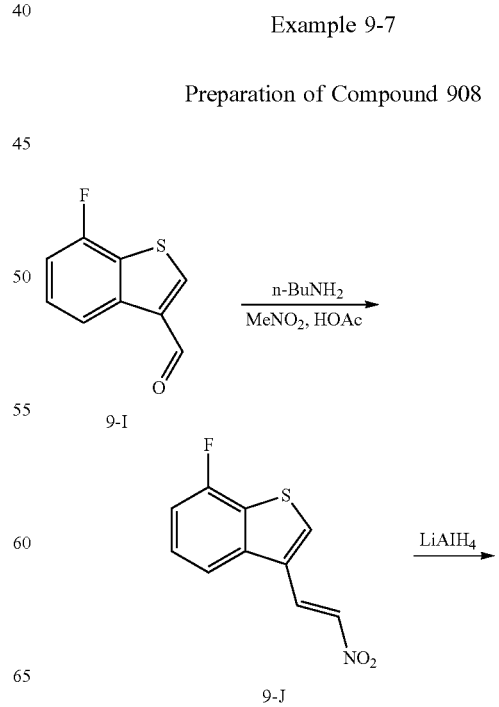

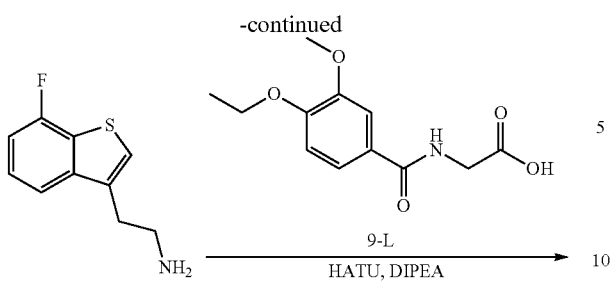

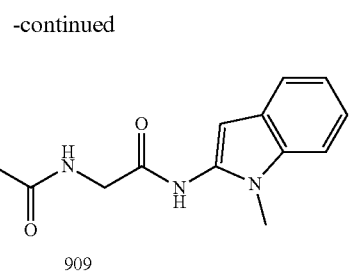

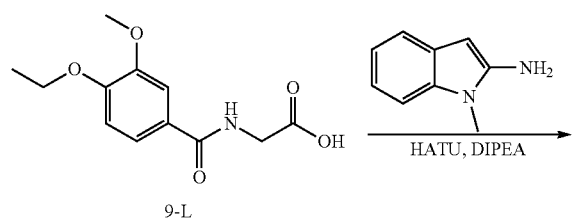

A mixture of 7-fluorobenzo[b]thiophene-3-carboxaldehyde (9-I) (1.0 g, 5.6 mol), n-BuNH$_2$ (0.49 g, 6.7 mmol) and MeNO$_2$ (1.1 g, 18 mmol) in HOAc (6 mL) was heated to 80° C. for 3 h. The mixture was poured into H$_2$O and extracted with DCM. The organic layer was removed. The crude product was recrystallized from EtOH to afford 9-J. $^1$H NMR (400 MHz, DMSO-d$_6$) δ 8.27 (d, J=13.8 Hz, 1H), 7.96 (s, 1H), 7.76 (s, 1H), 7.74 (d, J=5.4 Hz, 1H), 7.54-7.49 (m, 1H), 7.21-7.17 (m, 1H).

To a suspension of LiAlH$_4$ (860 mg, 22.6 mmol) in dry THF (6 mL) was added a solution of 9-J (900 mg, 45 mmol) in dry THF (3 mL) under N$_2$. The mixture was refluxed for 16 h, and then treated with 50% NaOH. The aqueous mixture was extracted with EA. The combined organic phase was dried, and concentrated to afford crude 9-K used directly for next step without purification.

To a solution of 2-(4-ethoxy-3-methoxybenzamido)acetic acid (9-L) (500 mg, 2.0 mmol), HATU (1.2 g, 3.2 mmol) and DIPEA (700 mg, 5.4 mmol) in anhydrous DCM (15 mL) was added 9-K (390 mg, 2.0 mmol). The mixture was stirred for 10 h and then diluted with 1.0 N aqueous NaHCO$_3$ solution, and extracted with DCM. The combined organic phase was dried over anhydrous Na$_2$SO$_4$, and concentrated. The residue was purified by recrystallization to afford the compound 908 (200 mg, 50%). ESI-LCMS: m/z 431[M+H]$^+$.

Example 9-8

Preparation of Compound 909

To a solution of 2-(4-ethoxy-3-methoxybenzamido)acetic acid (9-L) (152 mg, 0.6 mmol) in DCM (5 mL) was added HATU (380 mg, 1 mmol) and DIPEA (162 mg, 1.25 mmol), the mixture was stirred at rt, then was added 1-methyl-1H-indol-2-amine (110 mg, 0.5 mmol). The mixture was stirred at rt for additional 15 h. The mixture was washed with water and the organic layer was collected. The solvent was removed and the residue was purified by HPLC to afford compound 909 (35 mg, 18.4%) as a white solid. ESI-LCMS: m/z 382.0 [M+H]$^+$.

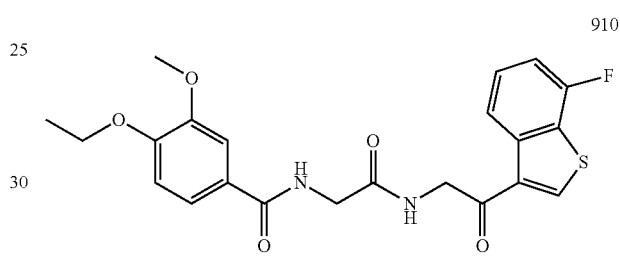

Compound 910 was obtained following the procedure for obtaining compound 909 using 2-amino-1-(7-fluorobenzo[b]thiophen-3-yl)ethanone in place of 1-methyl-1H-indol-2-amine. Compound 910 was obtained as a white solid (37 mg, 31.1%). +ESI-MS: m/z 445.0 [M+H]$^+$.

Example 9-9

Preparation of Compound 911

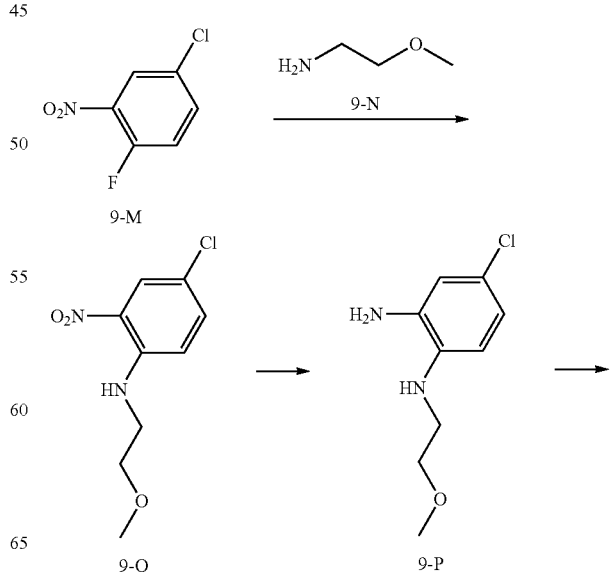

185
-continued

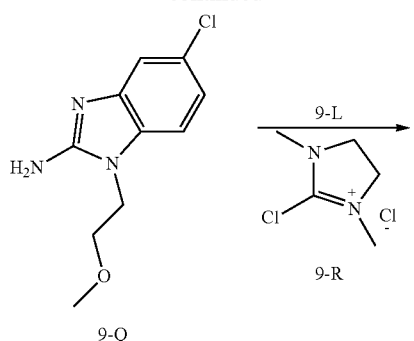

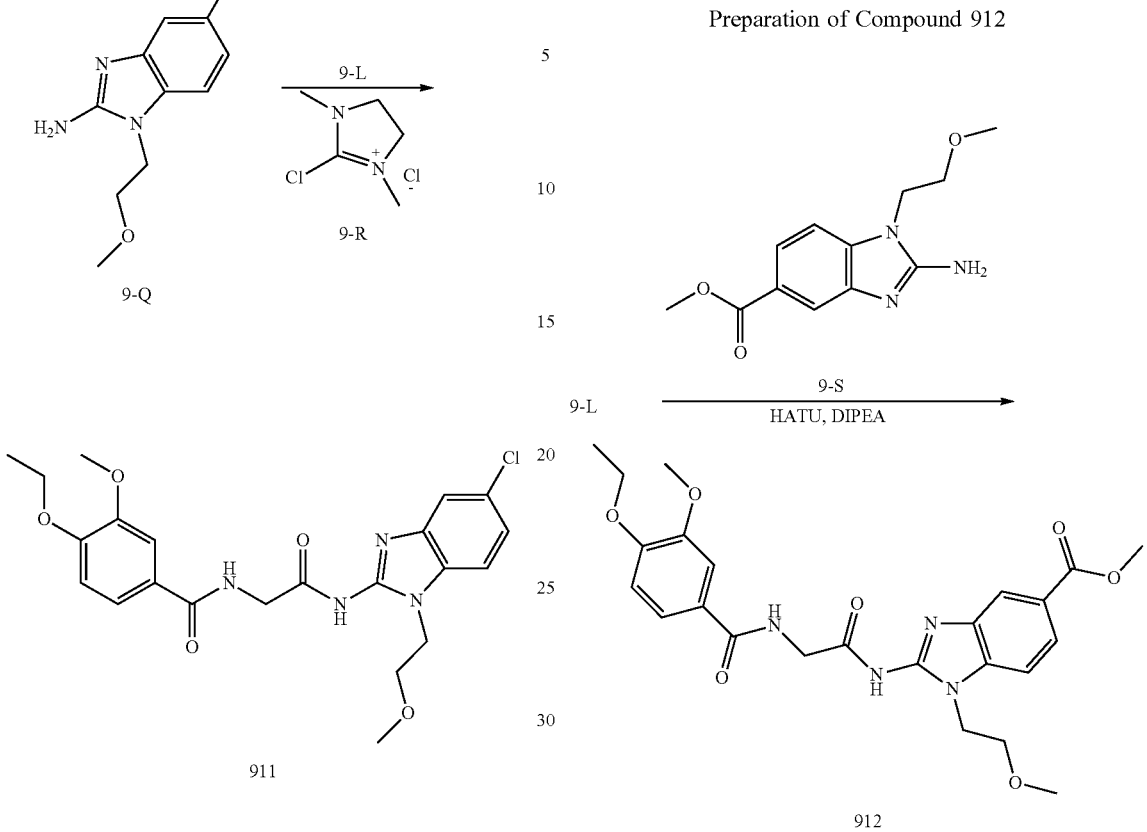

To a solution of 4-chloro-1-fluoro-2-nitrobenzene (9-M) (10 g, 57 mmol) in DMF (100 mL), K₂CO₃ (11.8 g, 85 mmol) was added. Then 2-methoxyethanamine (9-N) (5.12 g, 68.3 mmol) was added. The solution was stirred for 15 h at rt and then poured into water and extracted with EA. The organic phase was concentrated to afford crude 9-O (12 g, 91.5%).

To a solution of 9-O (6 g, 26 mmol) in DCM/MeOH (10/50 mL), NiCl₂.6H₂O (7.44 g, 31 mmol) was added. Then NaBH₄ (5.28 g, 0.138 mol) was added in portions until the solution turned dark. The mixture was treated with aqueous NaHCO₃ and extracted with EA. The organic phase was concentrated to afford crude 9-P (5 g, 96.15%).

To a solution of 9-P (3 g, 14.9 mmol) in ethanol, BrCN was added slowly at rt. The mixture was stirred for 15 h at rt. The mixture was treated with aqueous NaHCO₃ and extracted with EA. The organic phase was concentrated and the residue was recrystallized (PE:EA=1:1) to afford 9-Q (2 g, 59.7%).

To a mixture of 9-Q (112 mg, 0.442 mmol) in DMF (2 mL), 2-(4-ethoxy-3-methoxybenzamido)acetic acid (9-L) (100 mg, 0.442 mmol) and TEA (134 mg, 1.32 mmol) and 2-chloro-1,3-dimethylimidazolinium chloride (9-R) (150 mg, 0.884 mmol) were added. The mixture was stirred for 15 h under rt. The mixture was washed with water and extracted with EA. The organic phase was concentrated and the residue was purified by prep-HPLC to afford compound 911 (2 mg, 1.0%). +ESI-MS: m/z 461.0 [M+H]⁺.

186
Example 9-10

Preparation of Compound 912

To a solution of 2-(4-ethoxy-3-methoxybenzamido)acetic acid (9-L) (500 mg, 2.0 mmol), HATU (1.2 g, 3.2 mmol) and DIPEA (700 mg, 5.4 mmol) in anhydrous DCM (15 mL) was added methyl 2-amino-1-(2-methoxyethyl)-1H-benzo[d]imidazole-5-carboxylate (9-S) (491 mg, 2.0 mmol). The solution was stirred for 10 h and then diluted with 1.0 N aqueous NaHCO₃ solution, extracted with DCM. The combined organic phase was dried over anhydrous Na₂SO₄, and concentrated. The residue was purified by prep-HPLC to afford compound 912 (100 mg, 20%). +ESI-MS: m/z 485.1 [M+H]⁺.

Example 9-11

Preparation of Compound 913

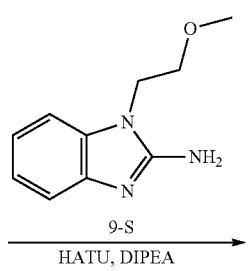

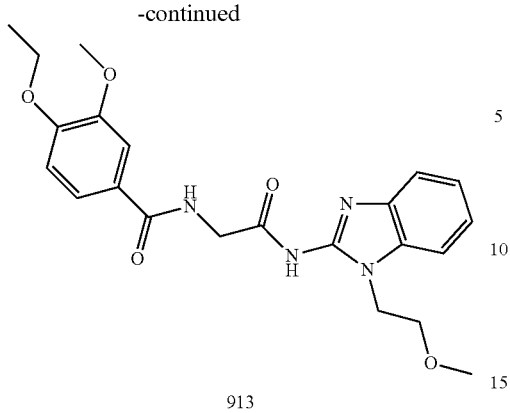

913

To a solution of 2-(4-ethoxy-3-methoxybenzamido)acetic acid (9-L) (600 mg, 2.4 mmol), HATU (1.3 g, 3.4 mmol) and DIPEA (780 mg, 6.0 mmol) in anhydrous DCM (15 mL) was added 9-S (453 mg, 2.4 mmol). The solution was stirred for 10 h and then diluted with 1.0 N aqueous NaHCO$_3$ solution, extracted with DCM. The combined organic phase dried over anhydrous Na$_2$SO$_4$, and concentrated. The residue was purified by prep-HPLC to afford compound 913 (100 mg, 20%). ESI-LCMS: m/z 427.0 [M+H]$^+$.

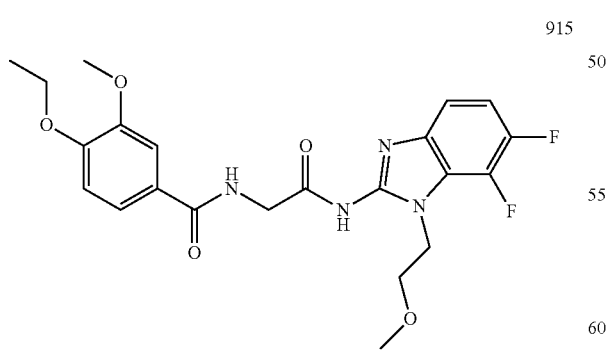

914

Compound 914 was obtained following the procedure for obtaining compound 911 modified as appropriate using 4-fluoro-2-nitroaniline. Compound 914 was obtained as a white solid (22 mg, 15.6%). ESI-LCMS: m/z 445.1 [M+H]$^+$.

915

Compound 915 was obtained following the procedure for obtaining compound 911 modified as appropriate using 2,3-difluoro-6-nitroaniline. Compound 915 was obtained as a white solid (35 mg, 18.8%). ESI-LCMS: m/z 463.2 [M+H]$^+$.

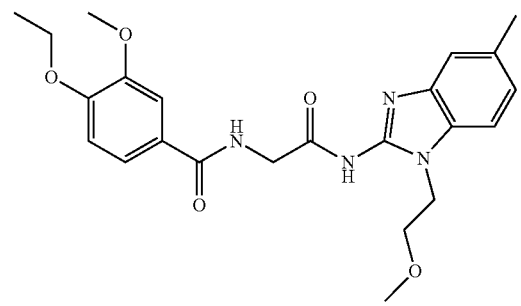

916

Compound 916 was obtained following the procedure for obtaining compound 911 using 1-(2-methoxyethyl)-5-methyl-1H-benzo[d]imidazol-2-amine in place of 9-Q. Compound 916 was obtained as a white solid (36 mg, 19.6%). ESI-LCMS: m/z 441.5 [M+H]$^+$.

Example 9-12

Preparation of Compound 917

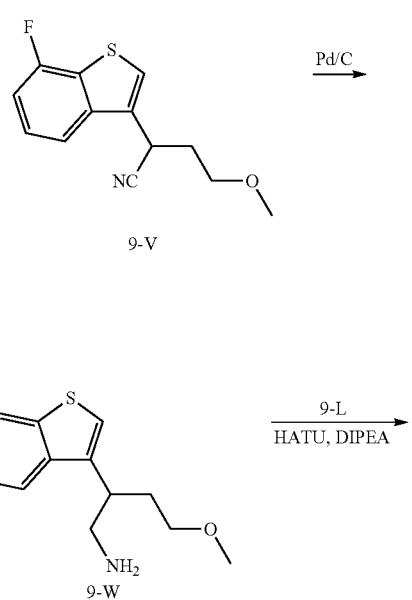

9-U

9-V

9-W

-continued

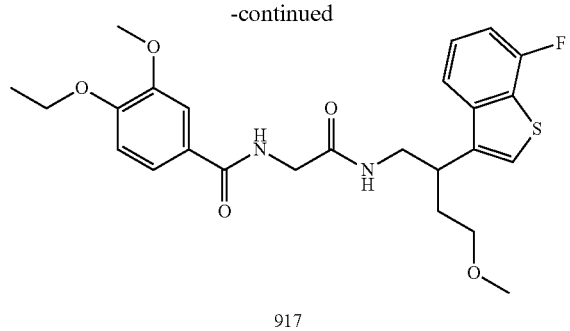

917

Solid t-BuOK was added to a stirred and cooled solution of 9-U (500 mg, 2.1 mmol) and tosylmethyl isocyanide (550 mg, 2.8 mmol) in a mixture of dioxane and EtOH (v/v=10:1) while keeping the temperature between 0° C. and 5° C. The solution was stirred at rt for 2 h. The mixture was poured in H₂O and extracted with EA. The organic layer was dried and concentrated. The residue was purified by TLC to afford 9-V. ¹H NMR (400 MHz, DMSO-d6) δ 7.96 (s, 1H), 7.79 (d, J=8.0 Hz, 1H), 7.55-7.49 (m, 1H), 7.35-7.30 (m, 1H), 4.73-4.69 (m, 1H), 3.52-3.39 (m, 2H). 3.26 (s, 1H), 2.33-2.17 (m, 2H).

A vessel under N₂ was charged with 9-V (150 mg, 0.60 mol), Pd/C (80 mg) in ethanol (5 mL) and HCl (0.2 mL). The vessel was placed under 1 atm of H₂ and then stirred at rt for 5 h. The solid was removed by filtration through a pad of celite and the filtrate was concentrated to afford crude 9-W used directly in next step without further purification.

To a solution of 2-(4-ethoxy-3-methoxybenzamido)acetic acid (9-L) (80 mg, 0.32 mmol), HATU (160 mg, 0.42 mmol) and DIPEA (103 mg, 0.8 mmol) in anhydrous DCM (3 mL) was added 9-W (80 mg, 0.32 mmol). The mixture was stirred for 10 h and then diluted with a 1.0 N aqueous NaHCO₃ solution, and extracted with EA. The combined organic phase was dried over anhydrous Na₂SO₄, and concentrated. The residue was purified by prep-HPLC to afford the compound 917 (5 mg). ESI-LCMS: m/z 489.1 [M+H]⁺.

Example 10

Preparation of Compound 1000

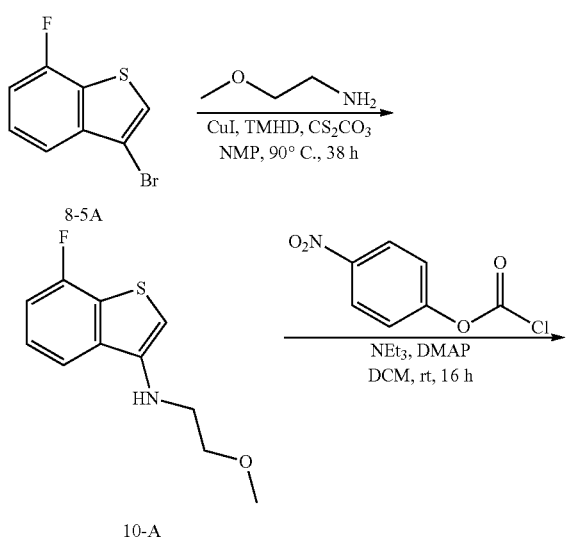

-continued

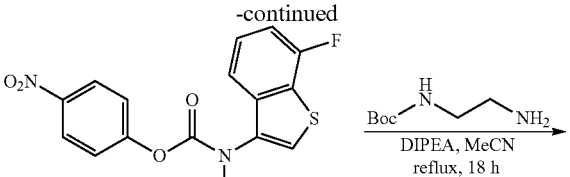

10-B

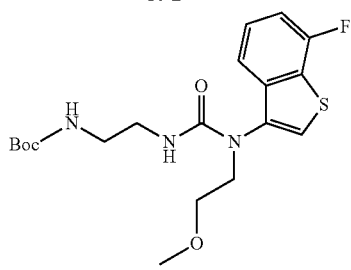

10-C

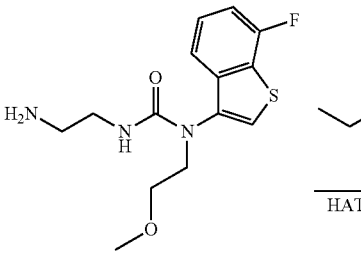

10-D

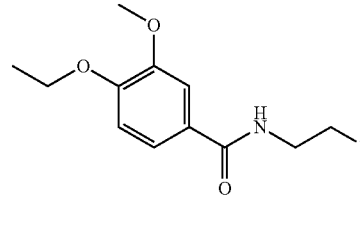

1000

To a mixture of 3-bromo-7-fluorobenzo[b]thiophene (8-5A) (1.13 g, 4.9 mmol), CuI (0.140 g, 0.15 eq.), TMHD (0.271 g, 0.30 eq.) and Cs₂CO₃ (3.19 g, 2 eq.) in NMP (10 mL) was added 2-methoxyethanamine (2.2 g, 6 eq.). The mixture was stirred at 90° C. for 38 h. The mixture was diluted with water and extracted with EA, the organic layer was collected and dried over anhydrous MgSO₄. After filtration, the solvent was removed and the residue was purified by silica gel column (PE/EA=20/1 to 5/1) to afford 10-A as a white solid (0.741 g, 67.2%). +ESI-MS: m/z 225.9 [M+H]⁺.

To a solution of 10-A (150 mg, 0.67 mmol), triethylamine (101 mg, 1.5 eq.), and DMAP (16 mg, 0.2 eq.) in DCM (10 mL) was added 4-nitrophenyl chloroformate (201 mg, 1.5 eq.). The mixture was stirred at rt for 16 h. The mixture was diluted with water and extracted with EA, the organic layer was collected and dried over anhydrous MgSO₄. After filtration, the solvent was removed and the residue was purified by silica gel column (PE/EA=10/1 to 3/1) to afford 10-B as a white solid (220 mg, 84.6%). +ESI-MS: m/z 390.8 [M+H]$^+$.

To a solution of 10-B (220 mg, 0.56 mmol) and DIPEA (218 mg, 3.0 eq.) in MeCN (20 mL) was added tert-butyl (2-aminoethyl)carbamate (451 mg, 5.0 eq.). The mixture was heated to reflux for 18 h. The mixture was allowed to cool to rt and then diluted with water. The aqueous mixture was extracted with EA, the organic layer was collected and dried over anhydrous MgSO$_4$. After filtration, the solvent was removed and the residue was purified by silica gel column (PE/EA=20/1 to 5/1) to afford 10-C as a white solid (200 mg, 86.2%). +ESI-MS: m/z 412.0 [M+H]$^+$.

Compound 10-C (200 mg, 0.49 mmol) was added to a HCl/EA (50 mL) solution. The mixture was stirred at rt for 1 hour. The formed precipitate was filtered and washed with EA (10 mL×3) and then dried to afford 10-D as a white solid (147 mg, 97%). +ESI-MS: m/z 311.9 [M+H]$^+$.

To a solution of 4-ethoxy-3-methoxybenzoic acid (93 mg, 0.47 mmol) in DMF (6 mL) was added HATU (357 mg, 2 eq.) and DIPEA (243 mg, 4 eq.), the mixture was stirred at rt for 30 mins, the mixture was then treated with 10-D (147 mg, 0.47 mmol). The mixture was stirred at rt for another 4 h. The mixture was washed with water and the organic layer was collected. The solvent was removed and the residue was purified by prep-HPLC to afford compound 1000 as a white solid (42 mg, 18.2%). +ESI-MS: m/z 490.2[M+H]$^+$.

Example 11

Preparation of Compound 1100

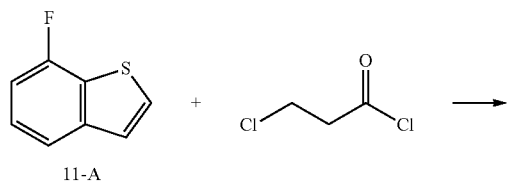
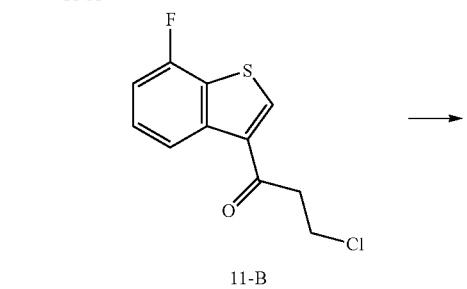
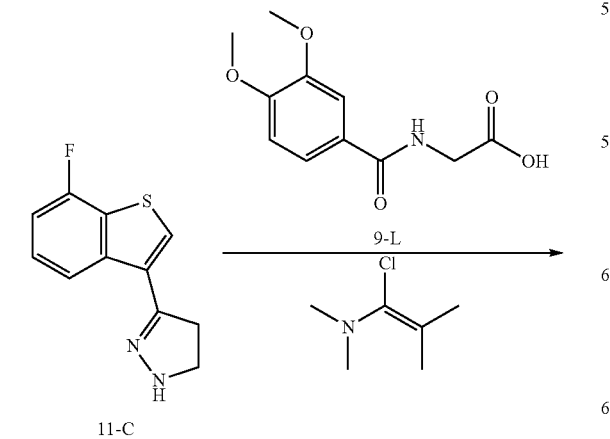

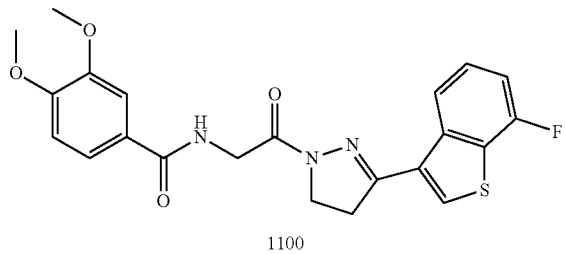

1100

To a mixture of aluminum trichloride (2.66 g, 20 mmol) in dry DCM (10 mL) cooled at 0° C. under N$_2$, was added a solution of 7-fluorobenzo[b]thiophene (11-A) (3.044 g, 20 mmol) and then 3-chloropropanoyl chloride (2.53 g, 20 mmol) in dry DCM (10 mL) was slowly added. The mixture was stirred at rt for 1 hour. The mixture was cooled to −78° C. (acetone-carbon dioxide bath) and a solution of 96% sulphuric acid (1 mL) and water 15 mL was slowly added. The organic layer was decanted, washed with water and dried over anhydrous MgSO$_4$. After filtration, the solvent was removed and the residue was purified by silica gel column (PE/EA=20/1 to 8/1) and then re-crystallization in PE/EA (30:1) to afford 11-B as a white solid (1.654 g, 34%). +ESI-MS: m/z 243.0 [M+H]$^+$.

To a solution of 11-B (300 mg, 1.2 mmol) in iso-propyl alcohol (10 mL) was added N$_2$H$_4$.xH$_2$O (119 mg, 3.6 mmol). The mixture was heated to reflux for 1 hour. Then the mixture was allowed to cool to rt and the solvent was evaporated to afford crude 11-C (270 mg, 99.3%), which was used for next step directly without further purification.

To a solution of 2-(3,4-dimethoxybenzamido)acetic acid (9-L) (586 mg, 2.45 mmol) in dry DCM (6 mL) cooled at 0° C. and under N$_2$, was added 1-chloro-N,N,2-trimethyl-1-propenylamine (360 mg, 2.70 mmol). The mixture was stirred at rt for 1 hour. The mixture was treated with crude 11-C (270 mg) in dry DCM (6 mL) and the mixture was allowed to stir at rt for one more hour. The mixture was diluted with water and extracted with EA. The organic layer was collected and dried over anhydrous MgSO$_4$. After filtration, the solvent was removed and the residue was purified by silica gel column (DCM/MeOH=40/1 to 10/1) to afford compound 1100 as a white solid (279 mg, 51.6%). +ESI-LCMS: m/z 442.1 [M+H]$^+$.

Example 11-1

Preparation of Compound 1101

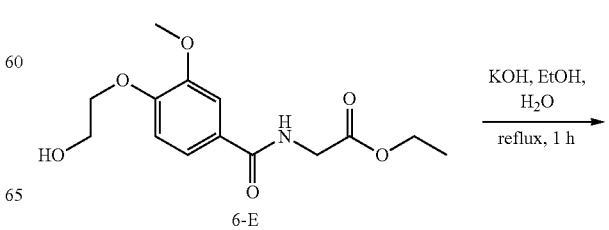

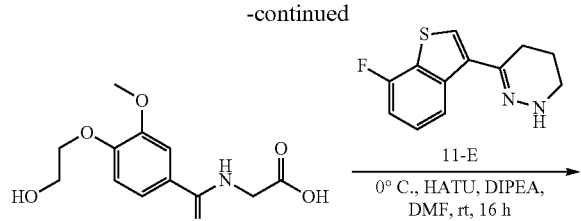
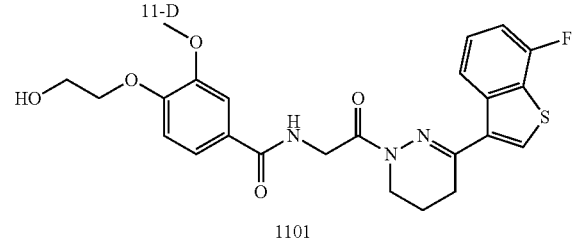

To a solution of ethyl 2-(4-(2-hydroxyethoxy)-3-methoxybenzamido)acetate (6-E) (2.00 g, 6.73 mmol) in EtOH (30 mL) was added a solution of KOH (4.48 g, 80 mmol) in H$_2$O (10 mL). The mixture was heated to reflux for 1 hour, then was cooled down to rt and diluted with H$_2$O (50 mL). The EtOH was removed and the remaining aqueous mixture was acidified with HCl aq. to adjust pH to 4-5 at 0° C. A white precipitate was formed. The precipitate was filtered and the residue was washed with EtOH (6 mL×3) to afford 2-(4-(2-hydroxyethoxy)-3-methoxybenzamido)acetic acid (11-D) (0.50 g, 27.6%) as a white component.

To a solution of 2-(4-(2-hydroxyethoxy)-3-methoxybenzamido)acetic acid (11-D) (34 mg, 1.28 mmol) and DIPEA (112 mg, 0.87 mmol) in DMF (2 mL) at 0° C. was added HATU (654 mg, 2.0 eq.). The mixture was stirred at 0° C. for 30 mins, then was added 3-(7-fluorobenzo[b]thiophen-3-yl)-1,4,5,6-tetrahydro-pyridazine (11-E) (200 mg, 0.86 mmol). The mixture was stirred at rt for another 16 h. The mixture was diluted with water and extracted with EA. The organic layer was collected and dried over anhydrous MgSO$_4$. After filtration, the solvent was removed and the residue was purified by prep-TLC (EA) and recrystallization from EA. Compound 1101 was obtained as a white solid (91.36 mg, 22.1%). +ESI-LCMS: m/z 486.1[M+H]$^+$.

Example 11-2

Preparation of Compound 11-F

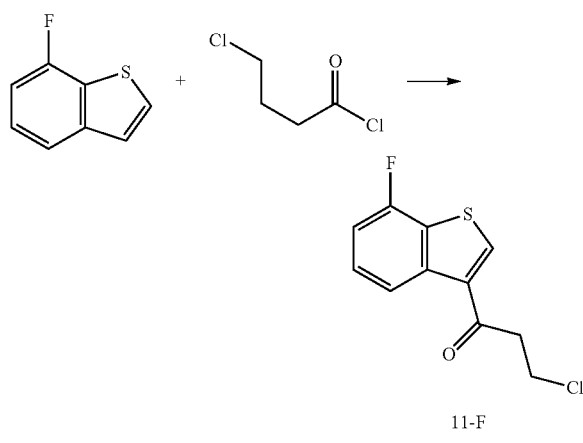

Compound 11-F was obtained following the procedure for obtaining 11-B using 4-chlorobutanoyl chloride in place of 3-chloropropanoyl chloride. Compound 11-F was obtained as a brown solid (1.067 g, 37.3%).

Example 12

Preparation of Compound 1200

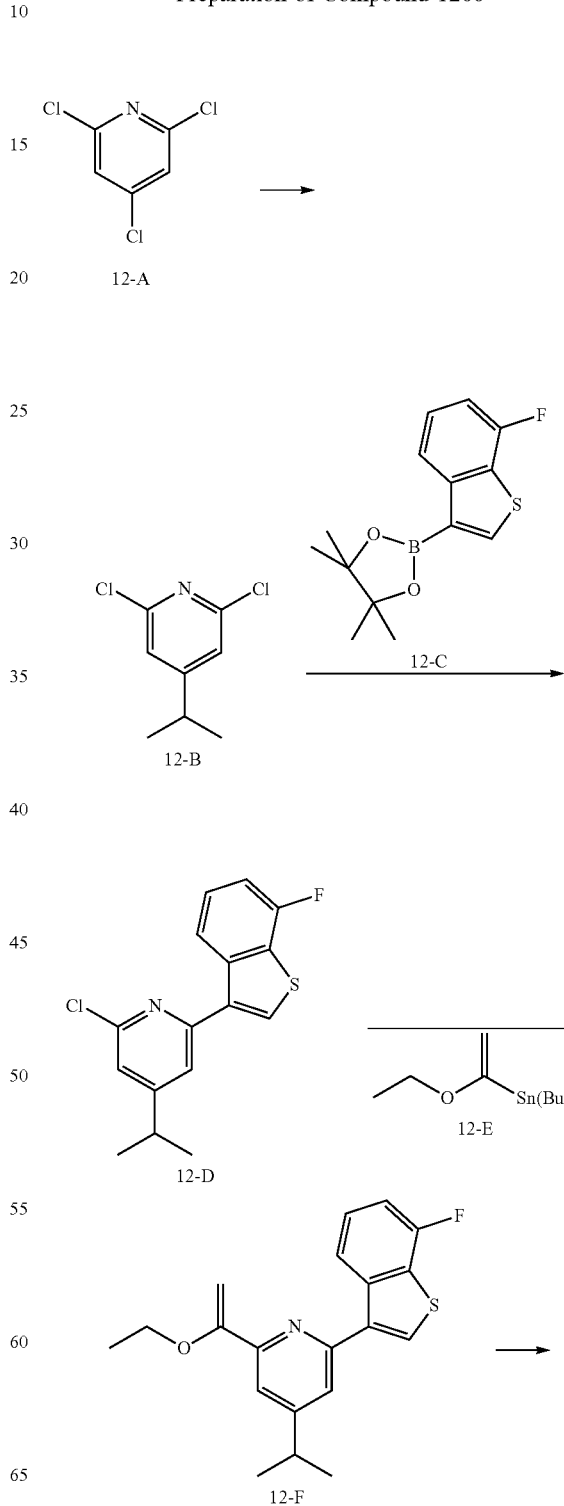

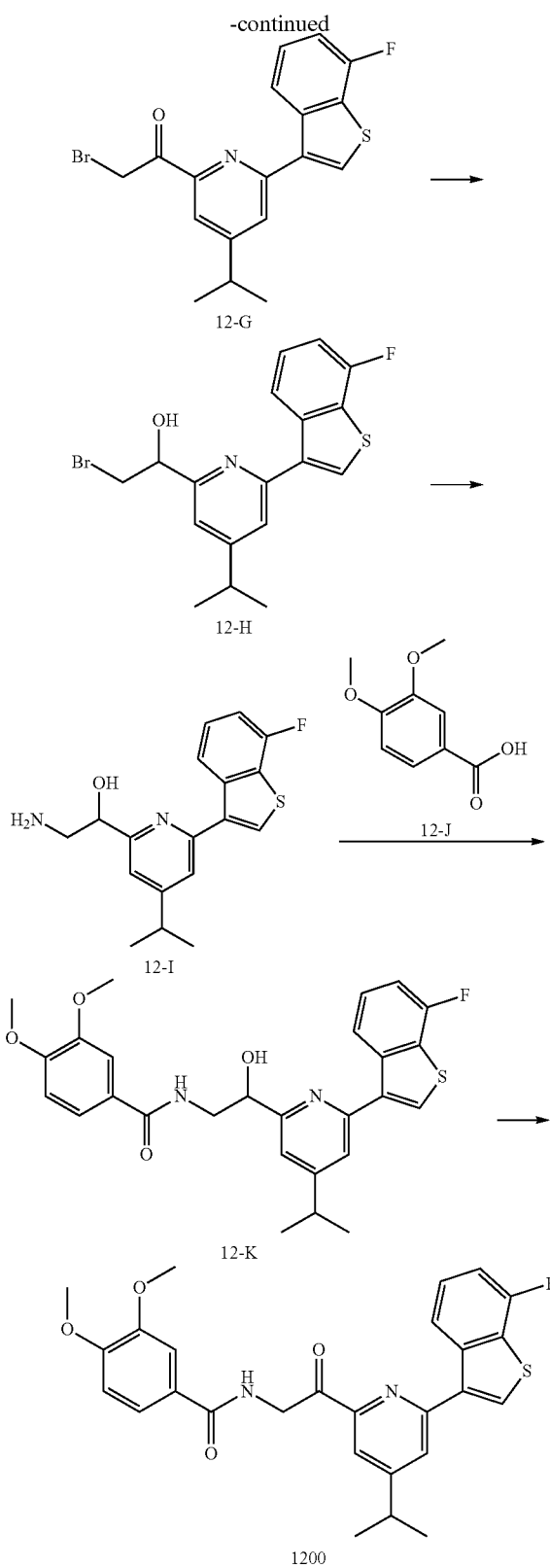

brine. The organic phase was concentrated to give crude 12-B as a colorless solid (2.4 g, 63.5%). +ESI-MS: m/z 190.1 [M+H]+.

To a mixture of 12-B (1 g, 5.29 mmol) and 12-C (1.03 g, 5.29 mmol) in DMF (30 mL) were added Pd(dppf)Cl$_2$ (420 mg, 0.529 mmol) and a freshly prepared KF solution (2.57 g in 10 mL of water). The system was degassed and then charged with nitrogen 3 times. The mixture was stirred under nitrogen at 70° C. using an oil bath for 8 h. The reaction solution was cooled to rt, diluted with EA and separated from the water layer. The EA solution was washed with brine, dried over Na$_2$SO$_4$ and concentrated. The residue was purified on a silica gel column to give 12-D as a colorless solid (0.5 g, 31%). +ESI-MS: m/z 306.0 [M+H]+.

To a mixture of 12-D (900 mg, 2.95 mmol), 12-E (1.07 g, 2.95 mmol) and KF (0.684 g, 11.8 mmol) in DMF (10 mL) was added Pd(dppf)Cl$_2$ (228 mg, 0.295 mmol). The system was degassed and then charged with nitrogen 3 times. The mixture was stirred under nitrogen at 70° C. using an oil bath for 8 h. The reaction solution was cooled to rt, diluted with EA and H$_2$O. The organic phase was washed with brine, dried over Na$_2$SO$_4$ and concentrated to give crude 12-F (1 g). +ESI-MS: m/z 342.1 [M+H]+.

A mixture of 12-F (1 g, 2.9 mmol) and NBS (516 mg, 2.9 mmol) in a mixture of THF (10 mL) and H$_2$O (1 mL) was stirred at rt for 30 mins. The solution was diluted with water and the aqueous layer was extracted with EtOAc. The combined organic layers were washed with a saturated Na$_2$S$_2$O$_3$ solution, followed by brine. The solution was dried over Na$_2$SO$_4$ and evaporated to give crude 12-G (1 g). +ESI-MS: m/z 392.0 [M+H]+.

To a solution of 12-G (1 g, 2.55 mmol) in a mixture of THF (5 mL) and MeOH (0.5 mL) was added NaBH$_4$ (193 mg, 5.1 mmol) at 0° C. The mixture was stirred at 0° C. for 30 mins with TLC monitoring. The reaction was quenched by the addition of H$_2$O and extracted with EA. The combined organic layers were washed with brine, dried over Na$_2$SO$_4$ and concentrated. The residue was purified on a silica gel column to give 12-H (200 mg, 20%). +ESI-MS: m/z 394.0 [M+H]+.

A mixture of 12-H (200 mg, 0.50 mmol) and saturated NH$_4$OH/EtOH (1 mL/5 mL) in a sealed tube was heated to 70° C. for 6 h. The solution was removed under reduced pressure to give crude 12-I (160 mg, 90.0%), which was used for next step directly without purification. +ESI-MS: m/z 331.1 [M+H]+.

To a solution of 12-J (65 mg, 0.363 mmol), HATU (172 mg, 0.45 mmol) and DIPEA (117 mg, 0.909 mmol) in anhydrous DMF (1 mL) was added 12-1 (100 mg 0.303 mmol) at 25° C. The solution was stirred for 10 h at rt. The solution was diluted with 1.0 N aqueous NaHCO$_3$ solution (40 mL×2) and extracted with EA (20 mL×2). The combined organic layers were washed with brine, dried over anhydrous Na$_2$SO$_4$, and concentrated under reduced pressure. The residue was purified on a silica gel column to give 12-K (100 mg, 67.1%). +ESI-MS: m/z 495.1 [M+H]+.

To a mixture of 12-K (100 mg, 0.203 mmol) in DCM (2 mL) were added DMP (517 mg, 1.4 mmol). The mixture was stirred at rt for 30 mins with TLC monitoring. The solution was quenched using an aqueous NaHCO$_3$ solution and extracted with EA. The combined organic layers were washed with saturated Na$_2$S$_2$O$_3$ and brine, dried over Na$_2$SO$_4$ and concentrated. The residue was purified by Pre-HPLC(FA) to give compound 1200 as a white solid (30 mg, 30%). +ESI-MS: m/z 493.0 [M+H]+.

To a mixture of 12-A (3.65 g, 20 mmol) in NMP:THF (2 mL/20 mL), Fe(acac)$_3$ (622 mg, 2 mmol) was added. The solution was cooled to 0° C. and i-PrMgCl (20 mL, 2N) was added slowly at 0° C. The solution was stirred for 2 h at 0° C. The solution was extracted with EA, and washed with

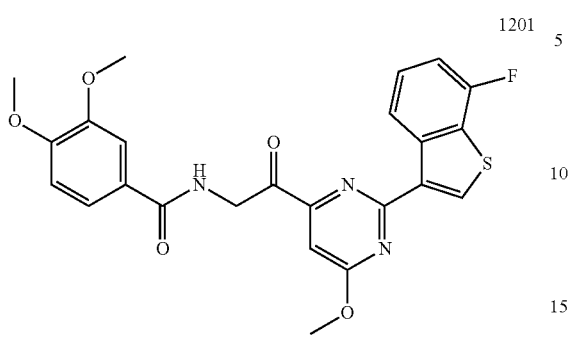

Compound 1201 was obtained following the procedure for obtaining compound 1200 by using 4-chloro-2-iodo-6-methoxypyrimidine as the starting material. Compound 1201 was obtained as a white solid. +ESI-MS: m/z 482.9 [M+H]$^+$.

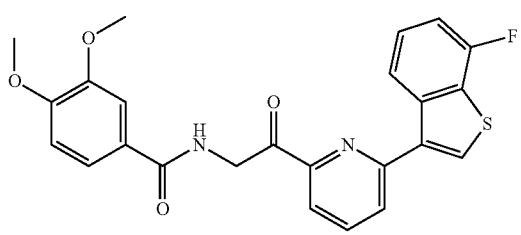

Compound 1202 was obtained following the procedure for obtaining compound 1200 by using 2,6-dichloropyridine as the starting material. Compound 1202 was obtained as a white solid. +ESI-MS: m/z 450.9 [M+H]$^+$.

Example 12-1

Preparation of Compound 12-L

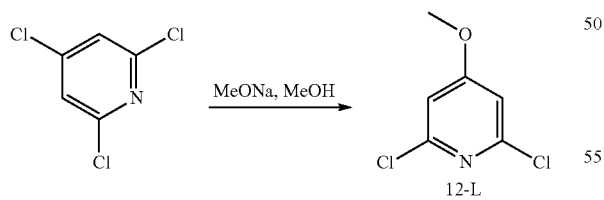

A solution of 2,4,6-trichloropyridine (6.5 g, 36 mmol) in anhydrous methanol (20 mL) was added MeONa (2.9 g, 54 mmol) at 0° C. The reaction mixture was stirred at rt for 12 h. The reaction was quenched with dry ice, and the mixture was filtered. The solution was concentrated under reduced pressure, and the residue was dissolved in EA. The mixture was washed with water, and the organic layers were dried over NaSO$_4$. The solvent was concentrated to give 12-L (4.2 g, 67%).

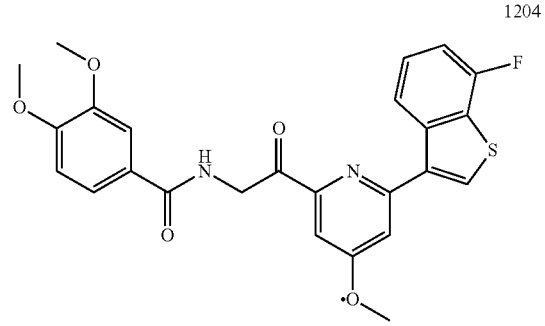

Compound 1204 was obtained following the procedure for obtaining Compound 1200 by using 12-L as the starting material. Compound 1204 was obtained as a white solid. Compound 1204: +ESI-MS: m/z 496.1 [M+H]$^+$.

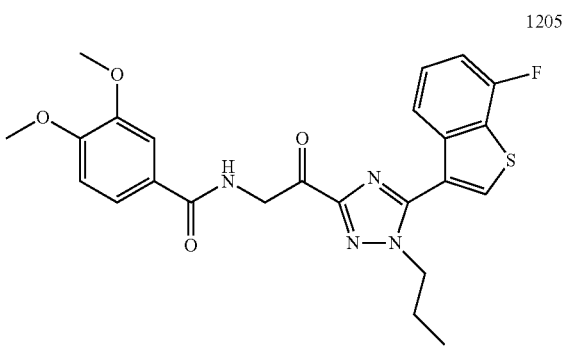 [SMILES: CCCn1nc(C(=O)CNC(=O)c2ccc(OC)c(OC)c2)nc1-c1csc2c(F)cccc12]

Compound 1205 was obtained following the procedure for obtaining compound 1200 by using 3,5-dibromo-1-propyl-1H-1,2,4-triazole as the starting material. Compound 1205 was obtained as a white solid. +ESI-MS: m/z 482.9 [M+H]$^+$.

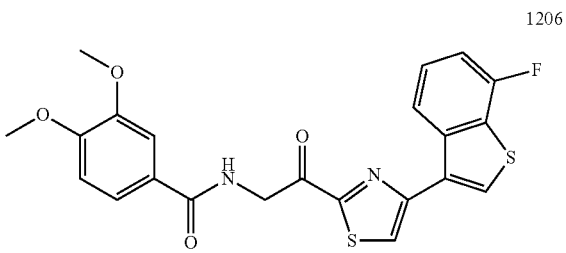 [SMILES: COc1ccc(C(=O)NCC(=O)c2nc(-c3csc4c(F)cccc34)cs2)cc1OC]

Compound 1206 was obtained following the procedure for obtaining compound 1200 by using 2,4-dibromothiazole as the starting material. Compound 1206 was obtained as a white solid. +ESI-MS: m/z 456.8[M+H]$^+$.

Example 12-2

Preparation of Compound 1207

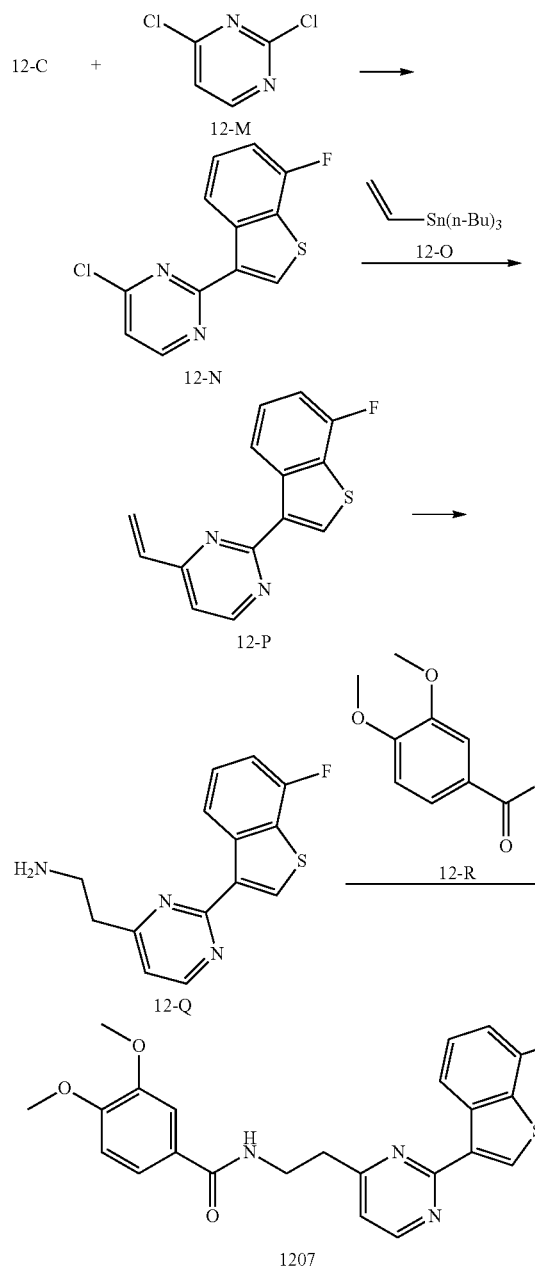

To a mixture of 12-M (1.94 g, 20.1 mmol) and 12-C (3.6 g, 20.0 mmol) in dioxane (20 mL) were added Pd(dppf)Cl₂ (800 mg, 0.94 mmol) and a freshly prepared KF solution (3.6 g in 8 mL of water). The system was degassed and then charged with nitrogen 3 times. The mixture was stirred under nitrogen at 70° C. using an oil bath for 6 h. The reaction solution was cooled to rt, diluted with EA and separated from the water layer. The EA solution was washed with brine, dried over Na₂SO₄ and concentrated. The residue was purified on a silica gel column to give crude 12-N (2.8 g), which used for the next step without purification.

To a mixture of 12-N (1.3 g, 5 mmol), 12-0 (1.6 g, 5 mmol) and KF (1.0 g, 16.6 mmol) in DMF (10 mL) were added Pd(dppf)Cl₂ (400 mg, 0.49 mmol). The system was degassed and then charged with nitrogen 3 times. The mixture was stirred under nitrogen at 70° C. using an oil bath for 8 h. The reaction solution was cooled to rt, and diluted with water and EtOAc. The EtOAc solution was washed with brine, dried over Na₂SO₄ and concentrated. The residue was purified on a silica gel column to give crude 12-P (0.8 g) as a liquid, which used for the next step without purification.

To a mixture of 12-P (0.8 g, 3.1 mmol) in EtOH (5 mL) were added NH₄OH (5 mL) in a sealed tube. The mixture was heated at 70° C. for 5 h with TLC monitoring. The solution was removed under reduced pressure to give crude 12-Q (0.5 g), which was used for next step directly without purification To a solution of 12-R (91 mg, 0.5 mmol), HATU (250 mg, 0.65 mmol) and DIPEA (200 mg, 1.5 mmol) in anhydrous DCM (3 mL) was added 12-Q (138 mg 0.5 mmol) at 25° C. The solution was stirred for 8 h at rt. The solution was diluted with 1.0 N aqueous NaHCO₃ solution (40 mL×2) and extracted with EA (40 mL×2). The combined organic layers were washed with brine, dried over anhydrous Na₂SO₄, and concentrated under reduced pressure. The residue was purified on a silica gel column (PE:EA=1:2) to give compound 1207 (100 mg) as a white solid. +ESI-MS: m/z 438.1[M+H]⁺.

Example 12-3

Preparation of Compound 1208

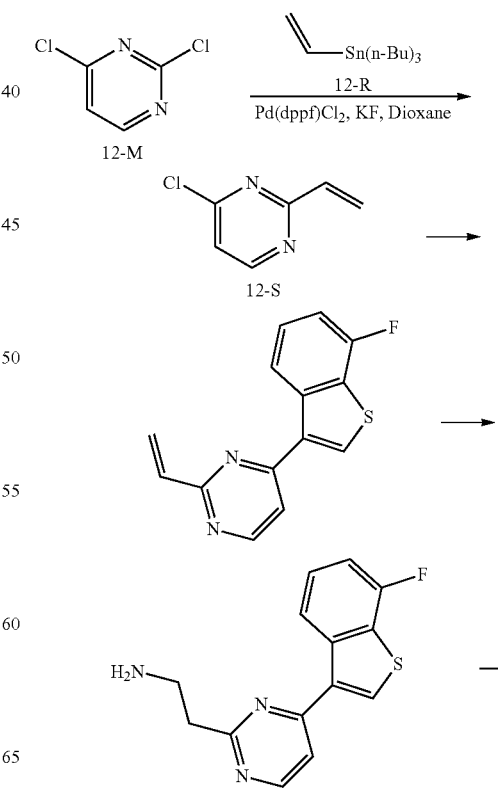

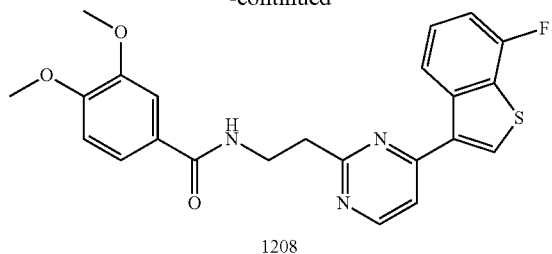

1208

To a mixture of 12-M (1.5 g, 10 mmol), 12-R (3.2 g, 10 mmol) and KF (1.8 g, 30.0 mmol) in DMF (6 mL) was added Pd(dppf)Cl$_2$ (400 mg, 0.49 mmol). The system was degassed and then charged with nitrogen 3 times. The mixture was stirred under nitrogen at 70° C. using an oil bath for 7 h. The reaction solution was cooled to rt. The mixture was diluted with H$_2$O and extracted with EtOAc. The EtOAc solution was washed with brine, dried over Na$_2$SO$_4$ and concentrated. The residue was purified on a silica gel column to give crude 12-S (0.8 g) as a liquid, which was used for the next step without purification.

Compound 1208 was obtained following the procedure for obtaining compound 1207 by using 12-S. Compound 1208 was obtained as a white solid. +ESI-MS: m/z 438.1 [M+H]$^+$.

Example 12-4

Preparation of Compound 1209

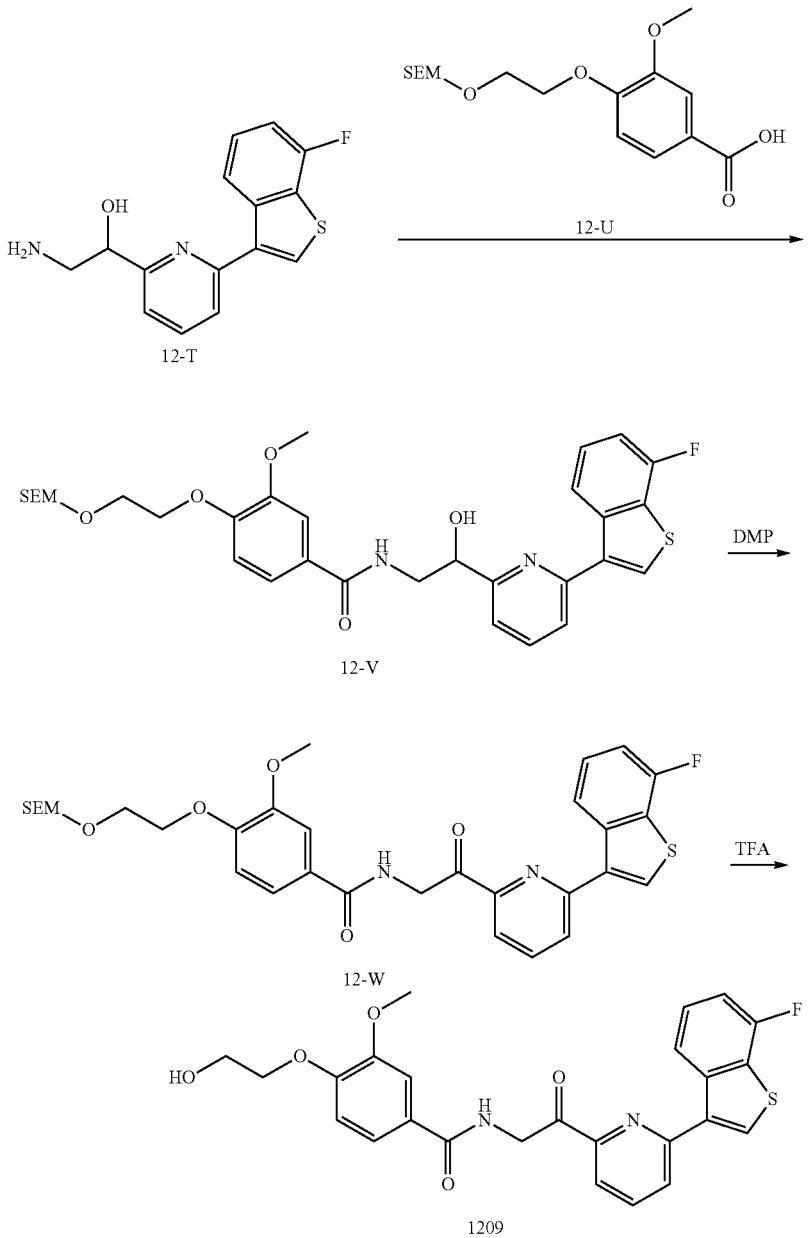

Compound 12-U (170 mg, 0.5 mmol), 12-T (140 mg, 0.5 mmol) and triethylamine (1 mmol) were dissolved in DMF (15 mL). HATU (380 mg, 1 mmol) was added to the solution. After 15-30 mins., the reaction was completed, and a saturated NaCl solution (100 mL) was added. The product was extracted with EtOAc (3×10 mL), and the combined organic phase was washed with 2N HCl solution, 5% $NaHCO_3$ solution, and brine. The organic phase was dried over $MgSO_4$, and concentrated in vacuum to give the crude product. The crude product was purified by silica gel column chromatography eluting with EtOAc/PE (1/1) to give 12-V as a white solid (240 mg, 80%). +ESI-MS: m/z 613.2 $[M+H]^+$.

To a stirred solution of 12-V (240 mg, 0.4 mmol) in $CH_2Cl_2$ (10 mL) was added DMP (426 mg, 1.0 mmol), the mixture was stirred at rt until the starting material was consumed completely. The mixture was concentrated to give a residue. Purification of the residue by silica gel column chromatography (PE/EA) gave 12-W as a solid (185 mg, 75%). +ESI-MS: m/z 611.2 $[M+H]^+$.

To 12-W (185 mg, 0.3 mmol) in DCM (10 mL) was added TFA (10 mL). The mixture was stirred for 2 h at rt. The solvent was evaporated under reduced pressure to give the crude product as an oil. The crude product was purified by Pre-HPLC to give compound 1209 (28 mg, 30%). +ESI-MS: m/z 480.9 $[M+H]^+$.

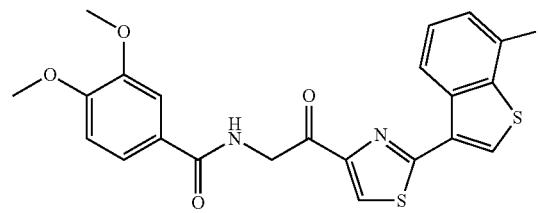

1210

Compound 1210 was obtained following the procedure for obtaining compound 1200 by using 2,4-dibromothiazole as the starting material. Compound 1210 was obtained as white solid. +ESI-MS: m/z 457.0 $[M+H]^+$.

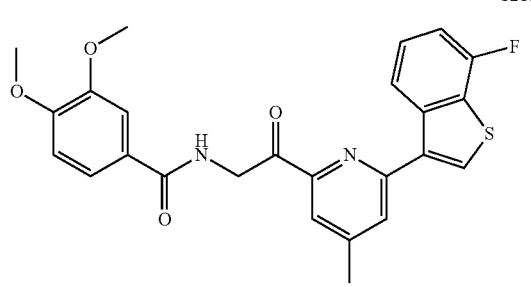

1211

Compound 1211 was obtained following the procedure for obtaining compound 1200 by using 2,4-dibromothiazole as the starting material. Compound 1211 was each obtained as a white solid. Compound 1211: +ESI-LCMS: m/z=464.9 $[M+H]^+$.

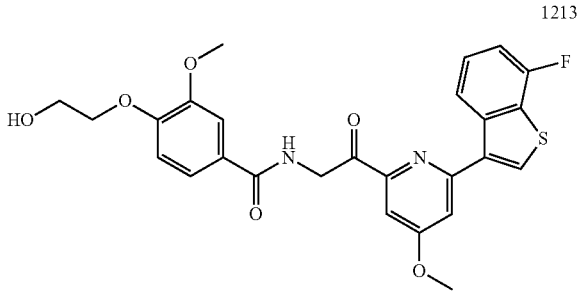 [SMILES: COc1cc(C(=O)CNC(=O)c2ccc(OCCO)c(OC)c2)nc(-c2csc3c(F)cccc23)c1]

1213

Compound 1213 was obtained following the procedures for obtaining compounds 1200 and 1209 by using 2,4,6-trichloropyridine as the starting material. Compound 1213 was obtained as a white solid. +ESI-MS: m/z 511.0 $[M+H]^+$.

Example 12-5

Preparation of Compound 12-AA

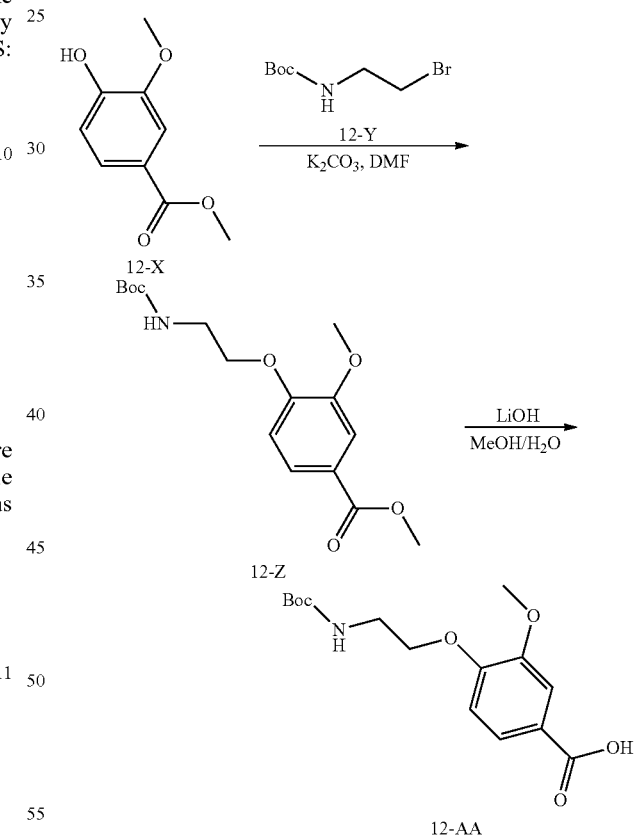

To a solution of 12-X (1.82 g, 10 mmol) and $K_2CO_3$ (6.9 g, 50 mmol) in DMF (20 mL) was added 12-Y (4.48 g, 20 mmol) at 25° C. The solution was stirred for 15 h at 90° C. The mixture was diluted with water and extracted with EA. The combined organic phase was dried over anhydrous $Na_2SO_4$, and concentrated under reduced pressure to give 12-Z (3.0 g). +ESI-MS: m/z 326.1 $[M+H]^+$.

To a solution of 12-Z (3.0 g, 9.23 mmol) in MeOH (20 mL) was added LiOH (2.3 g, 95.8 mmol) in $H_2O$ (10 mL). The solution was stirred for 3 h at 50° C. The mixture was concentrated, acidified with 2N HCl solution. The precipitate was collected by filtration and washed with H₂O to give the 12-AA (2.0 g). ¹H NMR: DMSO (400 MHz): δ=7.54-7.52 (dd, J=2.0 Hz, J=8.4 Hz, 1H), 7.44 (s, 1H), 7.04 (d, J=8.4 Hz, 1H), 6.98-6.95 (br s, 1H), 4.04-4.01 (m, 2H), 3.79 (s, 3H), 3.32-3.28 (m, 2H), 1.37 (m, 9H).

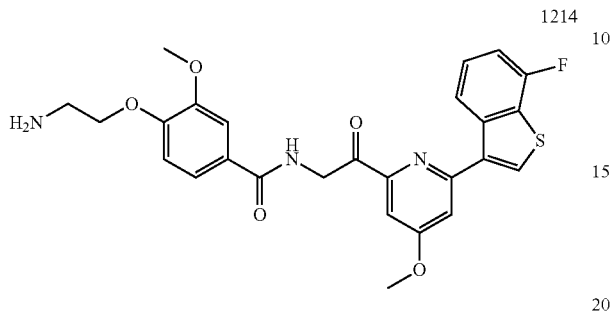

1214

Compound 1214 was obtained following the procedures for obtaining compounds 1200 and 1209 by using 2-amino-1-(6-(7-fluorobenzo[b]thiophen-3-yl)-4-methoxypyridin-2-yl) ethanol and 12-AA as the starting materials. Compound 1214 was obtained as a white solid. +ESI-MS: m/z 510.1 [M+H]⁺.

Example 12-6

Preparation of Compound 12-CC

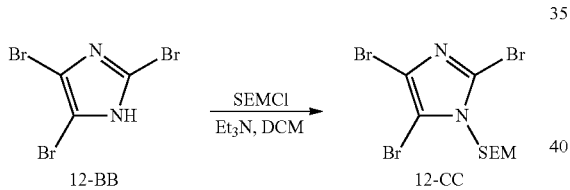

To a solution of 12-BB (30.0 g, 100.0 mmol) and SEMCl (16.6 g, 100.0 mmol) in DCM (800 mL) were added Et₃N (11 g, 108.9 mmol) at rt. The mixture was stirred at rt for 30 mins with TLC monitoring. The solution was removed under reduced pressure, and the residue was washed with H₂O and extracted with EtOAc. The combined organic layers were washed with brine, dried over Na₂SO₄ and concentrated to give crude 12-CC (25.0 g), which used for next step without purification.

Example 12-7

Preparation of Compound 12-II

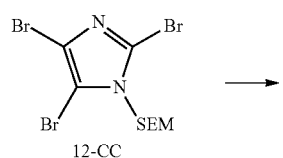

12-CC

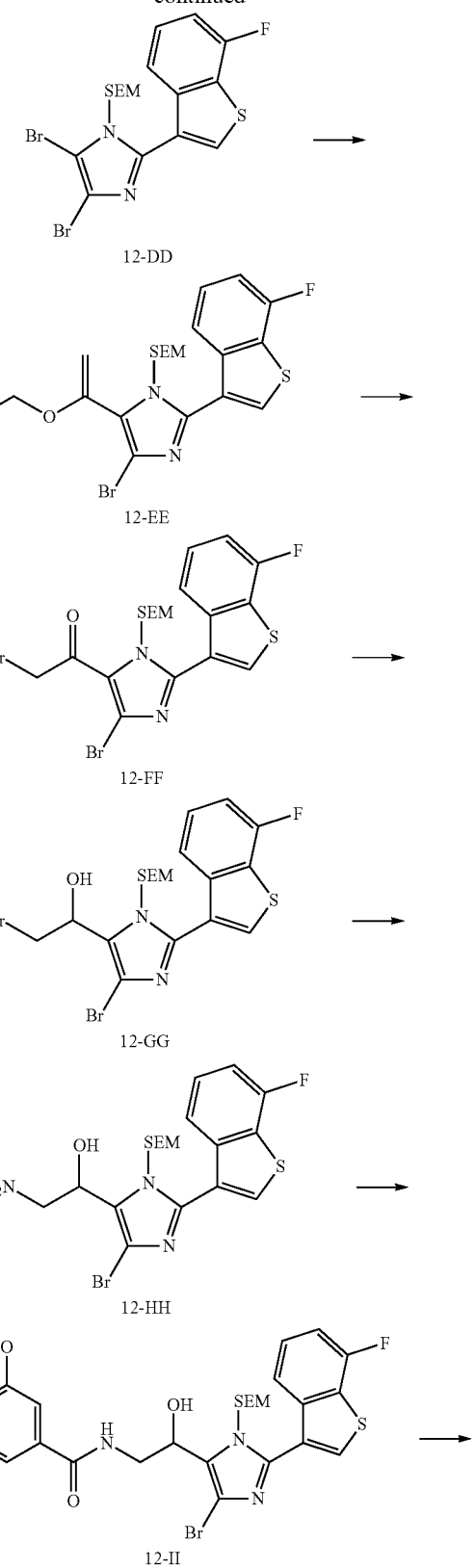

Compound 12-II was obtained following the procedures for obtaining compound 1200 by using 12-CC as the starting material.

Example 12-8

Preparation of Compound 1215

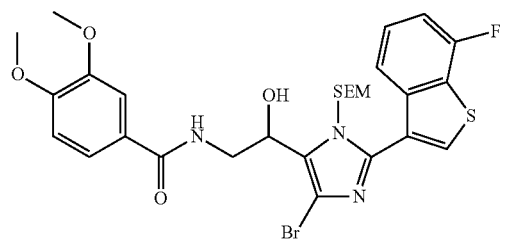
12-II

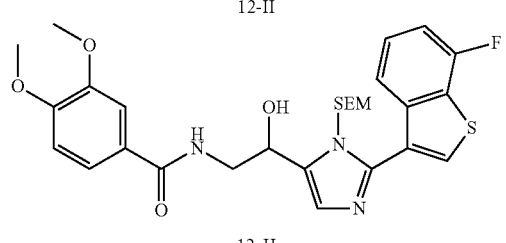
12-JJ

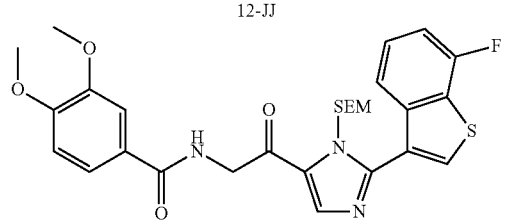
12-KK

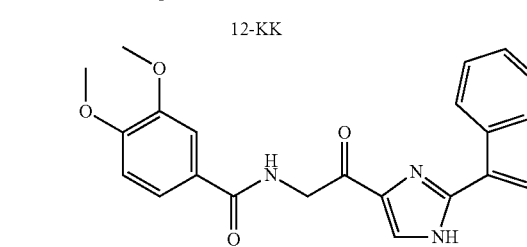
12-II

To a solution of 12-II (2.6 g, 4.6 mmol) in anhydrous THF (30 mL) was added t-BuLi (18 mL, 1.3 M in THF) dropwise under nitrogen atmosphere at −78° C. The mixture was stirred at −78° C. for 5 mins with TLC monitoring. The reaction was quenched by addition of aqueous NH$_4$Cl and extracted with EtOAc (3×100 mL). The organic layer was washed, dried and concentrated. The residue was purified on a silica gel column to give 12-JJ (2.1 g) as a solid, which was used without further purification. +ESI-MS: m/z 572.2 [M+H]$^+$.

To a solution of 12-JJ (2.1 g, 3.6 mmol) in DCM (25 mL) were added DMP (1.7 g, 4.0 mmol). The mixture was stirred at rt for 30 mins with TLC monitoring. The resulted solution was quenched by an aqueous NaHCO$_3$ solution and extracted with EtOAc. The combined organic layers were washed by saturated Na$_2$S$_2$O$_3$ and brine, dried over Na$_2$SO$_4$ and concentrated. The residue was purified by pre-HPLC to give 12-KK (600 mg) as a white solid. $^1$H NMR: CD3OD (400 MHz): δ=6.77 (d, J=4.0 Hz, 2H), 6.34 (d, J=8.4 Hz, 2H), 6.00-5.90 (m, 3H), 5.68-5.64 (m, 1H), 5.47 (d, J=8.4 Hz, 1H), 4.25 (s, 2H), 3.20 (s, 2H), 2.33 (s, 6H), 2.00-1.96 (m, 2H), 1.71-1.75 (m, 2H), 1.68 (s, 9H). +ESI-MS: m/z 570.2 [M+H]$^+$.

To a solution of 12-KK (300 mg, 0.53 mmol) in DCM (5 mL) was added TFA (5 mL) at 0° C. The solution was stirred at 40° C. for 2 h with TLC monitoring. The reaction was quenched by the addition of a saturated NaHCO$_3$ solution, and extracted with EtOAc. The combined organic layers were washed with brine, dried over Na$_2$SO$_4$ and concentrated. The residue was purified by—HPLC to give compound 1215 (15 mg) as a white solid. +ESI-MS: m/z 440.1 [M+H]$^+$.

Example 12-9

Preparation of Compound 12-OO

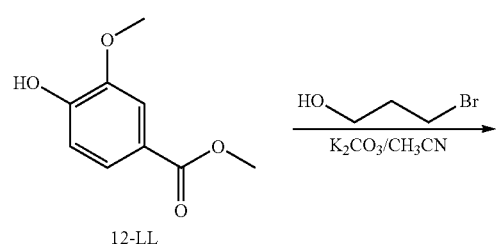
12-LL

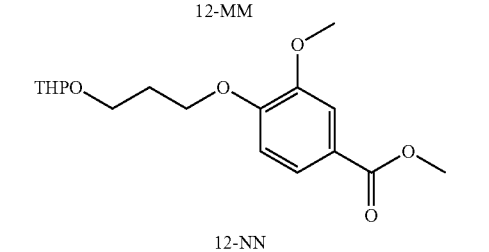
12-MM

12-NN

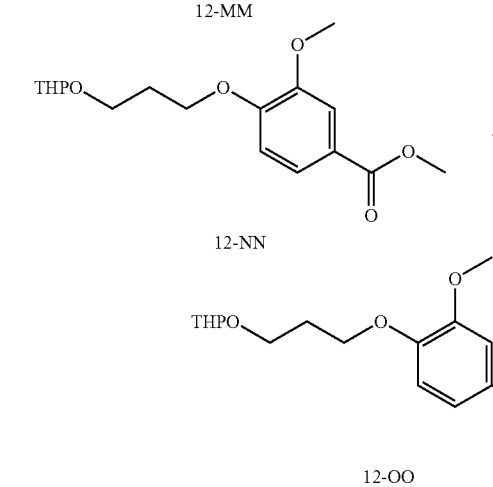
12-OO

To a solution of 12-LL (2.0 g, 11.0 mmol) in CH$_3$CN (10 mL) was added K$_2$CO$_3$ (4.55 g, 33.0 mmol) and 3-bromopropan-1-ol (4.55 g, 33.0 mmol). The mixture was heated to reflux for 12 h. The solution was evaporated and purified by column chromatography gel eluted with PE:EA=5:1 to give crude 12-MM (2.1 g, 70.7%). $^1$H-NMR (CDCl$_3$) δ=7.62-7.64 (d, 1H), 7.54-7.53 (d, 1H), 6.90-6.88 (d, 1H), 4.26-4.23 (m, 2H), 3.90-3.89 (m, 8H), 2.12-2.09 (m, 2H).

To a stirred solution of crude 12-MM (2.1 g, 8.75 mmol) in DCM (10 mL) was added TsOH (1.3 g, 13.12 mmol) and DHP (2.2 g, 13.12 mmol). The mixture was stirred at rt for 12 h. The solution was quenched with an aqueous NaHCO$_3$ solution, and the organic layer was combined and purified by column chromatography gel eluted with PE:EA=5:1 as elute to give 12-NN (1.6 g, 50.0%).

To a solution of 12-NN (1.6 g, 5.9 mmol) in THF (20 mL) was carefully added 2 N NaOH solution (9 mL, 18 mmol) and stirred at rt for 3 h. The solution was evaporated and dissolved with DCM. The solution was acidified to pH=7 with 1N HCl solution, and the aqueous layer was extracted with DCM. The organic layer was combined and purified by column chromatography gel eluted with PE:EA=3:1 as elute to give 12-OO (1.0 g, 65.4%).

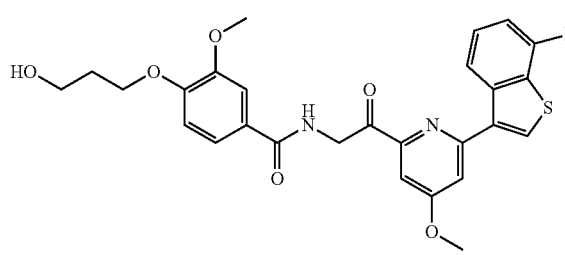

1216

Compound 1216 was obtained following the procedure for obtaining compound 1200 by using 12-OO and 2-amino-1-(6-(7-fluorobenzo[b]thiophen-3-yl)-4-methoxypyridin-2-yl) ethanol as the starting materials. Compound 1216 was obtained as a white solid. +ESI-MS: m/z 525.1 [M+H]+.

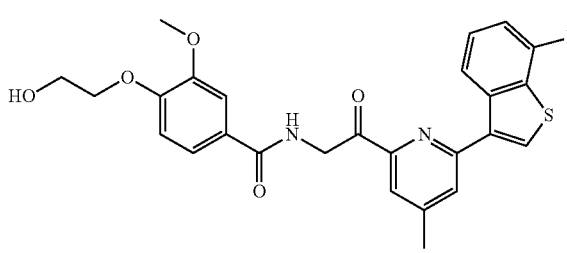

1217

Compound 1217 was obtained following the procedure for obtaining compound 1200 by using 3-methoxy-4-(2-((tetrahydro-2H-pyran-2-yl)oxy)ethoxy)benzoic acid and 2-amino-1-(6-(7-fluorobenzo[b]thiophen-3-yl)-4-methylpyridin-2-yl)ethanol as the starting materials. Compound 1217 was obtained as a white solid. +ESI-MS: m/z 495.1 [M+H]+.

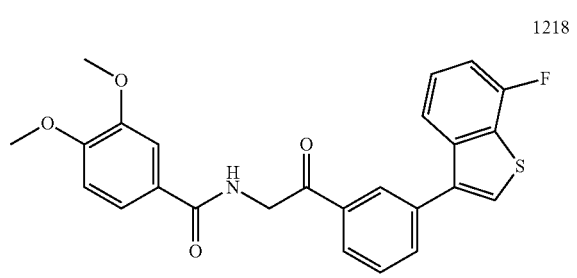 [SMILES: COc1ccc(C(=O)NCC(=O)c2cccc(-c3csc4c(F)cccc34)c2)cc1OC]

1218

Compound 1218 was obtained following the procedure for obtaining compound 1200 by using 1,3-dibromobenzene as the starting material. Compound 1218 was obtained as a white solid. +EST-MS: m/z 450.0 [M+H]+.

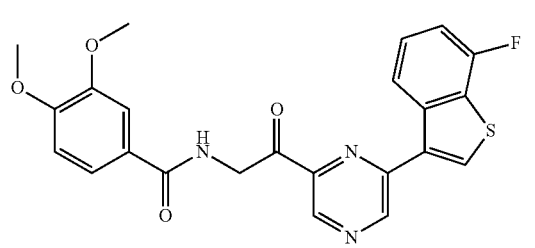

1219

Compound 1219 was obtained following the procedure for obtaining compound 1200 by using 2,6-dichloropyrazine as the starting material. Compound 1219 was obtained as a white solid (100 mg, 75%). +ESI-MS: m/z 452.1 [M+H]+.

Example 12-10

Preparation of Compound 12-RR

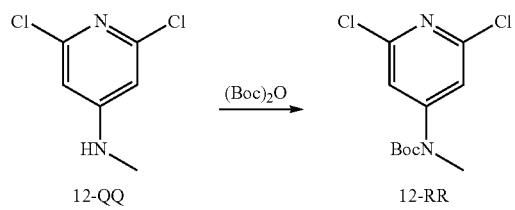

To a solution of 12-QQ (1.77 g, 10.0 mmol) in DCM (60 mL) was added Et₃N (2.02 g, 20.0 mmol) and (Boc)₂O (2.18 g, 10.0 mmol). The mixture was stirred at rt overnight. The mixture was neutralized with a saturated NaHCO₃ solution. The organic layer was evaporated to give the crude product. The residue was purified by a silica gel column using PE/EA=20/1 to 5/1 as elute to afford 12-RR as a white solid (2.5 g, 90.3%). +ESI-MS: m/z 277.0 [M+H]+.

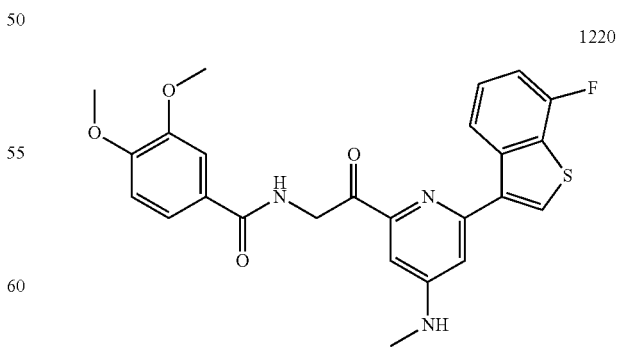

1220

Compound 1220 was obtained following the procedure for obtaining compound 1200 by using 12-RR as the starting material. +ESI-MS; m/z 480.1 [M+H]+.

Example 12-11

Preparation of Compound 12-TT

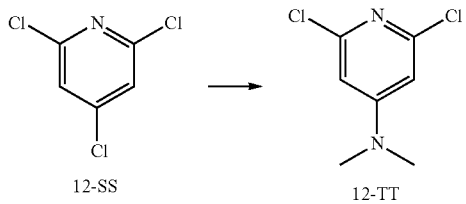

A mixture of 12-SS (10.0 g, 55.6 mmol), dimethylamine hydrochloride (4.5 g, 55.6 mmol) and Et$_3$N (8.0 g, 55.6 mmol) in DMF (80 mL) in a sealed tube was heated to 80° C. for 8 h. The mixture was diluted with water and extracted with EtOAc. The combined organic layers were washed with brine, dried over Na$_2$SO$_4$ and concentrated. The residue was purified on a silica gel column to give 12-TT (4.0 g) as a white solid. $^1$H-NMR: DMSO (400 MHz): δ=6.66 (s, 2H), 2.99 (s, 6H).

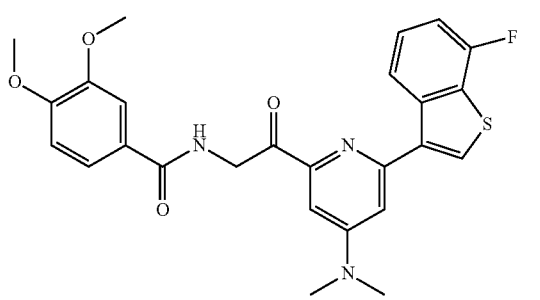

1221

Compound 1221 was obtained following the procedure for obtaining compound 1200 by using 12-TT as the starting material. Compound 1221 was obtained as a white solid +ESI-LCMS: m/z=494.0 [M+H]$^+$.

Example 12-12

Preparation of Compound 12-UU

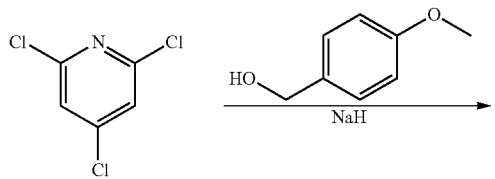

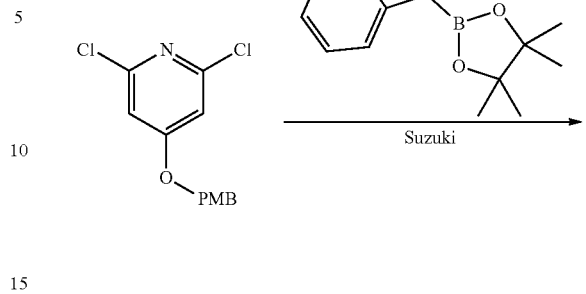

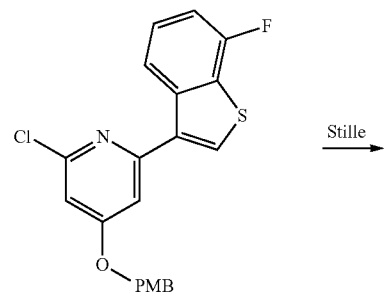

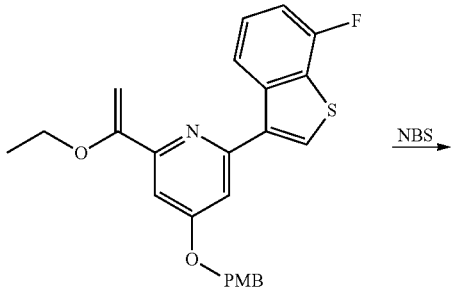

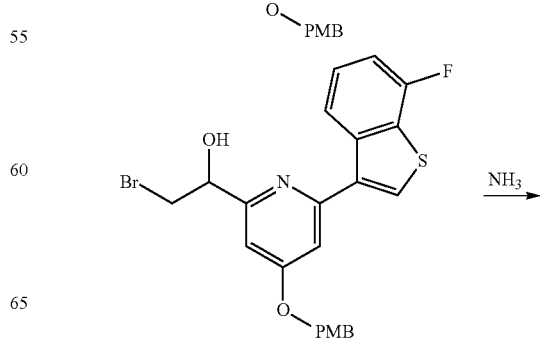

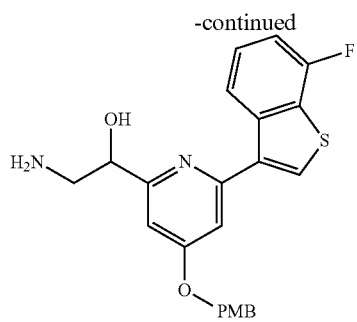

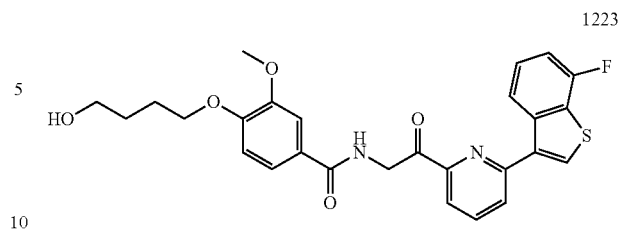

Compound 1223 was obtained following the procedure for obtaining compound 1200 by using 3-methoxy-4-((4-((2-(trimethylsilyl)ethoxy)methoxy)butoxy)benzoic acid and 2-amino-1-(6-(7-fluorobenzo[b]thiophen-3-yl)pyridin-2-yl)ethanol as the starting materials. Compound 1223 was obtained as a white solid +ESI-MS: m/z 509.0 [M+H]$^+$.

Example 12-13

Preparation of Compound 12-YY

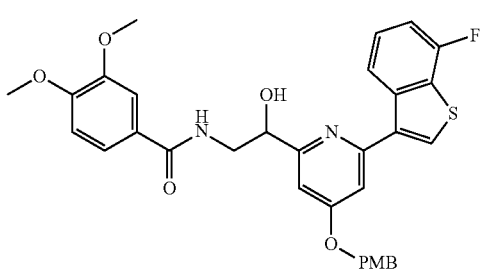

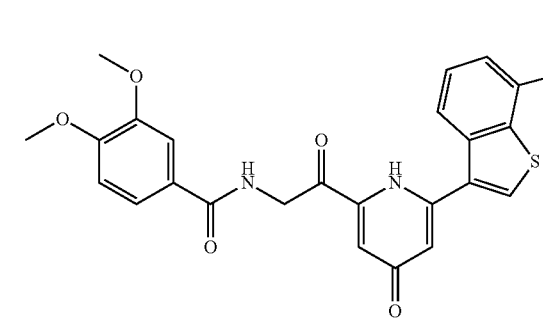

Compound 12-UU was obtained following the procedure for obtaining compound 1200 by using 2,4,6-trichloropyridine as the starting material.

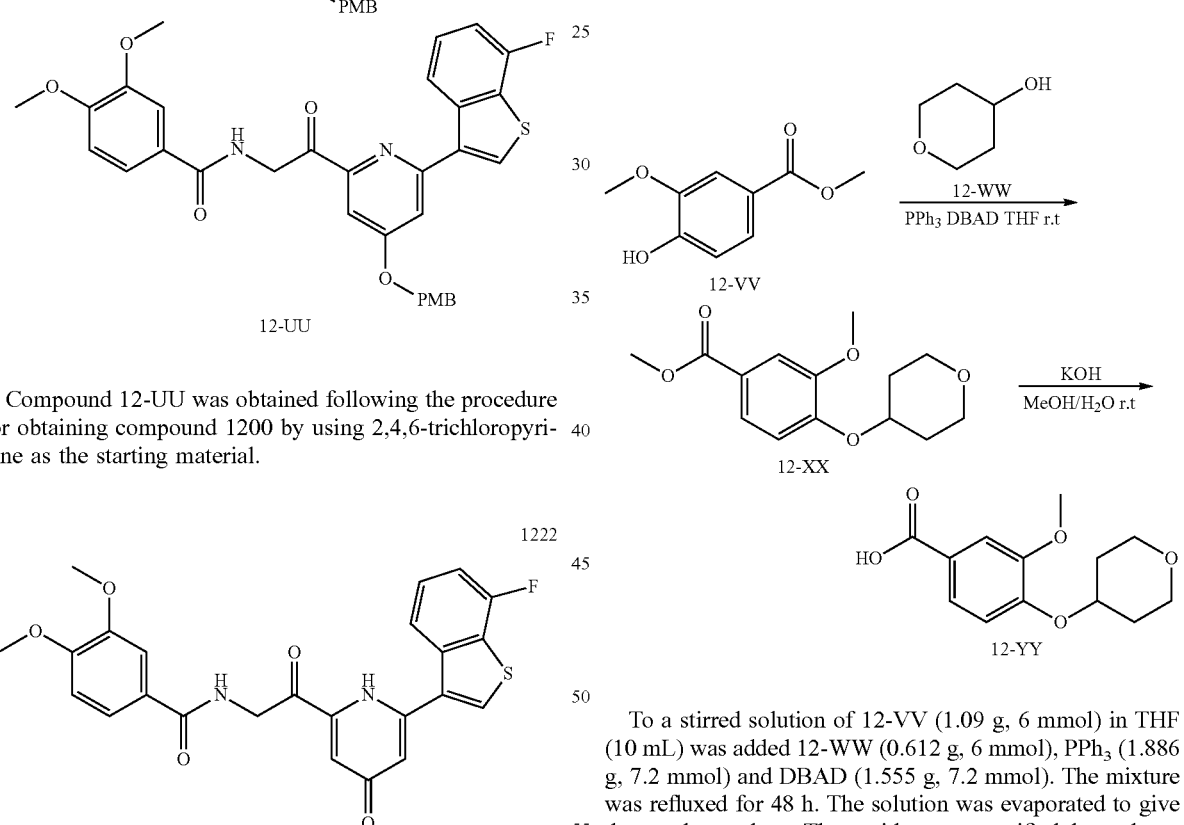

To a solution of 12-UU (90 mg, 0.15 mmol) in DCM/H$_2$O (1.5 mL, DCM/H$_2$O=10:1) was added DDQ (69 mg, 0.3 mmol). The mixture was stirred at 30° C. for 3 h. The mixture was neutralized with a saturated NaHCO$_3$ solution. The mixture was extracted with DCM (300 mL). The organic layers were combined, washed with brine, dried over Na$_2$SO$_4$ and concentrated. The residue was purified by column on silica gel using DCM:MeOH=50:1 to 30:1 as elute to give compound 1222 (30 mg, 43%). +ESI-MS: m/z 466.9 [M+H]+.

To a stirred solution of 12-VV (1.09 g, 6 mmol) in THF (10 mL) was added 12-WW (0.612 g, 6 mmol), PPh$_3$ (1.886 g, 7.2 mmol) and DBAD (1.555 g, 7.2 mmol). The mixture was refluxed for 48 h. The solution was evaporated to give the crude product. The residue was purified by column chromatography gel using PE:acetone=8:1 as the elute to give 12-XX (900 mg, 52.9%).

To a solution of crude 12-XX (800 mg, 3.38 mmol) in MeOH (15 mL) was added a solution of 1N KOH (757 mg, 13.53 mmol). The mixture was stirred at rt for 1 h. After complete conversion, as indicated by TLC (PE:EA=2:1), the solvent was washed with water and extracted with EtOAc. The aqueous phase was acidified to pH=3 with 1N critic acid solution. The solution was extracted with EtOAc, and the organic phase was concentrated to give crude 12-YY. After purification, 12-YY (660 mg, yield: 87.2%) was obtained.

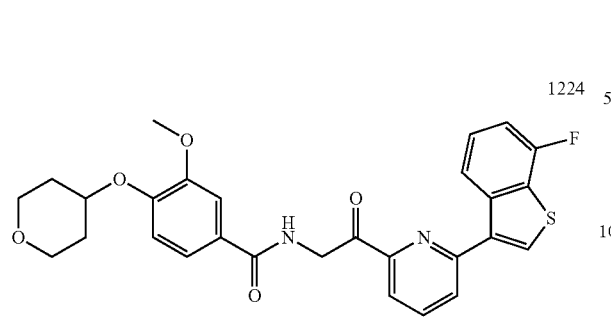

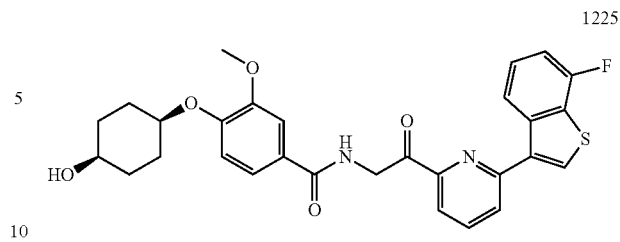

Compound 1224 was obtained following the procedure for obtaining compound 1200 by using 2-amino-1-(6-(7-fluorobenzo[b]thiophen-3-yl)pyridin-2-yl)ethanol and 12-YY as the starting materials. Compound 1224 was obtained as a white solid +ESI-MS: m/z 521.1 [M+H]+.

Compound 1225 was obtained following the procedure for obtaining compound 1200 by using 3-methoxy-4-(((1s,4s)-4-((2-(trimethylsilyl)ethoxy)methoxy)cyclohexyl)oxy)benzoic acid and 2-amino-1-(6-(7-fluorobenzo[b]thiophen-3-yl)pyridin-2-yl)ethanol as the starting materials. Compound 1225 was obtained as a white solid +ESI-MS: m/z 535.1 [M+H]+.

Example 12-14

Preparation of Compound 1226

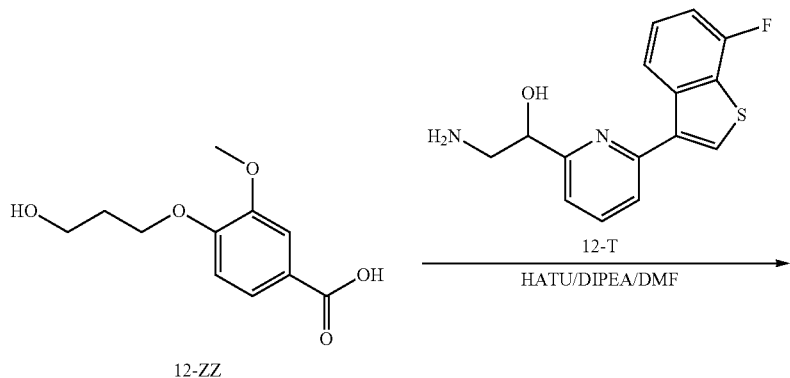

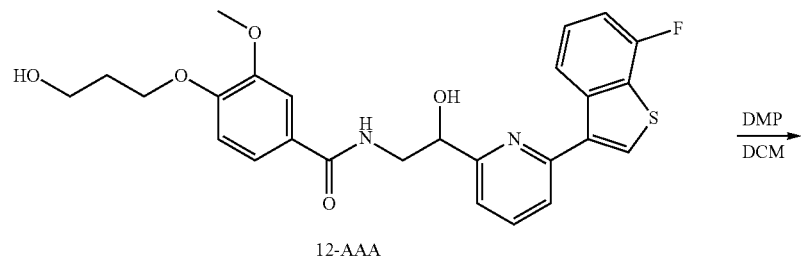

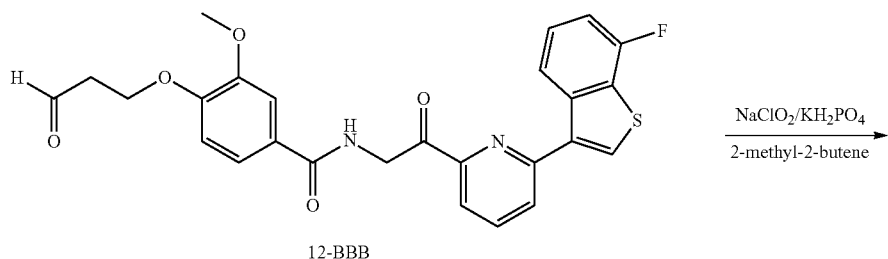

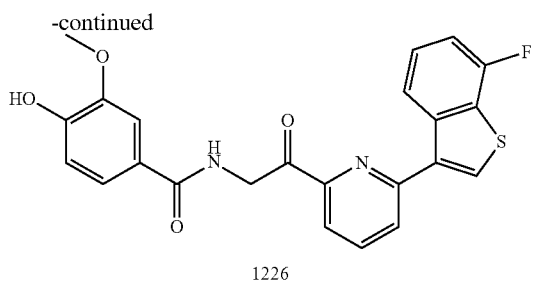

1226

To a solution of 12-ZZ (100 mg, 0.442 mmol), HATU (251 mg, 0.66 mmol) and DIPEA (170 mg, 1.32 mmol) in anhydrous DMF (2 mL) was added 12-T (127 mg 0.442 mmol) at 25° C. The solution was stirred for 10 h at rt and then diluted with 1.0 N aqueous NaHCO$_3$ solution (40 mL×2), extracted with EA (20 mL×2). The combined organic layers were washed with brine, dried over anhydrous Na$_2$SO$_4$, and concentrated under reduced pressure. The residue was purified on a silica gel column to give 12-AAA (120 mg, 54.8%). +ESI-MS: m/z 497.1 [M+H]$^+$.

To a mixture of 12-AAA (120 mg, 0.24 mmol) in DCM (10 mL) was added DMP (410 mg, 0.96 mmol). The mixture was stirred at rt for 30 mins with TLC monitoring. The solution was quenched with aqueous NaHCO$_3$ solution and extracted with EtOAc. The combined organic layers were washed with saturated Na$_2$S$_2$O$_3$ and brine, dried over Na$_2$SO$_4$ and concentrated. The residue was purified by prep-TLC to give 12-BBB (100 mg, 84.7%). +ESI-MS: m/z 493.1[M+H]$^+$.

To a solution of 12-BBB (100 mg, 0.2 mmol) in acetone: H$_2$O (1 mL/1 mL) were added KH$_2$PO$_4$ (23 mg, 0.22 mmol), NaClO$_2$ (36 mg, 0.4 mmol) and 2-methyl-2-butene (116 mg, 2 mmol) at 0° C. The mixture was stirred for 30 mins. The resulted solution was quenched with a Na$_2$S$_2$O$_3$ solution and extracted with EtOAc. The combined organic layers were washed with brine, dried over Na$_2$SO$_4$ and concentrated. The residue was purified by prep-HPLC(FA) to give compound 1226 (20 mg, 17.2%). +ESI-MS: m/z 436.9 [M+H]$^+$.

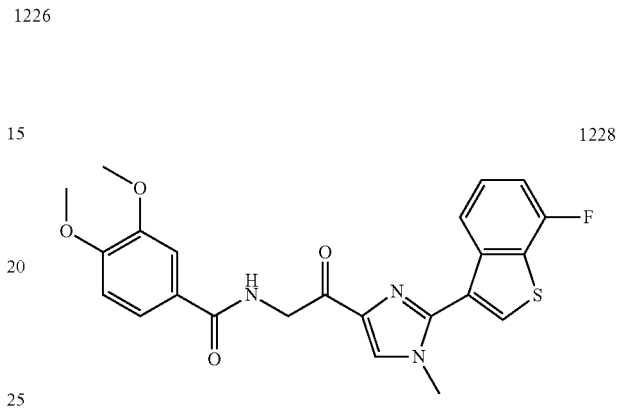

1228

To a mixture of compound 1215 (44 mg, 0.1 mmol) in DMF (4 mL) was added K$_2$CO$_3$ (27 mg, 0.2 mmol). The solution was heated to 60° C. and MeI (5.6 g, 20 mmol) was added. The solution was stirred for 2 h at 60° C. The water was added and extracted with EtOAc. The organic phase was concentrated to give the crude product. Further purification by prep-HPLC gave compound 1228 as a colorless solid (6 mg, 14%). +ESI-MS: m/z 454.0 [M+H]$^+$.

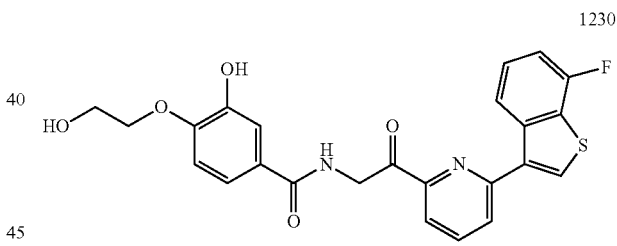

1230

Compound 1230 was obtained following the procedure for obtaining compound 1200 by using 2,6-dichloropyridine as the starting material. Compound 1230 was obtained as a white solid. +ESI-MS: m/z 467.1 [M+H]$^+$.

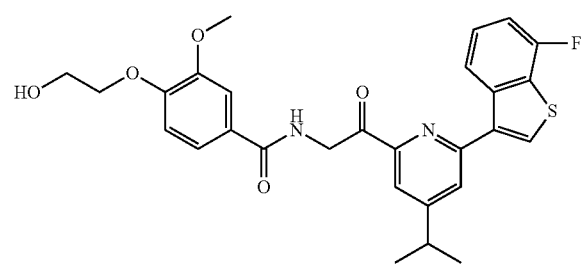

1227

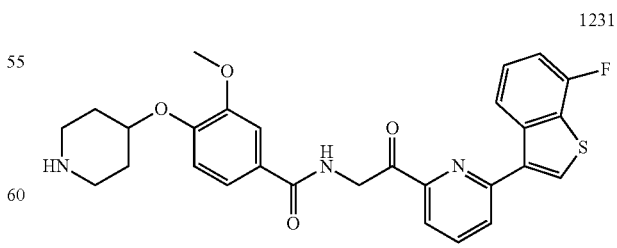

1231

Compound 1227 was obtained following the procedure for obtaining compound 1200 by using 2,4,6-trichloropyridine as the starting material. Compound 1227 was obtained as a white solid +ESI-MS: m/z 523.0 [M+H]$^+$.

Compound 1231 was obtained following the procedure for obtaining compound 1200 by using 4-((1-(tert-butoxycarbonyl)piperidin-4-yl)oxy)-3-methoxybenzoic acid and 2-amino-1-(6-(7-fluorobenzo[b]thiophen-3-yl)pyridin-2-yl)

ethanol as the starting materials. Compound 1231 was obtained as a yellow solid (50 mg, 50%). +ESI-MS: m/z 519.9 [M+H]+.

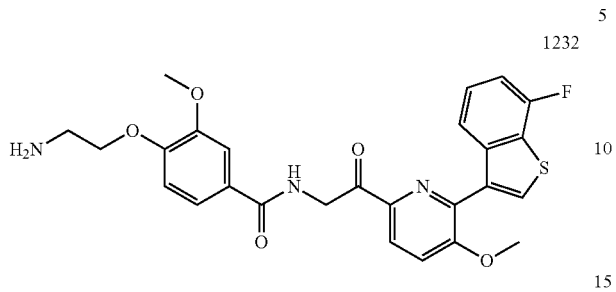

Compound 1232 was obtained following the procedure for obtaining compound 1200 by using 4-(2-((tert-butoxycarbonyl)amino)ethoxy)-3-methoxybenzoic acid and 2-amino-1-(6-(7-fluorobenzo[b]thiophen-3-yl)-5-methoxypyridin-2-yl)ethanol as the starting materials. Compound 1232 was obtained as a white solid. +ESI-MS: m/z 510.1 [M+H]+.

Compound 1233 was obtained following the procedure for obtaining compound 1200 by using 4-(2-((tert-butoxycarbonyl)amino)ethoxy)-3-methoxybenzoic acid and 2-amino-1-(6-(7-fluorobenzo[b]thiophen-3-yl)-5-methoxypyridin-2-yl)ethanol as the starting materials. Compound 1233 was obtained as a white solid. +ESI-MS: m/z 549.9 [M+H]+.

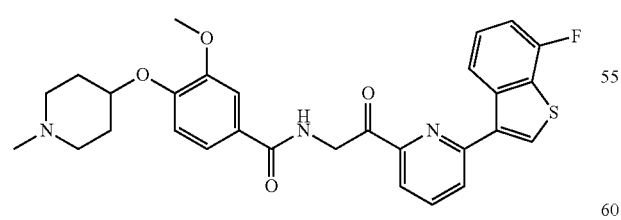

Compound 1234 was obtained following the procedure for obtaining compound 1200 by using 3-methoxy-4-((1-methylpiperidin-4-yl)oxy)benzoic acid and 2-amino-1-(6-(7-fluorobenzo[b]thiophen-3-yl)-5-methoxypyridin-2-yl)ethanol as the starting materials. Compound 1234 was obtained as a white solid. +ESI-MS: m/z 534.1 [M+H]+.

Example 12-15

Preparation of Compound 1236

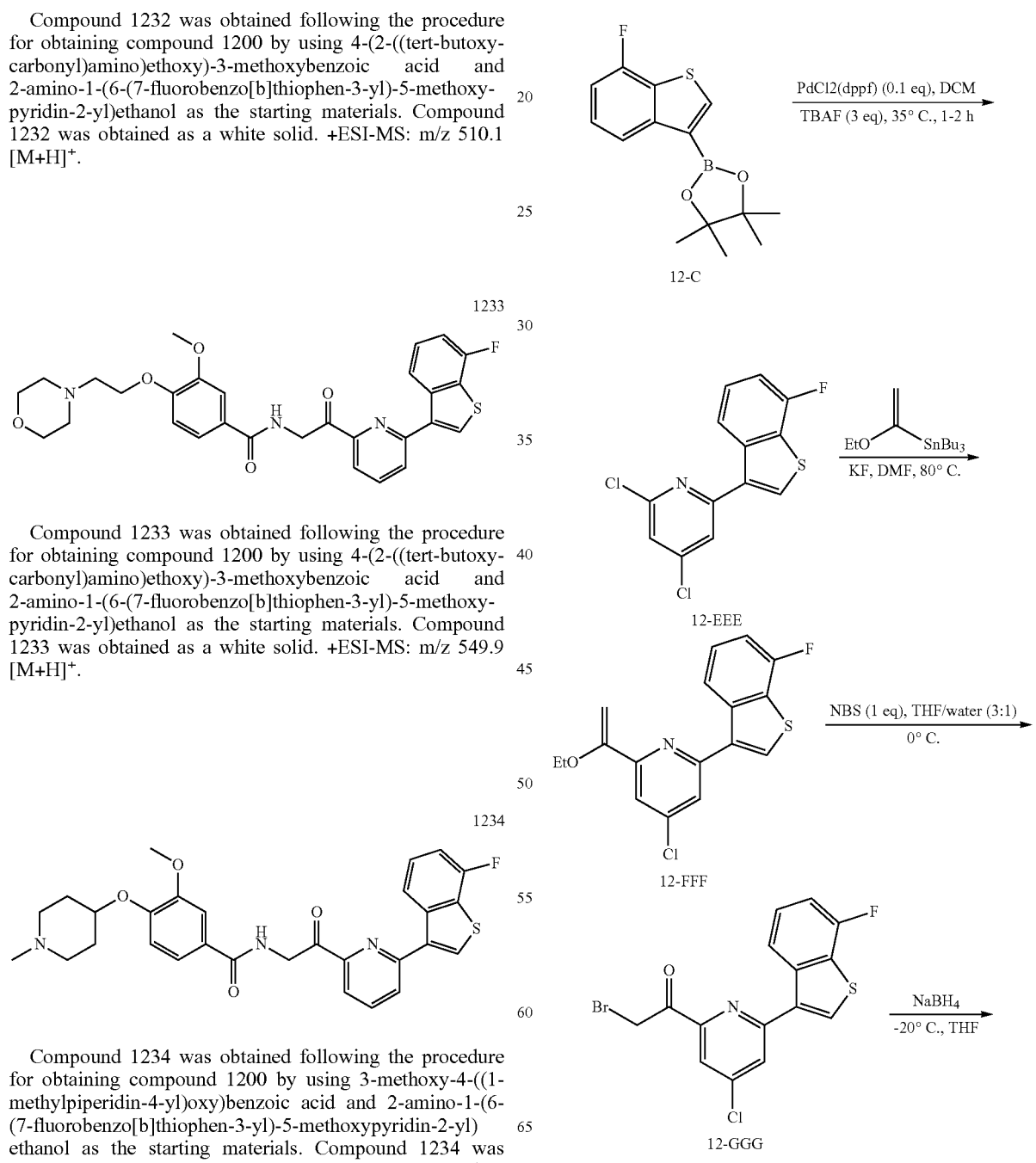

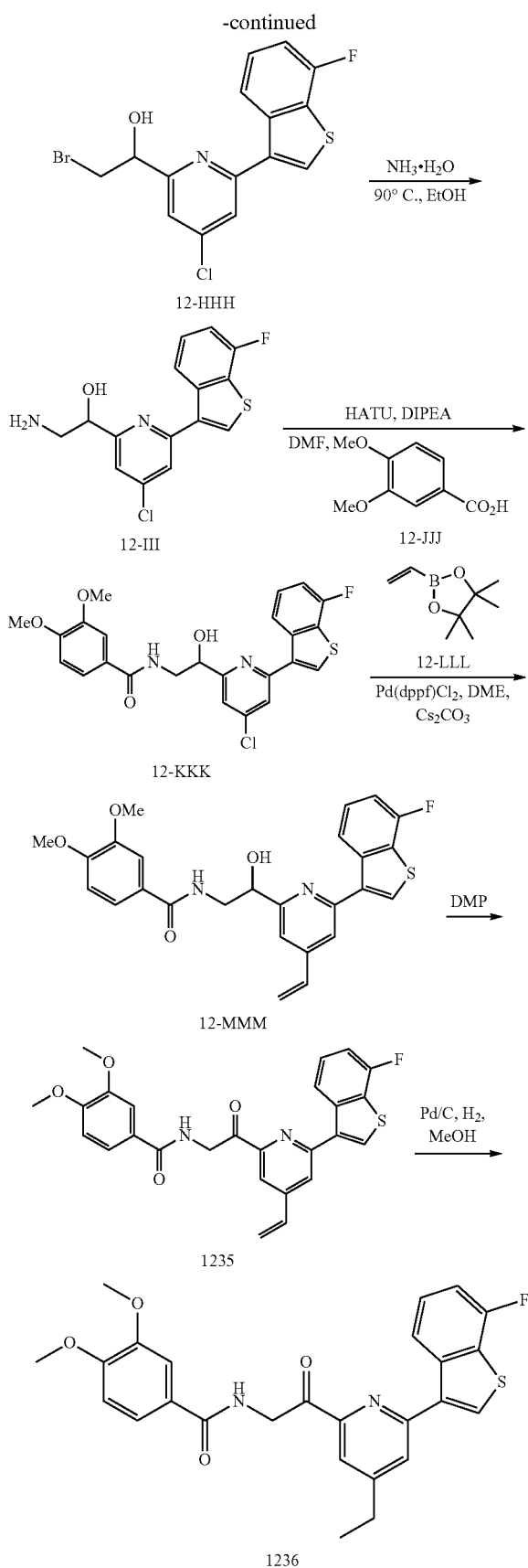

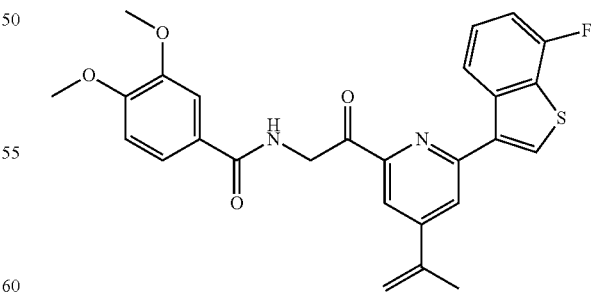

To a solution of 12-SS (18.2 g, 0.1 mol) in DCM (200 mL) was added 12-C (27.8 g, 0.1 mol), TBAF (78 g, 0.3 mol) and Pd(dppf)Cl$_2$ (7.31 g, 0.01 mol). The mixture was stirred at 30-40° C. for 2 h and monitored by TLC. The reaction solution was filtered and the filtrates were washed with brine. The organic layer was concentrated by rotary evaporator, and the product was purified by silica column chromatography (9 g, 30%). +ESI-MS: m/z 298.0 [M+H]$^+$.

Compound 12-EEE to 12-KKK were obtained following the procedure for obtaining Compound 1200 by using 12-EEE as the starting material.

To a solution of 12-KKK (972 mg, 2 mmol) in DME (15 mL) was added 12-LLL (616 mg, 4 mmol), Pd(dppf)Cl$_2$ (146 mg, 0.2 mmol) and Cs$_2$CO$_3$ (1.3 g, 4 mmol). The mixture was stirred for 16 h at 120° C. under N$_2$. The reaction solution was filtered and to give a clear solution. The solution was extracted with EtOAc (80 mL) and washed with brine (20 mL×3). Compound 12-MMM was purification by silica column chromatography using EA:PE=1:1 as the elute (900 mg, 94%). ESI-MS: m/z 478.9 [M+H]$^+$.

To a solution of 12-MMM (478 mg, 1 mmol) in DCM (10 mL) was added DMP (848 mg, 2 mmol) at 0° C. The reaction was allowed to proceed for 3 h. The mixture was washed with brine (5 mL×3), and the organic layer was dried and concentrated to give the crude product. The product was purified by silica column chromatography using PE:EA=2:1 as the elute to give the compound 1235 (220 mg, 46%). +ESI-MS: m/z 476.8 [M+H]$^+$ A mixture of compound 1235 (119 mg, 0.25 mmol) and Pd/C (50 mg) in MeOH (10 mL) was hydrogenated under H$_2$ (1 atm) for 1 h at rt. The suspension was filtered through a pad of Celite, and the filter cake was washed with MeOH (10 mL×3). The combined filtrates were concentrated to give the product. Compound 1236 was purified by prep-HPLC to give the product (15 mg, 12%). +ESI-MS: m/z 479.0 [M+H]$^+$.

Compound 1237 was obtained following the procedure for obtaining compound 1235 by using 4,4,5,5-tetramethyl-2-(prop-1-en-2-yl)-1,3,2-dioxaborolane and 12-KKK as the starting materials. Compound 1237 was obtained as a white solid. +ESI-MS: m/z 490.9 [M+H]$^+$.

1238

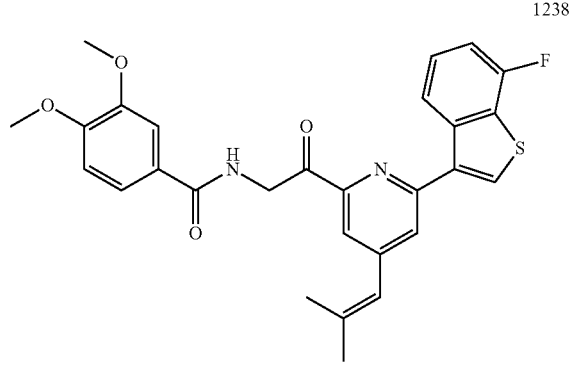

1239

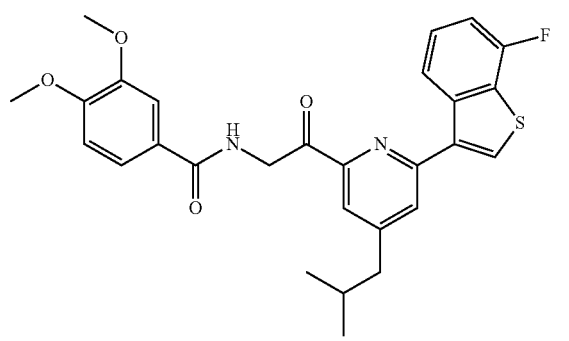

Compounds 1238 and 1239 were obtained following the procedure for obtaining compound 1235 by using 12-KKK and 4,4,5,5-tetramethyl-2-(2-methylprop-1-en-1-yl)-1,3,2-dioxaborolane as the starting materials. Compounds 1238 and 1239 were each obtained as a white solid. Compound 1238: +ESI-MS: m/z 504.9 [M+H]$^+$. Compound 1239: +ESI-MS: m/z 506.8 [M+H]$^+$.

1240

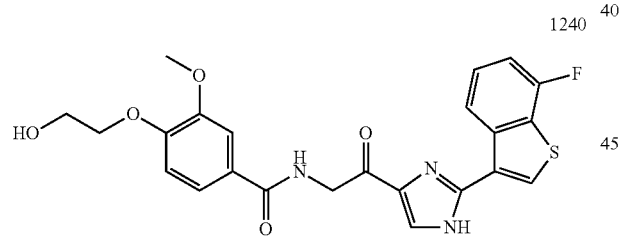

Compound 1240 was obtained following the procedure for obtaining compound 1215 by using 2,4,5-tribromo-1H-imidazole as the starting material. Compound 1240 was obtained as a white solid. +ESI-MS: m/z 469.8 [M+H]$^+$.

1241

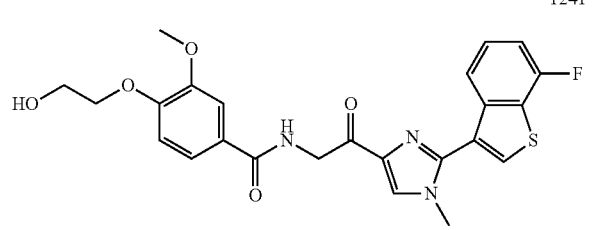

To a mixture of compound 1240 (100 mg, 0.2 mmol) in DMF (4 mL), K$_2$CO$_3$ (27 mg, 0.2 mmol) was added. The solution was heated to 60° C. and MeI (5.6 g, 20 mmol) was added. The solution was stirred for 2 h at 60° C. The water was added, and the solution was extracted with EtOAc. The organic phase was concentrated to give the crude product. Further purification by prep-HPLC gave compound 1241 as a colorless solid (50 mg, 48%). +ESI-MS: m/z 483.9 [M+H]$^+$.

Example 12-16

Preparation of Compound 12-QQQ

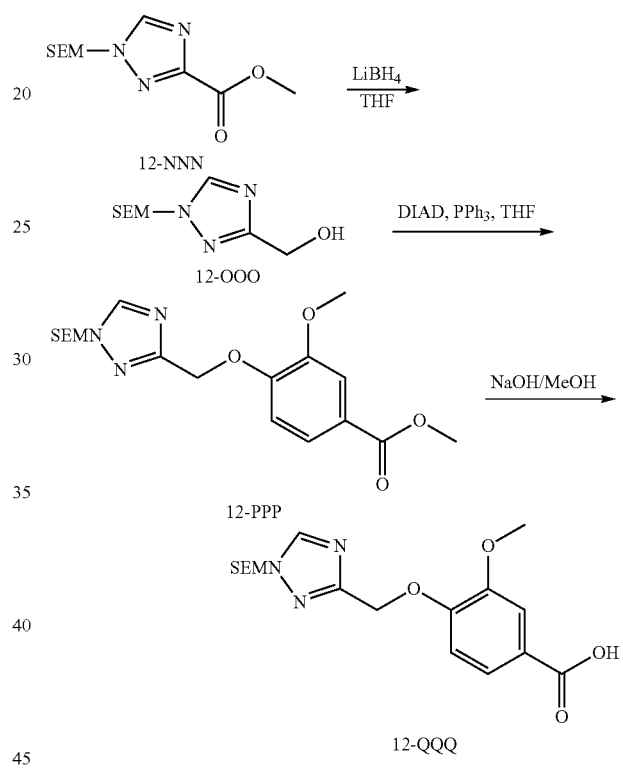

To a solution of 12-NNN (5 g, 19.4 mmol) in THF (30 mL) was added LiBH$_4$ (1.7 g, 77.8 mmol) at rt. The solution was heated to reflux and stirred for 2 h. The solution was quenched with H$_2$O and extracted with EtOAc. The combined organic layers were washed with brine, dried over Na$_2$SO$_4$ and concentrated to give 12-OOO (1.3 g, 73%).

To a solution of 12-OOO (3.3 g, 14.4 mmol) and methyl 4-hydroxy-3-methoxybenzoate (2.62 g, 14.4 mmol) in THF (20 mL) were added DIAD (3.49 g, 17.3 mmol) and PPh$_3$ (4.5 g, 17.3 mmol). The solution was heated to reflux and stirred for 15 h. The solution was washed with brine and extracted with EtOAc. The organic phase was concentrated, and the residue was used in the next step without further purification.

To a solution of 12-PPP (4 g crude, 10 mmol) in methanol (20 mL), was added NaOH aqueous (20 mL, 1M). The mixture was stirred for 4 h at 60° C. The solution was cooled to rt, acidified using 1N HCl and extracted with EtOAc. The organic phase was dried with anhydrous Na$_2$SO$_4$ and concentrated under reduced pressure to provide 12-QQQ (400 mg, 50%).

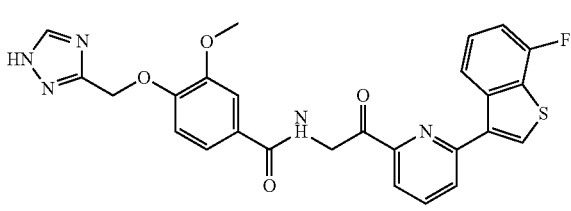

1242

Compound 1242 was obtained following the procedure for obtaining compound 1215 by using 2-amino-1-(6-(7-fluorobenzo[b]thiophen-3-yl)pyridin-2-yl)ethanol and 12-QQQ as the starting materials. Compound 1242 was obtained as a white solid. +ESI-MS: m/z 517.8 [M+H]$^+$.

1243

1244

Compounds 1243 and 1244 were obtained following the procedure for obtaining compound 1235 by using 12-KKK and 4,4,5,5-tetramethyl-2-(prop-1-en-1-yl)-1,3,2-dioxaborolane as the starting materials. Compounds 1243 and 1244 were each obtained as a white solid. Compound 1243: +ESI-MS: m/z 491.1[M+H]$^+$. Compound 1244: +ESI-MS: m/z 593.1 [M+H]$^+$.

1245

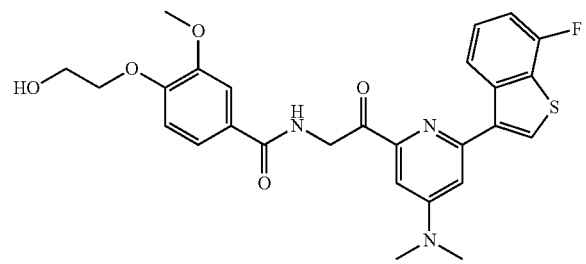

Compound 1245 was obtained following the procedure for obtaining compound 1221 by using 2,4,6-trichloropyridine as the starting material. Compound 1245 was each obtained as a white solid. +ESI-MS: m/z 524.1 [M+H]$^+$.

Example 12-17

Preparation of Compound 12-UUU

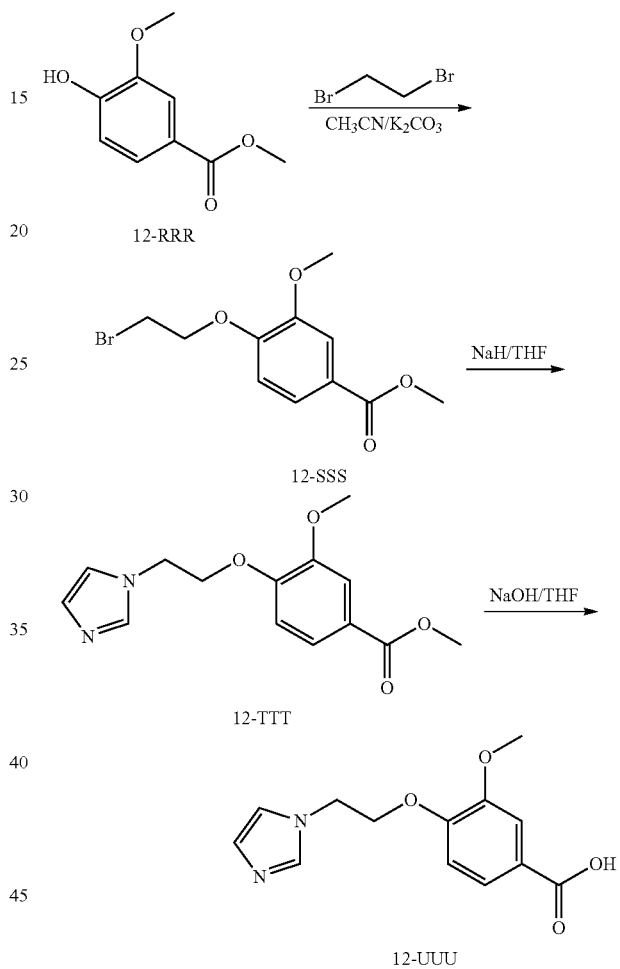

To a solution of 12-RRR (3.6 g, 20 mmol), 1,2-dibromoethane (7.4 g, 40 mmol) in CH$_3$CN (30 mL) were added K$_2$CO$_3$ (4.5 g, 22.2 mmol). The solution was heated to reflux and stirred for 15 h. The solution was washed with brine and extracted with EtOAc. The organic phase was concentrated, and the residue was directly used in the next step.

To a solution of imidazole (680 mg, 10.0 mmol) in THF (30 mL) were added NaH (480 mg, 22.2 mmol, 60% in mineral oil). The mixture was stirring at rt for 0.5 h, and 12-SSS (2.88 g, 10 mmol) in THF (10 mL) was added dropwise. The solution was stirred for 15 h at rt. The solution was washed with brine and extracted with EtOAc. The organic phase was concentrated, and the residue was directly used in the next step. +ESI-MS: m/z 277.1 [M+H]$^+$.

To a solution of 12-TTT (2.76 g crude, 10 mmol) in methanol (20 mL) was added NaOH aqueous (20 mL, 1M). The mixture was stirred for 4 h at 60° C. The solution was cooled to rt, acidified to pH=3 using 1N HCl solution and extracted with EtOAc. The organic phase was dried with anhydrous Na$_2$SO$_4$ and concentrated under reduced pressure to provide 12-UUU (1.4 g, 50%).

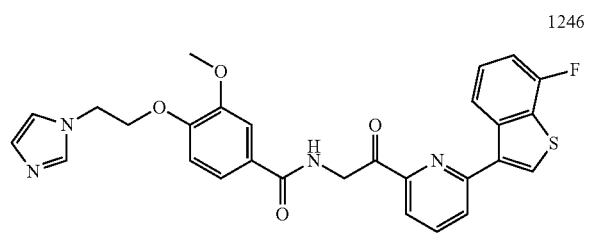 [SMILES: COc1cc(C(=O)NCC(=O)c2cccc(-c3csc4c(F)cccc34)n2)ccc1OCCn1ccnc1]

1246

Compound 1246 was obtained following the procedure for obtaining compound 1215 by using 2-amino-1-(6-(7-fluorobenzo[b]thiophen-3-yl)pyridin-2-yl)ethanol and 12-UUU as the starting materials. Compound 1246 was each obtained as a white solid. +ESI-MS: m/z 531.0 [M+H]$^+$.

Example 12-18

Preparation of Compound 12-AAAA

To a solution of 12-RRR (1.82 g, 10 mmol) and K$_2$CO$_3$ (2.76 g, 20 mmol) in CH$_3$CN (20 mL) at rt was slowly added 2-bromoacetonitrile (2.4 g, 20 mmol). The mixture was heated to reflux and stirred for 15 h. The solvent were removed under reduced pressure. Purification by column chromatography on silica gel (PE:EA=3:1) provided 12-VVV (2 g, 90%).

To a solution of 12-VVV (2.21 g, 10 mmol) in methanol (10 mL) was added NaOH aqueous (10 mL, 1M). The mixture was stirred for 4 h at 60° C. The solution was cooled to rt, acidified to pH=4 using 1N HCl solution and extracted with EtOAc. The organic phase was dried with anhydrous Na$_2$SO$_4$ and concentrated under reduced pressure to provide 12-YYY (1.1 g, 50%).

To a solution of 12-YYY (226 mg, 0.1 mmol) in DMF (3 mL) were added HATU (570 mg, 1.5 mmol) and DIPEA (387 mg, 3 mmol) at rt. The solution was stirred for 10 min at rt. Compound 12-ZZZ (287 mg, 1 mmol) was added and stirred for 1 h. The solution was extracted with EtOAc and washed with H$_2$O. The organic phase was concentrated and purified by prep-TLC to give 12-AAAA (200 mg, 40%). +ESI-MS: m/z 495.9 [M+H]$^+$.

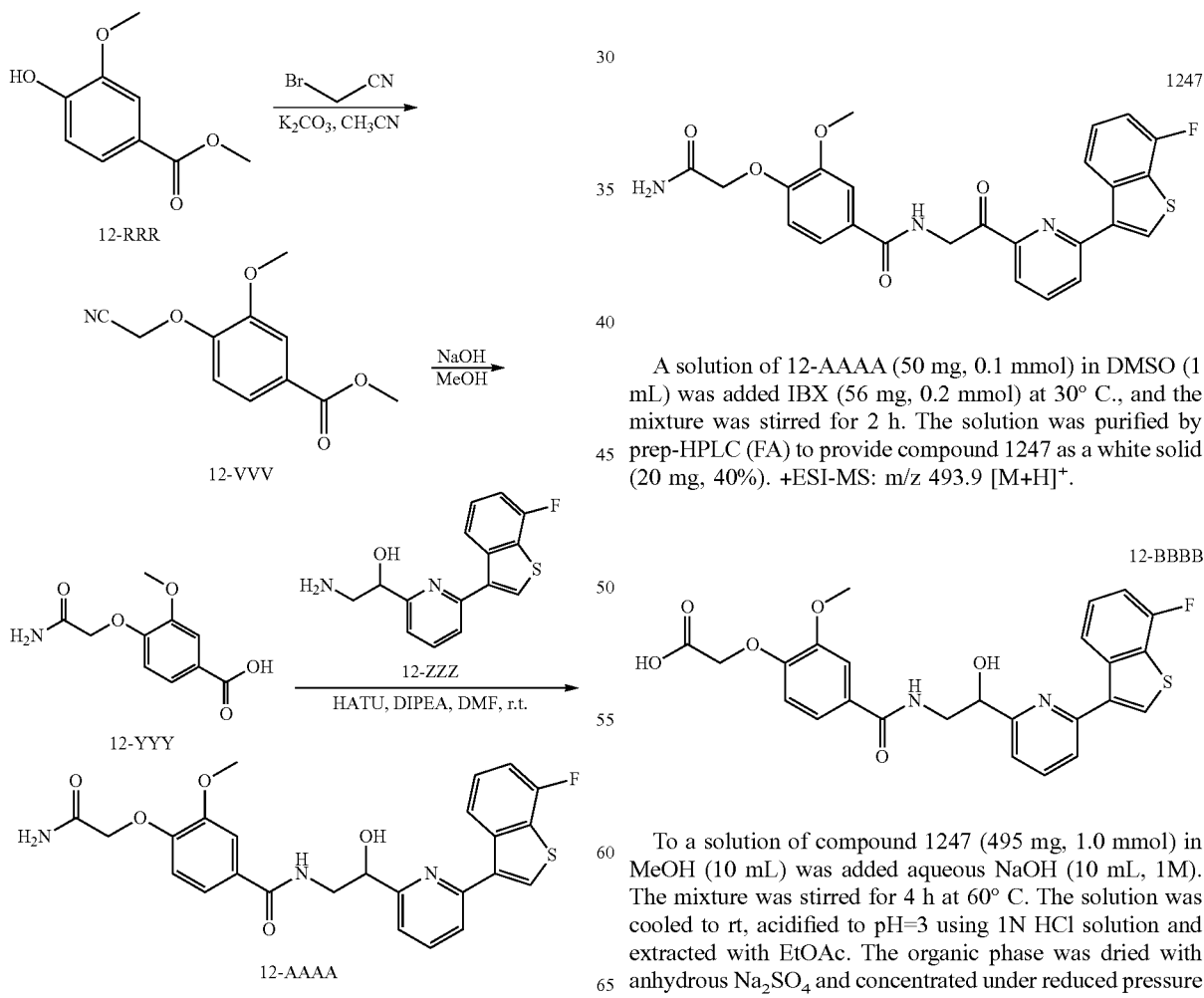

A solution of 12-AAAA (50 mg, 0.1 mmol) in DMSO (1 mL) was added IBX (56 mg, 0.2 mmol) at 30° C., and the mixture was stirred for 2 h. The solution was purified by prep-HPLC (FA) to provide compound 1247 as a white solid (20 mg, 40%). +ESI-MS: m/z 493.9 [M+H]$^+$.

To a solution of compound 1247 (495 mg, 1.0 mmol) in MeOH (10 mL) was added aqueous NaOH (10 mL, 1M). The mixture was stirred for 4 h at 60° C. The solution was cooled to rt, acidified to pH=3 using 1N HCl solution and extracted with EtOAc. The organic phase was dried with anhydrous Na$_2$SO$_4$ and concentrated under reduced pressure to provide 12-BBBB (490 mg, 99%). +ESI-MS: m/z 497.1 [M+H]$^+$.

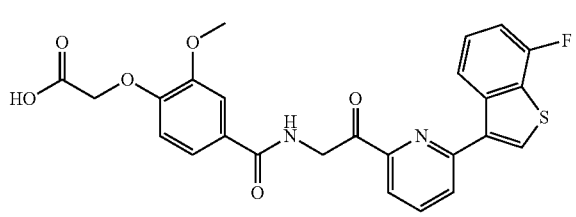

1248

To a solution of 12-BBBB (50 mg, 0.1 mmol) in DMSO (1 mL) was added IBX (56 mg, 0.2 mmol) at 30° C. and stirred for 2 h. The solution was purified by prep-HPLC (FA) to provide compound 1248 as a white solid (20 mg, 40%). +ESI-MS: m/z 494.7 [M+H]+.

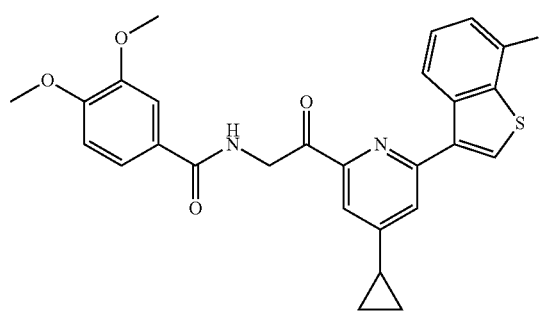

1249

Compound 1249 was obtained following the procedure for obtaining compound 1235 by using N-(2-(4-chloro-6-(7-fluorobenzo[b]thiophen-3-yl)pyridin-2-yl)-2-hydroxyethyl)-3,4-dimethoxybenzamide and 2-cyclopropyl-4,4,5,5-tetramethyl-1,3,2-dioxaborolane as the starting materials. Compound 1249 was each obtained as a white solid. +ESI-MS: m/z 491.0 [M+H]+.

1250

Compound 1250 was obtained following the procedure for obtaining compound 1235 by using N-(2-(4-chloro-6-(7-fluorobenzo[b]thiophen-3-yl)pyridin-2-yl)-2-hydroxyethyl)-3-methoxy-4-(2-((tetrahydro-2H-pyran-2-yl)oxy)ethoxy)benzamide and 4,4,5,5-tetramethyl-2-vinyl-1,3,2-dioxaborolane as the starting materials.

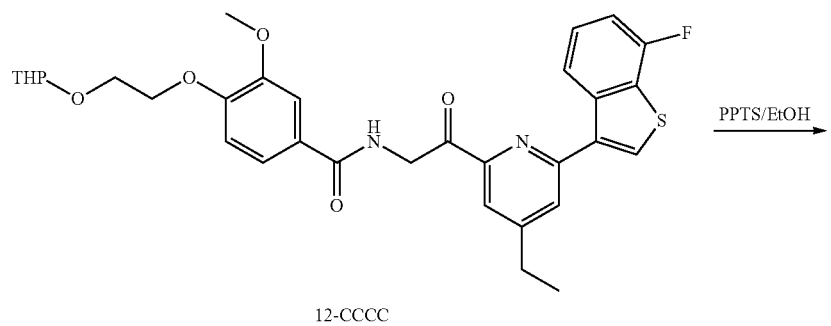

12-CCCC

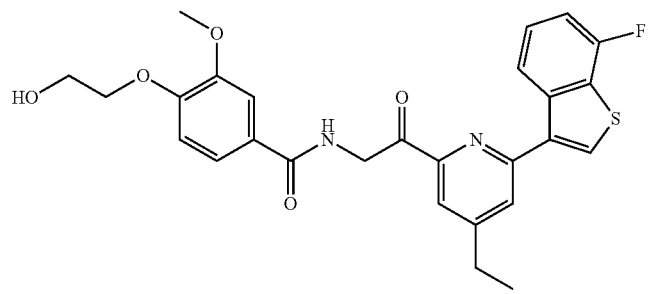

1250

To a solution of 12-CCCC (160 mg, 0.27 mmol) in EtOH (5 mL) was added PPTS (6.8 mg, 0.027 mmol), and stirred at 70° C. for 2 h. The mixture was diluted with water and extracted with EA. The organic layer was dried over sodium sulfate, and concentrated in vacuum to give the crude product, which was purified by prep-HPLC to give compound 1250 (50 mg) as a white solid. +ESI-MS: m/z 509.1 [M+H]$^+$.

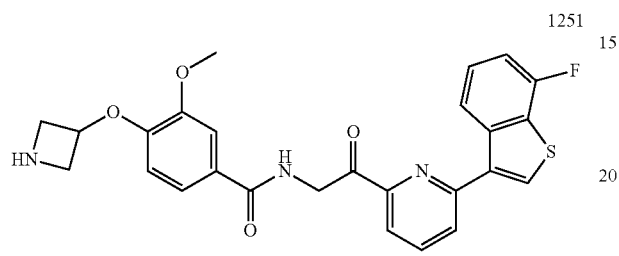

1251

Compound 1251 was obtained following the procedure for obtaining compound 1242 by using tert-butyl 3-hydroxyazetidine-1-carboxylate as the starting material.

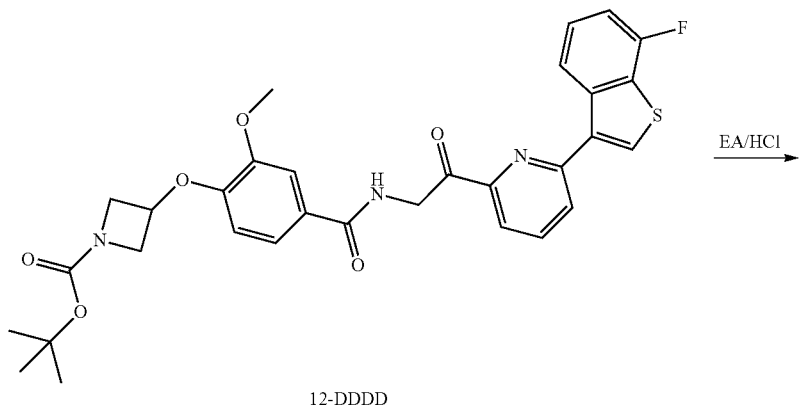

12-DDDD

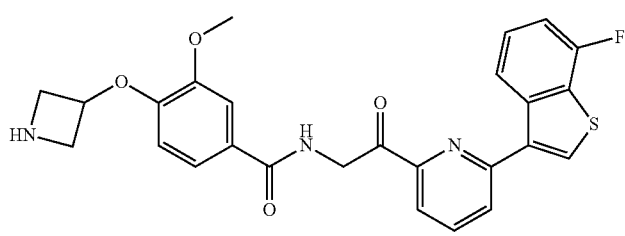

1251

To a solution of 12-DDDD (150 mg, 0.25 mmol) in EA (2 mL) was added HCl/EA (2 mL) at 0° C. and stirred for 0.5 h. The solvent was removed by bubbling with N₂. The residue was purified by prep-HPLC to provide compound 1251 as a white solid (20 mg, 16.3%). +ESI-MS: m/z 491.8 [M+H]⁺.

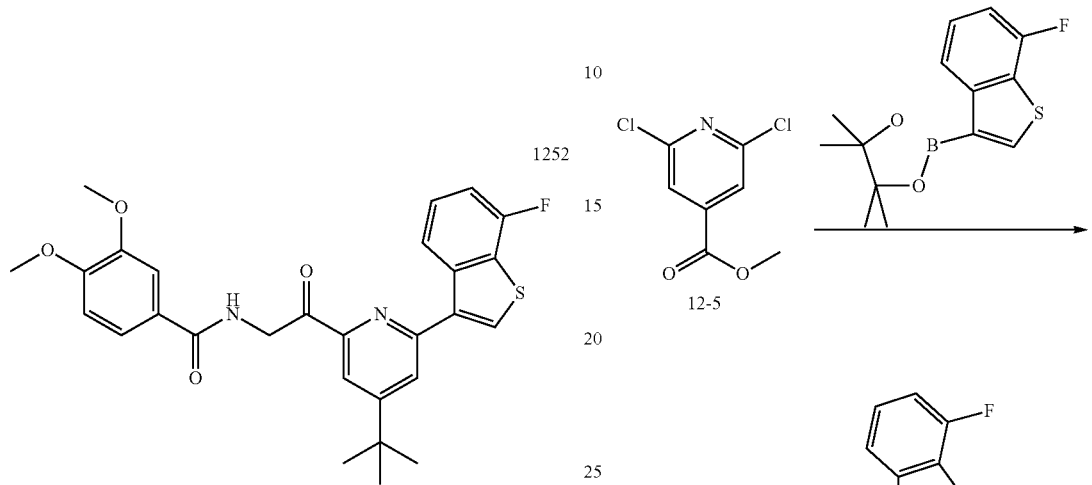

1252

Compound 1252 was obtained following the procedure for obtaining compound 1200 by using 4-(tert-butyl)-2,6-dichloropyridine as the starting material. Compound 1252 was obtained as a white solid. +ESI-MS: m/z 507.0 [M+H]⁺.

Example 12-19

Preparation of Compound 1253

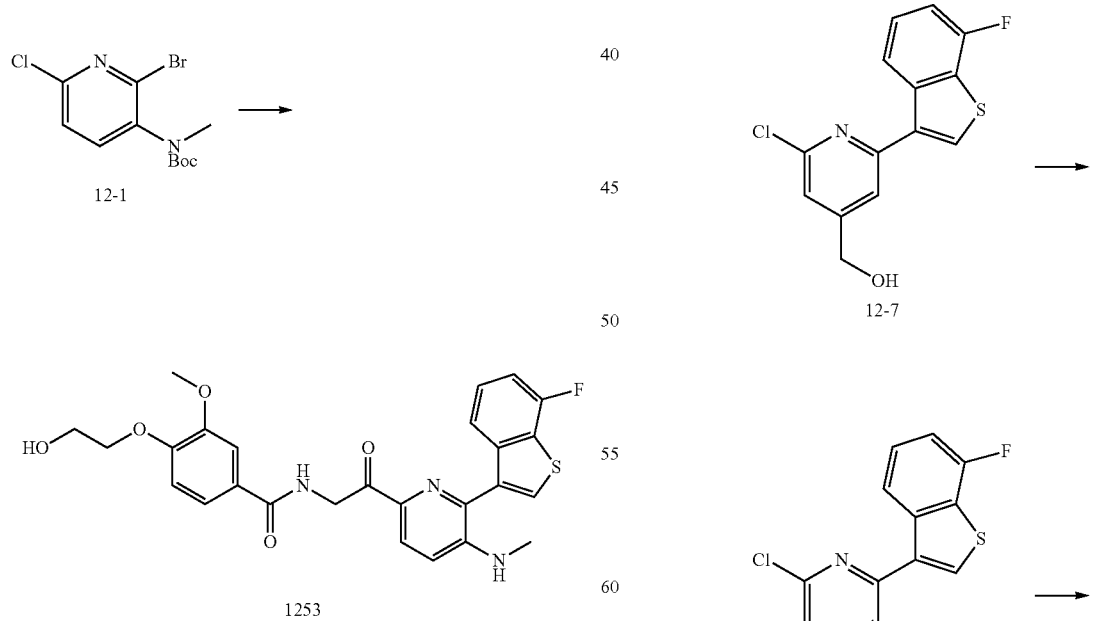

12-1

1253

Compound 1253 was obtained following the procedure for obtaining compound 1200 by using 12-1 as the starting material. Compound 1253 was obtained as a white solid. +ESI-MS: m/z: 509.9 [M+H]⁺.

Example 12-20

Preparation of Compound 1255

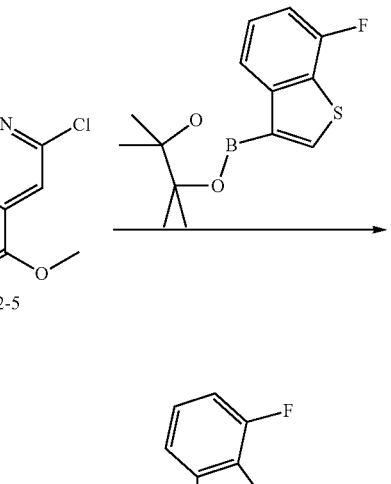

12-5

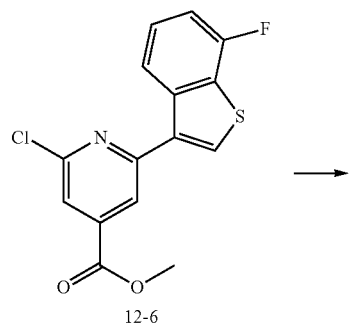

12-6

12-7

12-8

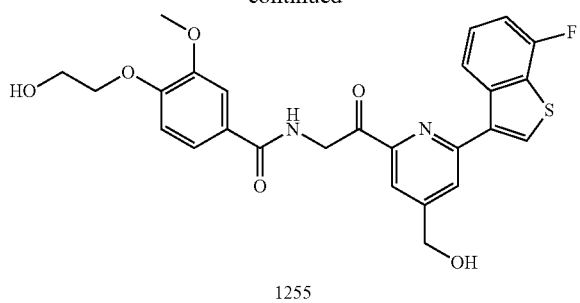

1255

To a mixture of 12-5 (4 g, 19.3 mmol) and the dioxaborolane (5.38 mg, 19.3 mmol) in dioxane/H₂O (10 mL/2 mL) were added Pd(dppf)Cl₂ (1.41 g, 1.93 mmol) and Cs₂CO₃ (7.527 g, 23.16 mmol). The system was degassed and then charged with nitrogen for 3 times. The mixture was stirred under nitrogen at 80° C. in an oil bath for 2 h. The solution was cooled to rt, diluted with EA and separated from the water layer. The EA solution was washed by brine, dried over Na₂SO₄ and concentrated. The residue was purified on a silica gel column to give 12-6 (32.4%). +ESI-MS: m/z 322.0 [M+H]+.

To a solution of 12-6 (1.8 g, 5.6 mmol) in THF (100 mL) was added LAH (0.428 g, 1.2 mmol) at −78° C. The solution was stirred for 10 mins. The solution was quenched with H₂O (0.4 mL). The solution was filtered and the filtrate was concentrated to give crude 12-7 (1.3 g, 78.8%). +ESI-MS: m/z 294.0 [M+H]+.

To a solution of 12-7 (1.3 g, 4.42 mmol) in DMF was added imidazole (0.601 g, 8.84 mmol) at rt. TBSCl (0.978 g, 4.8 mmol) was added. The solution was stirred for 18 h. The solution was washed with water and extracted with EtOAc. The organic phase was concentrated to give 12-8 (1.5 g, 83.3%). +ESI-MS: m/z 408.1 [M+H]+.

Compound 1255 was obtained following the procedure for obtaining compound 1200 by using 12-8 as the starting material. Compound 1255 was obtained as a white solid. +ESI-MS: m/z 511.1 [M+H]⁺.

Example 12-21

Preparation of Compound 1256

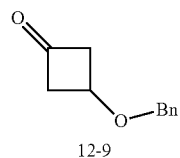

12-9

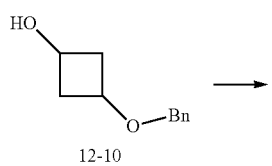

12-10

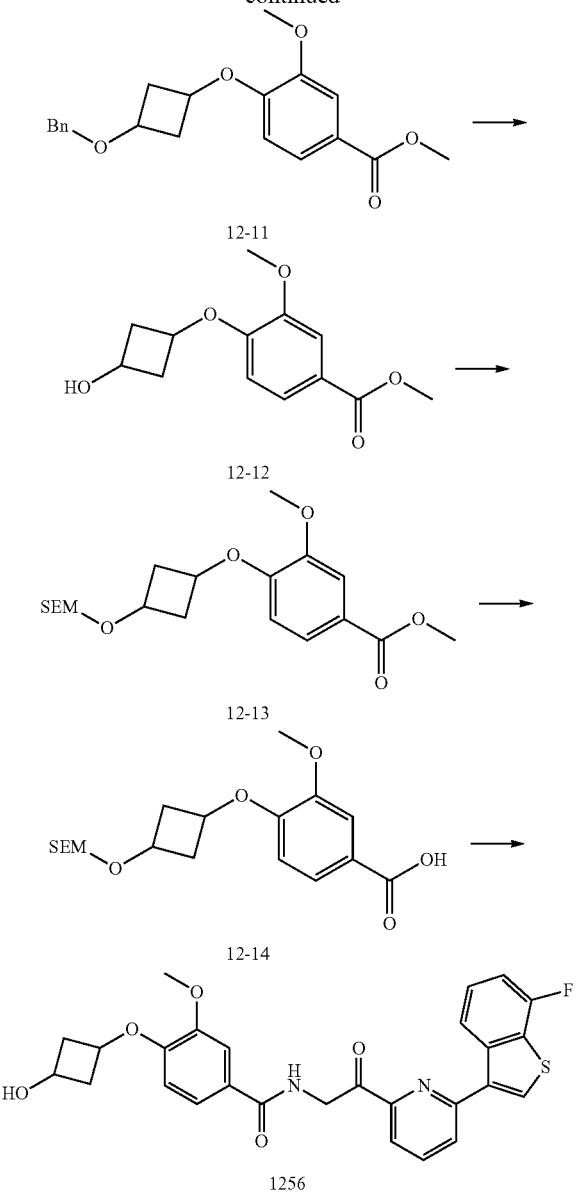

To a solution of 12-9 (3.5 g, 20 mmol) in THF/MeOH (v/v=1:2, 30 mL) was added NaBH₄ (1.2 g, 32 mmol) at rt. The solution was stirred at rt for 1 h with TLC monitoring. The reaction was quenched by addition of HCl (1.0 N in H₂O) and extracted by EtOAc. The combined organic layers were dried over Na₂SO₄ and concentrated to give crude 12-10 (3.0 g), which was used in next step without purification. ¹H-NMR: CDCl₃ (400 MHz): δ=7.35-7.27 (t, 5H), 4.40 (s, 2H), 3.91-3.87 (m, 1H), 3.63-3.59 (m, 1H), 2.73-2.66 (m, 2H), 1.95-1.88 (m, 2H).

A solution of 12-10 (3.0 g, 16.8 mmol), 4-hydroxy-3-methoxybenzoic acid (3.01 g, 16.8 mmol), and PPh₃ (6.6 g, 25.2 mmol) in dry THF (50 mL) was stirred at 0° C. under a nitrogen atmosphere. The mixture was added dropwise DIAD (5.1 g, 25.2 mmol) over a period of 5 mins. The mixture was stirred under nitrogen at 50° C. in an oil bath for 3 h with monitoring by TLC. The solvent was evaporated under reduced pressure and the oil was purified by flash column chromatography (PE/EA=10:1 to 2:1) to give 12-11 (2.5 g) as a white solid.

To a mixture of 12-11 (2.5 g, 7.3 mmol) in MeOH (15 mL) was added Pd/C (10%, 400 mg) under N₂. The suspension was degassed under vacuum and purged with H₂ three times. The mixture was stirred under H₂ (40 psi) at rt for 3 h. The suspension was filtered through a pad of Celite and the pad cake was washed with MeOH. The combined filtrates were concentrated to give crude 12-12 (2.2 g), which was used in next step without purification.

To a mixture of NaH (320 mg, 13.3 mmol) in DMF (20 mL) was added 12-12 (2.2 g, 8.7 mmol) under 0° C. SEMCl (2.2 g, 13.3 mmol) was added. The mixture was stirred at rt for 2 h with TLC monitoring. The reaction was quenched by addition of H₂O and extracted by EtOAc. The combined organic layers were washed by brine, dried over Na₂SO₄ and concentrated. The residue was purified on a silica gel column to give 12-13 (2.9 g).

A solution of 12-13 (2.9 g, 7.6 mmol) and 2N sodium hydroxide solution (35 mL) in MeOH (35 mL) was stirred under reflux for 1 hour. The mixture was neutralized using 2N hydrochloric acid solution, and extracted with EtOAc. The combined organic solutions were dried (MgSO4), and evaporated under reduced pressure to give 12-14 (2.0 g). ESI-LCMS: m/z=391 [M+Na]+.

Compound 1256 was obtained following the procedure for obtaining compound 1215 by using 12-14 and 2-amino-1-(6-(7-fluorobenzo[b]thiophen-3-yl)pyridin-2-yl)ethanol as the starting materials. Compound 1256 was obtained as a white solid. +ESI-LCMS: m/z=506.9 [M+H]⁺.

Example 12-22

Preparation of Compound 1257

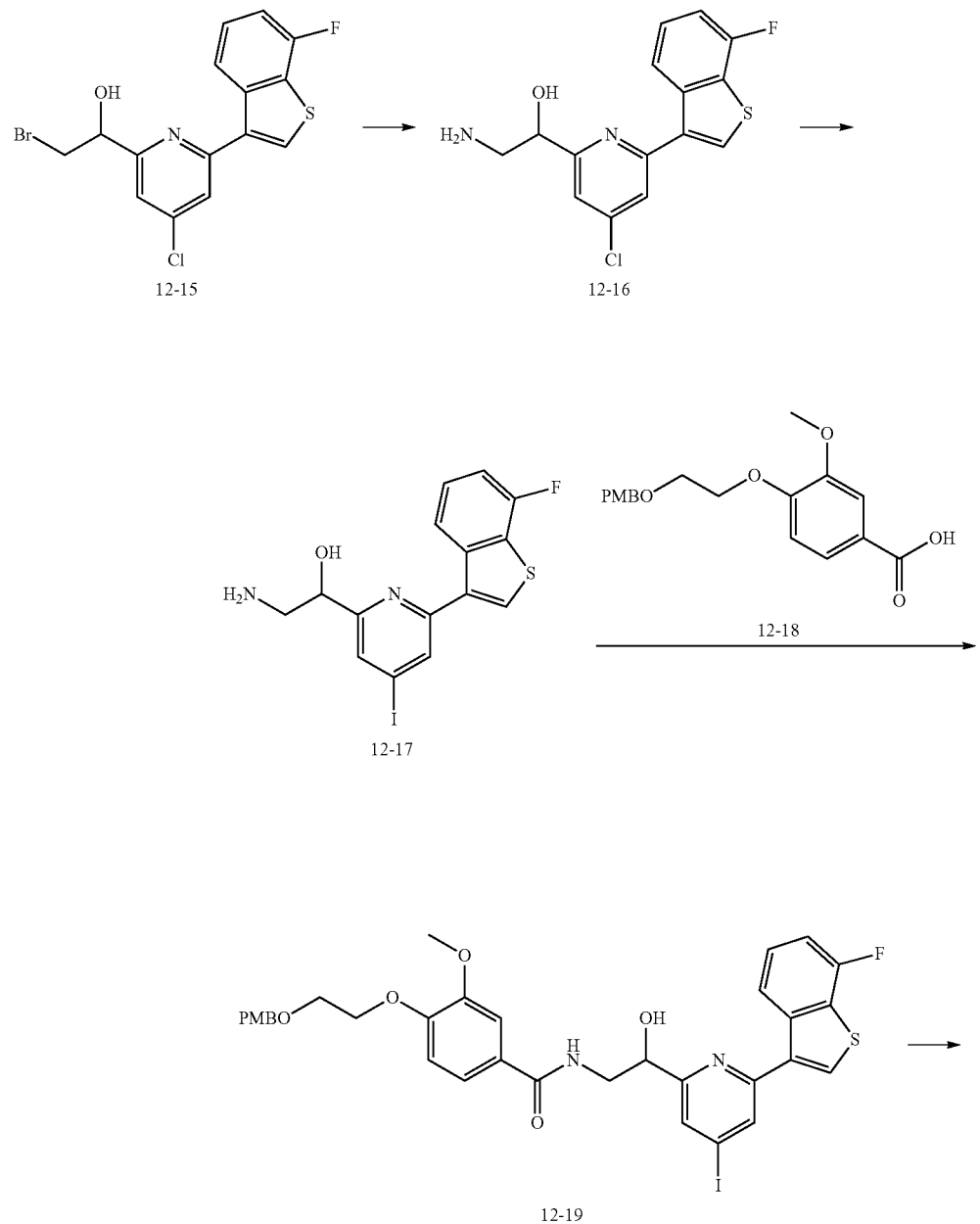

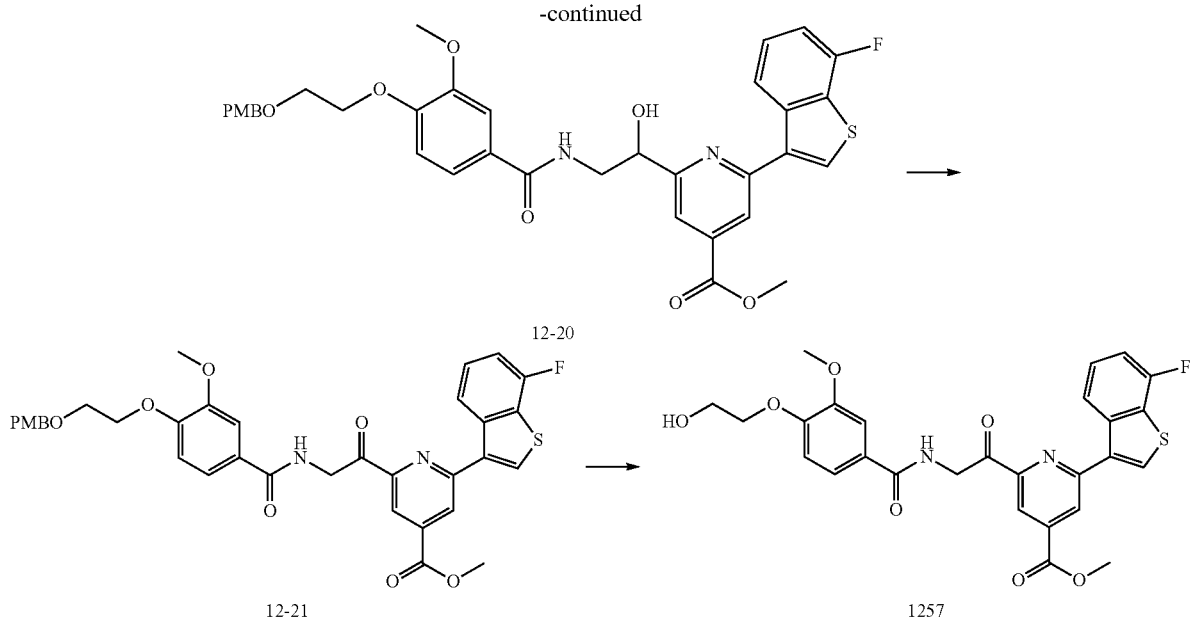

12-20

12-21

1257

To a solution of 12-15 (1.5 g, 38.7 mmol) in EtOH (5 mL) was added NH₄OH (4 mL) in a seal tube. The mixture was stirred at 100° C. for 1 h. The mixture was diluted with water and extracted with EA. The organic layer was dried over sodium sulfate, and concentrated in vacuum to the crude product, which was purified by column chromatography to give 12-16 (400 mg). +ESI-MS: m/z 323.0 [M+H]+.

To a solution of 12-16 (400 mg, 1.24 mmol) in EA (5 mL) was added HCl/EA (4 M, 2 mL). The mixture was stirred at rt for 20 mins, and concentrated in vacuum to give the HCl salt. The HCl salt was dissolved in CH₃CN (20 mL), and NaI (1.86 g, 12.4 mmol) was added, and the mixture was stirred at 110° C. overnight. The mixture was washed with NaHCO₃ solution, and extracted with EA. The organic layer was dried over sodium sulfate, and concentrated in vacuum to give the crude product, which was purified by column chromatography to give 12-17 (550 mg). +ESI-MS: m/z 415.0 [M+H]+.

To a solution of 12-18 (415 mg, 1.25 mmol) in DMF (20 mL) were added DIPEA (645 mg, 5.0 mmol), HATU (475 mg, 1.25 mmol), and the mixture was stirred at rt for 30 mins. Compound 12-17 (514 mg, 1.25 mmol) was added, and the mixture was stirred at rt for 2 h. The mixture was diluted with water and extracted with EA. The organic layer was dried over sodium sulfate, and concentrated in vacuum to give the crude product, which was purified by column chromatography to give 12-19 (650 mg). +ESI-MS: m/z 729.1.0 [M+H]+.

To a solution of 12-19 (0.55 g, 0.76 mmol) in MeOH (20 mL) were added Pd(PPh₃)₄ (174 mg, 0.15 mmol) and Et₃N (2.3 g, 2.28 mmol). The mixture was stirred at 80° C. under 40 psi of CO atmosphere overnight. The mixture was concentrated in vacuum to give the crude product, which was purified by column chromatography to give 12-20. (430 mg, yield: 87.2%)+ESI-MS: m/z 661.1 [M+H]+.

To a solution of 12-20 (520 mg, 0.79 mmol) in DCM (30 mL) was added DMP (1.02 g, 2.36 mmol), and the mixture was stirred at rt for 2 h. The mixture was diluted with EA and washed with water. The organic layer was dried over sodium sulfate, concentrated in vacuum to give 12-21 as white solid. +ESI-MS: m/z 659.1 [M+H]+.

Compound 12-21 (440 mg, 0.67 mmol) was dissolved in DCM/TFA (1:1, 10 mL), and the mixture was stirred at rt for 5 mins. The mixture was diluted with DCM and the pH of the mixture was adjusted to 7.0 by adding NaHCO₃ solution, The organic layer was dried over sodium sulfate and concentrated in vacuum to give the crude product, which was purified by TLC separation to give compound 1257 (23 mg) as a white solid. +ESI-LCMS: m/z=538.9 [M+H]⁺.

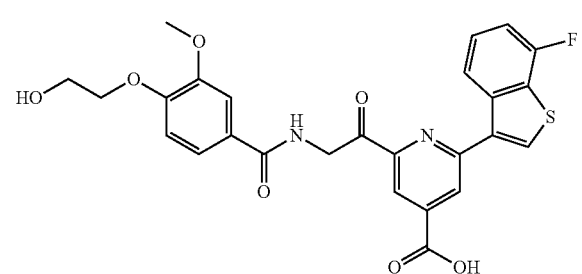

1258

To a solution of compound 1257 (180 mg, 0.335 mmol) in THF/H₂O (2:1, 10 mL) was added LiOH (40 mg, 1.67 mmol), and the mixture was stirred at rt for 15 mins. The mixture was diluted with water, and the pH of the aqueous layer was adjusted to around 5 by progressively adding NH₄Cl solution. The mixture was extracted with EA. The organic layers were dried over sodium sulfate and concentrated in vacuum to give the crude product, which was purified by prep-HPLC to give compound 1258 (32 mg) as a white solid. +ESI-LCMS: m/z=525.1 [M+H]⁺.

Example 13-1

Preparation of Compound 1300

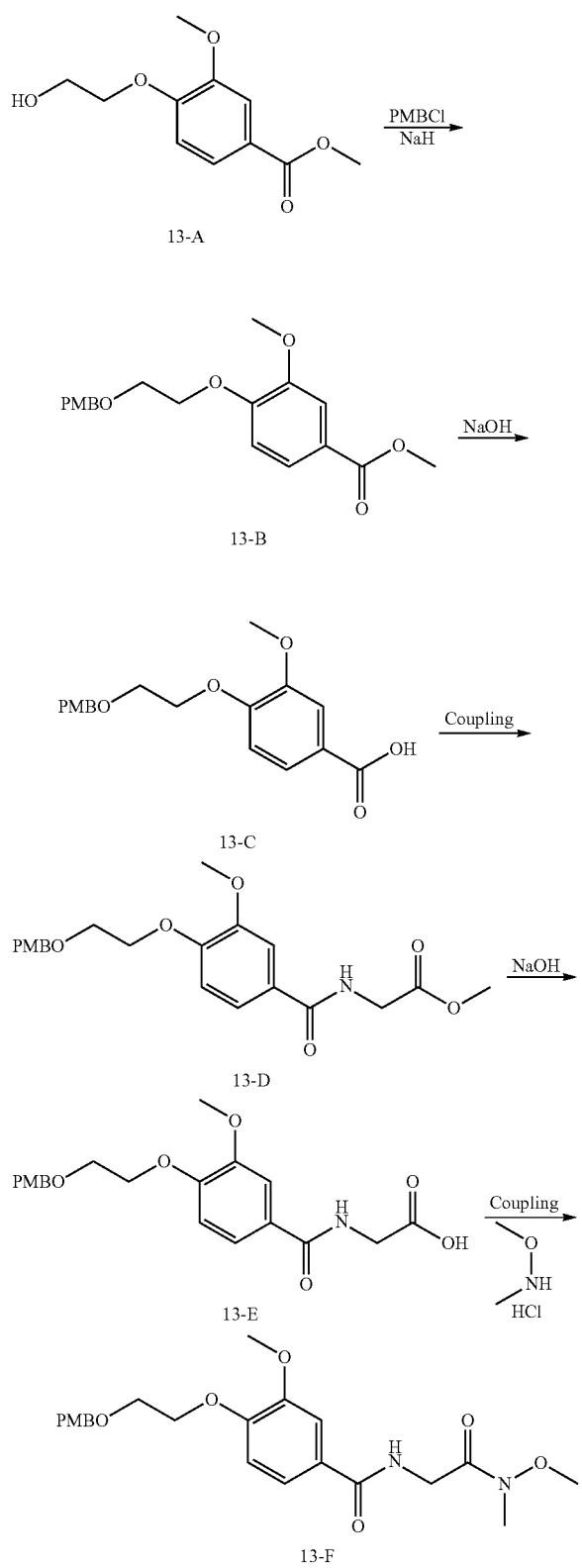

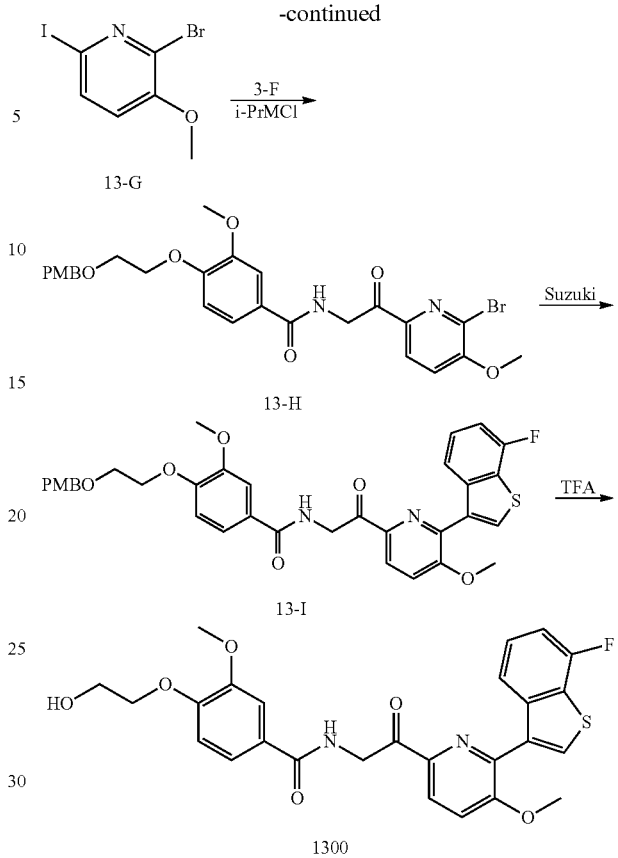

To a solution of crude 13-A (10 g, 44.0 mmol) in DMF (150 mL) was added NaH (7.0 g, 0.177 mol). The mixture was stirred at 0° C. for 30 mins. PMBCl (11.67 g, 74.8 mmol) was added. The mixture was stirred at rt overnight. The solution was then diluted with water and extracted with EtOAc. The organic phase was concentrated to give 13-B (11 g, 87.2%). $^+$ESI-MS: m/z 347.1 [M+H]$^+$.

To a solution of 13-B (11 g, 31.8 mmol) in MeOH (100 mL) was added KOH (7.0 g, 127 mmol), and stirred at rt overnight. The mixture was extracted with EA, and the pH of the aqueous layer was adjusted to approximately 5 by progressive addition of diluted HCl, followed by extraction with EA. The organic layers were dried over sodium sulfate and concentrated in vacuum to give 13-C (8.4 g), which was used in the next step without further purification. $^1$H-NMR (400 MHz, CDCl$_3$) δ=8.04 (s, 1H), 7.16 (d, J=8.0 Hz, 1H), 7.59 (s, 1H), 7.30-7.27 (m, 2H), 6.94-6.87 (m, 3H), 4.58 (s, 2H), 4.26 (t, J=4.8 Hz, 2H), 3.93 (s, 3H), 3.85 (t, J=4.8 Hz, 2H), 3.81 (s, 3H).

To a solution of 13-C (6.0 g, 18.0 mmol) in DMF (100 mL) were added HATU (10.3 g, 27 mmol) and DIPEA (7.0 g, 54 mmol). The mixture was stirred at rt for 30 mins. Methyl 2-aminoacetate hydrochloride (2.3 g, 18 mmol) was added and stirred at rt overnight. The mixture was concentrated in vacuum, diluted with water, and extracted with EA. The organic layer was dried over sodium sulfate and concentrated in vacuum to give crude 13-D, which was purified by column chromatography. +ESI-MS: m/z 404.1 [M+H]$^+$.

To a solution of 13-D (9.7 g, 24 mmol) in MeOH (100 mL) was added KOH (5.4 g, 96 mmol). The mixture was stirred at rt overnight, and then extracted with EA. The pH of the aqueous layer was adjusted to approximately 5 by progressively adding diluted HCl, followed by extraction with EA. The organic layers were dried over sodium sulfate and concentrated in vacuum to give 13-E (8.5 g), which was used in the next step without further purification. $^1$H NMR (400 MHz, d-DMSO) δ=8.70 (t, J=6.0 Hz, 1H), 7.43 (s, 2H), 7.24 (d, J=8.0 Hz, 2H), 7.01 (d, J=8.0 Hz, 1H), 6.88 (d, J=8.0 Hz, 2H), 5.02 (s, 2H), 4.45 (t, J=4.8 Hz, 2H), 4.41 (s, 2H), 3.88 (t, J=4.8 Hz, 2H), 3.78 (s, 3H).

To a solution of 13-E (8.5 g, 21.85 mmol) in DMF (200 mL) were added HATU (8.3 g, 21.85 mmol) and Et$_3$N (8.83 g, 87.4 mmol). The mixture was stirred at rt for 30 mins. N,O-dimethylhydroxylamine hydrochloride (2.12 g, 21.85 mmol) was added, and the mixture was stirred at rt overnight. The mixture was concentrated in vacuum, diluted with water, and extracted with EA. The organic layer was dried over sodium sulfate and concentrated in vacuum to give crude 13-F, which was purified by column chromatography. +ESI-MS: m/z 433.1 [M+H]$^+$.

To a solution of 13-F (3.71 g, 8.6 mmol) and 13-G (2.7 g, 8.6 mmol) in THF (50 mL) was added i-PrMgCl (17.2 mL, 34.4 mmol) in portions. The reaction was quenched after 3 mins with a NH$_4$Cl solution. The mixture was extracted with EA. The organic phase was dried over sodium sulfate, and then concentrated in vacuum to give the crude product, which was purified by column chromatography to give pure 13-H (2.4 g). +ESI-MS: m/z 558.1, 560.1 [M+H]$^+$.

To a solution of 13-H (2.2 g, 3.93 mmol) in dioxane/H$_2$O (10:1) (30 mL) were added Compound 12-C (1.09 g, 3.93 mmol), Pd(dppf)Cl$_2$ (288 mg, 0.393 mmol) and KOAc (0.94 g, 11.8 mmol). The mixture was bubbled with nitrogen gas and stirred at 90° C. for 3 h. The mixture was diluted with water and extracted with EA. The organic layer was dried over sodium sulfate, and then concentrated in vacuum to give the crude product, which was purified by column chromatography to give 13-I (1.2 g). +ESI-MS: m/z 631.1 [M+H]$^+$.

Compound 13-I (200 mg, 0.32 mmol) was dissolved in DCM/TFA (1:1) (34 mL) and then stirred at rt for 30 mins. The mixture was diluted with DCM and the pH of the mixture was adjusted to 7.0 by addition of a saturated NaHCO$_3$ solution. The organic layer was dried over sodium sulfate and concentrated in vacuum to give the crude product, which was purified by prep-HPLC to give compound 1300 (70 mg) as a white solid. $^1$H NMR: (400 MHz, d-DMSO): δ=8.71-8.69 (t, J=5.2 Hz, 1H), 8.25 (d, J=8.0 Hz, 1H), 8.47 (s, 1H), 8.25 (d, J=8.0 Hz, 1H), 8.09 (d, J=8.4 Hz, 1H), 7.84 (d, J=8.8 Hz, 1H), 7.55-7.51 (m, 3H), 7.36-7.31 (t, J=9.0 Hz, 1H), 7.06 (d, J=8.4 Hz, 1H), 4.94-4.87 (m, 3H), 4.06-4.01 (m, 5H), 3.82 (s, 3H), 3.77-3.74 (t, J=5.0 Hz, 2H).

Example 13-2

Preparation of Compound 1301

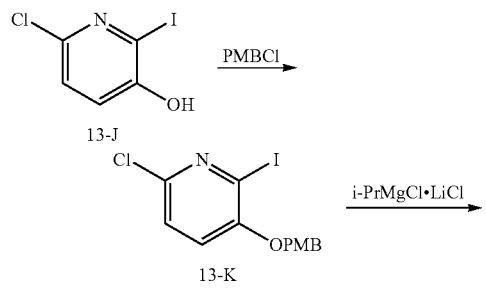

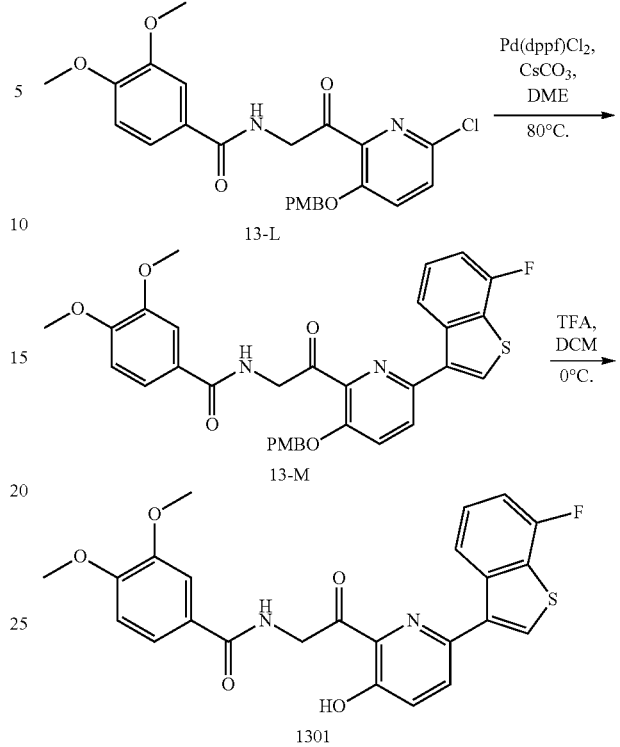

To a solution of 13-J (12.7 g, 50 mmol) in DCM (100 mL) was added PMBCl (9.4 g, 60 mmol) and TEA (7.5 g, 75 mmol). This mixture was stirred at rt overnight. The reaction solution was washed with brine, and the organic layer was concentrated to give crude 13-K, which was used in the next step without further purification. $^1$H-NMR: (400 MHz, d-DMSO): δ=7.46 (d, J=8.8 Hz, 2H), 7.38 (d, J=8.0 Hz, 2H), 6.94 (d, J=8.0 Hz, 2H), 5.14 (s, 2H), 3.73 (s, 3H).

A solution of 13-K (3.75 g, 10 mmol) in THF (30 mL) was added i-PrMgCl.LiCl (20 mmol) at rt. After 10 mins, the reaction was monitored by TLC. The mixture was diluted with water, and extracted with EA. The solution was evaporated at low pressure to give the crude product. The residue was purified by silica column chromatography using DCM:MeOH=50:1 as the elute to generate 13-L (3 g, 64%). +ESI-MS: m/z 471.1 [M+H]$^+$.

To a solution of crude 13-L (2.35 g, 5 mmol) in DME (20 mL) was added 2-(7-fluorobenzo[b]thiophen-3-yl)-4,4,5,5-tetramethyl-1,3,2-dioxaborolane (1.39 g, 5 mmol), cesium carbonate (3.25 g, 10 mmol) and Pd(dppf)Cl2 (109 mg, 0.15 mmol). The reaction was stirred for 2 h at 80° C. under N$_2$. The solution was filtered, and the filtrate was concentrated by rotary evaporator. The residue was dissolved in DCM, and the solution was washed with brine. The organic phase was evaporated at low pressure to give the crude product. The residue was purified by silica column chromatography with EA:PE=1:1 as the elute to give 13-M (2 g, 68%). +ESI-MS: m/z 587.1 [M+H]$^+$.

To a solution of 13-M (440 mg, 0.75 mmol) in dry DCM (5 mL) was added TFA (2 mL) at 0° C. After 1 h, the reaction was monitored by TLC. The reaction solution was washed with brine, and the DCM layer was concentrated by rotary evaporator. The product was purified by prep-TLC with EA:PE=2:1 as the elute to give 1301 (280 mg, 80%). $^1$HNMR (d-DMSO) δ=8.81 (s, 1H), 8.62 (d, J=8 Hz, 1H), 8.48 (s, 1H), 8.20 (d, J=8 Hz, 1H), 7.65 (d, J=8 Hz, 1H), 7.55-7.50 (m, 3H), 7.33 (t, J=8 Hz, 1H), 7.04 (d, J=8 Hz, 1H), 5.03 (s, 2H), 3.79 (s, 6H).

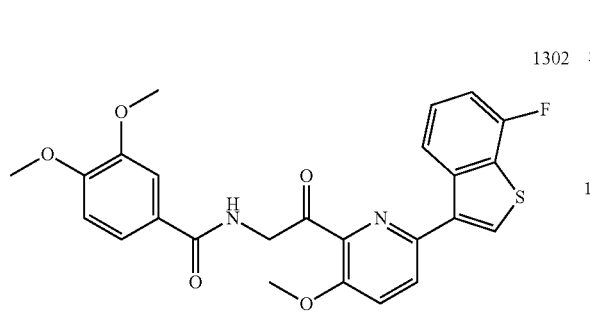

1302

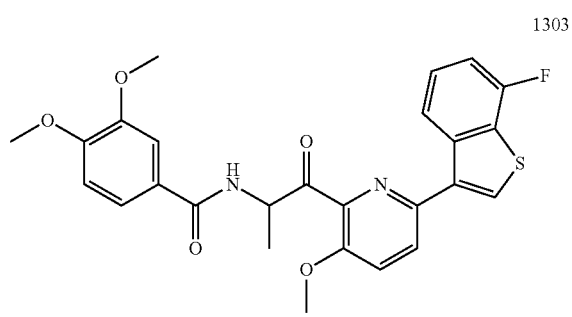

1303

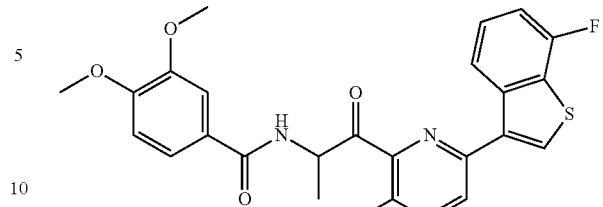

1304

To a solution of 1301 (93 mg, 0.2 mmol) in DMF (5 mL) was added K₂CO₃ (41 mg, 0.3 mml) and MeI (28 mg, 0.2 mmol). The reaction was stirred for 1 h. Water (20 mL) was poured into the reaction solution, and the solution was extracted with DCM. The organic layer was concentrated by rotary evaporator. The product was purified by prep-HPLC to give 1302 (15 mg, 17%), 1303 (10 mg) and 1304 (10 mg). Compound 1302: +ESI-MS: m/z 466.9 [M+H]⁺. Compound 1303: ¹H-NMR (d-DMSO) δ=8.60 (dd, J=8 Hz, J=1.2 Hz, 2H), 8.39 (s, 1H), 8.13 (d, J=8.4 Hz, 1H), 7.81 (d, J=4 Hz, 1H), 7.51-7.49 (m, 2H), 7.44 (s, 1H), 7.33-7.31 (m, 1H), 7.99 (d, J=8 Hz, 1H), 5.78-5.74 (m, 1H), 3.90 (s, 3H), 3.77 (d, J=6 Hz, 6H). ESI-MS: m/z 495.0 [M+H]⁺. Compound 1304: +ESI-MS: m/z 480.9 [M+H]⁺.

Example 13-3

Preparation of Compound 1305

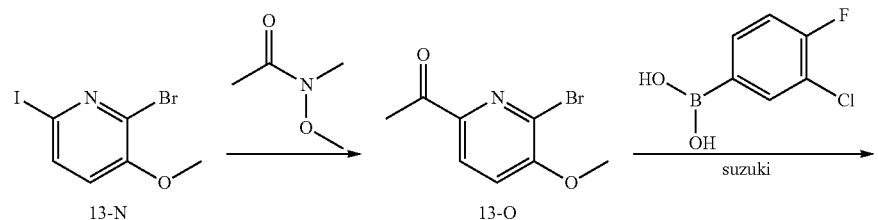

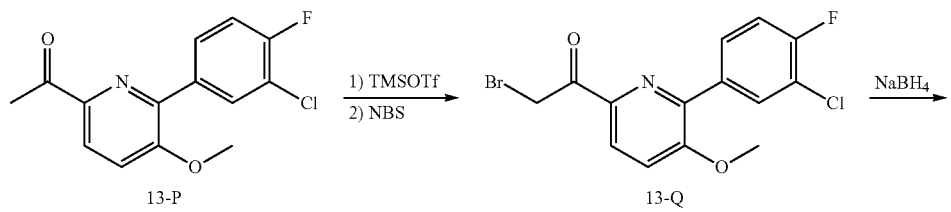

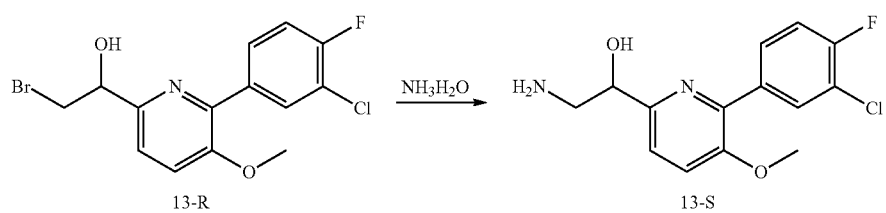

-continued

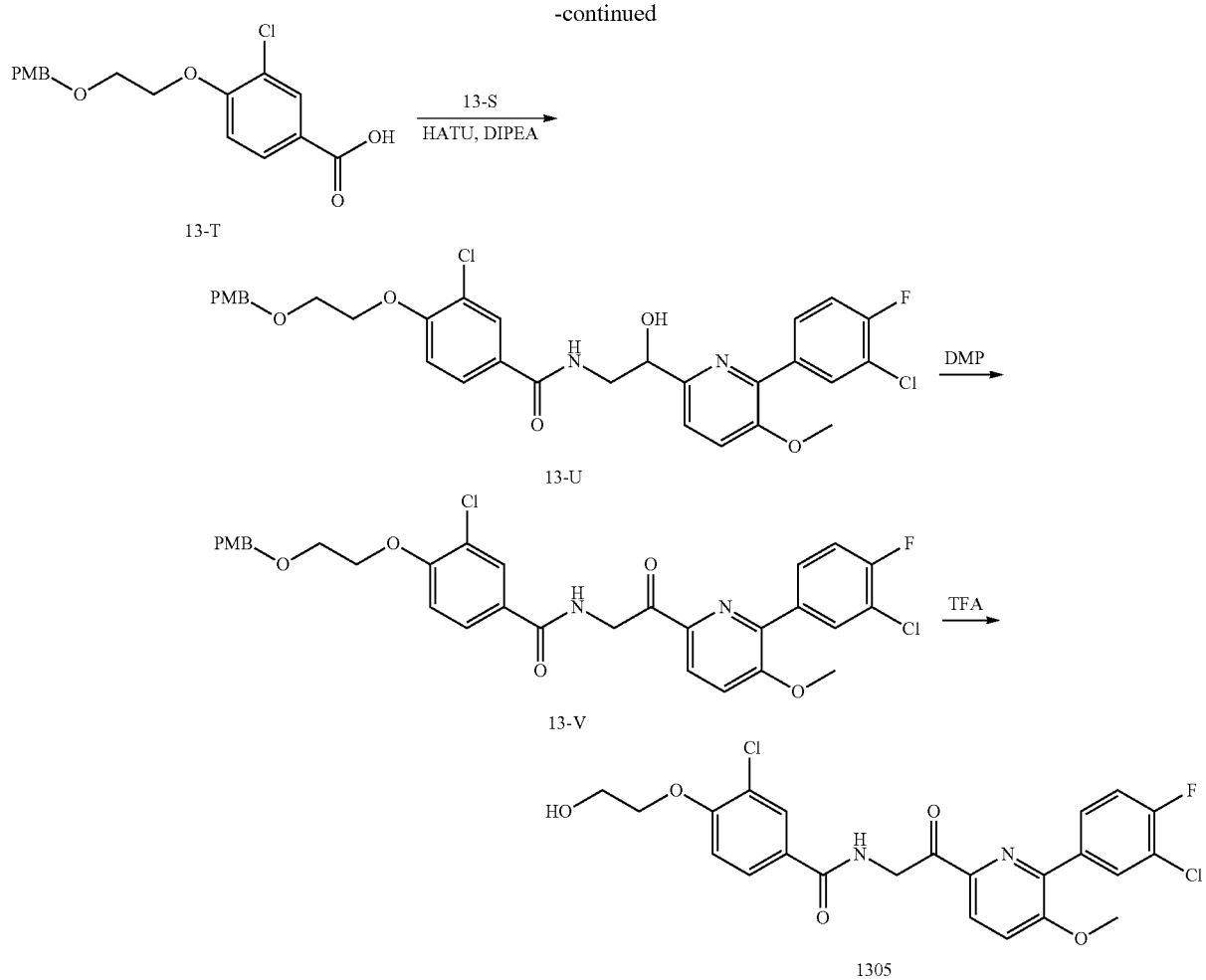

To a solution of 13-N (5 g, 16.0 mmol) and Weinerb amide (1.6 g, 16.0 mmol) in THF (10 mL) was added i-PrMgCl (10 mL, 19.2 mmol). The solution was stirred at rt for 5 mins and the concentrated. The solution was acidified to pH=7 with aq.NH$_4$Cl, and the aqueous layer was extracted with DCM. The organic layers were combined and purified by column chromatography with PE:EA=5:1 as the elute to give 13-O (1.9 g, 51.9%). $^1$H-NMR (d-DMSO) δ=7.97 (d, J=8.4 Hz, 1H), 7.63 (d, J=8.4 Hz, 1H), 3.97 (s, 3H), 2.53 (s, 3H).

To a solution of 13-O (700 mg, 1.12 mmol), (3-chloro-4-fluorophenyl)boronic acid (336 mg, 1.2 mmol) and Cs$_2$CO$_3$ (24.3 g, 74.2 mmol) in dioxane (20 mL) and H$_2$O (2 mL) were added Pd(dppf)$_2$Cl$_2$ (812 mg, 1.11 mmol). The mixture was degassed and then charged with nitrogen 3 times. The mixture was stirred under nitrogen at 80° C. using an oil bath for 5 h. The solution was cooled to rt, diluted with EA and separated from the aqueous layer. The organic solution was washed with brine, dried over Na$_2$SO$_4$ and concentrated. The residue was purified on a silica gel column to give 13-P (7.3 g, 70.5%), which used for next step without further purification. $^1$H-NMR (d-DMSO) δ=8.11 (d, J=7.2 Hz, 1H), 8.00-7.96 (m, 2H), 7.70 (d, J=8.4 Hz, 1H), 7.50 (d, J=8.8 Hz, 1H), 3.95 (s, 3H), 2.62 (s, 3H).

To a solution of 13-P (1.8 g, 6.4 mmol) in DCM (15 mL), were added DIPEA (3.3 g, 25.8 mmol) and TMSOTf (4.3 g, 19.4 mmol). The mixture was stirred at rt for 30 mins, and the solution was extracted with DCM (20 mL). The organic phase was evaporated at low pressure to generate the crude residue. The residue was treated with a solution of NBS (1.12 g, 6.4 mmol) in THF (10 mL) and H$_2$O (10 mL). After 10 mins, the solution was quenched by an aqueous NaHCO$_3$ solution and extracted with EtOAc. The combined organic layers were washed by saturated Na$_2$S$_2$O$_3$ and brine, dried over Na$_2$SO$_4$ and concentrated to give crude 13-Q (2.0 g) which can be used in the next step without further purification. $^1$H-NMR (CDCl$_3$) δ=8.11 (d, J=8.0 Hz, 2H), 7.95-7.93 (m, 1H), 7.40 (d, J=8.0 Hz, 2H), 7.25-7.21 (m, 1H), 4.85 (s, 2H), 3.99 (s, 3H).

To a solution of crude 13-Q (7.0 g, 19.6 mmol) in a mixture of THF (20 mL) and EtOH (8 mL) were added NaBH$_4$ (1.1 g, 19.6 mmol) at 0° C. The mixture was stirred at 0° C. for 30 mins. The reaction was quenched by the addition of H$_2$O and extracted by EtOAc. The combined organic layers were washed using brine, dried over Na$_2$SO$_4$ and concentrated. The residue was purified on a silica gel column to give 13-R (4.0 g, 57.1%). $^1$H-NMR (CDCl$_3$) δ=8.06 (d, J=7.2 Hz, 1H), 7.09-7.87 (m, 1H), 7.36-7.32 (m, 2H), 7.20 (t, J=8.8 Hz, 1H), 5.00-4.95 (m, 1H), 4.08 (d, J=9.6 Hz, 1H), 3.91 (s, 3H), 3.79-3.70 (m, 2H).

A mixture of 13-R (720 mg, 2.0 mmol), K$_2$CO$_3$ (552 mg, 4.0 mmol) and saturated NH$_3$/EtOH (15/15 mL) in a sealed tube was stirred at ambient temperature for 20 mins, then heated to 50° C. for 10 h. The solvent was removed under reduced pressure to give crude 13-S (0.6 g), which used for next step without further purification. ¹H-NMR (CDCl₃) δ=8.05 (d, J=8.0 Hz, 1H), 7.88-7.87 (m, 1H), 7.36-7.18 (m, 3H), 4.75-4.72 (m, 1H), 3.90 (s, 3H), 3.17-3.13 (m, 1H), 2.96-2.91 (m, 1H).

To a solution of 13-T (336 mg, 1.0 mmol), HATU (570 mg, 1.5 mmol) and DIPEA (320 mg, 2.5 mmol) in anhydrous DCM (10 mL) was added 13-5 (296 mg, 1.0 mmol) at 25° C. The solution was stirred for 3 h at 25° C. The mixture was diluted with 1.0 N aqueous NaHCO₃ solution, and extracted with DCM. The combined organic layers were washed using brine, dried over anhydrous Na₂SO₄, and concentrated under reduced pressure. The residue was purified on a silica gel column using PE:EA=2:1 to 1:3 as the elute to give crude 13-U (450 mg) as a white solid. +ESI-LCMS: m/z=615.2 [M+H]⁺.

To a solution of 13-U (450 mg, 0.73 mmol) in DCM (6 mL) was added DMP (600 mg, 1.41 mmol). The mixture was stirred at rt for 30 mins with TLC monitoring. The solution was quenched by an aqueous NaHCO₃ solution and extracted by EtOAc. The combined organic layers were washed by saturated Na₂S₂O₃ and brine, dried over Na₂SO₄ and concentrated. The residue was purified on a silica gel column using PE:EA=2:1 to 1:1 as the elute to give 13-V (300 mg). +ESI-LCMS: m/z=613.1 [M+H]⁺.

To a solution of 13-V (300 mg, 0.49 mmol) in DCM (5 mL) was added TFA (5 mL) at rt. The mixture was stirred at rt for 30 mins with TLC monitoring, quenched by an aqueous NaHCO₃ solution and extracted using DCM. The combined organic layers were dried over Na₂SO₄ and concentrated. The residue was purified by prep-HPLC to give compound 1305 (80 mg) as a white solid. +ESI-LCMS: m/z=493.0 [M+H]⁺.

Example 13-4

Preparation of Compound 13-Y

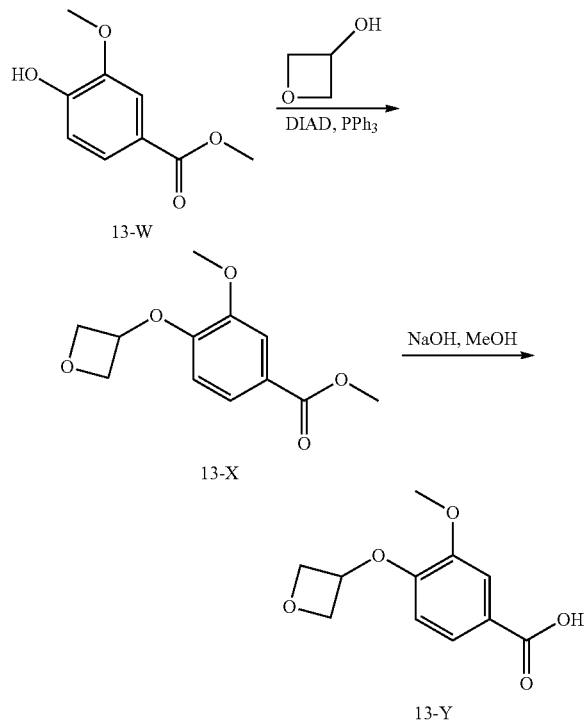

To a solution of 13-W (1 g, 5.95 mmol) and oxetan-3-ol (0.484 g, 6.54 mmol) in THF (10 mL) were added DEAD (1.243 g, 7.14 mmol) and PPh₃ (1.87 g, 7.14 mmol). The solution was heated to reflux and stirred for 15 h. The solution was diluted with brine and extracted with EtOAc. The organic phase was concentrated, and the residue was purified by chromatography to give 13-X (500 mg, 35.7%).

To a solution of 13-X (500 mg, 2.1 mmol) in MeOH (5 mL) was added NaOH aqueous (5 mL, 1M). The mixture was stirred for 4 h at 60° C., and the cooled to rt. The mixture was acidified to pH=3 by addition of 1N HCl solution, and extracted with EtOAc. The organic phase was dried with anhydrous Na₂SO₄ and concentrated under reduced pressure to give 13-Y (250 mg, 53.0%).

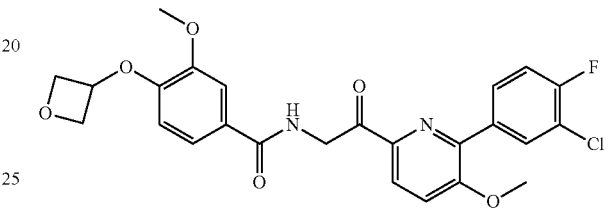

Compound 1306 was obtained following the procedure for obtaining compound 1351 by using 13-Y and 2-amino-1-(6-(3-chloro-4-fluorophenyl)-5-methoxypyridin-2-yl) ethanol as the starting materials. Compound 1306 was obtained as a white solid (40 mg, 26.8%). +ESI-MS: m/z 500.9 [M+H]⁺.

Example 13-5

Preparation of Compound 13-A2

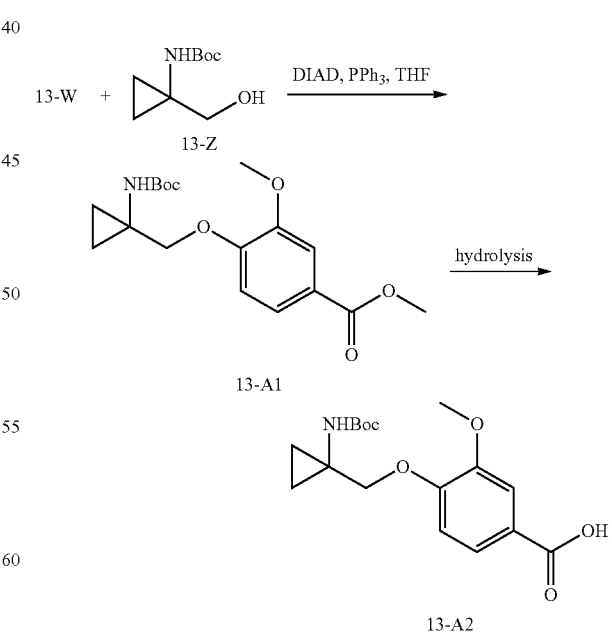

To a solution of 13-W (567 mg, 3.13 mmol) in THF (30 mL) was added 3-Z (750 mg, 3.75 mmol) and PPh₃ (982.5 mg, 3.75 mmol). The mixture was stirred at rt for 30 mins.

DIAD (757.5 mg, 3.75 mmol) was added, and the mixture was stirred at 70° C. overnight. The mixture was diluted with EtOAc and washed with brine. The organic layers were dried over sodium sulfate and concentrated in vacuum to give crude 13-A1, which was purified by column chromatography to give purified 13-A1 (600 mg). +ESI-MS: m/z 352.1 [M+H]+.

To a solution of 13-A1 (300 mg, 1.64 mmol) in EtOH/H$_2$O (2:1) 10 mL was added KOH (460 mg, 8.24 mmol), and the mixture was stirred at 50° C. for 1 h. The mixture was extracted with EA, and the pH of the aqueous layer was adjusted to approximately 5 by adding a NaHCO$_3$ solution, then extracted with EA. The organic layers were dried over sodium sulfate and concentrated in vacuum to give 13-A2 (150 mg). +ESI-MS: m/z 338.1 [M+H]+.

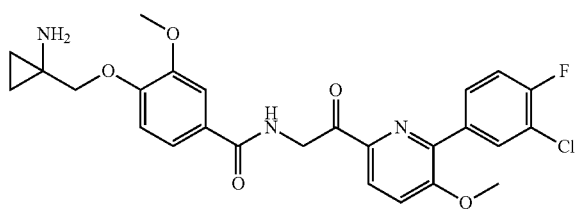

1307

Compound 1307 was obtained following the procedure for obtaining compound 1351 by using 13-A2 and 2-amino-1-(6-(3-chloro-4-fluorophenyl)-5-methoxypyridin-2-yl) ethanol as the starting materials. Compound 1307 was obtained as a white solid. +ESI-MS: m/z 338.1 [M+H]+.

1308

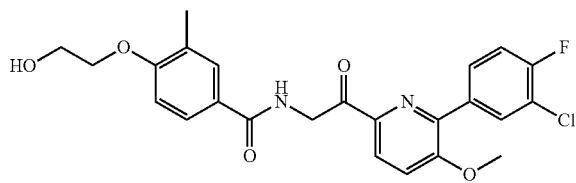

Compound 1308 was obtained following the procedure for obtaining compound 1351 by using 2-amino-1-(6-(3-chloro-4-fluorophenyl)-5-methoxypyridin-2-yl) ethanol and methyl 4-hydroxybenzoate as the starting materials. Compound 1308 was obtained as a white solid. +ESI-MS: m/z 338.1 [M+H]+.

1309

Compound 1309 was obtained following the procedure for obtaining compound 1351 by using 2-amino-1-(6-(3-chloro-4-fluorophenyl)-5-methoxypyridin-2-yl) ethanol and methyl 4-(2-hydroxyethoxy)-3-methylbenzoate as the starting materials. Compound 1309 was obtained as a white solid. +ESI-MS: m/z 473.1 [M+H]+.

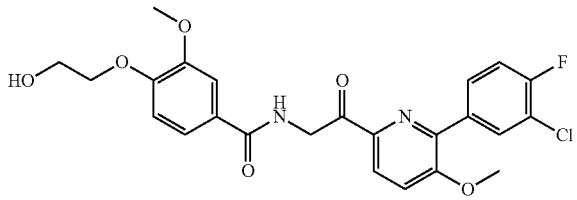

1310

Compound 1310 was obtained following the procedure for obtaining compound 1300 by using 2-amino-1-(6-(3-chloro-4-fluorophenyl)-5-methoxypyridin-2-yl) ethanol and methyl 4-hydroxybenzoate as the starting materials. Compound 1310 was obtained as a white solid. +ESI-MS: m/z 489.1 [M+H]+.

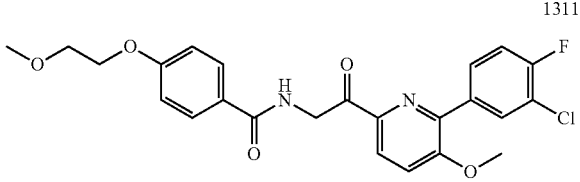 [SMILES: COCCOc1ccc(C(=O)NCC(=O)c2ccc(OC)c(-c3ccc(F)c(Cl)c3)n2)cc1]

1311

Compound 1311 was obtained following the procedure for obtaining compound 1351 by using 2-amino-1-(6-(3-chloro-4-fluorophenyl)-5-methoxypyridin-2-yl) ethanol and methyl 4-hydroxybenzoate as the starting materials. Compound 1311 was obtained as a white solid. +ESI-MS: m/z 473.1 [M+H]+.

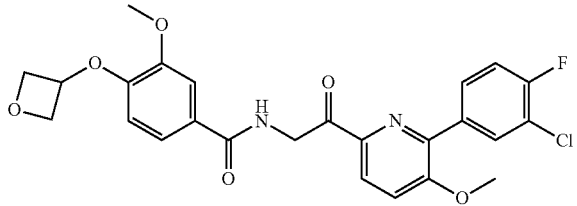

1312

Compound 1312 was obtained following the procedure for obtaining compound 1351 by using 2-amino-1-(6-(3-chloro-4-fluorophenyl)-5-methoxypyridin-2-yl) ethanol and 3-methoxy-4-(oxetan-3-yloxy) benzoic acid as the starting materials. Compound 1312 was obtained as a white solid (40 mg, 26.8%). +ESI-MS: m/z 500.9 [M+H]+.

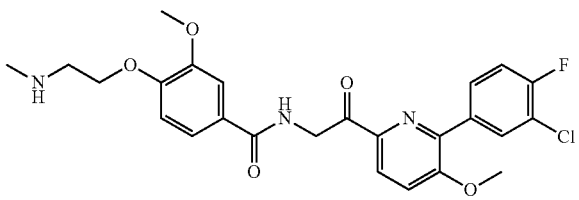

1313

Compound 1313 was obtained following the procedure for obtaining compound 1351 by using 2-amino-1-(6-(3- chloro-4-fluorophenyl)-5-methoxypyridin-2-yl) ethanol and methyl 4-hydroxy-3-methoxybenzoate as the starting materials. Compound 1313 was obtained as a white solid (15 mg, 18.07%). +ESI-MS: m/z 501.9 [M+H]+.

1314

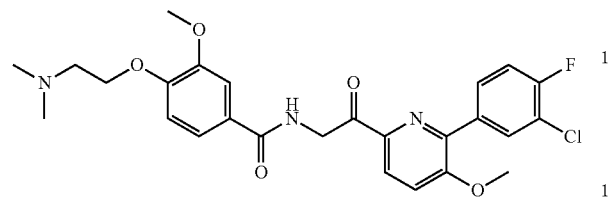

Compound 1314 was obtained following the procedure for obtaining compound 1351 by using 2-amino-1-(6-(3-chloro-4-fluorophenyl)-5-methoxypyridin-2-yl) ethanol and methyl 4-hydroxy-3-methoxybenzoate as the starting materials. Compound 1314 was obtained as a white solid (20 mg, 18.07%). +ESI-MS: m/z 516.1 [M+H]+.

1315

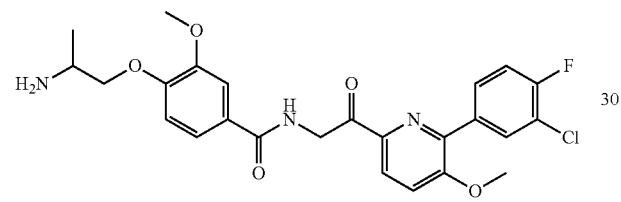

Compound 1315 was obtained following the procedure for obtaining compound 1351 by using 2-amino-1-(6-(3-chloro-4-fluorophenyl)-5-methoxypyridin-2-yl) ethanol and methyl 4-hydroxy-3-methoxybenzoate as the starting materials. Compound 1315 was obtained as a white solid (30 mg, 20.13%). +ESI-MS: m/z 502.1 [M+H]+.

Example 13-6

Preparation of Compound 13-A4

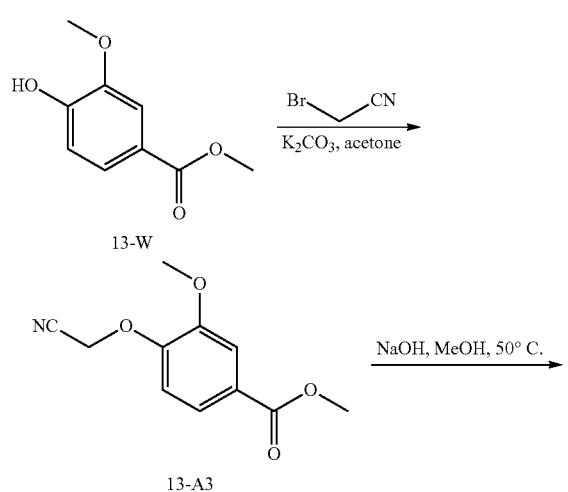

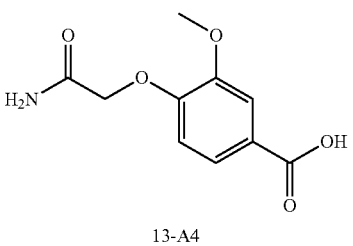

13-A4

To a solution of 13-W (10 g, 54.9 mmol) and 2-bromoacetonitrile (19.7 g, 165 mmol) in acetone (100 mL) were added K2CO3 (14.9 g, 108 mmol) at rt. The solution was heated to reflux and stirred for 4 h. The solid was removed by filtration and the filtrate was concentrated to give 13-A3 (10 g, 82.4%). +ESI-MS: m/z 222.0 [M+H]+.

To a solution of 13-A3 (4 g, 18.09 mmol) in methanol/THF (30 mL/30 mL) was added aqueous NaOH solution (36 mL, 1M). The mixture was stirred for 2 h at 60° C. The solution was cooled to rt and acidified to pH=3 by adding 1N HCl solution. The solid was collected by filtration, and the cake was washed with EtOAc and dried to give 13-A4 (1.2 g, 29.4%). +ESI-MS: m/z 226.0 [M+H]+.

1316

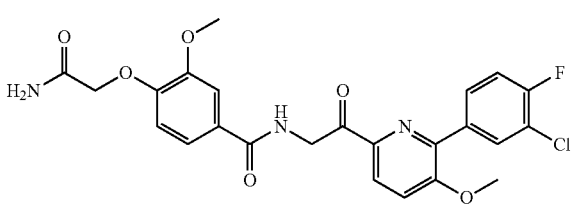

Compound 1316 was obtained following the procedure for obtaining compound 1351 by using 2-amino-1-(6-(3-chloro-4-fluorophenyl)-5-methoxypyridin-2-yl) ethanol and compound 13-A4 as the starting materials. Compound 1316 was obtained as a white solid (25 mg, 16.8%). +ESI-MS: m/z 501.9 [M+H]+.

1317

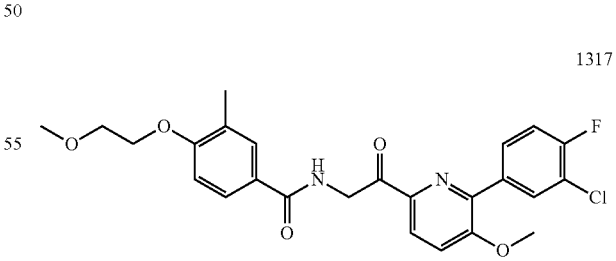

Compound 1317 was obtained following the procedure for obtaining compound 1351 by using 2-amino-1-(6-(3-chloro-4-fluorophenyl)-5-methoxypyridin-2-yl) ethanol and methyl 4-hydroxy-3-methylbenzoate as the starting materials. Compound 1317 was obtained as a white solid. +ESI-MS: m/z=487.1 [M+H]+.

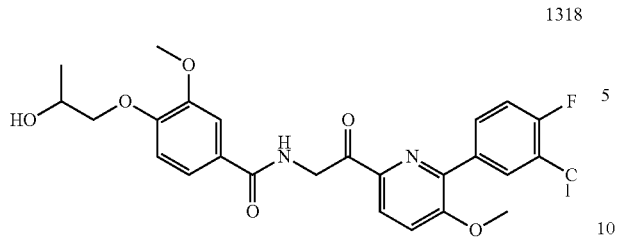
1318

Compound 1318 was obtained following the procedure for obtaining compound 1351 by using 2-amino-1-(6-(3-chloro-4-fluorophenyl)-5-methoxypyridin-2-yl) ethanol and methyl 4-hydroxy-3-methylbenzoate as the starting materials. Compound 1318 was obtained as a white solid. +ESI-MS: m/z 503.0 [M+H]$^+$.

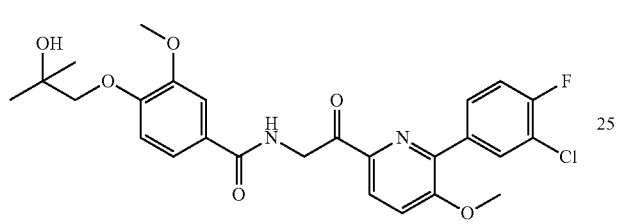
1319

Compound 1319 was obtained following the procedure for obtaining compound 1351 by using 2-amino-1-(6-(3-chloro-4-fluorophenyl)-5-methoxypyridin-2-yl) ethanol and methyl 4-hydroxy-3-methylbenzoate as the starting materials. Compound 1319 was obtained as a white solid. +ESI-MS: m/z 517.0 [M+H]$^+$.

Example 13-7

Preparation of Compound 13-A5

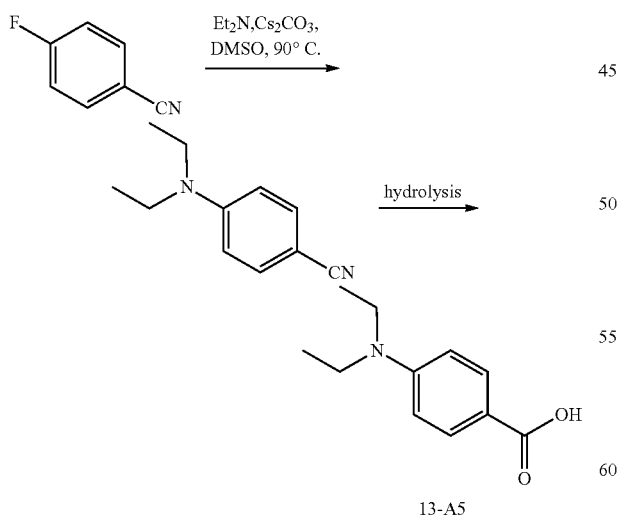

Compound 13-A5 was prepared according to the procedure in Shinozuka et al., *Chemistry Letters* (2006) 35(10): 1090-1091, which is hereby incorporated by reference for the limited purpose of the preparation of compound 13-A5.

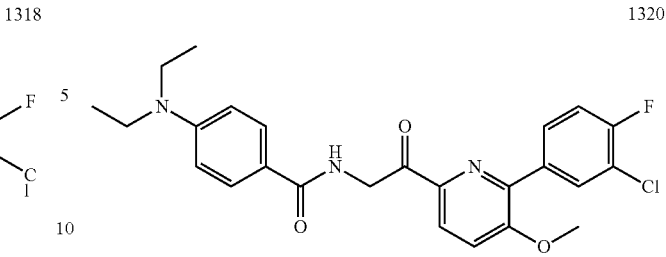
1320

Compound 1320 was obtained following the procedure for obtaining compound 1351 by using 2-amino-1-(6-(3-chloro-4-fluorophenyl)-5-methoxypyridin-2-yl) ethanol and 13-A5 as the starting materials. Compound 1320 was obtained as a white solid. $^1$H-NMR (400 MHz, CDCl$_3$) δ=8.15 (dd, J=2.0, 7.5 Hz, 1H), 8.10 (d, J=8.5 Hz, 1H), 8.03-7.98 (m, 1H), 7.78 (d, J=9.0 Hz, 2H), 7.41 (d, J=8.5 Hz, 1H), 7.26-7.23 (m, 1H), 7.00 (br. s., 1H), 6.67 (d, J=9.0 Hz, 2H), 5.20 (d, J=4.5 Hz, 2H), 4.00 (s, 3H), 3.42 (q, J=7.0 Hz, 4H), 1.20 (t, J=7.0 Hz, 6H).

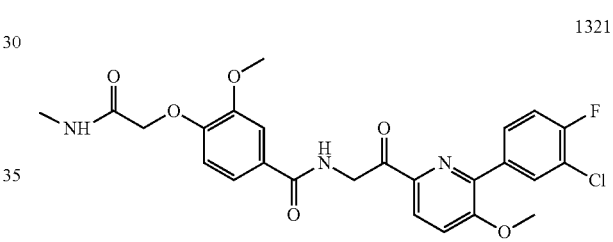
1321

Compound 1321 was obtained following the procedure for obtaining compound 1351 by using 2-amino-1-(6-(3-chloro-4-fluorophenyl)-5-methoxypyridin-2-yl) ethanol and methyl 4-hydroxy-3-methylbenzoate as the starting materials. Compound 1321 was obtained as a white solid. +ESI-MS: m/z 516.0 [M+H]$^+$;

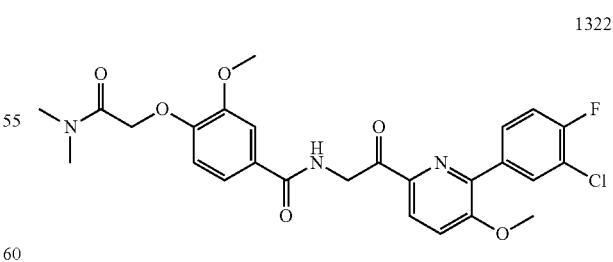
1322

Compound 1322 was obtained following the procedure for obtaining compound 1351 by using 2-amino-1-(6-(3-chloro-4-fluorophenyl)-5-methoxypyridin-2-yl) ethanol and methyl 4-hydroxy-3-methylbenzoate as the starting materials. Compound 1322 was obtained as a white solid. +ESI-MS: m/z 529.9 [M+H]$^+$.

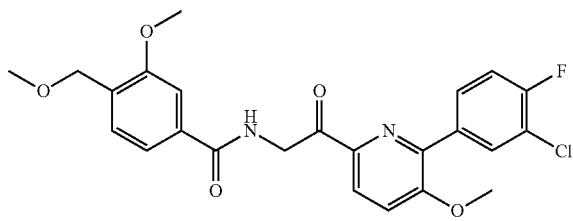

1323

Compound 1323 was obtained following the procedure for obtaining compound 1351 by using 2-amino-1-(6-(3-chloro-4-fluorophenyl)-5-methoxypyridin-2-yl) ethanol and 3-methoxy-4-(methoxymethyl)benzoic acid as the starting materials. Compound 1323 was obtained as a white solid (130 mg). +ESI-MS: m/z 473.1 [M+H]$^+$.

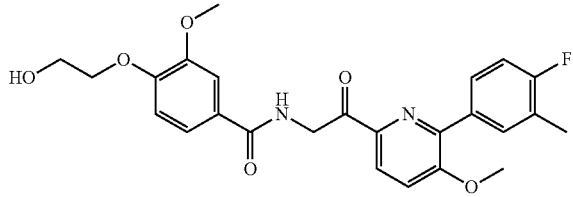

1325

To a stirred solution of 13-H (150 mg, 0.267 mmol) in dioxine/H$_2$O (50 mL) was added (4-fluoro-3-methylphenyl) boronic acid (51 mg, 0.3 mmol), KF (48 mg, 0.8 mmol) and Pd(dppf)Cl$_2$ (6.5 mg, 0.008 mmol). The mixture was stirred at 80° C. for 2 h. The solution was evaporated and purified by column chromatography gel eluted with PE:acetone=8:1 as the elute to give an intermediate compound (150 mg, 52.9%). +ESI-MS: m/z 589.2 [M+H]$^+$.

To a solution of the intermediate compound (150 mg, 0.34 mmol) in DCM (20 mL) was added TFA (2 mL). The mixture was stirred at rt for 5 mins (as determined by TLC, PE:EA=2:1). After conversion, the solution was diluted with CH$_2$Cl$_2$, and washed with saturated NaHCO$_3$ solution. The organic phase was concentrated to give crude compound 1325, which was purified by prep-HPLC to give purified compound 1325 (32 mg, 16.2%). +ESI-MS: m/z 469.2 [M+H]$^+$;

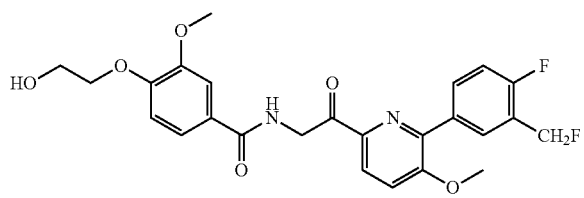

1326

Compound 1326 was obtained following the procedure for obtaining compound 1325 by using 2-(4-fluoro-3-(fluoromethyl)phenyl)-4,4,5,5-tetramethyl-1,3,2-dioxaborolane as the starting material. Compound 1326 was obtained as a white solid. +ESI-MS: m/z 487.1 [M+H]$^+$.

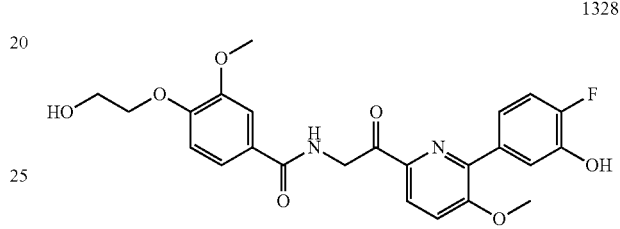

1327

Compound 1327 was obtained following the procedure for obtaining compound 1325 by using 2-(3-(difluoromethyl)-4-fluorophenyl)-4,4,5,5-tetramethyl-1,3,2-dioxaborolane as the starting material. Compound 1327 was obtained as a white solid. +ESI-MS: m/z 505.1 [M+H]$^+$.

1328

Compound 1328 was obtained following the procedure for obtaining Compound 1325 by using 2-fluoro-5-(4,4,5,5-tetramethyl-1,3,2-dioxaborolan-2-yl)phenol as the starting material. Compound 1328 was obtained as a white solid. +ESI-MS: m/z 471.1 [M+H]$^+$.

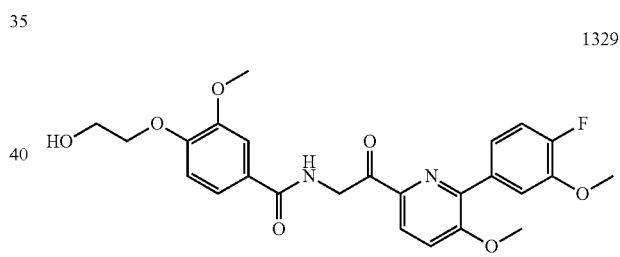

1329

Compound 1329 was obtained following the procedure for obtaining compound 1325 by using 2-(4-fluoro-3-methoxyphenyl)-4,4,5,5-tetramethyl-1,3,2-dioxaborolane as the starting material. Compound 1329 was obtained as a white solid. +ESI-MS: m/z 485.1 [M+H]$^+$.

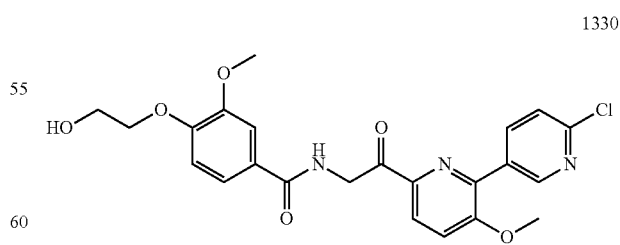

1330

Compound 1330 was obtained following the procedure for obtaining compound 1325 by using 2-(4-fluoro-3-methoxyphenyl)-4,4,5,5-tetramethyl-1,3,2-dioxaborolane as the starting material. Compound 1330 was obtained as a white solid. +ESI-MS: m/z 472.1 [M+H]$^+$.

1331

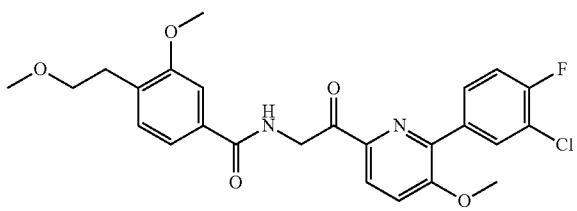

Compound 1331 was obtained following the procedure for obtaining compound 1325 by using 2-amino-1-(6-(3-chloro-4-fluorophenyl)-5-methoxypyridin-2-yl) ethanol and 3-methoxy-4-(2-methoxyethyl) benzoic acid as the starting materials. Compound 1331 was obtained as a white solid. +ESI-MS: m/z=487.1 [M+H]$^{+1}$.

1332

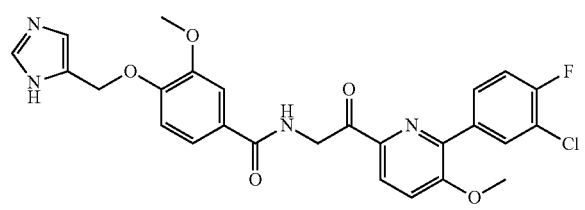

Compound 1332 was obtained following the procedure for obtaining compound 1325 by using 2-amino-1-(6-(3-chloro-4-fluorophenyl)-5-methoxypyridin-2-yl) ethanol and methyl 4-hydroxy-3-methoxybenzoate as the starting materials. Compound 1332 was obtained as a white solid. +ESI-MS: m/z=525.1 [M+H]$^+$.

1333

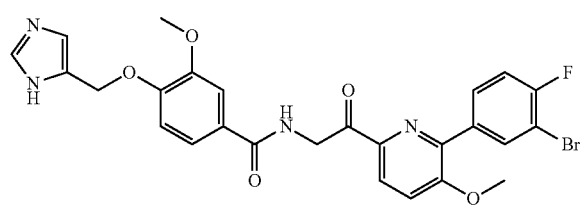

Compound 1333 was obtained following the procedure for obtaining compound 1325 by using 2-amino-1-(6-(3-bromo-4-fluorophenyl)-5-methoxypyridin-2-yl) ethanol and methyl 4-hydroxy-3-methoxybenzo as the starting materials. Compound 1333 was obtained as a white solid. +ESI-MS: m/z=568.0, 570.0 [M+H]$^+$.

1334

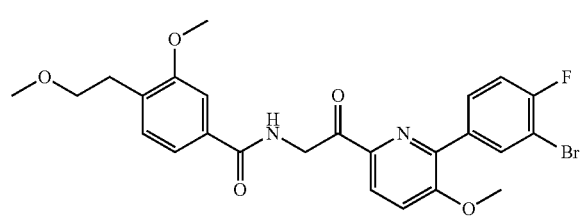

Compound 1334 was obtained following the procedure for obtaining compound 1325 by using 2-amino-1-(6-(3-chloro-4-fluorophenyl)-5-methoxypyridin-2-yl) ethanol and methyl 4-hydroxy-3-methoxybenzoate as the starting materials. Compound 1334 was obtained as a white solid. +ESI-MS: m/z=531.0 [M+H]$^+$.

Example 13-8

Preparation of Compound 1335

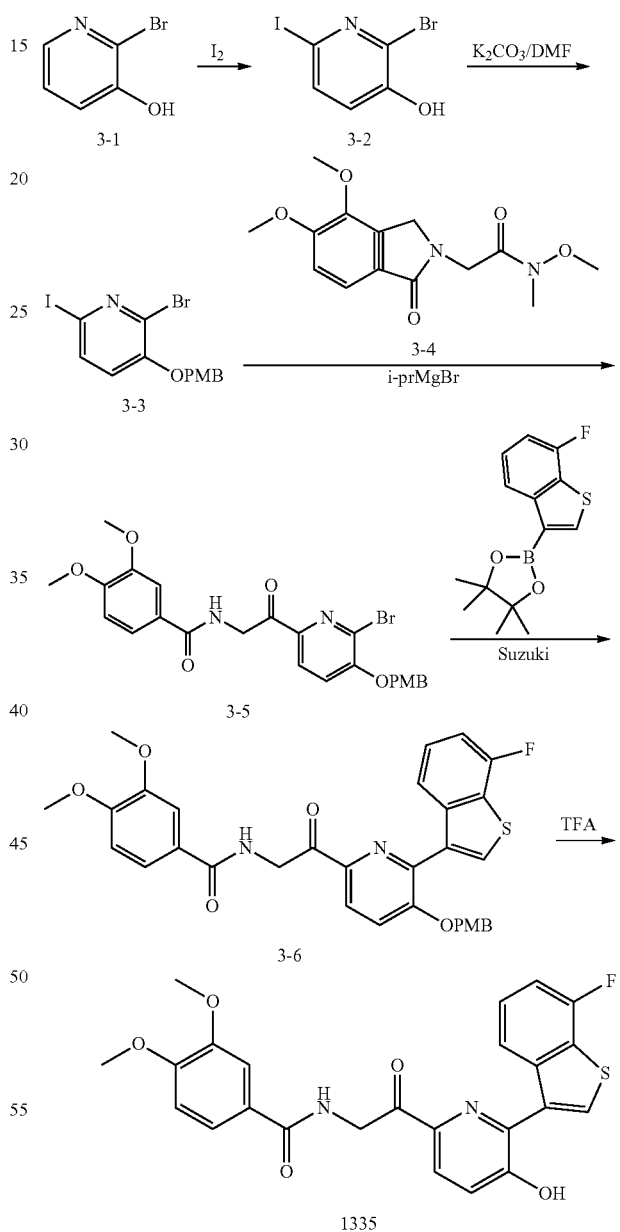

Compounds 3-2 and 3-3 were prepared according to procedures provided in PCT Publication Nos. WO 2011/109261 and WO 2011/068211, respectively, which are hereby incorporated by reference for the limited purpose of their respective disclosures of the preparation of compound 3-2 and 3-3.

To a solution of crude 3-3 (500 mg, 1.2 mmol) in THF (10 mL) was added 3-4 (338 mg, 1.2 mmol) and i-PrMgCl (2.4 mL, 4.8 mmol). The solution was stirred at rt for 5 mins. The solution was quenched by aq.NH$_4$Cl and the aqueous layer was extracted with DCM. The organic layer was combined and purified by column chromatograph gel eluted with PE:EA=1:3 to give 3-5 (0.30 g, yield: 48.6%). $^1$H NMR (400 MHz, d-DMSO) δ=8.60-8.76 (m, 1H), 8.02 (d, J=8.38 Hz, 1H), 7.79 (d, J=8.38 Hz, 1H), 7.36-7.56 (m, 5H), 6.94-7.07 (m, 4H), 5.31 (s, 2H), 4.79 (d, J=5.51 Hz, 2H), 3.82 (s, 3H), 3.81 (s, 3H), 3.77 (s, 3H).

To a solution of crude 3-5 (200 mg, 0.39 mmol) in DME:H$_2$O=10:1 (5 mL) under N$_2$ was added Cs$_2$CO$_3$ (381 mg, 1.17 mmol), Pd(dppf)$_2$Cl$_2$ (8.6 mg, 0.01 mmol) and the dioxaborolane (162.6 mg, 0.58 mmol). The mixture was heated to 85° C. for 3 h. The reaction was monitored by TLC (PE:EA=1:1). After conversion completed, the solvent was evaporated and the residue was purified by column chromatograph gel eluted with PE:EA=1:1 to give 3-6 (20 mg, yield: 8.7%).

To a stirred solution of 3-6 (200 mg, 0.34 mmol) in dry DCM (5 mL) was added TFA (0.2 mL). After complete conversion, the mixture was washed by saturated sodium carbonate. The organic phase was concentrated to dryness and purified by prep-HPLC to afford compound 1335 (10 mg, 6.3%). +ESI-MS: m/z=467.1 [M+H]$^+$.

1336

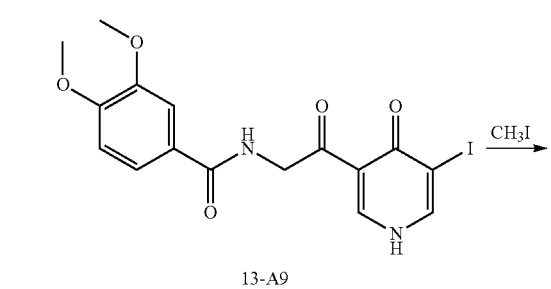

Compound 1336 was obtained following the procedure for obtaining compound 1300 by using N-(2-(6-bromo-5-methoxypyridin-2-yl)-2-oxoethyl)-3,4-dimethoxybenzamide and 2-(7-fluorobenzo[b]thiophen-3-yl)-4,4,5,5-tetramethyl-1,3,2-dioxaborolane as the starting materials. Compound 1336 was obtained as a white solid. +ESI-MS: m/z=481.1 [M+H]$^+$.

Example 13-9

Preparation of Compounds 13-A9 and 13-A10

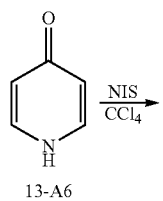

13-A6

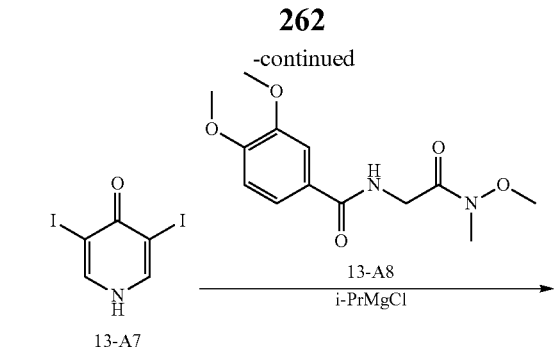

13-A7

13-A8 i-PrMgCl

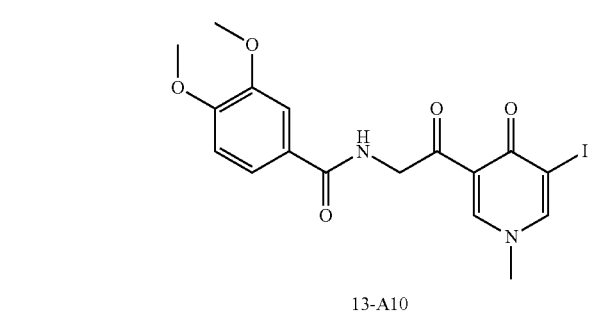

13-A9

CH$_3$I

13-A10

To a stirred solution of 13-A6 (1.0 g, 10.5 mmol) in CCl$_4$ (10 mL) was added NIS (4.7 g, 21 mmol), and the mixture was heated to reflux for 12 h. The solution was evaporated and dissolved with DCM. The solution was acidified to pH=8 with aqueous NaS$_2$O$_3$, and the aqueous layer was extracted with DCM. The organic layer was combined and purified by column chromatography gel eluted with PE:EA=1:3 as the elute to give 13-A7 (2.0 g, 55.6%). +ESI-MS: m/z=347.8 [M+H]$^+$.

To a solution of crude 13-A7 (1.0 g, 2.7 mmol) in THF (10 mL) was added 13-A8 (0.77 g, 2.7 mmol) and i-PrMgBr (7.7 mL, 10 mmol). The solution was stirred at rt for 5 mins and then evaporated. The solution was acidified to pH=8 with aqueous NH$_4$Cl, and the aqueous layer was extracted with DCM. The organic layer was combined and purified by column chromatography gel with PE:EtOAc=1:1 as the elute to give 13-A9 (0.5 g, 41.7%). +ESI-MS: m/z=442.0 [M+H]$^+$.

To a solution of 13-A9 (0.5 g, 1.1 mmol) in DMF (10 mL) was added K$_2$CO$_3$ (455.4 mg, 3.3 mmol) and MeI (156 mg, 1.1 mmol). After 30 mins, the solution was evaporated and purified by column chromatography gel eluted with PE:EA=1:5 as the elute to give 13-A10 (0.3 g, 60.1%). +ESI-MS: m/z=457.1 [M+H]$^+$.

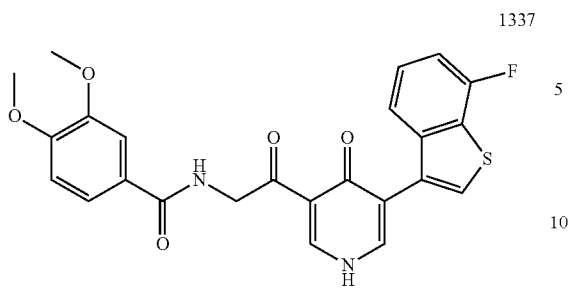

1337

To a solution of crude 13-A9 (200 mg, 0.9 mmol) in DME:H$_2$O=10:1 (2 mL) under N$_2$ was added Cs$_2$CO$_3$ (590 mg, 1.8 mmol), Pd(dppf)$_2$Cl$_2$ (20 mg, 0.027 mmol) and 12-C (500 mg, 1.8 mmol). The mixture was heated to 85° C. for 3 h (as monitored by TLC, PE:EA=1:3). After conversion, the mixture was filtered and purified by prep-HPLC to give compound 1337 (5 mg, 2.3%). +ESI-MS: m/z=467.1 [M+H]$^+$.

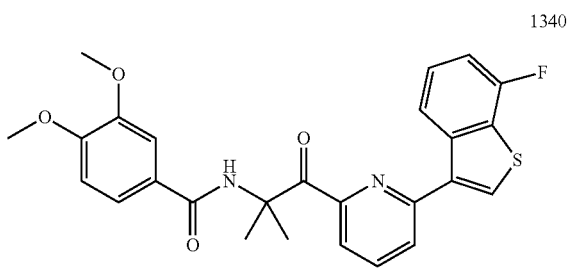 [SMILES: COc1ccc(C(=O)NC(C)(C)C(=O)c2cccc(-c3csc4c(F)cccc34)n2)cc1OC]

1340

Compound 1340 was obtained following the procedure for obtaining compound 1300 by using methyl 2-amino-2-methylpropanoate and 2,6-dibromopyridine as the starting materials. Compound 1340 was obtained as a white solid. +ESI-MS: m/z 479.1 [M+H]$^+$.

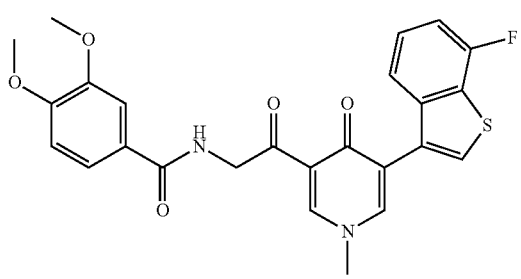

1338

To a solution of crude 13-A10 (200 mg, 0.44 mmol) in DME:H$_2$O=10:1 (5 mL) under N$_2$ was added Cs$_2$CO$_3$ (289 mg, 0.88 mmol), Pd (dppf)$_2$Cl$_2$ (9.6 mg, 0.013 mmol) and 12-C (245 mg, 0.88 mmol). The mixture was heated to 85° C. for 3 h (as monitored by TLC, PE:EA=1:3). After conversion, the mixture was filtered and purified by prep-HPLC to give compound 1338 (20 mg, 9.5%). +ESI-MS: m/z=481.1 [M+H]$^+$.

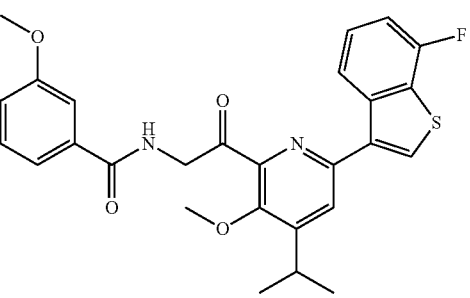

1341

Compound 1341 was obtained following the procedure for obtaining compound 1300 by using 2,6-diiodo-4-isopropyl-3-methoxypyridine as the starting material. Compound 1341 was obtained as a white solid. +ESI-MS: m/z 523.1 [M+H]$^+$.

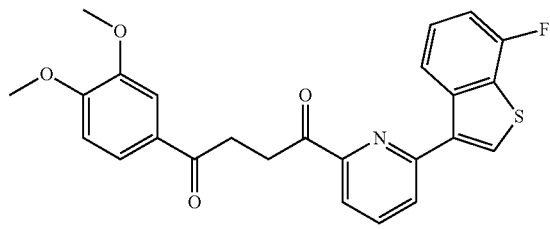

1339

Compound 1339 was obtained following the procedure for obtaining compound 1300 by using 4-(3,4-dimethoxyphenyl)-N-methoxy-N-methyl-4-oxobutanamide and 2,6-dibromopyridine as the starting materials. Compound 1339 was obtained as a white solid. +ESI-MS: m/z=450.1 [M+H]$^+$.

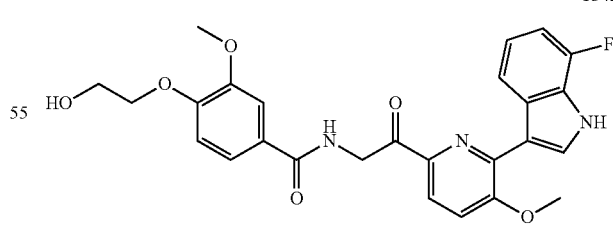

1342

Compound 1342 was obtained following the procedure for obtaining compound 1325 by using 7-fluoro-3-(4,4,5,5-tetramethyl-1,3,2-dioxaborolan-2-yl)-1-((2-(trimethylsilyl)ethoxy)methyl)-1H-indole as the starting material. Compound 1342 was obtained as a white solid. +ESI-MS: m/z 494.2; [M+H]$^+$.

1343

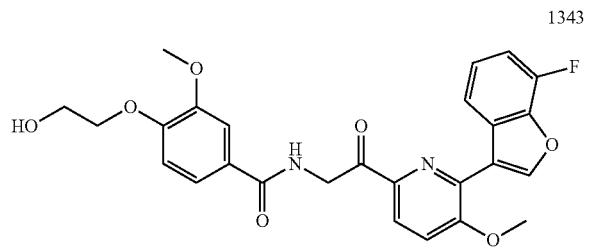 [SMILES: COc1cc(C(=O)NCC(=O)c2ccc(OC)c(-c3coc4c(F)cccc34)n2)ccc1OCCO]

Compound 1343 was obtained following the procedure for obtaining compound 1325 by using 2-(7-fluorobenzofuran-3-yl)-4,4,5,5-tetramethyl-1,3,2-dioxaborolane as the starting material. Compound 1343 was obtained as a white solid.

+ESI-MS: m/z 495.1 [M+H]$^+$.

1344

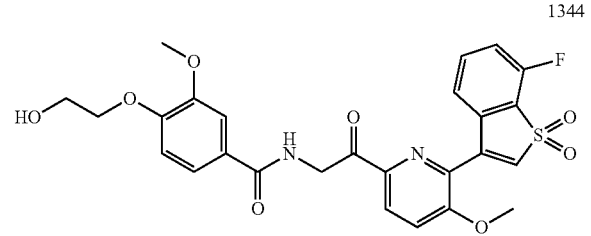 [SMILES: COc1cc(C(=O)NCC(=O)c2ccc(OC)c(C3=CS(=O)(=O)c4c(F)cccc43)n2)ccc1OCCO]

Compound 1344 was obtained following the procedure for obtaining compound 1325 by using 7-fluoro-3-(tributylstannyl)benzo[b]thiophene 1,1-dioxide as the starting material. Compound 1344 was obtained as a white solid. +ESI-MS: m/z 543.1 [M+H]$^+$.

1345

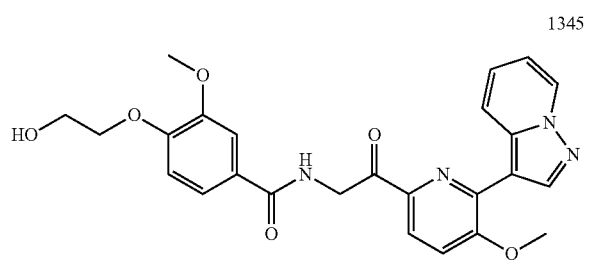 [SMILES: COc1cc(C(=O)NCC(=O)c2ccc(OC)c(-c3cnn4ccccc34)n2)ccc1OCCO]

Compound 1345 was obtained following the procedure for obtaining compound 1325 by using 3-(trimethylstannyl)pyrazolo[1,5-a]pyridine as the starting material. Compound 1345 was obtained as a white solid. +ESI-MS: m/z 476.9 [M+H]$^+$.

1346

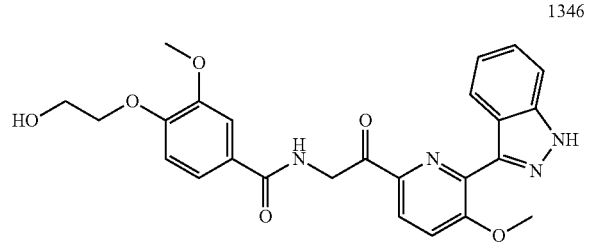 [SMILES: COc1cc(C(=O)NCC(=O)c2ccc(OC)c(-c3n[nH]c4ccccc34)n2)ccc1OCCO]

Compound 1346 was obtained following the procedure for obtaining compound 1325 by using 1-((2-(trimethylsilyl)ethoxy)methyl)-3-(trimethylstannyl)-1H-indazole as the starting material. Compound 1346 was obtained as a white solid. +ESI-MS: m/z 477.4 [M+H]$^+$.

Example 13-10

Preparation of Compound 13-A13

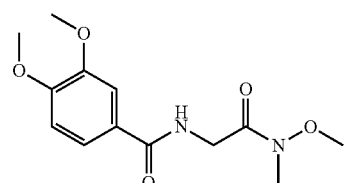

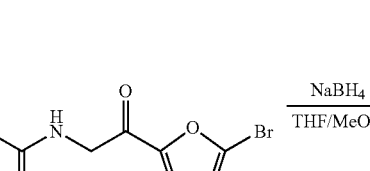

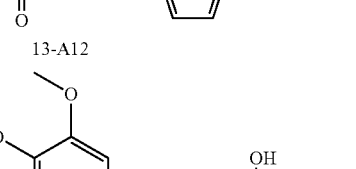

A 50 mL flask with a magnetic stirring bar was charged with 13-A11 (223 mg, 1.0 mmol), Weinreb amide (13-A8, 282 mg, 1.0 mmol), and THF (10 mL) under N$_2$ atmosphere. The solution was treated with i-PrMgCl (1.3 M, 2.0 eq.) dropwise at rt. The mixture was stirred for 1 h at rt. Water (50 mL) and EA (50 mL) were added. The organic layer was separated and the aqueous phase extracted with EA. The combined organic layers were dried with MgSO$_4$ and the volatiles were removed under reduced pressure. The residue was purified by column chromatography on silica gel (PE) to provide 13-A12 as a solid (332 mg, 90%). +ESI-MS: m/z 367.0, 369.0 [M+H]$^+$.

To a stirred solution of 13-A12 (368 mg, 1.0 mmol) in MeOH/THF (5 mL/5 mL) was added NaBH$_4$ (380 mg, 10 mmol) in portions until the starting materials was consumed. The volatiles were removed under reduced pressure. The residue was purified by column chromatography on silica gel (PE:EtOAc=2:1) to give 13-A13 as a colorless oil (370 mg, 100%). +ESI-MS: m/z 369.0, 371.0 [M+H]$^+$.

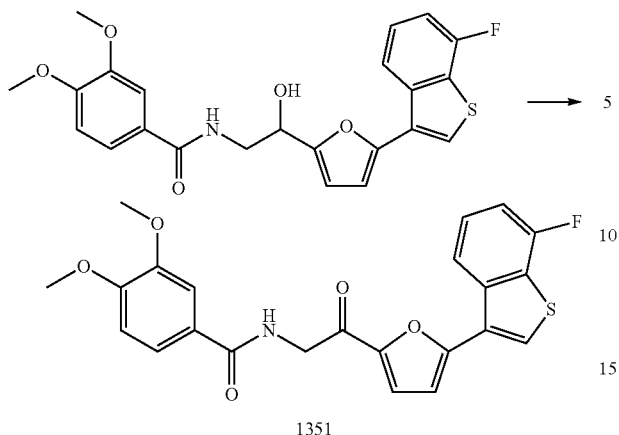

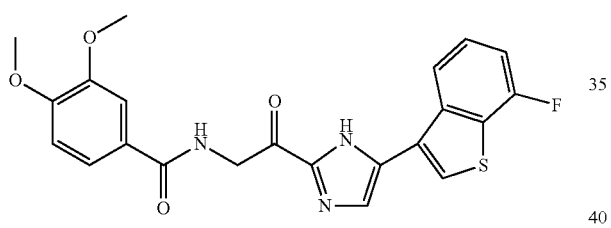

1351

To a solution of N-(2-(5-(7-fluorobenzo[b]thiophen-3-yl) furan-2-yl)-2-hydroxyethyl)-3,4-dimethoxybenzamide (88 mg, 0.2 mmol) in $CH_2Cl_2$ (10 mL) was added DMP (170 mg, 0.4 mmol). The mixture was stirred at rt until the starting material was consumed. The mixture was concentrated at low pressure to give the crude product, which was purified by silica gel column chromatography (PE/EA) to give compound 1351 as a white solid (68 mg, 80%). +ESI-MS: m/z 439.9 [M+H]$^+$.

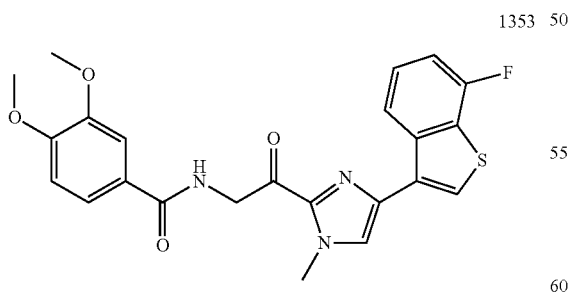

1352

Compound 1352 was obtained following the procedure for obtaining compound 1351 by using 2,5-dibromo-1-((2-(trimethylsilyl)ethoxy)methyl)-1H-imidazole and 2-(7-fluorobenzo[b]thiophen-3-yl)-4,4,5,5-tetramethyl-1,3,2-dioxaborolane as the starting materials. Compound 1352 was obtained as a white solid. +ESI-MS: m/z 440.0 [M+H]$^+$.

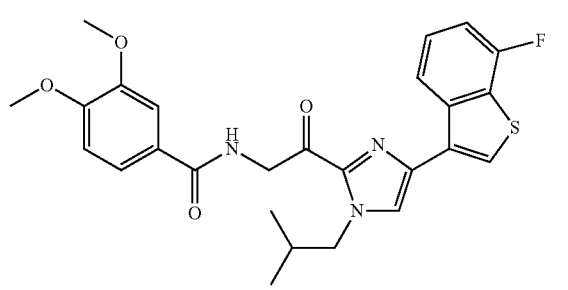

1353

Compound 1353 was obtained following the procedure for obtaining compound 1351 by using 2,4-dibromo-1-methyl-1H-imidazole and 2-(7-fluorobenzo[b]thiophen-3-yl)-4,4,5,5-tetramethyl-1,3,2-dioxaborolane as the starting materials. Compound 1353 was obtained as a white solid. +ESI-MS: m/z 453.8 [M+H]$^+$.

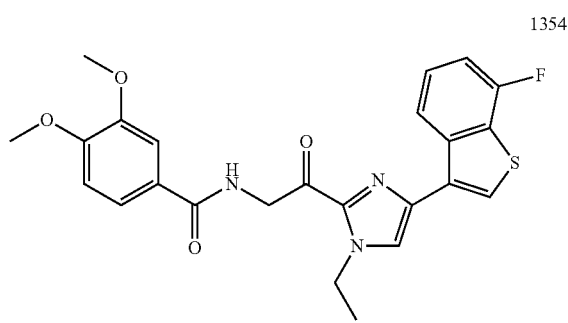 [SMILES: CCn1cc(-c2csc3c(F)cccc23)nc1C(=O)CNC(=O)c1ccc(OC)c(OC)c1]

1354

Compound 1354 was obtained following the procedure for obtaining compound 1351 by using 2,4-dibromo-1-ethyl-1H-imidazole and 2-(7-fluorobenzo[b]thiophen-3-yl)-4,4,5,5-tetramethyl-1,3,2-dioxaborolane as the starting materials. Compound 1354 was obtained as a white solid. +ESI-MS: m/z 468.1 [M+H]$^+$.

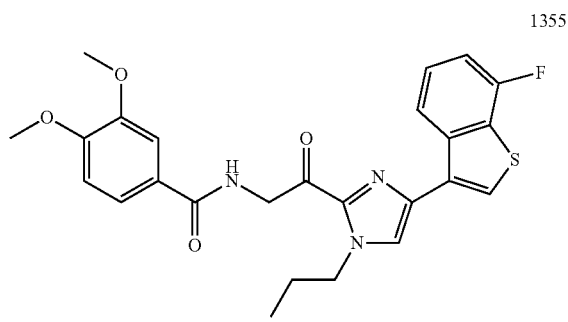 [SMILES: CCCn1cc(-c2csc3c(F)cccc23)nc1C(=O)CNC(=O)c1ccc(OC)c(OC)c1]

1355

Compound 1355 was obtained following the procedure for obtaining compound 1351 by using 2,4-dibromo-1-propyl-1H-imidazole and 2-(7-fluorobenzo[b]thiophen-3-yl)-4,4,5,5-tetramethyl-1,3,2-dioxaborolane as the starting materials. Compound 1355 was obtained as a white solid. +ESI-MS: m/z 482.5 [M+H]$^+$.

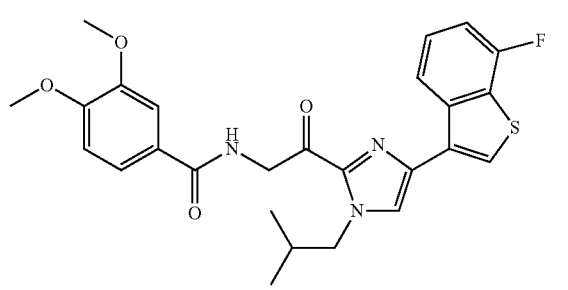

1356

Compound 1356 was obtained following the procedure for obtaining compound 1351 by using 2,4-dibromo-1-isobutyl-1H-imidazole and 2-(7-fluorobenzo[b]thiophen-3-yl)-4,4,5,5-tetramethyl-1,3,2-dioxaborolane as the starting materials. Compound 1356 was obtained as a white solid. +ESI-MS: m/z 496.1 [M+H]$^+$.

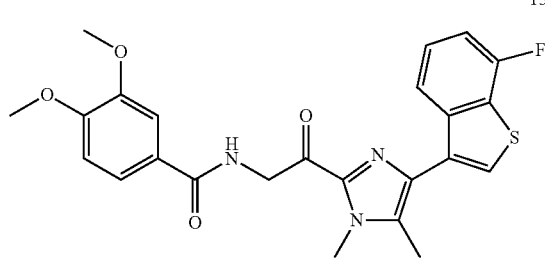

Compound 1358 was obtained following the procedure for obtaining compound 1351 by using 2,4-dibromo-1,5-dimethyl-1H-imidazole and 2-(7-fluorobenzo[b]thiophen-3-yl)-4,4,5,5-tetramethyl-1,3,2-dioxaborolane as the starting materials. Compound 1358 was obtained as a white solid. +ESI-MS: m/z 467.8 [M+H]+.

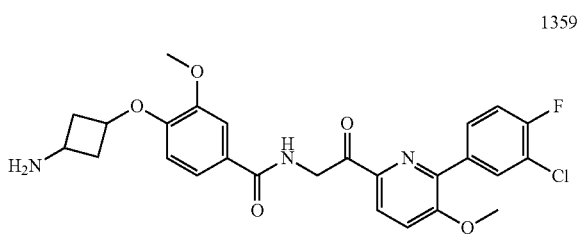 [SMILES: COc1cc(C(=O)NCC(=O)c2ccc(OC)c(-c3ccc(F)c(Cl)c3)n2)ccc1OC1CC(N)C1]

Compound 1359 was obtained following the procedure for obtaining compound 1310 by using 2-amino-1-(6-(3-chloro-4-fluorophenyl)-5-methoxypyridin-2-yl) ethanol and 4-(3-((tert-butoxycarbonyl) amino) cyclobutoxy)-3-methoxybenzoic acid as the starting materials. Compound 1359 was obtained as a white solid. +ESI-MS: m/z 513.9 [M+H]+.

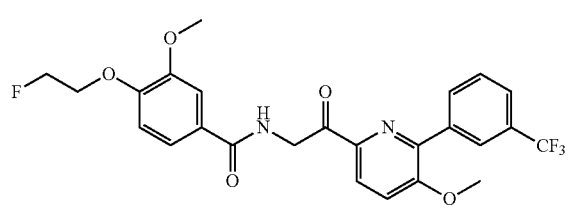

Compound 1360 was obtained following the procedure for obtaining compound 1325 by using 3-H and (3-(trifluoromethyl)phenyl)boronic acid as the starting material. Compound 1360 was obtained as a white solid. +ESI-MS: m/z 505.2 [M+H]+.

Example 14-1

Preparation of General Compound 1400A

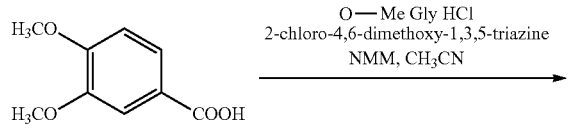

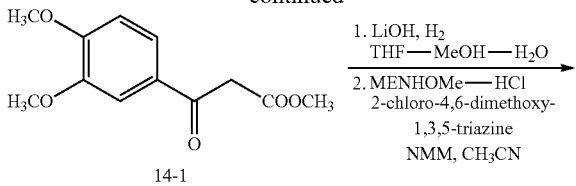

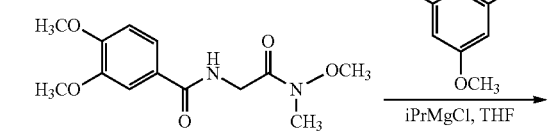

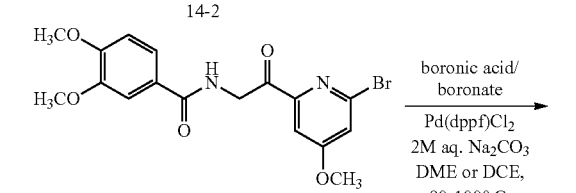

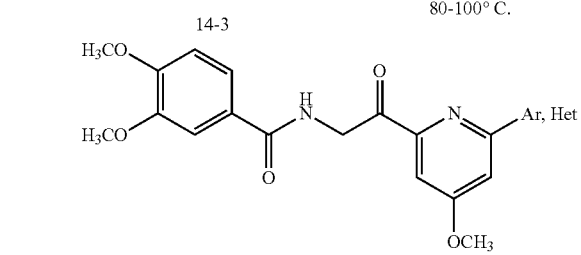

A mixture of 3,4-dimethoxybenzoic acid (15.0 g, 82.4 mmol), 2-chloro-4,6-dimethoxy-1,3,5-triazine (20.1 g, 115 mmol) and NMM (18.4 mL, 132 mmol) in CH₃CN (60 mL) was stirred at rt for 30 mins. Glycine methylester hydrochloride (12.4 g, 99.0 mmol) and NMM (10.9 mL, 99.0 mmol) were added and the reaction was stirred for 2 h. The volatiles were removed under reduced pressure. The residue was taken up with EtOAc and the organic portion was washed with water, dried (Na₂SO₄), filtered and concentrated under reduced pressure. Crude 14-1 (21.1 g) was used to the next step without further purification.

Monohydrate LiOH (11.0 g, 261 mmol) was added to 14-1 (21.1 g) dissolved in a 2:1:1 THF-MeOH—H₂O mixture (80 mL). The reaction was stirred at rt for 1 h. The organic solvents were removed under reduced pressure. The residue was taken up with water and the aqueous portion was extracted twice with EtOAc. The combined organic portions were dried (Na₂SO₄), filtered, and the solvents were removed under reduced pressure. The residue was dissolved in CH₃CN (60 mL) and 2-chloro-4,6-dimethoxy-1,3,5-triazine (14.4 g, 107 mmol) and NMM (14.5 mL, 132 mmol) were added to the mixture. After 30 mins, N,O-dimethylhydroxylamine hydrochloride (10.4 g, 107 mmol) and NMM (11.7 mL, 107 mmol) were added. The mixture was stirred at rt for 2 h. The volatiles were removed under reduced pressure. The residue was dissolved in EtOAc, and the organic portion was washed with water and brine, dried (Na₂SO₄), filtered and concentrated under reduced pressure to afford 14-2 (9.5 g). UPLC/MS (ES+), m/z: 283.10 [M+H]+.

A 2M solution of i-PrMgCl in THF (3.0 mL, 6.04 mmol) was added to a solution of 2,6-dibromo-4-methoxypyridine (800 mg, 3.02 mmol) in dry THF (6 mL). The mixture was stirred at rt for 30 mins and added via cannula to a solution of 14-2 (500 mg, 1.77 mmol) in THF (5 mL), which had been pre-heated to 40° C. The reaction was stirred at 40° C. for 1 h, cooled down to rt and quenched with a 1M aq HCl solution. The organic portion was diluted with EtOAc, washed twice with brine, dried (Na$_2$SO$_4$), filtered and concentrated under reduced pressure. Chromatography of the residue (cyclohexane-EtOAc, 100:0 to 0:100) afforded the 14-3 as a white solid (200 mg, 27%). UPLC/MS(ES$^+$), m/z: 409.10 [M+H]$^+$.

A mixture of 14-3 (170 mg, 0.390 mmol), boronic acid/ester (0.975 mmol), Pd(dppf)Cl$_2$ (14.0 mg, 0.019 mmol) and aq Na$_2$CO$_3$ (2M solution, 585 uL, 1.17 mmol) in DME (7 mL) was degassed and heated to 85° C. for 2 h (or until disappearing of the starting material). The volatiles were removed under reduced pressure. Chromatography of the residue (cyclohexane-EtOAc) afforded compound 1400A.

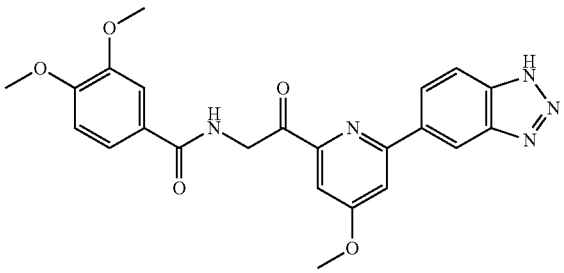

1401

Compound 1401 was obtained by reacting 14-3 with (4-hydroxyphenyl)boronic acid according to the procedure shown in Example 14-1. Compound 1401 was obtained as a white solid (26%). UPLC/MS(ES$^+$), m/z: 423.18 [M+H]$^+$.

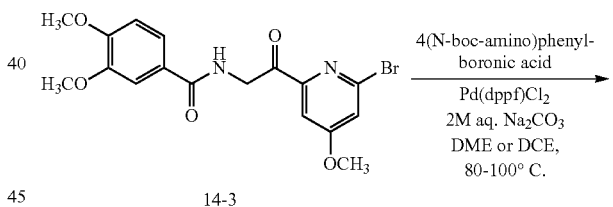

1402

Compound 1402 was obtained by reacting 14-3 with 1,4-benzodioxane-6-boronic acid according to the procedure shown in Example 14-1. Compound 1402 was obtained as a grey solid (42%). UPLC/MS(ES$^+$), m/z: 465.20 [M+H]$^+$.

1403

A mixture of 14-3 (100 mg, 0.240 mmol), 5-(tetramethyl-1,3,2-dioxaborolan-2-yl)-1-(triphenylmethyl)-1H-1,2,3-benzotriazole (233 mg, 0.480 mmol), Pd(dppf)Cl$_2$ (26.0 mg, 0.036 mmol) and aq Na$_2$CO$_3$ (2M solution, 360 uL, 0.720 mmol) in DME (2 mL) was degassed and stirred. The mixture was heated to 80° C. for 48 h. Water and DCM were added. The mixture was filtered and the organic portion was dried (Na$_2$SO$_4$), filtered and concentrated under reduced pressure. Chromatography of the residue (cyclohexane-EtOAc, 100:0 to 0:100) afforded 3,4-dimethoxy-N-(2-{4-methoxy-6-[1-(triphenylmethyl)-1H-1,2,3-benzotriazol-5-yl]pyridin-2-yl}-2-oxoethyl)benzamide (90 mg, 54%). This compound was dissolved in DCM (3 mL) and treated with TFA (1 mL). The volatiles were removed under reduced pressure. The residue was purified by prep-HPLC to afford 1403 as an off white solid (8 mg, 14%). UPLC/MS(ES$^+$), m/z: 448.22 [M+H]$^+$.

Example 14-2

Preparation of Compound 1404

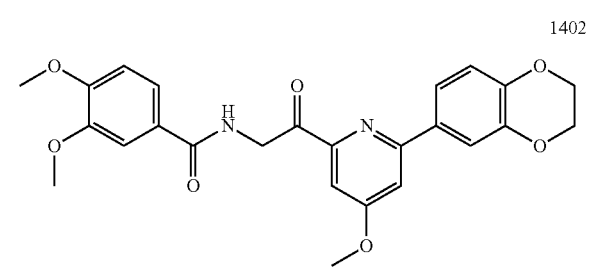 [SMILES: COc1cc(C(=O)CNC(=O)c2ccc(OC)c(OC)c2)nc(-c2ccc3c(c2)OCCO3)c1]

14-3

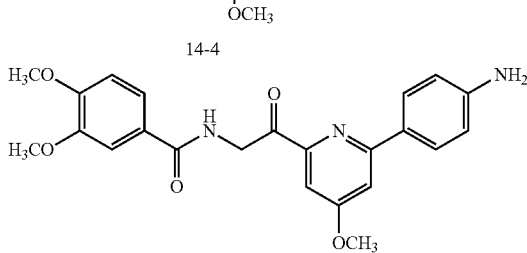

14-4

1404

A mixture of 14-3 (130 mg, 0.320 mmol), 4-(N-boc-amino)phenyl-boronic acid (111 mg, 0.470 mmol), Pd(dppf)Cl₂ (33.0 mg, 0.047 mmol) and aq Na₂CO₃ (2M solution, 320 uL, 0.640 mmol) in DME (3.2 mL) was degassed and stirred at 85° C. for 16 h. Water was added and the mixture was extracted twice with EtOAc. The combined organic portions were dried (Na₂SO₄), filtered and concentrated in vacuo. Chromatography of the residue (cyclohexane-EtOAc, 100:0 to 30:70) afforded 14-4 as a grey solid (75 mg, 45%). UPLC/MS(ES⁺), m/z: 522.20 [M+H]⁺.

TFA (300 uL) was added to a mixture of 14-4 (75 mg, 0.026 mmol) in DCM (1 mL). After 1 h, the reaction was diluted with DCM and the organic portion was washed with a saturated aq NaHCO₃ solution, dried (Na₂SO₄) and concentrated under reduced pressure. The residue was purified by prep-HPLC to afford 1404 as a grey solid (11 mg, 18%). UPLC/MS(ES⁺), m/z: 422.15 [M+H]⁺.

Example 14-3

Preparation of Compound 1405

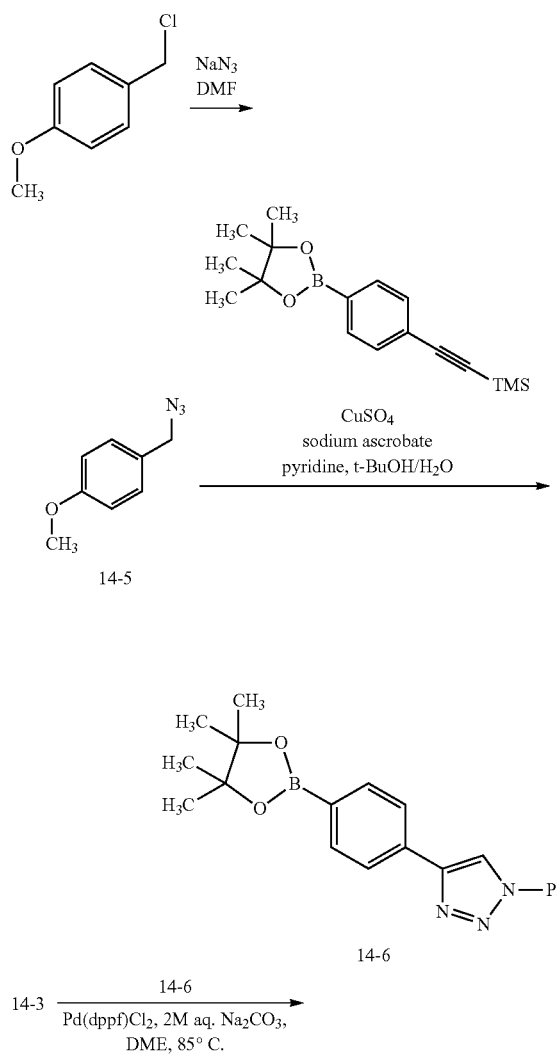

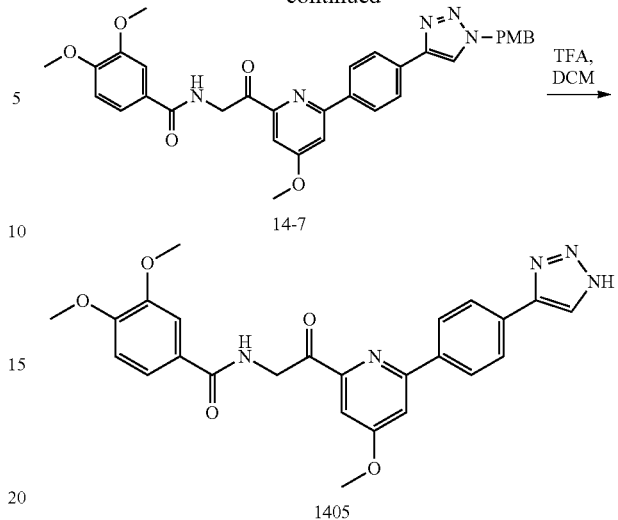

Sodium azide (249 mg, 3.83 mmol) was added to a solution of 1-(chloromethyl)-4-methoxybenzene (500 mg, 3.19 mmol) in DMF (5 mL). The mixture was stirred at rt for 1 h. Et₂O was added and the organic portion was washed with a saturated aq NH₄Cl solution. The aqueous portion was back-extracted with Et₂O. The combined organic portions were dried (Na₂SO₄), filtered and the volatiles were removed under reduced pressure to afford 14-5 as a colorless oil (500 mg, 96%). ¹H NMR (400 MHz, CDCl₃) δ ppm 3.85 (s, 3H), 4.30 (s, 2H), 6.95 (d, J=8.8 Hz, 2H), 7.28 (d, J=8.8 Hz, 2H).

A mixture of 14-5 (500 mg, 3.06 mmol), trimethyl({2-[4-(tetramethyl-1,3,2-dioxaborolan-2-yl)phenyl]ethynyl}) silane (120 mg, 0.399 mmol), CuSO₄ (7.0 mg, 0.041 mmol), 0.1M aq sodium ascorbate solution (416 uL, 0.041 mmol) and pyridine (504 uL, 6.24 mmol) in a 2:1 t-BuOH—H₂O mixture (3 mL) was stirred with heat at 60° C. for 18 h. The volatiles were removed under reduced pressure. The residue was partitioned between EtOAc and NH₄OH solution; the layers were separated and the aqueous phase was back-extracted with EtOAc. The combined organic portions were dried (Na₂SO₄), filtered and the volatiles were removed under reduced pressure to afford crude 14-6 (140 mg), which was used in the next step without further purification. ¹H NMR (400 MHz, METHANOL-d₄) δ ppm 1.96 (s, 12H), 3.82 (s, 3H), 5.59 (s, 2H), 6.97 (d, J=8.5 Hz, 2H), 7.37 (d, J=8.5 Hz, 2H), 7.71 (d, 1H), 7.78-7.84 (m, 3H), 8.32 (d, J=10.3 Hz, 1H).

A mixture of 14-3 (106 mg, 0.259 mmol), 14-6 (140 mg, 0.358 mmol), Pd(dppf)Cl₂ (28.4 mg, 0.038 mmol) and aq Na₂CO₃ (2M solution, 323 uL, 0.646 mmol) in DME (5 mL) was degassed and stirred with heat to 85° C. for 50 min. After cooling to rt, the mixture was diluted with water and extracted 3 times with EtOAc. The combined organic portions were dried (Na₂SO₄), filtered and the volatiles were removed under reduced pressure. Chromatography of the residue (cyclohexane-EtOAc, 100:0 to 0:100) afforded 14-7 as a white solid (43 mg, 28%). UPLC/MS(ES⁺), m/z: 594.20 [MH⁺].

Compound 14-7 was dissolved in TFA (5 mL), and the solution was heated to 65° C. After 48 h, the mixture was cooled to rt and diluted with EtOAc. The organic portion was washed with a 2M aq Na₂CO₃ solution, dried (Na₂SO₄), filtered and the volatiles were removed under reduced pressure. Chromatography of the residue (cyclohexane-EtOAc, 100:0 to 0:100) afforded 1405 as a light yellow solid (10 mg, 29%). UPLC/MS(ES⁺), m/z: 474.20 [M+H]⁺.

Example 15-1

Preparation of General Compound 1500A

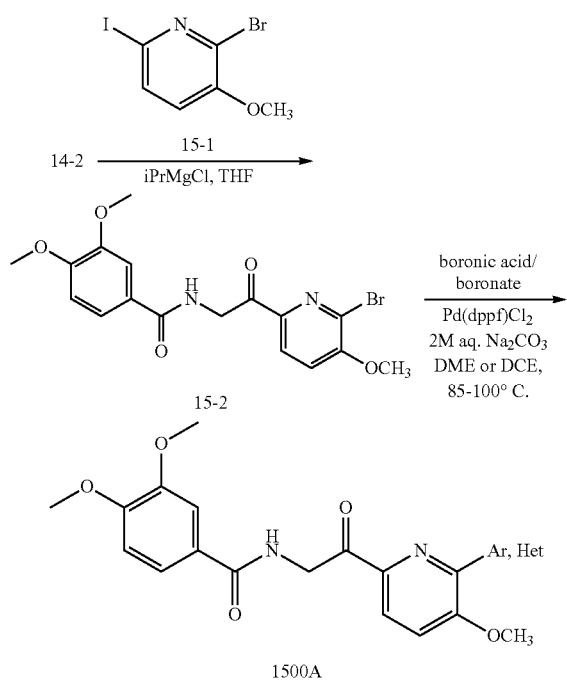

(Na₂SO₄), filtered and concentrated under reduced pressure. Chromatography of the residue afforded compound 1500A.

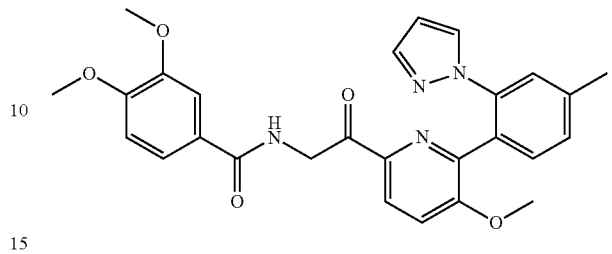

1501

Compound 1501 was obtained by reacting 15-2 with [4-methyl-2-(1H-pyrazol-1-yl)phenyl]boronic acid according to the procedure shown in Example 15-1, General Procedure A. Compound 1501 was obtained as a pale yellow solid (18%). UPLC/MS(ES⁺), m/z: 487.20 [M+H]⁺.

Example 15-2

Preparation of Compound 15-7

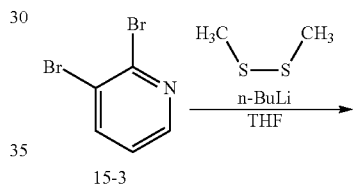

15-3

Isopropylmagnesium chloride (2M solution in THF, 22.0 mL, 44.0 mmol) was added dropwise to a solution of 15-1 (8.30 g, 13.2 mmol) and 14-2 (5.00 g, 8.80 mmol) in dry THF (60 mL). The reaction was stirred at rt for 30 mins. A 1M aq HCl solution was added and the mixture was extracted with EtOAc. The organic portion was dried (Na₂SO₄) filtered and evaporated under reduced pressure. Trituration of the residue with a 1:1 DCM-MeOH mixture 15-2 as an off white solid (3.80 g, 53%). ¹H NMR (400 MHz, CDCl₃) δ ppm 3.97 (s, 3H), 3.99 (s, 3H), 4.05 (s, 3H), 5.14 (d, J=4.5 Hz, 2H), 6.94 (d, J=8.3 Hz, 1H), 7.03 (br. s., 1H), 7.27 (d, J=8.5 Hz, 1H), 7.46 (dd, J=8.3, 2.0 Hz, 1H), 7.52 (d, J=2.0 Hz, 1H), 8.10 (d, J=8.3 Hz, 1H).

General Procedure A (1500A):

A mixture of 15-2 (0.390 mmol), boronic acid/ester (0.975 mmol), Pd(dppf)Cl₂ (0.019 mmol) and aq Na₂CO₃ (2M solution, 1.17 mmol) in DME (7 mL) was degassed and heated to 85° C. for 2 h (or until disappearing of the starting material). The volatiles were removed under reduced pressure. Chromatography of the residue afforded compound 1500A.

General Procedure B (1500A):

A mixture of N-(2-(6-bromo-5-methoxypyridin-2-yl)-2-oxoethyl)-3,4-dimethoxybenzamide (B-2, 0.245 mmol), KF (0.980 mmol), Pd(dppf)Cl₂ (0.025 mmol) and boronic acid/boronate (0.370 mmol) in dry DMF (1 mL) was heated to 85° C. When complete (TLC or UPLC monitoring), the mixture was cooled to rt, diluted with EtOAc and washed with water and brine. The organic portion was dried

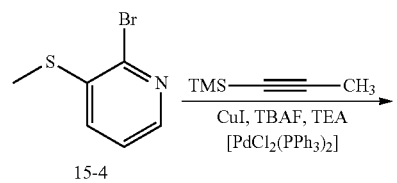

15-4

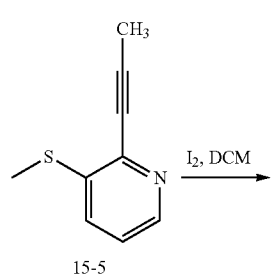

15-5

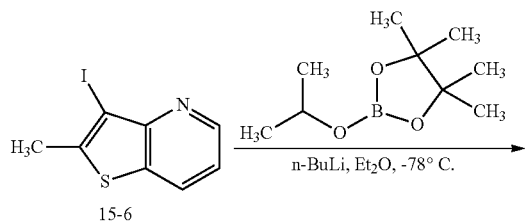

15-6

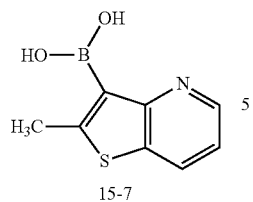

15-7 n-Butyllithium (1.6 M solution in hexane, 6.5 mL, 10.5 mmol) was added to a solution of 2,3-dibromopyridine (15-3, 2.50 g, 10.8 mmol) in dry THF (45 mL), which was pre-cooled to −78° C. After 1 h, dimethyl disulfide (2.25 mL, 21.5 mmol) was added and the mixture was stirred for an additional 1 h. The mixture was allowed to reach rt. Water was added and the aqueous portion was extracted twice with EtOAc. The combined organic portions were washed with water, dried ($Na_2SO_4$) filtered and evaporated. Chromatography of the residue (cyclohexane-EtOAc, 100:0 to 80:20) 15-4 as a brown oil (670 mg, 30%). $^1$H NMR ($CDCl_3$) δ: 2.45-2.57 (m, 3H), 7.24-7.30 (m, 1H), 7.41 (dd, J=7.9, 1.4 Hz, 1H), 8.15 (dd, J=4.5, 1.5 Hz, 1H).

To a mixture of 15-4 (1.2 g, 5.9 mmol), 1-(trimethylsilyl)propyne (662 mg, 5.90 mmol) and copper(I) iodide (55.0 mg, 0.290 mmol) in TEA (37.5 mL) was added tetrabutylammonium fluoride (1M solution in THF, 17.9 mL). The mixture was degassed for 30 mins. Bis(triphenylphosphine)palladium(II) dichloride (203 mg, 0.290 mmol) was added and the mixture was stirred at 40° C. under argon overnight. EtOAc was added and the organic portion was washed with water, dried ($Na_2SO_4$), filtered and concentrated under reduced pressure. Chromatography of the residue (cyclohexane-EtOAc, 100:0 to 80:20) afforded 15-5 as a yellow oil (200 mg, 20%). $^1$H NMR ($CDCl_3$) δ: 2.08-2.25 (m, 3H), 2.49 (s, 3H), 7.19 (dd, J=8.2, 4.6 Hz, 1H), 7.45 (dd, J=8.0, 1.0 Hz, 1H), 8.31 (d, J=3.8 Hz, 1H).

Iodine (464 mg, 1.83 mmol) dissolved in DCM (12.5 mL) was added dropwise to a solution of 15-5 (200 mg, 1.22 mmol) in DCM (12.5 mL). The mixture was stirred at rt for 1 h, diluted with DCM and washed with water. The organic portion were dried ($Na_2SO_4$) filtered and concentrated under reduced pressure. Chromatography of the residue (cyclohexane-EtOAc, 100:0 to 80:20) afforded 15-6 as a yellow solid (210 mg, 62%). $^1$H NMR ($CDCl_3$) δ: 2.70 (s, 3H), 7.25-7.28 (m, 1H), 8.06 (dd, J=8.0, 1.3 Hz, 1H), 8.76 (dd, J=4.5, 1.3 Hz, 1H).

n-Butyllithium (1.6M solution in hexane, 489 uL, 0.790 mmol) was added dropwise to a solution of 15-6 (210 mg, 0.760 mmol) in dry $Et_2O$ (4 mL), which had been pre-cooled to −78° C. The mixture was stirred at −78° C. for 1 h. 2-Isopropoxy-4,4,5,5-tetramethyl-1,3,2-dioxaborolane (162 uL, 0.790 mmol) was added and the mixture was left to stir at −78° C. overnight. The mixture was allowed to reach rt and water was added. The aqueous portion was extracted twice with EtOAc. The combined organic portions were dried ($Na_2SO_4$) filtered and evaporated. The residue was purified by reverse phase chromatography (water-$CH_3CN$, 100:0-0:100) to give 15-7 as a white solid (48 mg, 31%). UPLC/MS($ES^+$), m/z: 193.99 [M+H]$^+$.

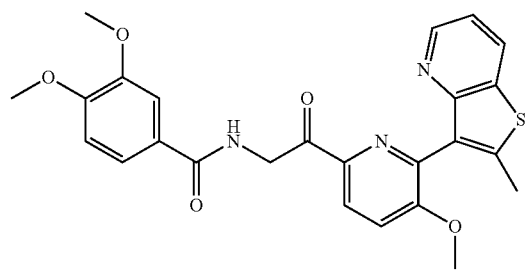

1502

Compound 1502 was obtained by reacting 15-2 with 15-7 according to the procedure shown in Example 15-1, General Procedure A. Compound 1502 was obtained as an off-white solid (50%). UPLC/MS($ES^+$), m/z: 478.15 [M+H]$^+$.

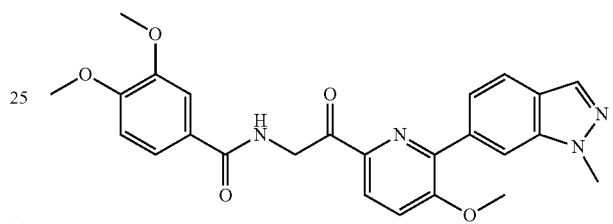

1503

Compound 1503 was obtained by reacting 15-2 with 1-methyl-1H-indazole-6-boronic acid according to the procedure shown in Example 15-1, General Procedure A. Compound 1503 was obtained as a pale yellow solid (53%). UPLC/MS($ES^+$), m/z: 461.18 [M+H]$^+$.

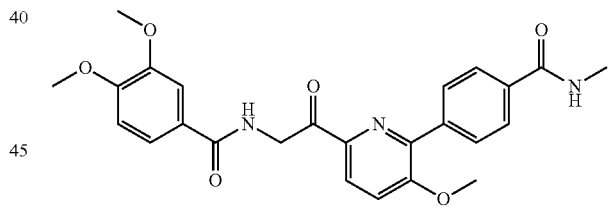

1504

Compound 1504 was obtained by reacting 15-2 with [4-(methylcarbamoyl)phenyl]boronic acid according to the procedure shown in Example 15-1, General Procedure A. Compound 1504 was obtained as a pale yellow solid (7%). UPLC/MS($ES^+$), m/z: 464.17 [M+H]$^+$.

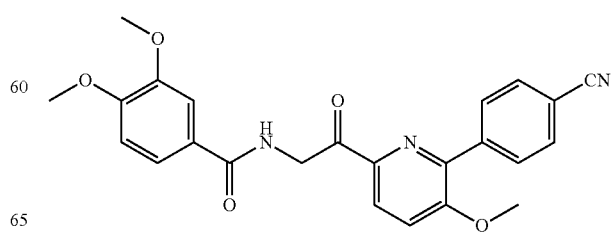

1505

Compound 1505 was obtained by reacting 15-2 with [(4-cyanophenyl)boronic acid according to the procedure shown in Example 15-1, General Procedure A. Compound 1505 was obtained as an off-white solid (48%). UPLC/MS (ES+), m/z: 432.15 [M+H]+.

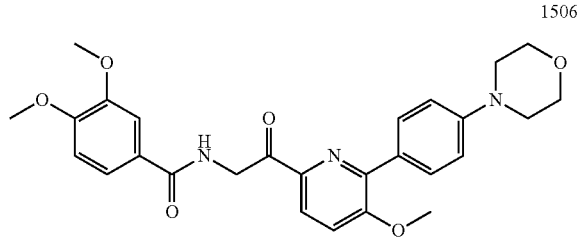 [SMILES: COc1ccc(C(=O)NCC(=O)c2ccc(OC)c(-c3ccc(N4CCOCC4)cc3)n2)cc1OC]

Compound 1506 was obtained by reacting 15-2 with 4-morpholine-phenyl-boronic acid according to the procedure shown in Example 15-1, General Procedure A. Compound 1506 was obtained as a light yellow solid (83%). UPLC/MS(ES+), m/z: 492.19 [M+H]+.

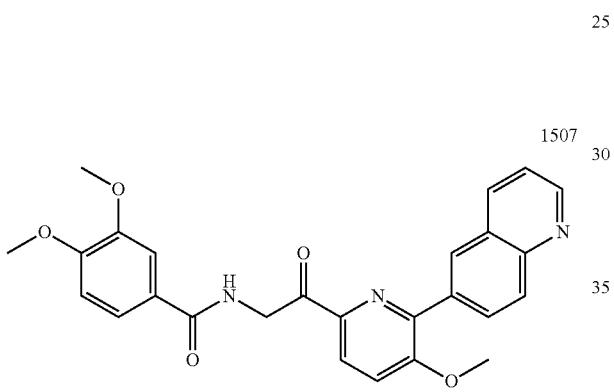

Compound 1507 was obtained by reacting 15-2 with (quinolin-6-yl)boronic acid according to the procedure shown in Example 15-1, General Procedure A. Compound 1507 was obtained as a yellow solid (62%). UPLC/MS (ES+), m/z: 458.20 [M+H]+.

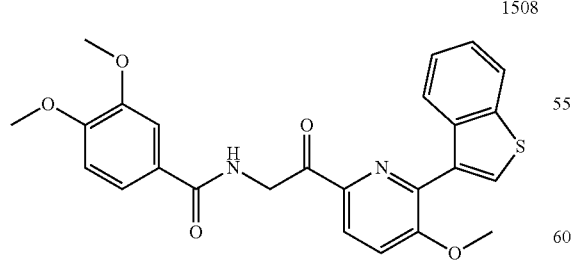

Compound 1508 was obtained by reacting 15-2 with (1-benzothiophen-3-yl)boronic acid according to the procedure shown in Example 15-1, General Procedure A. Compound 1508 was obtained as an off-white solid (59%). UPLC/MS(ES+), m/z: 463.13 [M+H]+.

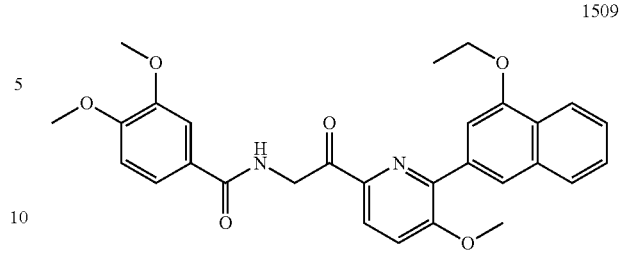

Compound 1509 was obtained by reacting 15-2 with (3-ethoxynaphthalen-1-yl)boronic acid according to the procedure shown in Example 15-1, General Procedure A. Compound 1509 was obtained as an off-white solid (31%). UPLC/MS(ES+), m/z: 501.20 [M+H]+.

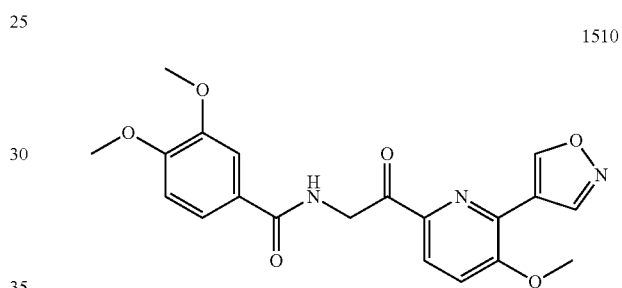

Compound 1510 was obtained by reacting 15-2 with (1,2-oxazol-4-yl)boronic acid according to the procedure shown in Example 15-1, General Procedure A. Compound 1510 was obtained as a white solid (43%). UPLC/MS(ES+), m/z: 398.09 [M+H]+.

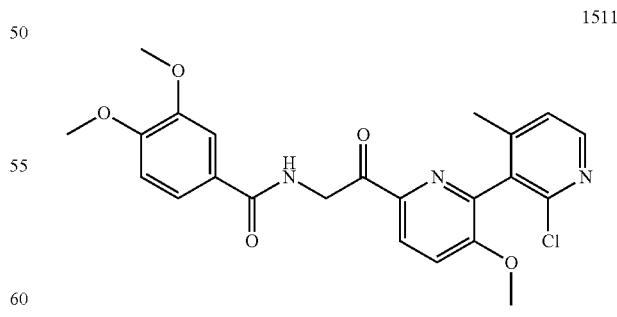

Compound 1511 was obtained by reacting 15-2 with (2-chloro-4-methylpyridin-3-yl)boronic acid according to the procedure shown in Example 15-1, General Procedure A. Compound 1511 was obtained as a pale yellow solid (19%). UPLC/MS(ES+), m/z: 456.14 [M+H]+.

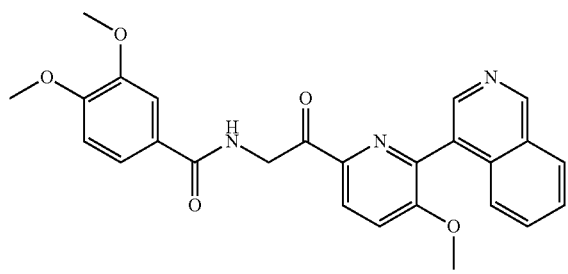

1512

Compound 1512 was obtained by reacting 15-2 with (isoquinolin-4-yl)boronic acid according to the procedure shown in Example 15-1, General Procedure A. Compound 1512 was obtained as an off-white solid (38%). UPLC/MS (ES$^+$), m/z: 458.17 [M+H]$^+$.

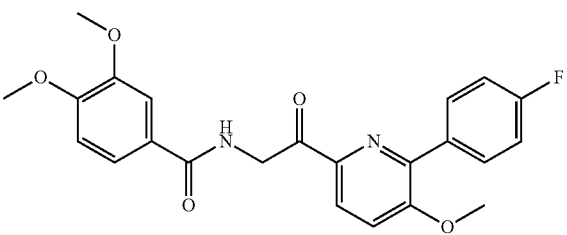

1515

Compound 1515 was obtained by reacting 15-2 with (4-fluorophenyl)boronic acid according to the procedure shown in Example 15-1, General Procedure A. Compound 1515 was obtained as a pale yellow solid (79%). UPLC/MS (ES$^+$), m/z: 425.16 [M+H]$^+$.

1513

Compound 1513 was obtained by reacting 15-2 with (naphthalen-1-yl)boronic acid according to the procedure shown in Example 15-1, General Procedure A. Compound 1513 was obtained as a white solid (38%). UPLC/MS(ES$^+$), m/z: 457.17 [M+H]$^+$.

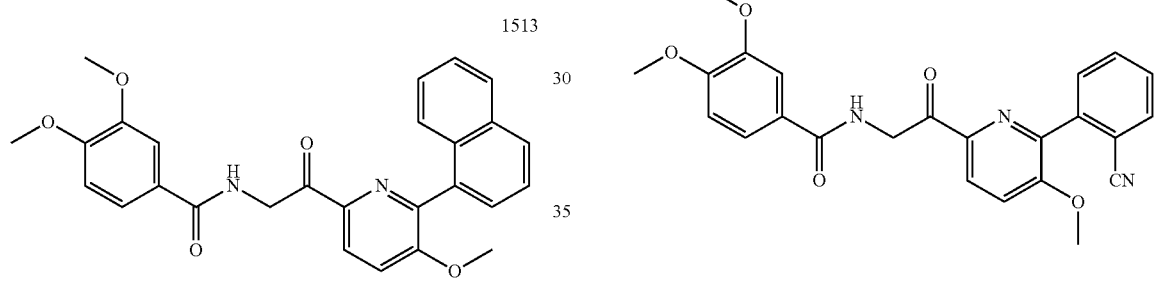

1516

Compound 1516 was obtained by reacting 15-2 with (2-cyanophenyl)boronic acid according to the procedure shown in Example 15-1, General Procedure A. Compound 1516 was obtained as a white solid (36%). UPLC/MS(ES$^+$), m/z: 432.16 [M+H]$^+$.

1514

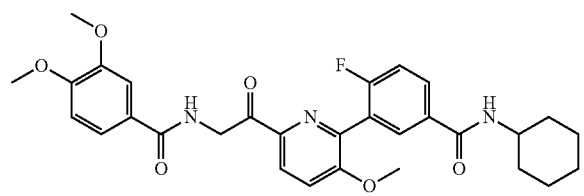

Compound 1514 was obtained by reacting 15-2 with [5-(cyclohexylcarbamoyl)-2-fluorophenyl]boronic acid according to the procedure shown in Example 15-1, General Procedure A. Compound 1514 was obtained as a pale yellow solid (45%). UPLC/MS(ES$^+$), m/z: 550.21 [M+H]$^+$.

1517

Compound 1517 was obtained by reacting 15-2 with (naphthalen-2-yl)boronic acid according to the procedure shown in Example 15-1, General Procedure A. Compound 1517 was obtained as a white solid (53%). UPLC/MS(ES$^+$), m/z: 457.16 [M+H]$^+$.

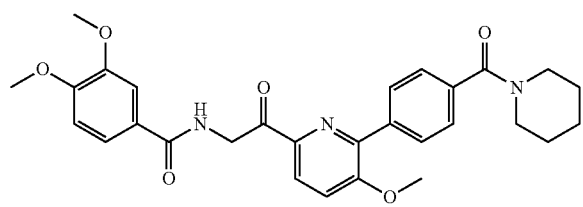

1518

Compound 1518 was obtained by reacting 15-2 with {4-[(piperidin-1-yl)carbonyl]phenyl}boronic acid according to the procedure shown in Example 15-1, General Procedure A. Compound 1518 was obtained as an off-white solid (79%). UPLC/MS(ES$^+$), m/z: 518.20 [M+H]$^+$.

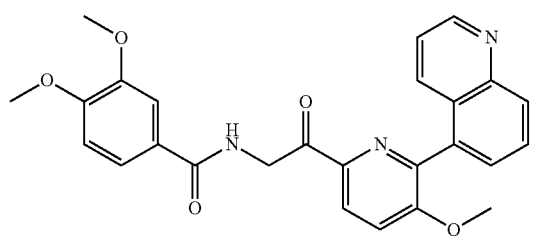

1519

Compound 1519 was obtained by reacting 15-2 with (quinolin-5-yl)boronic acid according to the procedure shown in Example 15-1, General Procedure A. Compound 1519 was obtained as an off-white solid (53%). UPLC/MS (ES$^+$), m/z: 458.20 [M+H]$^+$.

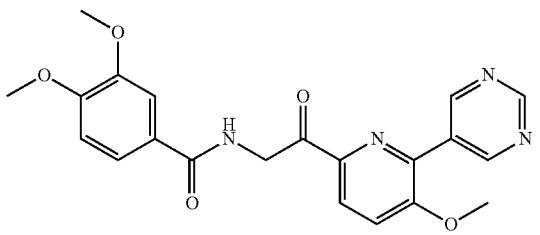

1520

Compound 1520 was obtained by reacting 15-2 with pyrimidine-5-boronic acid according to the procedure shown in Example 15-1, General Procedure A. Compound 1520 was obtained as a yellow solid (45%). UPLC/MS (ES$^+$), m/z: 409.16 [M+H]$^+$.

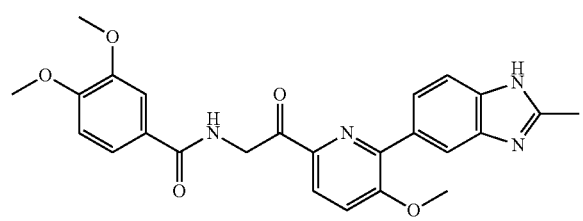

1521

Compound 1521 was obtained by reacting 15-2 with 2-methyl-6-(tetramethyl-1,3,2-dioxaborolan-2-yl)-1H-1,3-benzodiazole according to the procedure shown in Example 15-1, General Procedure A. Compound 1521 was obtained as a yellow solid (15%). UPLC/MS(ES$^+$), m/z: 461.17 [M+H]$^+$.

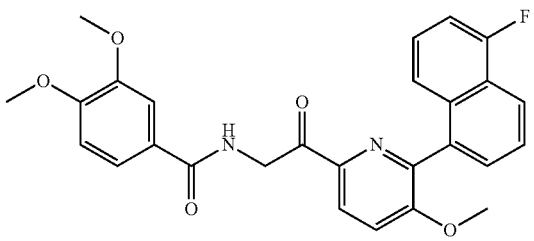

1522

Compound 1522 was obtained by reacting 15-2 with 2-(5-fluoronaphthalen-1-yl)-5,5-dimethyl-1,3,2-dioxaborinane according to the procedure shown in Example 15-1, General Procedure A. Compound 1522 was obtained as a light pink solid (80%). UPLC/MS(ES$^+$), m/z: 475.15 [M+H]$^+$.

2-(5-fluoronaphthalen-1-yl)-5,5-dimethyl-1,3,2-dioxaborinane: A mixture of 1-bromo-5-fluoronaphthalene (350 mg, 1.55 mmol), 2-(5,5-dimethyl-1,3,2-dioxaborinan-2-yl)-5,5-dimethyl-1,3,2-dioxaborinane (700 mg, 3.10 mmol), Pd(dppf)Cl$_2$ (56.0 mg, 0.077 mmol) and KOAc (608 mg, 6.20 mmol) in DMF (4.5 mL) was degassed and heated to 85° C. for 50 mins. After cooling to rt, water was added and the mixture was extracted with DCM. The organic portion was dried (Na$_2$SO$_4$), filtered and concentrated under reduced pressure. Chromatography of the residue (cyclohexane-EtOAc, 100:0 to 80:20) afforded the title compound as a white solid (320 mg, 80%). $^1$H NMR (400 MHz, CDCl$_3$) δ ppm 1.12 (s, 6H), 3.91 (s, 4H), 7.15 (dd, J=10.4, 7.6 Hz, 1H), 7.44 (td, J=8.1, 6.1 Hz, 1H), 7.55 (dd, J=8.2, 7.1 Hz, 1H), 8.12 (d, J=6.5 Hz, 1H), 8.23 (d, J=8.3 Hz, 1H), 8.58 (d, J=8.5 Hz, 1H).

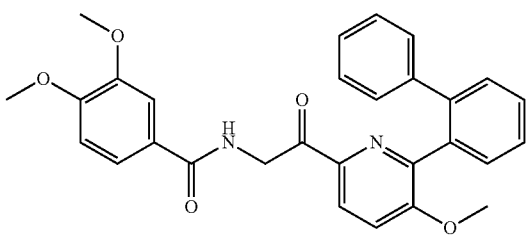

1523

Compound 1523 was obtained by reacting 15-2 with 2-biphenylboronic acid according to the procedure shown in Example 15-1, General Procedure A. Compound 1523 was obtained as an off-white solid (77%). UPLC/MS(ES$^+$), m/z: 483.19 [M+H]$^+$.

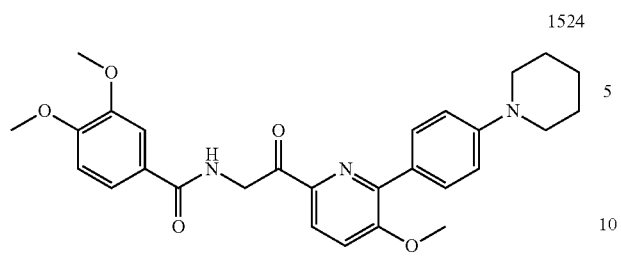

1524

Compound 1524 was obtained by reacting 15-2 with [4-(piperidin-1-yl)phenyl]boronic acid hydrochloride according to the procedure shown in Example 15-1, General Procedure A. Compound 1524 was obtained as a yellow solid (84%). UPLC/MS(ES$^+$), m/z: 490.22 [M+H]$^+$.

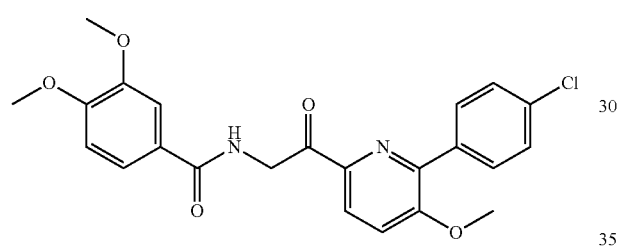

1525

Compound 1525 was obtained by reacting 15-2 with (4-chlorophenyl)boronic acid according to the procedure shown in Example 15-1, General Procedure A. Compound 1525 was obtained as an off-white solid (83%). UPLC/MS (ES$^+$), m/z: 441.13 [M+H]$^+$.

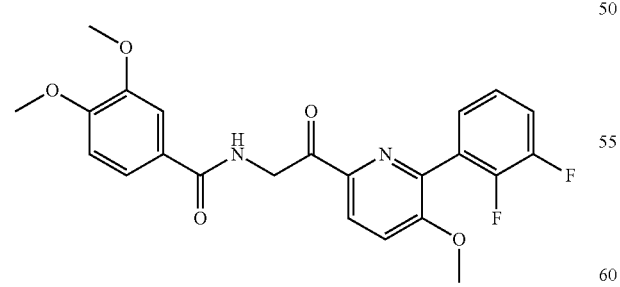

1526

Compound 1526 was obtained by reacting 15-2 with (2,3-difluorophenyl)boronic acid according to the procedure shown in Example 15-1, General Procedure A. Compound 1526 was obtained as an off-white solid (69%). UPLC/MS (ES$^+$), m/z: 443.13 [M+H]$^+$.

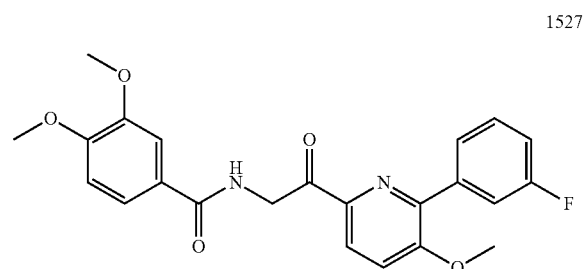

1527

Compound 1527 was obtained by reacting 15-2 with (3-fluorophenyl)boronic acid according to the procedure shown in Example 15-1, General Procedure A. Compound 1527 was obtained as a white solid (72%). UPLC/MS(ES$^+$), m/z: 425.17 [M+H]$^+$.

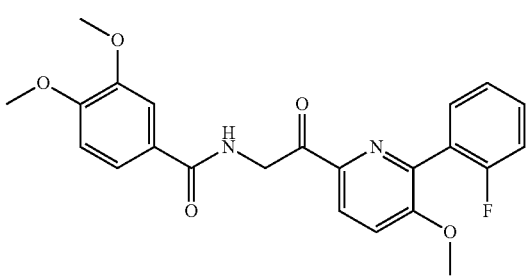

1528

Compound 1528 was obtained by reacting 15-2 with (2-fluorophenyl)boronic acid according to the procedure shown in Example 15-1, General Procedure A. Compound 1528 was obtained as a white solid (56%). UPLC/MS(ES$^+$), m/z: 425.15 [M+H]$^+$.

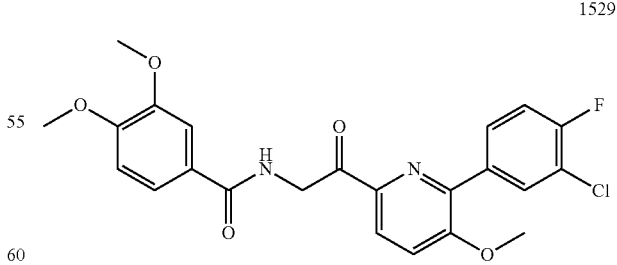

1529

Compound 1529 was obtained by reacting 15-2 with (3-chloro-4-fluorophenyl)boronic acid according to the procedure shown in Example 15-1, General Procedure A. Compound 1529 was obtained as a light yellow solid (87%). UPLC/MS(ES$^+$), m/z: 459.11 [M+H]$^+$.

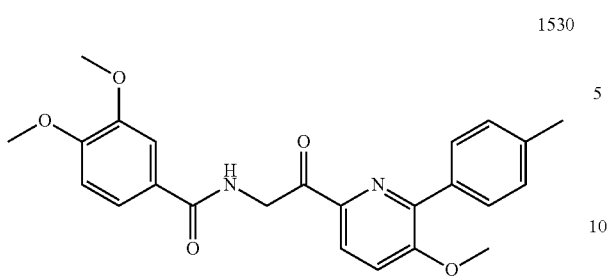

1530

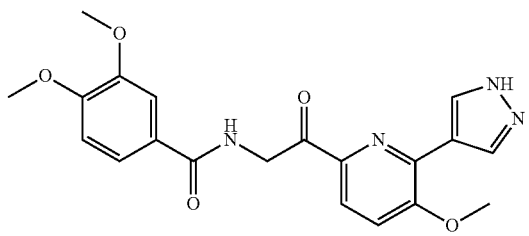

1533

Compound 1530 was obtained by reacting 15-2 with (4-methylphenyl)boronic acid according to the procedure shown in Example 15-1, General Procedure A. Compound 1530 was obtained as a light orange solid (72%). UPLC/MS(ES+), m/z: 421.17 [M+H]+.

Compound 1533 was obtained by reacting 15-2 with (1H-pyrazol-4-yl)boronic acid according to the procedure shown in Example 15-1, General Procedure A. Compound 1533 was obtained as a light yellow solid (55%). UPLC/MS(ES+), m/z: 397.15 [M+H]+.

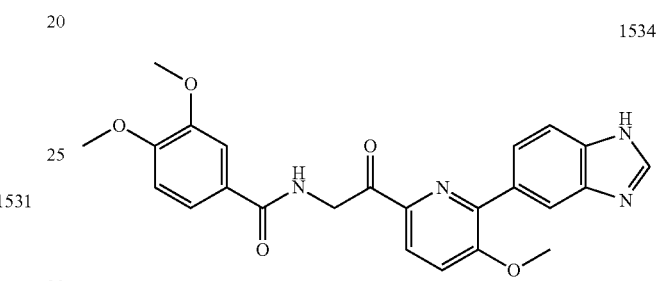

1534

Compound 1534 was obtained by reacting 15-2 with (1H-1,3-benzodiazol-5-yl)boronic acid according to the procedure shown in Example 15-1, General Procedure A. Compound 1534 was obtained as a light yellow solid (34%). UPLC/MS(ES+), m/z: 447.20 [M+H]+.

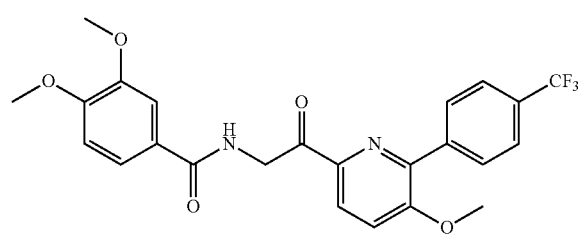

1531

Compound 1531 was obtained by reacting 15-2 with [4-(trifluoromethyl)phenyl]boronic acid according to the procedure shown in Example 15-1, General Procedure A. Compound 1531 was obtained as a white solid (79%).

UPLC/MS(ES+), m/z: 475.12 [M+H]+.

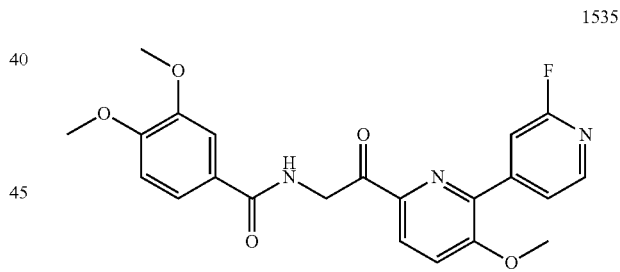

1535

Compound 1535 (75%). was obtained by reacting 15-2 with (2-fluoropyridin-4-yl)boronic acid according to the procedure shown in Example 15-1, General Procedure A. UPLC/MS(ES+), m/z: 426.16 [M+H]+.

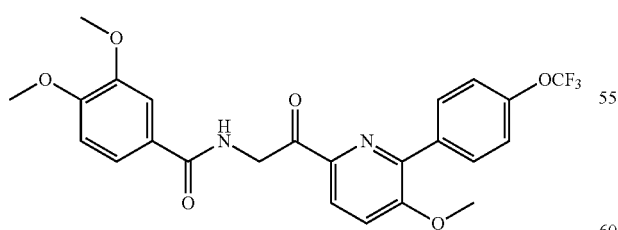

1532

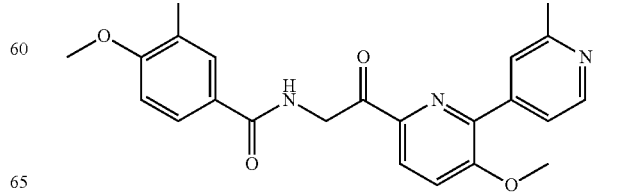

1536

Compound 1532 was obtained by reacting 15-2 with [4-(trifluoromethoxy)phenyl]boronic acid according to the procedure shown in Example 15-1, General Procedure A. Compound 1532 was obtained as a white solid (72%).

UPLC/MS(ES+), m/z: 491.13 [M+H]+.

Compound 1536 (61%) was obtained by reacting 15-2 with (2-chloropyridin-4-yl)boronic acid according to the procedure shown in Example 15-1, General Procedure A. UPLC/MS(ES+), m/z: 442.10 [M+H]+.

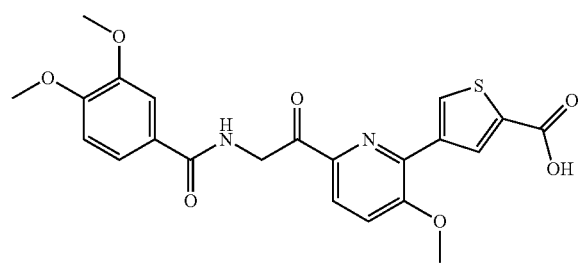

1537

Compound 1537 was obtained by reacting 15-2 with 4-(dihydroxyboranyl)thiophene-2-carboxylic acid according to the procedure shown in Example 15-1, General Procedure B. Compound 1537 was obtained as an off-white solid (7%). UPLC/MS(ES+), m/z: 457.10 [M+H]+.

1538

Compound 1538 was obtained by reacting 15-2 with 2-methyl-2H-indazol-6-yl-6-boronic acid according to the procedure shown in Example 15-1, General Procedure B. Compound 1538 was obtained as an off-white solid (21%). UPLC/MS(ES+), m/z: 461.20 [M+H]+.

1539

Compound 1539 was obtained by reacting 15-2 with 5-(4,4,5,5-tetramethyl-1,3,2-dioxaborolan-2-yl)benzo[d]thiazole according to the procedure shown in Example 15-1, General Procedure B. Compound 1539 was obtained as an off-white solid (37%). UPLC/MS(ES+), m/z: 464.10 [M+H]+.

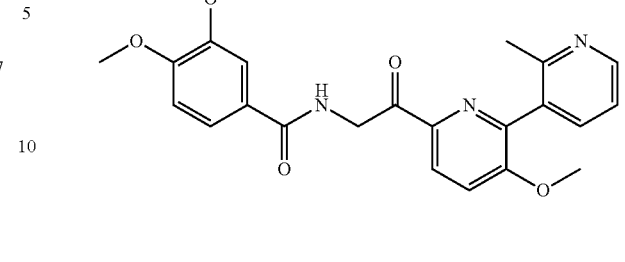

1540

Compound 1540 was obtained by reacting 15-2 with 2-methylpyridin-3-yl-3-boronic acid according to the procedure shown in Example 15-1, General Procedure B. Compound 1540 was obtained as a pale yellow solid (46%). UPLC/MS(ES+), m/z: 422.20 [M+H]+.

Example 15-3

Preparation of Compound 15-8

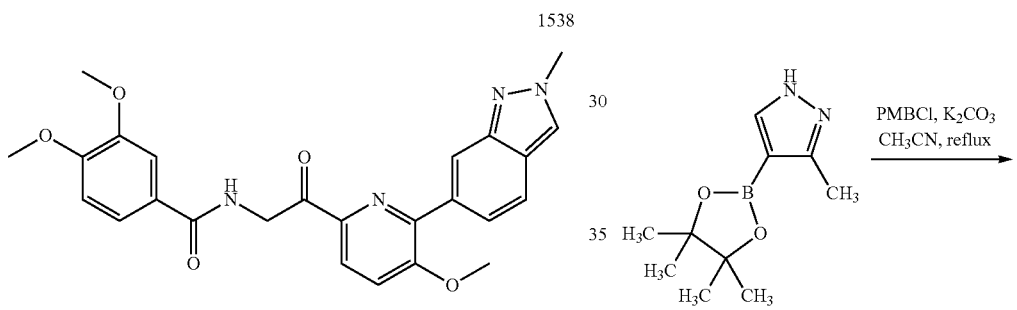

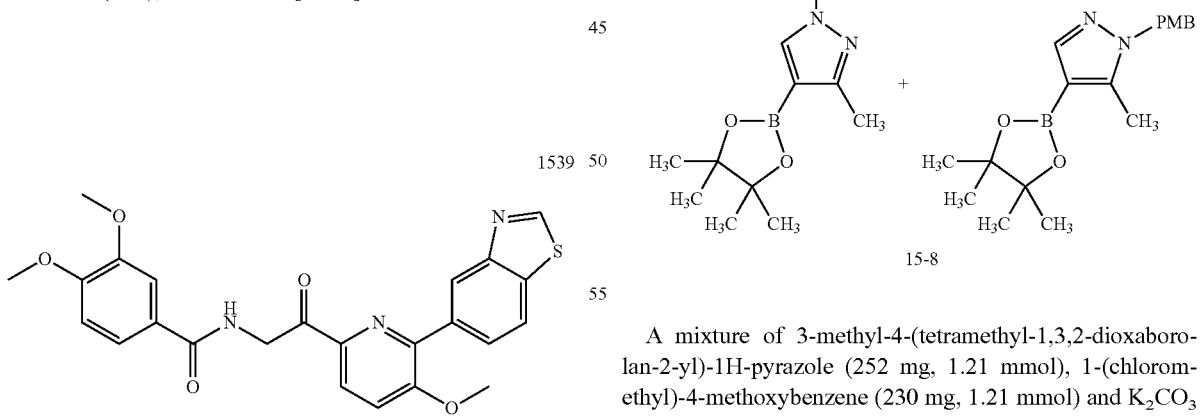

15-8

A mixture of 3-methyl-4-(tetramethyl-1,3,2-dioxaborolan-2-yl)-1H-pyrazole (252 mg, 1.21 mmol), 1-(chloromethyl)-4-methoxybenzene (230 mg, 1.21 mmol) and $K_2CO_3$ (167 mg, 1.21 mmol) in $CH_3CN$ (3 mL) was stirred with heat to reflux for 5 h. After cooling to rt, the mixture was filtered and the organic portion was concentrated under reduced pressure. Chromatography of the residue (cyclohexane-EtOAc, 100:0 to 80:20) 15-8 as a mixture of regioisomers (320 mg, 80%). UPLC/MS(ES+), m/z: 329.17 [M+H]+.

1541

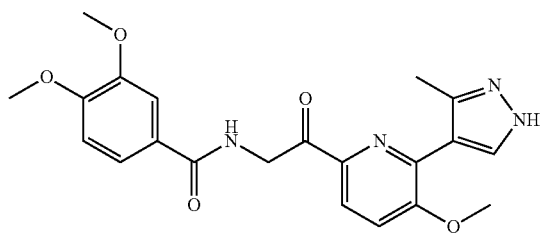

A mixture of 15-8 (250 mg, 0.761 mmol), 15-2 (124 mg, 0.300 mmol), Pd(Ph₃)₄ (51.0 mg, 0.150 mmol) and aq NaHCO₃ (2M solution, 450 uL, 0.900 mmol) in DME (2.5 mL) was heated to 120° C. under mw irradiation. After 30 mins, the mixture was diluted with EtOAc and washed with brine. The organic portion was dried (Na$_2$SO$_4$), filtered and the volatiles were removed under reduced pressure. The residue was dissolved in TFA and the solution was heated to 65° C. for 2 h. After cooling to rt, the mixture was diluted with EtOAc and poured in a 2M aq NaOH solution. The phases were separated and the organic portion was dried (Na$_2$SO$_4$), filtered and concentrated under reduced pressure. Chromatography of the residue (EtOAc-MeOH, 100:0 to 95:5) afforded 1541 as a light yellow solid (35 mg, 28% over two steps). UPLC/MS(ES$^+$), m/z: 411.21 [M+H]$^+$.

Example 16-1

Preparation of General Compound 1600A

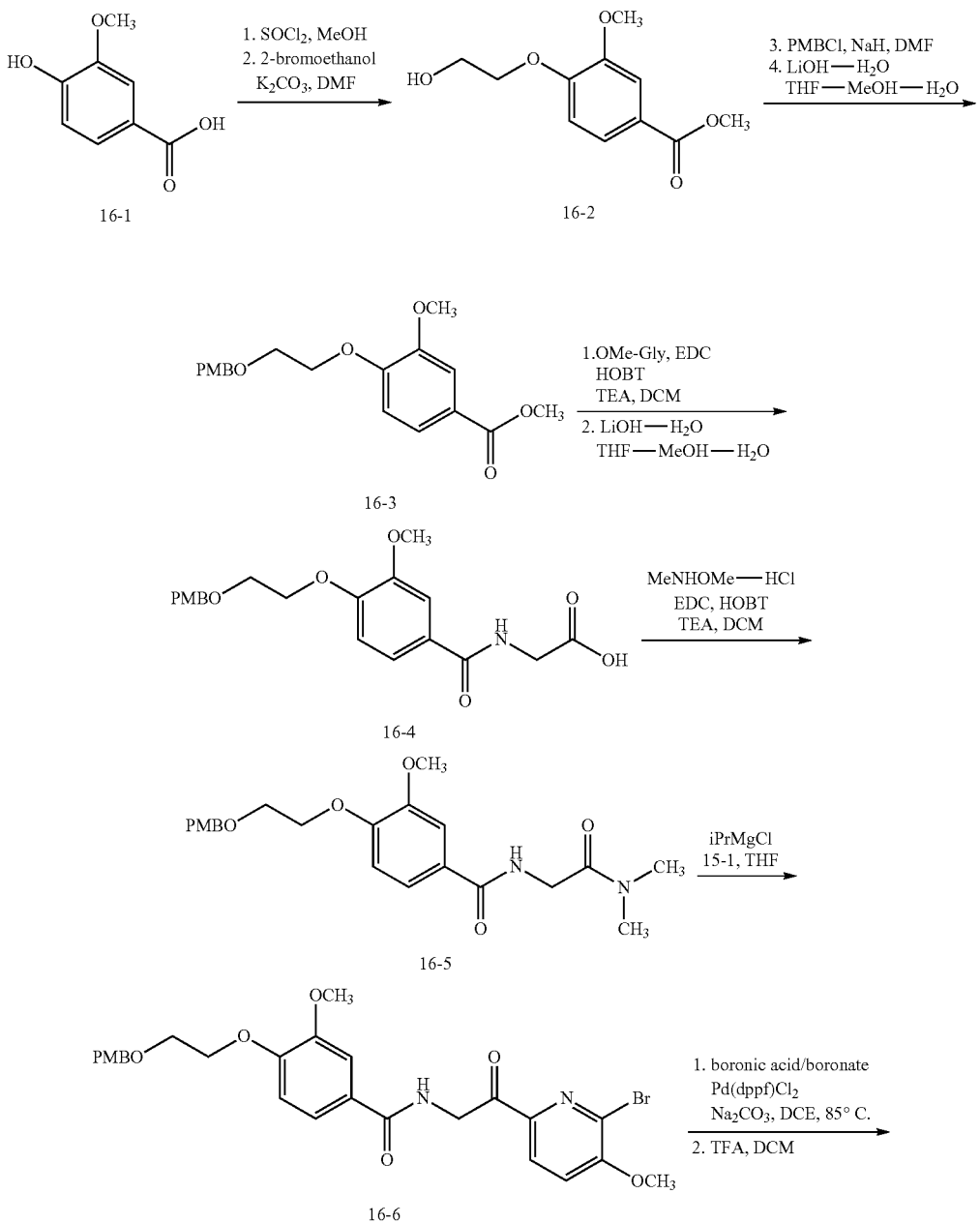

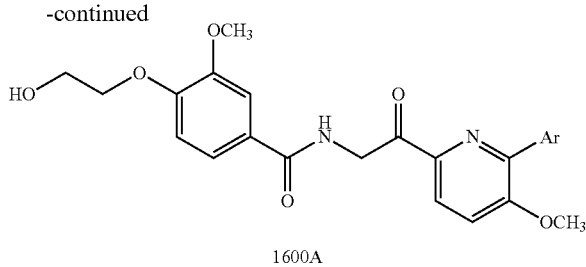

1600A

Thionyl chloride (64.8 mL, 892 mmol) was added to a suspension of vanillic acid (15.0 g, 89.2 mmol) in MeOH (150 mL), which had been pre-cooled to 0° C. The mixture was allowed to gradually reach rt and stirred for 18 h. The volatiles were removed under reduced pressure. The residue was dissolved in EtOAc and washed with saturated aq NaHCO$_3$ solution and brine. The organic portion was dried (Na$_2$SO$_4$), filtered and concentrated under reduced pressure to afford the crude methylester (18 g), which was used in the next step without further purification. The methylester was dissolved in DMF (80 mL). K$_2$CO$_3$ (36.9 g, 267 mmol) and 2-bromoethanol (13.4 g, 107 mmol) were added. The mixture was heated to 90° C. for 2 h, cooled down to room temp and stirred for a further 18 h. A 1M aq HCl solution was added and the aqueous portion was extracted twice with EtOAc. The combined organic portions were dried (Na$_2$SO$_4$), filtered and concentrated under reduced pressure. Chromatography of the residue (cyclohexane-EtOAc, 100:0 to 0:100) afforded 16-2 as a white solid (12.0 g, 55% over two steps). UPLC/MS(ES$^+$), m/z: 227.16 [M+H]$^+$.

Sodium hydride (2.54 g, 63.6 mmol) was added to a solution of 16-2 (12.0 g, 53.0 mmol) in DMF (60 mL), which had been pre-cooled to 0° C. After 10 mins, 1-(chloromethyl)-4-methoxybenzene (10.8 mL, 79.5 mmol) was added and the mixture was stirred at rt for 1 h. The mixture was poured into a saturated aq NH$_4$Cl solution; and the aqueous portion was extracted twice with EtOAc. The combined organic portions were dried (Na$_2$SO$_4$), filtered and concentrated under reduced pressure to afford the crude PMB-ether, which was used in the next step. The PMB-ether was dissolved in a 2:1:1 THF-MeOH—H$_2$O mixture (250 mL) and treated with LiOH*H$_2$O (6.68 g, 159 mmol). After 18 h of stirring at rt, the organic solvents were removed under reduced pressure. The supernatant aqueous portion was acidified with 1M aq HCl solution A precipitate formed, and the white solid was collected, washed with Et$_2$O and dried to afford 16-3 (14.9 g, 84%). UPLC/MS(ES$^-$), m/z: 331.22 [M+H]$^+$.

A mixture of 16-3 (12.0 g, 36.1 mmol), EDC (9.69 g, 50.5 mmol), HOBT (8.78 g, 65.0 mmol), glycine methyl ester hydrochloride (6.80 g, 54.1 mmol) and TEA (14.1 mL, 101 mmol) in DCM (250 mL) was stirred at rt for 3 h. A 1M aq HCl solution was added; and the precipitate was filtered off. The phases were separated and the organic portion was washed with 1M aq HCl solution, dried (Na$_2$SO$_4$) and filtered. The volatiles were removed under reduced pressure to afford the crude amide (16.0 g), which was used in the next step. The amide was dissolved in a 2:1:1 THF-MeOH—H$_2$O solution (160 mL) and treated with LiOH*H$_2$O (6.06 g, 144 mmol). After 18 h of stirring at rt, the organic solvents were removed under reduced pressure. The aqueous portion was acidified with 1M aq HCl solution; and formation of a white precipitate was observed. The white solid was collected, washed with water and Et$_2$O and dried to afford 16-4 (13.1 g, 93% over two steps). UPLC/MS(ES$^+$), m/z: 390.15 [M+H]$^+$.

A mixture of 16-4 (13.1 g, 33.8 mmol), EDC (9.06 g, 42.3 mmol), HOBT (8.21 g, 60.8 mmol), N,O-dimethylhydroxylamine hydrochloride (4.94 g, 50.6 mmol) and TEA (13.1 mL, 94.5 mmol) in DCM (250 mL) was stirred at rt for 2 h. A 1M aq HCl solution was added; and the layers were separated. The organic portion was dried (Na$_2$SO$_4$), filtered and concentrated under reduced pressure. Chromatography of the residue (cyclohexane-EtOAc) afforded the 16-5 as a white solid (25.3 g, 94%). UPLC/MS(ES$^+$), m/z: 433.19 [M+H]$^+$.

i-PrMgCl (2M solution in THF, 6.94 mL, 13.9 mmol) was added to a solution of 16-5 (3.00 g, 6.94 mmol) and 15-1 (3.26 g, 10.4 mmol) in THF (35 mL). The mixture was stirred at rt for 30 mins. The reaction was quenched with a saturated aq NH$_4$Cl solution and extracted with EtOAc. The organic portion was dried (Na$_2$SO$_4$), filtered and the volatiles were removed under reduced pressure. Chromatography of the residue (DCM-MeOH, 99:1) afforded 16-6 as a light yellow solid (2.26 g, 58%). UPLC/MS(ES$^+$), m/z: 559.09 [M+H]$^+$.

A mixture of 16-6 (0.390 mmol), boronic acid/ester (0.975 mmol), Pd(dppf)Cl$_2$ (0.019 mmol) and aq Na$_2$CO$_3$ (2M solution, 1.17 mmol) in DME (7 mL) was degassed and heated to 85° C. for 2 h (or until disappearing of the starting material). The volatiles were removed under reduced pressure. Chromatography of the residue afforded the title compound. This compound was dissolved in a 10:1 DCM-TFA mixture and the solution was stirred at rt until disappearing of the starting material. A 2M aq NaOH solution was added (final pH 9) and the layers were separated. The organic portion was dried (Na$_2$SO$_4$), filtered and concentrated under reduced pressure. Chromatography of the residue afforded Compound 1600A.

Example 16-2

Preparation of 1,3,2-dioxaborinanes

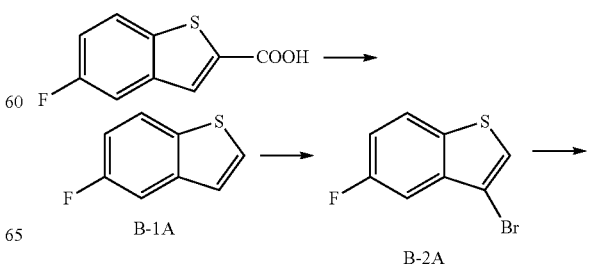

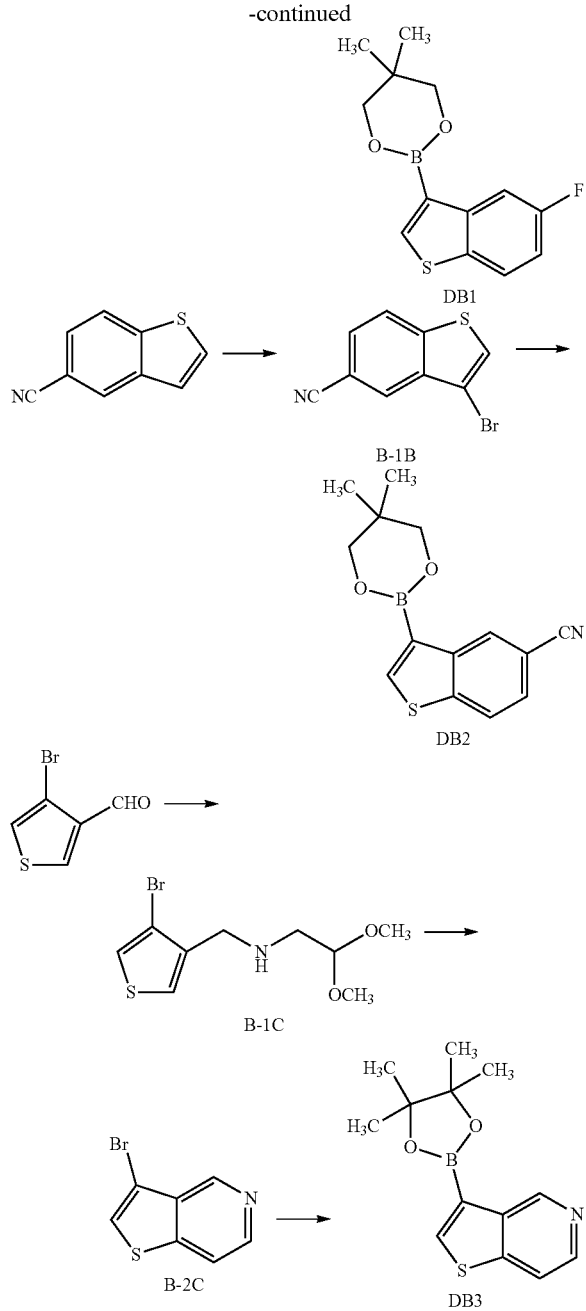

A mixture of 5-fluoro-1-benzothiophene-2-carboxylic acid (500 mg, 2.54 mmol) and powdered copper (110 mg, 3.81 mmol) in quinoline (2.3 mL) was stirred with heat at 150° C. for 20 h. After cooling to rt, the reaction was partitioned between EtOAc and 2N aq HCl solution. The phases were separated, and the organic portion was washed with 2N aq HCl, dried (Na$_2$SO$_4$), filtered and concentrated under reduced pressure. The residue, B-1A (340 mg) was directly progressed to the next step.

A mixture B-1A (340 mg) and NBS (238 mg, 1.34 mmol) in a 25:1 DCM-DMF solution was stirred at rt for 16 h. The mixture was washed with 10% aq Na$_2$S$_2$O$_3$ sol, 1M aq HCl and brine. The mixture was then dried (Na$_2$SO$_4$), filtered and concentrated under reduced pressure. The residue B-2A (284 mg) was directly progressed to the next step.

A mixture of B-2A (284 mg), 2-(5,5-dimethyl-1,3,2-dioxaborinan-2-yl)-5,5-dimethyl-1,3,2-dioxaborinane (505 mg, 2.24 mmol), KOAc (329 mg, 3.35 mmol) and Pd(dppf)Cl$_2$ (41 mg, 0.056 mmol) in DMF (2 mL) was stirred with heat at 90° C. for 1.5 h. After cooling down to rt, the mixture was diluted with water and extracted with DCM. The organic portion was dried (Na$_2$SO$_4$), filtered and concentrated under reduced pressure. Chromatography of the residue (cyclohexane-EtOAc, 100:0 to 80:20) afforded DB1 as a light yellow solid (150 mg, 22% over three steps). $^1$H NMR (400 MHz, DMSO-d$_6$) δ ppm 0.99 (s, 6H), 3.82 (s, 4H), 7.24 (td, J=8.8, 2.6 Hz, 1H), 7.96 (dd, J=10.5, 2.5 Hz, 1H), 8.05 (dd, J=8.8, 5.3 Hz, 1H), 8.26 (s, 1H).

A mixture 1-benzothiophene-5-carbonitrile (200 mg, 1.25 mmol), NBS (268 mg, 1.50 mmol) in a 25:1 DCM-DMF mixture (5.2 mL) was stirred at rt for 24 h. The mixture was washed with 10% aq Na$_2$S$_2$O$_3$ solution, 1M aq HCl sol and brine. The organic portion was dried (Na$_2$SO$_4$), filtered and concentrated under reduced pressure. The crude B-1B (300 mg) was progressed to the next step without further purification.

A mixture of B-1B (120 mg), 2-(5,5-dimethyl-1,3,2-dioxaborinan-2-yl)-5,5-dimethyl-1,3,2-dioxaborinane (170 mg, 0.752 mmol), KOAc (147 mg, 1.20 mmol) and Pd(dppf)Cl$_2$ (36.5 mg, 0.050 mmol) in DMF (2 mL) was deoxygenated and heated to 90° C. After 3.5 h the mixture was diluted with water; and the aqueous portion was extracted with DCM. The organic portion was dried (Na$_2$SO$_4$), filtered and concentrated under reduced pressure. Chromatography of the residue (cyclohexane-EtOAc, 100:0 to 80:20) afforded DB2.

4-bromothiophene-3-carbaldehyde (500 mg, 2.60 mmol) was dissolved in EtOH (6 mL) and treated with 2,2-dimethoxyethan-1-amine (275 mg, 2.60 mmol) and 4-methylbenzene-1-sulfonic acid monohydrate (24.7 mg, 0.130 mmol). The mixture was heated to reflux. After 4 h, the mixture was cooled to rt and NaBH$_4$ (95.0 mg, 2.60 mmol) was added portionwise. The mixture was stirred rt for 15 min, and then heated to reflux. The volatiles were removed under reduced pressure. The residue was dissolved in EtOAc, washed with saturated aq. NaHCO$_3$, water and brine. The organic portion was dried (Na$_2$SO$_4$), filtered and concentrated under reduced pressure. The crude B-1C was progressed to the next step without any further purification. UPLC/MS(ES$^+$), m/z. found 280.05 [MH$^+$], C$_9$H$_{14}$BrNO$_2$S requires 278.99. t$_R$: 0.36 min.

4-Methylbenzene-1-sulfonyl chloride (594 mg, 3.12 mmol) was added to a solution of B-1C and pyridine (617 mg, 7.80 mmol) in DCM (5 mL) which had been pre-cooled to 0° C. The mixture was stirred at 0° C. for 4 h. The mixture was then washed 3 times with 1M aq HCl solution, water and saturated aq. NaHCO$_3$ solution. The organic portion was dried (Na$_2$SO$_4$), filtered and concentrated under reduced pressure. Chromatography of the residue (cyclohexane-EtOAc, 100:0 to 80:20) afforded the sulphonamide (660 mg, 58% over two steps). The sulphonamide was dissolved in 1,4-dioxane (4 mL) and treated with 6N aq HCl solution. The mixture was heated to 100° C. and stirred for 18 h. The volatiles were removed under reduced pressure. Chromatography of the residue (EtOAc-MeOH, 100:0 to 90:10) afforded B-2C as a colourless oil (120 mg).

A mixture of B-2C (120 mg), 4,4,5,5-tetramethyl-2-(tetramethyl-1,3,2-dioxaborolan-2-yl)-1,3,2-dioxaborolane (426 mg, 1.68 mmol), KOAc (164 mg, 1.68 mmol) and Pd(dppf)Cl$_2$ (20.0 mg, 0.028 mmol) in DMF (2 mL) was degassed and heated to 90° C. After 2 h, volatiles were removed under reduced pressure. The crude DB3 was used without further purification.

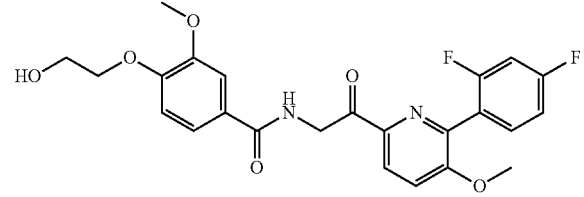

1601

Compound 1601 was obtained by reacting 16-6 with 2,4-difluorophenylboronic acid followed by PMB-group according to the procedure shown in Example 16-1. Compound 1601 was obtained as a yellow solid (47% over two steps). UPLC/MS(ES$^+$), m/z: 473.16 [M+H]$^+$.

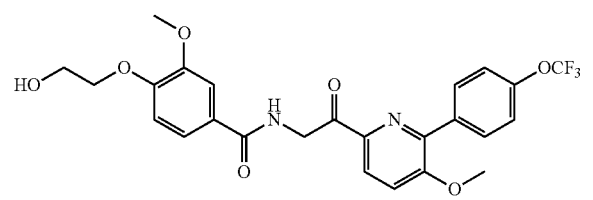

1602

Compound 1602 was obtained by reacting 16-6 with [4-(trifluoromethoxy)phenyl]boronic acid followed by PMB-group according to the procedure shown in Example 16-1. Compound 1602 was obtained as a white solid (57% over two steps). UPLC/MS(ES$^+$), m/z: 521.12 [M+H]$^+$.

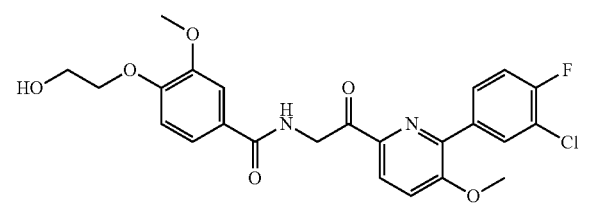

1603

Compound 1603 was obtained by reacting 16-6 with (3-chloro-4-fluorophenyl)boronic acid followed by PMB-group according to the procedure shown in Example 16-1. Compound 1603 was obtained as a white solid (24% over two steps). UPLC/MS(ES$^+$), m/z: 489.13 [M+H]$^+$.

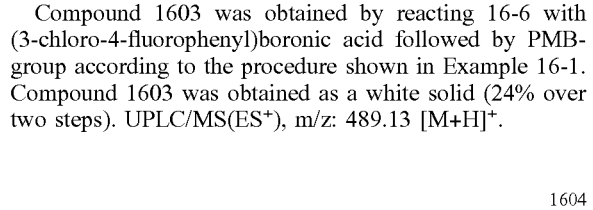

1604

Compound 1604 was obtained by reacting 16-6 with (4-methanesulfonylphenyl)boronic acid followed by PMB-group according to the procedure shown in Example 16-1. Compound 1604 was obtained as a white solid (52% over two steps). UPLC/MS(ES$^+$), m/z: 515.15 [M+H]$^+$.

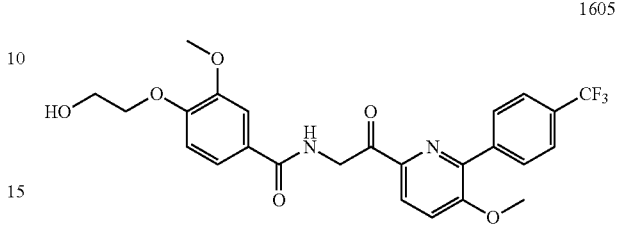

1605

Compound 1605 was obtained by reacting 16-6 with [4-(trifluoromethyl)phenyl]boronic acid followed by PMB-group according to the procedure shown in Example 16-1. Compound 1605 was obtained as a white solid (20% over two steps). UPLC/MS(ES$^+$), m/z: 505.13 [M+H]$^+$.

1606

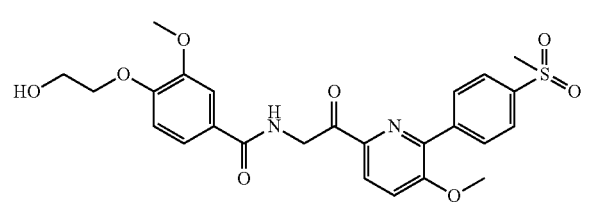

Compound 1606 was obtained by reacting 16-6 with 4-(methylphenyl)boronic acid followed by PMB-group according to the procedure shown in Example 16-1. Compound 1606 was obtained as a light yellow solid (58% over two steps). UPLC/MS(ES$^+$), m/z: 451.21 [M+H]$^+$.

1607

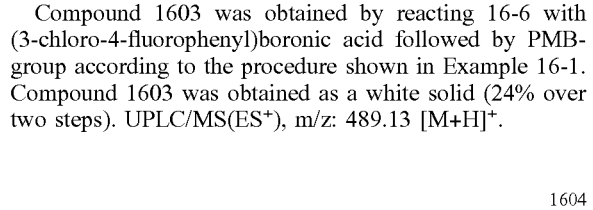

Compound 1607 was obtained by reacting 16-6 with (4-chlorophenyl)boronic acid followed by PMB-group according to the procedure shown in Example 16-1. Compound 1607 was obtained as a light yellow solid (50% over two steps). UPLC/MS(ES$^+$), m/z: 471.13 [M+H]$^+$.

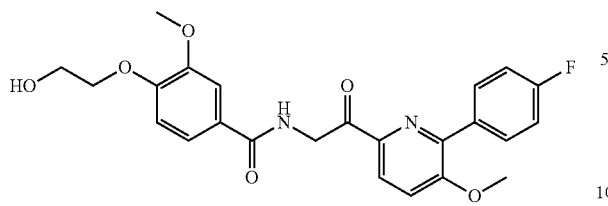

1608

Compound 1608 was obtained by reacting 16-6 with (4-fluorophenyl)boronic acid followed by PMB-group according to the procedure shown in Example 16-1. Compound 1608 was obtained as a light yellow solid (40% over two steps). UPLC/MS(ES$^+$), m/z: 455.15 [M+H]$^+$.

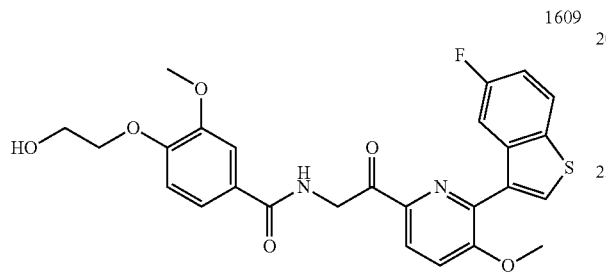

1609

Compound 1609 was obtained by reacting 16-6 with 2-(5-fluoro-1-benzothiophen-3-yl)-5,5-dimethyl-1,3,2-dioxaborinane followed by PMB-group according to the procedure shown in Example 16-1. Compound 1609 was obtained as a light yellow solid (69% over two steps). UPLC/MS(ES$^+$), m/z: 511.22 [M+H]$^+$.

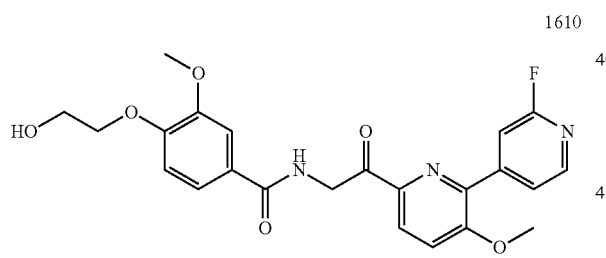

1610

Compound 1610 (29% over two steps) was obtained by reacting 16-6 with (2-fluoropyridin-4-yl)boronic acid followed by PMB-group according to the procedure shown in Example 16-1. UPLC/MS(ES$^+$), m/z: 456.11 [M+H]$^+$.

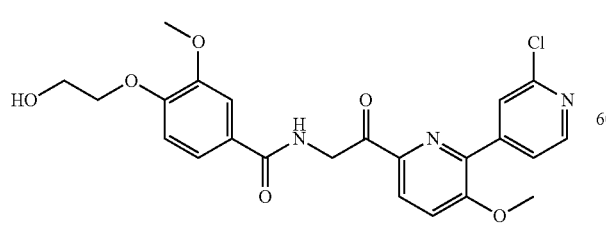

1611

Compound 1611 (28% over two steps) was obtained by reacting 16-6 with (2-chloropyridin-4-yl)boronic acid followed by PMB-group according to the procedure shown in Example 16-1. UPLC/MS(ES$^+$), m/z: 472.14 [M+H]$^+$.

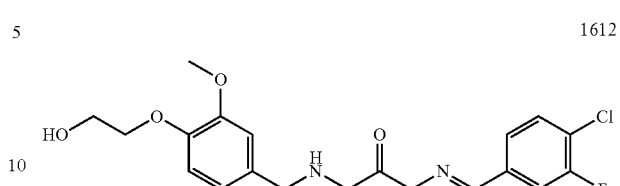

1612

Compound 1612 was obtained by reacting 16-6 with (4-chloro-3-fluorophenyl)boronic acid followed by PMB-group according to the procedure shown in Example 16-1. Compound 1612 was obtained as an off-white solid (33% over two steps). UPLC/MS(ES$^+$), m/z: 489.08 [M+H]$^+$.

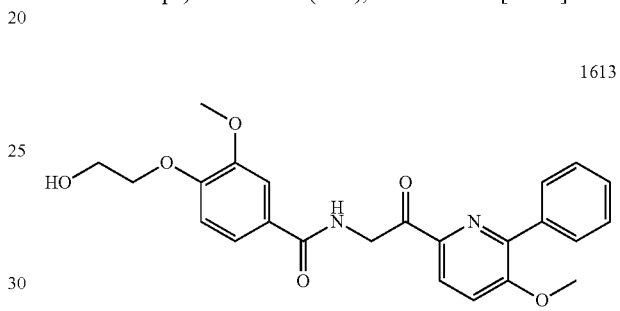

1613

Compound 1613 (71% over two steps) was obtained by reacting 16-6 with phenylboronic acid followed by PMB-group according to the procedure shown in Example 16-1. UPLC/MS(ES$^+$), m/z: 437.19 [M+H]$^+$.

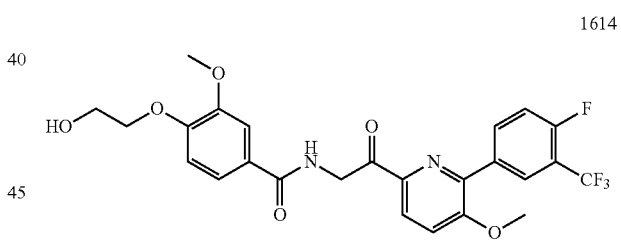

1614

Compound 1614 (64% over two steps) was obtained by reacting 16-6 with [4-fluoro-3-(trifluoromethyl)phenyl]boronic acid followed by PMB-group according to the procedure shown in Example 16-1. UPLC/MS(ES$^+$), m/z: 523.15 [M+H]$^+$.

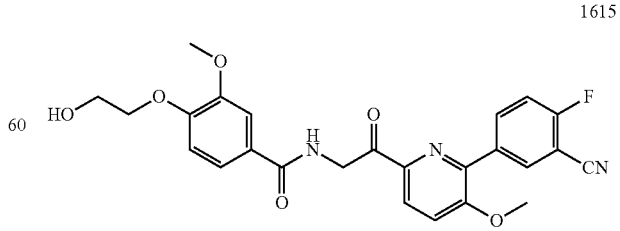

1615

Compound 1615 (56% over two steps) was obtained by reacting 16-6 with (3-cyano-4-fluorophenyl)boronic acid followed by PMB-group according to the procedure shown in Example 16-1. UPLC/MS(ES+), m/z: 480.18 [M+H]+.

1616

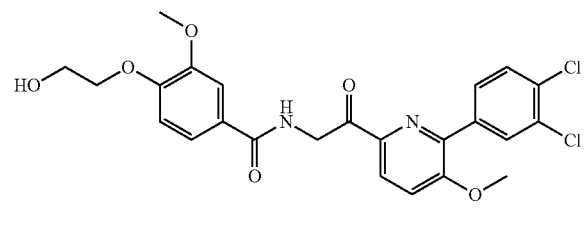

Compound 1616 (52% over two steps) was obtained by reacting 16-6 with (3,4-dichlorophenyl)boronic acid followed by PMB-group according to the procedure shown in Example 16-1. UPLC/MS(ES+), m/z: 505.05 [M+H]+.

1617

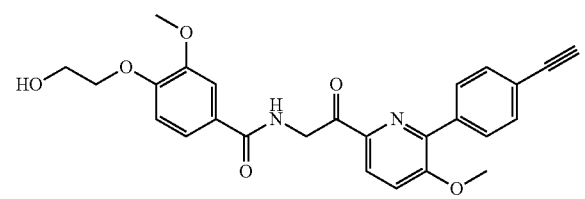

Compound 1617 (15% over two steps) was obtained by reacting 16-6 with trimethyl({2-[4-(tetramethyl-1,3,2-dioxaborolan-2-yl)phenyl]ethynyl}) silane followed by PMB-group according to the procedure shown in Example 16-1. UPLC/MS(ES+), m/z: 461.19 [M+H]+.

1618

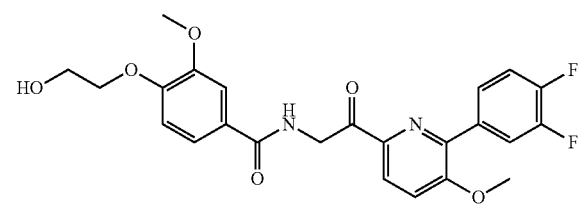

Compound 1618 (61% over two steps) was obtained by reacting 16-6 (3,4-difluorophenyl)boronic acid followed by PMB-group according to the procedure shown in Example 16-1. UPLC/MS(ES+), m/z: 473.19 [M+H]+.

1619

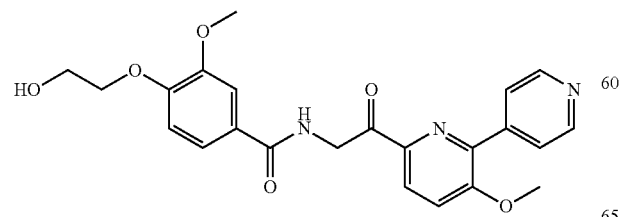

Compound 1619 (55% over two steps) was obtained by reacting 16-6 with (3,4-difluorophenyl)boronic acid (pyridin-4-yl)boronic acid followed by PMB-group according to the procedure shown in Example 16-1. UPLC/MS(ES+), m/z: 438.25 [M+H]+.

1620

Compound 1620 (27% over two steps) was obtained by reacting 16-6 with 3-(5,5-dimethyl-1,3,2-dioxaborinan-2-yl)-1-benzothiophene-5-carbonitrile followed by PMB-group according to the procedure shown in Example 16-1. UPLC/MS(ES+), m/z: 518.15 [M+H]+.

1621

Compound 1621 (37% over two steps) was obtained by reacting 16-6 with 3-(tetramethyl-1,3,2-dioxaborolan-2-yl)thieno[3,2-c]pyridine followed by PMB-group according to the procedure shown in Example 16-1. UPLC/MS(ES+), m/z: 494.19 [M+H]+.

1622

Compound 1622 (18% over two steps) was obtained by reacting 16-6 with (3-bromo-4-fluorophenyl)boronic acid followed by PMB-group according to the procedure shown in Example 16-1. UPLC/MS(ES+), m/z: 533.16 [M+H]+.

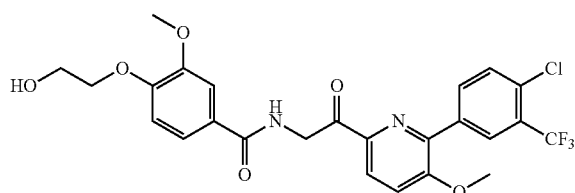

Compound 1623 (78% over two steps) was obtained by reacting 16-6 with [4-chloro-3-(trifluoromethyl)phenyl]boronic acid followed by PMB-group according to the procedure shown in Example 16-1. UPLC/MS(ES+), m/z: 539.18 [M+H]+.

Example 17-1

Preparation of Compound 1700

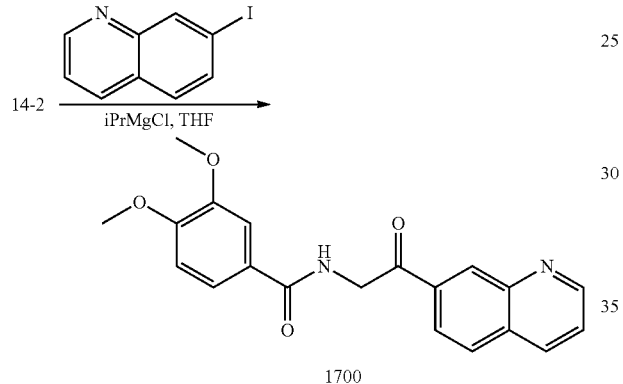

A 2M i-PrMgCl solution in THF (1.22 mL, 2.45 mmol) was added dropwise to a mixture of 7-iodoquinoline (267 mg, 1.05 mmol) and 14-2 (200 mg, 0.700 mmol) in THF (9 mL). The mixture was stirred at rt for 15 mins. Water was added and the organic solvents were removed under reduced pressure. The aqueous portion was extracted with EtOAc. The organic portion was dried (Na2SO4), filtered and concentrated under reduced pressure. Chromatography of the residue (cyclohexane-EtOAc, 100:0 to 30:70) afforded compound 1700 (44 mg, 18%). UPLC/MS(ES+), m/z: 351.13 [M+H]+.

Example 17-2

Preparation of Compound 1701

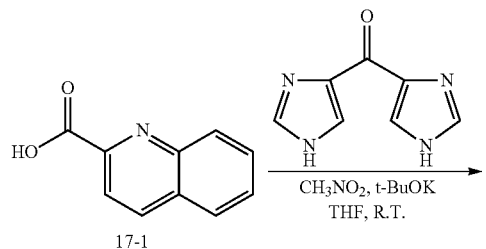

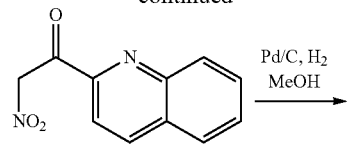

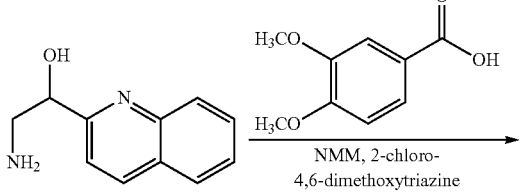

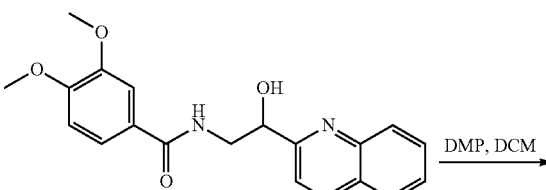

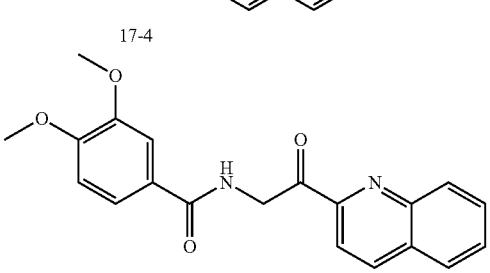

1,1'-Carbonyldiimidazole (1.17 g, 7.21 mmol) was added to a solution of 17-1 (1.00 g, 5.77 mmol) in THF (9.6 mL). The mixture was stirred at rt for 30 mins. CH3NO2 (1.87 mL, 34.62 mmol) and potassium tert-butoxide (2.58 g, 23.04 mmol) were then added, and the mixture was stirred for 2 h. The volatiles were removed under reduced pressure. EtOAc (50 mL) and 0.1M aq HCl solution (40 mL) were added. The yellow precipitate was collected and dried to afford 17-2 (1.13 g, 91%). UPLC/MS(ES+), m/z: 217.05 [M+H]+.

A mixture of 10% Pd/C (Degussa type, 60 mg) and 17-2 (60 mg, 0.270 mmol) in MeOH (9 mL) was stirred under H2 atmosphere for 1.5 h. The catalyst was filtered off and the organic portion was concentrated under reduced pressure to afford crude 17-3 (50 mg), which was directly in the next step.

A mixture of 3,4-dimethoxybenzoic acid (76 mg, 0.420 mmol), 4-methylmorpholine (57 µL, 0.52 mmol) and 2-chloro-4,6-dimethoxy-1,3,5-triazine (63 mg, 0.36 mmol) in CH3CN (4 mL) was stirred at rt for 1 h. 17-3 (50 mg) was added, and the mixture was stirred for 18 h. The volatiles were removed under reduced pressure. The residue was dissolved in EtOAc, and the organic portion was washed twice with water, dried (Na2SO4), filtered and concentrated under reduced pressure. Chromatography of the residue (cyclohexane-EtOAc, 70:30 to 0:100) afforded 17-4 as a grey solid (74 mg, 78% over two steps). UPLC/MS(ES+), m/z: 353.15 [M+H]+.

DMP (135 mg, 0.320 mmol) was added to a solution of 17-4 (74 mg, 0.21 mmol) in DCM (4 mL). After 1 h, the reaction was quenched with a 1:1 10% aq Na2S2O3 solution, saturated aq NaHCO3. The mixture was stirred for 30 mins. The aqueous portion was extracted with EtOAc. The combined organic portions were dried (Na$_2$SO$_4$), filtered and the volatiles were removed under reduced pressure. Chromatography of the residue (cyclohexane:EtOAc, 100:0 to 60:40) afforded compound 1701 as a yellowish solid (21 mg, 28%). UPLC/MS(ES$^+$), m/z: 351.15 [M+H]$^+$.
Example 17-3
Preparation of Compound 1702
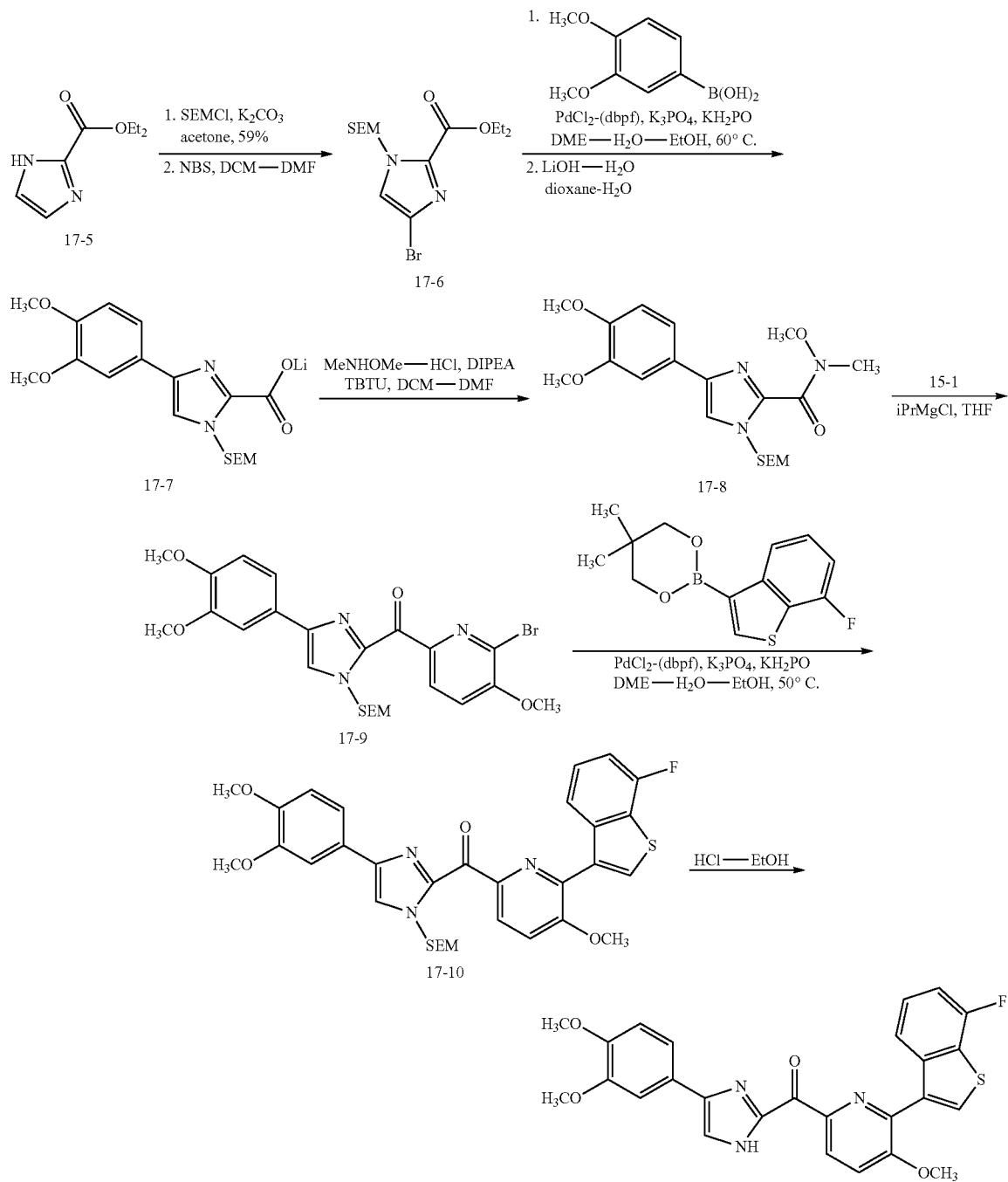

[2-(chloromethoxy)ethyl]trimethylsilane (3.23 mL, 18.2 mmol) was added to a stirred suspension of 17-5 (2.13 g, 15.2 mmol) and potassium carbonate (4.20 g, 30.4 mmol) in acetone (30 mL), and the mixture was stirred overnight at rt. The mixture was poured into water (100 mL) and EtOAc/cyclohexane (200 mL, 1:1). The phases were separated and the aqueous phase extracted with EtOAc/cyclohexane (100 mL, 1:1). The combined organic phases were washed with brine (50 mL), dried ($Na_2SO_4$) and evaporated under reduced pressure. Chromatography of the residue (cyclohexane-EtOAc, 90:10 to 40:60) afforded a SEM-protected intermediate as a colourless oil (2.43 g, 59%). This compound was dissolved in a 1:1 DCM-DMF (20 mL) and N-bromosuccinimide (2.40 g, 13.5 mmol) was added. The mixture was stirred overnight. The mixture was poured into water (100 mL) and 10% sodium thiosulphate solution (5 mL), and then extracted with EtOAc/cyclohexane (100 mL+50 mL, 1:1). The combined organic phases were washed with water/brine (2×100 mL, 1:1) and brine (100 mL), dried ($Na_2SO_4$), filtered and evaporated under reduced pressure. Chromatography of the residue (cyclohexane-EtOAc, 95:5 to 80:20) afforded 17-6 as a white solid (1.86 g, 60%). UPLC/MS(ES$^+$), m/z: 349.07 [M+H]$^+$.

A solution of monobasic potassium phosphate (0.69 g, 5.07 mmol) and tribasic potassium phosphate (1.08 g, 5.07 mmol) in water (20 mL) was added to a solution of (3,4-dimethoxyphenyl)boronic acid (1.20 g, 6.59 mmol) and 17-6 (1.77 g, 5.07 mmol) in DME (35 mL) and EtOH (10 mL) at rt. The mixture was deoxygenated, Pd(dbpf)Cl$_2$ (120 mg, 0.250 mmol) was added, and the mixture was stirred at 60° C. for 3 h. Additional Pd(dbpf)Cl$_2$ (240 mg, 0.500 mmol) was added and the mixture was stirred at 60° C. for 6 h. The mixture was partially evaporated under reduced pressure to remove the majority of the EtOH and DME. The residue was partitioned between EtOAc (150 mL) and half-saturated sodium bicarbonate solution (100 mL). The aqueous phase was extracted further with EtOAc (50 mL), and the combined organic phases were washed with brine (50 mL), dried ($Na_2SO_4$) and evaporated under reduced pressure. Chromatography of the residue (SNAP 100 using NH samplet, cyclohexane-EtOAc, 80:20 to 50:50) afforded the coupled intermediate as a pale yellow gum (1.61 g, 78%). This was dissolved in 1,4-dioxane (30 mL) and a solution of lithium hydroxide monohydrate (0.18 g, 4.36 mmol) in water (10 mL) was added. The mixture was heated to 50° C. for 4 h. The mixture was evaporated under reduced pressure to give 17-7 as a white solid (1.60 g, ~95 wt %).

TBTU (1.65 g, 5.14 mmol) was added to a stirred suspension of 17-7 (1.60 g), methoxy(methyl)amine hydrochloride (0.460 g, 4.74 mmol) and DIPEA (1.38 mL, 7.90 mmol) in a 1:1 DCM-DMF mixture (50 mL). After 30 mins, additional TBTU (2×200 mg) was added at 20 minute intervals after which the mixture became a homogeneous solution. The mixture was diluted with EtOAc (250 mL), washed with half saturated sodium bicarbonate solution (2×200 mL) and brine (200 mL). The organic phase was dried ($Na_2SO_4$) and evaporated under reduced pressure. Chromatography of the residue (cyclohexane-EtOAc, 90:10 to 50:50) afforded 17-8 as a pale yellow gum (1.57 g, 94%). UPLC/MS(ES$^+$), m/z: 422.20 [M+H]$^+$.

A 2M i-PrMgCl solution in THF (0.46 mL, 0.920 mmol) was added dropwise to a stirred solution of 15-1 (268 mg, 0.850 mmol) in THF (3 mL) at −5° C. The solution was stirred at −5° C. for 30 mins, then a solution of 17-8 (300 mg, 0.710 mmol) in THF (3 mL) was added. Stirring was continued for 90 mins allowing the temperature to reach 0° C. The reaction was quenched with water (5 mL), partitioned between EtOAc (50 mL) and half-saturated brine (50 mL). The aqueous phase was extracted further with EtOAc (25 mL). The combined organic phases were washed with brine (25 mL), dried ($Na_2SO_4$) and evaporated under reduced pressure. The residue was chromatographed on NH-modified silica gel eluting with a gradient of 10-50% EtOAc in cyclohexane to give 17-9 as an intense yellow gum/foam (305 mg, 78%). UPLC/MS(ES$^+$), m/z: 548.13 [M+H]$^+$.

A solution of monobasic potassium phosphate (75 mg, 0.550 mmol) and tribasic potassium phosphate (117 mg, 0.550 mmol) in water (4 mL) was added to a solution of 2-(7-fluoro-1-benzothiophen-4-yl)-5,5-dimethyl-1,3,2-dioxaborinane (261 mg, 0.990 mmol) and 17-9 (302 mg, 0.550 mmol) in DME (6 mL) and EtOH (2 mL) at rt. The mixture was deoxygenated with N$_2$ before the addition of Pd(dbpf)Cl$_2$ (13 mg, 0.027 mmol). The mixture was then stirred at 60° C. for 2 h. The mixture was partially evaporated under reduced pressure to remove most of the DME and EtOH. The residue was partitioned between EtOAc (50 mL) and half-saturated sodium bicarbonate solution (30 mL). The aqueous phase was extracted further with EtOAc (25 mL), and the combined organic phases were washed with brine (30 mL), dried ($Na_2SO_4$) and evaporated under reduced pressure. The residue was chromatographed on NH-modified silica gel eluting with a gradient of 10-60% EtOAc in cyclohexane to give the 17-10 as an intense yellow gum/foam (301 mg, 88%). UPLC/MS(ES$^+$), m/z: 620.20 [M+H]$^+$.

A 1M aq HCl solution (15 mL) was added to a stirred solution of 17-10 (298 mg, 0.480 mmol) in EtOH (15 mL). The mixture was then heated to 50° C. for 8 h. The mixture was partially evaporated under reduced pressure to remove most of the EtOH. The residue was basified with 1M aq NaOH solution and extracted with dichloromethane (50+25 mL). The combined organic phases were washed with brine (25 mL), dried ($Na_2SO_4$) and evaporated under reduced pressure. The residue was chromatographed on NH-modified silica gel eluting with a gradient of 50-100% EtOAc in cyclohexane to give compound 1702 as an intense yellow gum/foam (219 mg, 93%). UPLC/MS(ES$^+$), m/z: 490.20 [M+H]$^+$.

Example 17-4

Preparation of Compound 1703

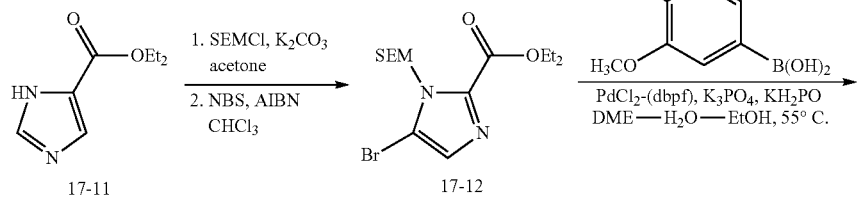

-continued
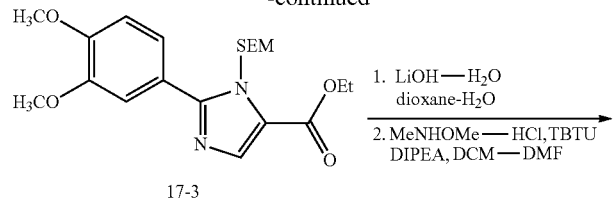
17-3
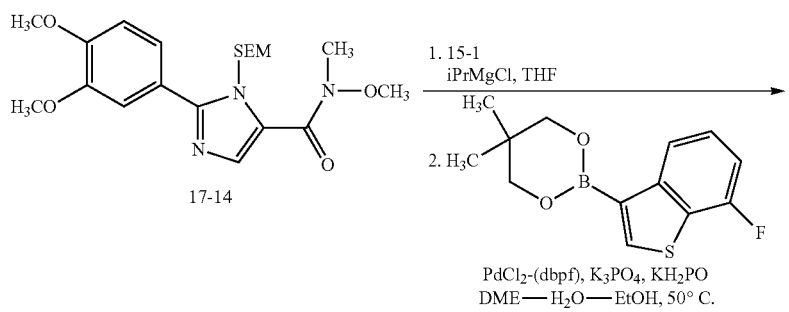
17-14
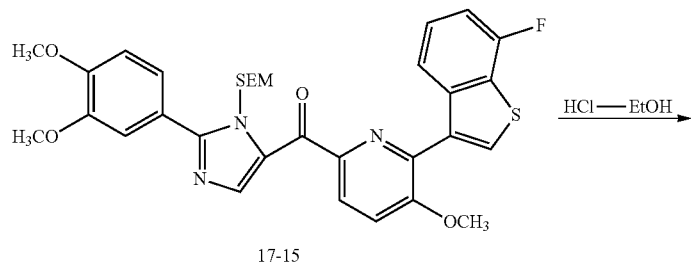
17-15
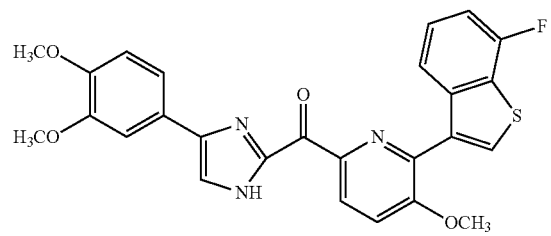
1703

Compound 1703 was prepared starting from ethyl 1H-imidazole-5-carboxylate by following a synthetic route, which closely follows that described for preparation of compound 1702. Compound 1703 was obtained as a pale yellow solid. UPLC/MS(ES+), m/z: 490.20 [M+H]+.

Example 18-1

Preparation of Compound 1800

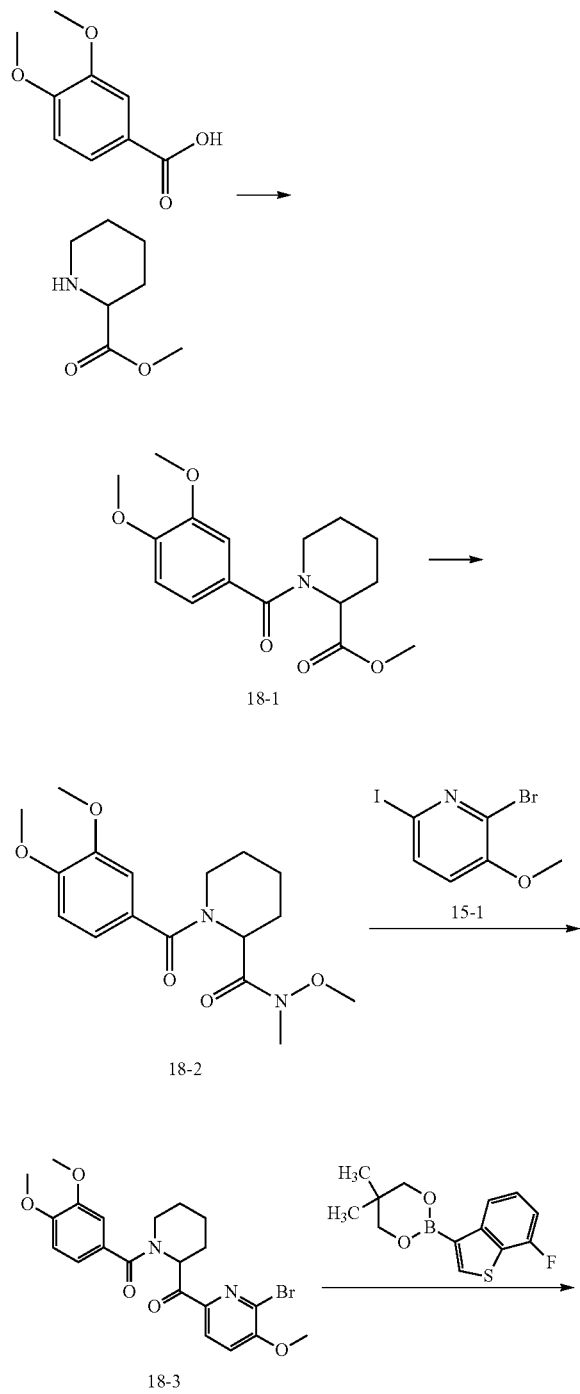

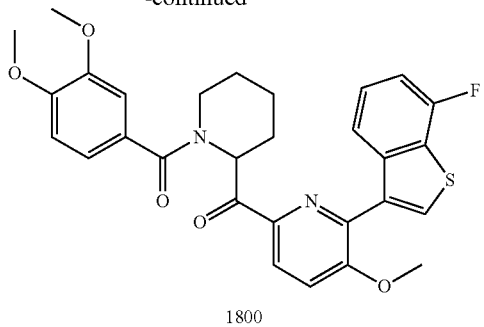

1800

A mixture of 3,4-dimethoxybenzoic acid (550 mg, 3.02 mmol), NMM (530 uL, 4.83 mmol) and 2-chloro-4,6-dimethoxytriazine (740 mg, 4.23 mmol) in CH₃CN (20 mL) was stirred at rt for 30 mins. Methyl piperidine-2-carboxylate (605 mg, 4.23 mmol) was added and the mixture was left to stir at rt for 1 h. DCM was added and the organic portion was washed with 1M aq HCl solution, dried (Na₂SO₄), filtered and concentrated under reduced pressure. Chromatography of the residue (cyclohexane-EtOAc, 50:50 to 0:100) afforded 18-1 as a colourless wax (529 mg, 57%). UPLC/MS(ES+), m/z: 308.15 [M+H]+.

Compound 18-1 (529 mg, 1.72 mmol) was suspended in a 2:1:1 THF-MeOH—H₂O mixture (6 mL) and treated with LiOH—H₂O (217 mg, 5.18 mmol). After 1 h stirring at rt, the mixture was concentrated under reduced pressure. The residue was taken up with EtOAc and water. The layers were separated and the aqueous portion was acidified with 1M aq HCl solution and extracted twice with EtOAc. The combined organic portions were dried (Na₂SO₄), filtered and the volatiles were removed under reduced pressure. The crude acid was directly used in to the next step.

The crude acid was dissolved in CH₃CN (15 mL). To the solution, NMM (251 uL, 2.28 mmol) and 2-chloro-4,6-dimethoxy-1,3,5-triazine (350 mg, 2.00 mmol) were added. After 30 mins, a mixture of N,O-dimethylhydroxylamine hydrochloride (217 mg, 2.24 mmol) and NMM (204 uL, 1.86 mmol) in CH₃CN (2 mL) was added, and the mixture was stirred at rt for 2 h. The volatiles were removed under reduced pressure. The residue was dissolved in EtOAc and the organic portion was washed with 1M aq HCl solution and brine, dried (Na₂SO₄), filtered and concentrated under reduced pressure. Crude 18-2 was used in the next step without further purification. ¹H NMR (400 MHz, CDCl₃) δ ppm 1.35-1.94 (m, 5H), 2.09 (d, J=12.5 Hz, 1H), 3.24 (br. s., 3H), 3.69-4.01 (m, 11H), 5.56 (br. s., 1H), 6.85 (d, J=8.5 Hz, 1H), 6.96-7.12 (m, 2H).

A 2M i-PrMgCl solution in THF (173 uL, 3.57 mmol) was added dropwise to a mixture of 18-2 and 15-1 (670 mg, 2.14 mmol) in dry THF (7 mL). The mixture was stirred at rt for 1 h and then quenched with 1M aq HCl solution. EtOAc was added and the organic portion was washed with 1M aq HCl solution and water, dried (Na₂SO₄), filtered and concentrated under reduced pressure. Chromatography of the residue (cyclohexane-EtOAc, 100:0 to 0:100) afforded 18-3 as a white foam (377 mg, 47% over three steps).

A mixture of 18-3 (220 mg, 0.476 mmol), 2-(7-fluoro-1-benzothiophen-3-yl)-5,5-dimethyl-1,3,2-dioxaborinane (251 mg, 0.952 mmol), Pd(dppf)Cl₂ (29 mg, 0.024 mmol) and 2M aq Na₂CO₃ (714 uL, 1.43 mmol) in DCE (7 mL) was degassed and heated to 85° C. for 2 h. The volatiles were removed under reduced pressure. Chromatography of the residue (cyclohexane-EtOAc, 80:20 to 30:70) afforded compound 1800 as a white solid (70.0 mg, 28%). UPLC/MS (ES+), m/z: 535.15 [M+H]+.

Example 18-2
Preparation of Compound 1801
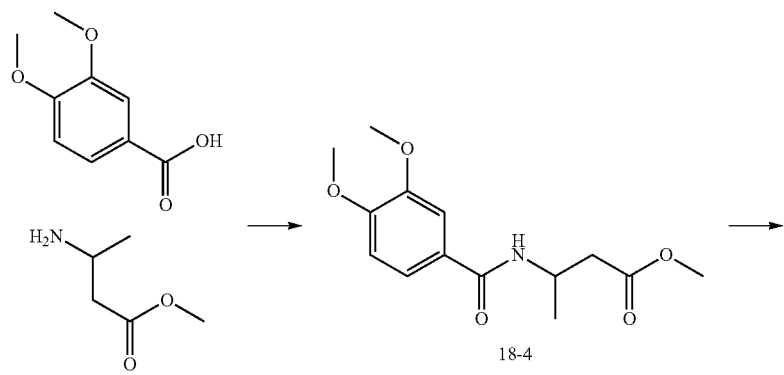
18-4
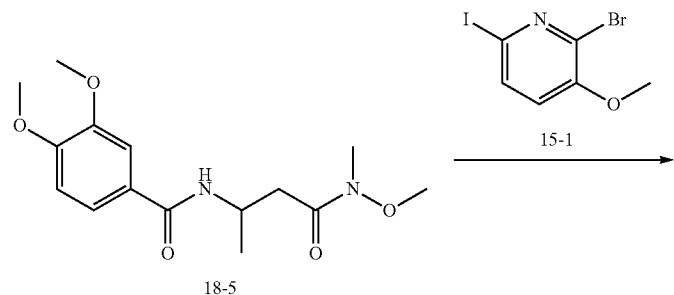
18-5
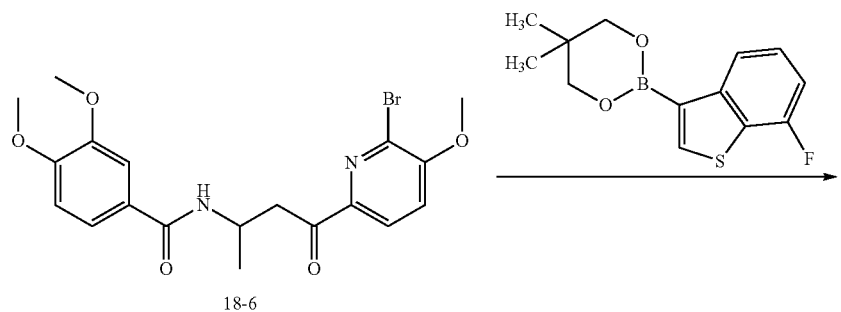
18-6
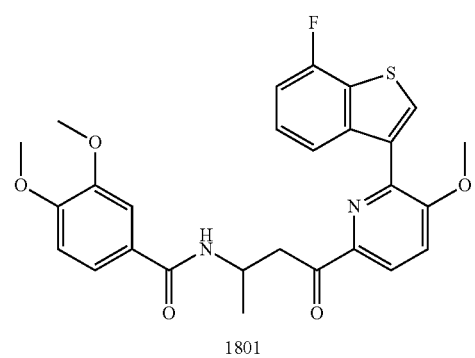
1801

A mixture of 3,4-dimethoxybenzoic acid (359 mg, 1.97 mmol), 2-chloro-4,6-dimethoxytriazine (483 mg, 2.76 mmol) and NMM (346 uL, 3.15 mmol) in CH$_3$CN (8 mL) was stirred at rt for 30 mins. Methyl 3-aminobutanoate (300 mg, 2.56 mmol) was added and the mixture was stirred at rt for an additional 1 h. The volatiles were removed under reduced pressure. The residue was dissolved in DCM and the organic portion washed with 1M aq HCl solution, dried (Na$_2$SO$_4$), filtered and concentrated under reduced pressure. Chromatography of the residue (cyclohexane-EtOAc, 100:0 to 0:100) 18-4 as a white solid (300 mg, 54%).

Compound 18-4 (300 mg, 1.06 mmol) was dissolved in a 2:1:1 THF-MeOH—H$_2$O mixture (10 mL) and treated with LiOH—H$_2$O (141 mg, 3.37 mmol). After 30 mins, the volatiles were removed under reduced pressure. The residue was partitioned between DCM and 1M aq HCl solution. The layers were separated and the organic portion was dried (Na$_2$SO$_4$), filtered and concentrated under reduced pressure to afford the acid, which was used in the next step.

The acid was dissolved in CH$_3$CN (10 mL) and 2-chloro, 4,6-dimethoxytriazine (203 mg, 1.16 mmol) and NMM (237 uL, 2.16 mmol) were sequentially added to the solution. After 30 mins, N,O-dimethyl hydroxylamine hydrochloride (105 mg, 1.08 mmol) was added and the mixture was stirred at room temp for an additional 1 h. The volatiles were removed under reduced pressure. The residue was dissolved in DCM and the organic portion washed with 1M aq HCl solution, dried (Na$_2$SO$_4$), filtered and concentrated under reduced pressure. Chromatography of the residue (EtOAc-MeOH, 100:0 to 80:20) afforded 18-5 as a colourless wax (223 mg, 68% over two steps). $^1$H NMR (400 MHz, DMSO-d$_6$) δ ppm 1.15-1.20 (m, 3H), 2.54-2.65 (m, 1H), 2.66-2.77 (m, 1H), 3.09 (s, 3H), 3.31 (s, 3H), 3.68 (s, 3H), 3.80 (s, 3H), 4.31-4.45 (m, 1H), 7.00 (d, J=8.3 Hz, 1H), 7.41 (d, J=1.8 Hz, 1H), 7.45 (dd, J=8.3, 2.0 Hz, 1H), 8.12 (d, J=8.0 Hz, 1H).

A 2M i-PrMgCl solution in THF (900 uL, 1.80 mmol) was added dropwise to a solution of 18-5 (223 mg, 0.719 mmol) and 15-1 (313 mg, 1.08 mmol) in THF (6 mL). The mixture was stirred at rt for 1 h and then quenched with 1M aq HCl solution. The aqueous portion was extracted twice with EtOAc. The combined organic portions were dried (Na$_2$SO$_4$), filtered and concentrated under reduced pressure. Chromatography of the residue (EtOAc-MeOH, 100:0 to 95:5) afforded 18-6 as a white solid (170 mg, 54%). $^1$H NMR (400 MHz, CDCl$_3$) δ ppm 1.41 (d, J=6.8 Hz, 3H), 3.28 (dd, J=16.3, 5.3 Hz, 1H), 3.65 (dd, J=16.3, 6.1 Hz, 1H), 3.93 (s, 3H), 3.94 (s, 3H), 4.01 (s, 3H), 4.70 (br. s., 1H), 6.84-6.93 (m, 2H), 7.23 (d, J=8.5 Hz, 1H), 7.27-7.31 (m, 1H), 7.43 (d, J=1.8 Hz, 1H), 8.05 (d, J=8.5 Hz, 1H).

A mixture of 18-6 (170 mg, 0.390 mmol), 2-(7-fluoro-1-benzothiophen-3-yl)-5,5-dimethyl-1,3,2-dioxaborinane (257 mg, 0.975 mmol), Pd(dppf)Cl$_2$ (14 mg, 0.019 mmol) and 2M aq Na$_2$CO$_3$ (585 uL, 1.17 mmol) in DCE (7 mL) was degassed and heated to 85° C. for 2 h. The volatiles were removed under reduced pressure. Chromatography of the residue (cyclohexane-EtOAc, 50:50 to 0:100) afforded compound 1801 as an off-white solid (137 mg, 69%). UPLC/MS(ES$^+$), m/z: 509.15 [M+H]$^+$.

Example 18-3

Preparation of Compound 1802

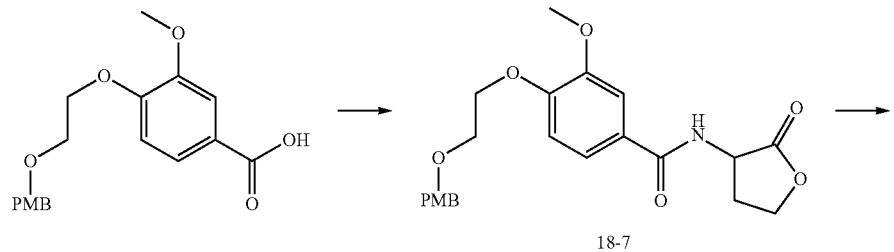

18-7

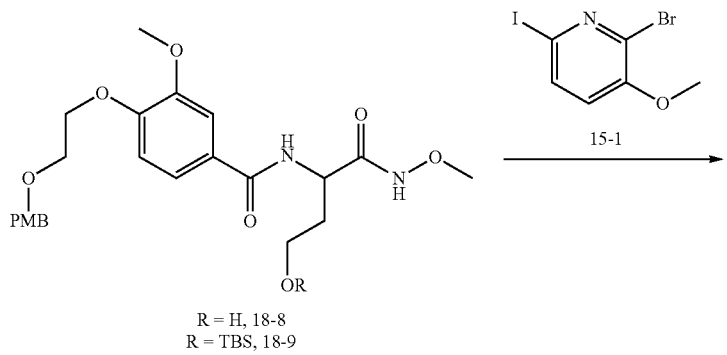

R = H, 18-8
R = TBS, 18-9

317
-continued
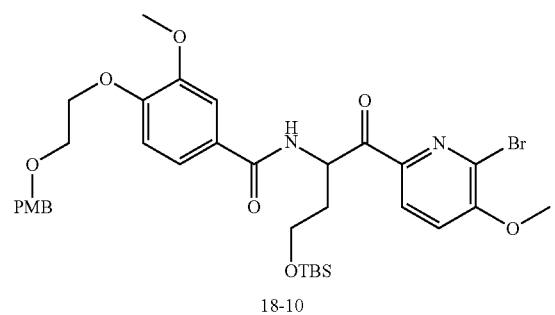 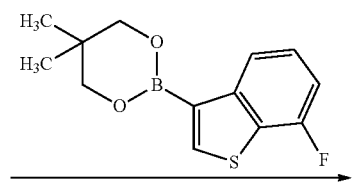
18-10
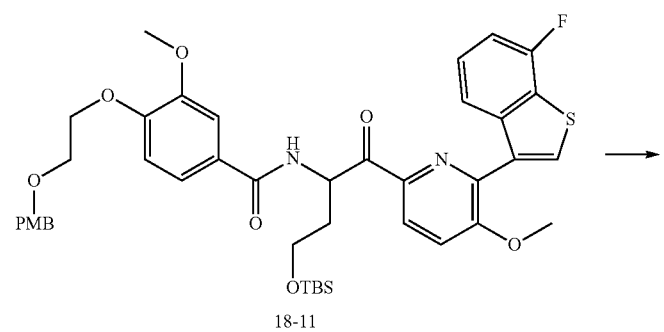
18-11
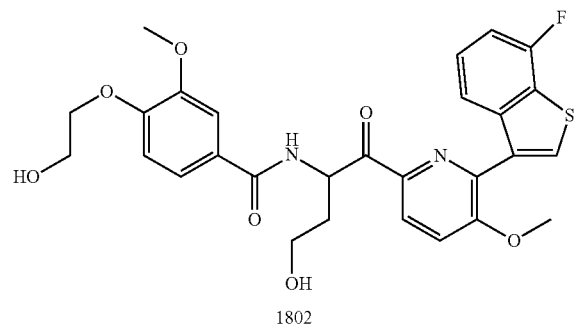
1802

A mixture of 3-methoxy-4-{2-[(4-methoxyphenyl)methoxy]ethoxy}benzoic acid (500 mg, 1.50 mmol), 2-chloro-4,6-dimethoxytriazine (368 mg, 2.10 mmol) and NMM (334 uL, 2.40 mmol) in CH$_3$CN (10 mL) was stirred at rt for 30 mins. 2-Amino-4-hydroxybutanoic acid (232 mg, 1.95 mmol) was added, and the mixture was stirred at rt for 1 h. The volatiles were removed under reduced pressure. The residue was dissolved in DCM and the organic portion was washed twice with 1M aq HCl solution. The combined organic portions were dried (Na$_2$SO$_4$), filtered and volatiles were removed under reduced pressure to afford 18-7 which was progressed to the next step without any further purification. UPLC/MS(ES$^+$), m/z: 416.20 [M+H]$^+$.

Pyridine (137 uL, 1.70 mmol) and AlMe$_3$ (2M solution in heptanes, 1.15 mL, 2.31 mmol) were added to a suspension of MeONHMe-HCl (224 mg, 2.31 mmol) in DCM (5 mL). The mixture was stirred under N$_2$ atmosphere for 15 mins. A solution of 18-7 in DCM (2 mL) was added dropwise. The mixture was stirred at rt for 2.5 h, cooled to 0° C. and quenched with 1M aq HCl solution. The organic portion was diluted with DCM and washed with 1M aq HCl sol and brine, dried (Na$_2$SO$_4$), filtered and concentrated under reduced pressure. Crude 18-8 was used in the next step without further purification.

Triethylamine (214 uL, 1.54 mmol) and TBSCl (151 mg, 1.0 mmol) were sequentially added to a solution of 18-8 in DCM (6 mL). The mixture was stirred at rt for 48 h, diluted with DCM and washed with water. The organic portion was dried (Na$_2$SO$_4$), filtered and volatiles were removed under reduced pressure. Crude 18-9 (263 mg) was used in the next step. $^1$H NMR (400 MHz, CDCl$_3$) δ ppm 0.07, 0.08 (2×s, 6H), 0.91 (s, 9H), 1.91-2.01 (m, 1H), 2.08-2.20 (m, 1H), 3.26 (s, 3H), 3.76-3.97 (m, 13H), 4.25 (t, J=5.1 Hz, 2H), 4.59 (s, 2H), 5.15-5.30 (m, 1H), 6.84-6.95 (m, 3H), 7.11-7.22 (m, 1H), 7.30-7.35 (m, 3H), 7.45 (d, J=1.8 Hz, 1H).

A 2M i-PrMgCl solution in THF (710 uL, 1.42 mmol) was added to a solution of 15-1 (209 mg, 0.670 mmol) and 18-9 (263 mg) in dry THF (4 mL). The mixture was stirred at rt for 15 mins. Methanol and water were added, and the volatiles were removed under reduced pressure. The residue was dissolved in EtOAc. The organic portion was washed twice with water, dried (Na$_2$SO$_4$), filtered and concentrated under reduced pressure. Chromatography of the residue (cyclohexane-EtOAc, 70:30 to 50:50) afforded 18-10 as an off-white solid (206 mg, 19% over four steps). $^1$H NMR (400 MHz, CDCl$_3$) δ ppm 0.01, 0.02 (2×s, 6H), 0.84 (s, 9H), 2.37 (d, J=5.5 Hz, 2H), 3.75-3.84 (m, 5H), 3.87 (t, J=5.1 Hz, 2H), 3.93 (s, 3H), 4.01 (s, 3H), 4.25 (t, J=5.1 Hz, 2H), 4.59 (s, 2H), 5.95 (d, J=5.3 Hz, 1H), 6.84-6.95 (m, 3H), 7.24 (d, J=8.5 Hz, 1H), 7.31 (d, J=8.5 Hz, 2H), 7.36 (dd, J=8.4, 1.9 Hz, 1H), 7.47 (d, J=1.8 Hz, 1H), 7.58 (d, J=6.5 Hz, 1H), 8.08 (d, J=8.5 Hz, 1H).

A mixture of 18-10 (74.0 mg, 0.104 mmol), (3-chloro-4-fluorophenyl)boronic acid (45.0 mg, 0.260 mmol), Pd(dppf)Cl$_2$ (4.0 mg, 0.005 mmol) and aq Na$_2$CO$_3$ (2M solution, 75 uL, 0.150 mmol) in DCE (5 mL) was degassed and stirred with heat at 85° C. for 1 h. Water and DCM were added. The layers were separated and the organic portion was dried (Na$_2$SO$_4$), filtered and concentrated under reduced pressure. Chromatography of the residue (cyclohexane-EtOAc, 100:0 to 60:40) afforded 18-11 as an off-white solid. UPLC/MS (ES$^+$), m/z: 789.27 [M+H]$^+$.

Trifluoroacetic acid (100 uL) was added to a solution of 18-11 in DCM (7 mL). The mixture was stirred at rt for 1 h, and then diluted with DCM. The organic portion was washed with 1M aq NaOH solution and brine, dried (Na$_2$SO$_4$), filtered and concentrated under reduced pressure. The residue was purified by reverse column chromatography (water-CH$_3$CN, 100:0 to 35:65) to afford compound 1802 as a white solid (7 mg, 12% over two steps). UPLC/MS(ES$^+$), m/z: 555.20 [M+H]$^+$.

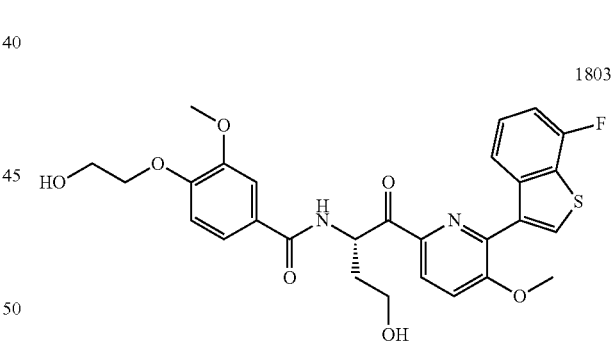

1803

Synthesis performed using L-homoserine lactone hydrochloride as a starting material afforded compound 1803 as a single enantiomer (S, er>98:2, t$_R$ 22.1 min, [Chiralpak IB column (25×2.0 cm, 5 uM), mobile phase: n-Hexane/(Ethanol/Methanol 1/1) 75/25% v/v, flow rate: 0.8 mL/min, UV detection DAD 220 nm]). UPLC and $^1$H NMR analyses of compound 1803 were identical to those for compound 1802.

Example 18-4

Preparation of Compounds 1804, 1805, 1806 and 1807

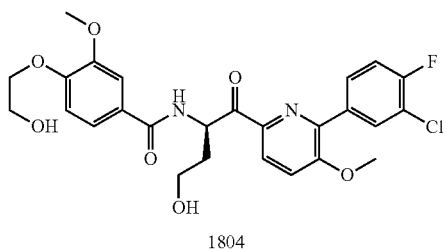
1804

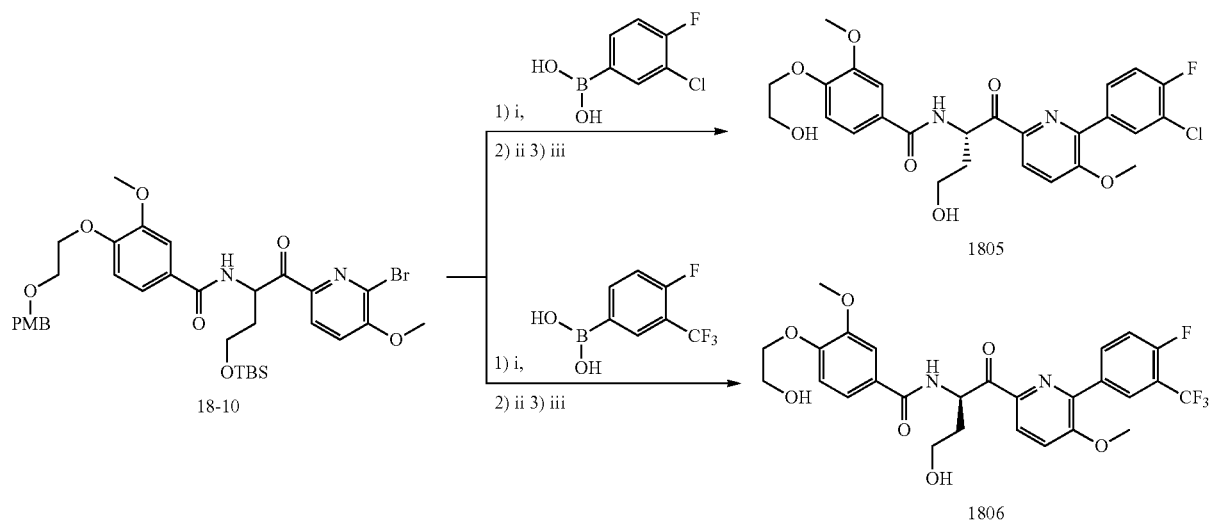

1805

1806

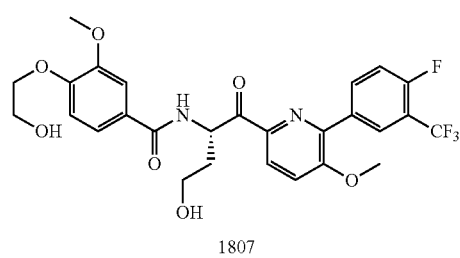
1807

Suzuki coupling of 18-10 with (3-chloro-4-fluorophenyl)boronic acid followed by removal of all the protecting groups (TFA-DCM) afforded a mixture of compounds 1804 and 1805 (27% over two steps). This mixture of compounds (42 mg) was resolved by using a prep-HPLC separation [Chiralpak IB column (25×2.0 cm, 5 uM), mobile phase: n-Hexane/(Ethanol/Methanol 1/1) 75/25% v/v, flow rate: 14 mL/min, UV detection DAD 220 nm] to obtain compound 1804 (15 mg, enantiomer 1 (R), $t_R$ 13.3 min) and compound 1805 (12 mg, enantiomer 2 (S), $t_R$ 15.3 min) based on the order of elution. UPLC and $^1$H NMR analyses for the two enantiomers were superimposible. UPLC/MS(ES$^+$), m/z: 533.32 [M+H]$^+$.

Suzuki coupling of 18-10 with [4-fluoro-3-(trifluoromethyl)phenyl]boronic acid followed by removal of all the protecting groups (TFA-DCM) afforded a mixture of compounds 1806 and 1807 (46% over two steps). This mixture of compounds (54 mg) was resolved by using a prep-HPLC separation [Chiralpak TB column (25×2.0 cm, 5 uM), mobile phase: n-Hexane/(Ethanol/Methanol 1/1) 72/28% v/v, flow rate: 14 mL/min, UV detection DAD 220 nm] to obtain to obtain compound 1806 (23 mg, enantiomer 1 (R), $t_R$ 12.2 min) and compound 1807 (27 mg, enantiomer 2 (S), $t_R$ 14.7 min) based on the order of elution. UPLC and $^1$H NMR analyses for the two enantiomers were superimposible. UPLC/MS(ES$^+$), m/z: 566.92 [M+H]$^+$.

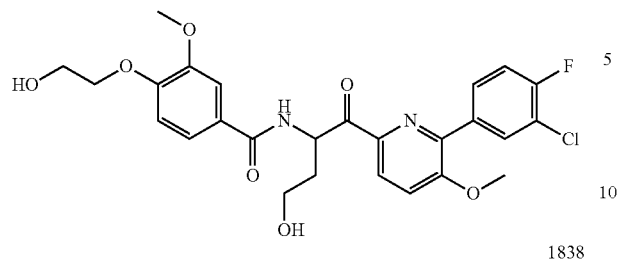
1837
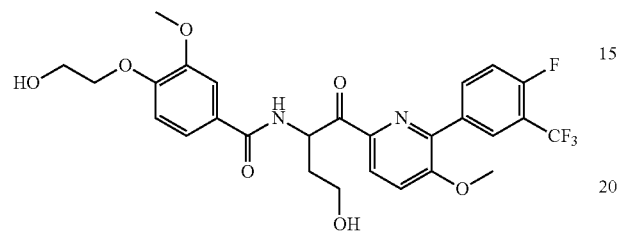
1838
Compounds 1837 and 1838 were obtained as described above in Example 18-4.
Example 18-5
Preparation of Compound 1808
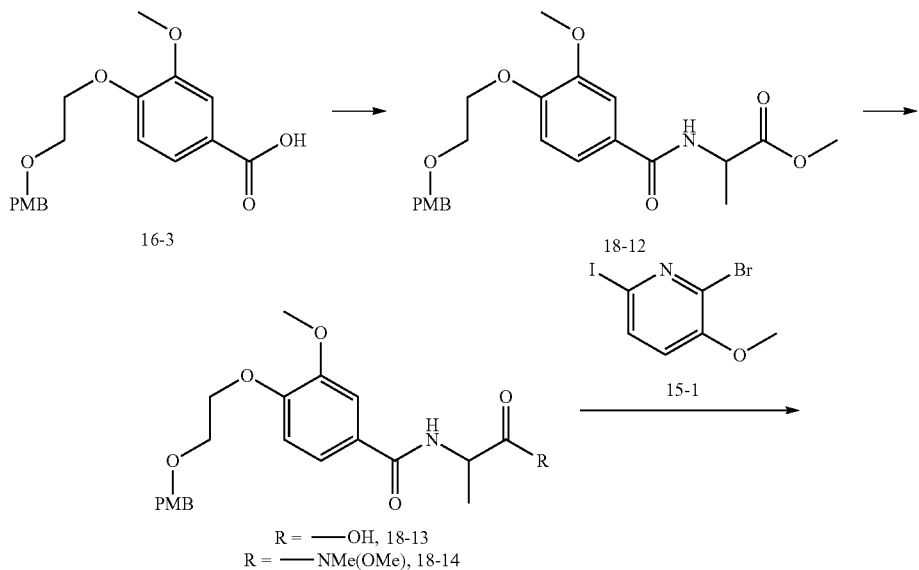
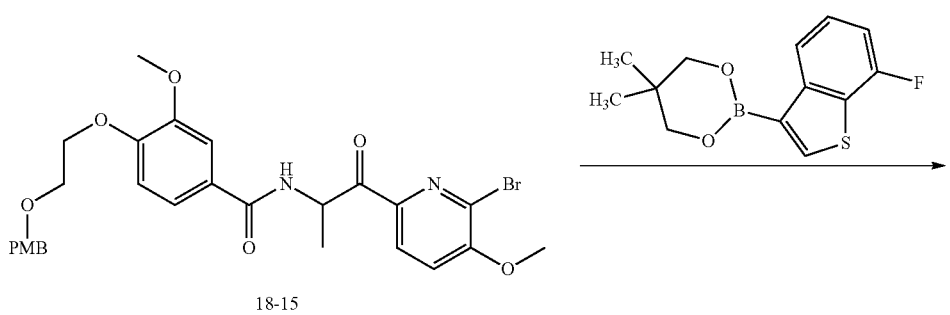

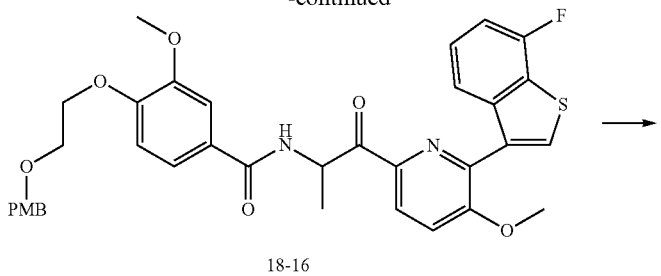

18-16

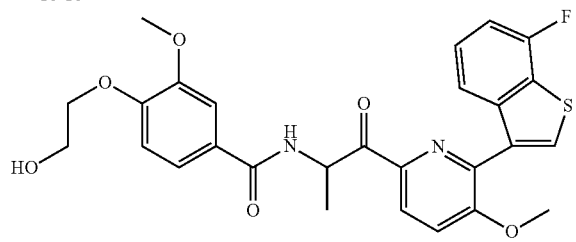

1808

4-Methylmorpholine (1.23 mL, 11.2 mmol) was added to a mixture of 2-chloro-4,6-dimethoxy-1,3,5-triazine (862 mg, 4.91 mmol) and 16-3 (1.12 g, 3.51 mmol) in CH$_3$CN (20 mL). The mixture was stirred at rt for 1 h. (DL)-Alanine methyl ester hydrochloride (764 mg, 5.49 mmol) was added, and the mixture was stirred at rt for an additional 1 h. The volatiles were removed under reduced pressure. The residue was dissolved in EtOAc, and the organic portion was washed with 1M aq HCl solution, dried (Na$_2$SO$_4$), filtered and concentrated under reduced pressure. Crude 18-12 (1.43 g) was used in the next step without further purification. UPLC/MS(ES$^+$), m/z: 418.20 [M+H]$^+$.

Amide 18-12 (1.43 g) was dissolved in a 2:1:1 THF-MeOH—H$_2$O mixture (12 mL) and treated with LiOH—H$_2$O (617 mg, 10.3 mmol). After 1 h, the volatiles were removed under reduced pressure. The residue was partitioned between DCM and 1M aq HCl solution, and the layers were separated. The organic portion was dried (Na$_2$SO$_4$), filtered and concentrated under reduced pressure to afford 18-13 (1.10 g). UPLC/MS(ES$^+$), m/z: 404.20 [M+H]$^+$.

A mixture of 18-13 (1.10 g, 2.71 mmol), HOBT (660 mg, 4.88 mmol), EDC (727 mg, 3.79 mmol), TEA (680 uL, 4.88 mmol) and N,O-Dimethylhydroxylamine hydrochloride (396 mg, 4.06 mmol) in DCM (22 mL) was stirred at rt for 18 h. A 1M aq HCl solution was added and the mixture was stirred at rt for 10 mins. The mixture was filtered from the precipitate and the phases were separated. The organic portion was washed with 1M aq HCl solution, dried (Na$_2$SO$_4$), filtered and concentrated under reduced pressure. Chromatography of the residue (EtOAc-MeOH, 100:0 to 90:10) afforded 18-14 (919 mg, 76%). UPLC/MS(ES$^+$), m/z: 447.20 [M+H]$^+$.

A 2M i-PrMgCl solution in THF (840 uL, 1.68 mmol) was added to a solution of 15-1 (313 mg, 1.00 mmol) and 18-14 (300 mg, 0.607 mmol) in dry THF (6 mL). The mixture was stirred at rt for 45 mins. Methanol and water were added, and the volatiles were removed under reduced pressure. The residue was dissolved in EtOAc and the organic portion was washed twice with water, dried (Na$_2$SO$_4$), filtered and concentrated under reduced pressure. Chromatography of the residue (cyclohexane-EtOAc, 70:30 to 0:100) afforded 18-15 as a yellow solid (240 mg, 63%). $^1$H NMR (400 MHz, CDCl$_3$) δ ppm 1.62 (d, J=7.3 Hz, 3H), 3.83 (s, 3H), 3.86-3.91 (m, 2H), 3.95 (s, 3H), 4.03 (s, 3H), 4.26 (t, J=5.1 Hz, 2H), 4.60 (s, 2H), 5.99 (t, J=7.1 Hz, 1H), 6.85-6.97 (m, 3H), 7.17 (d, J=7.3 Hz, 1H), 7.26 (d, J=8.5 Hz, 1H), 7.31 (d, J=8.5 Hz, 2H), 7.38 (dd, J=8.3, 2.0 Hz, 1H), 7.45-7.51 (m, 1H), 8.11 (d, J=8.3 Hz, 1H).

A mixture of 18-15 (240 mg, 0.420 mmol), 2-(7-fluoro-1-benzothiophen-3-yl)-5,5-dimethyl-1,3,2-dioxaborinane (280 mg, 1.05 mmol), Pd(dppf)Cl$_2$ (22.0 mg, 0.029 mmol) and aq Na$_2$CO$_3$ (2M solution, 360 uL, 1.26 mmol) in DCE (2 mL) was degassed and stirred with heat at 85° C. for 1 h. Water and DCM were added. The mixture was filtered from the solids, and the layers were separated. The organic phase was dried (Na$_2$SO$_4$), filtered and concentrated under reduced pressure. Crude 18-16 was used in the next step without further purification.

PMB-ether 18-16 was dissolved in a 1:1 DCM-TFA solution (3.4 mL). The mixture was stirred at rt for 1 h, then diluted with DCM and neutralized with saturated aq Na$_2$CO$_3$ solution. The aqueous phase was extracted with DCM. The combined organic portions were dried (Na$_2$SO$_4$), filtered and concentrated under reduced pressure. Chromatography of the residue (EtOAc-MeOH, 100:0 to 85:15) followed by trituration of the collected fractions with a CH$_3$CN-EtOAc-cyclohexane mixture afforded compound 1808 as a white solid (56.0 mg, 26% over two steps). UPLC/MS(ES$^+$), m/z: 525.20 [M+H]$^+$.

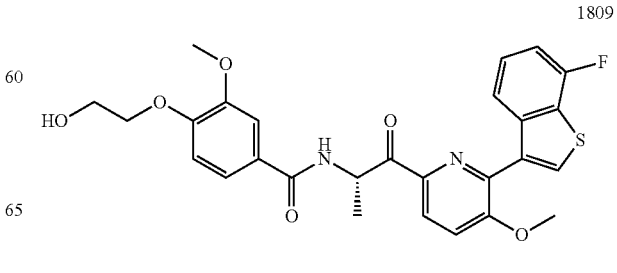

1809

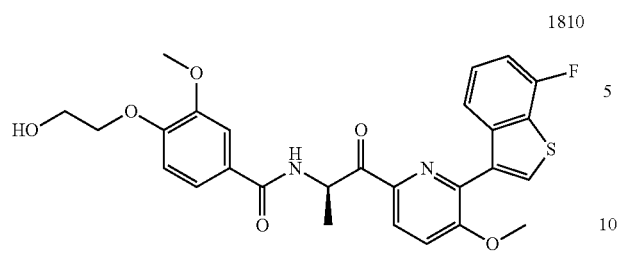

1810

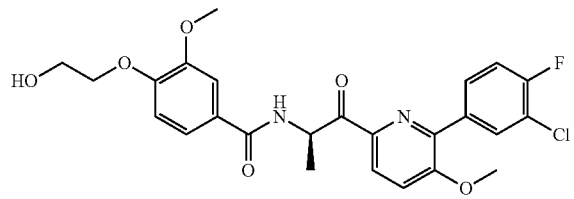

1813

Compounds 1809 and 1810 were prepared starting from enantiomerically pure (L)-alanine methyl ester hydrochloride by following a synthetic route, which closely follows that described for preparation of compound 1808. An unequal mixture of enantiomers was obtained. This mixture of compounds (92 mg) was resolved by using a prep-HPLC separation [Chiralpak IB column (25×2.0 cm, 5 uM), mobile phase: n-Hexane/(Ethanol/Methanol 1/1) 75/25% v/v, flow rate: 14 mL/min, UV detection DAD 220 nm] to obtain compound 1809 (13.2 mg, enantiomer 1 (R), $t_R$ 16.8 min) and compound 1810 (38.0 mg, enantiomer 2 (S), $t_R$ 18.1 min) based on the order of elution. UPLC and $^1$H NMR analyses for the two enantiomers were superimposible and identical to those for compound 1808.

1814

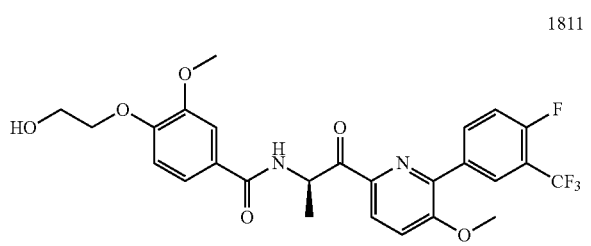

1811

Suzuki coupling of 18-15 (prepared starting from (L)-alanine methyl ester hydrochloride) with (3-chloro-4-fluorophenyl)boronic acid followed by PMB-group removal afforded a mixture of compounds 1813 and 1814 (er 26:74, 40% over two steps). This mixture of compounds (86 mg) was resolved by using a prep-HPLC separation [Chiralpak IB column (25×2.0 cm, 5 uM), mobile phase: n-Hexane/(Ethanol/Methanol 1/1) 70/30% v/v, flow rate: 14 mL/min, UV detection DAD 220 nm] to obtain compound 1813 (15.6 mg, enantiomer 1 (R), $t_R$ 11.1 min) and compound 1814 (24.0 mg, enantiomer 2 (S), $t_R$ 12.7 min) based on the order of elution. UPLC and $^1$H NMR analyses for the two enantiomers were superimposible. $^1$H NMR (400 MHz, DMSO-$d_6$) δ ppm 1.49 (d, J=7.3 Hz, 3H), 3.74 (q, J=5.2 Hz, 2H), 3.81 (s, 3H), 3.97-4.10 (m, 5H), 4.89 (t, J=5.4 Hz, 1H), 5.89 (t, J=7.0 Hz, 1H), 7.03 (d, J=8.3 Hz, 1H), 7.48 (d, J=1.8 Hz, 1H), 7.50-7.56 (m, 1H), 7.57-7.62 (m, 1H), 7.80 (d, J=8.8 Hz, 1H), 7.99-8.09 (m, 2H), 8.18 (dd, J=7.4, 2.1 Hz, 1H), 8.66 (d, J=6.8 Hz, 1H). UPLC/MS(ES$^+$), m/z: 503.18 [M+H]$^+$.

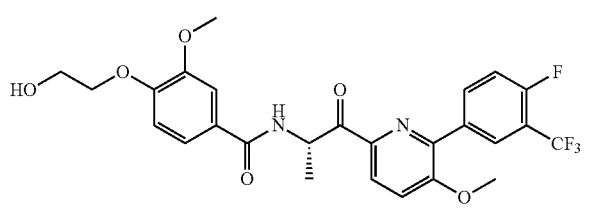

1812

Suzuki coupling of 18-15 (prepared starting from (L)-alanine methyl ester hydrochloride) with [4-fluoro-3-(trifluoromethyl)phenyl]boronic acid followed by PMB-group removal afforded a mixture of compounds 1811 and 1812 (er 6.2:93.8, 22% over two steps). This mixture of compounds (52 mg) was resolved by using a prep-HPLC separation [Chiralpak IB column (25×2.0 cm, 5 uM), mobile phase: n-Hexane/(Ethanol/Methanol 1/1) 70/30% v/v, flow rate: 14 mL/min, UV detection DAD 220 nm] to obtain to obtain compound 1811 (2.4 mg, enantiomer 1 (R), $t_R$ 11.1 min) and compound 1812 (38.0 mg, enantiomer 2 (S), $t_R$ 12.7 min) based on the order of elution. UPLC and $^1$H NMR analyses for the two enantiomers were superimposible. UPLC/MS (ES$^+$), m/z: 537.21 [M+H]$^+$.

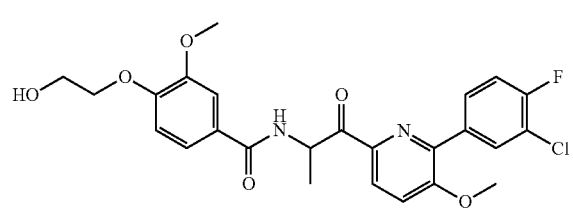

1839

Compound 1839 was obtained as described herein for the preparation for compounds 1813 and 1814.

Example 18-6

Preparation of Compounds 1815 and 1816

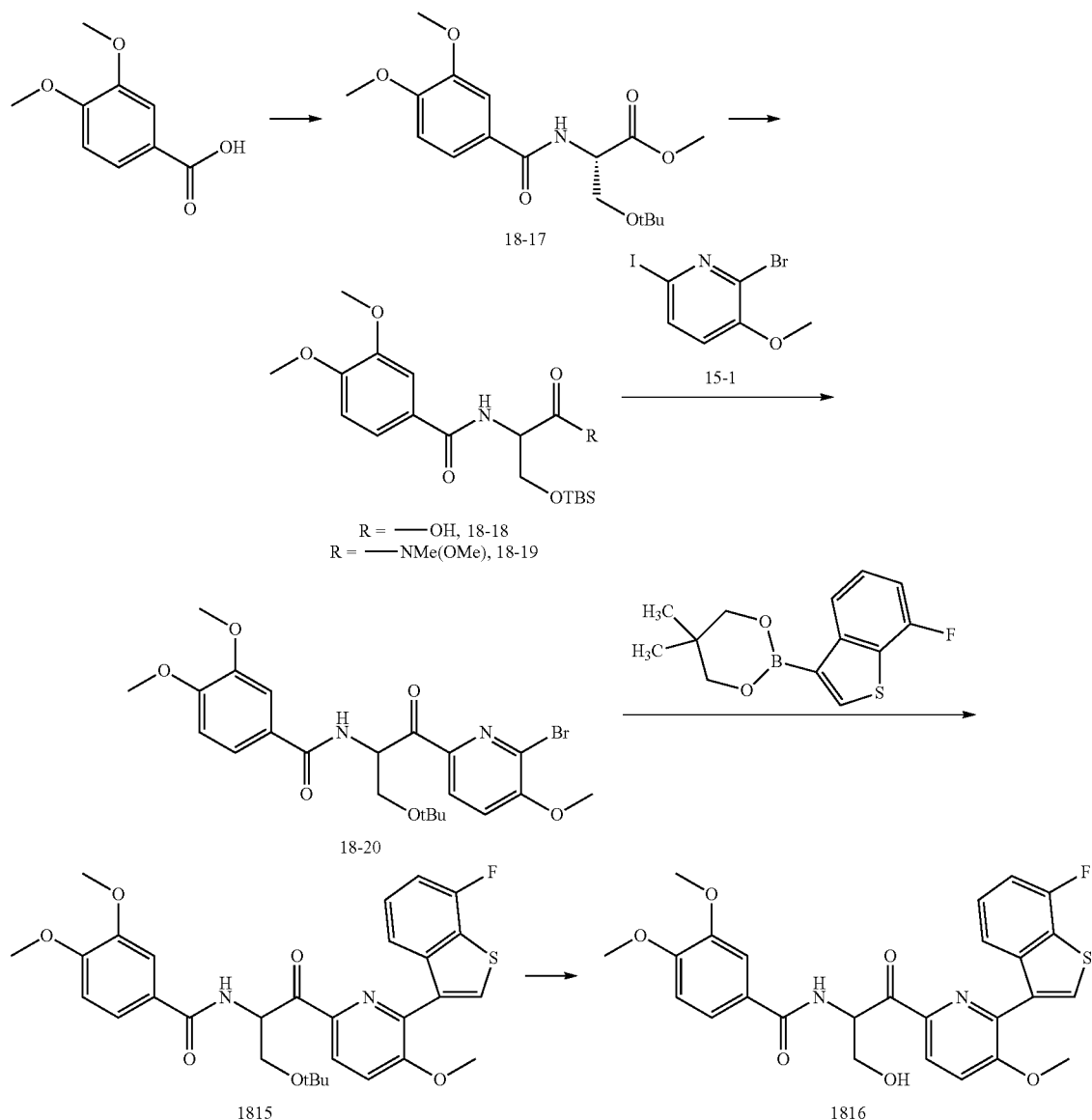

4-Methylmorpholine (900 uL, 8.22 mmol) was added to a mixture of 2-chloro-4,6-dimethoxy-1,3,5-triazine (1.34 g, 7.66 mmol) and 3,4-dimethoxybenzoic acid (1.00 g, 5.48 mmol) in $CH_3CN$ (30 mL). The mixture was stirred at rt for 30 mins, then O-tert-butyl-L-serine methyl ester hydrochloride (1.50 g, 7.12 mmol) was added. The mixture was stirred at rt for 1 h. The volatiles were removed under reduced pressure, and the residue was dissolved in EtOAc. The organic portion was washed twice with 1M aq HCl solution, dried ($Na_2SO_4$), filtered and concentrated under reduced pressure. Crude 18-17 was used in the next step without further purification. UPLC/MS(ES$^+$), m/z: 340.20 [M+H]$^+$.

Amide 18-17 was dissolved in a 2:1:1 THF-MeOH—$H_2O$ mixture (20 mL) and treated with LiOH—$H_2O$ (690 mg, 16.4 mmol). After 30 mins, the volatiles were removed under reduced pressure. The residue was partitioned between DCM and 1M aq HCl solution, and the layers were separated. The organic portion was dried ($Na_2SO_4$), filtered and concentrated under reduced pressure to afford 18-18. UPLC/MS(ES$^+$), m/z: 326.10 [M+H]$^+$.

A mixture of 18-18, HOBT (1.33 g, 9.86 mmol), EDC (1.47 g, 7.67 mmol), TEA (1.37 mL, 9.86 mmol) and N,O-Dimethylhydroxylamine hydrochloride (801 mg, 8.22 mmol) in DCM (20 mL) was stirred at rt for 18 h. A 1M aq HCl solution was added, and the mixture was stirred at rt for 10 mins. The mixture was filtered from the precipitate and the phases were separated. The organic portion was washed with 1M aq HCl solution, dried ($Na_2SO_4$), filtered and concentrated under reduced pressure. Chromatography of the residue (cyclohexane-EtOAc, 100:0 to 20:80) afforded 18-19 (1.70, 84% over three steps). UPLC/MS(ES⁺), m/z: 369.24 [M+H]⁺.

A 2M i-PrMgCl solution in THF (2.3 mL, 4.60 mmol) was added to a solution of 15-1 (1.08 g, 3.45 mmol) and 18-19 (850 mg, 2.30 mmol) in dry THF (20 mL). The mixture was stirred at rt. After 30 min, additional i-PrMgCl solution (1.67 mL, 3.45 mmol) was added and stirring was continued for 15 mins. The reaction was quenched with a saturated aq NH₄Cl solution. The aqueous portion was extracted with EtOAc, dried (Na₂SO₄), filtered and concentrated under reduced pressure. Chromatography of the residue (cyclohexane-EtOAc, 100:0 to 20:80) afforded 18-20 as a yellow solid (525 mg, 46%). UPLC/MS(ES⁺), m/z: 495.15 [M+H]⁺.

A mixture of 18-20 (200 mg, 0.404 mmol), 2-(7-fluoro-1-benzothiophen-3-yl)-5,5-dimethyl-1,3,2-dioxaborinane (212 mg, 0.806 mmol), Pd(dppf)Cl₂ (15 mg, 0.020 mmol) and aq Na₂CO₃ (2M solution, 606 uL, 1.21 mmol) in DCE (4 mL) was degassed and stirred with heat at 85° C. for 3 h. Water and DCM were added, and the layers were separated. The organic phase was dried (Na₂SO₄), filtered and concentrated under reduced pressure. Chromatography of the residue (cyclohexane-EtOAc, 100:0 to 50:50) afforded compound 1815 (181 mg, 79%). UPLC/MS(ES⁺), m/z: 567.26 [M+H]⁺.

Compound 1815 (135 mg, 0.238 mmol) was dissolved in a 10:1 DCM-TFA solution (4.4 mL). The mixture was stirred at rt for 7 h, then diluted with DCM and washed with 2M aq NaOH solution. The organic portion was dried (Na₂SO₄), filtered and concentrated under reduced pressure. The residue was purified by reverse phase chromatography (water-CH₃CN, 95:5 to 0:100) to afford compound 1816 as a white solid (29 mg, 24%). UPLC/MS(ES⁺), m/z: 511.17 [M+H]⁺.

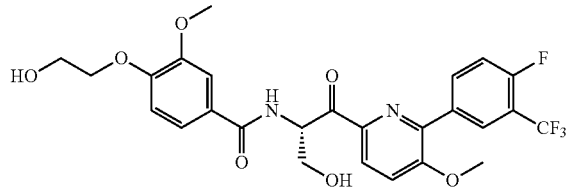

1818

Compounds 1817 and 1818 were prepared starting from 16-3 by following a synthetic route, which closely follows that described for preparation of compound 1815. Coupling of E-21 with [4-fluoro-3-(trifluoromethyl)phenyl]boronic acid followed by removal of the PMB-group (TFA-DCM) afforded a mixture of compounds 1817 and 1818. This mixture of compounds (51 mg) was resolved by using a prep-HPLC separation [Chiralpak IB column (25×2.0 cm, 5 uM), mobile phase: n-Hexane/(Ethanol/Methanol 1/1) 70/30% v/v, flow rate: 14 mL/min, UV detection DAD 220 nm] to obtain compound 1817 (11.8 mg, enantiomer 1 (R), t_R 12.9 min) and compound 1818 (10.0 mg, enantiomer 2 (S), t_R 14.6 min) based on the order of elution. UPLC and ¹H NMR analyses for the two enantiomers were superimposible. UPLC/MS(ES⁺), m/z: 553.20 [M+H]⁺.

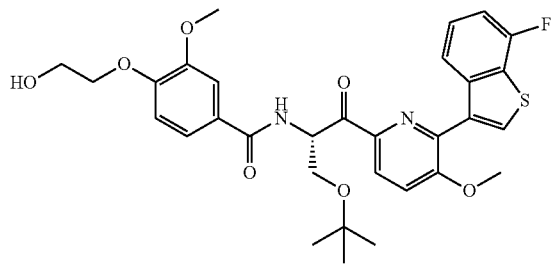

1819

Coupling of 18-21 with 2-(7-fluoro-1-benzothiophen-3-yl)-5,5-dimethyl-1,3,2-dioxaborinane followed by removal of the PMB-group by treatment with TFA afforded compound 1819 as a white solid. UPLC/MS(ES⁺), m/z: 597.30 [M+H]⁺.

Example 18-7

Preparation of Compounds 1820 and 1821

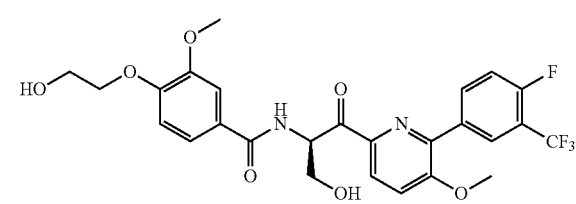

1817

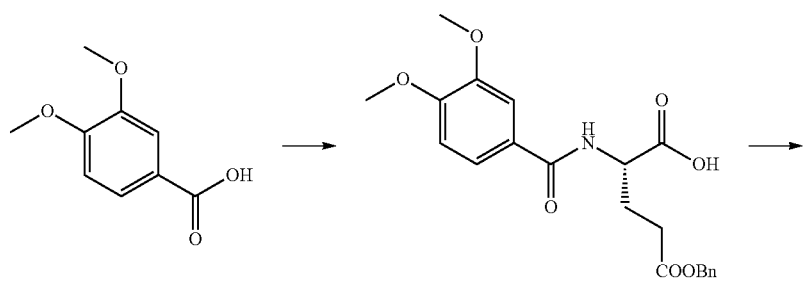

18-22

-continued

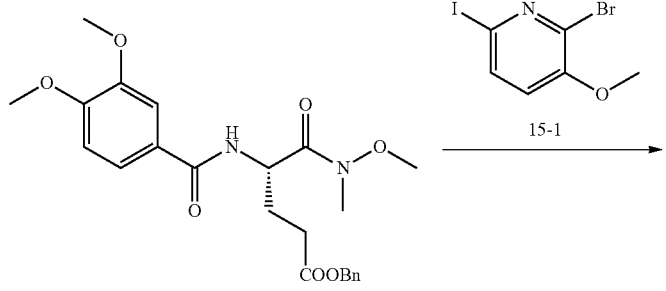

18-23

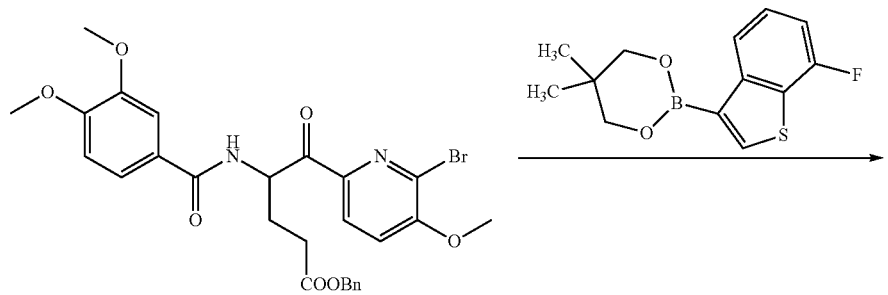

18-24

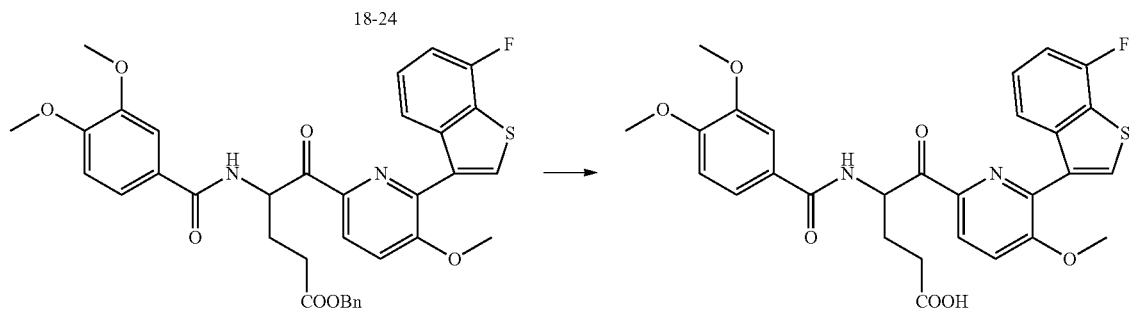

1820 → 1821

Thionyl chloride (2.0 mL, 27.5 mmol) was added to a mixture of 3,4-dimethoxybenzoic acid (1.00 g, 5.49 mmol) in toluene (8 mL). The mixture was stirred with heat to 120° C. for 18 h. The volatiles were removed under reduced pressure. The residue was dissolved in DCM (2 mL), and the solution was added to a mixture of (2S)-2-amino-5-(benzyloxy)-5-oxopentanoic acid (780 mg, 3.29 mmol) and TEA (2.29 mL, 16.5 mmol) in DCM (6 mL). After 1 h, the volatiles were removed under reduced pressure. Chromatography of the residue (cyclohexane-EtOAc, 100:0 to 0:100) afforded 18-22 (887 mg, 67%). UPLC/MS(ES+), m/z: 402.20 [M+H]+.

4-Methylmorpholine (631 uL, 5.74 mmol) was added to a mixture of 2-chloro-4,6-dimethoxy-1,3,5-triazine (542 mg, 3.09 mmol) and 18-22 (887 mg, 1.12 mmol) in CH₃CN (6 mL). The mixture was stirred at rt for 1 h. N,O-Dimethylhydroxylamine hydrochloride (278 mg, 2.87 mmol) was added, and the mixture was left to stir at rt for 1 h. The volatiles were removed under reduced pressure. Chromatography of the residue (cyclohexane-EtOAc, 100:0 to 0:100) afforded 18-23 as a pale yellow wax (308 mg, 62%). UPLC/MS(ES+), m/z: 445.20 [M+H]+.

A 2M i-PrMgCl solution in THF (862 uL, 1.72 mmol) was added to a solution of 15-1 (323 mg, 1.03 mmol) and 18-23 (308 mg, 0.69 mmol) in dry THF (6 mL). The mixture was stirred at rt for 20 mins and then quenched with 2M aq HCl solution. The aqueous portion was extracted with EtOAc, dried (Na₂SO₄), filtered and concentrated under reduced pressure. Chromatography of the residue (cyclohexane-EtOAc, 100:0 to 20:80) afforded 18-24 as a pale yellow solid (100 mg, 25%). UPLC/MS(ES+), m/z: 571.12 [M+H]+.

A mixture of 18-24 (100 mg, 0.175 mmol), 2-(7-fluoro-1-benzothiophen-3-yl)-5,5-dimethyl-1,3,2-dioxaborinane (115 mg, 0.437 mmol), Pd(dppf)Cl₂ (9 mg, 0.012 mmol) and aq Na₂CO₃ (2M solution, 262 uL, 0.525 mmol) in DCE (3 mL) was degassed and stirred with heat at 85° C. for 3 h. Chromatography of the mixture (cyclohexane-EtOAc, 90:10 to 0:100) afforded compound 1820 (109 mg). UPLC/MS (ES+), m/z: 643.20 [M+H]+.

A solution of compound 1820 (57.0 mg, 0.089 mmol) in DCM (2 mL) was treated with a 33% HBr solution in acetic acid (700 uL). After 2 h stirring at rt, saturated aq NaHCO₃ solution was added. The layers were separated and the aqueous portion was extracted with DCM. The combined organic portions were dried (Na₂SO₄), filtered and the volatiles were removed under reduced pressure. Chromatography of the residue (EtOAc-MeOH, 100:0 to 70:30) afforded compound 1821 as a white solid (21 mg, 43%). UPLC/MS(ES+), m/z: 553.10 [M+H]+.

Example 18-8

Preparation of Compound 1822

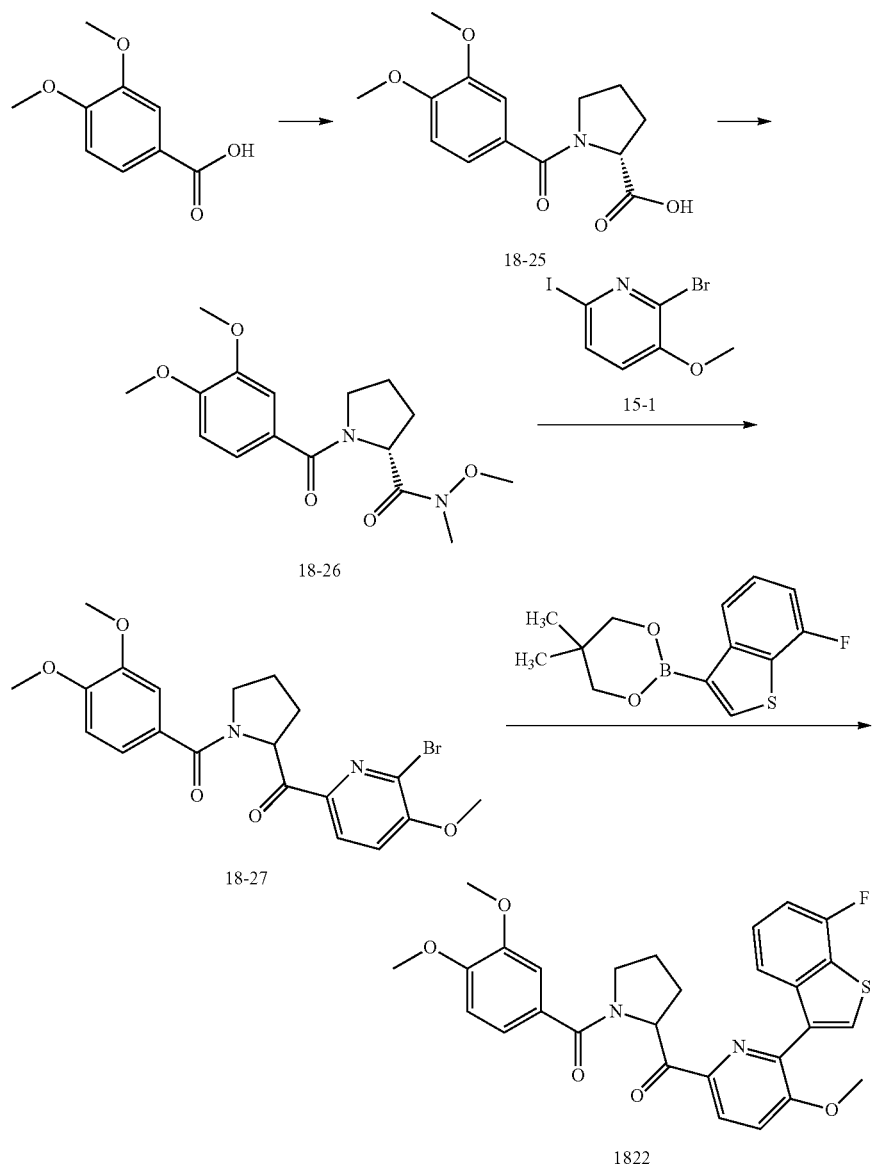

4-Methylmorpholine (610 uL, 4.38 mmol) was added to a mixture of 2-chloro-4,6-dimethoxy-1,3,5-triazine (672 mg, 3.83 mmol) and 3,4-dimethoxybenzoic acid (500 mg, 2.74 mmol) in CH$_3$CN (14 mL). The mixture was stirred at rt for 1 h, then D-proline (706 mg, 4.38 mmol) was added. The mixture was left to stir at rt for 1 h. The volatiles were removed under reduced pressure. The residue was dissolved in EtOAc and washed with 1M aq HCl solution. The organic portion was (Na$_2$SO$_4$), filtered and concentrated under reduced pressure to afford 18-25 as a white solid (1.01 g). UPLC/MS(ES$^+$), m/z: 280.09 [M+H]$^+$.

A mixture of 18-25 (1.01 g), HOBT (875 mg, 6.48 mmol), EDC (966 mg, 5.04 mmol), TEA (903 uL, 46.5 mmol) and N,O-dimethylhydroxylamine hydrochloride (526 mg, 5.40 mmol) in DCM (30 mL) was stirred at rt overnight. A 1M aq HCl solution was added and the mixture was stirred at rt for 10 mins. The mixture was filtered from the solids and the layers were separated. The organic portion was washed with 1M aq HCl solution, dried (Na$_2$SO$_4$), filtered and concentrated under reduced pressure. Crude 18-26 (1.07 g) was used in the next step without further purification. UPLC/MS(ES$^+$), m/z: 323.14 [M+H]$^+$.

A 2M i-PrMgCl solution in THF (3.80 mL, 7.75 mmol) was added to a solution of 15-1 (1.40 g, 4.65 mmol) and 18-26 (1.0 g, 3.10 mmol) in dry THF (10 mL). The mixture was stirred at rt for 30 mins and then quenched with a 1M aq HCl solution. The aqueous portion was extracted with EtOAc. The combined organic portions were dried (Na$_2$SO$_4$), filtered and concentrated under reduced pressure. Chromatography of the residue (EtOAc) afforded 18-27 as an off-white solid (214 mg, 17% over three steps). UPLC/MS(ES$^+$), m/z: 449.07 [M+H]$^+$.

A mixture of 18-27 (100 mg, 0.220 mmol), 2-(7-fluoro-1-benzothiophen-3-yl)-5,5-dimethyl-1,3,2-dioxaborinane (145 mg, 0.550 mmol), Pd(dppf)Cl$_2$ (8 mg, 0.011 mmol) and aq Na$_2$CO$_3$ (2M solution, 165 uL, 0.330 mmol) in DCE (2 mL) was degassed and stirred with heat at 85° C. for 3 h. Water and DCM were added, and the layers were separated. The organic portion was dried (Na$_2$SO$_4$), filtered and concentrated under reduced pressure. Chromatography of the mixture (cyclohexane-EtOAc, 20:80 to 0:100) afforded compound 1822 (20 mg, 17%). UPLC/MS(ES$^+$), m/z: 521.15 [M+H]$^+$.

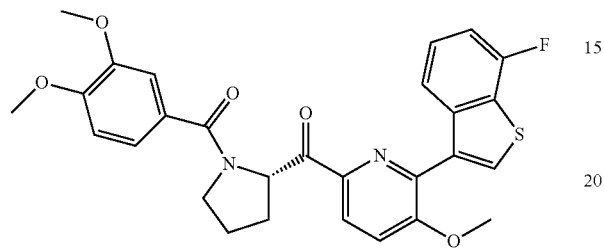

1823

Compound 1823 was prepared starting from L-proline by following a synthetic route, which closely follows that described for preparation of compound 1822. UPLC/MS (ES$^+$), m/z: 521.15 [M+H]$^+$.

Example 18-9

Preparation of Compound 1824

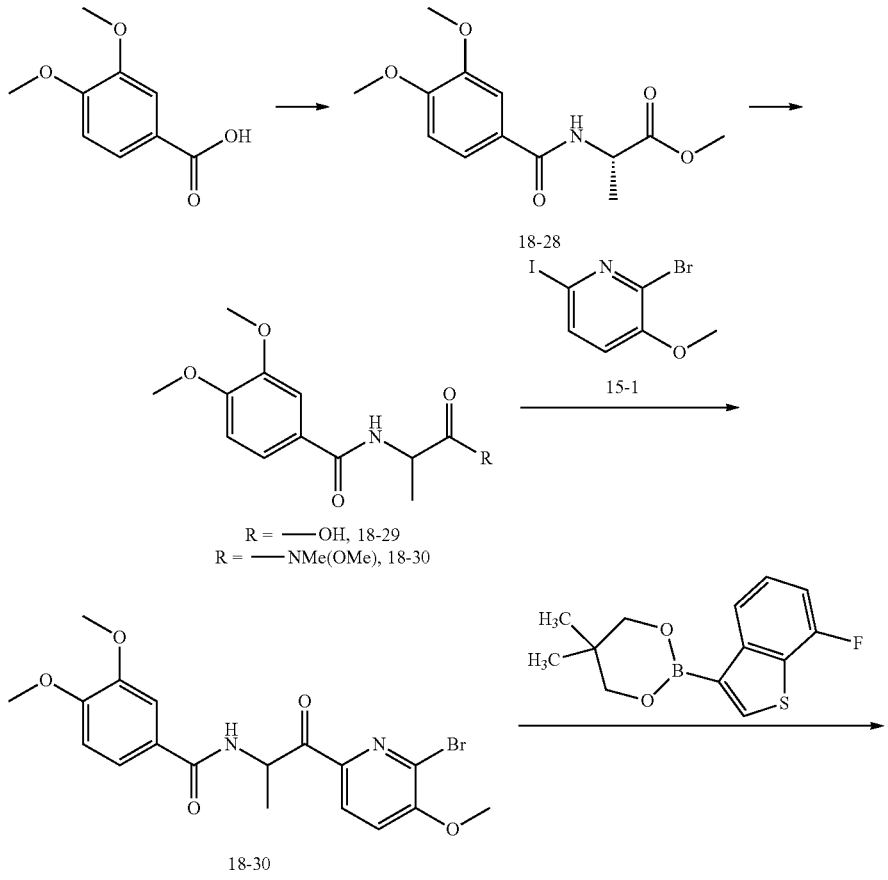

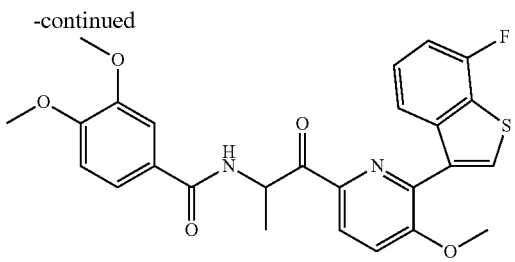

1824

A mixture of 3,4-dimethoxybenzoic acid (700 mg, 3.84 mmol), HOBT (934 mg, 6.91 mmol), EDC (1.03 g, 5.38 mmol), methyl (2S)-2-aminopropanoate hydrochloride (804 mg, 5.76 mmol) and TEA (1.50 mL, 10.8 mmol) in DCM (17 mL) was stirred at rt for 2 h. A 1M aq HCl solution was added and the mixture was stirred until a white solid precipitated. The mixture was filtered from the solids and the layers separated. The organic portion was washed with 1M aq HCl solution, dried (Na$_2$SO$_4$), filtered and concentrated under reduced pressure. Crude 18-28 (1.03 g) was used in the next step. UPLC/MS(ES$^+$), m/z: 268.11 [M+H]$^+$.

Amide 18-28 (1.03 g) was dissolved in a 4:2:1 THF-MeOH—H$_2$O mixture (17.5 mL) and treated with LiOH—H$_2$O (461 mg, 9.60 mmol). After 30 mins, the volatiles were removed under reduced pressure. The residue was partitioned between EtOAc and 1M aq HCl solution, and the layers were separated. The organic portion was dried (Na$_2$SO$_4$), filtered and concentrated under reduced pressure to afford 18-29 (909 mg). UPLC/MS(ES$^+$), m/z: 254.09 [M+H]$^+$.

A mixture of 18-29 (900 mg), HOBT (865 mg, 6.40 mmol), EDC (744 mg, 7.63 mmol), TEA (1.39 mL, 9.96 mmol) and N,O-Dimethylhydroxylamine hydrochloride (744 mg, 7.63 mmol) in DCM (20 mL) was stirred at rt for 1 h. vA 1M aq HCl solution was added and the mixture was stirred at rt for 10 mins. The mixture was filtered from the precipitate and the phases were separated. The organic portion was washed with 1M aq HCl solution, dried (Na$_2$SO$_4$), filtered and concentrated under reduced pressure. Crude 18-30 (914 mg) was used in the next step without further purification. UPLC/MS(ES$^+$), m/z: 297.10 [M+H]$^+$.

A 2M i-PrMgCl solution in THF (6.35 mL, 12.7 mmol) was added dropwise to a solution of 15-1 (2.0 g, 6.37 mmol) in dry THF (10 mL). After 40 mins, a Grignard reagent was added to a solution of 18-30 (1.20 g, 4.26 mmol) in THF (10 mL), which had been pre-heated to 40° C. The mixture was stirred at 40° C. for 1 h. The mixture was partitioned between saturated aq NH$_4$Cl solution and EtOAc, and the layers were separated. The organic portion was dried (Na$_2$SO$_4$), filtered and concentrated under reduced pressure. Chromatography of the residue (cyclohexane-EtOAc, 100:0 to 0:100) afforded 18-31.

A mixture of 18-31, 2-(7-fluoro-1-benzothiophen-3-yl)-5,5-dimethyl-1,3,2-dioxaborinane (86 mg, 0.325 mmol), Pd(dppf)Cl$_2$ (21.6 mg, 0.030 mmol) and KF (69.0 mg, 1.18 mmol) in DMF (4 mL) was degassed and stirred with heat at 85° C. for 4 h. The mixture was diluted with water and extracted three times with EtOAc. The combined organic portions were dried (Na$_2$SO$_4$), filtered and concentrated under reduced pressure. Chromatography of the residue (cyclohexane-EtOAc, 100:0 to 0:100) followed by trituration of the collected fractions with MeOH afforded compound 1824 as a white solid (35 mg). UPLC/MS(ES$^+$), m/z: 495.14 [M+H]$^+$.

Example 18-10

Preparation of Compound 1825

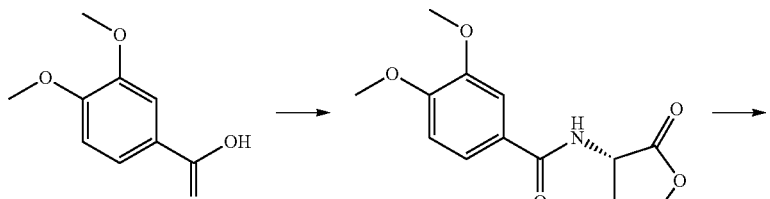

18-32

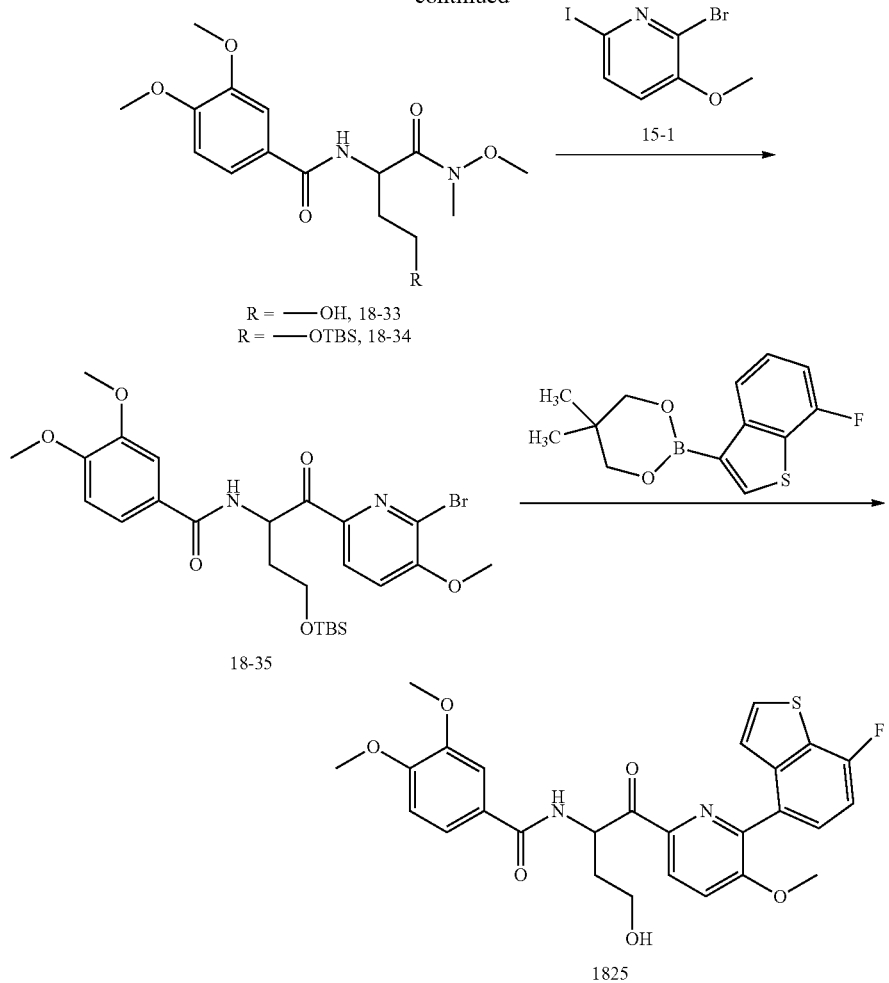

A mixture of 3,4-dimethoxybenzoic acid (500 mg, 2.74 mmol), NMM (452 uL, 4.12 mmol) and 2-chloro-4,6-dimethoxy-1,3,5-triazine (671 mg, 3.84 mmol) in CH$_3$CN (10 mL) was stirred at rt for 30 mins. A mixture of (3S)-3-aminooxolan-2-one hydrochloride (484 mg, 3.56 mmol) and NMM (391 uL, 3.56 mmol) in CH$_3$CN-DMF (2:1, 3 mL) was added and the mixture was stirred at rt for 1.5 h. The volatiles were removed under reduced pressure and the residue was dissolved in EtOAc. The organic portion was washed with 1M aq HCl and brine, dried (Na$_2$SO$_4$), filtered and concentrated under reduced pressure. Crude 18-32 (1.0 g) was used in the next step without further purification. UPLC/MS(ES$^+$), m/z: 266.10 [M+H]$^+$.

Pyridine (301 uL, 3.73 mmol) and AlMe$_3$ (2M solution in heptanes, 2.52 mL, 5.07 mmol) were added to a suspension of MeONHMe-HCl (492 mg, 5.07 mmol) in DCM (6 mL). After 15 mins, a solution of 18-32 (450 mg) in DCM (2 mL) was added dropwise. The mixture was stirred at rt for 18 h, then cooled to 0° C. and quenched with 1M aq HCl solution. The organic portion was diluted with DCM and washed with 1M aq HCl solution and brine, dried (Na$_2$SO$_4$), filtered and concentrated under reduced pressure. Crude 18-33 (310 mg) was used in the next step without further purification.

DIPEA (331 uL, 1.90 mmol) and TBSCl (214 mg, 1.42 mmol) were added to a solution of 18-33 (310 mg) in DCM. After 16 h at rt, the mixture was diluted with DCM and washed with water and brine, dried (Na$_2$SO$_4$), filtered and concentrated under reduced pressure. Chromatography of the residue (cyclohexane-EtOAc, 100:0 to 0:100) afforded 18-34 (220 mg). UPLC/MS(ES$^+$), m/z: 441.30 [M+H]$^+$.

A 2M i-PrMgCl solution in THF (852 uL, 1.70 mmol) was added dropwise to a solution of 18-34 (300 mg, 0.682 mmol) and 15-1 (319 mg, 1.02 mmol) in dry THF (12 mL). The mixture was stirred at rt for 1 h and then quenched with 1M aq HCl solution. The aqueous portion was extracted with EtOAc. The combined organic portions were dried (Na$_2$SO$_4$), filtered and concentrated under reduced pressure. Crude 18-35 was used in the next step without further purification.

A 1M TBAF solution in THF (1.5 mL) was added to a stirred solution of 18-35 in THF (1.5 mL). After 2 h, the mixture was diluted with EtOAc and washed with water. The organic portion was dried (Na$_2$SO$_4$), filtered and concentrated under reduced pressure. Crude 18-36 (structure not shown) was used in the next step without further purification.

A mixture of 18-36, 2-(7-fluoro-1-benzothiophen-3-yl)-5,5-dimethyl-1,3,2-dioxaborinane (100 mg, 0.378 mmol), Pd(dppf)Cl$_2$ (10 mg, 0.014 mmol) and aq Na$_2$CO$_3$ (2M solution, 150 uL, 300 mmol) in DCE (2 mL) was degassed and stirred with heat at 85° C. for 2 h. Water and DCM were added, and the layers were separated. The organic portion was dried (Na$_2$SO$_4$), filtered and concentrated under reduced pressure. Chromatography of the mixture (EtOAc-MeOH, 100:0 to 95:5) afforded compound 1825 (25 mg, 7% over three steps). UPLC/MS(ES$^+$), m/z: 525.15 [M+H]$^+$.

Example 18-11
Preparation of Compound 1826
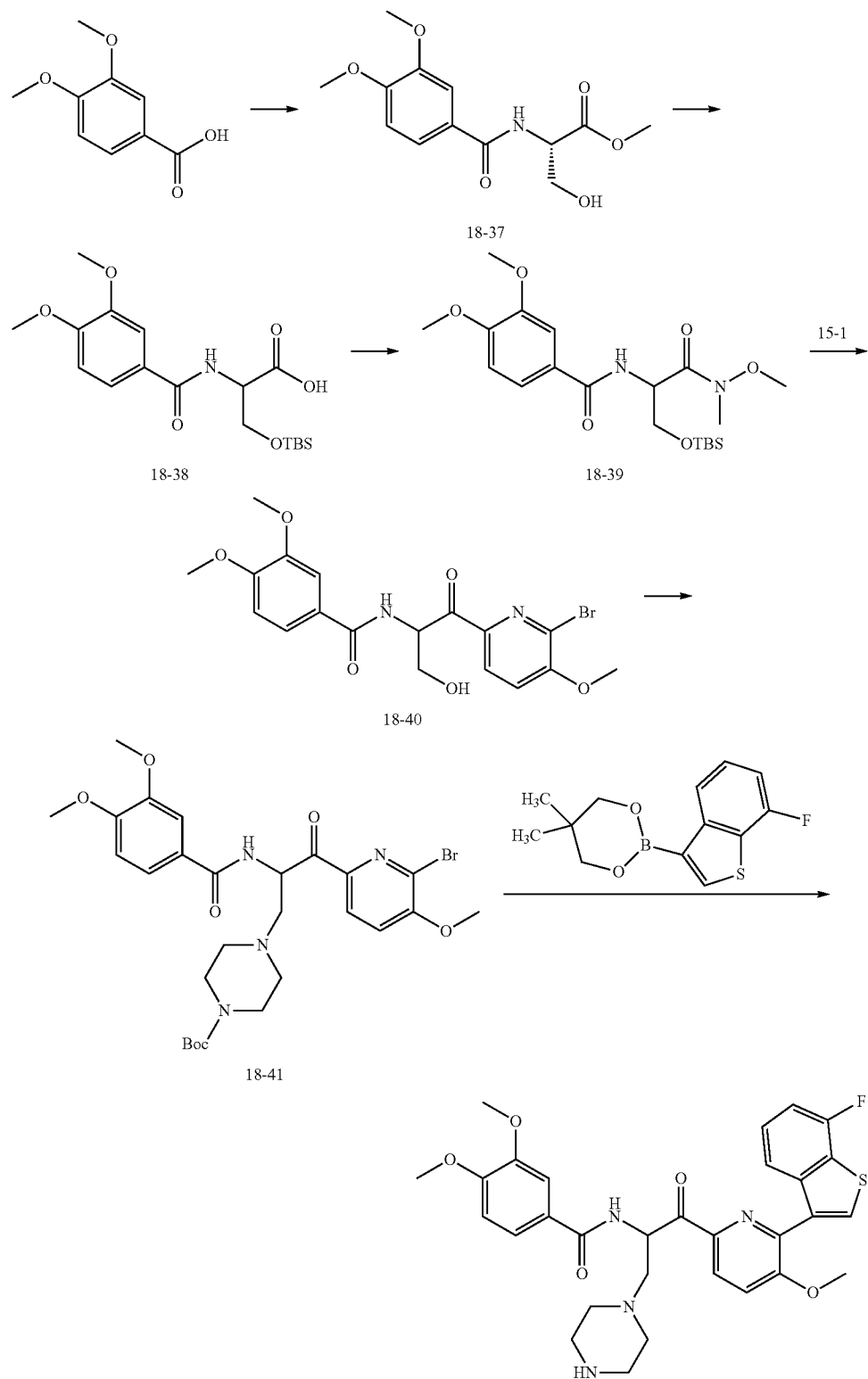

4-Methylmorpholine (1.80 mL, 16.9 mmol) was added to a mixture of 2-chloro-4,6-dimethoxy-1,3,5-triazine (1.60 g, 9.10 mmol) and 3,4-dimethoxybenzoic acid (1.20 g, 6.50 mmol) in $CH_3CN$ (35 mL). The mixture was stirred at rt for 1 h, then (DL)-serine methyl ester hydrochloride (1.60 g, 10.4 mmol) was added. The mixture was stirred at rt for 1 h. The volatiles was removed under reduced pressure. The residue was dissolved in EtOAc and washed with 1M aq HCl solution. The organic portion was dried ($Na_2SO_4$), filtered and concentrated under reduced pressure to afford crude 18-37 (2.0 g).

A mixture of 18-37 (350 mg, 1.24 mmol), TBSCl (224 mg, 1.49 mmol) and TEA (258 uL, 1.85 mmol) in DCM (7 mL) was stirred at rt for 20 h. The mixture was washed with water. The organic portion was dried ($Na_2SO_4$), filtered and concentrated under reduced pressure to afford the crude TBS-protected alcohol, which was used in the next step. The crude TBS-protected alcohol was dissolved in a 2:1 THF-MeOH mixture (3 mL). A solution of $LiOH-H_2O$ (156 mg, 3.72 mmol) in water (1 mL) was added and the mixture was stirred at rt for 30 mins. The organic solvents were removed under reduced pressure. The aqueous portion was acidified with saturated aq $NH_4Cl$ solution and extracted three times with DCM. The combined organic portions were dried ($Na_2SO_4$), filtered and concentrated under reduced pressure to afford crude 18-38, which was used in the next step without further purification. UPLC/MS($ES^+$), m/z: 387.20 $[M+H]^+$.

A solution of 18-38, EDC (357 mg, 1.86 mmol), HOBT (251 mg, 1.86 mmol), MeNHOMe*HCl (144 mg, 1.50 mmol) and TEA (345 uL, 2.48 mmol) in DCM (4 mL) was stirred at rt for 2 h. The mixture was diluted with DCM. The organic portion was washed twice with saturated aq $NH_4Cl$ solution, dried ($Na_2SO_4$), filtered and concentrated under reduced pressure to give crude 18-39 (471 mg), which was used in the next step without further purification.

A 2M i-PrMgCl solution in THF (1.55 mL, 3.10 mmol) was added dropwise to a solution of 18-39 (471 mg) and 15-1 (580 mg, 1.86 mmol) in dry THF (5 mL). The mixture was stirred at rt for 10 mins, then further i-PrMgCl (500 uL) was added. After 10 mins, the reaction was quenched with saturated aq $NH_4Cl$ solution and the aqueous portion was extracted with EtOAc. The combined organic portions were dried ($Na_2SO_4$), filtered and concentrated under reduced pressure. Chromatography of the residue (cyclohexane-EtOAc, 70:30 to 0:100) afforded the desired TBS-protected alcohol as a pale yellow wax (305 mg, 57% over four steps). $^1$H NMR (400 MHz, $CDCl_3$) δ ppm −0.05, −0.12 (2×s, 6H), 0.81 (s, 9H), 3.95-4.01 (m, 7H), 4.05 (s, 3H), 4.21 (dd, J=10.5, 3.3 Hz, 1H), 4.42 (dd, J=10.5, 3.0 Hz, 1H), 6.00-6.08 (m, 1H), 6.95 (d, J=8.3 Hz, 1H), 7.24-7.29 (m, 1H), 7.37 (d, J=7.5 Hz, 1H), 7.44-7.53 (m, 2H), 8.10 (d, J=8.5 Hz, 1H).

The TBS-protected alcohol was dissolved in THF (5 mL) and TBAF (1M solution in THF, 1.07 mL, 1.07 mmol) was added to the solution. After 45 mins, EtOAc was added. The organic portion was washed with brine, dried ($Na_2SO_4$), filtered and concentrated under reduced pressure. Crude 18-40 was used in the next step without further purification. UPLC/MS($ES^+$), m/z: 439.04 $[M+H]^+$.

A solution of 18-40, MsCl (65 uL, 0.828 mmol) and TEA (115 uL, 0.828 mmol) in DCM (3 mL) was stirred at rt for 5 h. The volatiles were removed under reduced pressure. The residue was dissolved in TEA (1 mL) and 1-Boc piperazine (720 mg, 3.86 mmol) was added. The mixture was heated to 50° C. and stirred for 18 h. The volatiles were removed under reduced pressure. Crude 18-41 was directly progressed to the next step.

A mixture of 18-41, 2-(7-fluoro-1-benzothiophen-3-yl)-5,5-dimethyl-1,3,2-dioxaborinane (100 mg, 0.378 mmol), Pd(dppf)$Cl_2$ (10 mg, 0.014 mmol) and aq $Na_2CO_3$ (2M solution, 150 uL, 300 mmol) in DCE (2 mL) was degassed and stirred with heat at 85° C. for 2 h. Water and DCM were added, and the layers were separated. The organic portion was dried ($Na_2SO_4$), filtered and concentrated under reduced pressure. Chromatography of the mixture (EtOAc-MeOH, 100:0 to 95:5) afforded the Boc-protected piperazine (55 mg, 15% overall yield). The Boc-protected piperazine (20 mg, 0.029 mmol) was dissolved in MeOH (2 mL) and treated with a 1M HCl solution in $Et_2O$ (1 mL). The mixture was stirred at rt for 3 h. The volatiles were removed under reduced pressure. The residue was purified by reverse phase chromatography (water-$CH_3CN$, 100:0 to 0:100) to afford compound 1826 as an off-white solid (4 mg, 24%). UPLC/MS($ES^+$), m/z: 579.20 $[M+H]^+$.

Example 18-12

Preparation of Compounds 1829 and 1830

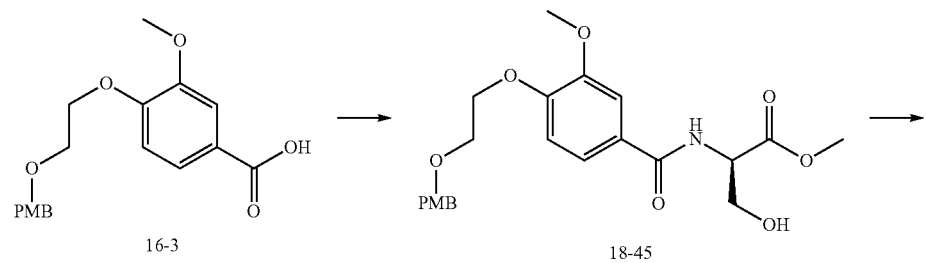

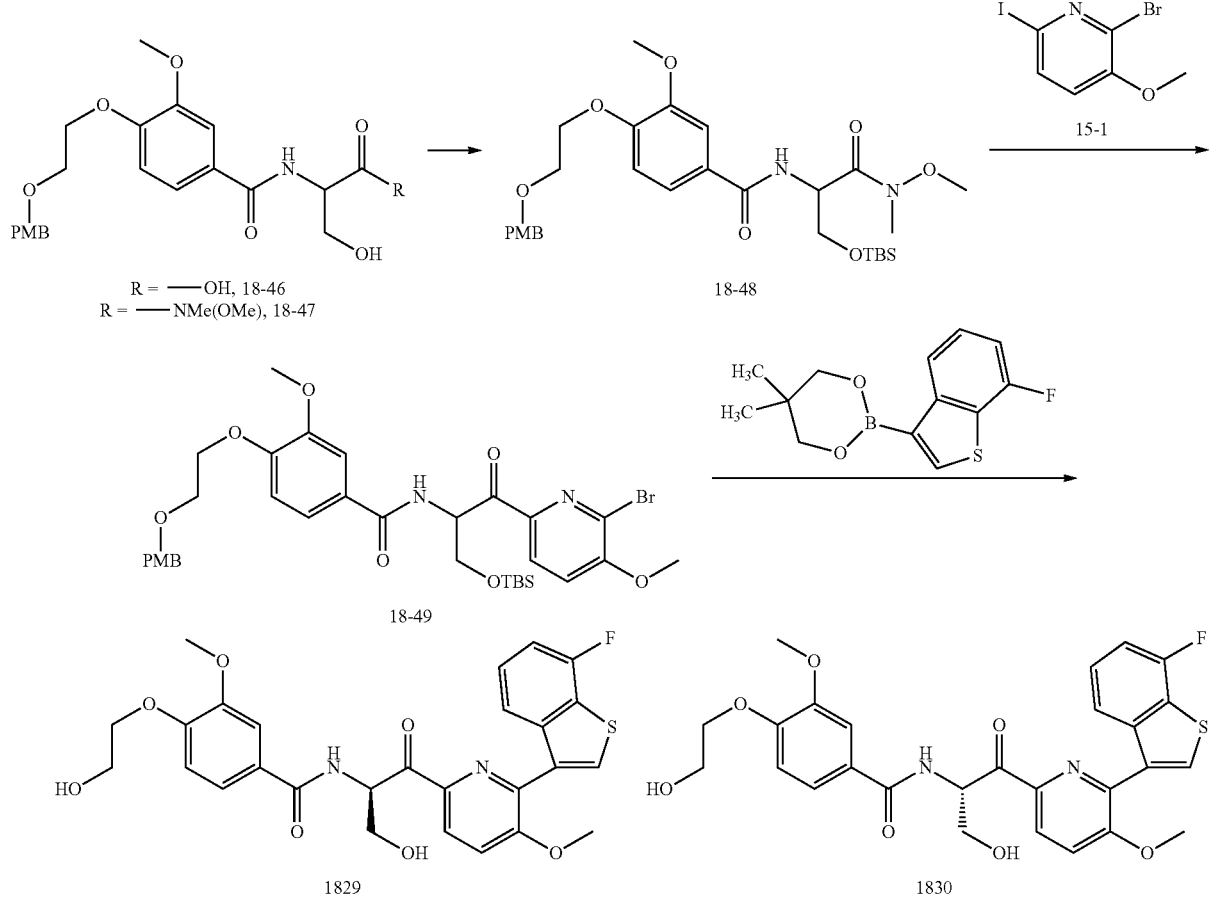

A mixture of acid 16-3 (1.00 g, 3.01 mmol), HOBT (732 mg, 5.42 mmol), EDC (807 mg, 4.21 mmol), TEA, 750 uL, 5.42 mmol) and D-serine methyl ester hydrochloride (700 mg, 4.51 mmol) in DCM (18 mL) was stirred at rt for 2 h. A 1M HCl solution was added and the mixture was stirred at rt for 10 mins. The mixture was filtered from the solids and the layers were separated. The organic portion was washed with 1M aq HCl solution, dried (Na$_2$SO$_4$), filtered and concentrated under reduced pressure. Crude 18-45 was used the next step without further purification. UPLC/MS (ES$^+$), m/z: 434.25 [M+H]$^+$.

Amide 18-45 was dissolved in a 2:1:1 THF-MeOH—H$_2$O mixture (20 mL) and treated with LiOH—H$_2$O (379 mg, 9.03 mmol). After 30 mins, the volatiles were removed under reduced pressure. The residue was partitioned between DCM and 1M aq HCl solution. The layers were separated and the organic portion was dried (Na$_2$SO$_4$), filtered and concentrated under reduced pressure to afford 18-46 (1.13 g). UPLC/MS(ES$^+$), m/z: 420.24 [M+H]$^+$.

A mixture of 18-46 (1.13 g), HOBT (654 mg, 4.84 mmol), EDC (722 mg, 3.77 mmol), TEA (670 mL, 4.84 mmol) and N,O-Dimethylhydroxylamine hydrochloride (394 mg, 4.03 mmol) in DCM (16 mL) was stirred at rt for 1 h. A 1M aq HCl solution was added and the mixture was stirred at rt for 10 mins. The mixture was filtered from the precipitate and the phases were separated. The organic portion was washed with 1M aq HCl solution, dried (Na$_2$SO$_4$), filtered and concentrated under reduced pressure. Crude 18-47 (1.15 g) was used the next step without further purification. UPLC/MS(ES$^+$), m/z: 463.20 [M+H]$^+$.

A mixture of 18-47 (1.15 g), TEA (1.03 mL, 7.44 mmol) and TBSCl (744 mg, 4.96 mmol) in DCM (10 mL) was stirred at rt for 72 h. The volatiles were removed under reduced pressure. Chromatography of the residue (cyclohexane-EtOAc, 80:20 to 40:60) afforded 18-48 as a colourless oil (742 mg, 43% over four steps). UPLC/MS(ES$^+$), m/z: 577.43 [M+H]$^+$.

A 2M i-PrMgCl solution in THF (1.58 mL, 3.17 mmol) was added dropwise to a solution of 15-1 (599 mg, 1.91 mmol) and 18-48 (735 mg, 1.27 mmol) in dry THF (15 mL). The mixture was stirred at rt for 1 h and then quenched with MeOH and water. The volatiles were removed under reduced pressure. The aqueous portion was extracted with EtOAc, dried (Na$_2$SO$_4$), filtered and concentrated under reduced pressure. Chromatography of the residue (cyclohexane-EtOAc, 80:20 to 50:50) afforded 18-49 as a pale yellow solid (437 mg, 49%). UPLC/MS(ES$^+$), m/z: 703.21 [M+H]$^+$.

A mixture of 18-49 (0.600 mmol), -(7-fluoro-1-benzothiophen-3-yl)-5,5-dimethyl-1,3,2-dioxaborinane (1.51 mmol), Pd(dppf)Cl$_2$ (0.042 mmol) and aq Na$_2$CO$_3$ (2M solution, 1.50 mmol) in DME (5 mL) was degassed and heated to 85° C. The reaction was monitored by TLC and UPLC. The mixture was diluted with water and extracted three times with EtOAc. The combined organic portions were dried (Na$_2$SO$_4$), filtered, concentrated under reduced pressure, and chromatographed. The compound was dissolved in a 10:1 DCM-TFA solution. The mixture was stirred at rt until disappearing of the starting material. The mixture was diluted with DCM and the organic portion was washed with 1M aq NaOH solution and brine, dried (Na$_2$SO$_4$), filtered and concentrated under reduced pressure. The mixture of compounds (29 mg) was resolved by using a prep-HPLC separation [Chiralpak IB column (25×2.0 cm, 5 uM), mobile phase: n-Hexane/(Ethanol/Methanol 1/1) 75/25% v/v, flow rate: 14 mL/min, UV detection DAD 220 nm] to obtain compound 1829 (8.0 mg, enantiomer 1 (R), $t_R$ 14.5 min) and compound 1830 (11.9 mg, enantiomer 2 (S), $t_R$ 16.4 min) based on the order of elution. UPLC and $^1$H NMR analyses for the two enantiomers were superimposible. UPLC/MS (ES$^+$), m/z: 541.19 [M+H]$^+$.

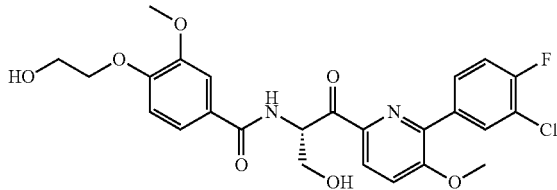

1832

Compounds 1831 and 1832 (40 mg, 14% over two steps) were prepared starting from 18-49 and (3-chloro-4-fluorophenyl)boronic acid by following a synthetic route, which closely follows that described for preparation of compounds 1829 and 1830. Compound 1831 (22.2 mg, enantiomer 1 (R), $t_R$ 14.4 min) and compound 1832 (14.9 mg, enantiomer 2 (S), $t_R$ 16.7 min) based on the order of elution. UPLC and $^1$H NMR analyses for the two enantiomers were superimposible. UPLC/MS(ES$^+$), m/z. found 519.25 [M+H]$^+$.

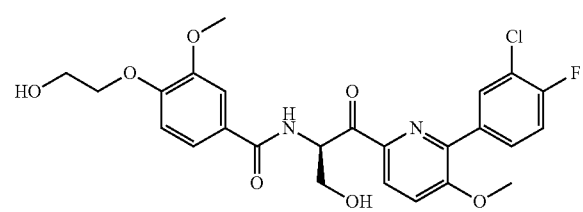

1831

Example 18-13

Preparation of Compounds 1833 and 1834

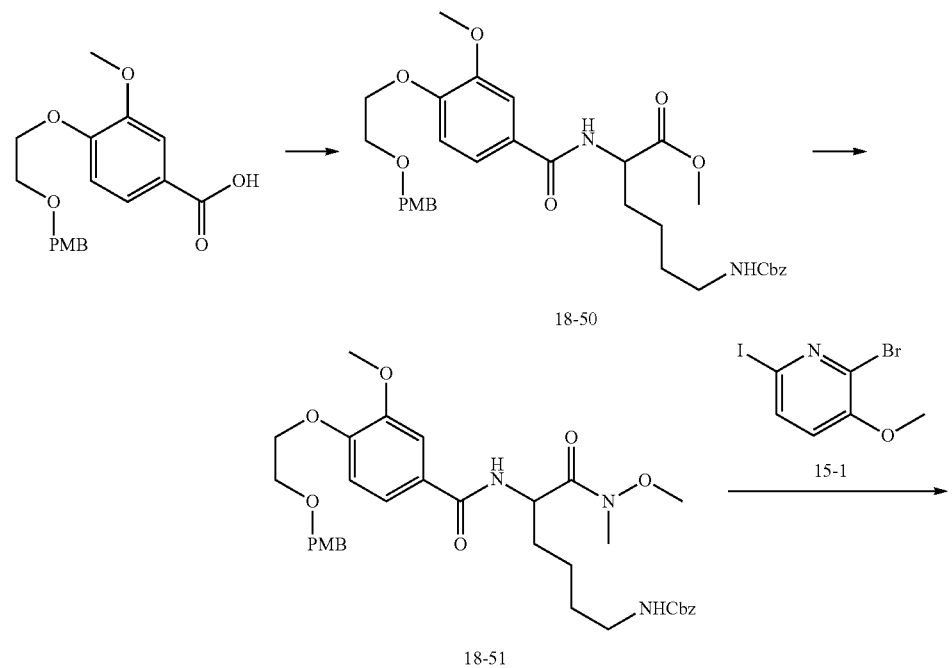

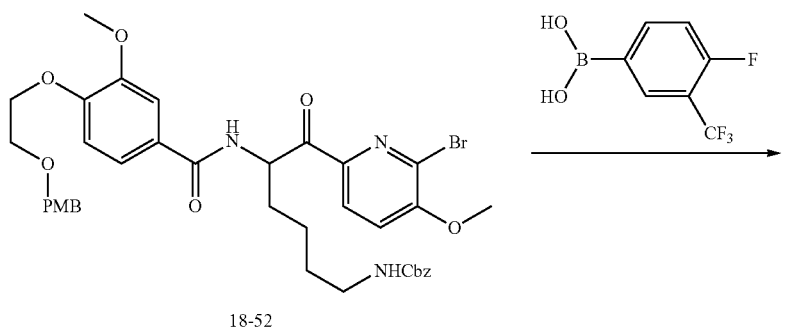

-continued

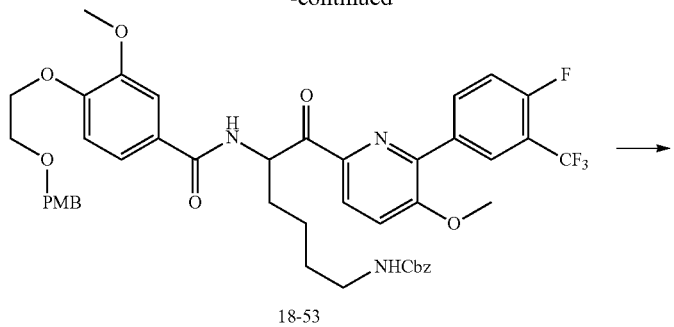

18-53

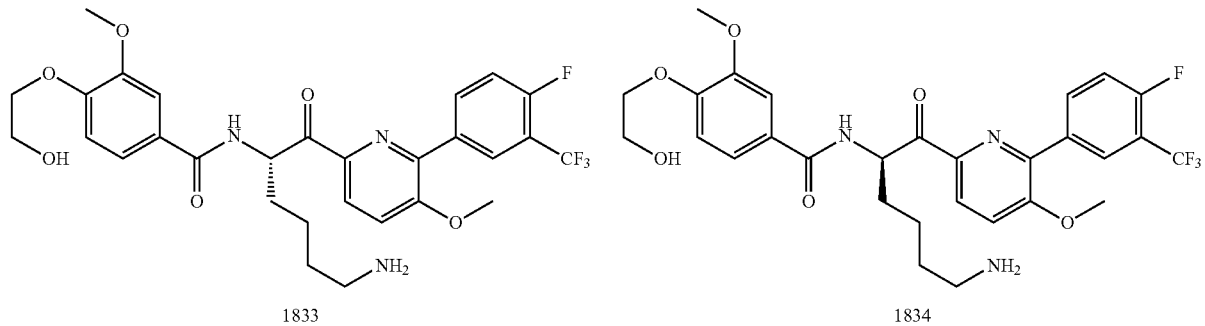

1833

1834

A mixture of acid 16-3 (750 mg, 2.25 mmol), HOBT (548 mg, 4.06 mmol), EDC (603 mg, 3.15 mmol), TEA (565 uL, 4.06 mmol) and methyl 2-amino-6-{[(benzyloxy)carbonyl]amino}hexanoate (990 mg, 3.37 mmol) in DCM (18 mL) was stirred at room temp for 3 h. A 1M HCl solution was added and the mixture was stirred at room temp for 10 mins. The mixture was filtered from the solids and the layers were separated. The organic portion was washed with 1M aq HCl solution, dried (Na$_2$SO$_4$), filtered and concentrated under reduced pressure. Chromatography of the residue (cyclohexane-EtOAc, 60:40 to 30:70) afforded 18-50 (2.10 g). UPLC/MS(ES$^+$), m/z: 609.40 [M+H]$^+$.

Amide 18-50 (2.10 g) was dissolved in a 2:1:1 THF-MeOH—H$_2$O mixture (24 mL) and treated with LiOH—H$_2$O (435 mg, 10.3 mmol). After 30 mins, the volatiles were removed under reduced pressure. The residue was partitioned between DCM and 1M aq HCl solution. The layers were separated and the organic portion was dried (Na$_2$SO$_4$), filtered and concentrated under reduced pressure to afford the acid (1.60 g), which was used in the next step. The acid was dissolved in DCM (20 mL), and HOBT (656 mg, 4.80 mmol), EDC (722 mg, 3.77 mmol), TEA (670 mL, 4.84 mmol) and N,O-Dimethylhydroxylamine hydrochloride (394 mg, 4.05 mmol) were added to the solution. The mixture was stirred at rt for 3 h. A 1M aq HCl solution was added and the mixture was stirred at rt for 10 mins. The mixture was filtered from the precipitate and the phases were separated. The organic portion was washed with 1M aq HCl solution, dried (Na$_2$SO$_4$), filtered and concentrated under reduced pressure. Chromatography of the residue (cyclohexane-EtOAc, 60:40 to 0:100) afforded 18-51 (820 mg, 57% over three steps). UPLC/MS(ES$^+$), m/z: 638.45 [M+H]$^+$.

A 2M i-PrMgCl solution in THF (1.60 mL, 3.20 mmol) was added dropwise to a solution of 15-1 (600 mg, 1.92 mmol) and 18-51 (820 mg, 1.28 mmol) in dry THF (16 mL). The mixture was stirred at rt for 30 mins and then quenched with 1M aq HCl solution. The aqueous portion was extracted with EtOAc, dried (Na$_2$SO$_4$), filtered and concentrated under reduced pressure. Chromatography of the residue (cyclohexane-EtOAc, 60:40 to 20:80) afforded 18-52 as an off-white solid (420 mg, 43%). UPLC/MS(ES$^+$), m/z: found 764.57 [M+H]$^+$.

Suzuki coupling. A mixture of 18-52 (0.410 mmol), [4-fluoro-3-(trifluoromethyl)phenyl]boronic acid (1.04 mmol), Pd(dppf)Cl$_2$ (0.020 mmol) and aq Na$_2$CO$_3$ (2M solution, 1.04) in DCE (2.5 mL) was degassed and heated to 85° C. The reaction was monitored by TLC and UPLC. The mixture was diluted with water and extracted three times with EtOAc. The combined organic portions were dried (Na$_2$SO$_4$), filtered, concentrated under reduced pressure and chromatographed.

PMB-group removal. A solution of PMB-ether (0.10 mmol) in a 10:1 DCM-TFA mixture (1.1 mL) was stirred at rt until disappearing of the starting material. The mixture was diluted with DCM. The organic portion was washed with 1M aq NaOH solution and brine, dried (Na$_2$SO$_4$), filtered, concentrated under reduced pressure and chromatographed.

Hydrogenation for Cbz-removal. A mixture of Pd/C (10% wet, Degussa type, catalytic) and Cbz-protected amine (0.110 mmol) in EtOH (2 mL) was stirred under H$_2$ atmosphere (1 atm) for 2 h. The mixture was filtered and concentrated under reduced pressure to afford the crude amine, a mixture of compounds 1833 and 1834. This mixture of compounds (20 mg) was resolved by using a prep-HPLC separation [Chiralpak IB column (25×2.0 cm, 5 uM), mobile phase: n-Hexane/(Ethanol/Methanol 1/1) 75/25% v/v, flow rate: 15 mL/min, UV detection DAD 220 nm] to obtain compound 1833 (1.5 mg, enantiomer 1, t$_R$ 12.2 min) and compound 1834 (1.0 mg, enantiomer 2, t$_R$ 14.3 min) based on the order of elution. UPLC and $^1$H NMR analyses for the two enantiomers were superimposible. UPLC/MS (ES$^+$), m/z. found 594.27 [M+H]$^+$.

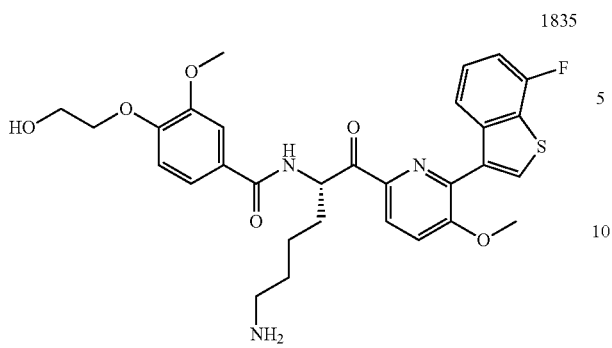

1835

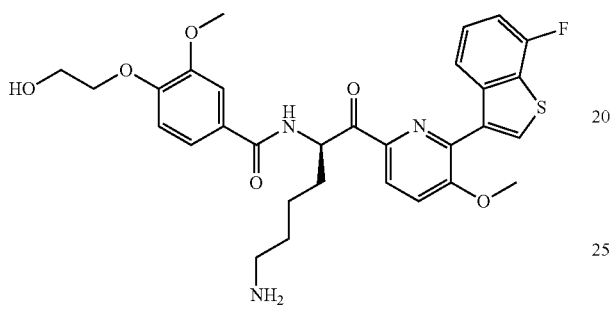

1836

Compounds 1835 and 1836 (200 mg) were prepared starting from 18-52 and 2-(7-fluoro-1-benzothiophen-3-yl)-5,5-dimethyl-1,3,2-dioxaborinane by following a synthetic route, which closely follows that described for preparation of compounds 1833 and 1834.

Compound 1835 (22 mg, enantiomer 1, $t_R$ 21.0 min) and compound 1836 (17 mg, enantiomer 2, $t_R$ 27.6 min) based on the order of elution separation [Chiralpak IC (25×0.46 cm), 5 um), mobile phase: n-Hexane/(Ethanol+0.1% isopropylamine) 80/20% v/v]. UPLC and $^1$H NMR analyses for the two enantiomers were superimposible. UPLC/MS(ES$^+$), m/z. found 582.27 [M+H]$^+$.

Example 19-1

Preparation of Compounds 1900, 1901 and 1902

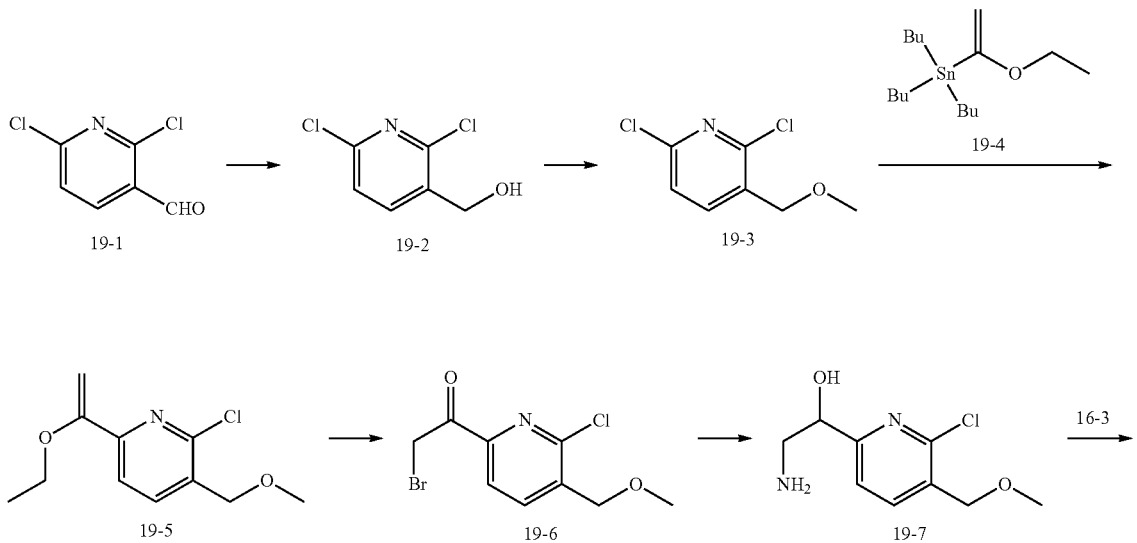

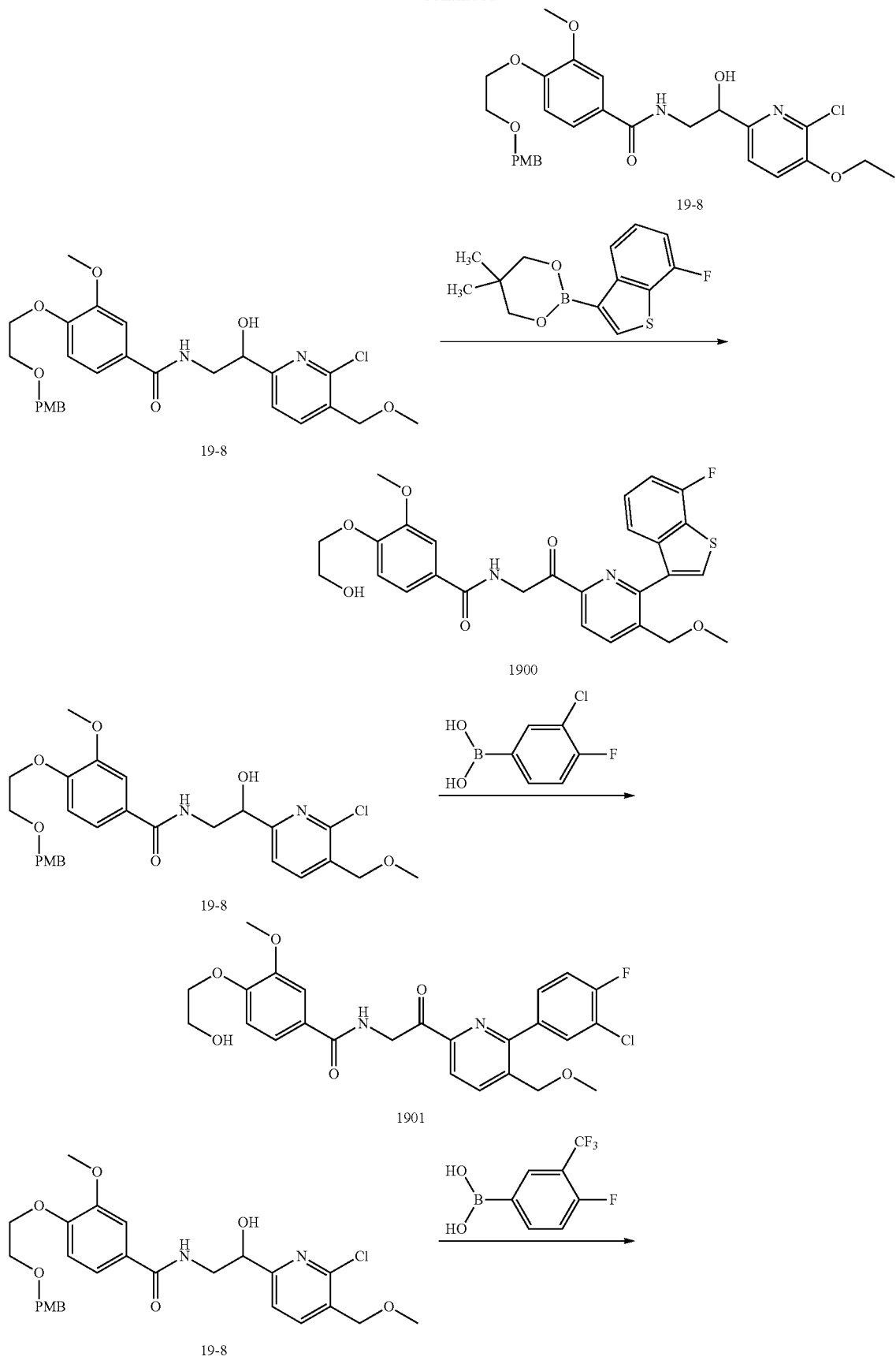

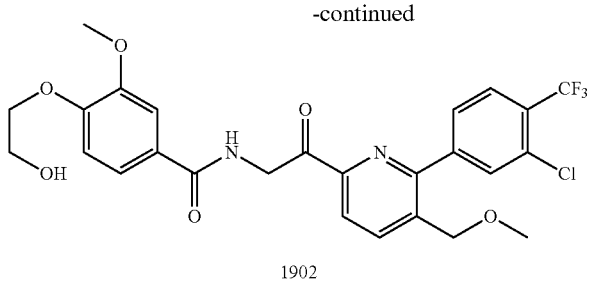

1902

NaBH₄ (476 mg, 12.5 mmol) was added to a solution of 19-1 (2.00 g, 11.4 mmol) in MeOH (25 mL), which had been pre-cooled to 0° C. The mixture was allowed to warm to rt and stirred for 30 mins. A 1M aq HCl solution was added and the organic solvent was removed under reduced pressure. The aqueous phase was extracted three times with DCM. The combined organic portions were dried (Na₂SO₄), filtered and concentrated under reduced pressure to afford crude 19-2 (2.05 g), which was used in the next step without further purification. UPLC/MS(ES⁺), m/z: 178.00 [M+H]⁺.

NaH (547 mg, 13.7 mmol) was added to a solution of 19-2 (2.05 g) in dry THF (20 mL), which had been pre-cooled to 0° C. After 20 mins, MeI (1.78 g, 12.5 mmol) was added and the mixture was allowed to warm to rt. After 1 h, the reaction was quenched with 1M aq HCl solution. The layers were separated and the organic portion was washed with brine, dried (Na₂SO₄), filtered and concentrated under reduced pressure. Crude 19-3 (2.50 g) was used in the next step without further purification.

A mixture of 19-3 (2.50 g), Pd(PPh₃)₂Cl₂ (365 mg, 0.52 mmol) and 19-4 (1.77 mL, 5.23 mmol) in 1,4-dioxane (9 mL) was degassed and heated to 90° C. After 1.5 h, the mixture was diluted with EtOAc. The organic portion was washed twice with brine, dried (Na₂SO₄), filtered and concentrated under reduced pressure to afford crude 19-5, which was used in the next step without further purification.

NBS (1.40 g, 7.84 mmol) was added to a solution of 19-5 in THF (16 mL), which had been pre-cooled to 0° C. The mixture was stirred at 0° C. for 45 mins, and then warmed to rt. The reaction was quenched with water, and the layers were separated. The organic portion was washed with brine, dried (Na₂SO₄), filtered and concentrated under reduced pressure. Chromatography of the residue (cyclohexane-EtOAc, 100:0 to 50:50) afforded 19-6 as a white solid (410 mg, 28% over three steps). UPLC/MS(ES⁺), m/z: 277.99 [M+H]⁺

NaBH₄ (56.0 mg, 1.48 mmol) was added to a solution of 19-6 (410 mg, 1.48 mmol) in MeOH (15 mL). The mixture was stirred at rt for 30 mins. A 1M aq HCl solution was added and the organic solvent was removed under reduced pressure. The aqueous phase was extracted three times with DCM. The combined organic portions were dried (Na₂SO₄), filtered and concentrated under reduced pressure to afford the crude alcohol (396 mg), which was used the next step without further purification. The crude alcohol was dissolved in a 7M NH₃-MeOH solution (10 mL). The mixture was stirred at rt for 28 h. The volatiles were removed under reduced pressure to give crude 19-7 which was used in the next step without further purification. UPLC/MS(ES⁺), m/z: 217.10 [M+H]⁺.

A mixture of 19-7, acid 16-3 (637 mg, 1.92 mmol), EDC (426 mg, 2.22 mmol), HOBT (300 mg, 2.22 mmol) and TEA (411 uL, 2.96 mmol) in DCM (7 mL) was stirred at rt for 14 h. The mixture was washed twice with 1M aq HCl solution. The organic portion was dried (Na₂SO₄), filtered and concentrated under reduced pressure. Chromatography of the residue (cyclohexane-EtOAc, 100:0 to 0:100) afforded 19-8 as a white foam (400 mg, 51% over three steps). UPLC/MS (ES⁺), m/z: 531.20 [M+H]⁺.

A mixture of 19-8 (100 mg, 0.188 mmol), the dioxaborinane (124 mg, 0.470 mmol), Pd(dppf)Cl₂ (9.6 mg, 0.013 mmol) and aq Na₂CO₃ (2M solution, 282 uL, 0.564 mmol) in DME (2 mL) was degassed and heated to 85° C. After 2 h, the volatiles were removed under reduced pressure. Chromatography of the residue (cyclohexane-EtOAc, 80:20 to 0:100) afforded the protected intermediate (120 mg).

Dess-Martin periodinane (133 mg, 0.315 mmol) was added to a solution of the protected intermediate (120 mg) in dry DCM (4 mL). The mixture was stirred at rt for 2 h. A 1:1 saturated aq NaHCO₃ solution-saturated aq Na₂S₂O₃ solution was added. The mixture was stirred at rt for 30 mins and the layers were separated. The organic portion was washed with water, dried (Na₂SO₄), filtered and concentrated under reduced pressure. The crude ketone was dissolved in DCM (3 mL) and treated with TFA (200 uL). The mixture was stirred at rt for 1 h. A 2M aq NaOH solution (1 mL) was added and the mixture was stirred at rt for 10 mins. The layers were separated and the aqueous portion was extracted with DCM. The combined organic portions were dried (Na₂SO₄), filtered and concentrated under reduced pressure. Chromatography of the residue (EtOAc-MeOH, 100:0 to 80:20) afforded compound 1900 as a white solid (6 mg, 6% over three steps). UPLC/MS(ES⁺), m/z: 525.16 [M+H]⁺.

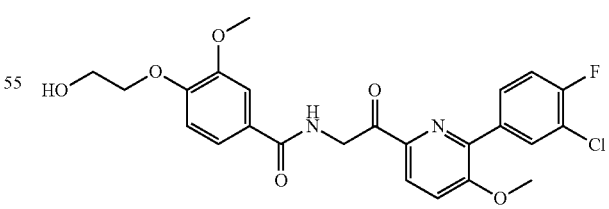

1901

Compound 1901 was prepared starting from 19-8 and (3-chloro-4-fluorophenyl)boronic acid by following a synthetic route, which closely follows that described for preparation of compound 1900. Compound 1901 was obtained as an off-white solid (5% over three steps). UPLC/MS(ES⁺), m/z: 503.13 [M+H]⁺.

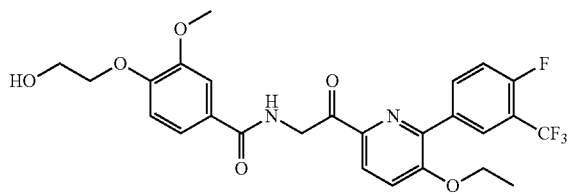

1902

Compound 1902 was prepared starting from 19-8 and [4-fluoro-3-(trifluoromethyl)phenyl]boronic acid by following a synthetic route, which closely follows that described for preparation of compound 1900. Compound 1902 was obtained as an off-white solid (7% over three steps). UPLC/MS(ES⁺), m/z: 537.20 [M+H]⁺.

Example 19-2

Preparation of Compound 1903

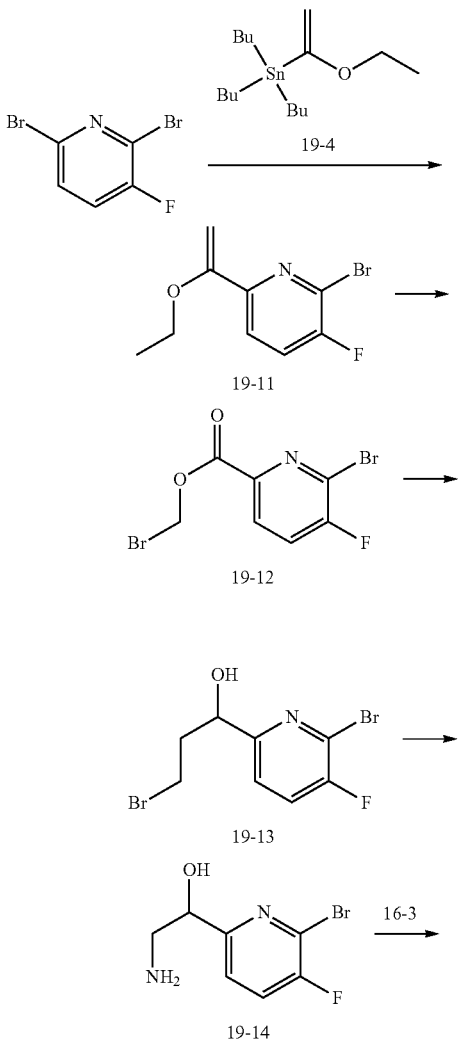

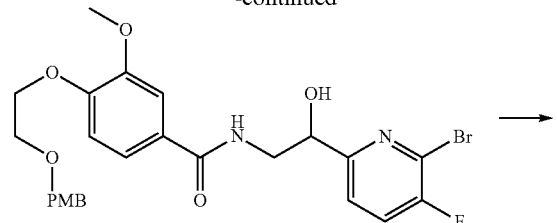

19-15

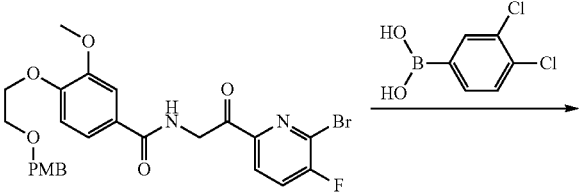

19-16

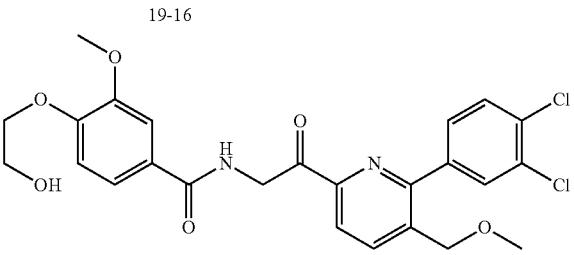

1903

A mixture of 2,6-dibromo-3-fluoropyridine (940 mg, 3.68 mmol), Pd(PPh₃)₂Cl₂ (258 mg, 0.368 mmol) and tributyl(1-ethoxyethenyl)stannane (19-4, 1.24 mL, 3.68 mmol) in 1,4-dioxane (9 mL) was degassed and heated to 90° C. After 1.5 h, the mixture was diluted with EtOAc. The organic portion was washed twice with brine, dried (Na₂SO₄), filtered and concentrated under reduced pressure. Crude 19-11 was used in the next step without further purification.

NBS (984 mg, 5.53 mmol) was added to a solution 19-11 in THF (10 mL), which had been pre-cooled to 0° C. The mixture was stirred for 45 min at 0° C., then warmed to reach rt. The reaction was quenched with water and the layers were separated. The organic portion was washed with brine, dried (Na₂SO₄), filtered and concentrated under reduced pressure. Chromatography of the residue (cyclohexane-EtOAc, 100:0 to 70:30) afforded 19-12 (420 mg, 38% over two steps). ¹H NMR (400 MHz, DMSO-d₆) δ ppm 4.97 (s, 2H), 8.04-8.23 (m, 2H).

NaBH₄ (59 mg, 1.56 mmol) was added to a solution of 19-12 (420 mg, 1.40 mmol) in MeOH (5 mL). The mixture was stirred at rt for 1 h and then quenched with 1M aq HCl solution. The methanolic portion was removed under reduced pressure and the aqueous phase was extracted three times with DCM. The combined organic portions were dried (Na₂SO₄), filtered and concentrated under reduced pressure to afford crude 19-13 (380 mg), which was used in the next step. ¹H NMR (400 MHz, DMSO-d₆) δ ppm 3.66-3.74 (m, 1H), 3.76-3.86 (m, 1H), 4.88 (q, J=4.8 Hz, 1H), 6.20 (d, J=5.3 Hz, 1H), 7.61 (dd, J=8.4, 3.6 Hz, 1H), 7.90 (t, J=8.3 Hz, 1H).

Bromide 19-13 (380 mg) was dissolved in a 7M NH₃-MeOH solution (5 mL) and the mixture was stirred at rt for 6 h. The volatiles were removed under reduced pressure to afford 19-14, which was used in the next step.

A mixture of 19-14, 3-methoxy-4-{2-[(4-methoxyphenyl)methoxy]ethoxy}benzoic acid (16-3, 548 mg, 1.65 mmol), EDC (364 mg, 1.90 mmol), HOBT (257 mg, 1.90 mmol) and TEA (353 uL, 2.54 mmol) in DCM (10 mL) was stirred at rt for 18 h. The mixture was washed with 1M aq HCl solution. The organic portion was dried ($Na_2SO_4$), filtered and concentrated under reduced pressure. Chromatography of the residue (DCM-MeOH, 100:0 to 95:5) afforded 19-15 (55.0 mg, 8% over three steps). UPLC/MS($ES^+$), m/z: 549.22 $[M+H]^+$.

Dess-Martin periodinane (72 mg, 0.170 mmol) was added to a solution of 19-15 (55 mg, 0.100 mmol) in DCM (4 mL). The mixture was stirred at rt for 1 h and additional DMP (13.0 mg, 0.030 mmol) was added. After 30 mins, a 1:1 saturated aq $NaHCO_3$ solution-saturated aq $Na_2S_2O_3$ solution was added. The mixture was stirred at rt for 40 mins and the layers were separated. The organic portion was washed with water, dried ($Na_2SO_4$), filtered and concentrated under reduced pressure to afford crude 19-16, which was used in the next step. UPLC/MS($ES^+$), m/z: 547.23 $[M+H]^+$.

A mixture of 19-16, (3,4-dichlorophenyl)boronic acid (38.0 mg, 0.200 mmol), Pd(dppf)$Cl_2$ (3.6 mg, 0.050 mmol) and aq $Na_2CO_3$ (2M solution, 150 uL, 0.300 mmol) in DCE (1.5 mL) was degassed and heated to 85° C. After 2 h, water was added to the mixture and the layers were separated. The organic portion was washed with water, dried ($Na_2SO_4$), filtered and concentrated under reduced pressure. The residue was dissolved in a 10:1 DCM-TFA solution (4 mL) and the solution was stirred at rt for 20 mins. A 2M aq NaOH solution was added and the layers were separated. The organic portion was dried ($Na_2SO_4$), filtered and concentrated under reduced pressure. Chromatography of the residue EtOAc-MeOH, 100:0 to 90:10) afforded compound 1903 as a light yellow solid (5.0 mg, 10% over three steps). UPLC/MS($ES^+$), m/z: 493.18 $[M+H]^+$.

Example 20-1

Preparation of Compound 2000

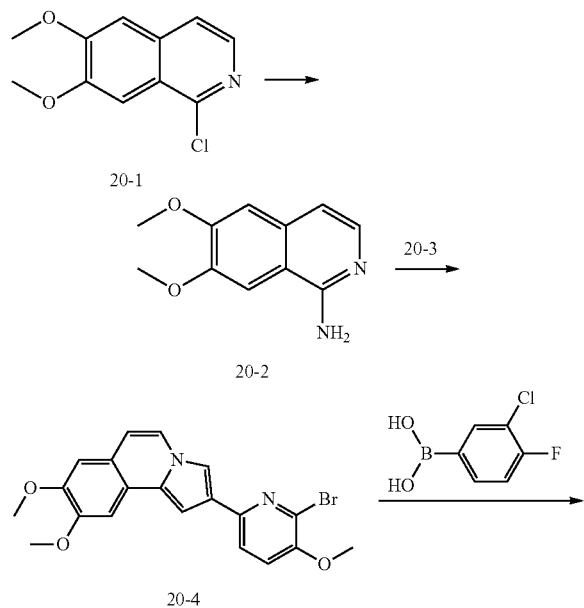

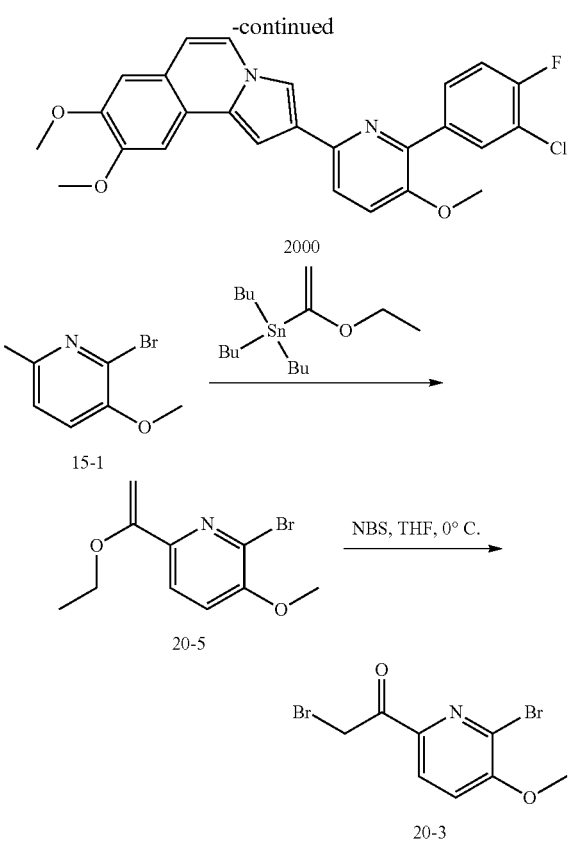

A mixture of 15-1 (1.00 g, 3.19 mmol), Pd(PPh$_3$)$_2$Cl$_2$ (224 mg, 0.319 mmol) and tributyl(1-ethoxyethenyl)stannane (0.97 mL, 2.87 mmol) in 1,4-dioxane (10 mL) was degassed, heated to 90° C. and stirred at that temp for 3 h. The reaction was quenched with saturated aq KF solution and stirred for 10 mins. The organic portion was diluted with EtOAc and washed twice with brine, dried ($Na_2SO_4$), filtered and concentrated under reduced pressure to afford crude 20-5, which was used in the next step.

NBS (738 mg, 4.15 mmol) was added to a solution of 20-5 in THF (20 mL), which had been pre-cooled to 0° C. The mixture was stirred at 0° C. for 1 h and then quenched with saturated aq $Na_2S_2O_3$ solution. The organic portion was washed with brine, dried ($Na_2SO_4$), filtered and concentrated under reduced pressure. Chromatography of the residue (cyclohexane-EtOAc, 60:40 to 30:70) afforded 20-3 as a white solid. UPLC/MS($ES^+$), m/z: 307.96 $[M+H]^+$.

To a mixture of 20-1 (200 mg, 0.890 mmol) and phenol (686 mg, 7.30 mmol) was added powdered KOH (86.5 mg, 1.54 mmol). The mixture was heated to 140° C. and stirred at that temp for 3 h. After cooling to rt, the mixture was diluted with 3M aq NaOH solution. The aqueous portion was extracted twice with DCM. The combined organic portions were dried ($Na_2SO_4$), filtered and concentrated under reduced pressure to give a phenol-ether, which was used in the next step. This phenol-ether was mixed with ammonium acetate (562 mg, 7.30 mmol). The mixture was heated to 150° C. After 18 h, the mixture was diluted with 3M aq NaOH solution. The aqueous portion was extracted twice with DCM. The combined organic portions were washed with 1M aq HCl solution, dried ($Na_2SO_4$), filtered and concentrated under reduced pressure to give 20-2 (100 mg), which was used in the next step.

A mixture of 20-2 (100 mg) and 20-3 (180 mg, 0.588 mmol) in EtOH (3 mL) was heated to reflux. After 18 h, the volatiles were removed under reduced pressure to afford crude 20-4, which was used in the next step.

A mixture of 20-4 (50 mg), (3-chloro-4-fluorophenyl) boronic acid (42.1 mg, 0.242 mmol), Pd(dppf)Cl$_2$ (2.0 mg, 0.003 mmol) and aq Na$_2$CO$_3$ (2M solution, 141 uL, 0.242 mmol) in DCE (2 mL) was degassed and heated to 85° C. After 1 h, the volatiles were removed under reduced pressure. Chromatography of the residue (cyclohexane-EtOAc, 100:0 to 0:100) afforded compound 2000 (A/1454/52/3) as a white solid (18 mg). UPLC/MS(ES$^+$), m/z: 464.16 [M+H]$^+$.

Example 21-1

Preparation of Compound 2100

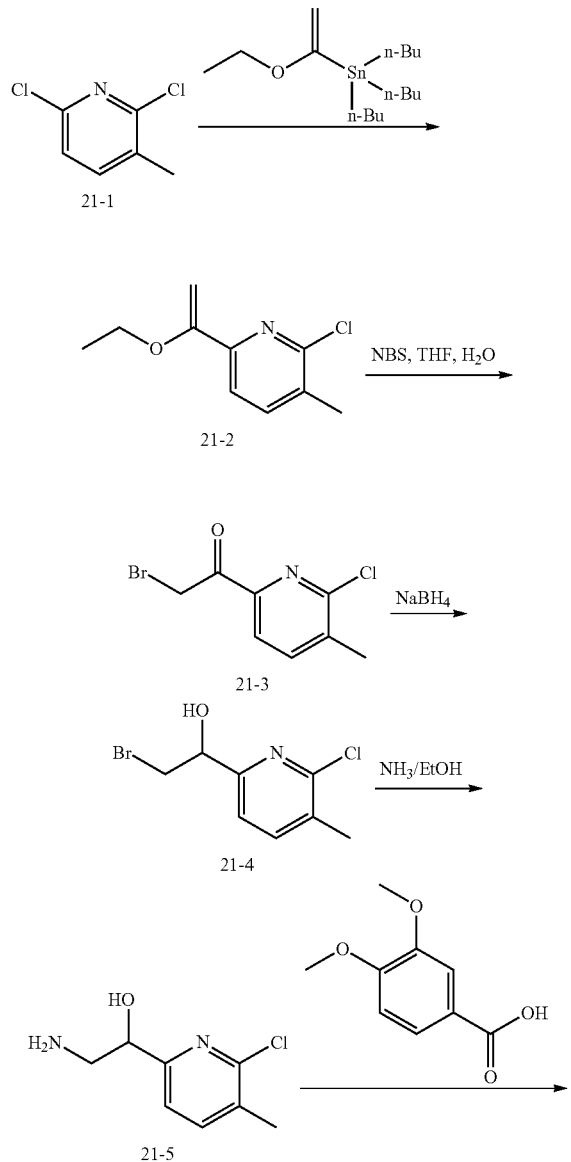

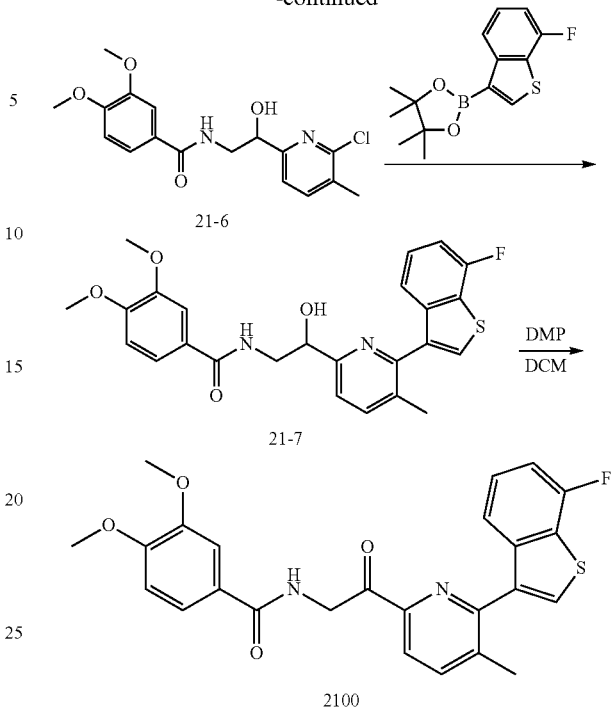

To a solution of 21-1 (2.5 g, 15.6 mmol), the tin reagent (5.6 g, 15.6 mmol) and KF (1.9 g, 31.7 mmol) in DMF (10 mL) was added Pd(dppf)Cl$_2$ (330 mg, 0.46 mmol). The system was degassed and then charged with nitrogen three times. The mixture was stirred under nitrogen at 70° C. in an oil bath for 10 h. The solution was cooled to rt. The mixture was washed with H$_2$O and diluted with EA. The EA solution was washed by brine, dried over Na$_2$SO$_4$ and concentrated. The residue was purified on a silica gel column to give crude 21-2 (2.3 g), which used in next step without purification. +ESI-MS: m/z 197.9 [M+H]$^+$.

To a solution of 21-2 (2.2 g, 11.2 mmol) in a mixture of THF (10 mL) and H$_2$O (1 mL) was added NBS (2.1 g, 11.8 mmol), and stirred at rt for 30 mins. The solution was washed with water and the aqueous was extracted by EA. The combined organic layers were washed by brine, dried over Na$_2$SO$_4$ and evaporated to give crude 21-3 (2.0 g), which was used in next step without purification.

To a solution of 21-3 (2.05 g, 8.1 mmol) in a mixture of THF (10 mL) and MeOH (10 mL) was added NaBH$_4$ (0.9 g, 23.7 mmol) at −30° C. The mixture was stirred at −30° C. for 30 mins. The reaction was quenched by addition of H$_2$O and extracted by EA. The combined organic layers were washed by brine, dried with Na$_2$SO$_4$ and concentrated. The residue was purified on a silica gel column to give 21-4 (1.5 g) as an oil. +ESI-MS: m/z 250.0 [M+H]$^+$.

A mixture of 21-4 (1.5 g, 5.3 mmol) and saturated NH$_3$/EtOH (10 mL) in a sealed tube was heated to 70° C. for 6 h. The solution was removed under reduced pressure to give crude 21-5 (1.0 g), which was used in next step without purification. +ESI-MS: m/z 186.9 [M+H]$^+$.

To a solution of 3,4-dimethoxybenzoic acid (364 mg, 2.0 mmol), HATU (1.1 g, 2.9 mmol) and DIPEA (700 mg, 5.4 mmol) in anhydrous DCM (5 mL) was added 21-5 (372 mg, 2.0 mmol) at 25° C. The solution was stirred for 5 h at this temperature and then diluted with 1.0 N aqueous NaHCO$_3$ solution. The mixture was extracted with EA. The combined organic layers were washed with brine, dried over anhydrous Na₂SO₄, and concentrated under reduced pressure. The residue was purified on a silica gel column (PE:EA=1:1) to give 21-6 (300 mg) as a white solid. +ESI-MS: m/z 351.0 [M+H]⁺.

To a solution of 21-6 (300 mg, 0.86 mmol) and the dioxaborolane reagent (262 mg, 0.94 mmol) in dioxane (6 mL) were added Pd(PPh₃)₂Cl₂ (30 mg, 0.04 mmol) and a freshly prepared KF solution (200 mg in 1 mL of water). The system was degassed and then charged with nitrogen three times. The mixture was stirred under nitrogen at 70° C. in an oil bath for 8 h. The solution was cooled to rt, diluted with EA and separated from the water layer. The EA solution was washed with brine, dried over Na₂SO₄ and concentrated. The residue was purified on a silica gel column (PE:EA=1:2) to give crude 21-7 (180 mg), which was used in next step without purification.

To a solution of 21-7 (150 mg, 0.32 mmol 1) in DCM (5 mL) were added DMP (550 mg, 1.3 mmol). The mixture was stirred at rt for 30 mins with TLC monitoring. The solution was quenched with aq. NaHCO₃ solution and extracted by EA. The combined organic layers were washed with saturated Na₂S₂O₃ and brine, dried over Na₂SO₄ and concentrated. The residue was purified by pre-HPLC to give compound 2100 (30 mg) as a white solid. +ESI-MS: m/z 464.9 [M+H]⁺.

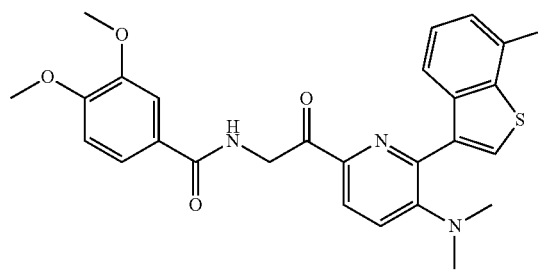

2101

Compound 2101 was prepared starting from 2,6-dibromo-N,N-dimethylpyridin-3-amine by following a synthetic route, which closely follows that described for preparation of compound 2100. Compound 2101 was obtained as white solids. +ESI-MS: m/z 493.9 [M+H]⁺.

Example 21-2

Preparation of Compound 21-9

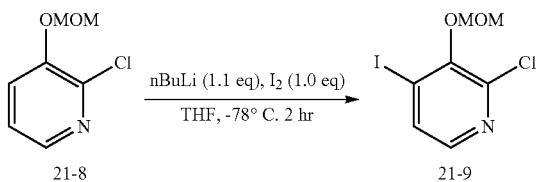

Compound 21-8 was prepared according to the procedure in PCT Publication No. WO 2005/074513. Compound 21-9 was prepared according to the procedure in PCT Publication No. WO 2010/018874. PCT Publication Nos. WO 2005/074513 and WO 2010/018874 are incorporated by reference for limited purpose of the preparation of compounds 21-8 and 21-9, respectively.

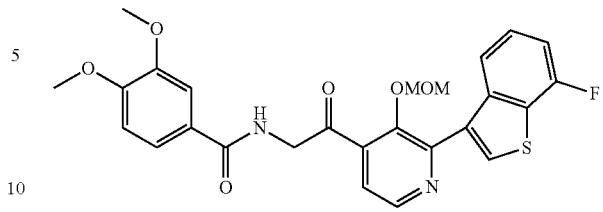

21-10

Compound 21-10 was prepared essentially as described in the preparation of compound 2100 by using 21-9 as the starting material. Compound 21-10 was obtained as white solids. +ESI-MS: m/z 511.0 [M+H]⁺.

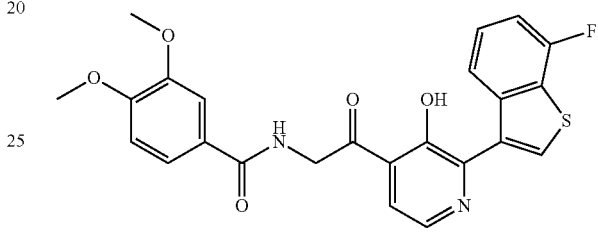

2102

To a solution of crude 21-10 (30 mg, 0.0588 mmol) in DCM (10 mL) was added TFA (7 mL). The mixture was stirred at rt for 30 mins. The mixture was washed with water and extracted with EA. The solution was evaporated at low pressure to give the crude product. The residue was purified by prep-HPLC to generate compound 2102 (4 mg, 8.7%). +ESI-MS: m/z 467.0 [M+H]⁺.

Example 21-3

Preparation of 2,6-diiodo-3-methoxy-4-methylpyridine

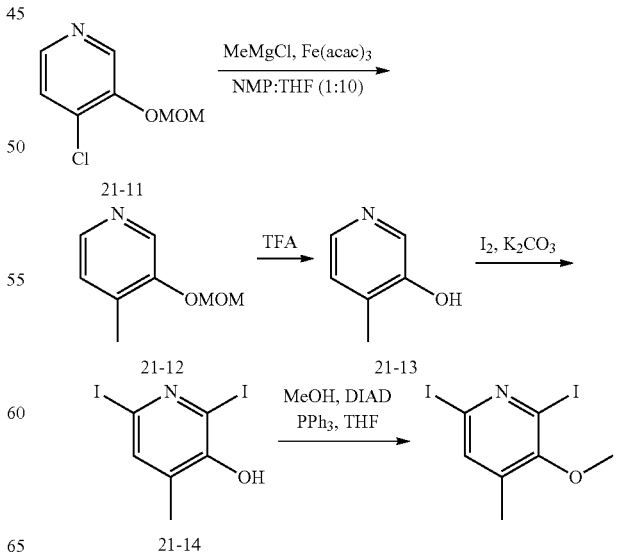

To a solution of 21-11 (2.1 g, 11.6 mmol) in NMP:THF=1:10 (10 mL) at 0° C. was added Fe(acac)$_3$ (0.84 g, 23.2 mmol). After 30 mins, MeMgCl (38.6 mL, 116 mmol) was added and the mixture was stirred at rt for 8 h with TLC monitoring. The solution was quenched with MeOH and extracted by EA. The combined organic layers were washed with brine, dried over MgSO$_4$, and concentrated under low pressure. The residue was purified on a silica gel column (PE:EA=5:1) to give 21-12 (1.2 g, 67.8%) as a liquid.

The compound 21-13 was prepared essentially as described in the preparation of compound 2102 by using 21-12 as starting material. Compound 21-13 was obtained as white solids. +ESI-MS: m/z 174.0 [M+H]$^+$.

To a solution of 21-13 (800 mg, 7.3 mmol) and K$_2$CO$_3$ (3.0 g, 14.6 mmol) in H$_2$O (8 mL)/THF (8 mL) was added I$_2$ (3.7 g, 14.6 mmol) at rt. The mixture was stirred at rt for 30 mins with TLC monitoring. The solution was removed under reduced pressure. The residue was dissolved in EA, and washed with brine. The organic layers were dried over MgSO$_4$, and concentrated at low pressure. The residue was purified on a silica gel column (PE:EA=5:1) to give 21-14 (2.2 g, 83.0%). +ESI-MS: m/z 375.9 [M+H]$^+$.

To a solution of 21-14 (2.0 g, 5.5 mmol) and PPh$_3$ (2.9 g, 11.0 mmol) in THF (800 mL) were added MeOH (1 mL) and DIAD (2.2 g, 11.0 mmol) at rt. The mixture was stirred at 80° C. for 2 h with TLC monitoring. The solution was removed under reduced pressure. The residue was purified on a silica gel column (PE:EA=100:1) to give 2,6-diiodo-3-methoxy-4-methylpyridine (1.4 g, 67.3%). $^1$H-NMR (400 MHz, CDCl$_3$), δ=7.44 (s, 1H), 3.81 (s, 3H) 2.27 (s, 3H).

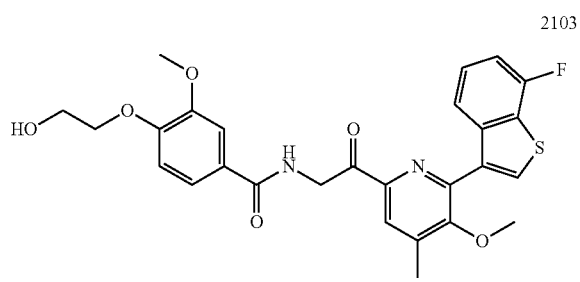 [SMILES: COc1cc(C(=O)NCC(=O)c2cc(C)c(OC)c(-c3csc4c(F)cccc34)n2)ccc1OCCO]

2103

Compound 2103 was prepared starting from 2,6-diiodo-3-methoxy-4-methylpyridine by following a synthetic route, which closely follows that described for preparation of compound 2100. Compound 2103 was obtained as white solids. +ESI-MS: m/z 524.9 [M+H]$^+$.

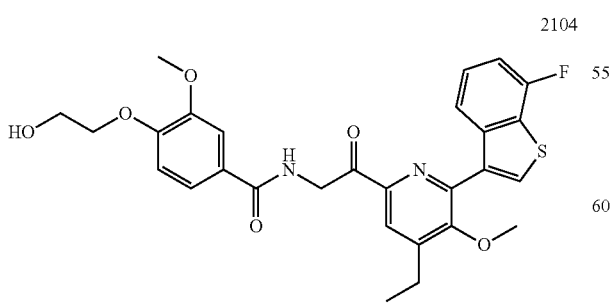

2104

Compound 2104 was prepared starting from pyridine-3-ol by following a synthetic route, which closely follows that described for preparation of compound 2102. Compound 2104 was obtained as white solids. +ESI-MS: m/z 539.0 [M+H]$^+$.

Example 21-4

Preparation of 2,6-dichloro-3-ethylpyridine

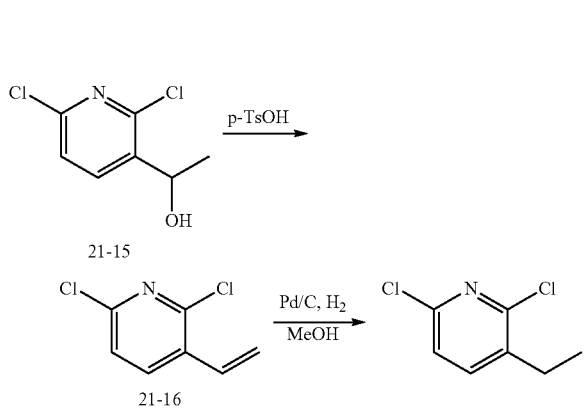

To a solution of 21-15 (2.0 mg, 11.1 mmol) in chlorobenzene (8 mL) were added p-TsOH (2.1 g, 12.2 mmol) at rt. The mixture was stirred at 140° C. in an oil bath for 5 h with TLC monitoring. The reaction was quenched by addition of saturated NaHCO$_3$ solution and extracted with EA. The EA solution was washed with brine, dried over Na$_2$SO$_4$ and concentrated at low pressure. The residue was purified on silica gel column to give 21-16 (0.9 g). $^1$H-NMR CDCl$_3$ (400 MHz): δ 7.83 (d, J=8.0 Hz, 1H), 7.27 (m, 1H), 7.01-6.94 (m, 1H), 5.79 (d, J=17.6 Hz, 1H), 5.53 (d, J=11.2 Hz, 1H).

A mixture of 21-16 (2.5 g, 14.4 mmol) in MeOH (10 mL) was added Pd/C (10%, 300 mg). The system was degassed and then charged with H$_2$ for 3 times and stirred under H$_2$ balloon at rt for 1 h. The suspension was filtered through a pad of celite. The combined filtrates were concentrated to give 2,6-dichloro-3-ethylpyridine (2.0 g) as a white solid.

2105

Compound 2105 was prepared starting from 2,6-dichloro-3-ethylpyridine by following a synthetic route, which closely follows that described for preparation of compound 2100. Compound 2105 was obtained as white solids. +ESI-MS: m/z 478.9 [M+H]$^+$.

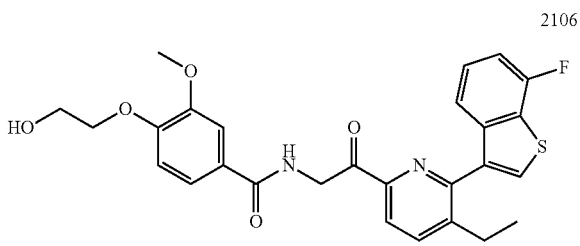 [SMILES: CCc1ccc(C(=O)CNC(=O)c2ccc(OCCO)c(OC)c2)nc1-c1csc2c(F)cccc12]

Compound 2106 was prepared starting from 2,6-dichloro-3-ethylpyridine by following a synthetic route, which closely follows that described for preparation of compound 2100. Compound 2106 was obtained as white solids. +ESI-MS: m/z 508.9 [M+H]+.

Example 21-5

Preparation of 2-bromo-6-iodo-3-(trifluoromethoxy)pyridine

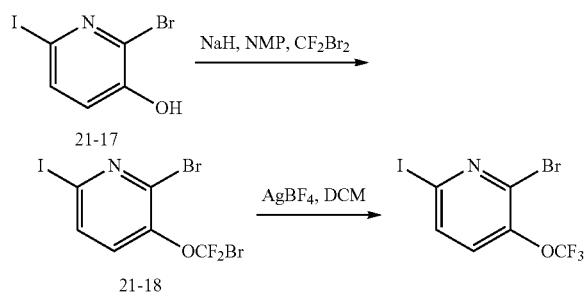

To a solution of 21-17 (2.0 g, 6.7 mmol) in NMP (10 mL) were added NaH (536 mg, 13.4 mmol) at rt. After 30 mins, CF$_2$Br$_2$ (1.68 g, 8.0 mmol) was added, and the mixture was stirred at rt for 1 h with TLC monitoring. The solution was quenched with MeOH and diluted with EA. The combined organic layers were washed with brine, dried over Na$_2$SO$_4$, and concentrated at low pressure. The residue was purified on a silica gel column (PE:EA=10:1) to give 21-18 (1.0 g, 35.1%).

To a solution of 21-18 (0.8 g, 1.88 mmol) in DCM (10 mL) at −78° C. was added AgBF$_4$ (0.8 g, 4.3 mmol). The mixture was stirred at rt for 8 h with TLC monitoring. The solution was diluted with CH$_2$Cl$_2$. The solution were washed by brine, and dried over MgSO$_4$, and concentrated at low pressure. The residue was purified on a silica gel column (PE:EA=10:1) to give 2-bromo-6-iodo-3-(trifluoromethoxy)pyridine (0.5 g, 72.5%) as a liquid. +ESI-MS: m/z 367.9 [M+H]+.

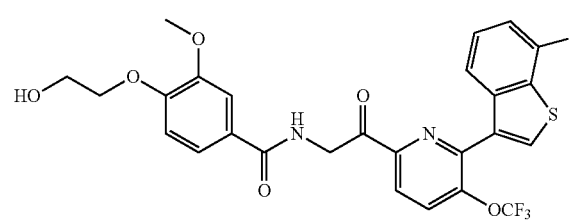

Compound 2107 was prepared starting from 2-bromo-6-iodo-3-(trifluoromethoxy)pyridine by following a synthetic route, which closely follows that described for preparation of compound 2100. Compound 2107 was obtained as white solids. +ESI-MS: m/z 564.9 [M+H]+.

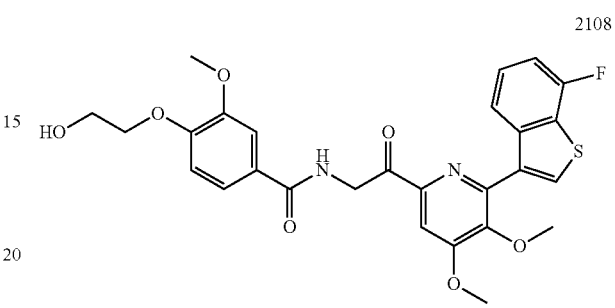

Compound 2108 was prepared starting from pyridine-3-ol by following a synthetic route, which closely follows that described for preparation of compound 2102. Compound 2108 was obtained as white solids. +ESI-MS: m/z 541.1 [M+H]+.

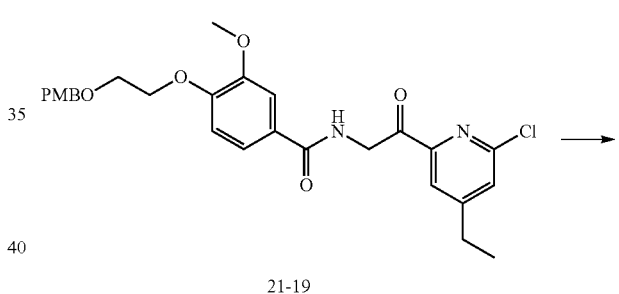

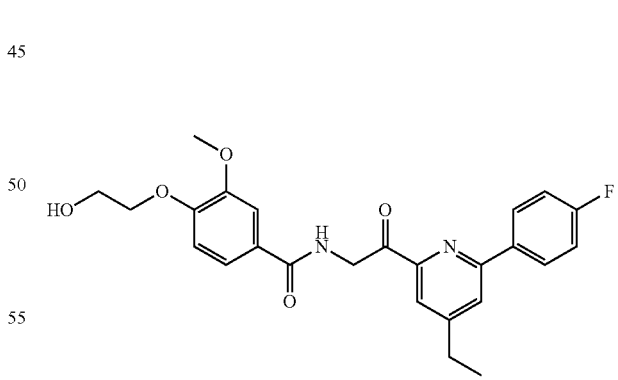

Compound 2109 was prepared starting from 2-(4-fluorophenyl)-4,4,5,5-tetramethyl-1,3,2-dioxaborolane and 21-19 by following a synthetic route, which closely follows that described for preparation of compound 2102. Compound 2109 was obtained as white solids. +ESI-MS: m/z=453.9 [M+H]+.

Example 21-6

Preparation of Compound 21-25

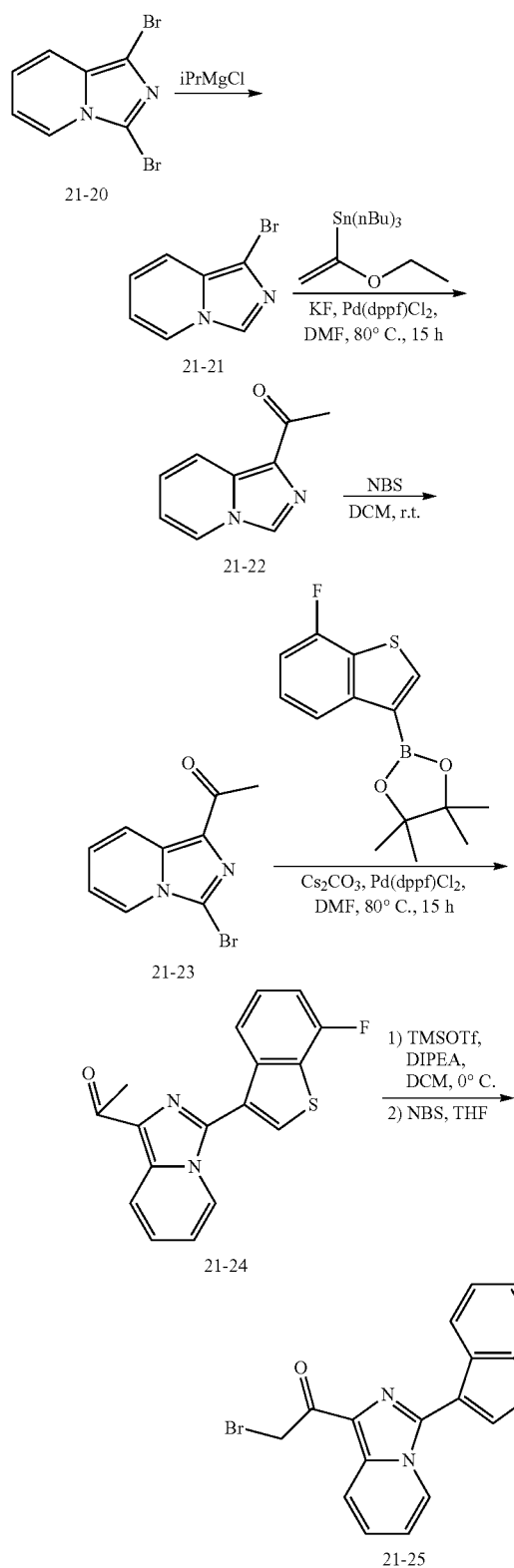

To a solution of 21-20 (7.5 g, 27.17 mmol) in THF (100 mL) was added slowly i-PrMgCl (25 mL, 2M in THF) at rt, and the mixture stirred for 10 mins. The solution was quenched with MeOH and diluted with DCM (20 mL). The solution was washed by brine, dried over $Na_2SO_4$ and concentrated to give crude 21-21 (5 g, 94.3%).

To a solution of 21-21 (1 g, 5.1 mmol), the tin reagent (3.71 g, 10.2 mmol) and KF (1.18 g, 20.4 mmol) in DMF (10 mL) was added $Pd(dppf)Cl_2$ (372 mg, 0.51 mmol). The system was degassed and then charged with nitrogen for 3 times. The mixture was stirred under nitrogen at 80° C. in an oil bath for 15 h. The solution was cooled to rt. The mixture was diluted with EA. The EA solution was washed by brine, dried over $Na_2SO_4$ and concentrated to give crude 21-22 (360 mg, 44.2%)

To a solution of 21-22 (360 mg, 2.25 mmol) in DCM (5 mL) was added NBS (480 mg, 2.7 mmol). The mixture was stirred at rt for 30 mins with TLC monitoring. The solution was quenched by aqueous $Na_2S_2O_3$ solution and extracted by EA. The combined organic layers were dried over $Na_2SO_4$ and concentrated. The residue was purified by prep-HPLC(FA) to give 21-23 (250 mg, 46.2%).

To a solution of 21-23 (480 mg, 2 mmol) and the dioxaborolane reagent (558 mg, 2 mmol) in dioxane/$H_2O$ (10 mL/2 mL) were added $Pd(dppf)Cl_2$ (146 mg, 0.2 mmol) and $Cs_2CO_3$ (975 mg, 3 mmol). The system was degassed and then charged with nitrogen for 3 times. The mixture was stirred under nitrogen at 80° C. in an oil bath for 15 h. The solution was cooled to rt, diluted with EA and separated from the water layer. The EA solution was washed by brine, dried over $Na_2SO_4$ and concentrated. The residue was purified on a silica gel column to give 21-24 (400 mg, 64.5%).

To a solution of 21-24 (550 mg, 1.77 mmol) in DCM (5 mL) was added DIPEA (685 mg, 5.31 mmol) and TMSOTf (589 mg, 2.65 mmol) at 0° C. The solution was stirred for 2 h at rt. The solution was concentrated and the residue was dissolved in THF (10 mL) and $H_2O$ (1 mL). NBS (471 mg, 2.65 mmol) was added at rt, and stirred for 1.5 h. The solution was evaporated at low pressure. The residue was purified by chromatography (PE:EA=3:1) to give 21-25 (600 mg, 86.9%).

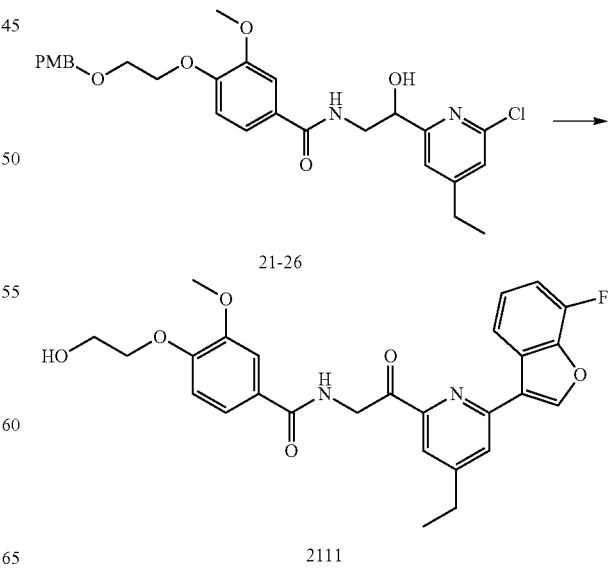

Compound 2111 was prepared starting from 21-26 and 2-(7-fluorobenzofuran-3-yl)-4,4,5,5-tetramethyl-1,3,2-dioxaborolane by following a synthetic route, which closely follows that described for preparation of compound 2100. Compound 2111 was obtained as white solids. +ESI-MS: m/z=493.0 [M+H]⁺.

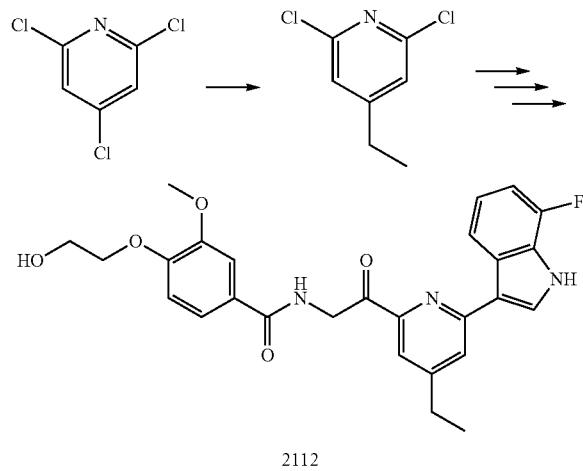

2112

Compound 2112 was prepared starting from 2,4,6-trichloropyridine by following a synthetic route, which closely follows that described for preparation of compound 2100. Compound 2112 was obtained as white solids. +ESI-MS: m/z 492.2 [M+H]⁺.

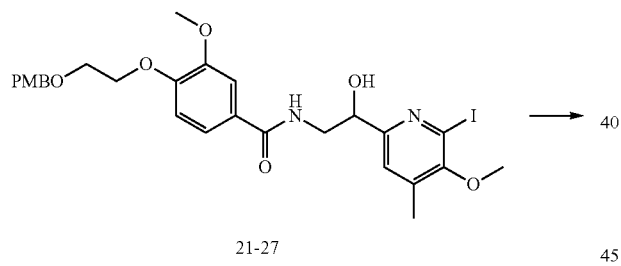

21-27

2113

Compound 2113 was prepared starting from 7-fluoro-3-(4,4,5,5-tetramethyl-1,3,2-dioxaborolan-2-yl)-1-((2-(trimethylsilyl)ethoxy)methyl)-1H-indole and 21-27 by following a synthetic route, which closely follows that described for preparation of compound 2100. Compound 2113 was obtained as white solids. +ESI-MS: m/z 508.0 [M+H]⁺.

2114

Compound 2114 was prepared starting from 2-(3-chloro-4-fluorophenyl)-4,4,5,5-tetramethyl-1,3,2-dioxaborolane and 21-27 by following a synthetic route, which closely follows that described for preparation of compound 2100. Compound 2114 was obtained as white solids. +ESI-MS: m/z 502.9 [M+H]⁺.

2115

Compound 2115 was prepared starting from (3-chloro-4-fluorophenyl) boronic acid and 2,4,6-trichloropyridine by following a synthetic route, which closely follows that described for preparation of compound 2100. Compound 2115 was obtained as white solids. +ESI-MS: m/z 514.9 [M+H]⁺.

Example 22-1

Preparation of Compound 2200

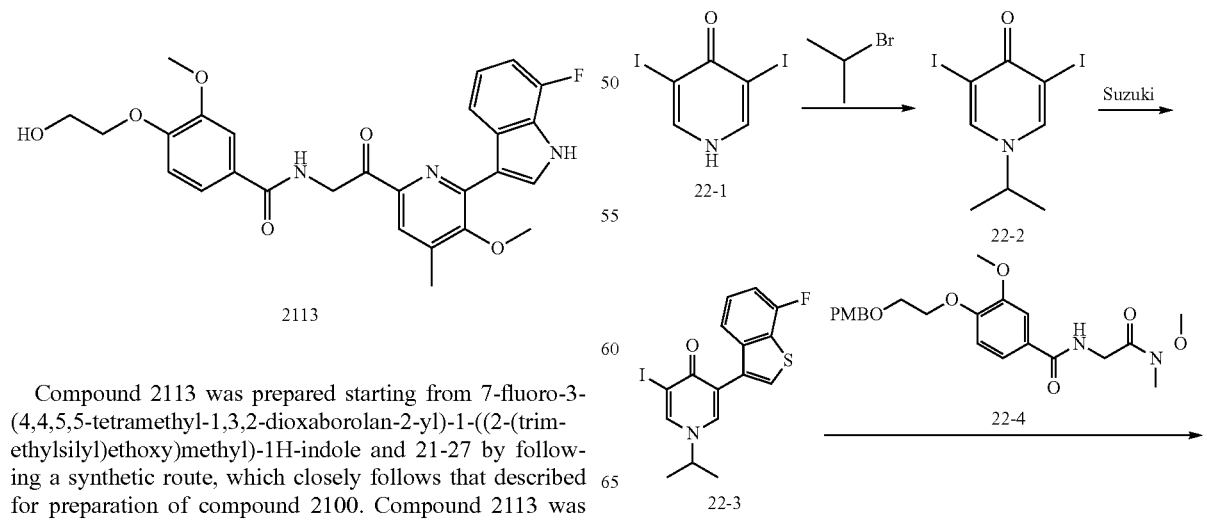

-continued

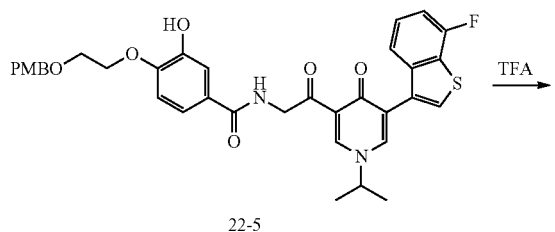

22-5

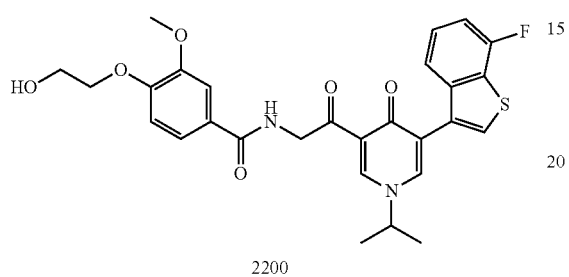

2200

To a stirred solution of 22-1 (2.4 g, 6.9 mmol) in DMF (10 mL) was added K$_2$CO$_3$ (1.98 g, 14 mmol) and i-PrBr (1.8 g, 14 mmol), and the mixture was heated to 80° C. for 48 h. The solution was evaporated and purified by column chromatograph gel using PE:EA=3:1 as the elute to give 22-2 (1.0 g, 37.3%). +ESI-MS: m/z 389.9 [M+H]$^+$.

To a solution of 22-2 (2.5 g, 6.4 mmol) in DME:H$_2$O=10:1 (10 mL) under N$_2$ was added Cs$_2$CO$_3$ (4.2 g, 12.8 mmol), Pd(dppf)$_2$Cl$_2$ (140 mg, 0.2 mmol) and 2-(7-fluorobenzo[b]thiophen-3-yl)-4,4,5,5-tetramethyl-1,3,2-dioxaborolane (1.95 g, 7 mmol). The mixture was heated to 85° C. for 3 h and monitored by TLC (PE:EA=1:3). After conversion, the mixture was filtered and purified by prep-HPLC to give 22-3 (500 mg, 18.9%). $^1$H-NMR (400 MHz, CD$_3$OD), δ=8.52 (d, J=2.21 Hz, 1H), 8.44 (s, 1H), 8.10 (d, J=2.21 Hz, 1H), 7.73 (s, 1H), 7.31-7.52 (m, 2H), 7.00-7.19 (m, 1H), 4.38-4.49 (m, 1H), 1.51-1.56 (m, 7H).

To a solution of 22-3 (300 mg, 0.7 mmol) and 22-4 (289 mg, 0.7 mmol) in THF (10 mL) was added i-PrMgCl (2.2 mL, 2.8 mmol), and stirred at rt for 5 mins. The solution was acidified to pH=8 with aq.NH$_4$Cl and the aqueous layer was extracted with DCM. The organic layer was combined and concentrated at low pressure. The residue was purified by column chromatograph gel using PE:EA=1:3 as the elute to give 22-5 (80 mg, yield: 17.4%). +ESI-MS: m/z 645.2 [M+H]$^+$.

To a solution of 22-5 (70 mg, 0.11 mmol) in DCM (2 mL) was added TFA (1 mL). The mixture was stirred for 3 h and monitored by TLC, PE:EA=1:3. After conversion, the mixture was concentrated and purified by prep-HPLC to generate compound 2200 (2 mg, 3.5%). $^1$H-NMR (400 MHz, CD$_3$OD), δ=8.68 (br. s., 1H), 8.17 (br. s., 1H), 7.71-7.98 (m, 1H), 7.56-7.71 (m, 1H), 7.53 (br. s., 2H), 7.47 (br. s., 1H), 7.40 (br. s., 1H), 7.01-7.19 (m, 2H), 4.13 (br. s., 2H), 3.83-3.97 (m, 7H), 1.56-1.64 (m, 6H).

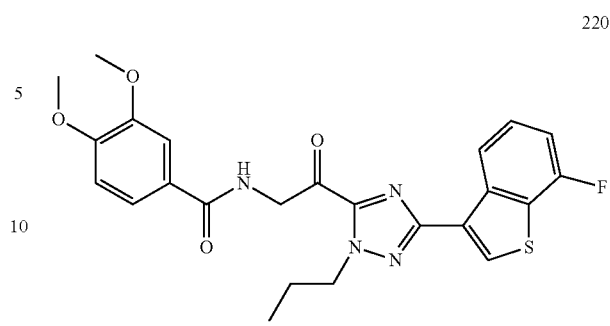

2203

Compound 2203 was prepared using 3,5-dibromo-1H-1,2,4-triazole and by following a synthetic route, which closely follows that described for preparation of compound 1354. Compound 2203 was obtained as a white solid. +ESI-MS: m/z 483.0 [M+H]$^+$.

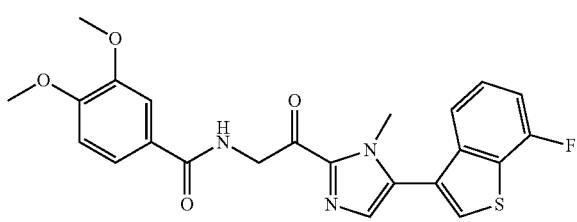

2204

Compound 2204 was prepared using 2,4,5-tribromo-1H-imidazole and by following a synthetic route, which closely follows that described for preparation of compound 1354. Compound 2204 was obtained as a white solid. +ESI-MS: m/z 454.0 [M+H]$^+$.

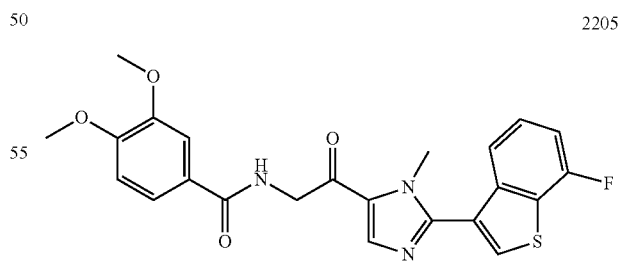

2205

Compound 2205 was prepared using 2,4,5-tribromo-1H-imidazole and by following a synthetic route, which closely follows that described for preparation of compound 1355. Compound 2205 was obtained as a white solid. +ESI-MS: m/z 454.0 [M+H]$^+$.

Example 23-1

Preparation of Compound 23-3

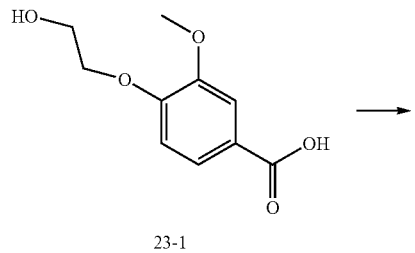

23-1

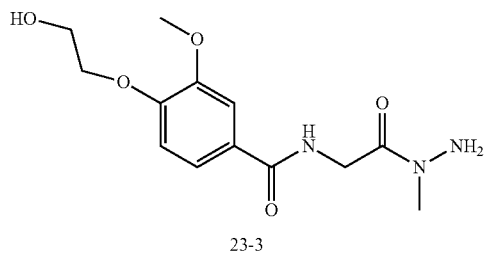

23-2

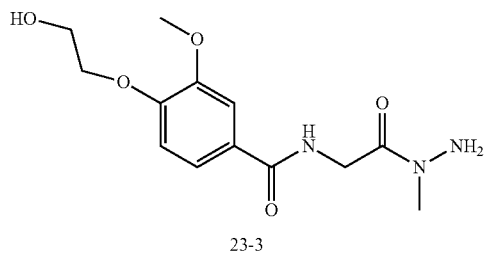

23-3

To a solution of 23-1 (6.0 g, 28 mmol), HATU (15 g, 39 mmol) and DIPEA (9 g, 70 mmol) in anhydrous DCM (100 mL) was added ethyl 2-aminoacetate (3.9 g, 28 mmol) at 25° C. The solution was stirred for 10 h at this temperature. The solution was then diluted with 1.0 N aqueous NaHCO$_3$ solution, and extracted with EA. The combined organic phase was dried over anhydrous Na$_2$SO$_4$, and concentrated under reduced pressure. The residue was purified by chromatograph to give 23-2 (4.0 g, 45%). $^1$H-NMR DMSO (400 MHz), δ=8.78-8.75 (br, 1H), 7.45 (m, 1H), 7.43 (s, 1H), 7.01 (d, J=8.4 Hz, 1H), 4.87-4.84 (m, 1H), 4.11-4.06 (m, 2H), 4.02-3.95 (m, 4H), 3.78 (s, 3H), 3.72-3.69 (m, 2H), 1.19-1.15 (m, 3H).

To a solution of 23-2 (2.5 g, 8.4 mol) in anhydrous EtOH (15 mL) was added methyl-hydrazine (18.3 g, 39 mmol). The solution was stirred for 10 h at 70° C. and then cooled to rt. The solution was concentrated under reduced pressure. The residue was purified by prep-HPLC to give 23-3 (300 mg). $^1$H-NMR DMSO (400 MHz): δ=8.26 (br, 1H), 7.47 (m, 1H), 7.45 (s, 1H), 7.02 (d, J=8.4 Hz, 1H), 4.23 (m, 2H), 4.04-4.01 (m, 2H), 3.80 (s, 3H), 3.74-3.72 (m, 2H), 3.12 (d, J=3.6 Hz, 3H).

Example 23-2

Preparation of Compound 23-7

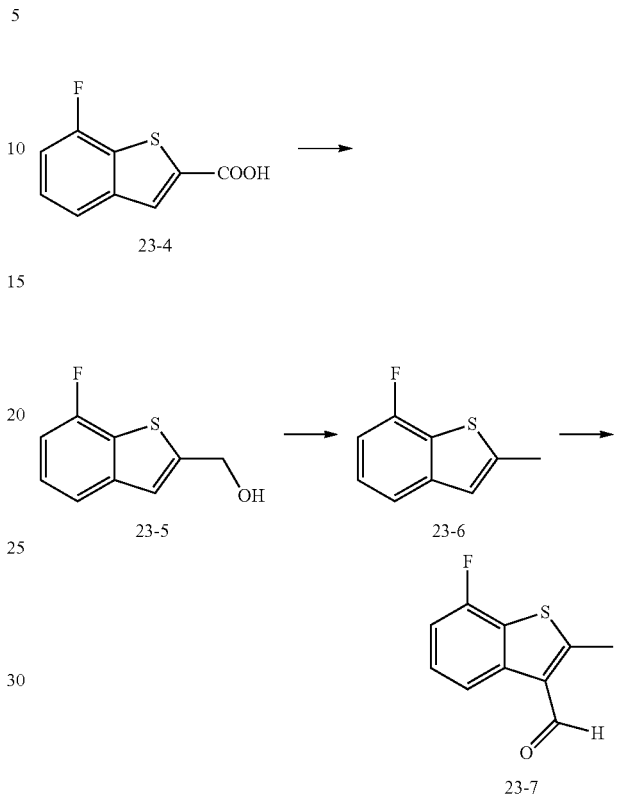

To a solution of 23-4 (3.0 g, 15.3 mmol) in anhydrous THF (8 mL) was added BH$_3$/THF (18 mmol) under an argon atmosphere. The solution was stirred at 50° C. for 6 h and cooled to rt. The reaction was quenched by addition of MeOH. The mixture was concentrated. The residue was purified on a silica gel column to give 23-5 (2.1 g) as a white solid. $^1$H-NMR CDCl$_3$ (400 MHz): δ=7.62 (d, J=8.0 Hz, 1H), 7.39-7.34 (m, 2H), 7.18-7.13 (m, 1H), 4.77 (d, J=0.40 Hz, 1H).

To a solution of 23-5 (2.1 g, 11.5 mmol) and triethylsilane (2.5 g, 21.5 mmol) in anhydrous EtOH (6 mL) was added a catalytic amount of palladium chloride (10 mol %) under an argon atmosphere. The solution was stirred at rt for 1 h. The mixture was filtered over a pad of celite and the filtrate was concentrated in vacuo. The residue was chromatographed on a silica gel column to give 23-6 (1.66 g) as a white solid. $^1$H NMR: CDCl$_3$ (400 MHz): δ=7.44 (d, J=7.6 Hz, 1H), 7.29-7.24 (m, 1H), 7.01-6.93 (m, 2H), 2.61 (s, 3H).

Compound 23-6 (1.66 g, 10 mmol) and dichloro(methoxy) methane (1.60 g, 14.1 mmol) were dissolved in anhydrous DCM (20 mL). Titanium tetrachloride (2.7 g, 14.4 mmol) was added. After 1 h at rt, the mixture was poured into a mixture of saturated aqueous NaHCO$_3$ and ice. The mixture was stirred for about 30 mins and then extracted with DCM. The organic layer was dried and concentrated. The residue was purified by chromatograph (PE:EA=60:1 to 10:1) to give 23-7. (1.5 g, 70%). $^1$H-NMR CDCl$_3$ (400 MHz): δ=10.35 (s, 1H), 8.35 (d, J=8.4 Hz, 1H), 7.44-7.39 (m, 1H), 7.10-7.05 (m, 1H), 2.94 (s, 3H).

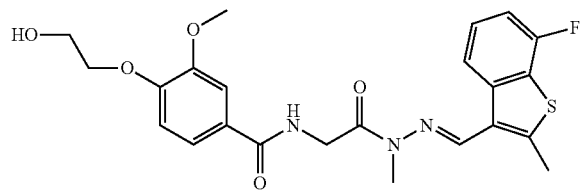

2300

To a solution of 23-3 (297 mg, 1.0 mmol) in anhydrous EtOH (6 mL)/AcOH (0.6 mL) was added 23-7 (195 mg, 1.0 mmol). The solution was stirred at 70° C. for 10 h and then cooled to rt. The precipitate was collected by filtration. The solid was washed with EA and EtOH to give compound 2300 (150 mg, 30%). +ESI-LCMS: m/z=474.1 [M+H]$^+$.

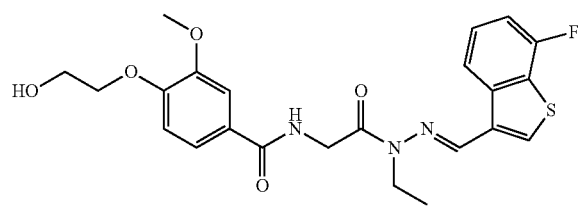

2301

Compound 2301 was prepared starting from 7-fluorobenzo[b]thiophene-3-carbaldehyde by following a synthetic route, which closely follows that described for preparation of compound 2300. Compound 2301 was obtained as a white solid. +ESI-MS: m/z 473.9 [M+H]$^+$.

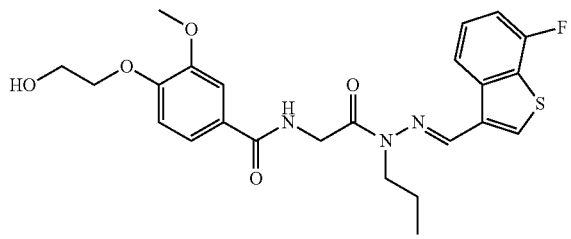

2302

Compound 2302 was prepared starting from 7-fluorobenzo[b]thiophene-3-carbaldehyde by following a synthetic route, which closely follows that described for preparation of compound 2300. Compound 2302 was obtained as a white solid. +ESI-MS: m/z 488.0 [M+H]$^+$.

Example 23-3

Preparation of Compound 23-12

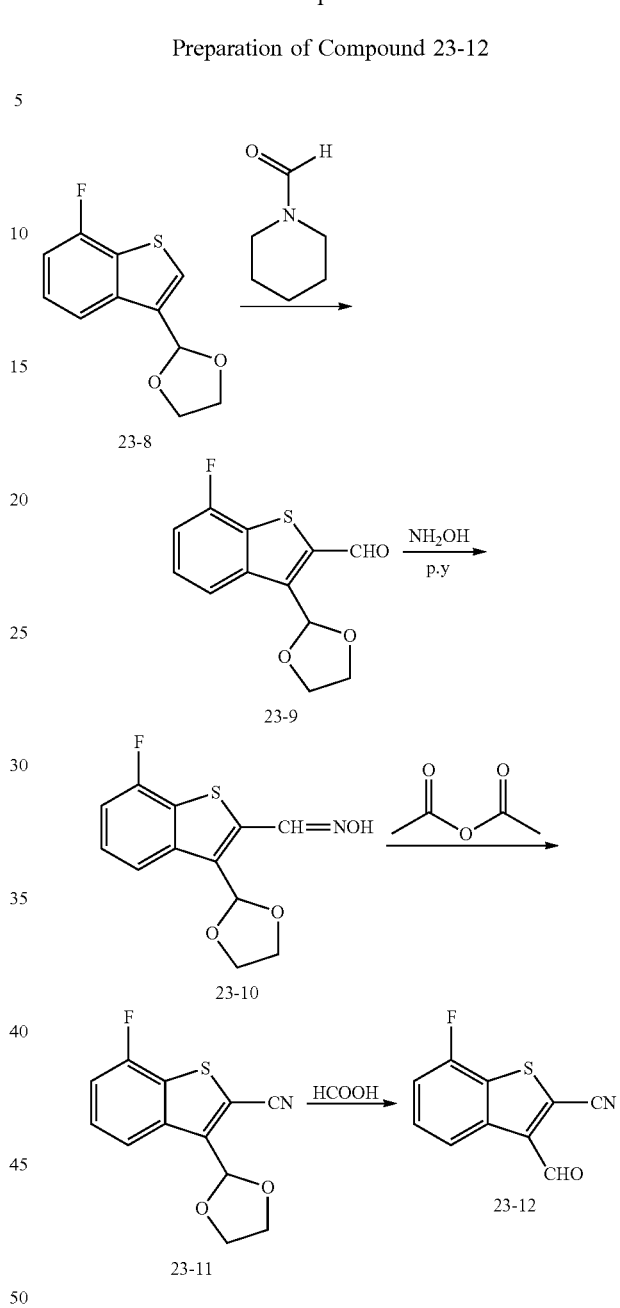

To a solution of 23-8 (224 mg, 1 mmol) in anhydrous THF (10 mL) was added n-BuLi (2.5M, 400 μL), and the mixture stirred at −78° C. for 15 mins. Piperidine-1-carbaldehyde (226 mg, 2 mmol) was added, and the mixture was stirred at −78° C. for 30 mins. The mixture was washed with water and extracted with EA. The organic layer was concentrated at low pressure. The residue was purified by silica gel column (PE/EA=20/1 to 5/1) to afford 23-9 (1.82 mg, 72.2%) as a white solid.

To a solution of 23-9 (224 mg, 1.0 mmol) in pyridine (10 mL) was added NH$_2$OH.HCl (690 mg, 10.0 mmol). The mixture was stirred at rt overnight. The mixture was diluted with EA, and washed with brine. The organic layer was dried over MgSO$_4$, and concentrated at low pressure. The residue was purified by silica gel column (PE/EA=20/1 to 5/1) to afford 23-10 (1.83 mg, 68.5%) as a white solid.

Compound 23-10 (267 mg, 1.0 mmol) was dissolved in acetic anhydride (20 mL), and stirred at 80° C. overnight. The mixture was diluted with EA, and washed with saturated NaHCO₃ solution. The organic layer was dried over anhydrous MgSO₄, and concentrated at low pressure. The residue was purified by silica gel column (PE/EA=20/1 to 5/1) to afford 23-11 (1.83 mg, 79.5%) as a white solid. $^1$H-NMR (DMSO-d₆, 400 MHz), δ=7.96 (d, J=8 Hz, 1H), 7.60-7.61 (m, 2H), 6.36 (s, 1H), 4.06-4.13 (m, 4H).

Compound 23-11 (249 mg, 1.0 mmol) was dissolved in formic acid (20 mL), and stirred at 80° C. overnight. The mixture was diluted with EA, and washed with saturated NaHCO₃ solution. The organic layer was dried over anhydrous MgSO₄, and concentrated at low pressure. The residue was purified by silica gel column (PE/EA=20/1 to 5/1) to afford 23-12 (1.83 mg, 89.2%) as a white solid. $^1$H-NMR (DMSO-d₆, 400 MHz), δ=10.4 (s, 1H), 8.48 (d, J=8 Hz, 1H), 7.51-7.57 (m, 1H), 7.28 (t, J=8 Hz 1H).

Example 23-4

Preparation of Compound 2303

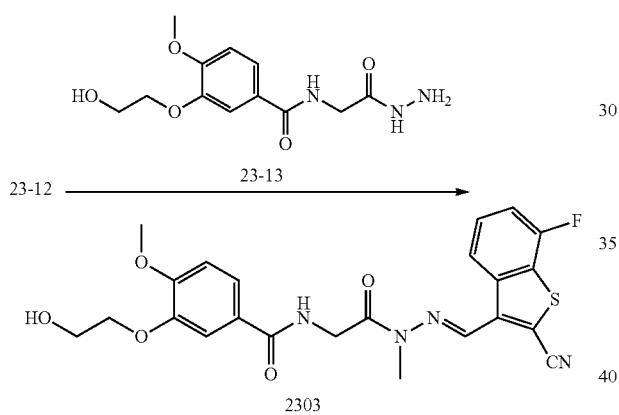

Compound 2303 was prepared starting from 23-12 and 23-13 by following a synthetic route, which closely follows that described for preparation of compound 2300. Compound 2303 was obtained as a white solid. +ESI-MS: m/z 484.9 [M+H]⁺.

Example 23-5

Preparation of Compound 2304

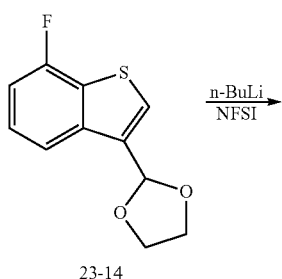

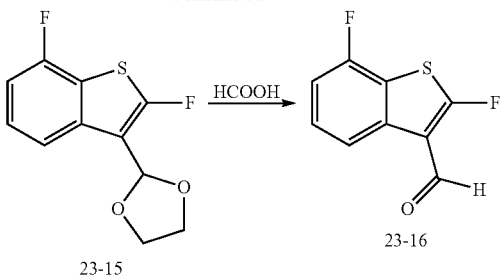

Compound 23-16 was by following a synthetic route, which closely follows that described for preparation of compound 23-12.

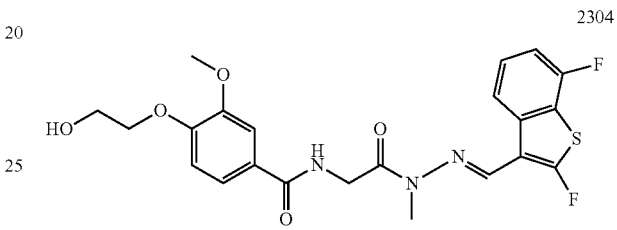

Compound 2304 was prepared starting from 23-16 and 23-13 by following a synthetic route, which closely follows that described for preparation of compound 2300. Compound 2304 was obtained as a white solid. +ESI-MS: m/z 478.0 [M+H]⁺.

Example 23-6

Preparation of Compound 23-18

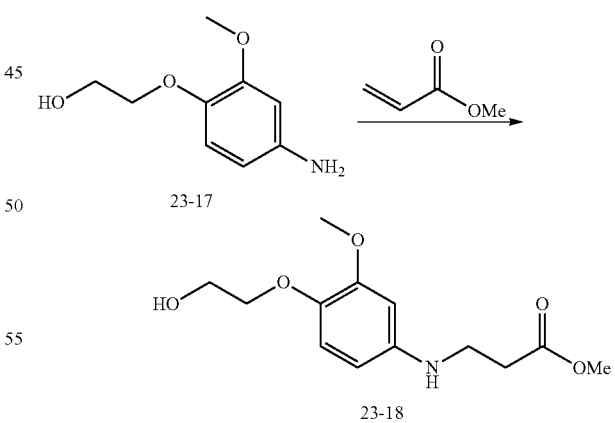

A solution of crude 23-17 (1.2 g, 6.6 mmol) and methyl acrylate (10 mL) was heated to reflux for 30 h. The solution was evaporated and dissolved with DCM. The solution was acidified to pH=8 with aq.NaHCO₃ and the aqueous layer was extracted with DCM. The organic layer was combined and purified by column chromatograph gel eluted with PE:EA=2:1 to give crude 23-18 (0.40 g, 22.5%).

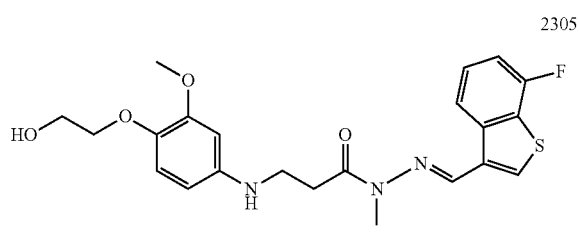 [SMILES: COc1cc(NCCC(=O)N(C)/N=C/c2csc3c(F)cccc23)ccc1OCCO]

Compound 2305 was prepared starting from 23-18 and 7-fluorobenzo[b]thiophene-3-carbaldehyde by following a synthetic route, which closely follows that described for preparation of compound 2300. Compound 2305 was obtained as a white solid. +ESI-MS: m/z 445.9 [M+H]⁺.

Example 23-7

Preparation of Compound 23-22

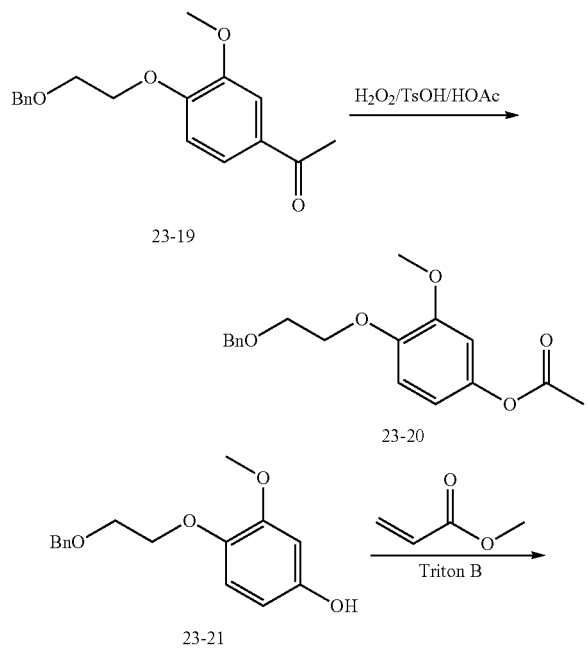

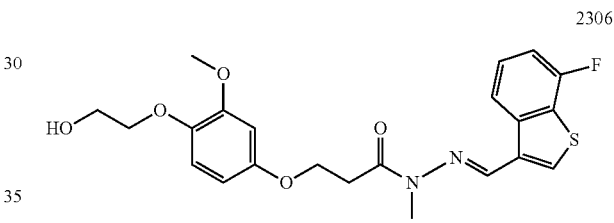

To a solution of 23-19 (900 mg, 3 mmol), TsOH.H₂O (275 mg, 1.5 mmol) in HOAc (10 mL) at rt was added H₂O₂ (2 mL, 30%). The mixture was heated to 70° C. and stirred for 2 h. The solution was poured into water and extracted with EA. The organic phase was dried with anhydrous Na₂SO₄ and concentrated under reduced pressure to give crude 23-20 (800 mg, 84%).

After converting 23-20 to 23-21, a solution of 23-21 (548 mg, 2 mmol) and methyl acrylate (5 mL) was combined with Triton B (0.2 mL). The mixture was stirred for 1.5 h at 80° C. The solution was poured into water and extracted with EA. The organic phase was dried over anhydrous Na₂SO₄ and concentrated under reduced pressure to give crude 23-22 (200 mg, 28.0%).

Compound 2306 was prepared starting from 23-22 and 7-fluorobenzo[b]thiophene-3-carbaldehyde by following a synthetic route, which closely follows that described for preparation of compound 2300. Compound 2306 was obtained as a white solid. +ESI-MS: m/z 446.9 [M+H]⁺.

Example 24-1

Preparation of Compound 2400

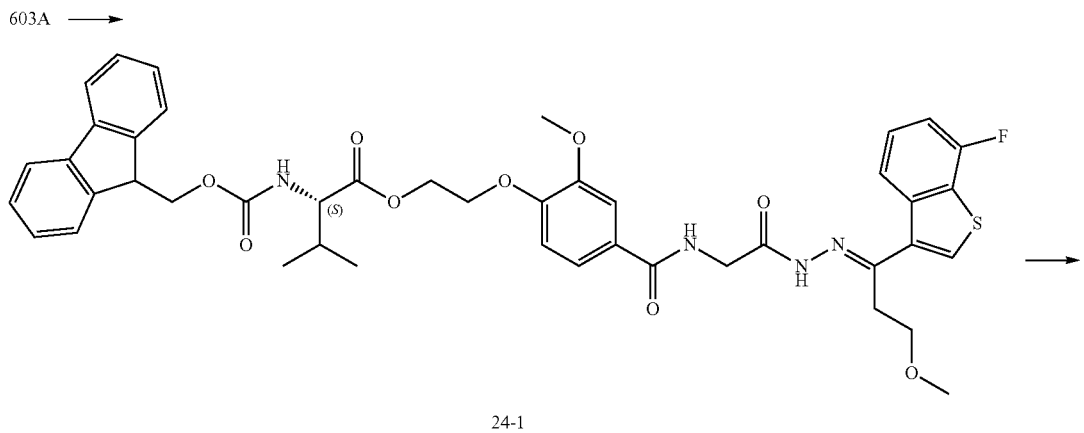

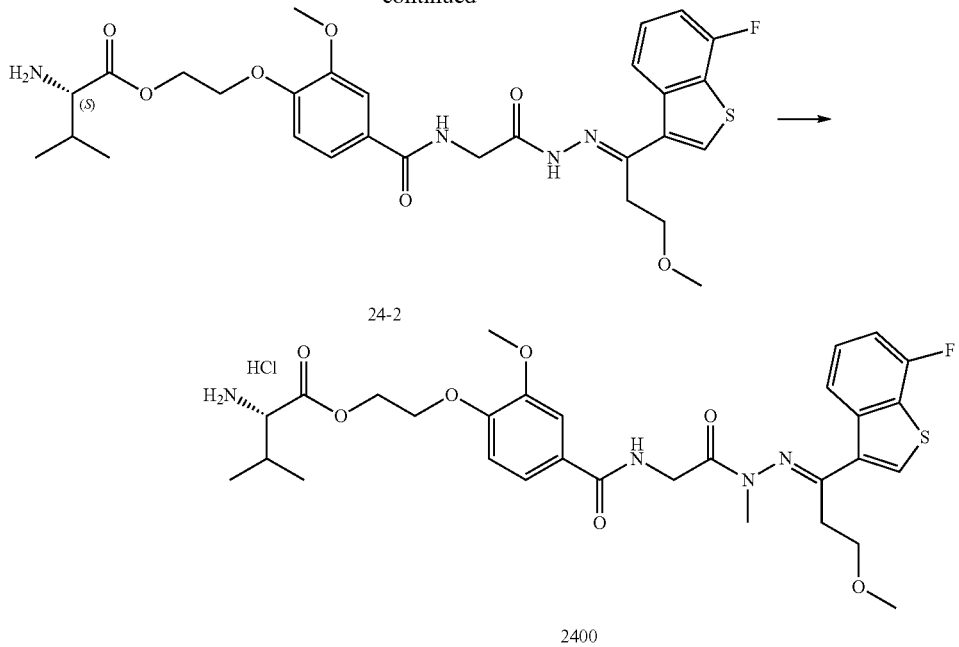

24-2

2400

A mixture of compound 603A (150 mg g, 0.3 mmol), DMAP (15 mg 0.12 mmol), DCC (186 mg, 0.9 mmol) and Fmoc-Val-OH (305 mg, 0.9 mmol) in THF (3 mL) was stirred at rt for 3 h. The mixture was diluted with EA, washed with water twice, dried over sodium sulfate, and concentrated. Chromatography on silica gel with 20-65% EA in dichloromethane 2 times gave of 24-1 (197 mg) as white foam.

Compound 24-1 was dissolved in DMF (2 mL) and 10% piperidine in DMF (2 mL) added. The solution stood at rt for 30 mins and was then concentrated to dryness under high vacuum. Chromatography on silica gel with 4-7% methanol in dichloromethane gave pure 24-2 (135 mg) as a white foam. Compound 24-2 (135 mg, 0.224 mmol) was dissolved in MeOH (5 mL) and ammonium chloride (12.0 mg, 0.224 mmol) was added. After standing for 5 mins, the methanol was evaporated on a rotary evaporator, and then the residue was co-evaporated with methanol 4 times. The residue was dissolved water, filtered, and lyophilized to give compound 2400 (141 mg) as a white foam: +ESI-LCMS: m/z 603.7 [M+H]$^+$.

Example 24-2

Preparation of Compound 2401

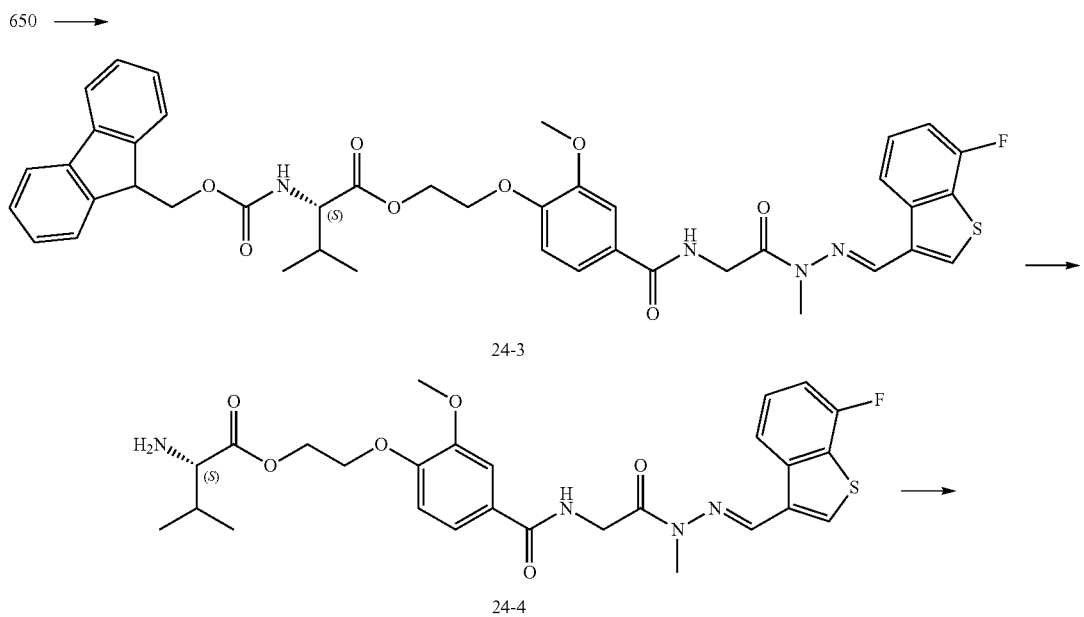

24-3

24-4

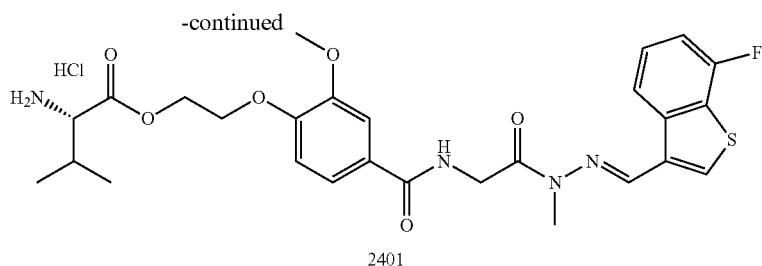

2401

A mixture of compound 650 (138 mg g, 0.3 mmol), DMAP (15 mg 0.12 mmol), DCC (186 mg, 0.9 mmol) and Fmoc-Val-OH (305 mg, 0.9 mmol) in THF 3 mL) was stirred at rt overnight. DMF (0.8 mL) was added, and the mixture stirred for an additional 3 h. The mixture was diluted with EA, washed with water 4 times, dried over sodium sulfate, and concentrated. Chromatography on silica gel with 1-2% methanol in dichloromethane 2 times gave 24-3 as a white foam, which was dissolved in 5% piperidine in DMF (4 mL). The solution stood at rt for 30 mins and then concentrated to dryness under high vacuum. Chromatography con silica gel with 2-6% MeOH in dichloromethane gave pure 24-4 (143 mg).

Pure 24-4 (143 mg, 0.256 mmol) was dissolved in MeOH (5 mL) and ammonium chloride (13.7 mg, 0.256 mmol) added. After standing for 5 mins, the methanol was evaporated on a rotary evaporator, and then the residue was co-evaporated with methanol once. The residue was dissolved water, filtered, and lyophilized to give compound 2401 (152 mg) as a white foam. +ESI-LCMS: m/z 559.4 [M+H]$^+$.

Example 25-1

Preparation of Compound 2500

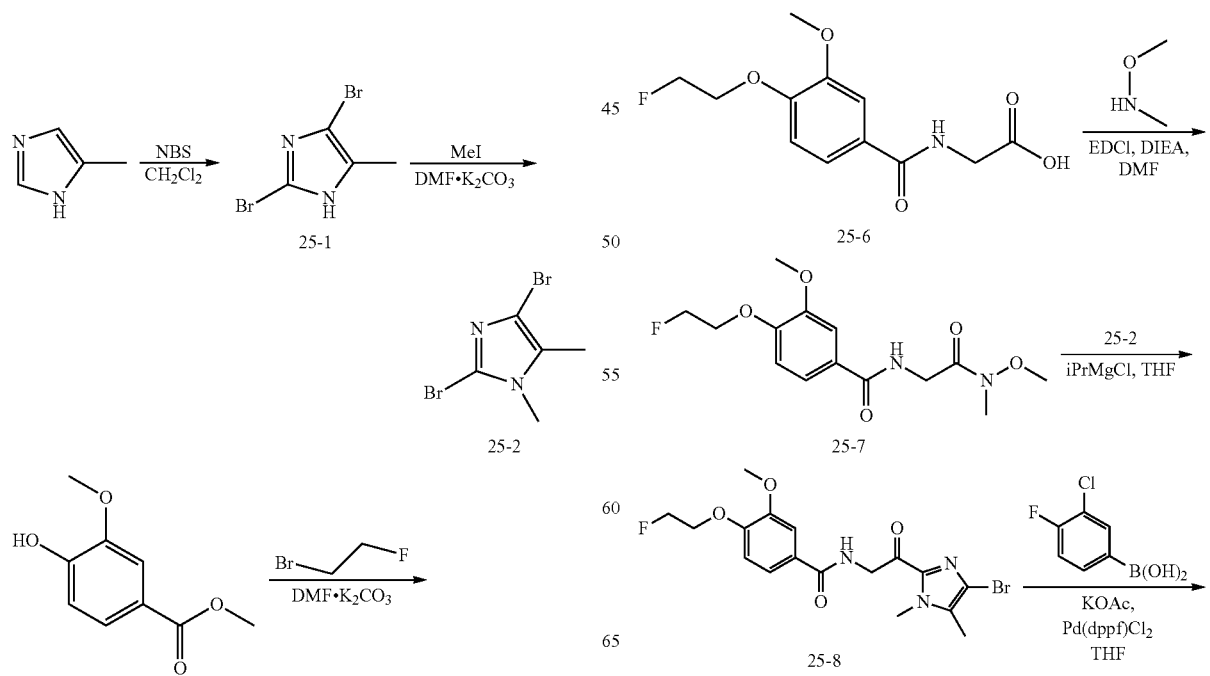

389

-continued

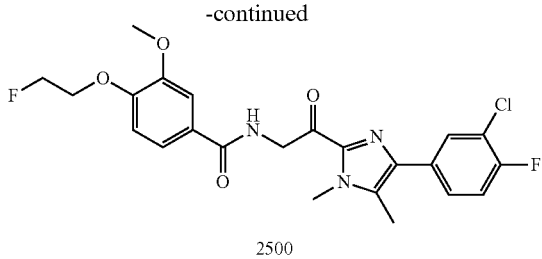

2500

To a solution of 4(5)-methylimidazole (2 g, 24 mmol) in CH$_2$Cl$_2$ (150 mL) was added bromine (2.5 mL, 48 mmol) at 0° C. The solution was stirred for 1H at rt. The product was filtered and partitioned between EA and saturated NaHCO$_3$. The product was precipitated from MeOH/CH$_2$Cl$_2$ to provide 25-1 (4.31 g, 75%). $^1$H NMR (400 MHz, DMSO-d$_6$): δ 2.06 (s, 3H).

To a solution of 25-1 (3.6 g, 15 mmol) and K$_2$CO$_3$ (4.1 g, 30 mmol) in DMF (18 mL) was added iodomethane (1.4 mL, 23 mmol) at 25° C. The solution was stirred for 15 h. The mixture was poured into water and extracted with EA The combined organic phase was dried over anhydrous Na$_2$SO$_4$, and the residue was purified by chromatography on silica gel (EA/hexane) to give 25-2 (1.6 g, 41%). $^1$H NMR (400 MHz, CDCl$_3$): δ 3.52 (s, 3H), 2.21 (s, 3H).

To a solution of methyl vanillate (7.06 g, 39 mmol) and K$_2$CO$_3$ (10.7 g, 78 mmol) in DMF (25 mL) was added 1-bromo-2-fluoroethane (4.3 mL, 58 mmol) at 25° C. The solution was stirred for 2 days. The mixture was poured into water and extracted with EA. The combined organic layers were dried over anhydrous Na$_2$SO$_4$, and concentrated. The residue was purified by chromatography on silica gel (EA/hexane) to give 25-3 (8.92 g, 103%).). $^1$H NMR (400 MHz, CDCl$_3$): δ 7.63 (dd, J=2.15, 8.41, 1H), 7.55 (d, J=8.41, 1H), 4.72-4.86 (m, 2H), 4.27-4.35 (m, 2H), 3.90 (s, 3H), 3.88 (s, 3H).

To a solution of 25-3 (8.92 g, 39 mmol) in MeOH (150 mL) was added 2 N NaOH (40 mL, 78 mmol). The solution was stirred for 2 h at 70° C. The mixture was concentrated, acidified with 2N HCl and extracted with EA to provide 25-4. (5.0 g, 30%). $^1$H NMR (400 MHz, DMSO-d$_6$): δ 7.47 (dd, J=1.96, 8.41, 1H), 7.38 (d, J=1.96, 1H), 6.99 (d, J=8.41, 1H), 4.61-4.76 (m, 2H), 4.17-4.27 (m, 2H).

To a solution of 25-4 (3.07 g, 14.3 mmol), glycine methyl ester HCl salt (3.6 g, 29 mmol), HATU (6.5 g, 17 mmol) in DMF (15 mL) was added DIEA (10 mL, 57 mmol). The solution was stirred for 18 h at rt. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 25-5 (2.02 g, 51%). $^1$H NMR (400 MHz, CDCl$_3$): δ 7.43 (d, J=2.15, 1H), 7.30 (dd, J=2.15, 8.42), 6.90 (d, J-8.42, 1H), 6.57 (br. t, 1H), 4.72-4.85 (m, 2H), 4.22-4.35 (m, 2H), 4.25 (d, J=5.08, 2H) 3.85 (s, 3H), 3.79 (s, 3H).

To a solution of 25-5 (2.02 g, 7.1 mmol) in MeOH (50 mL) was added 2 N NaOH (10 mL, 20 mmol). The solution was stirred for 2 h at rt. The mixture was concentrated, acidified with 2N HCl and extracted with EA to provide 25-6. (1.38 g, 72%). $^1$H NMR (400 MHz, CD$_3$OD): δ 7.49 (m, 2H), 7.04 (d, J=8.42, 1H), 4.62-4.85 (m, 2H), 4.25-4.34 (m, 2H), 4.08 (s, 2H), 3.90 (s, 3H).

To a solution of 25-6 (0.52 g, 1.9 mmol), N,O-dimethyl-hydroxylamine hydrochloride (0.23 g, 3.8 mmol), EDCI (0.38 g, 2.3 mmol) in DMF (3 mL) was DIEA (1.0 mL, 5.8 mmol). The solution was stirred for 2 h at rt. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 25-7 (0.28 g, 47%). $^1$H NMR (400 MHz, CDCl$_3$): δ 7.43 (d, J=1.96, 1H), 7.33 (dd, J=1.96, 8.22, 1H), 6.90 (d, J=8.22, 1H), 4.71-4.84 (m, 2H), 4.26-4.36 (m, 4H), 3.91 (3, 3H), 3.76 (s, 3H), 3.25 (s, 3H).

Isopropylmagnesium chloride (2.0M, 0.48 mL, 0.95 mmol) was added dropwise to a solution of 25-7 (0.12 g, 0.38 mmol) and 25-2 (0.13 g, 0.50 mmol) in THF (1.0 mL). The solution was stirred for 2 h at rt. The reaction was quenched with 1N HCl, diluted with EA and washed with brine. The organic solution was filtered to 25-8 (0.030 g, 20%). $^1$H NMR (400 MHz, CDCl$_3$): δ 7.49 (d, J=2.15, 1H), 7.38 (dd, J=2.15, 8.21, 1H), 7.03 (t, J=5.09, 1H), 4.93 (d, J=5.09, 2H), 4.74-4.96 (m, 2H), 4.28-4.37 (m, 2H), 3.96 (s, 3H), 3.93 (s, 3H), 2.22 (s, 3H).

A solution of 25-8 (30 mg, 0.070 mmol), 3-chloro-4-fluorophenylboronic acid (24 mg, 0.14 mmol), potassium acetate (21 mg, 0.21 mmol) and Pd(dppf)Cl$_2$ (10 mg, 0.014 mmol) was heated under microwave irradiation for 1 h at 110° C. The mixture was concentrated and purified by chromatography on silica gel (EA/hexane) to give compound 2500 (24 mg, 72%). LC/MS: [M+H] 478.10.

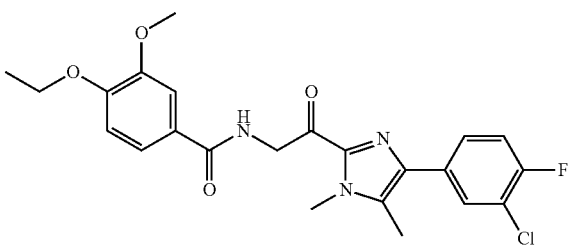

2502

Compound 2502 was prepared using iodoethane in the alkylation step and by following a synthetic route, which closely follows that described for preparation of compound 2500. LC/MS: [M+H] 460.05.

Example 25-2

Preparation of Compound 2504

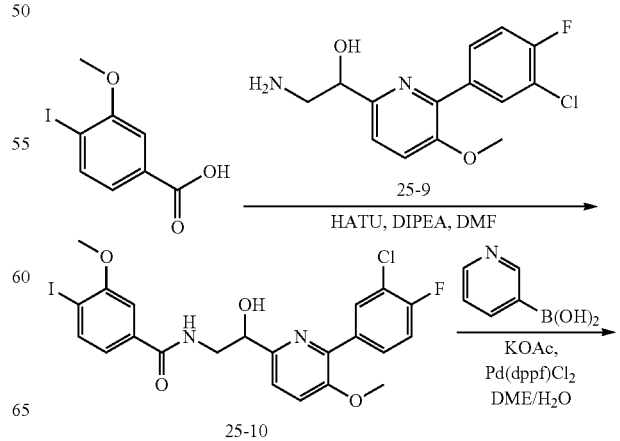

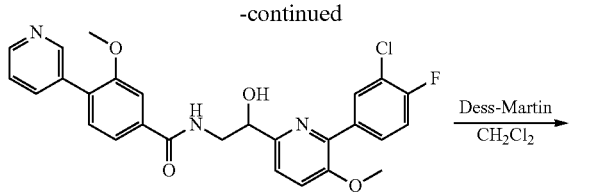

25-11

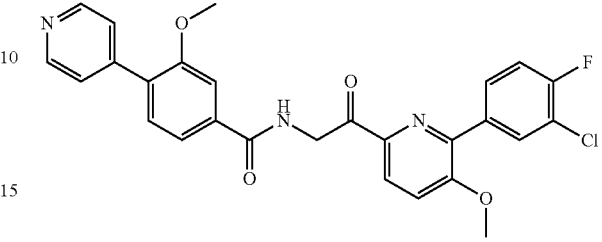

2504

To a solution of 3-methoxy-4-iodobenzoic acid (0.45 g, 1.6 mmol), 25-9 (0.485 g, 1.6 mmol), HATU (0.75 g, 2.0 mmol) in DMF (3 mL) was added DIEA (0.71 mL, 4.1 mmol). The solution was stirred for 18 h at rt. The mixture was diluted with EA. The organic phase was washed with water, 1N HCl, NaHCO$_3$ and brine, dried over anhydrous Na$_2$SO$_4$, and concentrated. The residue was purified by chromatography on silica gel (MeOH/CH$_2$Cl$_2$) to give 25-10 (0.176 g, 51%). $^1$H NMR (400 MHz, CDCl$_3$): δ 7.99 (dd, J=2.15, 7.24, 1H), 7.81-7.85 (m, 1H), 7.75 (d, J=8.02, 1H), 7.37-7.42 (m, 2H), 7.26-7.27 (m, 1H), 7.25 (t, J=8.71, 1H), 6.93 (dd, J=1.96, 8.02), 6.83-6.86 (m, 1H), 4.97-4.99 (m, 1H), 3.99-4.13 (m, 1H), 3.90 (s, 3H), 3.89 (s, 3H), 3.54-3.72 (m, 1H).

A solution of 25-10 (25 mg, 0.045 mmol), pyridine-3-boronic acid (11 mg, 0.09 mmol), potassium acetate (13 mg, 0.13 mmol) and Pd(dppf)Cl$_2$ (6 mg, 0.009 mmol) in DME (0.5 mL) and H$_2$O (0.05 mL) was heated under microwave irradiation for 1 h at 110° C. The mixture was concentrated and purified by chromatography on silica gel (MeOH/CH$_2$Cl$_2$) to give 25-11 (22 mg, 88%). $^1$H NMR (400 MHz, CDCl$_3$): δ 8.74-8.90 (br. s, 1H), 8.60-8.72 (br. s, 1H), 8.00, dd, J=2.15, 7.24), 7.85-7.88 (m, 2H), 7.34-7.45 (m, 5H), 7.17, (t, J=8.80, 1H), 6.94-6.97 (m, 1H), 4.98-5.01 (m, 1H), 4.00-4.09 (m, 1H), 3.88 (s, 3H), 3.82 (s, 3H0, 3.68-3.75 (m, 1H).

Dess-Martin periodinane (25 mg, 0.061 mmol) was added to a solution of 25-11 (22 mg, 0.043 mmol) in CH$_2$Cl$_2$, and stirred for 2 h. The mixture was diluted with CH$_2$Cl$_2$, washed with saturated Na$_2$CO$_3$, and brine, dried over MgSO$_4$, and concentrated under reduced pressure. The crude product was purified by chromatography on silica gel (EA/hexane) to give compound 2504 (6.1 mg, 28%). LC/MS: [M+H] 506.10.

2506

Compound 2506 was prepared using pyrazole-4-boronic acid pinacol ester in the Suzuki reaction and by following a synthetic route, which closely follows that described for preparation of compound 2504. LC/MS: [M+H] 495.10.

2507

Compound 2507 was prepared using pyridine-4-boronic acid pinacol ester in the Suzuki reaction and by following a synthetic route, which closely follows that described for preparation of compound 2504. LC/MS: [M+H] 506.10.

2508

Compound 2508 was prepared using pyrimidine-4-boronic acid pinacol ester in the Suzuki reaction and by following a synthetic route, which closely follows that described for preparation of compound 2504. LC/MS: [M+H] 507.10.

Example 26-1

Preparation of Compound 2600

26-1

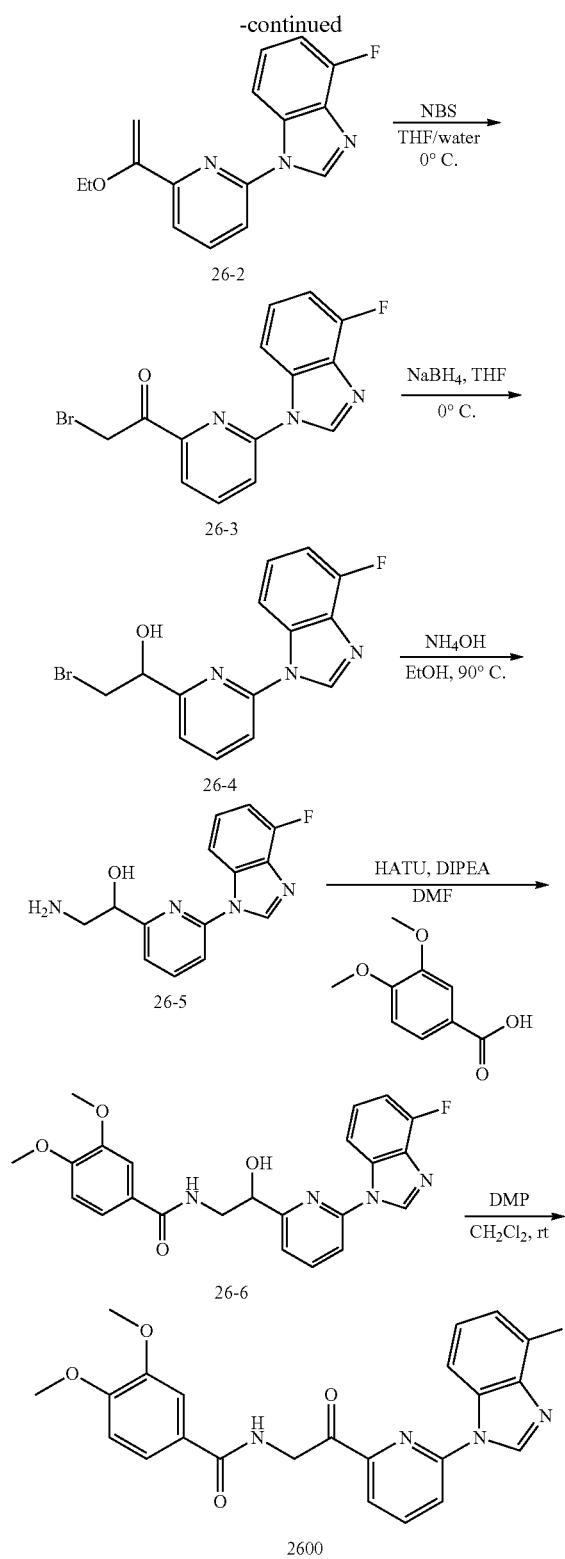

(2×25 mL). The combined organic layers were dried over MgSO₄, filtered, and concentrated under reduced pressure. Chromatography of the residue afforded 26-1 (300 mg) as a white solid. LCMS: 248.1 m/z [M+H]⁺.

To a stirring mixture of 26-1 (300 mg, 1.056 mmol), KF (184 mg, 3.2 mmol), Pd(dppf)Cl₂ (155 mg, 0.2 mmol) in dry DMF (2 mL, deoxygenated prior to use) was added tributyl (1-ethoxyvinyl)stannane (381 mg, 1.056 mmol). The mixture was stirred at 85° C. for 1 h. The mixture was cooled to rt and directly loaded into a silica gel column to give 26-2 as a colorless oil. LCMS: 284.2. m/z [M+H]⁺.

To a stirred solution of 26-2 (130 mg, 0.46 mmol) in THF/water (1.6 mL/0.8 mL) at 0° C. was added NBS (86 mg, 0.48 mmol). The mixture was stirred at 0° C. for 15 mins. The mixture was then quenched with a saturated NaHCO₃ solution. The aqueous layer was extracted with EtOAc (2×25 mL). The organic layers were dried (Na₂SO₄), filtered and concentrated under reduced pressure. Crude 26-3 was used in the next step without any purification.

To this stirring mixture of 26-3 in MeOH/THF (1:3, 4 mL total volume) at 0° C. was added NaBH₄ (17.5 mg). The mixture was stirred for 10 mins at 0° C. The reaction was quenched with a saturated NaHCO₃ solution. The aqueous layer was extracted with EtOAc (2×25 mL). The organic layers were dried (Na₂SO₄), filtered and concentrated under reduced pressure. Crude 26-4 was used in the next step without any purification.

To a stirring mixture of 26-4 in EtOH (2 mL) was added an ammonia hydrate solution (2 mL) in a sealed tube. The mixture was heated at reflux for 1 h and then cooled to rt. The mixture was diluted with toluene and concentrated under reduced pressure. This process was repeated twice. The mixture was used in the next step without further purification.

To a stirring mixture of 3,4-dimethoxybenzoic acid (54 mg, 0.3 mmol) in DMF (2 mL) at rt were added HATU (127 mg, 0.33 mmol) and DIPEA (83 mg, 0.64 mmol). The mixture was reacted at rt for 10 mins. To this mixture was added a solution of 26-5 in DMF (1 mL). The mixture was stirred at rt for 1 h and then quenched with a saturated NaHCO₃ solution. The aqueous layer was extracted with EtOAc (2×25 mL). The organic layers were dried (Na₂SO₄), filtered and concentrated under reduced pressure. Chromatography of the residue afforded 26-6 (100 mg) as a yellow oil. LC/MS: 437.25 m/z [M+H]⁺.

To a stirring mixture of 26-6 (100 mg, 0.22 mmol) in DCM (2 mL) at rt was added Dess-Martin periodinane (650 mg, 1.53 mmol). The mixture was stirred at rt for 1 h and then slowly quenched with 5% NaHSO₃ and a saturated NaHCO₃ solution. The aqueous layer was extracted with EtOAc (2×25 mL). The organic layers were dried (Na₂SO₄), filtered and concentrated under reduced pressure. The crude product mixture was purified using prep-HPLC to afford compound 2600 as a while solid. LCMS: 435.25 m/z [M+H]⁺.

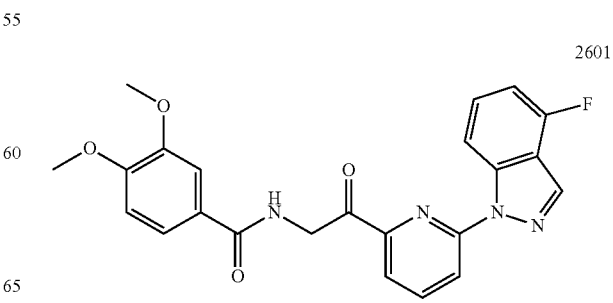

2601

To a stirring mixture of 2,6-dichloropyridine (270 mg, 1.82 mmol) and 7-fluoro-1H-benzo[d]imidazole (248 mg, 1.82 mmol) in DMF (3 mL) was added Cs₂CO₃ (709 mg, 2.2 mmol). The mixture was reacted at 120° C. for 2 h and then cooled to rt. The mixture was diluted with EtOAc and washed with a saturated NaCl solution. The layers were separated. The aqueous layer was extracted with EtOAc Compound 2601 was prepared using 2,6-dichloropyridine and 7-fluoro-1H-indazole and by following a synthetic route, which closely follows that described for preparation of compound 2600. LCMS: 435.30 m/z [M+H]+.

Compound 2604 was prepared using 2,4,6-trichloropyridine and 2-(7-fluorobenzo[b]thiophen-3-yl)-4,4,5,5-tetramethyl-1,3,2-dioxaborolane, and by following a synthetic route, which closely follows that described for preparation of compound 2600. LCMS: 485.25 m/z [M+H]+.

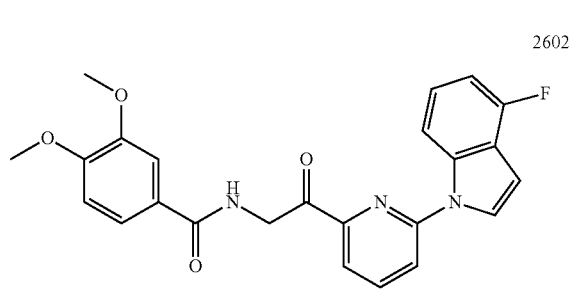 [SMILES: COc1ccc(C(=O)NCC(=O)c2cccc(-n3ccc4c(F)cccc43)n2)cc1OC]

2602

Compound 2602 was prepared using 2,6-dichloropyridine and 7-fluoro-1H-indole and by following a synthetic route, which closely follows that described for preparation of compound 2600. LCMS: 434.25 m/z [M+H]+.

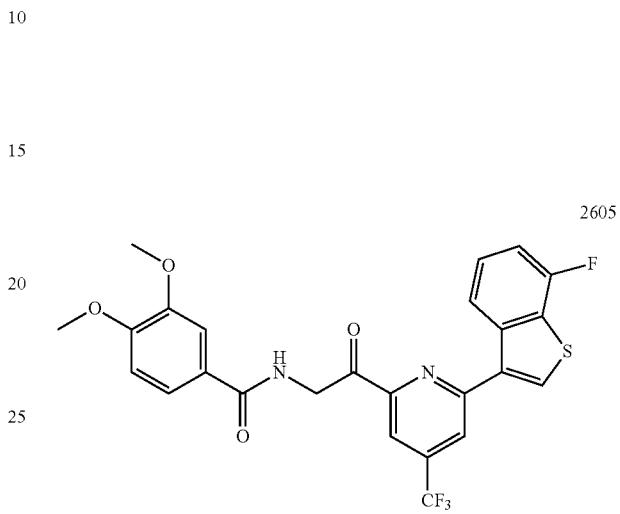

2605

Compound 2605 was prepared using 2,6-dichloro-4-(trifluoromethyl)pyridine and by following a synthetic route, which closely follows that described for preparation of compound 2604. LCMS: 519.1 m/z [M+H]+.

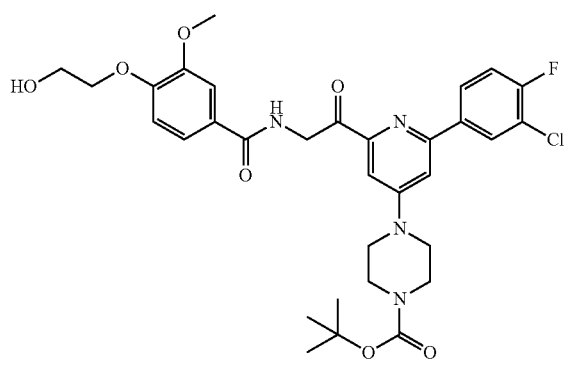 [SMILES: COc1cc(C(=O)NCC(=O)c2cc(N3CCN(C(=O)OC(C)(C)C)CC3)cc(-c3ccc(F)c(Cl)c3)n2)ccc1OCCO]

Compound 2603 was prepared using 1-piperazinecarboxylic acid, 4-(2,6-dichloro-4-pyridinyl)-, 1,1-dimethylethyl ester and by following a synthetic route, which closely follows that described for preparation of compound 2600. LCMS: 643.20 m/z [M+H]+.

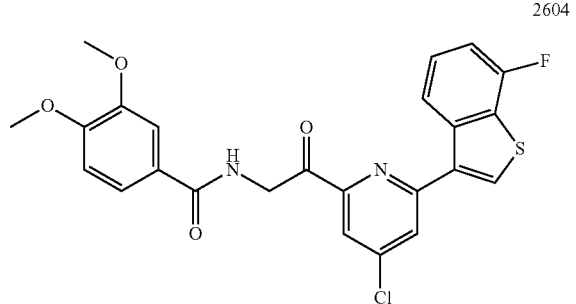 [SMILES: COc1ccc(C(=O)NCC(=O)c2cc(Cl)cc(-c3csc4c(F)cccc34)n2)cc1OC]

2604

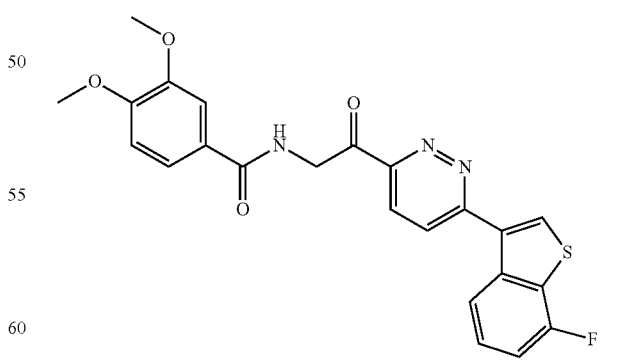

2606

Compound 2606 was prepared using 3,6-dichloropyridazine and by following a synthetic route, which closely follows that described for preparation of compound 2605. LCMS: 452.05 m/z [M+H]+.

Example 26-2

Preparation of Compound 2607

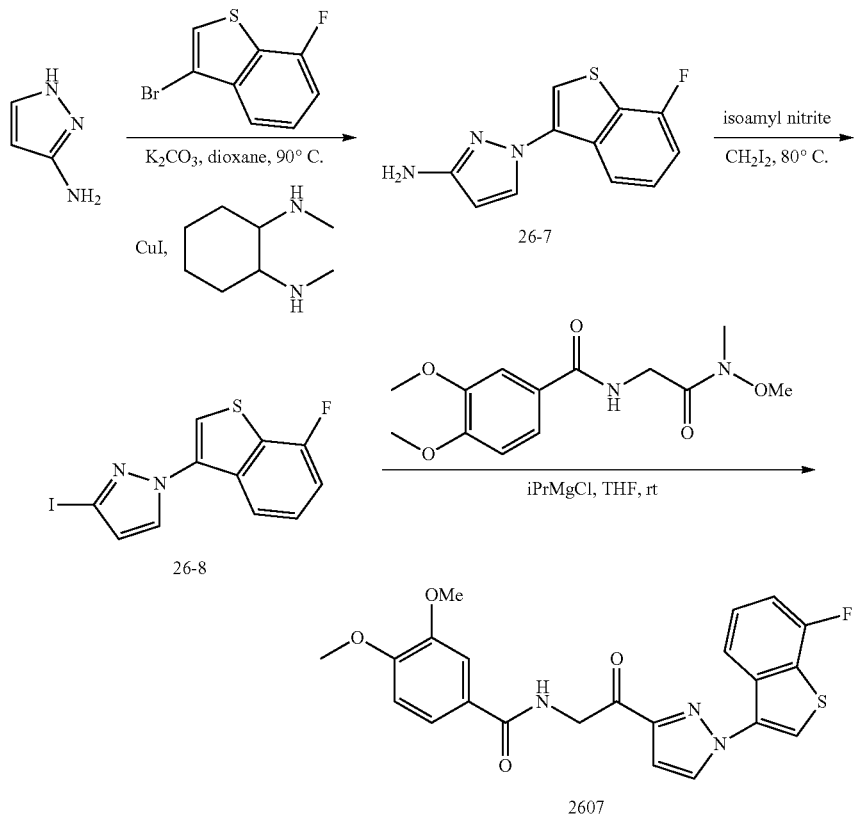

To a stirring mixture of 1H-pyrazol-3-amine (250 mg, 3 mmol) in dioxane (2 mL, deoxygenated prior to use) were added CuI (115 mg, 0.6 mmol), N1,N2-dimethylcyclohexane-1,2-diamine (102 mg, 0.72 mmol), K$_2$CO$_3$ (1.2 g, 9.04 mmol), and 3-bromo-7-fluorobenzo[b]thiophene (580 mg, 2.51 mmol). The mixture was heated at reflux for 2 h and then cooled to rt. The mixture was diluted with EtOAc and quenched with 10% NH$_4$OH. The aqueous layer was extracted with EtOAc. The organic layers were dried (Na$_2$SO$_4$), filtered and concentrated under reduced pressure. The crude product was purified by silica column chromatograph to afford 26-7 as a yellow solid (240 mg, 55% yield). LC/MS: 234.14 m/z [M+H]$^+$.

To a stirring mixture of 26-7 (180 mg, 0.77 mmol) in CH$_2$I$_2$ (3 mL) was added isoamyl nitrite (888 mg, 7.7 mmol). The mixture was stirred at 80° C. for 1 h and then cooled to rt. The crude mixture was concentrated under reduced pressure. The crude product was purified via silica column chromatograph to afford 26-8 as a yellow oil (230 mg). LCMS: 345.05 m/z [M+H]$^+$.

To a stirring mixture of 3,4-dimethoxy-N-(2-(methoxy (methyl)amino)-2-oxoethyl)benzamide (62 mg, 0.21 mmol) and 26-8 (80 mg, 0.26 mmol) in THF at rt under argon was added a solution of iPrMgCl in THF (0.35 mL, 0.65 mmol). The mixture was stirred at rt for 20 mins and then diluted with EtOAc. The reaction was slowly quenched with a saturated NH$_4$Cl solution. The organic layers were dried (Na$_2$SO$_4$), filtered and concentrated under reduced pressure. The crude product was purified by silica gel column and the product mixture was further purified via prep-HPLC to afford compound 2607 as a yellow solid. LCMS: 440.25 m/z [M+H]$^+$.

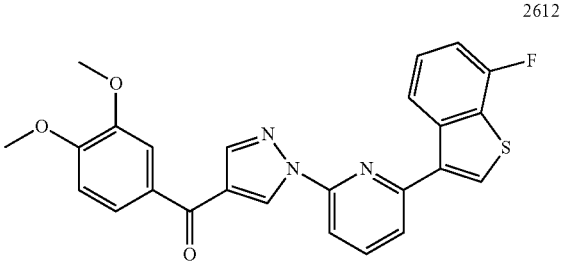 [SMILES: COc1ccc(C(=O)c2cnn(-c3cccc(-c4csc5c(F)cccc45)n3)c2)cc1OC]

2612

Compound 2612 was prepared using 2,6 dichloro pyridine and by following a synthetic route, which closely follows that described for preparation of compound 2607. LCMS: 460.05 m/z [M+H]$^+$.

Example 26-3

Preparation of Compound 2613

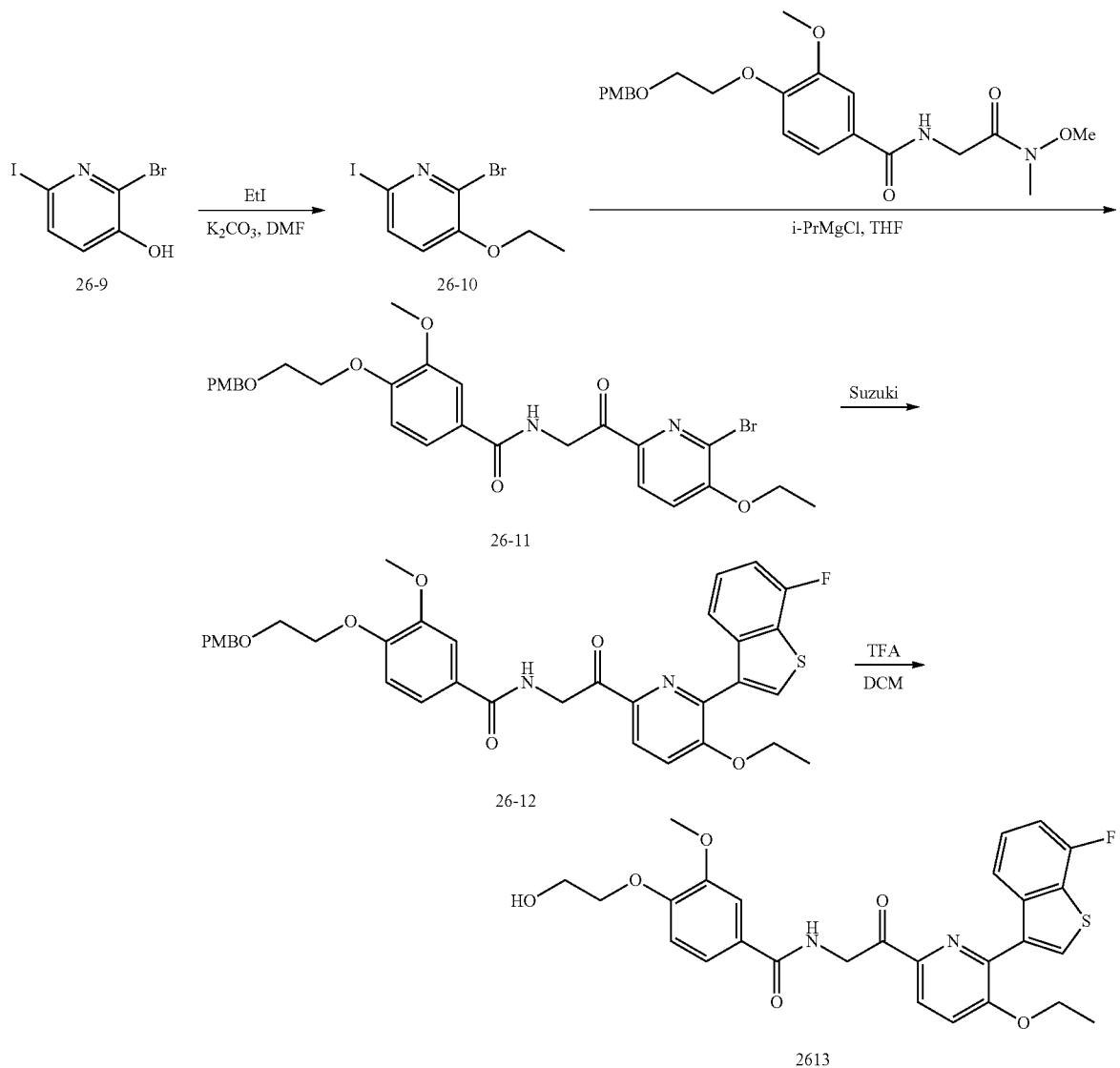

To a solution of 26-9 (300 mg, 1.0 mmol) in DMF (4 mL) was added K$_2$CO$_3$ (276 mg, 2.0 mmol) and EtI (163 mg, 1.05 mmol). The mixture was stirred at rt for 1 h and then diluted with EtOAc. The aqueous layer was extracted with EtOAc. The organic layers were dried (Na$_2$SO$_4$), filtered and concentrated under reduced pressure. The crude product was purified by silica gel column to afford 26-10 as a white solid. LCMS: 327.80 m/z [M+H]$^+$.

To a solution of 26-10 (91 mg, 0.28 mmol) and 3-methoxy-N-(2-(methoxy(methyl)amino)-2-oxoethyl)-4-(2-((4-methoxybenzyl)oxy)ethoxy)benzamide (80 mg, 0.18 mmol) in THF (0.28 mL) was added a solution of i-PrMgCl (0.28 mL, 0.56 mmol) in THF in portions. The mixture was reacted for 15 mins and slowly quenched with a saturated NH$_4$Cl solution and extracted with EA. The organic phase was dried over sodium sulfate, and then concentrated in vacuum to give crude 26-11, which was purified by column chromatography to give purified 26-11 (45 mg). LCMS: 573.0 m/z [M+H]$^+$.

To a solution of 26-11 (70 mg, 0.122 mmol) in dioxane/H$_2$O (10:1) (1.65 mL) were added a benzo-thiophene-based boronic ester (34 mg, 0.122 mmol), Pd(dppf)Cl$_2$ (25 mg, 0.025 mmol) and KOAc (35 mg, 0.36 mmol). The mixture stirred at 120° C. for 1 h under microwave conditions. The mixture was cooled to rt and concentrated under reduced pressure. The crude mixture was purified by column chromatography to give 26-12 as a yellow oil. LCMS: 645 m/z [M+H]$^+$.

To a stirring mixture of 26-12 (20 mg) in DCM (1.0 mL) at rt was added TFA (0.1 mL). The mixture was stirred for 5 mins, diluted with EtOAc and slowly quenched with a cold saturated NaHCO$_3$ solution, until pH >7. The aqueous layer was extracted with EtOAc. The organic layers were dried (Na₂SO₄), filtered and concentrated under reduced pressure. The crude product was purified by prep-HPLC to afford compound 2613 as a white solid. LCMS: 525.10 m/z [M+H]⁺.

2614

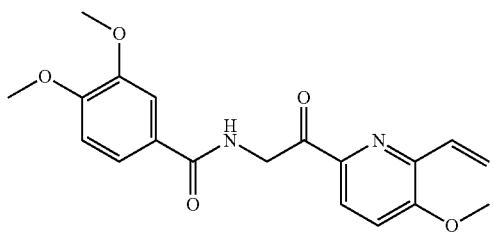

Compound 2614 was prepared using N-(2-(6-bromo-5-methoxypyridin-2-yl)-2-oxoethyl)-3,4-dimethoxybenzamide and vinyl boronic ester, and by following a synthetic route, which closely follows that described for preparation of compound 2613. LCMS: 357.10 m/z [M+H]⁺.

2615

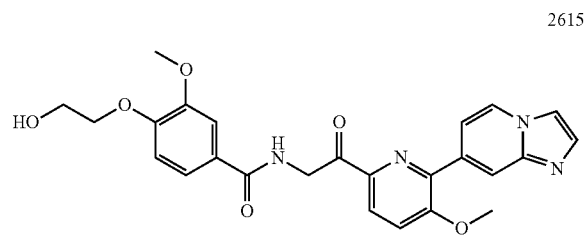 [SMILES: COc1cc(C(=O)NCC(=O)c2ccc(OC)c(-c3ccn4ccnc4c3)n2)ccc1OCCO]

Compound 2615 was prepared using N-(2-(6-bromo-5-ethoxypyridin-2-yl)-2-oxoethyl)-3-methoxy-4-(2-((4-methoxybenzyl)oxy)ethoxy)benzamide with 7-(4,4,5,5-tetramethyl-1,3,2-dioxaborolan-2-yl)imidazo[1,2-a]pyridine followed by the removal of PMB ether, and by following a synthetic route, which closely follows that described for preparation of compound 2613. LCMS: 477.15 m/z [M+H]⁺.

Example 26-4

Preparation of Compound 2616

2616

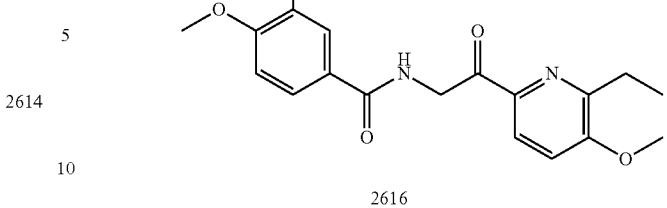

To a stirring mixture of 3,4-dimethoxy-N-(2-(5-methoxy-6-vinylpyridin-2-yl)-2-oxoethyl)benzamide (10 mg, 0.028 mmol) in EtOAc/EtOH (5 mL/1.0 mL) was added Pd/C (5 mg). The mixture was placed under hydrogen balloon and stirred for 20 mins. The crude mixture was filtered through a plug of celite and the plug was washed several times with EtOAc (2×10 mL). The mixture was concentrated under reduced pressure and purified via prep-HPLC to afford compound 2616 as a white solid. LCMS: 359.10 m/z [M+H]⁺.

2617

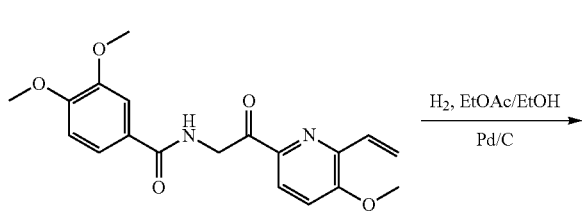

Compound 2617 was prepared using 2-bromo-6-iodopyridin-3-ol and (bromomethyl)cyclopropane were used as starting materials for the first alkylation step, and by following a synthetic route, which closely follows that described for preparation of compound 2613. LCMS: 551.10 m/z [M+H]⁺.

Example 26-5

Preparation of Compound 2618

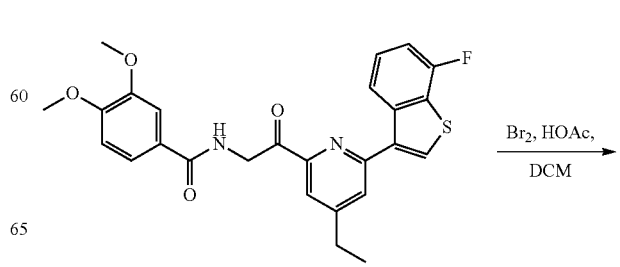

-continued

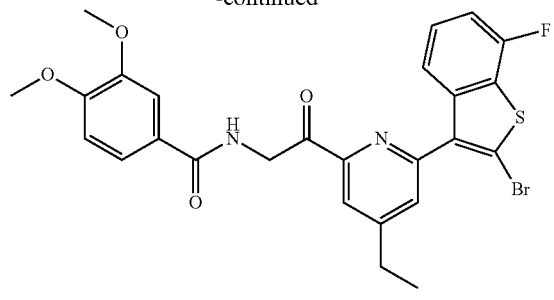

2618

To a stirring mixture N-(2-(4-ethyl-6-(7-fluorobenzo[b]thiophen-3-yl)pyridin-2-yl)-2-oxoethyl)-3,4-dimethoxybenzamide (30 mg, 0.06 mmol) in HOAc (0.5 mL) at rt was added a solution of bromine (20 mg) in DCM (0.25 mL). The mixture was stirred at rt until the starting material was consumed. The mixture was diluted with EtOAc and slowly quenched with $Na_2S_2O_3$. The aqueous layer was extracted with EtOAc. The organic layers were dried ($Na_2SO_4$), filtered and concentrated under reduced pressure. The crude mixture was purified via prep-HPLC to afford compound 2618 as a white solid. LCMS: 557.0 m/z [M+H]$^+$.

2619

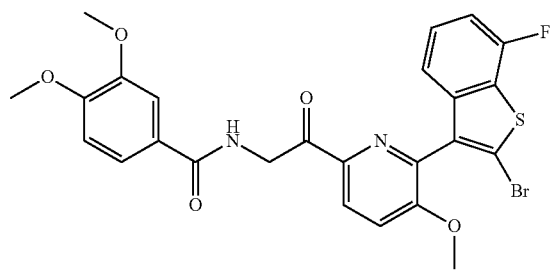

Compound 2619 was prepared using N-(2-(6-(7-fluorobenzo[b]thiophen-3-yl)-5-methoxypyridin-2-yl)-2-oxoethyl)-3,4-dimethoxybenzamide and bromine in DCM in the presence of HOAc, and by following a synthetic route, which closely follows that described for preparation of compound 2618. LCMS: 559.0 m/z [M+H]$^+$.

Example 26-6

Preparation of Compound 2620

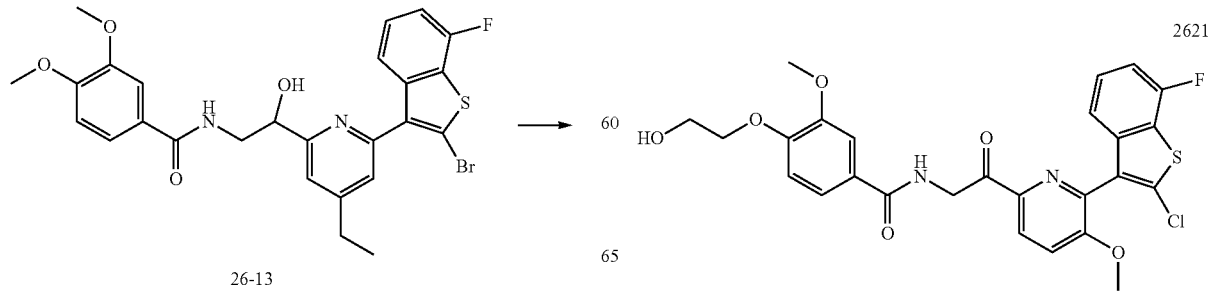

26-13

-continued

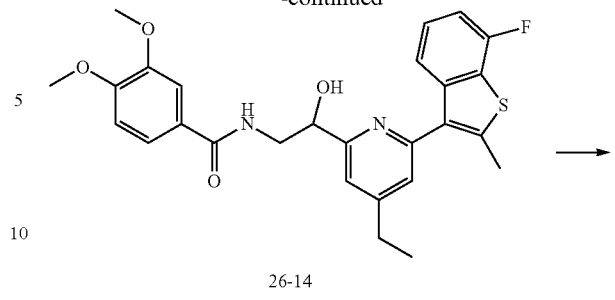

26-14

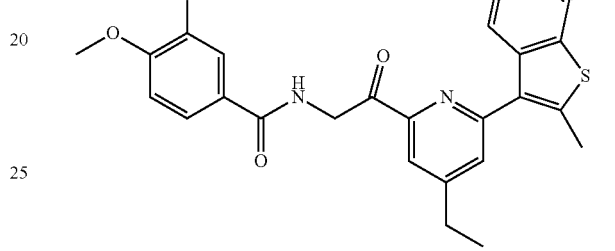

2620

To a stirring mixture of 26-13 (20 mg, 0.036 mmol) in THF (1 mL) were added bis(tri-tert-butylphosphine)palladium(0) (3.6 mg, 0.008 mmol), and a solution of MeZnCl in THF (0.055 mL, 0.11 mmol). The mixture was stirred under microwave condition at 100° C. for 1 h. The mixture was cooled to rt, diluted with EtOAc and slowly quenched with a saturated $NH_4Cl$ solution. The mixture was stirred at rt for 20 mins and then the layers were separated. The aqueous layer was extracted with EtOAc. The organic layers were dried ($Na_2SO_4$), filtered and concentrated under reduced pressure. The crude product mixture was purified via silica gel column to afford 26-14 as a colorless oil. LCMS: 495.1 m/z [M+H]$^+$.

To a stirring mixture of 26-14 (18 mg, 0.036 mmol) in DCM (2 mL) at rt was added Dess-Martin periodinane (154 mg, 0.36 mmol). The mixture was stirred at rt for 1 h and then slowly quenched with 5% $NaHSO_3$ and a saturated $NaHCO_3$ solution. The aqueous layer was extracted with EtOAc (2×25 mL). The organic layers were dried ($Na_2SO_4$), filtered and concentrated under reduced pressure. The crude product mixture was purified using prep-HPLC to afford compound 2620 as a while solid. LCMS: 493.15 m/z [M+H]$^+$.

2621

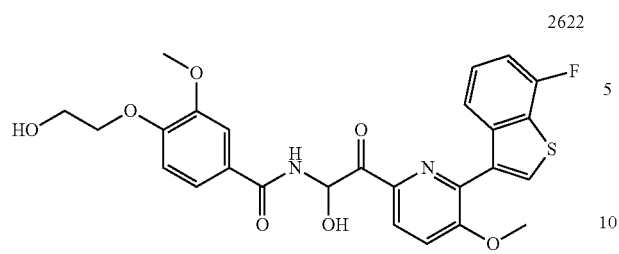

2622

To a stirring mixture of N-(2-(6-(7-fluorobenzo[b]thiophen-3-yl)-5-methoxypyridin-2-yl)-2-oxoethyl)-4-(2-hydroxyethoxy)-3-methoxybenzamide (40 mg, 0.67 mmol) in THF/water (0.5 mL/0.05 mL) at rt was added NCS (27 mg, 2 mmol). The mixture was heated at 70° C. for 1 h and then quenched with a saturated NaHCO$_3$. The mixture was diluted with EtOAc and the aqueous layer was extracted with EtOAc. The organic layers were dried (Na$_2$SO$_4$), filtered and concentrated under reduced pressure. The crude mixture was purified via prep-HPLC to afford compounds 2621 and 2622. Compound 2621: LCMS: 545.10 m/z [M+H]$^+$. Compound 2622: LCMS: 527.1 m/z [M+H]$^+$.

Example 26-7

Preparation of Compound 2623

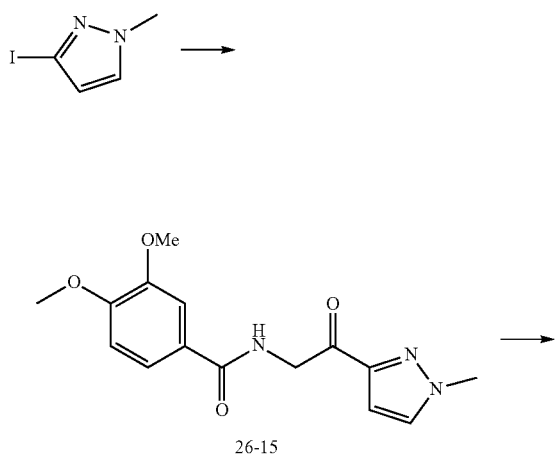

26-15

26-16

2623

To a stirring mixture of 3-iodo-1-methyl-1H-pyrazole (250 mg, 0.96 mmol) and 3,4-dimethoxy-N-(2-(methoxy (methyl)amino)-2-oxoethyl)benzamide (220 mg, 0.8 mmol) in THF was added a solution of i-PrMgCl (1.7 mL, 3.36 mmol) in THF (2.0M). The mixture was stirred for 20 mins, diluted with EtOAc and slowly quenched with a saturated NH$_4$Cl solution. The mixture was stirred at rt for 20 mins and the layers were separated. The aqueous layer was extracted with EtOAc. The organic layers were dried (Na$_2$SO$_4$), filtered and concentrated under reduced pressure. The crude product mixture was purified via silica gel column to afford 26-15 as a white solid (160 mg). LCMS: 304.1 m/z [M+H]$^+$.

To a stirring mixture of 26-15 (160 mg, 0.37 mmol) in CH$_3$CN in a presence of TFA (0.01 mL) was added NIS (130 mg, 0.59 mmol). The mixture was heated at 60° C. for 2 h and then cooled to rt. The mixture was stirred for 20 mins, diluted with EtOAc and quenched with a saturated NaHCO$_3$ solution. The mixture was stirred at rt for 20 mins and the layers were separated. The aqueous layer was extracted with EtOAc. The organic layers were dried (Na$_2$SO$_4$), filtered and concentrated under reduced pressure. The crude mixture was purified via silica gel chromatography to afford 26-16 as a white solid. LCMS: 430.0 m/z [M+H]$^+$.

To a stirring mixture of 26-16 (40 mg, 0.093 mmol) in dioxane/water (10:1, 1.5 mL total volume) were added 2-(7-fluorobenzo[b]thiophen-3-yl)-4,4,5,5-tetramethyl-1,3,2-dioxaborolane (30 mg, 0.1 mmol), PdCl$_2$(dppf) (12 mg, 0.014 mmol), and KOAc (32 mg, 0.33 mmol). The mixture was heated at 100° C. for 2 h. The mixture was cooled to rt and concentrated under reduced pressure. The crude product mixture was purified via silica gel chromatography and further purified via prep-HPLC to afford compound 2623 as a white solid. LCMS: 454.1 m/z [M+H]$^+$.

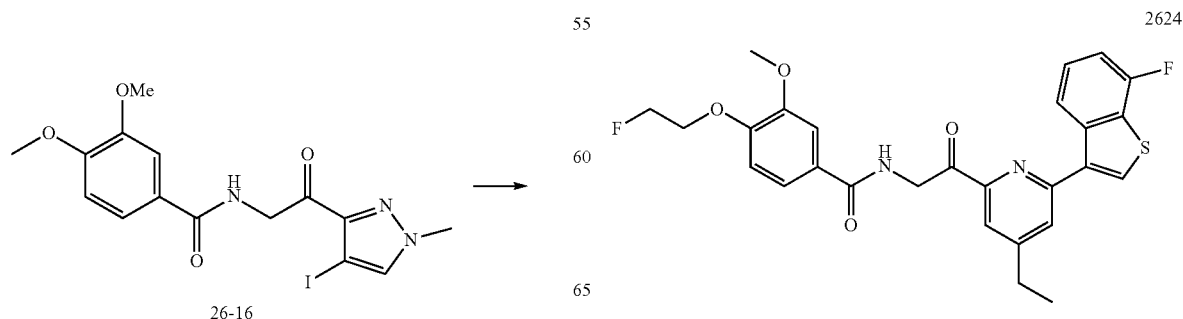

2624

To a stirring mixture of N-(2-(4-ethyl-6-(7-fluorobenzo[b]thiophen-3-yl)pyridin-2-yl)-2-oxoethyl)-4-(2-hydroxyethoxy)-3-methoxybenzamide (10 mg, 0.02 mmol) was added DAST (16 mg, 0.1 mmol) at 0° C. The mixture was reacted at 0 C for 1 h and then warmed to rt for 5 mins. The mixture was diluted with EtOAc and slowly quenched with a cold saturated NaHCO$_3$ solution. The aqueous layer was extracted with EtOAc. The organic layers were dried (Na$_2$SO$_4$), filtered and concentrated under reduced pressure. The crude product mixture was purified via prep-HPLC to afford compound 2624 as a white solid. LCMS: 511.15 m/z [M+H]$^+$.

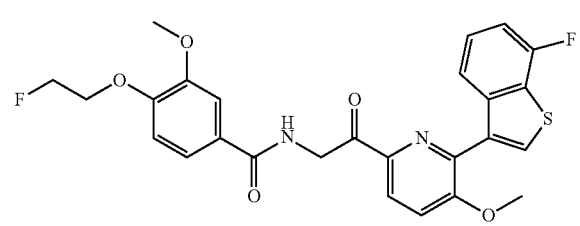

2625

Compound 2625 was prepared using N-(2-(6-(7-fluorobenzo[b]thiophen-3-yl)-5-methoxypyridin-2-yl)-2-oxoethyl)-4-(2-hydroxyethoxy)-3-methoxybenzamide and by following a synthetic route, which closely follows that described for preparation of compound 2624. LCMS: 513.10 m/z [M+H]$^+$.

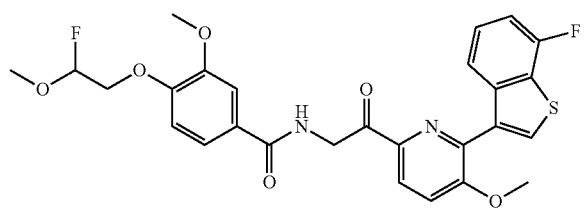

2626

Compound 2626 was prepared using N-(2-(6-(7-fluorobenzo[b]thiophen-3-yl)-5-methoxypyridin-2-yl)-2-oxoethyl)-4-(2-hydroxy-2-methoxyethoxy)-3-methoxybenzamide and by following a synthetic route, which closely follows that described for preparation of compound 2624. LCMS: 543.15 m/z [M+H]$^+$.

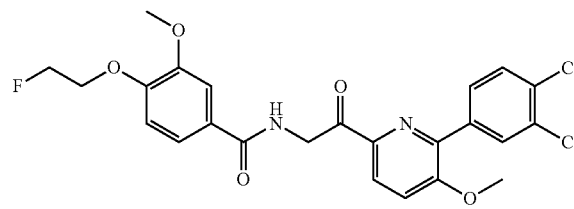

2627

Compound 2627 was prepared using N-(2-(6-(3,4-dichlorophenyl)-5-methoxypyridin-2-yl)-2-oxoethyl)-4-(2-hydroxyethoxy)-3-methoxybenzamide with DASF in DCM, and by following a synthetic route, which closely follows that described for preparation of compound 2624. LCMS: 507.05 m/z [M+H]$^+$.

Example 26-8

Preparation of Compound 2638

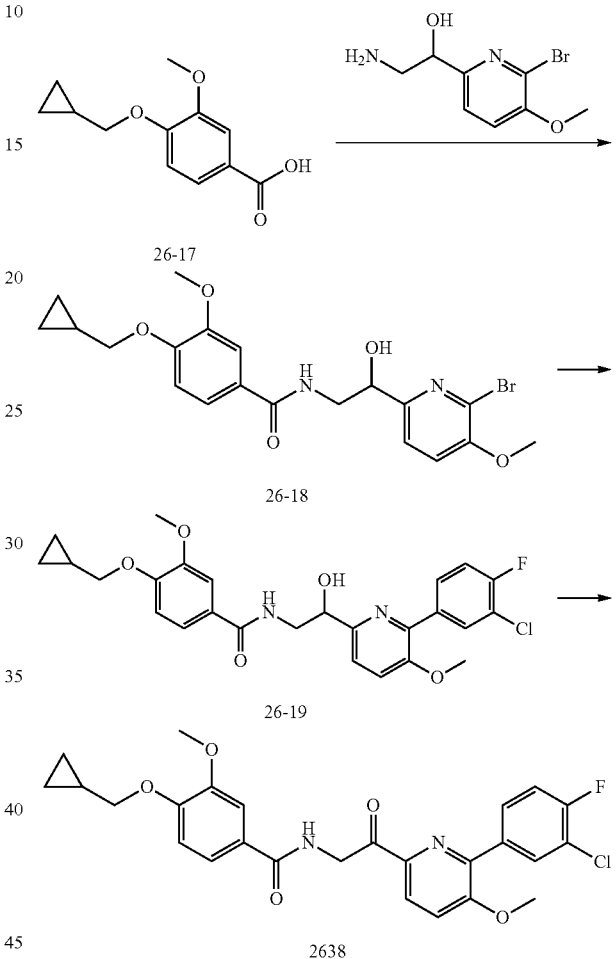

To a stirring mixture of 26-17 (44 mg, 0.197 mmol) in DMF were added HATU (83 mg, 0.218 mmol) and DIPEA (51 mg, 0.4 mmol). The mixture was stirred at rt for 10 min and a solution of 2-amino-1-(6-bromo-5-methoxypyridin-2-yl)ethan-1-ol was added. The mixture was stirred at rt for 1 h, diluted with EtOAc and quenched with a saturated NaHCO$_3$ solution. The mixture was stirred at rt for 10 mins and the layers were separated. The aqueous layer was extracted with EtOAc. The organic layers were dried (Na$_2$SO$_4$), filtered and concentrated under reduced pressure. The crude product was purified via silica gel chromatography to afford 26-18. LCMS: 451.05 m/z [M+H]$^+$.

To a stirring mixture of 26-18 (28 mg, 0.062 mmol) in DME/water (10:1, 2.2 mL) were added Cs$_2$CO$_3$ (60 mg, 0.19 mmol), PdCl$_2$dppf (10 mg, 0.012 mmol), and (3-chloro-4-fluorophenyl)boronic acid (11 mg, 0.062 mmol). The mixture was stirred under microwave conditions at 110° C. for 1 h. The crude product mixture was cooled to rt and concentrated under reduced pressure. The crude mixture was purified via silica gel chromatography to afford 26-19. LCMS: 501.15 m/z [M+H]$^+$.

To a stirring mixture of 26-19 (30 mg, 0.06 mmol) in DCM (2 mL) at rt was added Dess-Martin periodinane (400 mg, 0.9 mmol). The mixture was stirred at rt for 1 h and then slowly quenched with 5% NaHSO$_3$ and a saturated NaHCO$_3$ solution. The aqueous layer was extracted with EtOAc (2×25 mL). The organic layers were dried (Na$_2$SO$_4$), filtered and concentrated under reduced pressure. The crude product mixture was purified using prep-HPLC to afford compound 2638 as a while solid. LCMS: 499.15 m/z [M+H]$^+$.

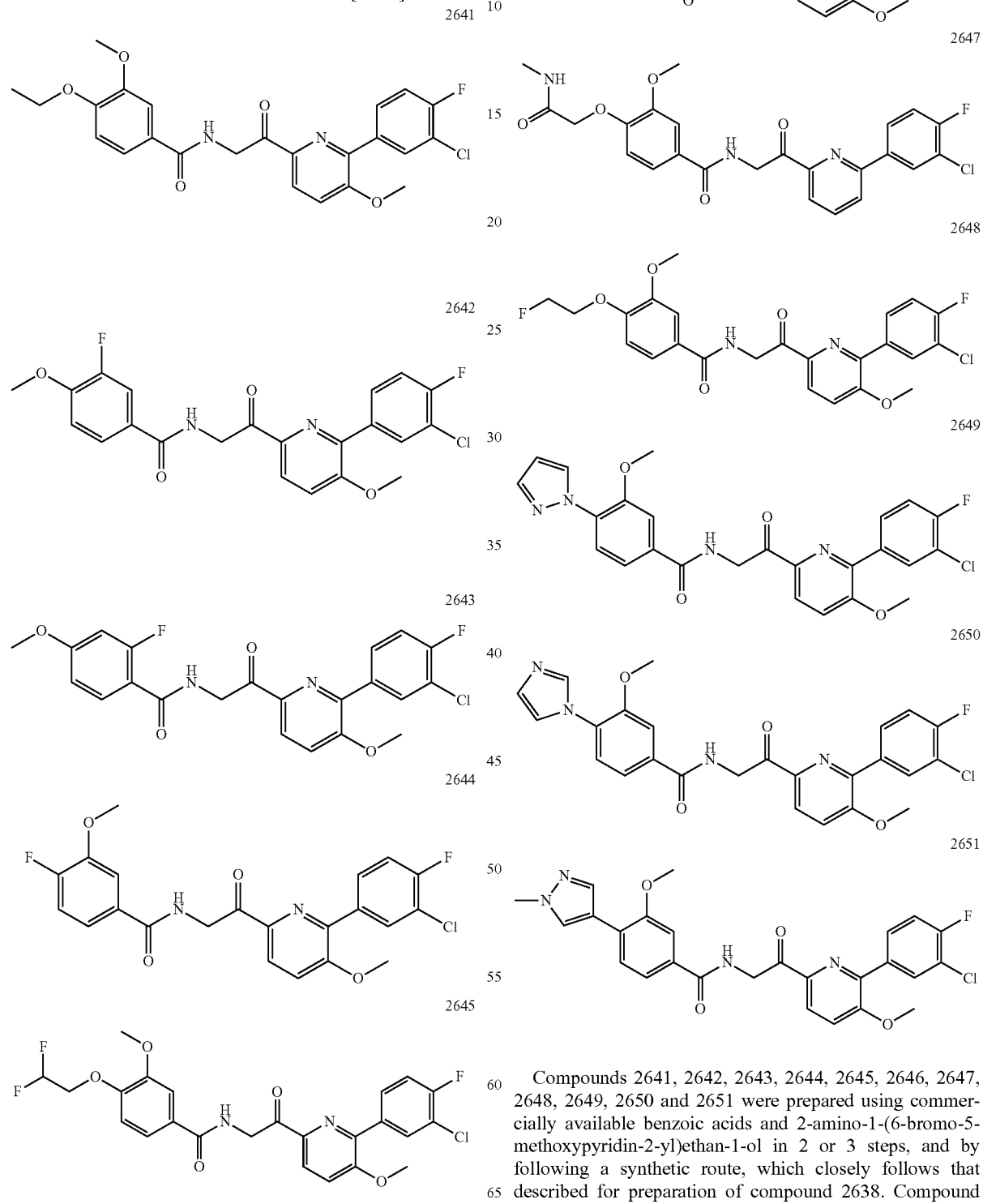

Compounds 2641, 2642, 2643, 2644, 2645, 2646, 2647, 2648, 2649, 2650 and 2651 were prepared using commercially available benzoic acids and 2-amino-1-(6-bromo-5-methoxypyridin-2-yl)ethan-1-ol in 2 or 3 steps, and by following a synthetic route, which closely follows that described for preparation of compound 2638. Compound 2641: LCMS: 473.10 m/z [M+H]$^+$. Compound 2642: LCMS: 447.05 m/z [M+H]$^+$. Compound 2643: LCMS:

447.05 m/z [M+H]+. Compound 2644: LCMS: 447.05 m/z [M+H]+. Compound 2645: LCMS: 509.05 m/z [M+H]+. Compound 2646: LCMS: 495.10 m/z [M+H]+. Compound 2647: LCMS: 486.05 m/z [M+H]+. Compound 2648: LCMS: 491.05 m/z [M+H]+. Compound 2649: LCMS: 495.05 m/z [M+H]+. Compound 2650: LCMS: [M+H] 495.05. Compound 2651: LCMS: [M+H] 509.1.
Example 26-9
Preparation of Compound 2652
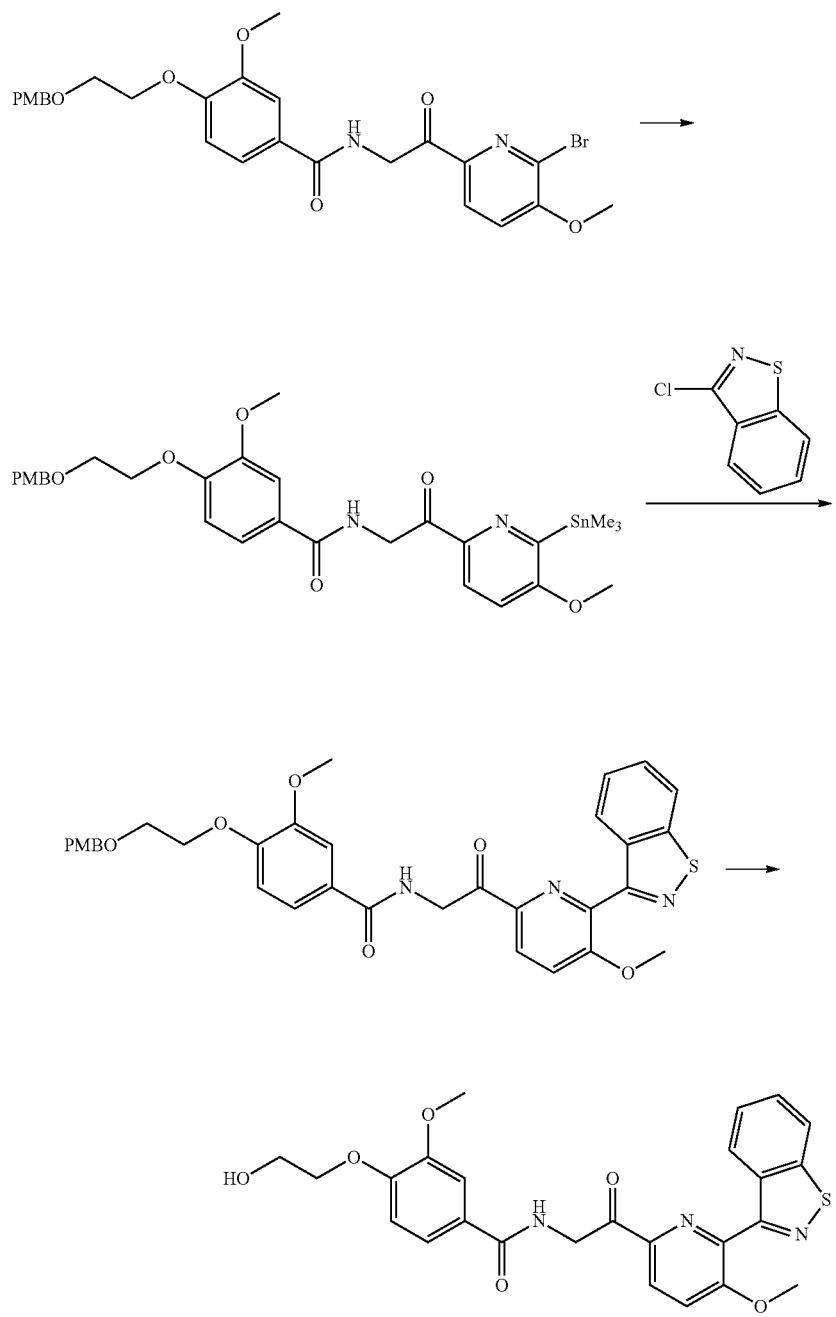

To a stirring mixture of N-(2-(6-bromo-5-methoxypyridin-2-yl)-2-oxoethyl)-3-methoxy-4-(2-((4-methoxybenzyl)oxy)ethoxy)benzamide (80 mg, 0.14 mmol) in dioxane (2 mL, deoxygenated prior to use) were added copper (I) thiophene carboxylate (5 mg), Pd(PPh$_3$)$_4$ (35 mg, 0.03 mmol), and Me$_6$Sn$_2$ (80 mg, 0.28 mmol). The mixture was heated under microwave irradiation for 1 h at 110° C. The mixture was cooled rt and the crude mixture was filtered through a plug of celite. The plug was washed with EtOAc. The filtrate was concentrated under reduced pressure and used in the next step without further purification. LCMS: 645.1 m/z [M+H]$^+$.

The crude stannane intermediate was dissolved in dioxane (1.0 mL). Copper (I) thiophene carboxylate (5 mg), Pd(PPh$_3$)$_4$ (35 mg, 0.03 mmol) and 3-chlorobenzo[d]isothiazole (48 mg, 0.48 mmol) was added. The mixture was heated at 90° C. for 1 h and then cooled to rt. This mixture was directly loaded into a silica gel column to afford the PMB protected ether. The PMB ether was removed using TFA in DCM at rt to afford compound 2652. LCMS: 494.05 m/z [M+H]$^+$.

Example 26-10

Preparation of Compound 2653

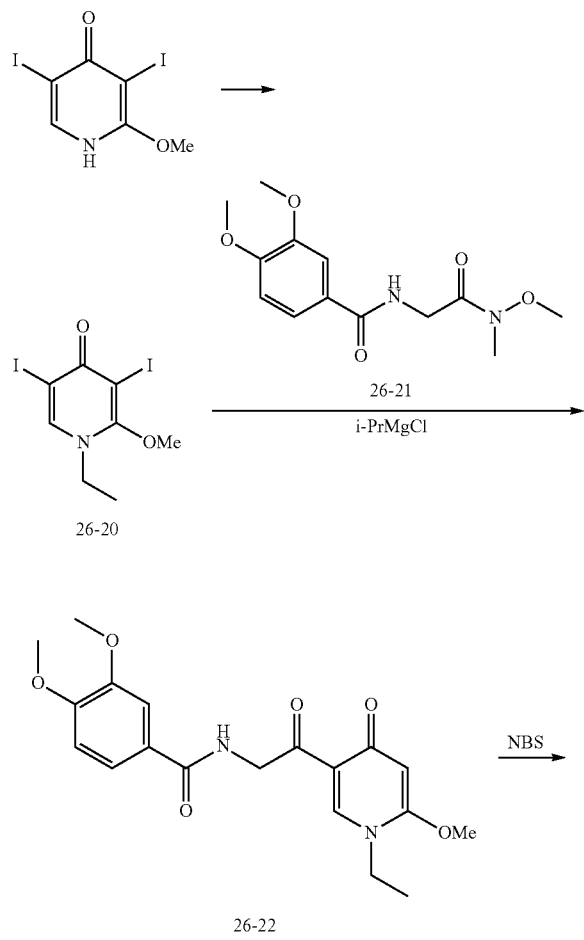

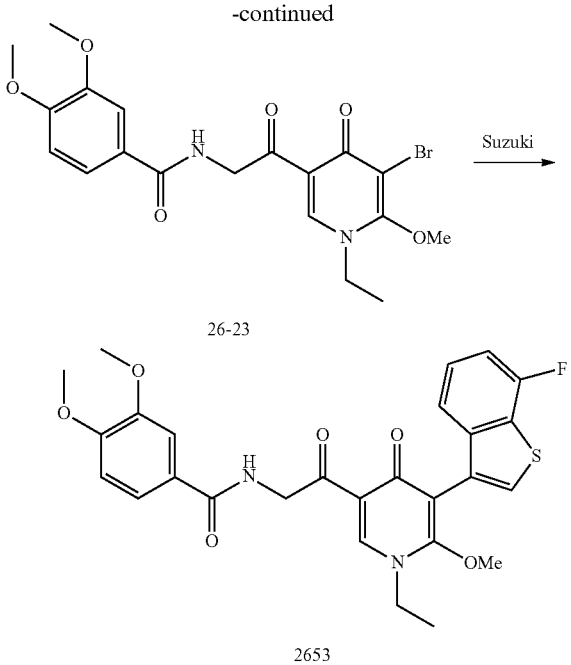

To a stirring mixture of 3,5-diiodo-2-methoxypyridin-4(1H)-one (380 mg, 1 mmol) in DMF (3 mL) were added K$_2$CO$_3$ (301 mg, 2.2 mmol) and ethyl iodide (0.12 mL, 1.51 mmol). The mixture was stirred at 75° C. for 2 h and then cooled to rt. The mixture was diluted with EtOAc and washed with a saturated NaCl solution. The aqueous layer was washed with EtOAc (2×20 mL). The organic layers were dried (Na$_2$SO$_4$), filtered and concentrated under reduced pressure. The crude mixture was purified via silica gel column to afford 26-20 as a white solid. LCMS: 406.0 m/z [M+H]$^+$.

To a stirring mixture of 26-20 (130 mg, 0.32 mmol) and 26-21 (55 mg, 0.19 mmol) in THF at rt was added a solution of iPrMgCl in THF (0.48 mL, 0.95 mmol). The mixture was stirred at rt for 10 mins, diluted with EtOAc and quenched slowly with a saturated NH$_4$Cl solution. The organic layers were dried (Na$_2$SO$_4$), filtered and concentrated under reduced pressure. The crude product mixture was purified via silica gel chromatography to afford 26-22 (55 mg, 73%) as a white solid. LCMS: 375.1 m/z [M+H]$^+$.

To a stirring mixture of 26-22 (55 mg, 0.147 mmol) in DMF (0.5 mL) at rt was added NBS (78.5 mg, 0.44 mmol). The mixture was stirred at 70° C. for 15 mins, cooled to rt and diluted with EtOAc. The reaction was quenched with a saturated NaHCO$_3$ solution. The aqueous layer was washed with EtOAc (2×20 mL). The organic layers were dried (Na$_2$SO$_4$), filtered and concentrated under reduced pressure. The crude product was purified via prep-HPLC to afford 26-23 (20 mg) as a white product. LCMS: 453.0 m/z [M+H]$^+$.

To a stirring mixture 26-23 (20 mg, 0.044 mmol) in dioxane/water (10:1, 2.2 mL total volume) were added 2-(7-fluorobenzo[b]thiophen-3-yl)-4,4,5,5-tetramethyl-1,3,2-dioxaborolane (15 mg, 0.054 mmol), PdCl$_2$(dppf) (13 mg, 0.018 mmol), KOAc (13 mg, 0.132 mmol). The mixture was heated under microwave irradiation for 1 h at 110° C. The mixture was cooled to rt and concentrated under reduced pressure. The crude product mixture was purified via silica gel chromatography and further purified via prep-HPLC to afford compound 2653 (2.6 mg) as a white solid. LCMS: 525.1 m/z [M+H]$^+$.

Example 26-11
Preparation of Compound 2654
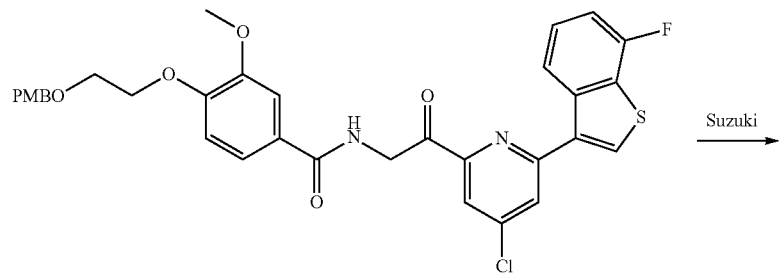
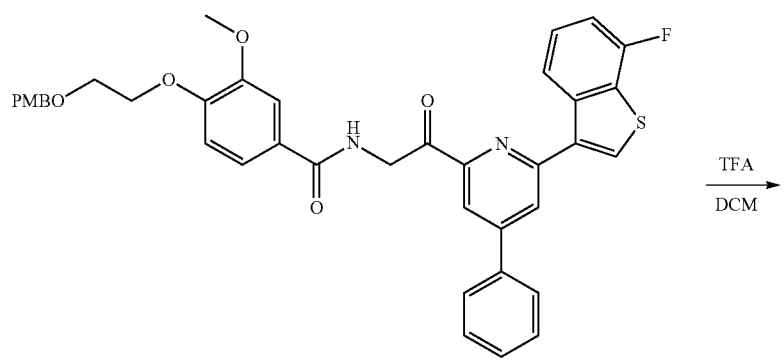
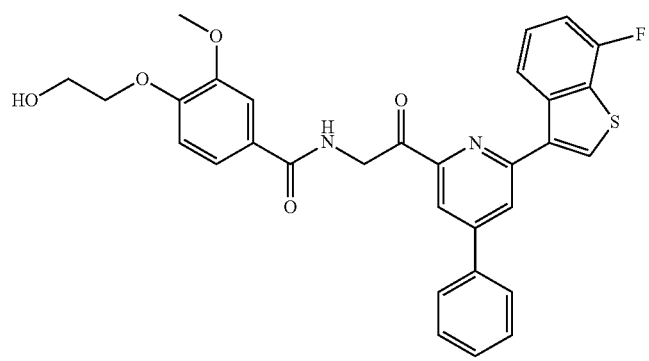
2654

To a stirring mixture of N-(2-(4-chloro-6-(7-fluorobenzo[b]thiophen-3-yl)pyridin-2-yl)-2-oxoethyl)-3-methoxy-4-(2-((4-methoxybenzyl)oxy)ethoxy)benzamide (30 mg, 0.044 mmol) in dioxane/water (10:1:2.2 mL total volume) were added PdCl$_2$(dppf) (7.3 mg, 0.01 mmol), KOAc (17 mg, 0.176 mmol), and phenyl boronic acid (11 mg, 0.088 mmol). The mixture was stirred was heated under microwave irradiation for 1 h at 110° C. The mixture was cooled to rt and concentrated under reduced pressure. The crude product mixture was purified via silica gel chromatography to afford the PMB ether. The PMB ether was removed using TFA in DCM at rt. The crude product was concentrated under reduced pressure and purified via prep-HPLC to afford compound 2654 (2.6 mg) as a white solid. LCMS: 557.15 m/z [M+H]$^+$.

Example 27-1

Preparation of Compound 27-13

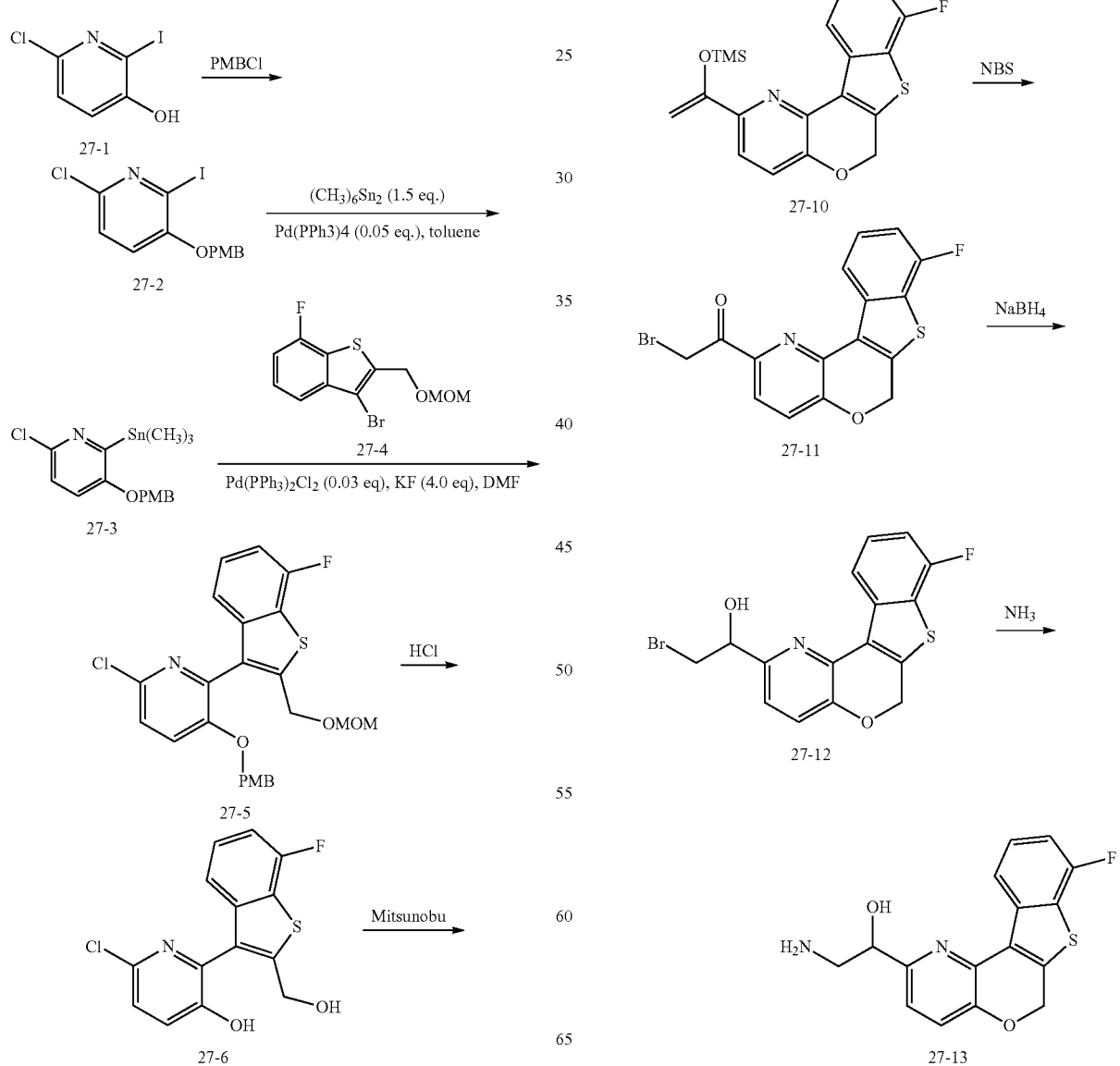

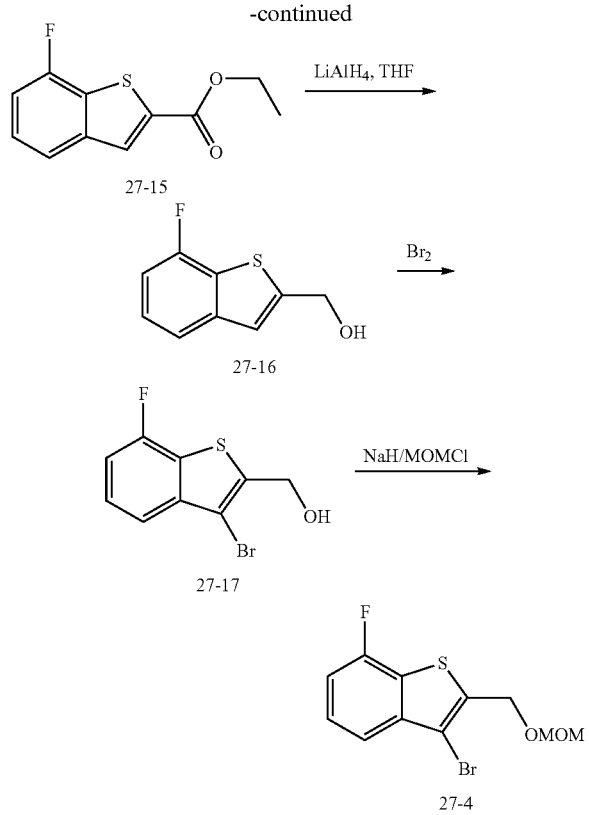

To a solution of 27-1 (10 g, 44.0 mmol) in DMF (150 mL) was added NaH (7.0 g, 0.177 mol), and the mixture was stirred at 0° C. for 30 mins. The solution was treated with PMBCl (11.67 g, 0.0748 mol), and stirred at rt overnight. After complete conversion, the reaction was quenched with MeOH and H$_2$O, and extracted with EA. The organic phase was concentrated to give 27-2 (11 g, 87.2%). +ESI-MS: m/z 375.9 [M+H]$^+$.

To a solution of 27-2 (36 g, 96 mmol) in toluene (400 mL) was added (CH$_3$)$_6$Sn$_2$ (47.0 g, 144.0 mmol). The mixture was bubbled with nitrogen gas and stirred at 100° C. for 3 h. The mixture was concentrated in vacuum to give the crude product, which was purified by column chromatography to give 27-3 (22 g). +ESI-MS: m/z 414.0 [M+H]$^+$.

To a solution of 27-15 (30 g, 134 mmol) in anhydrous THF (500 mL) was added LiAlH$_4$ (7.6 g, 200 mmol) in portions at 0° C., and the mixture was stirred at rt for 2 h (monitored by TLC). The reaction was quenched with a saturated NH$_4$Cl solution, and extracted with EA to give the crude product, which was purified by column chromatography to give 27-16 (22 g). +ESI-MS: m/z 183.0 [M+H]$^+$.

To a solution of 27-16 (22 g, 121 mmol) in THF (400 mL) was added NBS (25.7 g, 145 mmol), and the mixture was stirred at rt overnight (monitored by TLC). The reaction was quenched with a saturated Na$_2$S$_2$O$_3$ solution, and extracted with EA to give the crude product, which was purified by column chromatography to give 27-17 (23 g). +ESI-MS: m/z 460.9 [M+H]$^+$.

To a solution of 27-17 (22 g, 84.6 mmol) in anhydrous THF (200 mL) was added NaH (8.12 g, 33.85 mmol) in portions at 0° C., and the mixture was stirred at 0° C. for 30 mins. MOMCl (27.08 g, 338.5 mmol) was added, and the mixture was stirred at rt for 4 h. The reaction was quenched with water and extracted with EA. The organic layer was dried over sodium sulfate, and concentrated in vacuum to give the crude product, which was purified by column chromatography to give 27-4 (21 g). +ESI-MS: m/z 304.9 [M+H]$^+$.

To a solution of 27-3 (6.36 g, 15.4 mmol) in DMF (50 mL) were added 27-4 (4.7 g, 15.4 mmol), KF (3.7 g, 61.6 mmol) and Pd(PPh$_3$)$_2$Cl$_2$ (324 mg, 0.46 mmol). The mixture was bubbled with nitrogen gas and stirred at 100° C. overnight. The mixture was diluted with water and extracted with EA. The organic layer was dried over sodium sulfate, and concentrated in vacuum to give the crude product, which was purified by column chromatography to give 27-5 (3.8 g). +ESI-MS: m/z 474.1 [M+H]$^+$.

To a solution of 27-5 (4.5 g, 9.51 mmol) in THF (30 mL) was added 10% HCl (30 mL), and stirred 110° C. overnight. The mixture was cooled to rt, and the pH was adjusted to 7.0 by adding a saturated NaHCO$_3$ solution. The mixture was extracted with EA. The organic layer was dried over sodium sulfate, and concentrated in vacuum to give 27-6 (2.0 g), which was used in the next step without purification. +ESI-MS: m/z 310.0 [M+H]$^+$.

To a solution of 27-6 (1.3 g, 4.2 mmol) in THF (100 mL) was added PPh$_3$ (1.32 g, 5.05 mmol), and the mixture was stirred at rt for 10 mins. DIAD (1.01 g, 5.05 mmol) was added in portions, and the mixture stirred at refluxed for 4 h. The mixture was concentrated in vacuum to give the crude product, which was purified by column chromatography to give 27-7 (0.7 g). +ESI-MS: m/z 292.0 [M+H]$^+$.

To a solution of 27-7 (600 mg, 2.06 mmol) in DMF (20 mL) was added 27-8 (1.12 g, 3.10 mmol), KF (494.4 mg, 8.24 mmol) and Pd(PPh$_3$)$_2$Cl$_2$ (43.4 mg, 0.062 mmol). The mixture was bubbled with nitrogen gas and stirred at 100° C. for 10 h. The mixture was diluted with water and extracted with EA. The organic layer was dried over sodium sulfate and concentrated in vacuum to give the crude product, which was purified by column chromatography to give 27-9 (500 mg). +ESI-MS: m/z 300.0 [M+H]$^+$.

To a solution of 27-9 (400 mg, 1.34 mmol) in dichloromethane (20 mL) at 0° C. was added DIPEA (689.6 mg, 5.36 mmol) and TMSOTf (891.2 mg, 4.01 mmol), and the mixture stirred at 0° C. for 30 mins, and then for 1 h at rt. The mixture was diluted with water and extracted with EA. The organic phase was dried over sodium sulfate, and concentrated in vacuum to give crude 27-10.

To a solution of crude 27-10 (450 mg) in THF/H$_2$O (4:1, 20 mL) was added NBS (212.8 mg, 1.21 mmol) at 0° C., and the mixture was stirred at 0° C. for 1 h. The mixture was extracted with EA. The organic layer was dried over sodium sulfate, and then concentrated in vacuum to give crude product, which was purified by column chromatography to give 27-11 (650 mg). +ESI-MS: m/z 377.9 [M+H]$^+$.

To a solution of 27-11 (600 mg, 1.6 mmol) in THF (50 mL) was added NaBH$_4$ (300 mg, 7.96 mmol), and the mixture was stirred at 0° C. for 2 mins. The solution was treated with MeOH (5 mL) very slowly for 10 mins (monitored by TLC). The mixture was treated with ice and extracted with EA. The organic layer was dried over sodium sulfate, and concentrated in vacuum to give the crude product, which was purified by column chromatography to give 27-12 (400 mg). +ESI-MS: m/z 379.9 [M+H]$^+$.

To a solution of 27-12 (400 mg, 1.06 mmol) in EtOH 20 mL was added NH$_3$—H$_2$O (10 mL) in a seal tube, and the mixture was stirred at 100° C. for 1 h. The mixture was diluted with water and extracted with EA. The organic layer was dried over sodium sulfate, and concentrated in vacuum to give the crude product, which was purified by column chromatography to give 27-13 (340 mg). +ESI-MS: m/z 317.1 [M+H]$^+$.

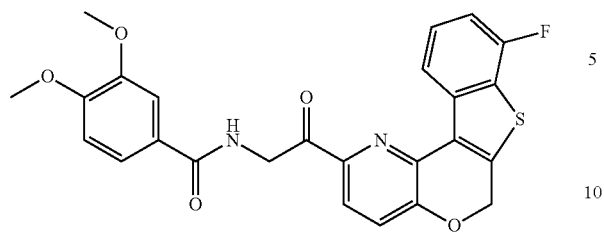
2701
To a solution of N-(2-(8-fluoro-6H-benzo[4',5']thieno[3', 2':4,5]pyrano[3,2-b]pyridin-2-yl)-2-hydroxyethyl)-3,4-dimethoxybenzamide (120 mg, 0.25 mmol) in DMSO (3 mL) was added IBX (210 mg, 0.75 mmol), and stirred at 30° C. overnight. The mixture was purified by prep-HPLC to give 2701 (30 mg) as a white solid. +ESI-MS: m/z 479.1 [M+H]$^+$.
Example 27-2
Preparation of Compound 2703
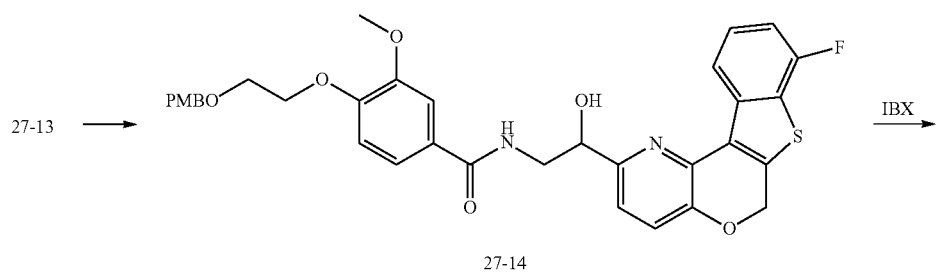
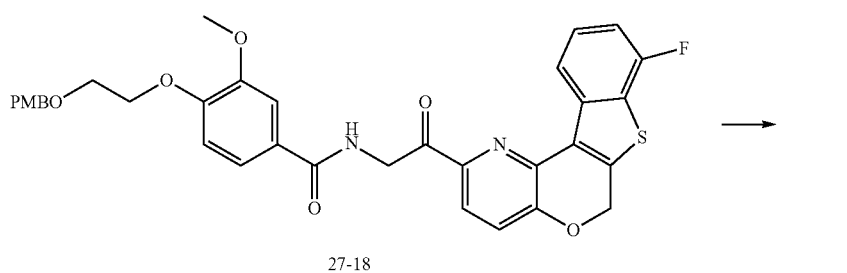
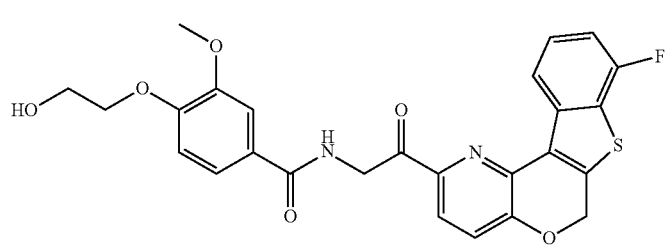
2703

Compound 27-18 (200 mg, 0.318 mmol) was dissolved in TFA/DCM (20 mL), and the mixture was stirred at rt for 1 h (monitored by TLC). The mixture was extracted with EA, and washed with a saturated NaHCO₃ solution. The organic layer was dried over sodium sulfate, and concentrated in vacuum to give the crude product, which was purified by prep-HPLC to give compound 2703 (28 mg) as a white solid. +ESI-MS: m/z 509.1 [M+H]⁺.

Example 28-1

Preparation of Compound 28-7

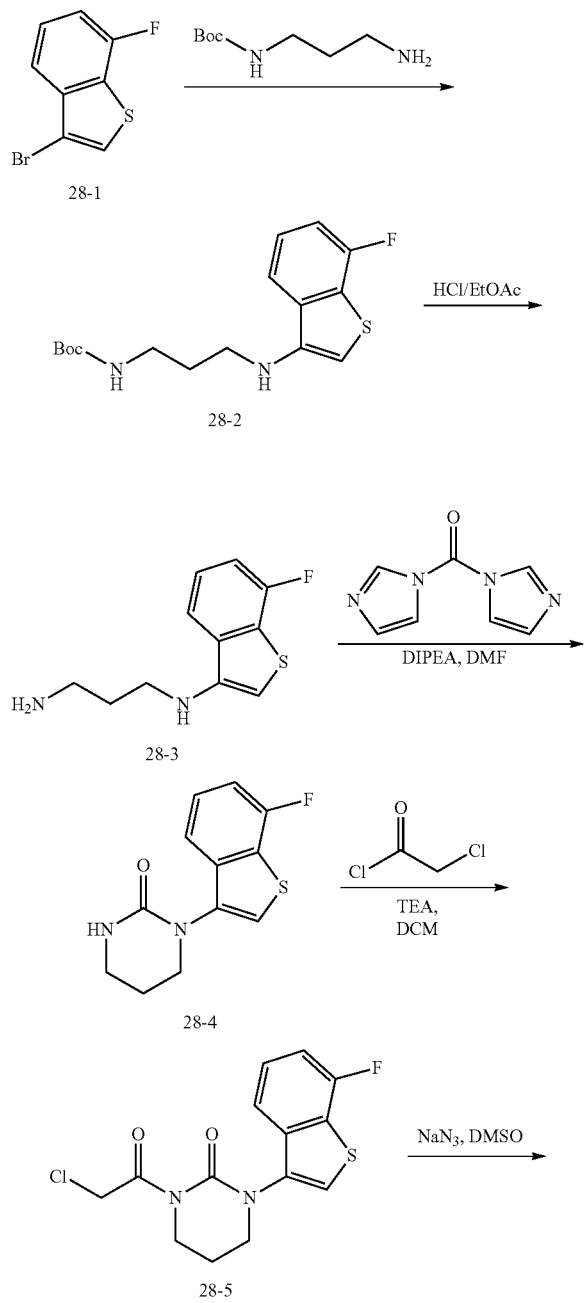

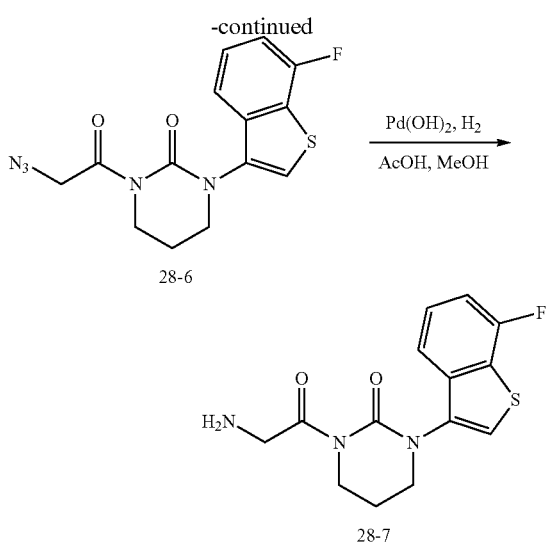

Compound 28-1 (10 g, 43.5 mmol), CuI (1.653 g, 8.7 mmol), L-proline (2 g, 17.4 mmol) and K₂CO₃ (9 g, 65.25 mmol) were added to Schleck flask. The flask was evacuated and backfilled with argon, and then degassed DMSO (44 mL) was added. Tert-butyl (3-aminopropyl) carbonate (11.35 g, 65.25 mmol) was added, and the mixture was heated to 80° C. until completion. The reaction was quenched with water, and extracted with EtOAc. The combined organic layers were washed with water and brine, dried over Na₂SO₄ and concentrated at low pressure. The residue was purified by column on silica gel (PE:EA=4:1) to give 28-2 (8.4 g, 59% yield). +ESI-MS: m/z 325.1 [M+H]⁺.

A round bottom flask was charged with 28-2 (4.6 g, 14.2 mmol) and 4 M HCl in EtOAc (7 mL) was added dropwise. The mixture was stirred at 0° C. for 30 mins. The solvent was removed to give crude 28-3 used in next step without further purification, To a solution of 28-3 (3.18 g, 14.2 mmol) in DMF (69 mL) was added DIPEA (7.78 g, 56.8 mmol) and CDI (2.53 g, 15.62 mmol). The mixture was stirred at 5° C. for 2 h and then heated at 90° C. for 10 h. The mixture was extracted with EtOAc and washed with water, dried over Na₂SO₄, and concentrated. The residue was purified by column on silica gel (DCM:MeOH=50:1) to give 28-4 (6 mg, 24%). +ESI-MS: m/z 251.0 [M+H]⁺

To a solution of 28-4 (1.5 g, 6 mmol) in DCM (30 mL) was added TEA (2.7 mL) and 2-chloroacetyl chloride (1.2 mL, 18 mmol) at 0° C. under argon. The reaction was quenched with water, extracted with EtOAc. The organic lays was washed with brine, dried over Na₂SO₄, and concentrated. The residue was purified by column on silica gel (PE:EA=10:1) to give 28-5 (500 mg, 25%). +ESI-MS: m/z 327.0 [M+H]⁺.

Compound 28-5 (500 mg, 1.534 mmol) and NaN₃ (398 mg, 6.136 mmol) was added to DMSO (7 mL). The mixture was stirred at 50° C. for 2 h. The mixture was extracted with EtOAc, washed with water, dried over Na₂SO₄, and concentrated. The residue was purified by column on silica gel (PE:EA=3:1) to give 28-6 (260 mg, 51%). +ESI-MS: m/z 334.1 [M+H]⁺.

To a solution of 28-6 (100 mg, 0.3 mmol) in MeOH (5 mL) was added Pd(OH)₂ (6 mL) and one drop of AcOH. The mixture was stirred at rt under H₂ atmosphere for 1 h. The mixture was filtered and the filtrate was dissolved in EtOAc. The solution was washed with aq. NaHCO₃ and brine, dried over Na₂SO₄, and concentrated. Crude 28-7 was used in next step without further purification.

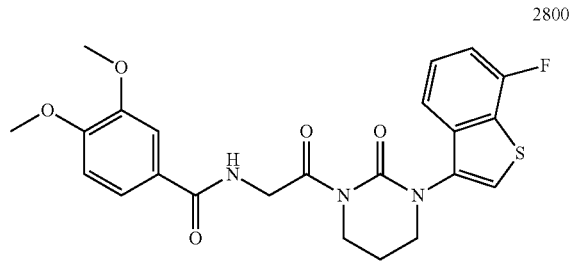 [SMILES: COc1ccc(C(=O)NCC(=O)N2CCCN(c3csc4c(F)cccc34)C2=O)cc1OC]

To a solution of 3,4-dimethoxybenzoic acid (110 mg, 0.6 mmol) in DIPEA (0.2 mL) and DMF (1 mL) was added HATU (230 mg, 0.6 mmol). The mixture was stirred at 40° C. for 30 mins. Compound 28-7 (93 mg, 0.3 mmol) was added. The mixture was stirred at 40° C. for 10 h. The reaction was quenched with water and extracted with EtOAc. The organic layers was washed with brine, dried over Na$_2$SO$_4$, and concentrated. The crude product was purified by prep-HPLC to give compound 2800 (32 mg, 22%). +ESI-MS: m/z 471.8 [M+H]$^+$.

Example 28-2

Preparation of Compound 2801

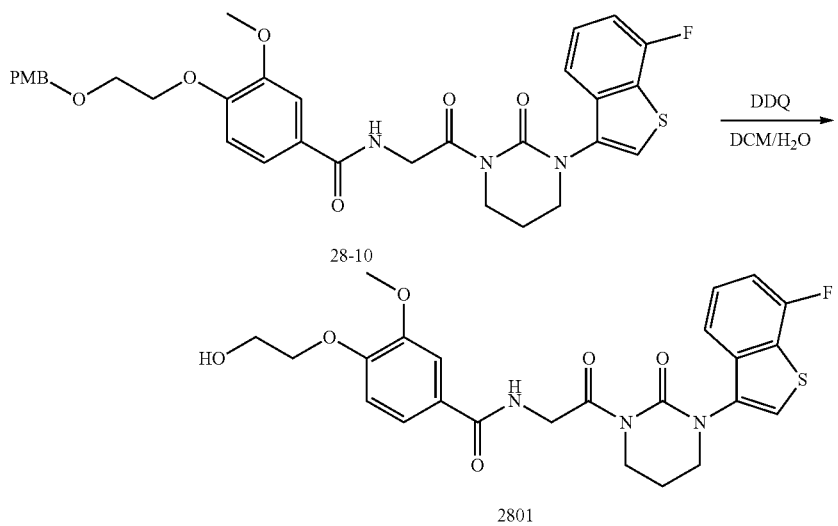

Compound 28-10 (60 mg, 25%) was prepared using 3-methoxy-4-(2-((4-methoxybenzyl)oxy)ethoxy)benzoic acid and by following a synthetic route, which closely follows that described for preparation of compound 2800. +ESI-MS: m/z 622.1 [M+H]$^+$.

To a solution of 28-10 (60 mg, 0.1 mmol) in DCM (2 mL) and H$_2$O (0.2 mL) was added DDQ (45 mg, 0.2 mmol). The mixture was stirred for 2 h. at rt. The mixture was dissolved in DCM (30 mL), and washed with a saturated NaHCO$_3$ solution. The organic phase was washed with brine, and dried over Na$_2$SO$_4$, and concentrated at low pressure. The residue was purified by prep-HPLC to give compound 2801 (12 mg, 25%). +ESI-MS: m/z 501.8 [M+H]$^+$.

Example 28-3

Preparation of Compound 2802

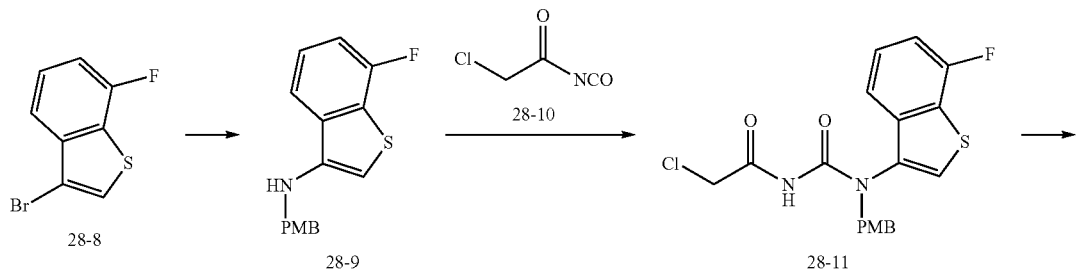

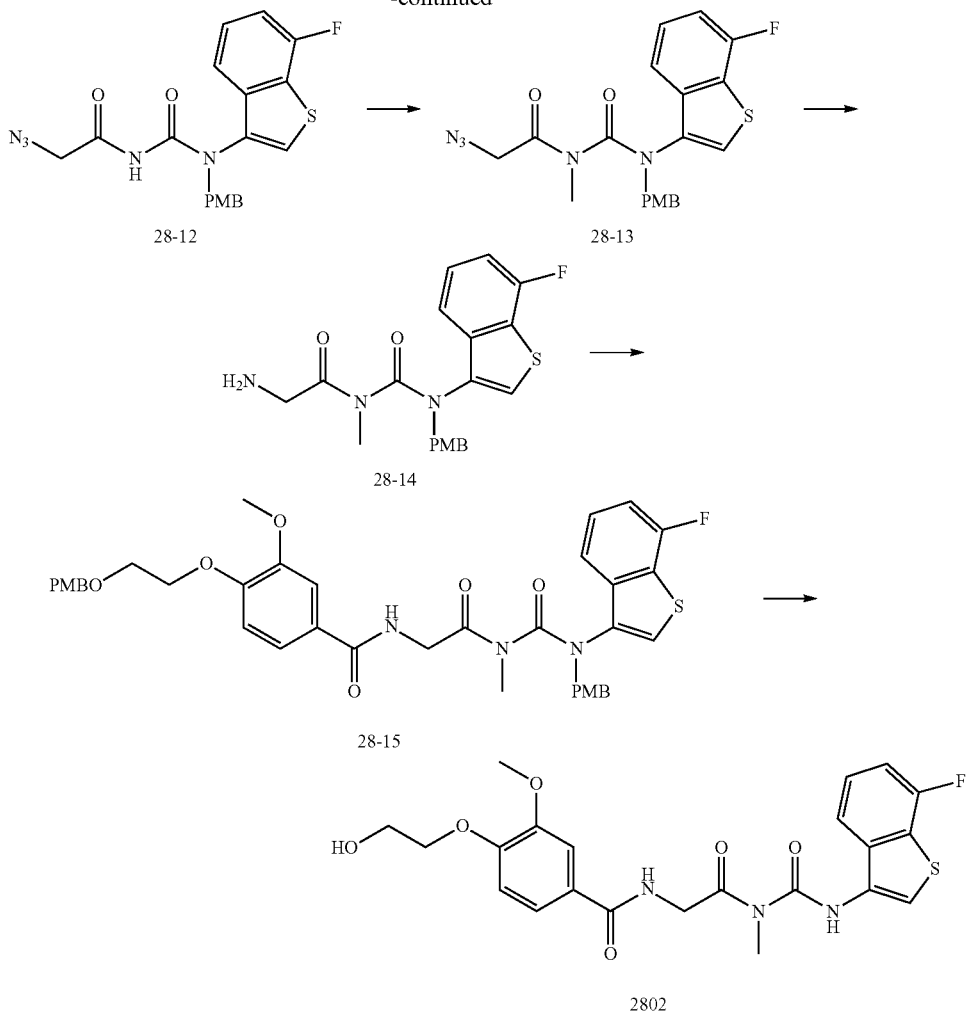

Compound 28-8 (10 g, 43.5 mmol), CuI (1.653 g, 8.7 mmol), L-proline (2 g, 17.4 mmol) and $K_2CO_3$ (9 g, 65.25 mmol) were in a Schlenk flask. The flask was evacuated and backfilled with argon and then degassed DMSO (44 mL) was added. $PMBNH_2$ (3-aminopropyl)carbamate (12 g, 87.60 mmol) was added and the mixture was heated to 80° C. The reaction was quenched with water, and extracted with EtOAc. The combined organic layers were washed with water and brine, dried over $Na_2SO_4$ and concentrated. The residue was purified by column on silica gel (PE:EA=4:1) to give 28-9 (5.5 g, 43% yield). +ESI-MS: m/z 288.1 $[M+H]^+$.

A round bottom flask was charged with 28-9 (1.44 g, 5.0 mmol) and THF (10 mL), and 28-10 in THF (7 mL) was added dropwise. The mixture was stirred at 0° C. for 30 mins. The solvent was removed to give crude 28-11, which was used in next step without further purification. +ESI-MS: m/z 406.8 $[M+H]^+$.

To a solution of 28-11 (2.03 g, 5.0 mmol) in DMF (10 mL) was added $NaN_3$ (680 mg, 10.0 mmol), and the mixture was stirred at rt until the starting materials were consumed. The mixture was extracted with EtOAc and washed with water, dried over $Na_2SO_4$, and concentrated to give 28-12. +ESI-MS: m/z 414.1 $[M+H]^+$ To a solution of 28-12 (2.07 g, 5 mmol) in DMF (30 mL) was added $K_2CO_3$ (1.33 g, 10 mmol) and MeI (1.41 g, 10 mmol) at rt. The mixture was stirred at 50° C. until the starting materials were consumed. The reaction was quenched with water, and extracted with EtOAc. The organic lays was washed with brine, dried over $Na_2SO_4$, and concentrated. The residue was purified by column on silica gel (PE:EA=10:1) to give 28-13 (190 mg, 90%). +ESI-MS: m/z 428.1 $[M+H]^+$.

To a solution of 28-13 (85 mg, 0.2 mmol) in MeOH (10 mL) was added Pd/C (10 mg) and one drop of concentrated HCl. The mixture was stirred at room temperature under $H_2$ atmosphere for 1 h. The mixture was filtered and the filtrate was dissolved in EtOAc. The solution was washed with aq. $NaHCO_3$ and brine, dried over $Na_2SO_4$, and concentrated. Crude 28-14 was used in next step without further purification. +ESI-MS: m/z 401.8 $[M+H]^+$.

To a solution of the substituent benzoic acid (66 mg, 0.2 mmol) in DIPEA (0.2 mL) and DMF (5 mL) was added HATU (115 mg, 0.3 mmol). The mixture was stirred at 40° C. for 30 mins and then 28-14 (80 mg, 0.2 mmol) was added. The mixture was stirred at 40° C. for 1 h. The mixture was quenched with water and extracted with EtOAc. The organic layers was washed with brine, dried over $Na_2SO_4$, and concentrated. The crude product was purified by silical gel to give 28-15 (135 mg, 90%). +ESI-MS: m/z 715.9 $[M+H]^+$.

To a solution of 28-15 (140 mg, 0.2 mmol) in DCM (4 mL) and TFA (2 mL) was added $Et_3SiH$ (1 mL). The mixture was stirred at 0° C. for 1 h. The organic layers was washed with brine, dried over Na$_2$SO$_4$, and concentrated. The crude product was purified by prep-HPLC to give compound 2802 (57 mg, 60%). +ESI-MS: m/z 475.8 [M+H]$^+$.

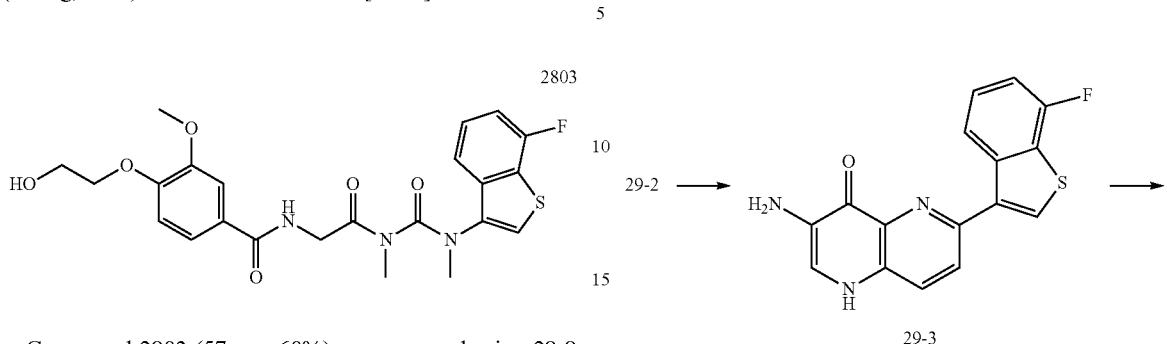

2803

Compound 2803 (57 mg, 60%) was prepared using 28-8 and methylamine hydrochloride, and by following a synthetic route, which closely follows that described for preparation of compound 2802. +ESI-MS: m/z 489.9 [M+H]$^+$.

Example 29-1

Preparation of Compound 29-2

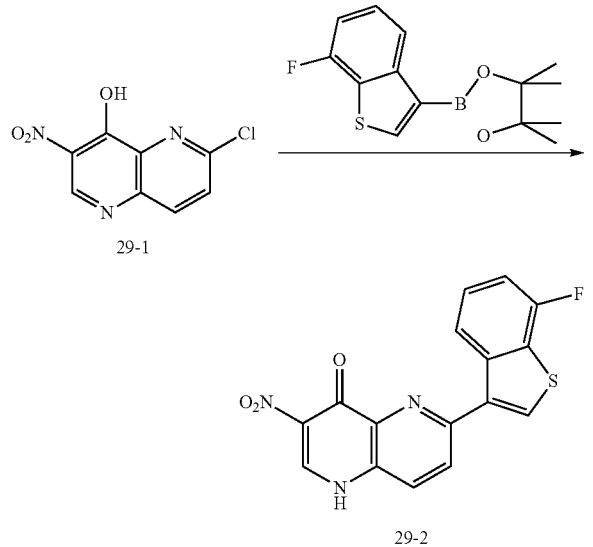

29-2

Compound 29-1 was prepared according to the procedure in PCT Publication No. 2012/034526, which hereby is incorporated by reference for the limited purpose of preparing 29-1.

To a solution of 29-1 (1.6 g, 7.11 mmol) in DMF/H$_2$O (30 mL) were added the dioxaborolane (1.98 g, 7.11 mmol), and KF (3.7 g, 61.6 mmol) and Pd(PPh$_3$)$_2$Cl$_2$ (150 mg, 0.21 mmol) and K$_2$CO$_3$ (1.96 g, 14.22 mmol). The mixture was bubbled with nitrogen gas and stirred at 90° C. overnight. The mixture was diluted with water and extracted with EA. The organic layer was dried over sodium sulfate and concentrated in vacuum to give the crude product, which was purified by column chromatography to give 29-2 (1.4 g). +ESI-MS: m/z 342.0[M+H]$^+$.

Example 29-2

Preparation of Compound 2900

29-2 →

[Structure 29-3]

[Structure 2900]

To a solution of 29-2 (500 mg, 1.47 mmol) in MeOH/DMF (10 mL) was added Pd/C (200 mg), and the mixture was stirred at rt under hydrogen gas balloon for 1 h. The mixture was concentrated in vacuum to give 29-3 (250 mg). +ESI-MS: m/z 312.0[M+H]$^+$.

To a solution of 29-3 (150 mg, 0.48 mmol) in DCM (30 mL) was added Et$_3$N (97.4 mg, 0.96 mmol) and 3,4-dimethoxybenzoyl chloride (96 mg, 0.48 mmol), and the mixture was stirred at rt for 3 h. The mixture was concentrated in vacuum to give the crude product, which was purified by TLC and prep-HPLC to give compound 2900 (4.0 mg). +ESI-MS: m/z 476.1[M+H]$^+$.

Example 29-3

Preparation of Compound 2901

29-2 →

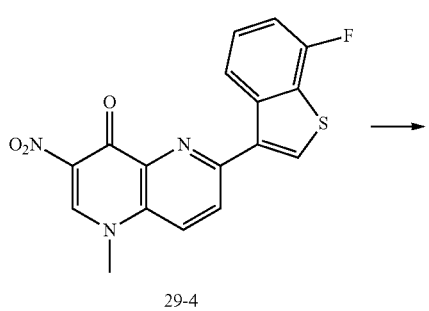

29-4

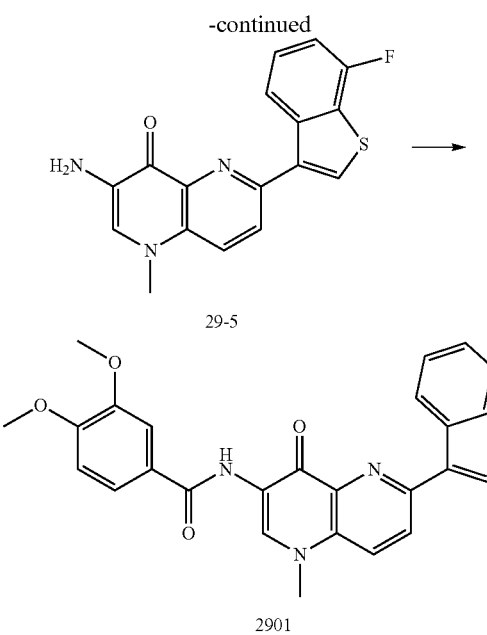

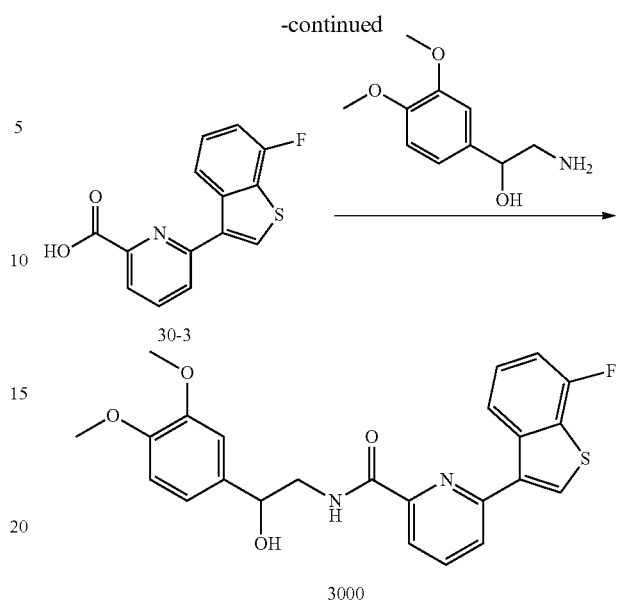

To a solution of 29-2 (400 mg, 1.17 mmol) in DMF (100 mL) was added $K_2CO_3$ (684 g, 4.69 mmol) and $CH_3I$ (668 mg, 4.69 mmol), and the mixture was stirred at rt overnight (monitored by LCMS). The mixture was concentrated in vacuum to give the crude product, which was purified by column chromatography to give 29-4 (350 mg). +ESI-MS: m/z 356.0[M+H]$^+$.

Compound 2901 was prepared using 29-4 and by following a synthetic route, which closely follows that described for preparation of compound 2900. +ESI-MS: m/z 489.9 [M+H]$^+$.

Example 30-1

Preparation of Compound 3000

Compound 30-1 (1.08 g, 5 mmol), the dioxaborolane (1.526 g, 5.5 mmol), $K_2CO_3$ (1.03 g) and Pd(dppf)Cl$_2$ (366 mg, 0.5 mmol) were dissolved in dioxane (10 mL) and $H_2O$ (5 mL), and the mixture stirred under argon at 90° C. for 10 h. The solvent was removed to give the crude product. The residue was purified by column on silica gel (PE:EA=10:1) to give 30-2 (440 mg, 30.6%). +ESI-MS: m/z 288.0 [M+H]$^+$.

To a solution of 30-2 (220 mg, 0.8 mmol) in MeOH (3 mL) and $H_2O$ (1 mL) was added KOH (67 mg, 1.2 mmol). The mixture was refluxed for 1 h., and concentrated at low pressure. The residue was dissolved in $H_2O$ and EtOAc, and acidified to pH (3-4) by adding HCl solution (2M, 0.5 mL). The organic phase was concentrated at low pressure to give 30-3 (200 mg, 91.5%). +ESI-MS: m/z 274.0 [M+H]$^+$.

To a solution of 30-3 (100 mg, 0.37 mmol), 2-amino-1-(3,4-dimethoxyphenyl)ethanol (108 mg, 0.55 mmol), DIPEA (0.2 mL) in DMF (1.5 mL) was added HATU (209 mg, 0.55 mmol). The mixture was stirred at 25° C. for 10 h. The mixture was purified by prep-TLC (PE:EA=1:1) to give compound 3000 (40 mg, 24%). +ESI-MS: m/z 474.9 [M+Na]$^+$.

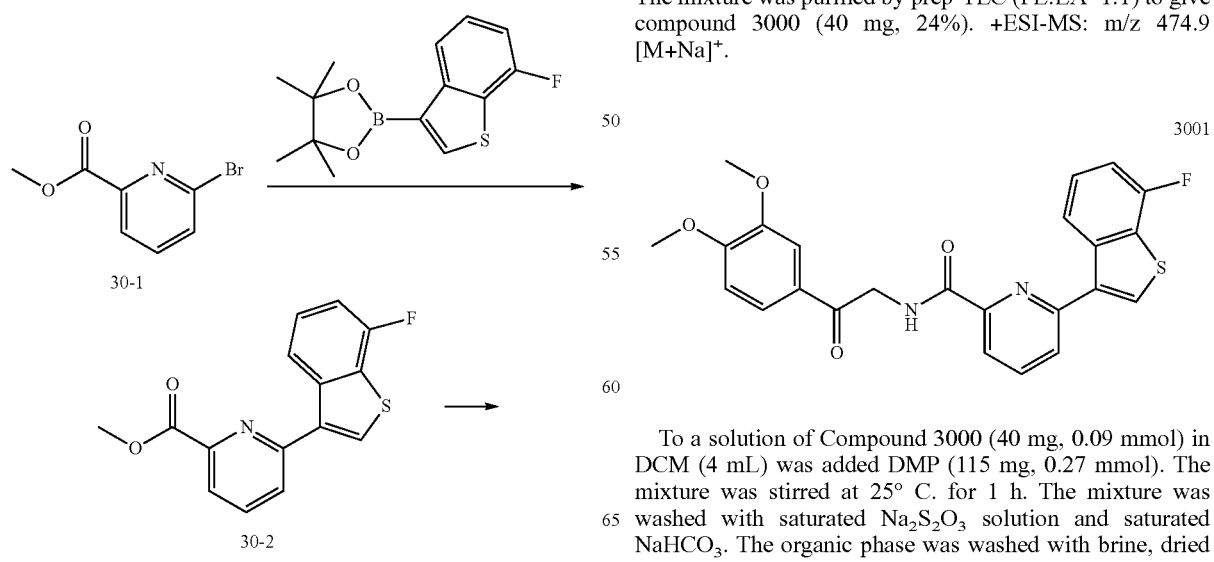

To a solution of Compound 3000 (40 mg, 0.09 mmol) in DCM (4 mL) was added DMP (115 mg, 0.27 mmol). The mixture was stirred at 25° C. for 1 h. The mixture was washed with saturated $Na_2S_2O_3$ solution and saturated $NaHCO_3$. The organic phase was washed with brine, dried over $Na_2SO_4$, and concentrated at low pressure. The residue was purified by column on silica gel (PE:EA=1:1) to give compound 3001 (15 mg, 30%). +ESI-MS: m/z 450.9 [M+H]+.

Example 31-1

Preparation of Compound 3100

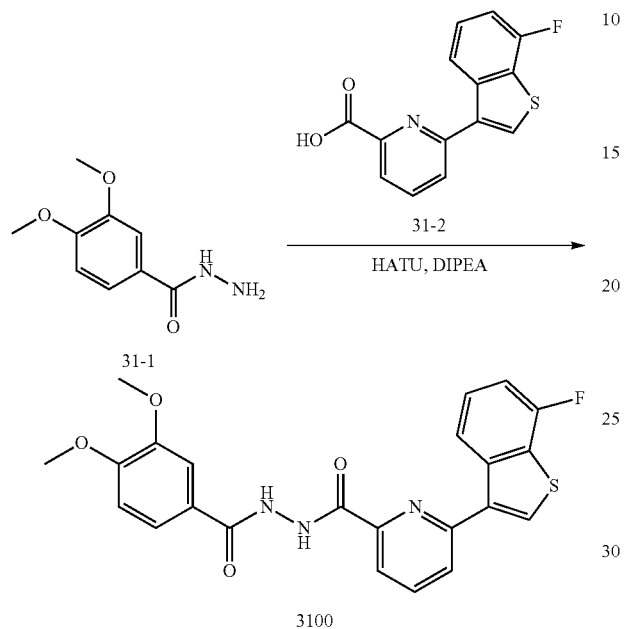

3100

Compound 31-1 was prepared according to the procedure in Murty et al., *Letters in Drug Design & Discovery* (2012) 9(3):276-281, which hereby is incorporated by reference for the limited purpose of preparing 31-1.

To a solution of 31-1 (100 mg, 0.36 mmol), HATU (200 mg, 0.52 mmol) and DIPEA (140 mg, 1.08 mmol) in anhydrous DCM (3 mL) was added 31-2 (76 mg, 0.36 mmol) at 25° C. The solution was stirred for 8 h at this temperature and then diluted with 1.0 N aqueous NaHCO3 solution (30 mL×2), and extracted with EA (30 mL×2). The combined organic layers were washed by brine, dried over anhydrous Na2SO4, and concentrated under reduced pressure. The residue was purified by prep-HPLC to give compound 3100 (8 mg) as a white solid. +ESI-MS: m/z 452.0 [M+H]+.

Example 31-2

Preparation of Compound 3101

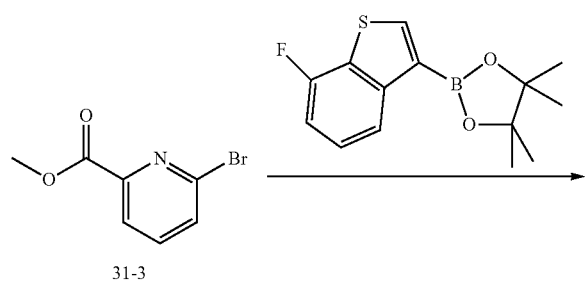

31-3

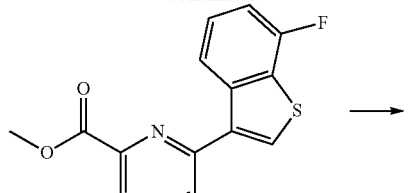

31-4

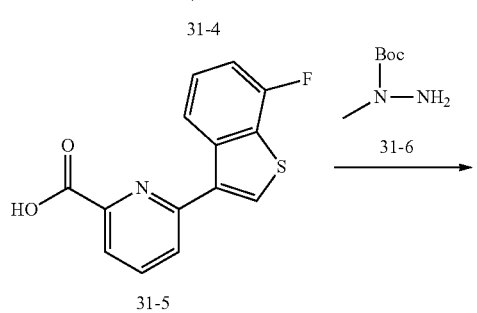

31-5

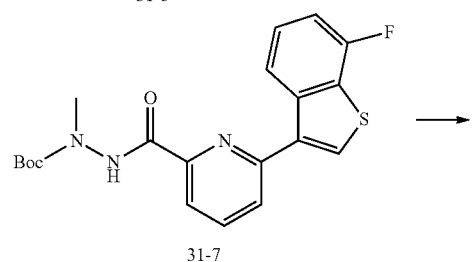

31-7

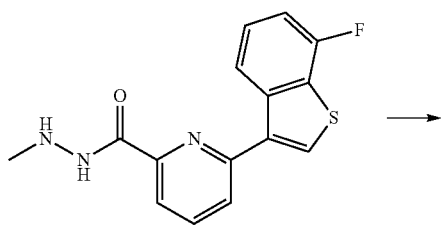

31-8

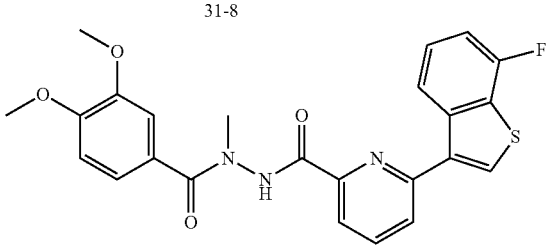

3101

To a solution of 31-3 (1.0 g, 4.6 mmol) and the dioxaborolane (1.6 g, 5.7 mmol) in dioxane (10 mL) were added Pd (PPh3)2Cl2 (50 mg, 0.06 mmol) and a freshly prepared K2CO3 solution (0.95 g in 2 mL of water). The system was degassed and then charged with nitrogen 3 times. The mixture was stirred under nitrogen at 70° C. in an oil bath for 2 h. The solution was cooled to rt, diluted with EA and separated from the water layer. The EA solution was washed by brine, dried over Na2SO4 and concentrated. The residue was chromatographed on silica gel to give 31-4 (0.9 g) as a white solid. +ESI-MS: m/z=287.7 [M+H]+.

To a solution of 31-4 (0.9 g, 3.1 mmol) in MeOH (5 mL) was added NaOH (5 mL, 2.5M NaOH in H2O). The solution was stirred at 60° C. for 1 h. After the solvent evaporated to a small volume, H2O (50 mL) was added and the solution was extracted with DCM (2×20 mL). The aqueous phase was cooled on an ice-water bath. The pH was adjusted to 7 by adding 25% v/v HCl. The precipitate was filtered and dried under vacuum to give 31-5 (700 mg) as a white solid. +ESI-MS: m/z=273.8 [M+H]⁺.

To a solution of 31-5 (600 mg, 2.2 mmol), HATU (1.1 g, 2.9 mmol) and DIPEA (700 mg, 5.4 mmol) in anhydrous DCM (5 mL) was added 31-6 (400 mg, 2.7 mmol) at 25° C. The solution was stirred for 10 h at this temperature and then diluted with 1.0 N aqueous NaHCO₃ solution (40 mL×2), and extracted with EA (50 mL×2). The combined organic layers were washed by brine, dried over anhydrous Na₂SO₄, and concentrated under reduced pressure. The residue was purified by chromatograph on a silica gel column to give 31-7 (800 mg) as a white solid. +ESI-MS: m/z=401.9 [M+H]⁺.

To a solution of 31-7 (800 mg, 2.0 mmol) in EtOAc (10 mL) was added HCl/EA (8 mL) at 0° C. The solution was stirred at 25° C. for 1 h with TLC monitoring. A precipitate formed and was collected by filtration. The solid was washed with EA to give 31-8 (800 mg) as a white solid. +ESI-MS: m/z=302.0 [M+H]⁺.

To a solution of 3,4-dimethoxybenzoic acid (60 mg, 0.33 mmol), HATU (180 mg, 0.47 mmol) and DIPEA (120 mg, 0.95 mmol) in anhydrous DCM (3 mL) was added 31-8 (100 mg, 0.33 mmol) at 25° C. The solution was stirred for 8 h. at this temperature and then diluted with 1.0 N aqueous NaHCO₃ solution (50 mL×2), and extracted with EA (50 mL×2). The combined organic layers were washed by brine, dried over anhydrous Na₂SO₄, and concentrated under reduced pressure. The residue was purified by prep-HPLC to give compound 3101 (40 mg) as a white solid. +ESI-MS: m/z=466.1 [M+H]⁺.

Example 31-3

Preparation of Compound 3102

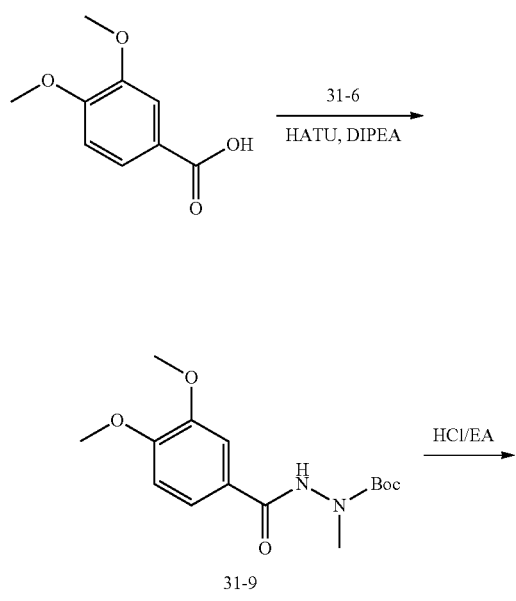

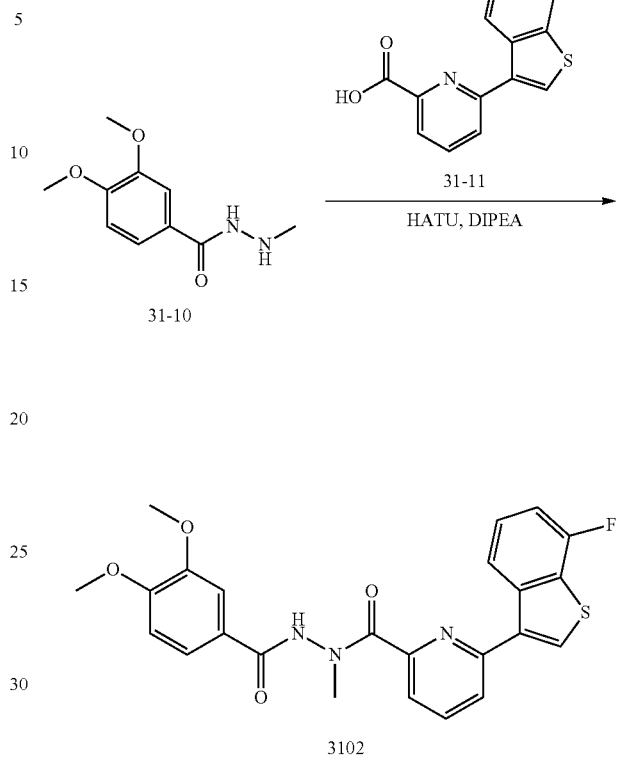

To a solution of 3,4-dimethoxybenzoic acid (1.82 g, 10 mmol), HATU (4.5 g, 11.8 mmol) and DIPEA (3.8 g, 29.4 mmol) in anhydrous DCM (10 mL) was added 31-6 (1.47 mg, 10.0 mmol) at 25° C. The solution was stirred for 10 h at this temperature and then diluted with 1.0 N aqueous NaHCO₃ solution (80 mL×2), extracted with EA (80 mL×2). The combined organic layers were washed by brine, dried over anhydrous Na₂SO₄, and concentrated under reduced pressure. The residue was purified on a silica gel column to give 31-9 (1.8 g) as a white solid. +ESI-MS: m/z=311.1 [M+H]⁺

To a solution of 31-9 (800 mg, 2.6 mmol) in EA (10 mL) was added HCl/EA (8 mL) at 0° C. The solution was stirred at 25° C. for 1 h with TLC monitoring. A precipitate formed and was collected by filtration. The solid was washed with EA to give 31-10 (500 mg) as a white solid. +ESI-MS: m/z=211.1 [M+H]⁺

To a solution of 31-11 (130 mg, 0.48 mmol), HATU (250 mg, 0.65 mmol) and DIPEA (200 mg, 1.55 mmol) in anhydrous DCM (3 mL) was added 31-10 (100 mg, 0.48 mmol) at 25° C. The solution was stirred for 8 h at this temperature and then diluted with 1.0 N aqueous NaHCO₃ solution (30 mL×2), and extracted with EA (30 mL×2). The combined organic layers were washed by brine, dried over anhydrous Na₂SO₄, and concentrated under reduced pressure. The residue was purified on a silica gel column to give compound 3102 (60 mg) as a white solid. +ESI-MS: m/z=466.1[M+H]⁺.

Example 31-4

Preparation of Compound 3103

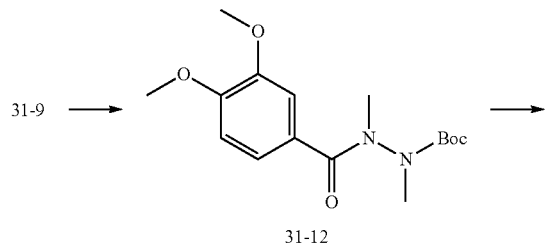

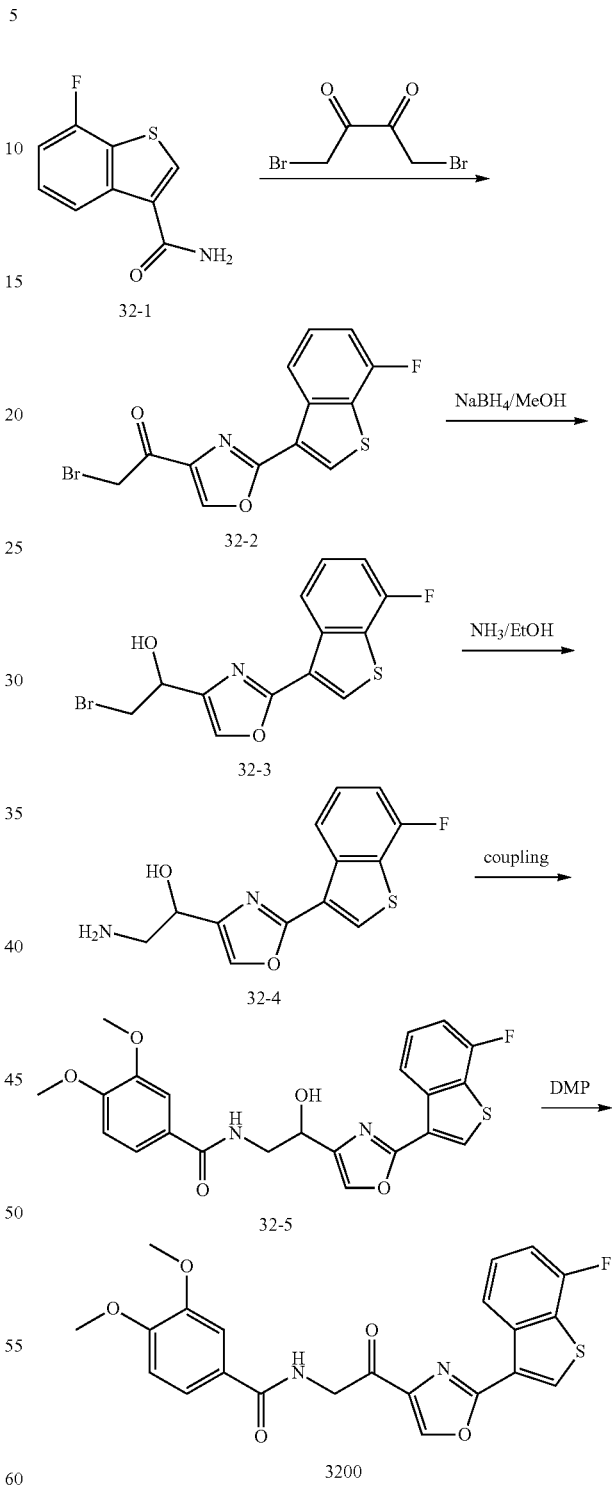

A mixture of 31-9 (1.0 g, 3.2 mmol), K$_2$CO$_3$ (1.7 g, 12 mmol) and CH$_3$I (2.3 g, 16 mmol) in DMF in a seal tube was stirred at 70° C. for 8 h. The mixture was diluted with EA. The organic layer was washed with brine, dried over anhydrous Na$_2$SO$_4$ and concentrated at low pressure. The residue was purified on a silica gel column to give 31-12 (800 mg) as a white solid. +ESI-MS: m/z=325.1[M+H]$^+$.

To a solution of 31-12 (800 mg, 2.4 mmol) in EA (10 mL) was added HCl/EA (8 mL) at 0° C. The solution was stirred at 25° C. for 1 h with TLC monitoring. A precipitate formed and was collected by filtration. The solid was washed with EA to give 31-13 (400 mg) as a white solid. +ESI-MS: m/z=225.1[M+H]$^+$ To a solution of 31-11 (100 mg, 0.37 mmol), HATU (250 mg, 0.65 mmol) and DIPEA (200 mg, 1.55 mmol) in anhydrous DCM (3 mL) was added 31-13 (80 mg, 0.38 mmol) at 25° C. The solution was stirred for 8 h at this temperature and then diluted with 1.0 N aqueous NaHCO$_3$ solution (30 mL×2), and extracted with EA (30 mL×2). The combined organic layers were washed by brine, dried over anhydrous Na$_2$SO$_4$, and concentrated under reduced pressure. The residue was purified on a silica gel column to give compound 3103 (120 mg) as a white solid. +ESI-MS: m/z=480.1[M+H]$^+$.

Example 32-1

Preparation of Compound 3200

To a solution of 32-1 (196 mg, 1.0 mmol), 1,4-dibromobutane-2,3-dione (241 mg, 1.0 mmol) in DCM (3 mL) was added AgOTf (255 mg, 1.0 mmol). The reaction was carried out at 80° C. under microwave irradiation for 15 mins. The mixture was concentrated at low pressure. The residue was purified by silica gel column (PE/EA) to 32-2 (270 mg, 80%). +ESI-MS: m/z 339.9 [M+H]$^+$.

To a solution of 32-2 (340 mg, 1.0 mmol) in MeOH (10 mL) was added NaBH$_4$ (380 mg, 10 mmol) in portions until the starting materials was consumed. The volatiles were removed under reduced pressure, and the residue was purified by column chromatography on silica gel (PE:EtOAc=2:1) to give 32-3 (340 mg, 99%). +ESI-MS: m/z 341.9 [M+H]$^+$.

Compound 32-3 was dissolved in EtOH/NH$_4$OH (10 mL/10 mL). After sealing in autoclave, the mixture was stirred at 90° C. for 10 h., and then extracted with EtOAc. The organic phase was dried over anhydrous Na$_2$SO$_4$, and concentrated at low pressure to give 32-4. +ESI-MS: m/z 279.0 [M+H]$^+$.

The carboxyl acid (90 mg, 0.5 mmol), amine (140 mg, 0.5 mmol) and triethylamine (1 mmol) are dissolved in DMF (15 mL), and HATU (380 mg, 1 mmol) was added to the solution. After 15-30 mins, saturated NaCl solution (100 mL) was added. The solution was extracted with EtOAc (3×10 mL). The combined organics were washed with 2N HCl and 5% NaHCO$_3$. The organic phase were dried over MgSO$_4$, and concentrated at low pressure to give the crude product. The crude was purified by silica gel column chromatography with EtOAc/PE (1/1) as the elute to give 32-5 (100 mg, 48%). +ESI-MS: m/z 442.9 [M+H]$^+$.

To a solution of 32-5 (88 mg, 0.2 mmol) in CH$_2$Cl$_2$ (10 mL) was added DMP (170 mg, 0.4 mmol), and the mixture was stirred at rt until the starting material was consumed. After work-up, the solution was concentrated to give the crude product. The residue was purified by silica gel column chromatography (PE/EA) to give compound 3200 (62 mg, 70%). +ESI-MS: m/z 441.0 [M+H]$^+$.

Example 32-2

Preparation of Compound 3201

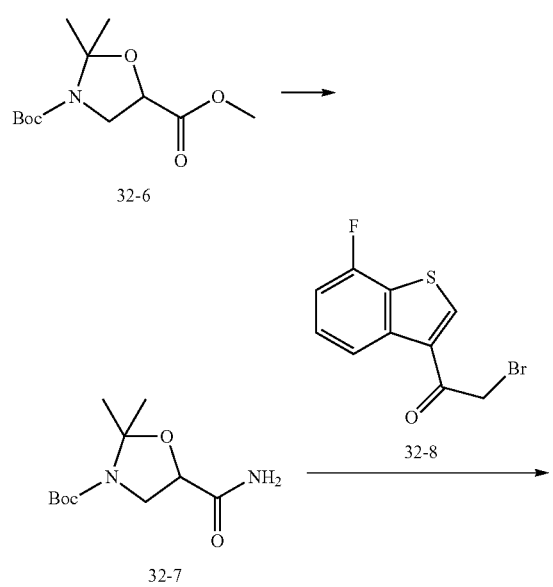

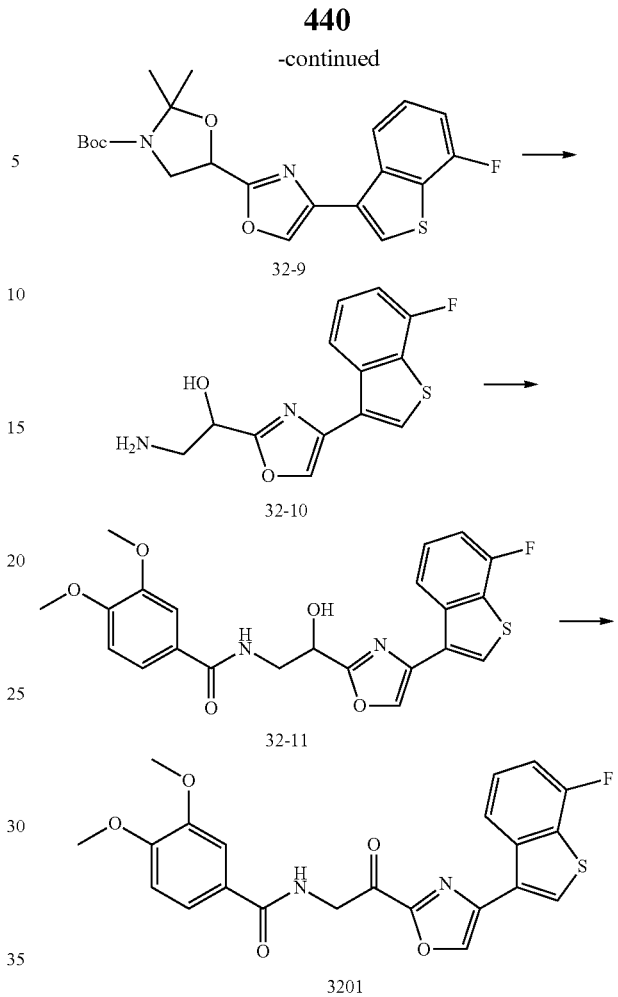

A solution of 32-6 (2.59 g, 0.01 mol) in NH$_3$/MeOH (20 mL) was stirred at rt for 30 mins. The solvent was removed by rotary evaporator. The residue, 32-7, was used in next step.

A mixture of 32-7 (2.44 g, 0.01 mol) 32-8 (2.73 g, 0.01 mol) and AgSbF$_6$ (5.14 g, 0.015 mol) in DME (20 mL) was stirred for 2 h at 120° C. under microwave irradiation. The mixture was filtrated. The filtrate was concentrated by rotary evaporator to give crude 32-9 (5 g), which was used in next step without further purification.

To a solution of 32-9 (5 g) in EtOAc (10 mL) was added HCl-EtOAc (30 mL). The solution was stirred for 10 h. The solvent was concentrated by rotary evaporator. The product was purified by prep-HPLC to give 32-10 (250 mg). ESI-MS: m/z 278.8 [M+H]$^+$.

To a solution of 32-10 (145 mg, 0.8 mmol) in DMF (10 mL) was added HATU (343 mg, 0.9 mmol), DIEA (155 mg, 1.2 mmol), and stirred for 5 min. 3,4-dimethoxybenzoic acid (250 mg, 0.8 mmol) was added and the mixture was stirred for 5 h. Water (100 mL) was poured into the solution, and a solid precipitated. The solid was purified by silica column chromatograph (PE:EA=1:1) to give 32-11 (158 mg, 45%). ESI-MS: m/z 442.9 [M+H]$^+$.

To a solution of 32-11 (158 mg, 0.35 mmol) in dry DCM (5 mL) was added DMP (300 mg, 0.7 mmol) at 0° C. and the mixture was stirred for 1 h (monitored by TLC). The product was purified by prep-HPLC to give compound 3201 (15 mg, yield 10%). +ESI-MS: m/z 440.9 [M+H]$^+$.

Example 33-1

Preparation of Compound 3300

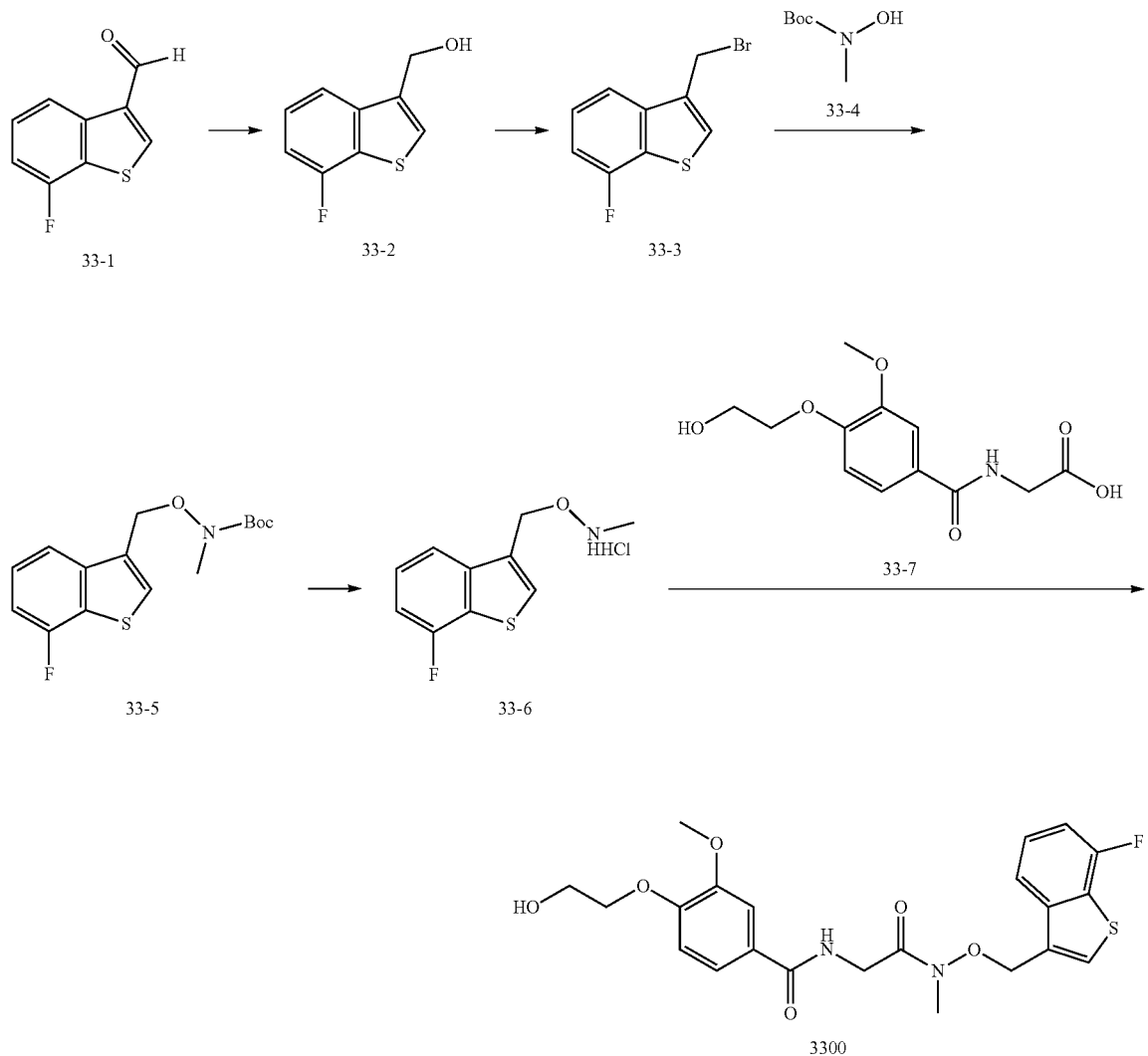

To a solution of 33-1 (2 g, 11 mmol) in THF (20 mL) and MeOH (2 mL) was added NaBH$_4$ (386 mg, 11.2 mmol) at 0° C., and the mixture was stirred for 30 mins (monitored by TLC). The reaction was quenched by addition of H$_2$O and extracted by EA. The combined organic layers were washed by brine, dried over Na$_2$SO$_4$ and concentrated. The residue was purified on a silica gel column to give 33-2 (1.5 g, 75%).

To a solution of 33-2 (1.09 g, 6 mmol) in DCM (10 mL) was added PBr3 (2 mL), and the mixture was stirred for 30 mins at rt. The solution was quenched with water and extracted with DCM. The organic phase was dried over Na$_2$SO$_4$ and concentrated. The residue was purified on a silica gel column to give 33-3 (0.5 g, 34%)

To a solution of 33-3 (490 mg, 2 mmol) in THF (5 mL) was added NaH (96 mg, 4 mmol) at 0° C. The solution was stirred for 30 mins at 0° C. Compound 33-4 (294 mg, 2 mmol)(prepared according to Hunt et al., *Org. Lett.* (2009) 11(22):5210-5213, which hereby is incorporated by reference for the limited purpose of preparing 33-4) was added. The solution was stirred for 30 mins at rt. The mixture was washed with H$_2$O and diluted with EA. The solution was washed by brine, dried over Na$_2$SO$_4$ and concentrated to give crude 33-5 (400 mg, 64.0%).

A solution of 33-5 (311 mg, 1 mmol) in EA (2 mL) was added EA/HCl (2 mL). The solution was stirred for 30 mins. The solid was collected to give 33-6 (247 mg, 100%)

To a solution of 33-7 (100 mg, 0.37 mmol), HATU (172 mg, 0.45 mmol) and DIPEA (117 mg, 0.909 mmol) in anhydrous DMF (1 mL) was added 33-6 (100 mg 0.404 mmol) at 25° C. The solution was stirred for 10 h at this temperature, diluted with 1.0 N aqueous NaHCO$_3$ solution (40 mL×2), and extracted with EA (20 mL×2). The combined organic layers were washed by brine, dried over anhydrous Na$_2$SO$_4$, and concentrated under reduced pressure. The residue was purified on a silica gel column to give compound 3300 (20 mg, 11.7%). +ESI-MS: m/z 463.1 [M+H]$^+$.

Example 33-2

Preparation of Compound 3302

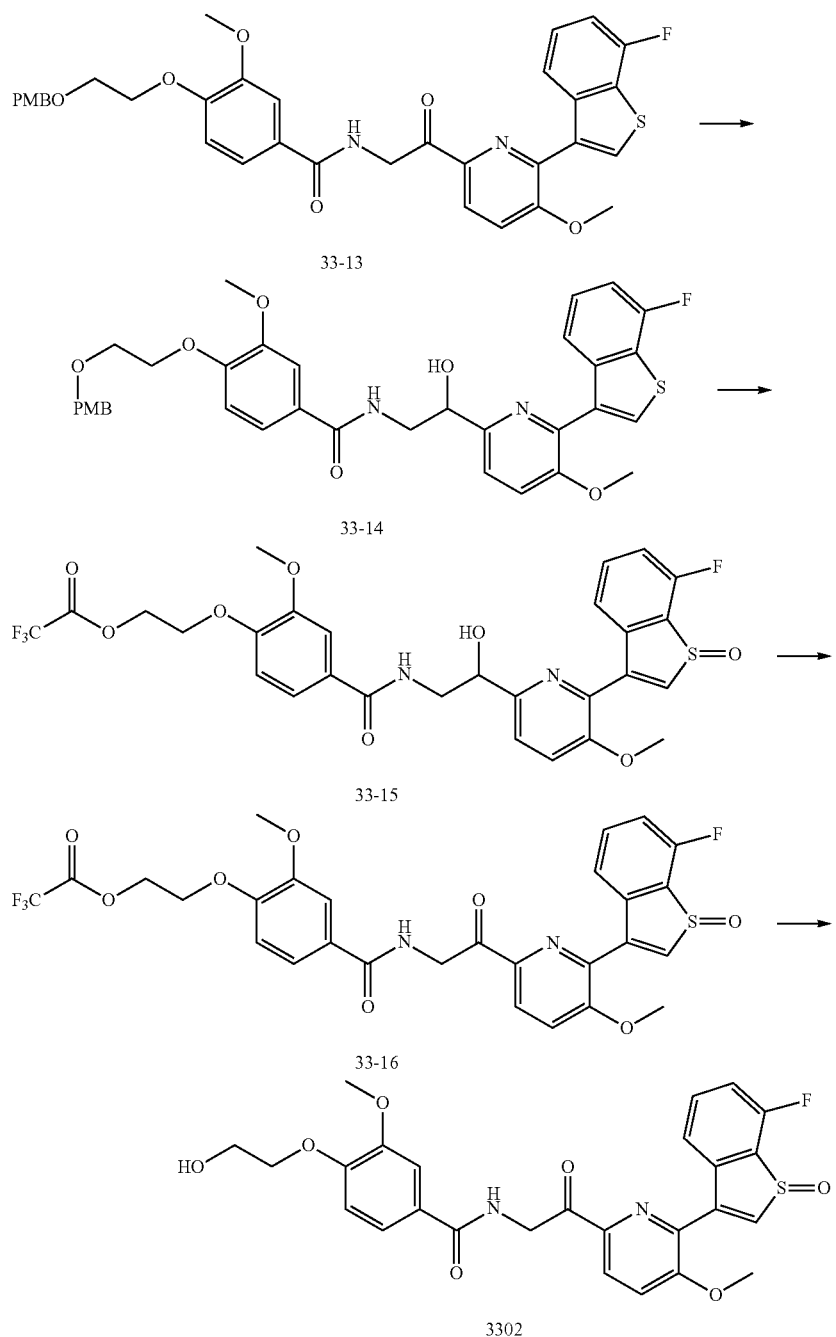

To a solution of 33-13 (190 mg, 0.30 mmol) in THF (5 mL) was added NaBH$_4$ (20 mg, 0.6 mmol) at rt. MeOH (1 mL) was added, and the mixture was stirred at 20° C. for 1 h. The residue was purified by column chromatography on silica gel (PE) to provide 33-14 (190 mg, 99%).

To a solution of 33-14 (190 mg, 0.3 mmol) in DCM (3 mL) was added TFA (0.5 mL) and H$_2$O$_2$ (0.2 mL, 30%, 2 eq), and the mixture was stirred for 30 mins. The mixture was neutralized with a saturated NaHCO$_3$ solution, and extracted with DCM (10 mL×3). The solution was concentrated to give crude 33-15 (200 mg), which was used in the next step without further purification. +ESI-MS: m/z 625.0 [M+H]$^+$.

To a solution of 33-15 (200 mg, 0.3 mmol) in CH$_2$Cl$_2$ (5 mL) was added DMP (170 mg, 0.4 mmol), and the mixture was stirred at rt until the starting material was consumed. After work up, 33-16 was obtained and used in the next step without further purification.

To a solution of 33-16 (200 mg, 0.3 mmol) in MeOH (10 mL) was added one drop of concentrated HCl (1 mL). The mixture was stirred at rt until the starting material was consumed. Work up and concentration of the residue provided compound 3302. Purification by prep-HPLC gave compound 3302 (13 mg, 7%). +ESI-MS: m/z 526.9 [M+H]⁺.

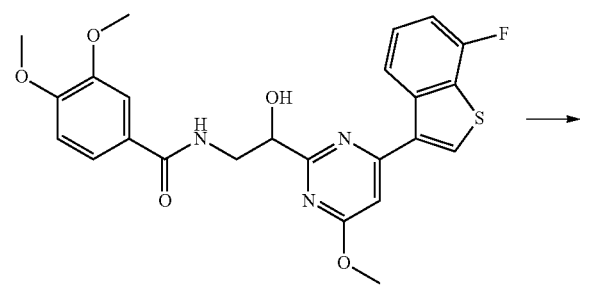

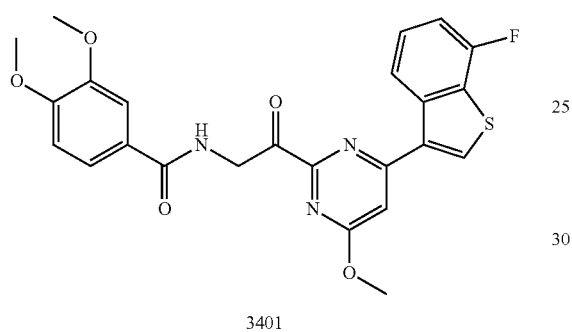

3401

To a stirred solution of N-(2-(4-(7-fluorobenzo[b]thiophen-3-yl)-6-methoxypyrimidin-2-yl)-2-hydroxyethyl)-3,4-dimethoxybenzamide (96 mg, 0.2 mmol) in DCM (10 mL) was added DMP (170 mg, 0.4 mmol). The mixture was stirred at rt until the starting material was consumed. The mixture was diluted with dichloromethane (20 mL), and washed with saturated $Na_2S_2O_3$ solution and $NaHCO_3$ solution. The organic phase was dried over anhydrous MgSO4, and concentrated to give the crude product. The residue was purified by silica gel column chromatography (PE/EA) to give compound 3401 (74 mg, 80%). +ESI-MS: m/z 482.9 [M+H]⁺.

3500

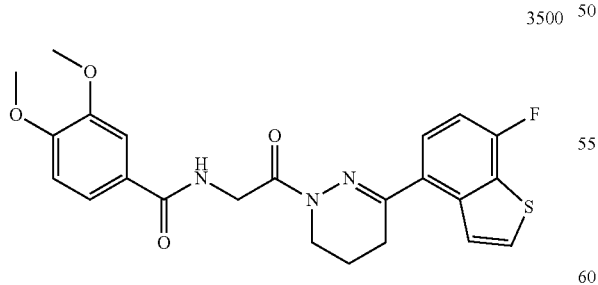

Compound 3500 was prepared using methyl 3,4-dimethoxybenzoic acid and 2,3-difluorobenzaldehyde, and by following a synthetic route, which closely follows that described for preparation of compound 200. Compound 3500 was obtained as a white solid (168.9 mg, 35.2%). +ESI-MS: m/z 456.1[M+H]⁺.

3501

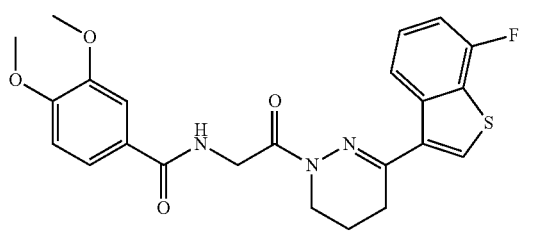

Compound 3501 was prepared using methyl 3,4-dimethoxybenzoic acid and 2,3-difluorobenzaldehyde, and by following a synthetic route, which closely follows that described for preparation of compound 200. Compound 3501 was obtained as a white solid (76.4 mg, 14.9%). +ESI-MS: m/z 456.0[M+H]⁺.

Example 34-1

Preparation of Compound 3800

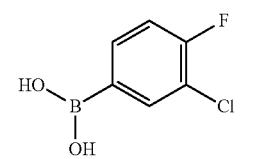

38-1

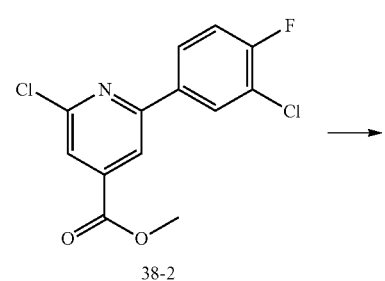

38-2

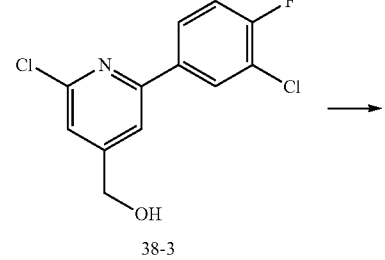

38-3

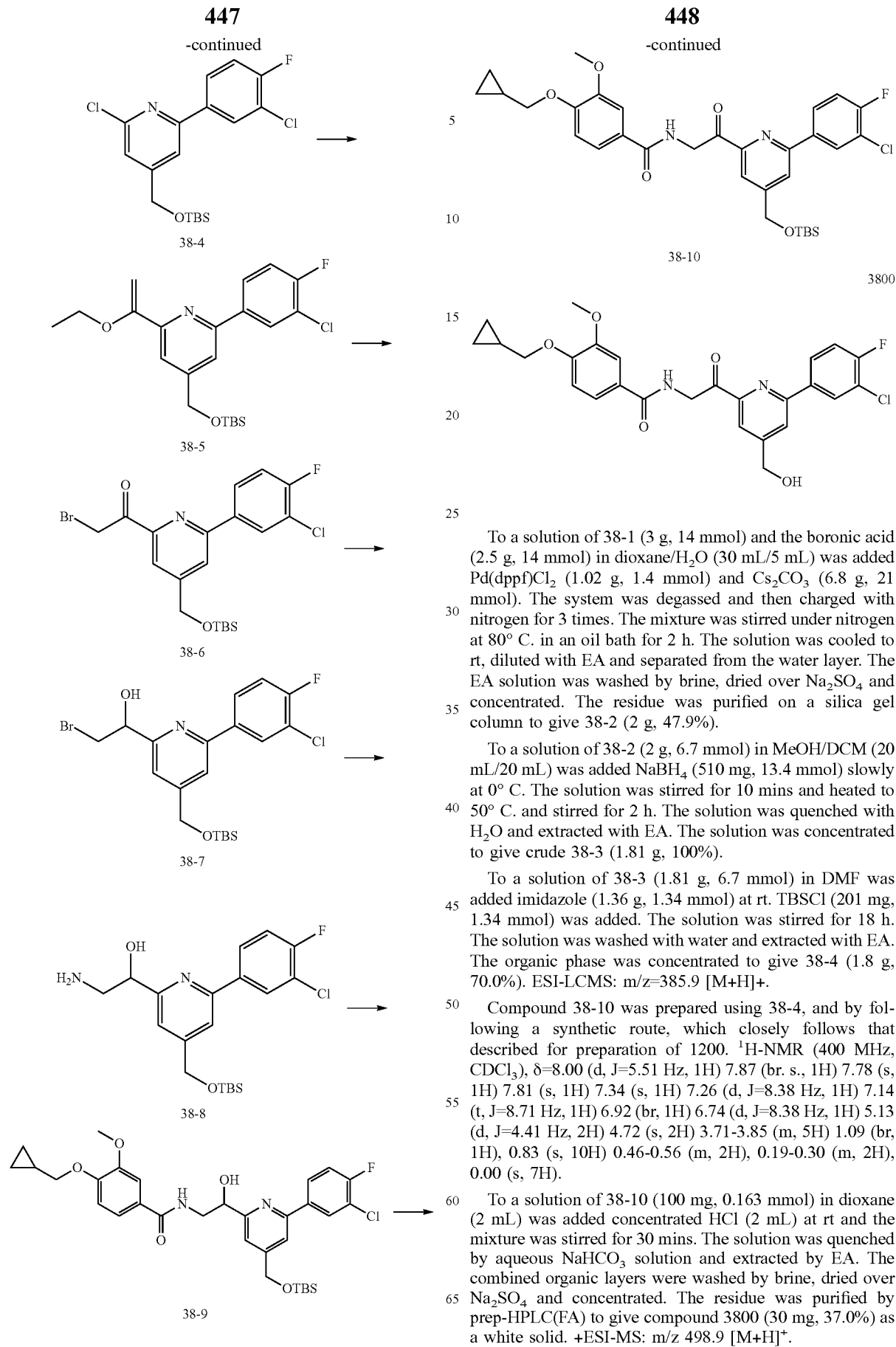

To a solution of 38-1 (3 g, 14 mmol) and the boronic acid (2.5 g, 14 mmol) in dioxane/H$_2$O (30 mL/5 mL) was added Pd(dppf)Cl$_2$ (1.02 g, 1.4 mmol) and Cs$_2$CO$_3$ (6.8 g, 21 mmol). The system was degassed and then charged with nitrogen for 3 times. The mixture was stirred under nitrogen at 80° C. in an oil bath for 2 h. The solution was cooled to rt, diluted with EA and separated from the water layer. The EA solution was washed by brine, dried over Na$_2$SO$_4$ and concentrated. The residue was purified on a silica gel column to give 38-2 (2 g, 47.9%).

To a solution of 38-2 (2 g, 6.7 mmol) in MeOH/DCM (20 mL/20 mL) was added NaBH$_4$ (510 mg, 13.4 mmol) slowly at 0° C. The solution was stirred for 10 mins and heated to 50° C. and stirred for 2 h. The solution was quenched with H$_2$O and extracted with EA. The solution was concentrated to give crude 38-3 (1.81 g, 100%).

To a solution of 38-3 (1.81 g, 6.7 mmol) in DMF was added imidazole (1.36 g, 1.34 mmol) at rt. TBSCl (201 mg, 1.34 mmol) was added. The solution was stirred for 18 h. The solution was washed with water and extracted with EA. The organic phase was concentrated to give 38-4 (1.8 g, 70.0%). ESI-LCMS: m/z=385.9 [M+H]+.

Compound 38-10 was prepared using 38-4, and by following a synthetic route, which closely follows that described for preparation of 1200. $^1$H-NMR (400 MHz, CDCl$_3$), δ=8.00 (d, J=5.51 Hz, 1H) 7.87 (br. s., 1H) 7.78 (s, 1H) 7.81 (s, 1H) 7.34 (s, 1H) 7.26 (d, J=8.38 Hz, 1H) 7.14 (t, J=8.71 Hz, 1H) 6.92 (br, 1H) 6.74 (d, J=8.38 Hz, 1H) 5.13 (d, J=4.41 Hz, 2H) 4.72 (s, 2H) 3.71-3.85 (m, 5H) 1.09 (br, 1H), 0.83 (s, 10H) 0.46-0.56 (m, 2H), 0.19-0.30 (m, 2H), 0.00 (s, 7H).

To a solution of 38-10 (100 mg, 0.163 mmol) in dioxane (2 mL) was added concentrated HCl (2 mL) at rt and the mixture was stirred for 30 mins. The solution was quenched by aqueous NaHCO$_3$ solution and extracted by EA. The combined organic layers were washed by brine, dried over Na$_2$SO$_4$ and concentrated. The residue was purified by prep-HPLC(FA) to give compound 3800 (30 mg, 37.0%) as a white solid. +ESI-MS: m/z 498.9 [M+H]$^+$.

Example 35-1

Preparation of Compound 3900

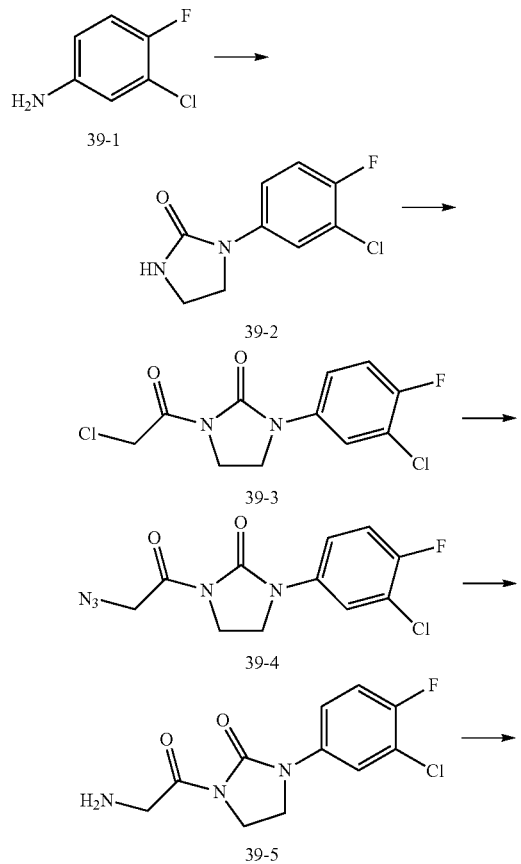

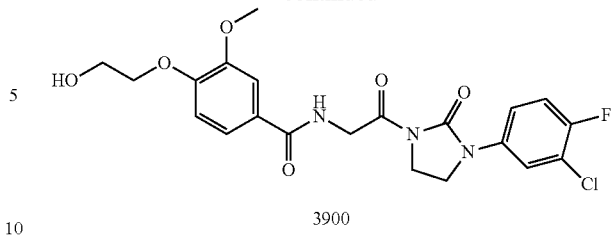

A round bottom flask was charged with 39-1 (1.45 g, 10.0 mmol) in THF (20 mL). 1-chloro-2-isocyanatoethane (1.2 g, 11 mmol) was added dropwise. The mixture was stirred at rt for 30 mins. NaH (400 mg, 10 mmol, 60% in mineral oil) was added. The mixture was stirred at 50° C. for 3 h. The reaction was quenched with MeOH, and diluted with EA (50 mL). The solution was washed with brine. The organic solution was dried over anhydrous MgSO4, and concentrated at low pressure. The residue was purified by chromatograph to give 39-2 (1.04 g, 50%). +ESI-MS: m/z 214.9 [M+H]$^+$ A round bottom flask was charged with 39-2 (214 mg, 1.0 mmol), 2-chloroacetic anhydride (340 mg, 2 eq) in PhMe (20 mL). The mixture was stirred at 120° C. for 3 h. The solvent was removed in vacuum. The residue was purified by column on silica gel (PE:EA=5:1) to give 39-3 (260 mg, 90%). +ESI-MS: m/z 291.1 [M+H]$^+$.

Compound 3900 was prepared using 39-3, and by following a synthetic route, which closely follows that described for preparation of compound 2800. +ESI-MS: m/z 465.8 [M+H]$^+$.

Example 35-2

Preparation of Compound 3901

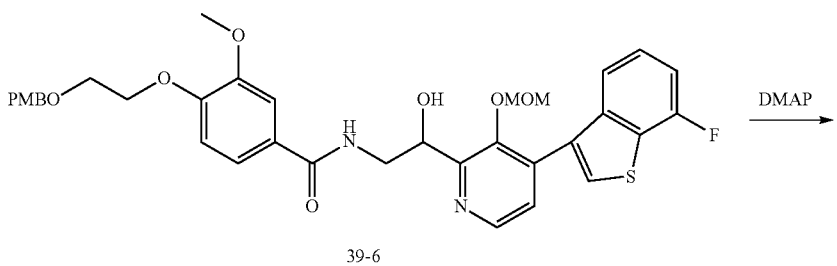

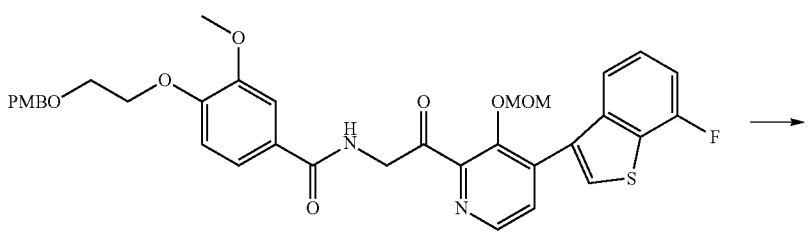

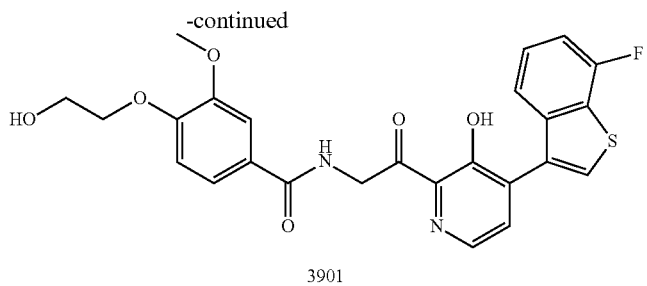

3901

Compound 39-7 was prepared using 2-chloro-4-iodo-3-(methoxymethoxy) pyridine, and by following a synthetic route, which closely follows that described for preparation of 1200.

To a solution of crude 39-7 (150 mg, 0.226 mmol) in DCM (20 mL) was added TFA (2 mL). The mixture was stirred at rt for 30 mins. The solution was washed with water and extracted with EA. The organic layer was dried over anhydrous MgSO$_4$, and concentrated at low pressure. The residue was purified by prep-HPLC to generate compound 3901 (29 mg, 8.7%). +ESI-MS: m/z 496.9 [M+H]$^+$.

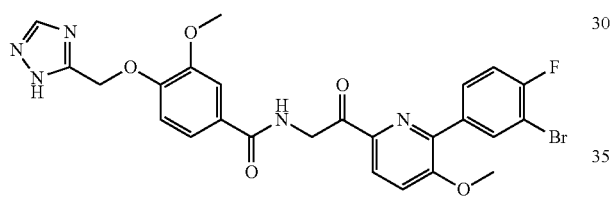

3903

Compound 3903 was prepared using 2-amino-1-(6-(3-bromo-4-fluorophenyl)-5-methoxypyridin-2-yl) ethanol, and by following a synthetic route, which closely follows that described for preparation of compound 1310. +ESI-MS: m/z 569.9 [M+H]$^+$.

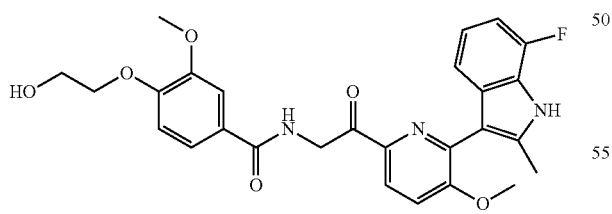

4002

Compound 4002 was prepared using N-(2-(6-bromo-5-methoxypyridin-2-yl)-2-oxoethyl)-3-methoxy-4-(2-((4-methoxybenzyl)oxy)ethoxy)benzamide and 7-fluoro-2-methyl-3-(4,4,5,5-tetramethyl-1,3,2-dioxaborolan-2-yl)-1-((2-(trimethylsilyl)ethoxy)methyl)-1H-indole, and by following a synthetic route, which closely follows that described for preparation of compound 1300. +ESI-MS: m/z 508.3 [M+H]$^+$.

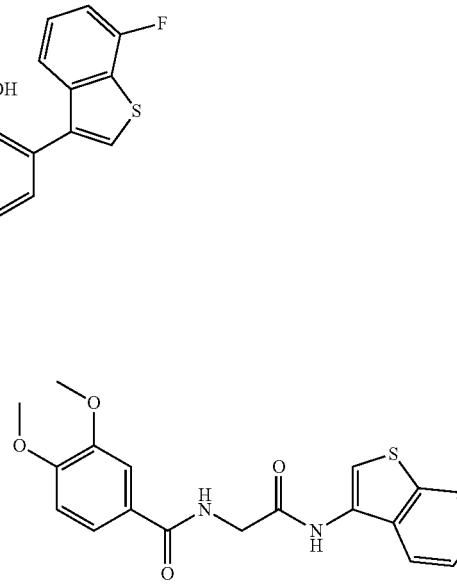

4100

Compound 4100 was prepared using 3,4-dimethoxybenzoic acid and benzo[b]thiophen-3-amine, and by following a synthetic route, which closely follows that described for preparation of compound 200. Compound 4100 was obtained as a white solid. ESI-LCMS: m/z=371.0 [M+H]$^+$.

Example 36-1

Preparation of Compound 4101

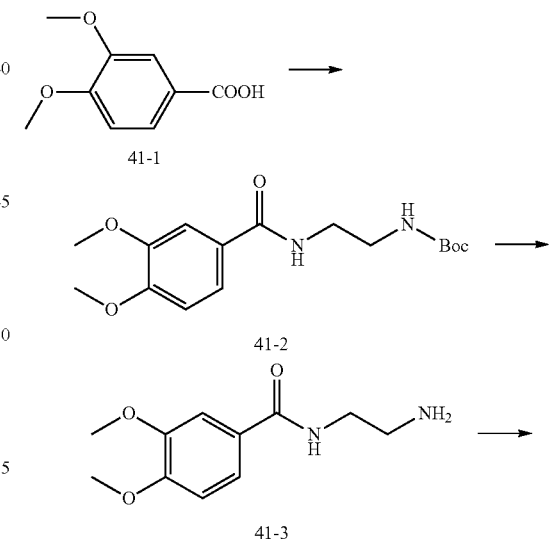

To a solution of 41-1 (3.0 g, 16.5 mmol) in DCM (50 mL) was added HATU (9.4 g, 24.7 mmol) and DIPEA (8.4 g, 65.0 mmol), and the mixture was stirred at rt for 30 mins. The mixture was treated with tert-butyl (2-aminoethyl)carbamate (4.0 g, 24.7 mmol). The mixture was then stirred at rt for 15 h. The mixture was washed with water and the organic layer was separated. The organic phase was dried over sodium sulfate and concentrated to dryness. The residue was purified by column chromatograph on silica gel (PE:EA=50:1 to 10:1) to afford 41-2 as a white solid (3.2 g, 60.3%). +ESI-LCMS: m/z=324.9 [M+H]$^+$.

Compound 41-2 (3.2 g, 9.7 mmol) was dissolved in HCl/EtOAc (6.0 M, 60 mL) and stirred at rt for 15 h. The mixture was concentrated to dryness. The residue was dissolved in water, basified with saturated $Na_2CO_3$, extracted with EA and purified by column chromatograph on silica gel (eluent: PE:EA=20:1 to 2:1) to give 41-3 as a white solid (1.9 g, 87%). +ESI-LCMS: m/z=224.9 [M+H]$^+$.

To a solution of 41-3 (450 mg, 2.00 mmol) and benzo[b]thiophene-3-carbaldehyde (350 mg, 1.85 mmol) in $ClCH_2CH_2Cl$ (10 mL) was added $NaBH_4$ (150 mg, 3.95 mmol), and the mixture was stirred at 50° C. for 15 h. The reaction was quenched with water (10 mL). The organic layer was separated, washed with saturated $NH_4Cl$, and dried over $Na_2SO_4$. The organic solvent was concentrated at low pressure. The residue was finally purified by column chromatograph on silica gel (eluent: PE:EA=20:1 to 1:1) to afford compound 4101 as a white solid (236 mg, 29.8%). ESI-LCMS: m/z=371.0 [M+H]$^+$.

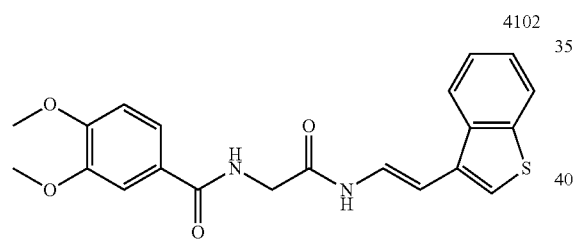

4102

Compound 4102 (30 mg, 2.6%) was prepared using 3,4-dimethoxybenzoic acid and 1-(benzo[b]thiophen-3-yl)ethanone, and by following a synthetic route, which closely follows that described for preparation of 200. Compound 4102 was obtained as a white solid. +ESI-MS: m/z 436.9 [M+MeCN]$^+$.

Example 36-2

Preparation of Compound 4103

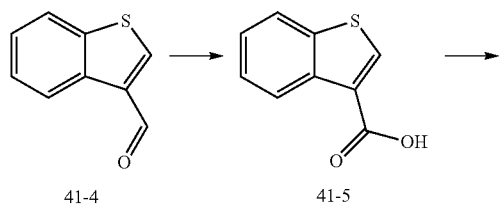

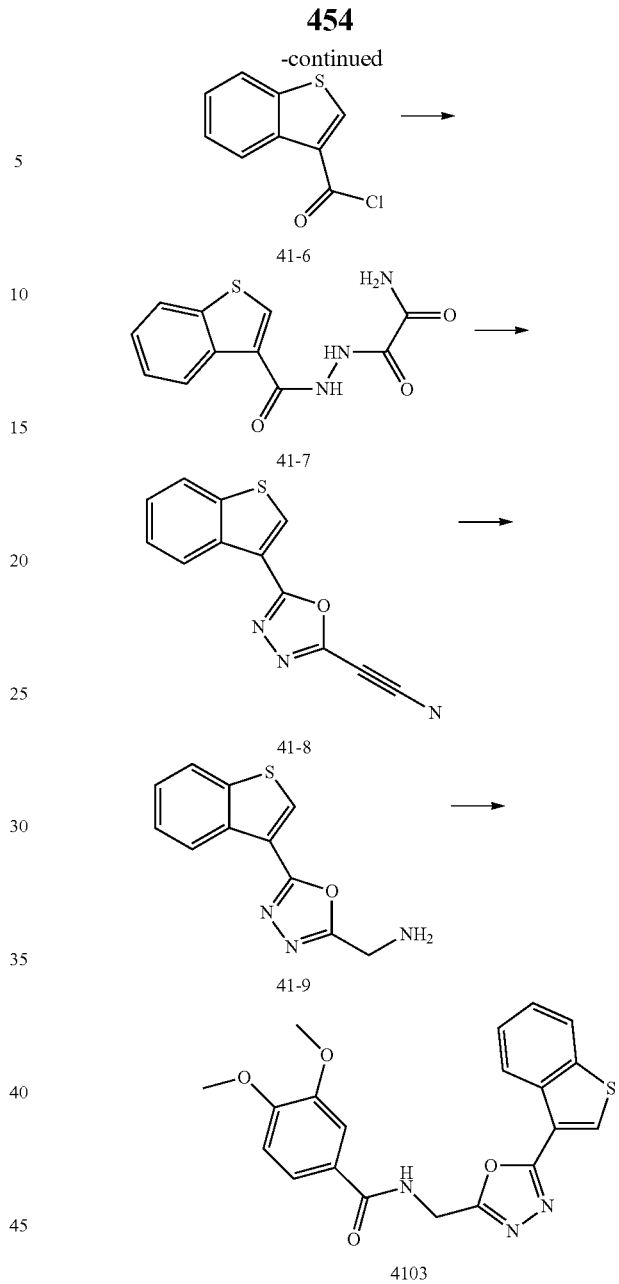

To a solution of 41-4 (6 g, 37 mmol) in MeOH (25 mL) and $H_2O$ (250 Ml) was added $KMnO_4$ (23 g, 145 mmol). The mixture was stirred at 80° C. for 13 h. The mixture was filtered, and the filtrate was concentrated, and acidified to pH=3.0 with 2N HCl solution. The precipitate was collected by filtration and washed with $H_2O$ to give 41-5. ESI-LCMS: m/z=178.9 [M+H]$^+$.

A mixture of 41-5 (1.5 g, 8.4 mmol) and $SOCl_2$ (5 g, 42 mmol) was refluxed for 4 h. Excess $SOCl_2$ was removed under reduced pressure and the residue was concentrated to give crude 41-6, which was used for next step without purification.

To a solution of 41-6 (1.5 g, 7.6 mmol) in dioxane (3 mL) was added a mixture 2-hydrazinyl-2-oxoacetamide (0.79 g, 7.6 mmol) and $NaHCO_3$ (0.64 g, 7.6 mmol) in dioxane (30 mL) dropwise. The mixture was refluxed for 4 h, and filtered hot. The filtrate was concentrated in vacuum to afford crude 41-7, which was used in next step without purification. ESI-LCMS: m/z=263.9 [M+H]$^+$.

A suspension of 41-7 in POCl₃ (20 mL) was heated to 100° C. for 3 h. POCl₃ was evaporated in vacuum. The mixture was diluted with EA (50 mL), and neutralized with an ice-cold saturated NaHCO₃ solution. The organic layer was dried over sodium sulfate and concentrated to give crude 41-8, which was used in next step without purification. ESI-LCMS: m/z=227.8 [M+H]⁺.

A mixture of 41-8 (220 mg, 0.97 mmol), concentrated HCl (3 mL) and Pd/C (100 mg) in EtOH (15 mL) was stirred under hydrogen (15 psi) for 13 h. The mixture was filtered over a pad of celite and the filtrate was concentrated in vacuum. The residue was diluted by DCM and water. The aqueous phase was basified by aq. NaOH (5 N), and extracted with DCM. The combined organic phase was dried over sodium sulfate, and concentrated at low pressure to give crude 41-9, which was used in next step without purification.

To a solution of 3,4-dimethoxybenzoic acid (24 mg, 0.13 mmol), HATU (60 mg, 0.16 mmol) and DIPEA (45 mg, 0.35 mmol) in anhydrous DCM (3 mL) was added 41-9 (30 mg, 0.13 mmol). The solution was stirred for 10 h at rt and then diluted with 1.0 N aqueous NaHCO₃ solution. The mixture was extracted with DCM. The combined organic phase was dried over anhydrous Na₂SO₄ and concentrated under reduced pressure. The residue was purified by prep-HPLC to give compound 4103 (15 mg, 30%). ESI-LCMS: m/z=396.0 [M+H]⁺.

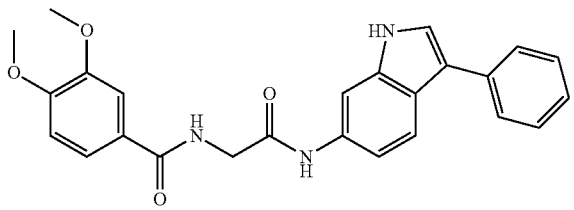

4104

Compound 4104 (4 mg, 2.1%) was prepared using 3,4-dimethoxybenzoic acid, (3-nitro-phenyl)-hydrazine and phenyl-acetaldehyde, and by following a synthetic route, which closely follows that described for preparation of compound 200. Compound 4104 was obtained as a white solid. +ESI-MS: m/z 430.2[M+H]⁺.

Example 36-3

Preparation of Compound 4105

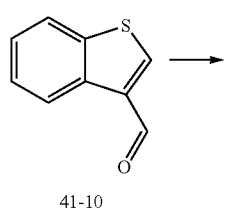

41-10

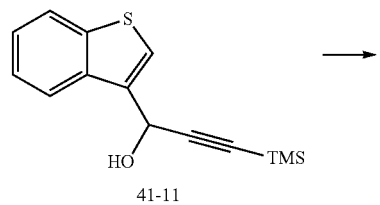

41-11

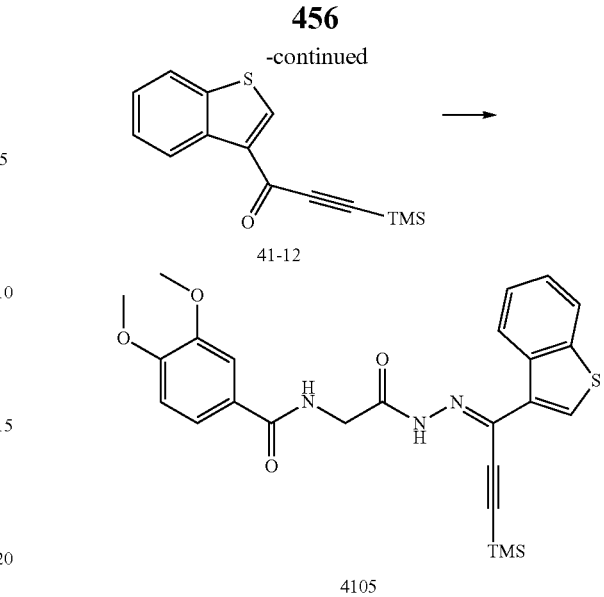

4105

To a stirred solution of ethynyltrimethylsilane (667 mg, 6.79 eq) in DMF (5 mL) was added sodium hydride (296 mg, 7.4 mmol), and the mixture was stirred at rt over 1 h. Benzo[b]thiophene-3-carbaldehyde (41-10, 1.0 g, 6.17 mmol) was added portion-wise. The mixture was stirred at rt for more than 2 h., and then quenched with water. The mixture was extracted with EA, and concentrated at low pressure. The residue was purified by silica gel (PE/EA=5/1) to give 41-11 (600 mg, 37%). ¹H-NMR (CDCl₃, 400 MHz), δ=7.87-7.3 (m, 3H), 7.42-7.34 (m, 2H), 4.93 (s, 1H), 0.22 (s, 9H).

To a solution of 41-11 (0.6 g, 2.3 mmol) in DCM was added PCC (993 mg, 4.6 mmol), and the mixture was stirred at rt for more than 4 h. The reaction was quenched with saturated NH₄Cl solution. The solution was extracted with DCM, and concentrated at low pressure. The residue was purified by silica gel (PE/EA=8/1) to give 41-12 (200 mg, 34%). ¹H-NMR (CDCl₃, 400 MHz), δ=8.76-7.74 (d, J=8.0 Hz, 1H), 8.65 (s, 1H), 7.88-7.86 (d, J=8.0 Hz, 1H), 7.53-7.49 (t, J=3.6 Hz, 1H), 7.46-7.42 (t, J=3.6 Hz, 1H), 0.32 (s, 9H).

To a solution of 41-12 (0.1 g, 0.387 mmol) in EtOH (5 mL) was added N-(2-hydrazinyl-2-oxoethyl)-3,4-dimethoxybenzamide (98 mg, 0.387 mmol), and the mixture was stirred at rt for more than 6 h. The mixture was then slowly heated to 70° C. for 2 h. The mixture was concentrated at low pressure. The residue was purified by prep-HPLC to give compound 4105 (20 mg, 10%). +ESI-MS: m/z 494.2 [M+H]⁺.

Example 37-1

Preparation of Compound 4200A

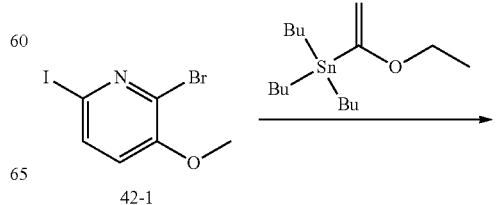

42-1

-continued

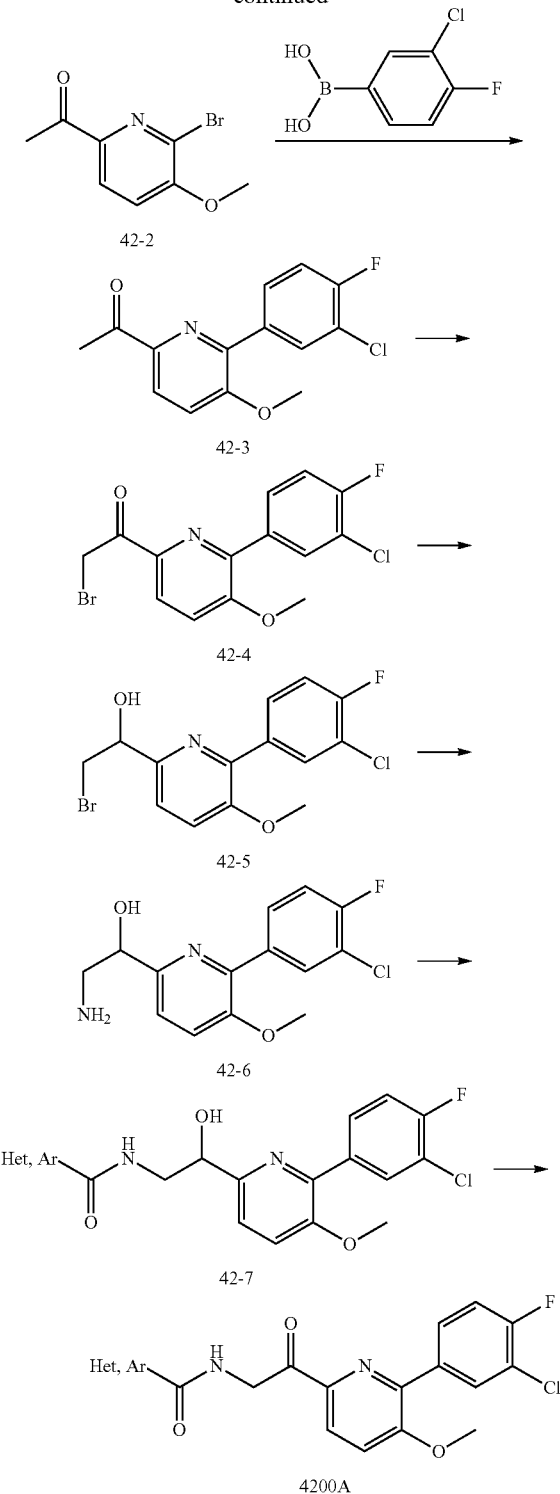

A mixture of 42-1 (6.00 g, 19.2 mmol), Pd(PPh₃)₂Cl₂ (133 mg, 0.19 mmol) and tributyl(1-ethoxyethenyl)stannane (6.0 mL, 17.7 mmol) in 1,4-dioxane (55 mL) was degassed and heated to 90° C. After 1.5 h, the mixture was diluted with EtOAc. The organic portion was washed twice with brine, dried (Na₂SO₄), filtered and concentrated under reduced pressure. Chromatography of the residue (cyclohexane-EtOAc, 100:0 to 85:15) afforded 42-2 as a pale yellow solid (2.36 g, 54%). ¹H NMR (400 MHz, DMSO-d6) δ ppm 2.56 (s, 3H) 3.99 (s, 3H) 7.66 (d, J=8.28 Hz, 1H) 8.01 (d, J=8.53 Hz, 1H).

A mixture of 42-2 (2.36 g, 10.3 mmol), (3-chloro-4-fluorophenyl)boronic acid (2.70 g, 15.4 mmol), Pd(dppf)Cl₂ (500 mg, 0.721 mmol) and aq Na₂CO₃ (2M solution, 12.9 mL, 25.7 mmol) in DCE (30 mL) was degassed and heated to 85° C. After 1 h, the mixture was diluted with DCM and filtered through a pad of celite. The volatiles were removed under reduced pressure. Chromatography of the residue (cyclohexane-EtOAc, 100:0 to 80:20) gave 42-3 as a white solid (1.70 g, 60%). ¹H NMR (400 MHz, DMSO-d₆) δ ppm 2.65 (s, 3H) 3.98 (s, 3H) 7.55 (t, J=8.91 Hz, 1H) 7.75 (d, J=8.78 Hz, 1H) 7.96-8.08 (m, 2H) 8.16 (dd, J=7.40, 2.13 Hz, 1H).

Br₂ (500 uL, 10.0 mmol) was added to a mixture of 42-3 (1.70 g, 6.1 mmol) in 30% HBr-acetic acid (6.6 mL), which had been pre-cooled to 0° C. The mixture was stirred at 0° C. for 1 h, then allowed to reach rt and stirred for 1.5 h. The mixture was poured into cold saturated aq. NaHCO₃ solution. The aqueous portion was extracted twice with DCM. The combined organic portions were dried (Na₂SO₄) and filtered. The volatiles were removed under reduced pressure. Chromatography of the residue (cyclohexane-DCM, 75:25 to 60:40) afforded 42-4 as a white solid (935 mg, 43%). ¹H NMR (400 MHz, DMSO-d₆) d ppm 3.99 (s, 3H) 5.08 (s, 2H) 7.55 (t, J=9.03 Hz, 1H) 7.77-7.81 (m, 1H) 8.03-8.11 (m, 2H) 8.21 (dd, J=7.40, 2.13 Hz, 1H).

NaBH₄ (109 mg, 2.86 mmol) was added to a solution of 42-4 (930 mg, 2.60 mmol) in MeOH (20 mL), which had been pre-cooled to 0° C. The mixture warmed to rt. After 30 mins, a 1M aq HCl solution was added and the methanolic portion was removed under reduced pressure. The aqueous phase was extracted 3 times with DCM. The combined organic portions were washed with brine, dried (Na₂SO₄), filtered and concentrated under reduced pressure. Crude 42-5 (887 mg) was in without further purification. ¹H NMR (400 MHz, DMSO-d₆) δ ppm 3.74 (dd, J=10.1, 6.1 Hz, 1H) 3.83-3.93 (m, 4H) 4.81-4.93 (m, 1H) 5.96 (d, J=5.2 Hz, 1H) 7.44-7.54 (m, 2H) 7.63 (d, J=8.5 Hz, 1H) 7.98 (ddd, J=8.7, 4.9, 2.1 Hz, 1H) 8.12 (dd, J=7.4, 2.1 Hz, 1H).

A mixture of 42-5 (870 mg) in 7M NH₃-MeOH (28 mL) was stirred at rt for 36 h. The volatiles were removed under reduced pressure. The residue was purified by reverse phase chromatography (water-CH₃CN, 80:20 to 60:40) to afford 42-6 as a white solid (472 mg, 61% over two steps). ¹H NMR (400 MHz, DMSO-d₆) δ ppm 3.03 (dd, J=12.7, 8.9 Hz, 1H), 3.27 (dd, J=12.7, 3.4 Hz, 1H), 3.90 (s, 3H), 4.79-4.92 (m, 1H), 6.20 (d, J=4.8 Hz, 1H), 7.46-7.57 (m, 2H), 7.68 (d, J=8.8 Hz, 1H), 7.84-7.84 (m, 1H), 7.90 (br. s., 2H), 7.98 (ddd, J=8.7, 4.9, 2.3 Hz, 1H), 8.10 (dd, J=7.5, 2.0 Hz, 1H).

A mixture of 42-6 (50.0 mg, 0.168 mmol), EDC (48.0 mg, 0.252 mmol), HOBT (34.0 mg, 0.252 mmol), TEA (50 uL, 0.336 mmol) and acid (0.201 mmol) in DCM (1 mL) was stirred at rt for 1 h. The mixture was washed with 1M aq HCl solution, dried (Na₂SO₄), filtered and concentrated under reduced pressure. Compound 42-7 was used in the next step without further purification.

Dess-Martin periodinane (0.252 mmol) was added to a solution of 42-7 in DCM (2 mL). The mixture was stirred at rt for 1 h. A 1:1 saturated aq NaHCO₃ solution-saturated aq Na₂S₂O₃ solution was added. The mixture was stirred at rt for 30 mins and the layers were separated. The organic portion was washed with water, dried (Na₂SO₄), filtered and concentrated under reduced pressure. Chromatography of the residue afforded compound 4200A.

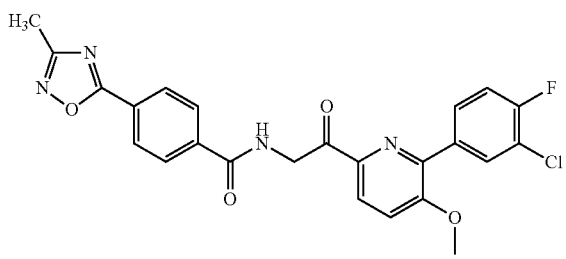

4201

Compound 4201 was prepared by coupling 42-6 with 4-(3-methyl-1,2,4-oxadiazol-5-yl)benzoic acid followed by DMP oxidation, and by following a synthetic route, which closely follows that described for preparation of compound 4200A. Compound 4201 was obtained as an off-white solid (10% over two steps). UPLC/MS(ES$^+$), m/z 481.15 [M+H]$^+$.

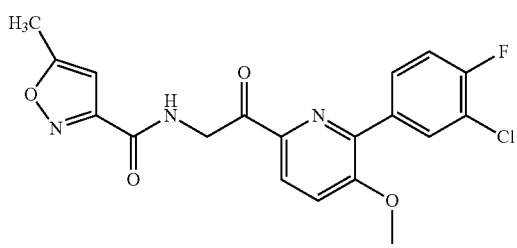

4202

Compound 4202 was prepared by coupling 42-6 with 5-methyl-1,2-oxazole-3-carboxylic acid followed by DMP oxidation, and by following a synthetic route, which closely follows that described for preparation of compound 4200A. Compound 4202 was obtained as a white solid (31% over two steps). UPLC/MS(ES$^+$), m/z: 404.10 [M+H]$^+$.

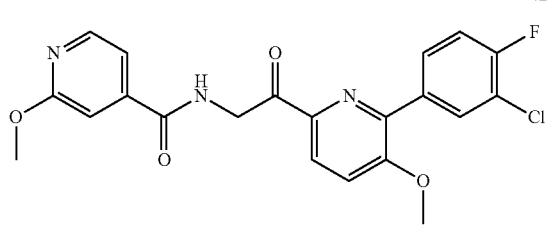

4203

Compound 4203 was prepared by coupling 42-6 with 2-methoxypyridine-4-carboxylic acid followed by DMP oxidation, and by following a synthetic route, which closely follows that described for preparation of compound 4200A. Compound 4203 was obtained as a pale yellow solid (14% over two steps). UPLC/MS(ES$^+$), m/z: 430.21 [M+H]$^+$.

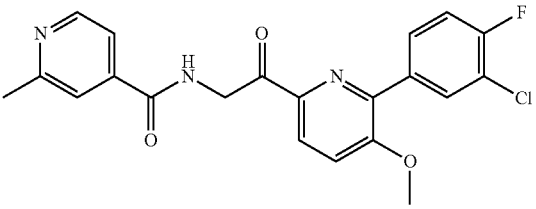

4204

Compound 4204 was prepared by coupling 42-6 with 2-methylpyridine-4-carboxylic acid followed by DMP oxidation, and by following a synthetic route, which closely follows that described for preparation of compound 4200A. Compound 4204 was obtained as an off-white solid (24% over two steps). UPLC/MS(ES$^+$), m/z: 414.10 [M+H]$^+$.

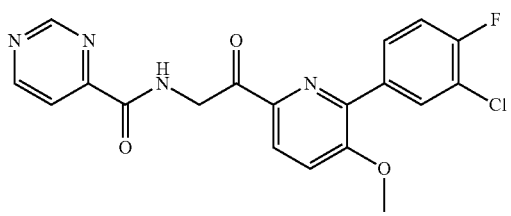

4205

Compound 4205 was prepared by coupling 42-6 with pyrimidine-4-carboxylic acid followed by DMP oxidation, and by following a synthetic route, which closely follows that described for preparation of compound 4200A. Compound 4205 was obtained as a pale yellow solid (25% over two steps). UPLC/MS(ES$^+$), m/z: 401.15 [M+H]$^+$.

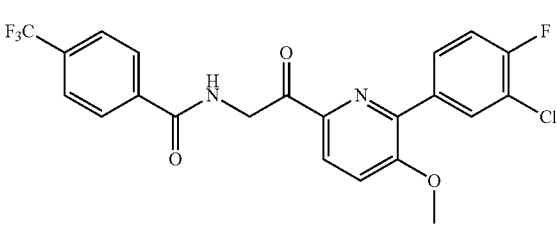

4206

Compound 4206 was prepared by coupling 42-6 with 4-(trifluoromethyl)benzoic acid followed by DMP oxidation, and by following a synthetic route, which closely follows that described for preparation of compound 4200A. Compound 4206 was obtained as an off-white solid (48% over two steps). UPLC/MS(ES$^+$), m/z: 467.18 [M+H]$^+$.

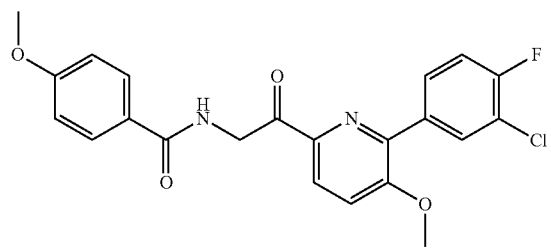

4207

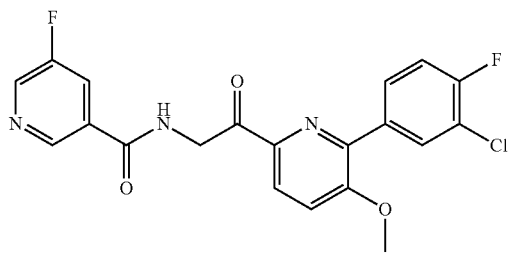

4210

Compound 4207 was prepared by coupling 42-6 with 4-methoxybenzoic acid followed by DMP oxidation, and by following a synthetic route, which closely follows that described for preparation of compound 4200A. Compound 4207 was obtained as a white solid (61% over two steps). UPLC/MS(ES+), m/z: 429.22 [M+H]+.

Compound 4210 was prepared by coupling 42-6 with 5-fluoropyridine-3-carboxylic acid followed by DMP oxidation, and by following a synthetic route, which closely follows that described for preparation of compound 4200A. Compound 4210 was obtained as a white solid (31% over two steps). UPLC/MS(ES+), m/z: 418.16 [M+H]+.

Example 37-2

Preparation of Compound 4212

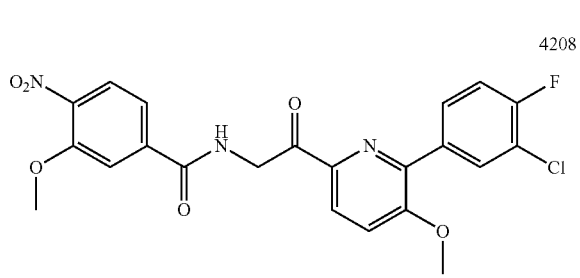 [SMILES: COc1cc(C(=O)NCC(=O)c2ccc(OC)c(-c3ccc(F)c(Cl)c3)n2)ccc1[N+](=O)[O-]]

4208

Compound 4208 was prepared by coupling 42-6 with 3-methoxy-4-nitrobenzoic acid followed by DMP oxidation, and by following a synthetic route, which closely follows that described for preparation of compound 4200A. Compound 4208 was obtained as a white solid (70% over two steps). UPLC/MS(ES+), m/z: 474.20 [M+H]+.

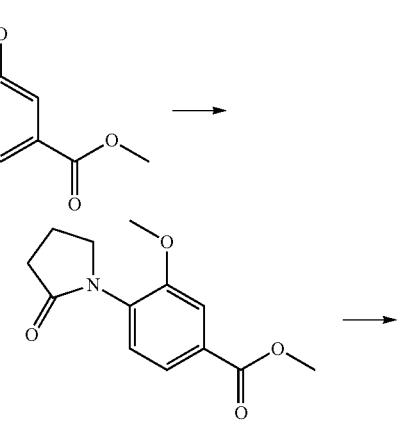

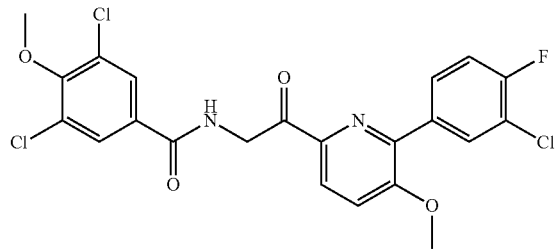

4209

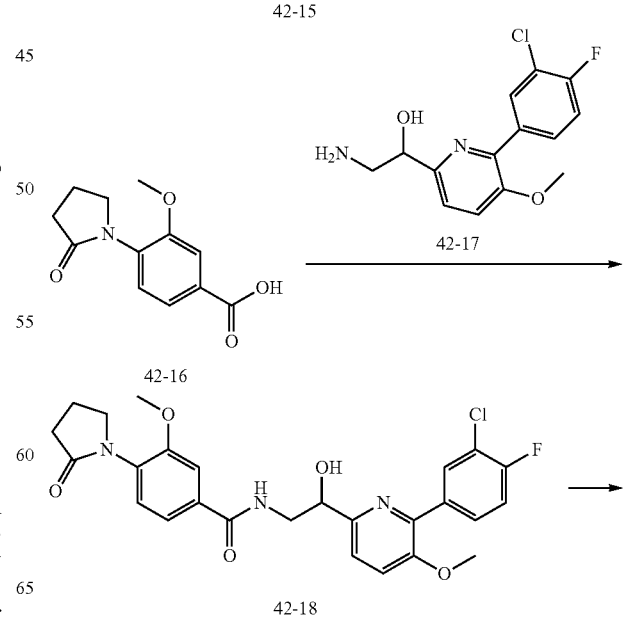

Compound 4209 was prepared by coupling 42-6 with 3,5-dichloro-4-methoxybenzoic acid followed by DMP oxidation, and by following a synthetic route, which closely follows that described for preparation of compound 4200A. Compound 4209 was obtained as a white solid (52% over two steps). UPLC/MS(ES+), m/z: 497.09 [M+H]+.

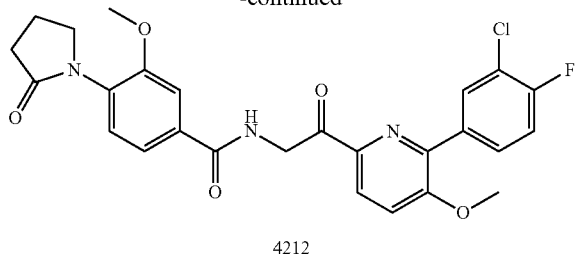

4212

To a solution of methyl 3-methoxy-4-iodobenzoate (250 mg, 0.85 mmol) in toluene (2 mL) was added pyrrolidinone (150 mg, 1.7 mmol), potassium phosphate (0.55 g, 2.2 mmol), xantphos (25 mg, 0.43 mmol) and tris(dibenzylideneacetone)dipalladium(0) (40 mg, 0.43 mmol). The mixture was heated at 110° C. for 3 h. The mixture was then diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 42-15 (0.178 g, 83%). LC/MS: [M+H] 478.10.

To a solution of 42-15 (0.178 g, 0.72 mmol) in methanol (6 mL) was added NaOH (2.0 M, 2.0 ml) at 25° C. The solution was stirred for 15 h, acidified with 2N HCl and extracted with EA. The combined organic phase was dried over anhydrous Na$_2$SO$_4$ to give 42-16 (0.152 g, 90%). $^1$H NMR (400 MHz, CDCl$_3$): δ 7.52 (dd, J=1.77, 8.22 Hz, 1H), 7.51 (d, J=1.77 Hz, 1H), 7.30 (d, J=8.22 Hz, 1H), 3.82 (s, 3H), 3.75 (t, J=7.04 Hz, 2H), 2.55 (t, J=8.02 Hz, 2H), 2.0-2.3 (m, 2H).

To a solution of 42-16 (0.152 g, 0.65 mmol), 42-17 (0.19 g, 0.65 mmol), HATU (0.37 g, 0.97 mmol) in DMF (1 mL) was added DIEA (0.23 ml, 1.3 mmol). The solution was stirred for 2 h at rt. The mixture was diluted with EA. The organic phase was washed with water, 1N HCl, NaHCO$_3$ and brine, dried over anhydrous Na$_2$SO$_4$, and concentrated. The residue was purified by chromatography on silica gel (EA/hexane) to give 42-18 (0.172 g, 51%). LC/MS: [M+H] 478.10.

Dess-Martin periodinane (220 mg, 0.50 mmol) was added to a solution of 42-18 (172 mg, 0.34 mmol) in CH$_2$Cl$_2$, and the mixture was stirred for 2 h. The mixture was diluted with CH$_2$Cl$_2$ and washed with saturated Na$_2$CO$_3$, and brine, dried over MgSO$_4$, and concentrated under reduced pressure. The crude product was purified by chromatography on silica gel (EA/hexane) to give compound 4212 (77 mg, 45%) as white solid. LC/MS: [M+H] 512.10.

Example 37-3

Preparation of Compound 4216

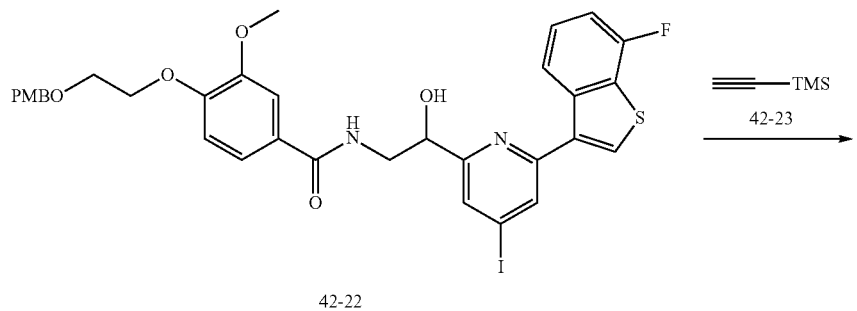

42-22

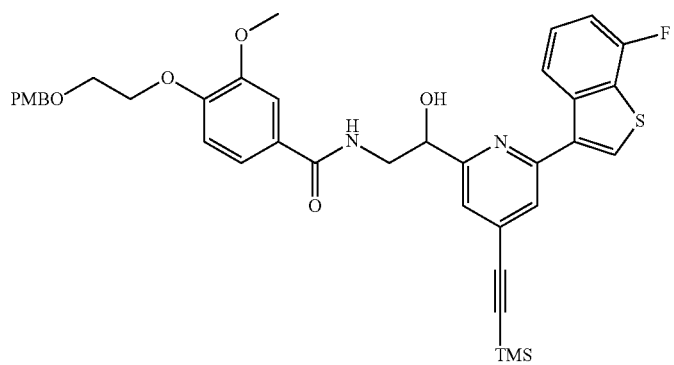

42-24

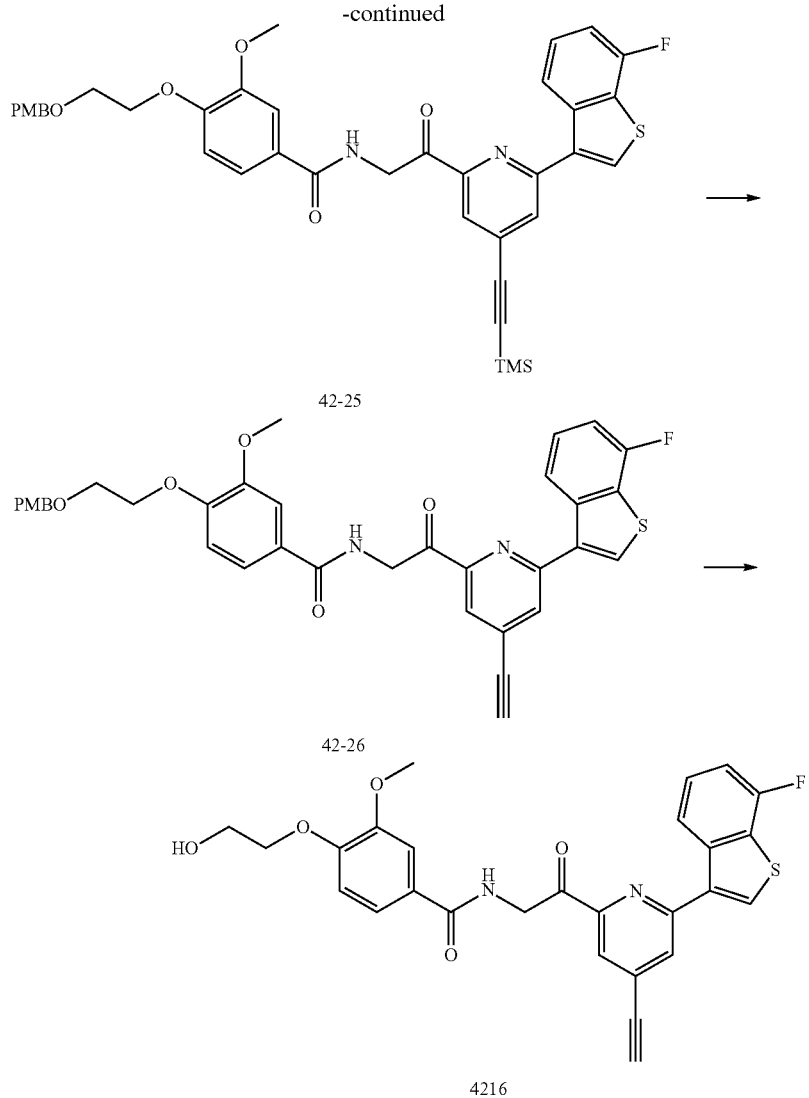

To a mixture of 42-22 (200 mg, 0.275 mmol) in THF (5 mL), was added 42-23 (41.2 mg, 0.42 mmol), Et$_3$N (110.46 mg, 1.09 mmol), CuI (1.04 mg, 0.0055 mmol) and Pd(PPh$_3$)$_4$ (6.34 mg, 0.0055 mol). The mixture was bubbled with nitrogen gas and stirred at rt for 1 h. The mixture was washed with water and extracted with EA. The organic layer was dried over anhydrous sodium sulfate, and concentrated in vacuum. The residue was purified by column chromatography to provide 42-24 (130 mg, 66.9%). +ESI-MS: m/z: 699.2 [M+H]$^+$.

To a solution of 42-24 (110 mg, 0.158 mmol) in DCM (10 mL) was added DMP (135 mg, 0.315 mmol). The mixture was stirred at rt overnight. The solution was then washed with water and extracted with EA. The organic layer was dried over sodium sulfate, concentrated in vacuum to give the desired residue, which was purified by column chromatography to give the desired 42-25 as a white solid (100 mg, 90.8%). +ESI-MS: m/z: 670.2 [M+H]$^+$.

To a solution of 42-25 (140 mg, 0.20 mmol) in MeOH/THF (1:1, 4 mL) was added KF (13.99 mg, 0.24 mmol). The mixture was stirred at rt for 1 h. The mixture was diluted with water, and extracted with EA. The organic layer was dried over anhydrous sodium sulfate, and concentrated in vacuum to give 42-26 as a white solid (120 mg, 96.0%). +ESI-MS: m/z: 625.1 [M+H]$^+$.

To a solution of 42-26 (110 mg, 0.18 mmol) in DCM (3 mL) was added TFA (3 mL), and stirred at rt for 10 mins. The mixture was diluted with EA, and washed with NaHCO$_3$ solution. The organic layer was dried over anhydrous sodium sulfate, and concentrated at low pressure to give the crude product, which was purified by prep-HPLC to give compound 4216 (9.3 mg, 10.2%). +ESI-MS: m/z: 504.9 [M+H]$^+$.

The foregoing syntheses are exemplary and can be used as a starting point to prepare a number of additional compounds. Additional compounds of Formula (I) and Formula (II) are shown in Table 1. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

TABLE 1
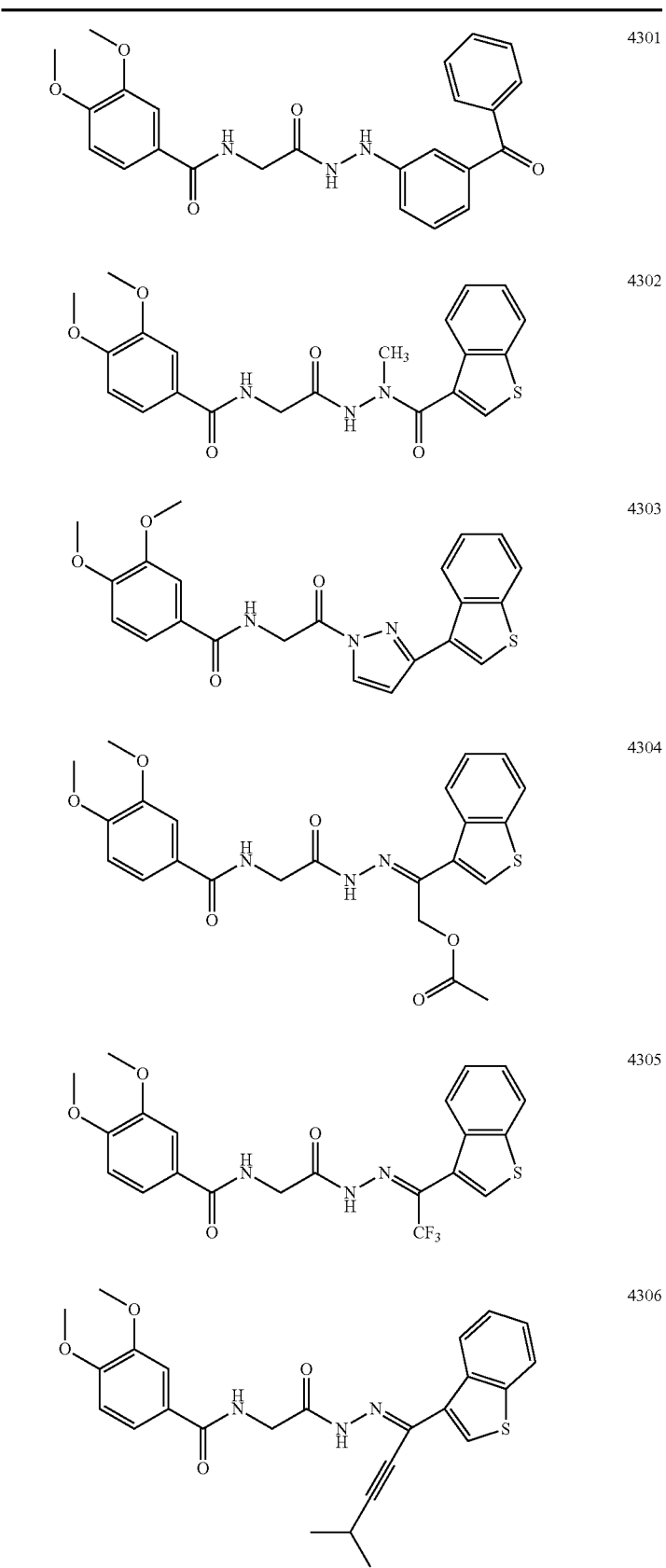

TABLE 1-continued
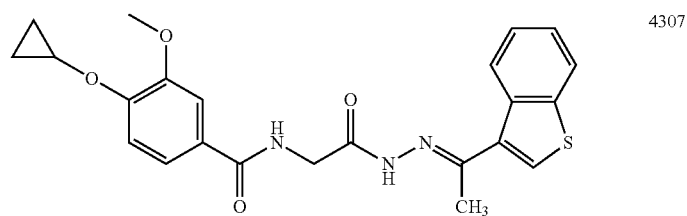
4307
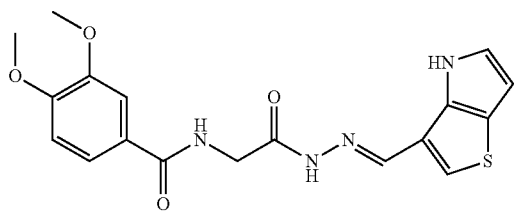 [SMILES: COc1ccc(C(=O)NCC(=O)N/N=C/c2csc3cc[nH]c23)cc1OC]
4308
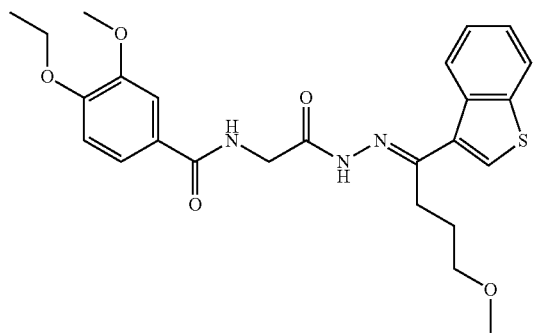 [SMILES: CCOc1ccc(C(=O)NCC(=O)N/N=C(\CCCOC)c2csc3ccccc23)cc1OC]
4309
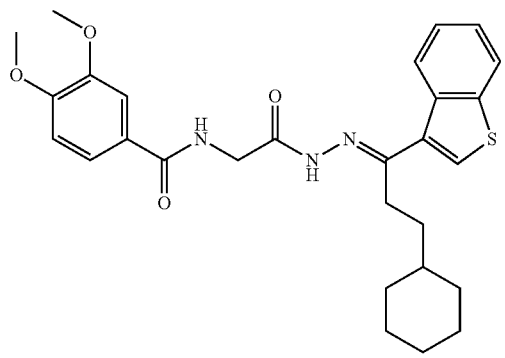 [SMILES: COc1ccc(C(=O)NCC(=O)N/N=C(\CCC2CCCCC2)c2csc3ccccc23)cc1OC]
4310
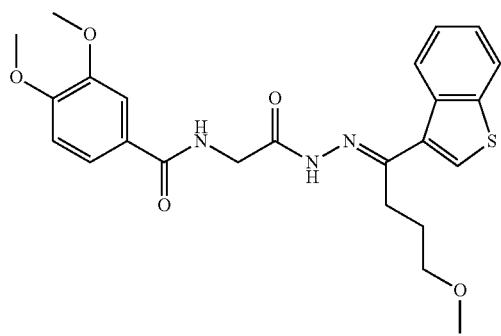 [SMILES: COCCC/C(=N\NC(=O)CNC(=O)c1ccc(OC)c(OC)c1)c1csc2ccccc12]
4311

TABLE 1-continued

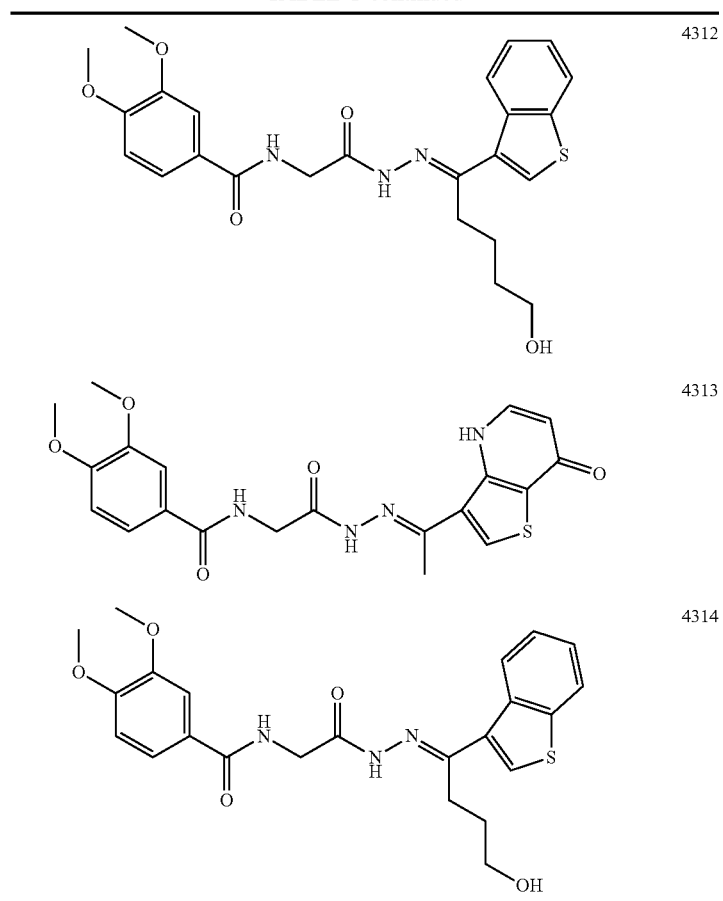

Example A

RSV Antiviral Assay

CPE reduction assays are performed as described by Sidwell and Huffman et al., Appl. Microbiol. (1971) 22(5): 797-801 with slight modifications. HEp-2 cells (ATCC#, CCL-23) are seeded at a density of 1,500 cells/30 μl/well into the 384-well cell plate(s) (Corning#3701) one day prior to the assay. Compounds are added into 384-well cell plates by Labcyte POD 810 Plate Assembler system. Each of the test compounds is provided to duplicate wells of a 384-well cell plate at final concentrations starting from 100 μM or 1 μM using ⅓ stepwise dilutions for 9 points. Quick-thaw Respiratory Syncytial Virus (RSV) long strain (ATCC#VR-26) stock in a 37° C. water bath. Place on ice until ready to use. Viruses are diluted to the concentration of 100 TCID$_{50}$/30 μl with medium and 30 μl diluted RSV are added into related wells of 384-well cell plates. For each plate, sixteen wells are set aside as uninfected, untreated cell controls (CC), and nine wells per test plate receive virus only as a control for virus replication (VC). The final DMSO concentration of all wells is 1%. Place the plates at 37° C., 5% CO$_2$ for 5 days.

After 5 days incubation, observe the CPE of cells in all wells. Cell controls should be natural and have no cell fusion; Cells in the virus control wells should exhibit signs of virus cytopathology (giant cell formation, syncytia). Six μl of cell counting kit-8 reagent (CCK-8, Dojindo Molecular Technologies Inc., CK04-20) are added to each well, which allows colorimetric assays to determine the number of viable cells through the dehydrogenase activity detection. After 3-4 hour incubation, the absorbance of each well is measured with a spectrophotometric plate reader at 450 nm wavelength, using a 630 nm filter as background according to manufacturer's instruction. The 50% effective concentration (EC$_{50}$) is calculated by using regression analysis, based on the mean O.D. at each concentration of compound.

Compounds of Formula (I) and Formula (II) are active in the assay against the RSV virus as demonstrated in Tables 2 and 3. Table 2 includes compounds with an EC$_{50}$ value that is less than 1 μM. Table 3 includes compounds with an EC$_{50}$ value that is equal to or higher than 1 μM and less than 50 μM. Other tested compounds disclosed herein had an EC$_{50}$ value of 50 μM or greater.

TABLE 2

| Compound | Compound | Compound | Compound | Compound | Compound |
|---|---|---|---|---|---|
| 238 | 490 | 605 | 1250 | 1335 | 1613 |
| 246A | 492 | 650 | 1252 | 1336 | 1614 |
| 300 | 493 | 651 | 1253 | 1342 | 1616 |
| 411 | 494 | 1101 | 1255 | 1343 | 1618 |
| 415 | 400-1 | 1200 | 1256 | 1358 | 1622 |
| 423 | 400-4 | 1209 | 1300 | 1359 | 1623 |
| 427 | 400-7 | 1211 | 1309 | 1360 | 1803 |
| 446 | 400-15 | 1213 | 1310 | 1505 | 1806 |
| 455A | 400-23 | 1214 | 1312 | 1508 | 1807 |
| 457 | 400-25 | 1216 | 1316 | 1515 | 1808 |
| 458A | 400-26 | 1217 | 1318 | 1525 | 1809 |
| 459 | 502 | 1220 | 1319 | 1529 | 1812 |

TABLE 2-continued

| Compound | Compound | Compound | Compound | Compound | Compound |
|---|---|---|---|---|---|
| 460 | 510 | 1221 | 1322 | 1531 | 1816 |
| 461 | 513 | 1227 | 1323 | 1601 | 1819 |
| 462A | 514A | 1232 | 1325 | 1602 | 1821 |
| 462B | 514B | 1235 | 1326 | 1603 | 1824 |
| 463A | 600 | 1236 | 1327 | 1605 | 1825 |
| 463B | 601 | 1237 | 1328 | 1606 | 1830 |
| 464 | 602 | 1241 | 1329 | 1607 | 1831 |
| 475 | 603A | 1244 | 1332 | 1608 | 1832 |
| 476 | 603B | 1245 | 1333 | 1609 | 1835 |
| 488 | 604 | 1247 | 1334 | 1612 | 1837 |
| 1839 | 2111 | 2302 | 2638 | 3501 | |
| 2103 | 2112 | 2613 | 2641 | 3800 | |
| 2104 | 2115 | 2617 | 2646 | 3903 | |
| 2106 | 2200 | 2621 | 2648 | 4002 | |
| 2108 | 2300 | 2625 | 3302 | | |
| 2109 | 2301 | 2627 | 3500 | | |

TABLE 3

| Compound | Compound | Compound | Compound | Compound | Compound |
|---|---|---|---|---|---|
| 215 | 453 | 400-13 | 1218 | 1338 | 1522 |
| 231 | 454 | 400-14 | 1223 | 1340 | 1523 |
| 235 | 456 | 400-16 | 1224 | 1341 | 1524 |
| 238 | 466 | 400-17 | 1225 | 1344 | 1526 |
| 245 | 467 | 400-18 | 1226 | 1345 | 1527 |
| 247 | 468 | 400-19 | 1228 | 1346 | 1528 |
| 400 | 469 | 400-21 | 1230 | 1351 | 1530 |
| 401 | 470 | 400-22 | 1238 | 1352 | 1532 |
| 402 | 471 | 400-24 | 1239 | 1353 | 1533 |
| 403 | 474 | 400-27 | 1240 | 1355 | 1534 |
| 409 | 477 | 400-28 | 1242 | 1356 | 1535 |
| 413 | 478 | 500 | 1243 | 1401 | 1536 |
| 414 | 479 | 501 | 1246 | 1402 | 1537 |
| 418 | 480 | 503 | 1248 | 1403 | 1538 |
| 422 | 481 | 504 | 1249 | 1404 | 1539 |
| 426 | 482 | 505 | 1251 | 1405 | 1540 |
| 430 | 483 | 506 | 1257 | 1502 | 1541 |
| 434 | 486 | 507 | 1258 | 1503 | 1604 |
| 436 | 489 | 508 | 1301 | 1504 | 1610 |
| 438 | 491 | 509 | 1302 | 1506 | 1611 |
| 439 | 495 | 511 | 1303 | 1507 | 1615 |
| 440 | 496 | 512 | 1307 | 1509 | 1619 |
| 441 | 497 | 606 | 1308 | 1510 | 1620 |
| 442 | 498 | 839 | 1311 | 1511 | 1621 |
| 443 | 400-2 | 840 | 1313 | 1512 | 1700 |
| 444 | 400-3 | 911 | 1314 | 1513 | 1701 |
| 445 | 400-5 | 1100 | 1315 | 1514 | 1800 |
| 447 | 400-6 | 1202 | 1317 | 1516 | 1801 |
| 448A | 400-8 | 1204 | 1320 | 1517 | 1822 |
| 449 | 400-9 | 1205 | 1321 | 1518 | 1836 |
| 450 | 400-10 | 1206 | 1330 | 1519 | 1900 |
| 451 | 400-11 | 1210 | 1331 | 1520 | 2100 |
| 452 | 400-12 | 1215 | 1337 | 1521 | 2101 |
| 2102 | 2305 | 2604 | 2703 | 3101 | 4105 |
| 2105 | 2306 | 2642 | 2800 | 3103 | 4202 |
| 2107 | 2504 | 2647 | 2801 | 3300 | 4204 |
| 2203 | 2507 | 2649 | 2802 | 3401 | 4205 |
| 2303 | 2600 | 2651 | 2803 | 3900 | 4216 |
| 2304 | 2601 | 2701 | 3100 | 3901 | |

Example B

Cytotoxicity Determination

In order to determine the compound cytotoxicity, in parallel, each of the compounds is applied to duplicate wells in a 384-well cell plate at serial final concentrations starting from 100 μM using ½ stepwise dilutions for 7 points without addition of virus. Incubate the cells at 37° C., 5% $CO_2$ for 5 days. Add 6 μl CCK-8 into each well and incubate in a $CO_2$ incubator at 37° C. for 3-4 hours. Read the plates to obtain the optical densities which are used to calculate 50% cytotoxicity concentration ($CC_{50}$).

Compounds of Formula (I) and Formula (II) are not cytotoxic as shown in Tables 4 and 5. Table 4 includes compounds with a $CC_{50}$ value that is greater than 100 μM. Table 5 includes compounds with a $CC_{50}$ value that is equal to or less than 100 μM and greater than 10 μM. Other tested compounds disclosed herein had a $CC_{50}$ value of less than 10 μM.

TABLE 4

| Compound | Compound | Compound | Compound | Compound | Compound |
|---|---|---|---|---|---|
| 101 | 400-15 | 423 | 440 | 455A | 473 |
| 215 | 400-16 | 424 | 441 | 456 | 475 |
| 235 | 400-18 | 425 | 442 | 459 | 476 |
| 242 | 400-21 | 427 | 443 | 460 | 477 |
| 243 | 400-23 | 428 | 444 | 462A | 480 |
| 247 | 400-24 | 429 | 445 | 463A | 481 |
| 400-1 | 400-25 | 430 | 446 | 463B | 488 |
| 400-3 | 400-26 | 431 | 447 | 464 | 490 |
| 400-5 | 400-27 | 434 | 449 | 466 | 491 |
| 400-6 | 400-28 | 435 | 450 | 467 | 492 |
| 400-10 | 403 | 436 | 451 | 468 | 493 |
| 400-13 | 420 | 438 | 452 | 470 | 494 |
| 400-14 | 421 | 439 | 454 | 471 | 497 |
| 498 | 1201 | 1300 | 1402 | 1603 | 2205 |
| 500 | 1202 | 1302 | 1403 | 1604 | 2301 |
| 502 | 1204 | 1308 | 1404 | 1606 | 2303 |
| 503 | 1207 | 1309 | 1502 | 1609 | 2306 |
| 508 | 1208 | 1310 | 1504 | 1610 | 2601 |
| 513 | 1210 | 1311 | 1505 | 1611 | 2604 |
| 514A | 1211 | 1312 | 1508 | 1612 | 2613 |
| 514B | 1213 | 1316 | 1509 | 1613 | 2617 |
| 600 | 1215 | 1317 | 1514 | 1614 | 2621 |
| 601 | 1217 | 1318 | 1515 | 1615 | 2625 |
| 602 | 1218 | 1319 | 1517 | 1616 | 2627 |
| 603A | 1219 | 1320 | 1520 | 1618 | 2641 |
| 603B | 1220 | 1322 | 1524 | 1619 | 2642 |
| 604 | 1221 | 1325 | 1525 | 1621 | 2647 |
| 650 | 1222 | 1326 | 1526 | 1622 | 2648 |
| 651 | 1224 | 1327 | 1527 | 1623 | 2802 |
| 839 | 1225 | 1328 | 1528 | 1700 | 2803 |
| 840 | 1235 | 1329 | 1529 | 1701 | 2900 |
| 904 | 1236 | 1330 | 1530 | 1801 | 2901 |
| 906 | 1238 | 1336 | 1531 | 1806 | 3200 |
| 907 | 1239 | 1337 | 1533 | 1807 | 3300 |
| 908 | 1240 | 1340 | 1534 | 1816 | 3401 |
| 909 | 1243 | 1341 | 1535 | 1824 | 3500 |
| 913 | 1245 | 1342 | 1536 | 1825 | 3900 |
| 914 | 1249 | 1343 | 1537 | 1830 | 3903 |
| 915 | 1250 | 1345 | 1538 | 2101 | 4103 |
| 916 | 1251 | 1346 | 1539 | 2108 | 4104 |
| 917 | 1252 | 1351 | 1540 | 2111 | 4202 |
| 1000 | 1253 | 1353 | 1541 | 2112 | 4204 |
| 1101 | 1257 | 1356 | 1601 | 2200 | 4205 |
| 1200 | 1258 | 1360 | 1602 | 2203 | |

TABLE 5

| Compound | Compound | Compound | Compound | Compound | Compound |
|---|---|---|---|---|---|
| 119 | 245 | 412 | 422 | 458A | 479 |
| 215 | 246A | 413 | 426 | 461 | 482 |
| 231 | 300 | 414 | 432 | 462B | 483 |
| 236 | 400 | 415 | 433 | 465 | 486 |
| 237 | 401 | 416 | 437 | 469 | 487 |
| 238 | 402 | 417 | 448A | 472 | 489 |
| 240 | 409 | 418 | 453 | 474 | 495 |
| 241 | 411 | 419 | 457 | 478 | 496 |
| 400-2 | 911 | 1248 | 1401 | 1819 | 2305 |
| 400-4 | 912 | 1255 | 1405 | 1821 | 2600 |
| 400-7 | 1100 | 1256 | 1503 | 1822 | 2638 |
| 400-8 | 1205 | 1301 | 1506 | 1831 | 2646 |
| 400-9 | 1206 | 1303 | 1507 | 1832 | 2649 |
| 400-11 | 1209 | 1304 | 1510 | 1835 | 2651 |

475

TABLE 5-continued

| Compound | Compound | Compound | Compound | Compound | Compound |
|---|---|---|---|---|---|
| 400-12 | 1214 | 1313 | 1511 | 1836 | 2701 |
| 400-17 | 1216 | 1314 | 1513 | 1837 | 2703 |
| 400-19 | 1223 | 1315 | 1516 | 1839 | 2800 |
| 400-22 | 1226 | 1321 | 1518 | 1900 | 2801 |
| 501 | 1227 | 1323 | 1519 | 2100 | 3100 |
| 504 | 1228 | 1331 | 1521 | 2102 | 3101 |
| 505 | 1230 | 1332 | 1522 | 2103 | 3102 |
| 509 | 1231 | 1333 | 1532 | 2104 | 3103 |
| 510 | 1232 | 1334 | 1605 | 2105 | 3201 |
| 511 | 1233 | 1335 | 1607 | 2106 | 3302 |
| 512 | 1234 | 1338 | 1608 | 2107 | 3501 |
| 605 | 1237 | 1339 | 1620 | 2109 | 3800 |
| 606 | 1241 | 1344 | 1800 | 2115 | 3901 |
| 700 | 1242 | 1352 | 1803 | 2204 | 4002 |
| 860 | 1244 | 1354 | 1808 | 2300 | 4102 |
| 902 | 1246 | 1355 | 1809 | 2302 | 4105 |
| 910 | 1247 | 1358 | 1812 | 2304 | |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (II), or a pharmaceutically acceptable salt thereof, having the structure:

$$A^b\text{-}L^b\text{-}Y^b \quad (II)$$

wherein:

$L^b$ is

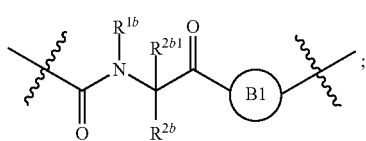

(IIb)

$A^b$ is phenyl, wherein the phenyl is unsubstituted or substituted with one or more groups selected from the group consisting of:
(a) hydroxy,
(b) halogen,
(c) nitro,
(d) alkyl optionally substituted with one or more substituents selected from the group consisting of halogen, hydroxy, and —O($C_{1-6}$ alkyl),
(e) amino optionally substituted with one or two alkyl groups,
(f) —O-(alkyl) optionally substituted with one or more substituents selected from the group consisting of hydroxy, halogen, alkoxy, cyano, amino optionally substituted with one or two alkyl groups, cycloalkyl, C-carboxy, and C-amido, and
(g) —O-(cycloalkyl) optionally substituted with one or more substituents selected from the group consisting of hydroxy, halogen, alkyl, alkoxy, and amino optionally substituted with one or two alkyl groups;

476

$Y^b$ is benzothiophenyl optionally substituted with one or more groups selected from the group consisting of halogen, alkyl optionally substituted with one or more halogen groups, hydroxy, alkenyl, alkynyl, alkoxy optionally substituted with one or more halogen groups, haloalkoxy, cyano, C-carboxy, —C-amido, sulfonyl, and aryl;

$R^{1b}$ is hydrogen or an unsubstituted $C_{1-4}$ alkyl;

$R^{2b}$ and $R^{2b1}$ are each independently hydrogen or $C_{1-4}$ alkyl optionally substituted with one or more groups selected from the group consisting of hydroxy, alkoxy, amino, and C-carboxy, and when more than one $R^{2b}$ and/or more than one $R^{2b1}$ are present, each $R^{2b}$ and each $R^{2b1}$ is the same or different; and ring B1 is pyridinyl optionally substituted with one or more substituents selected from the group consisting of hydrogen, halogen, hydroxy, alkenyl, alkynyl, cycloalkyl, aryl, alkoxy optionally substituted with one or more halogen groups, amino optionally substituted with one or more alkyl groups, C-carboxy, and alkyl optionally substituted with one or more groups selected from hydroxy, alkoxy, halo, and cycloalkyl.

2. A pharmaceutical composition comprising an effective amount of a compound of claim 1, or a pharmaceutically acceptable salt thereof, and a pharmaceutically acceptable carrier, diluent, excipient, or combination thereof.

3. The pharmaceutical composition of claim 2, wherein the compound is

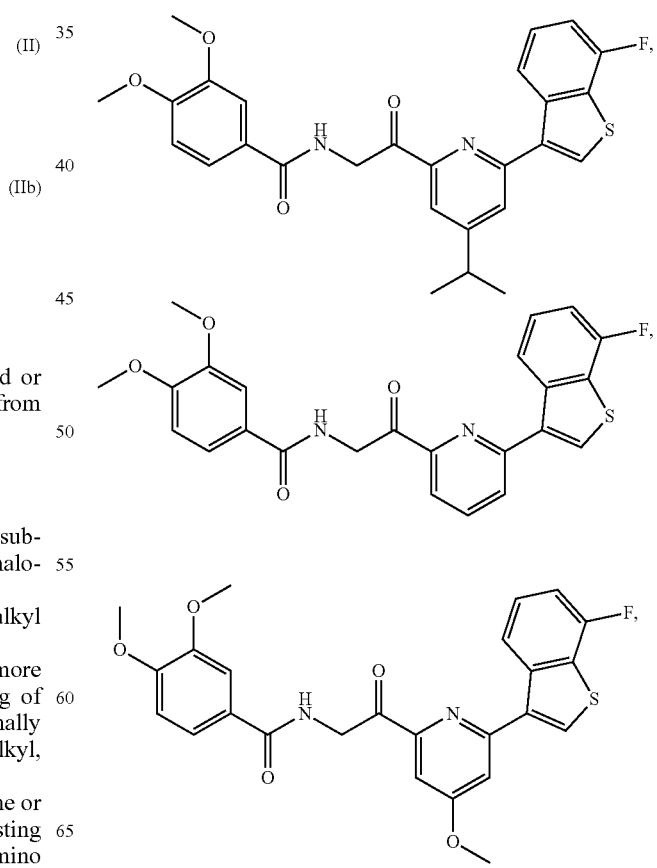

477
-continued
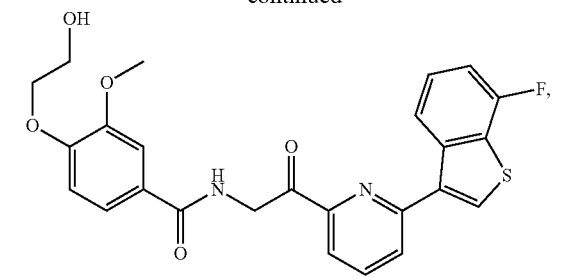
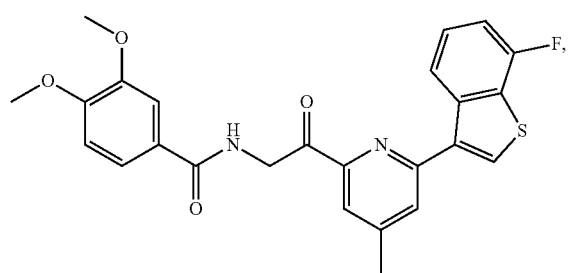
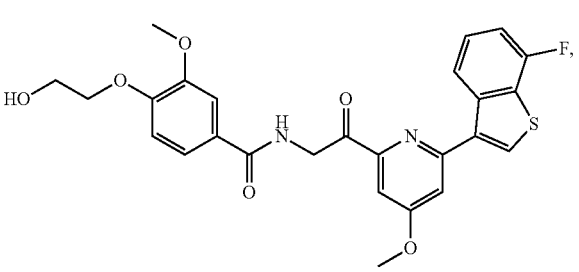
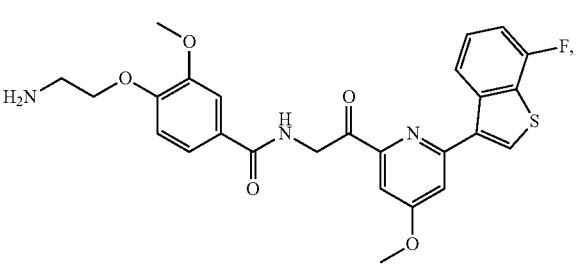
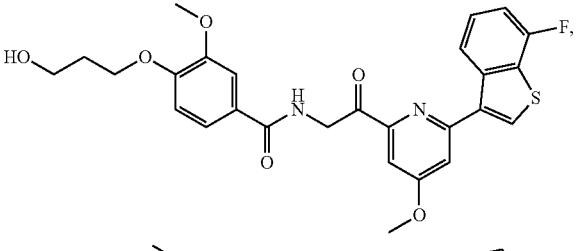
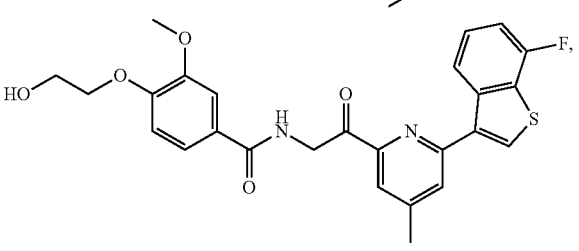
478
-continued
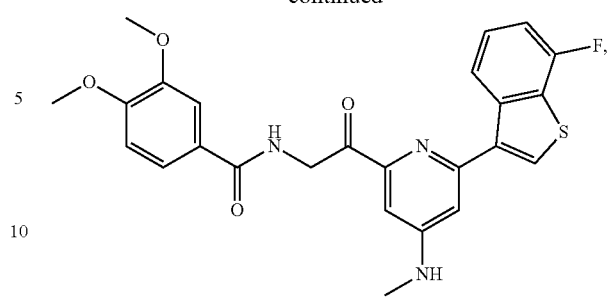
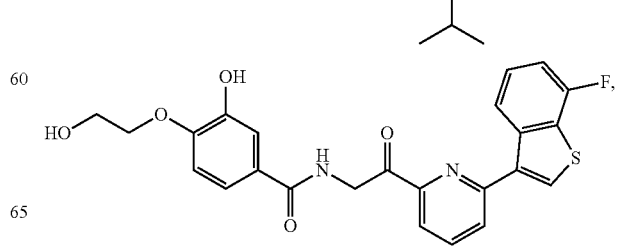

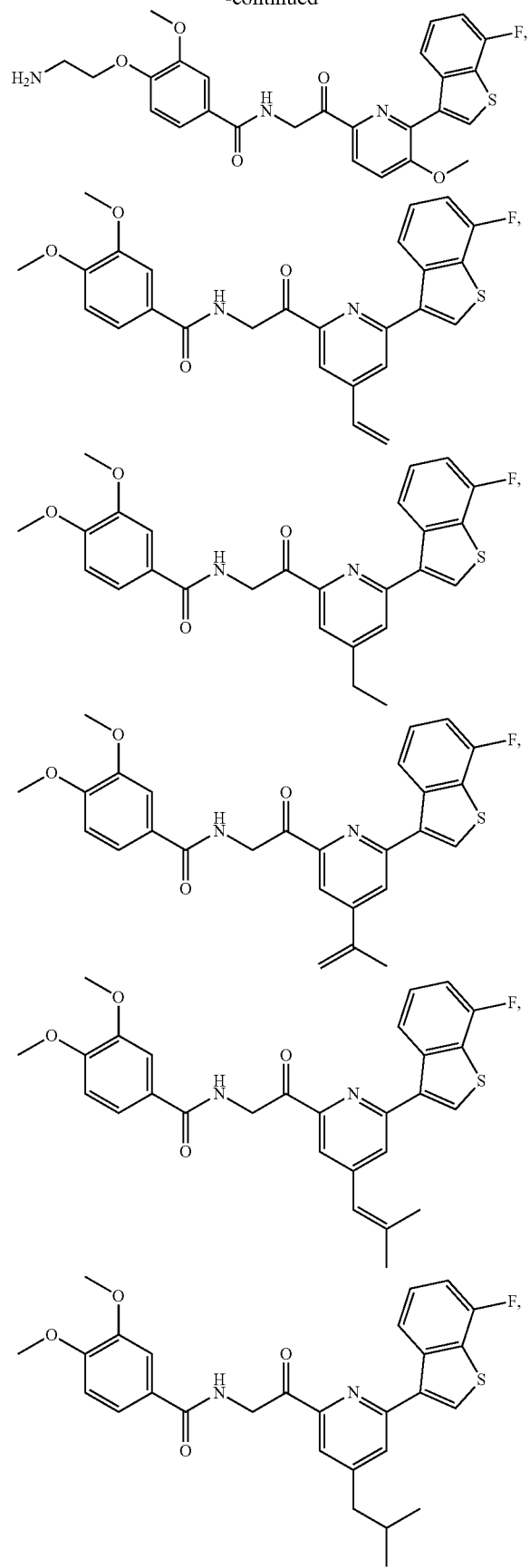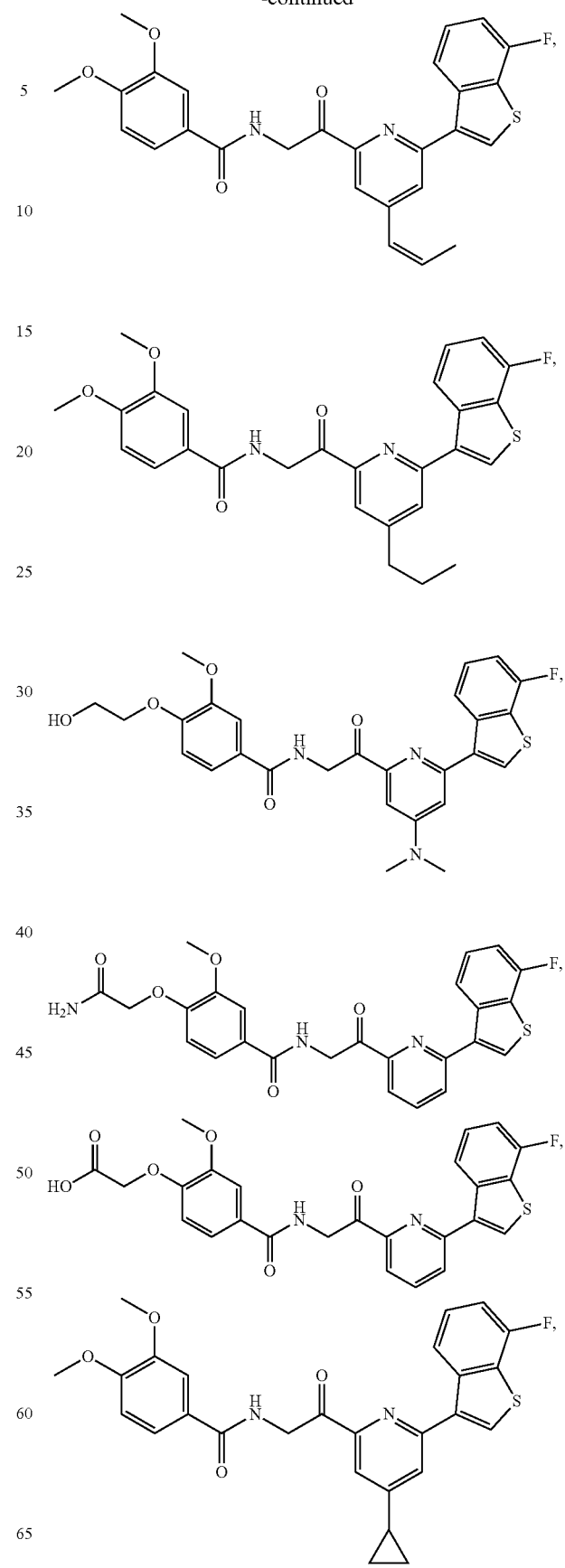

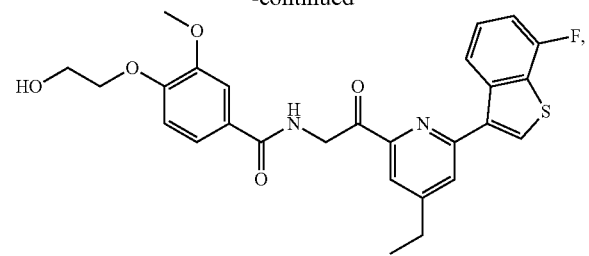
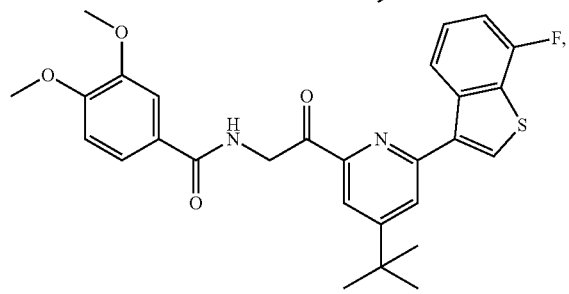
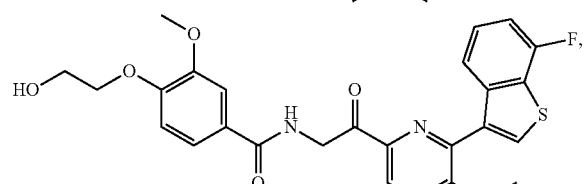
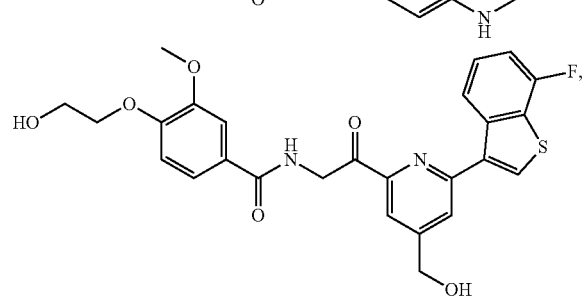
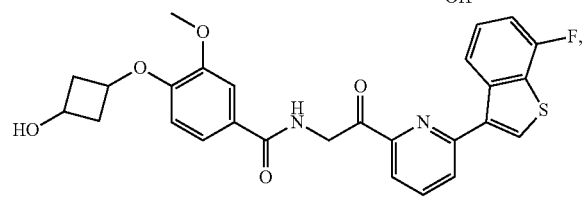
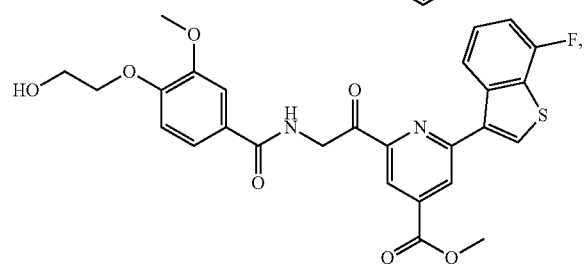
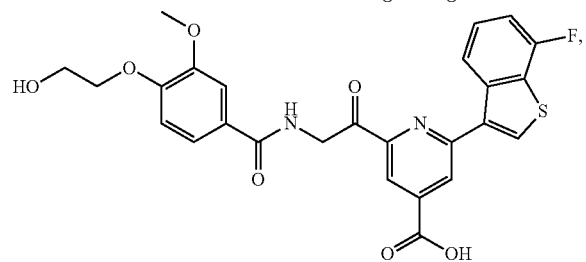
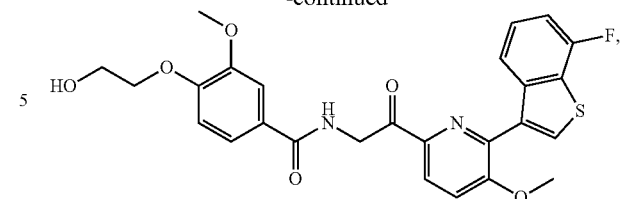
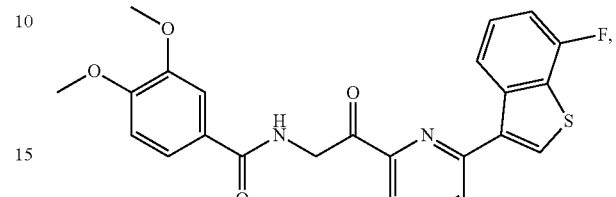
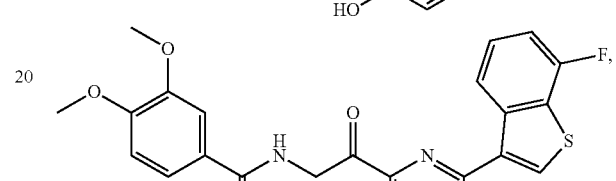
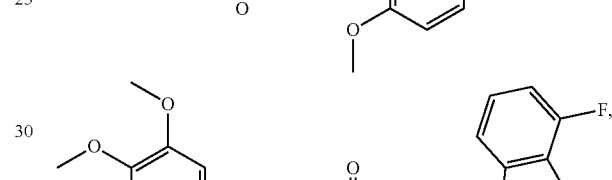
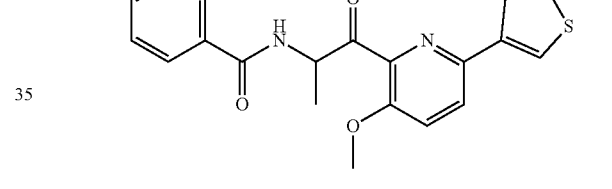
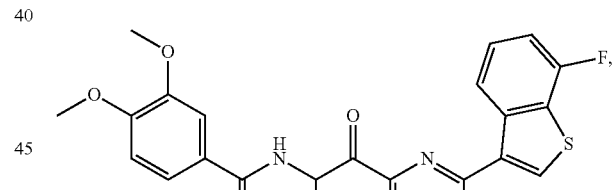
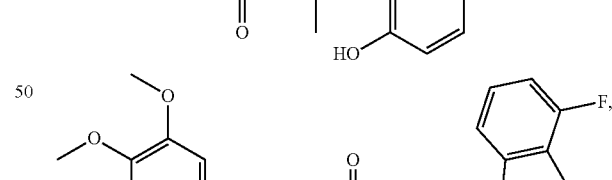
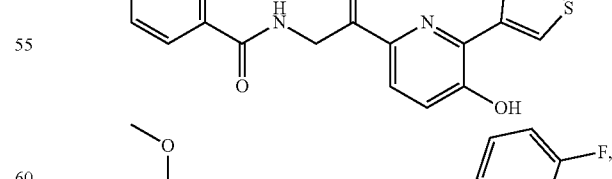
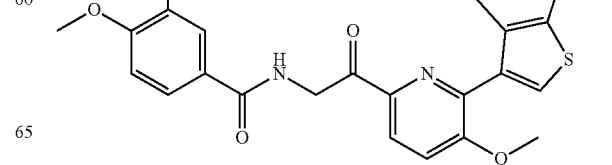

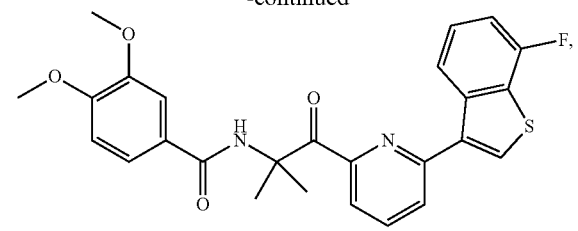
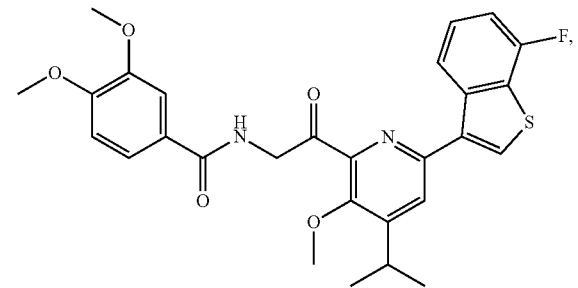
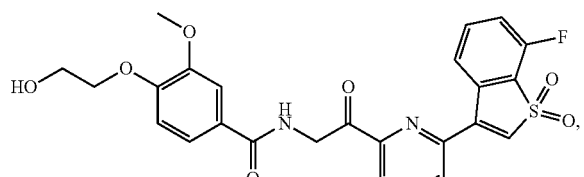
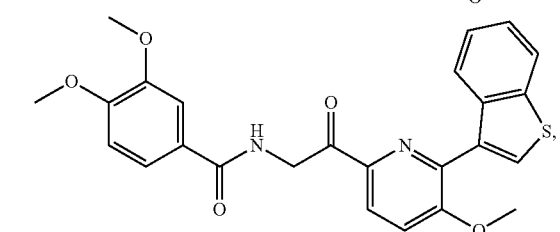
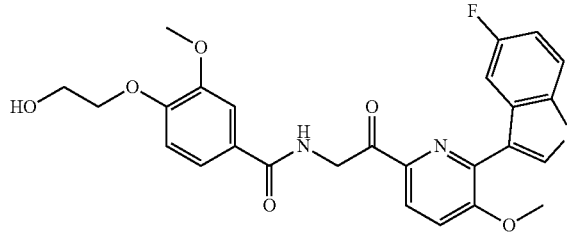
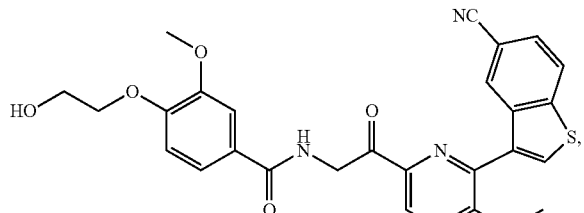
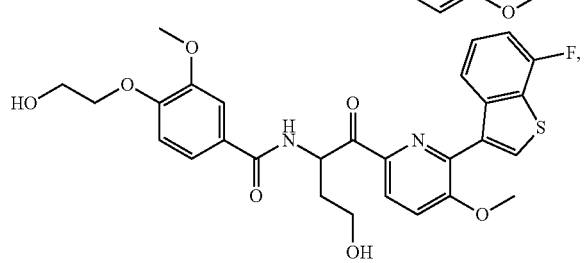
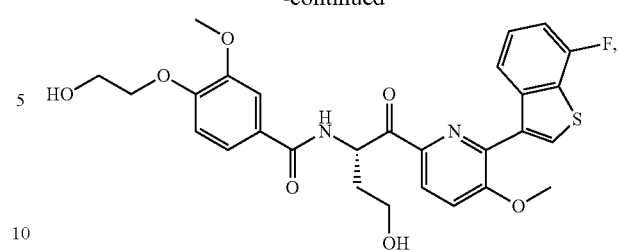
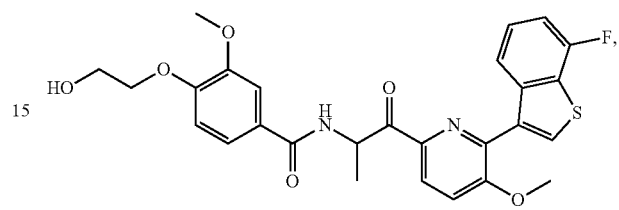
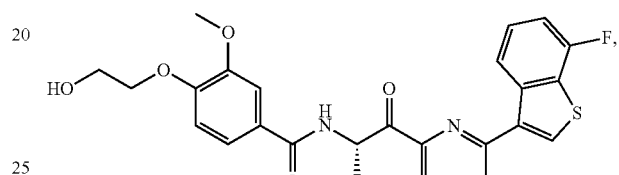
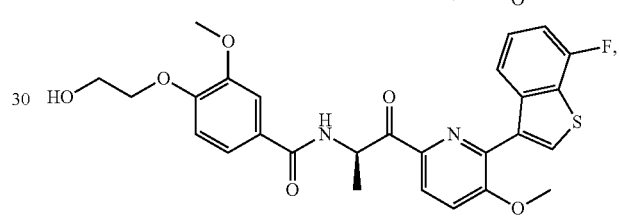
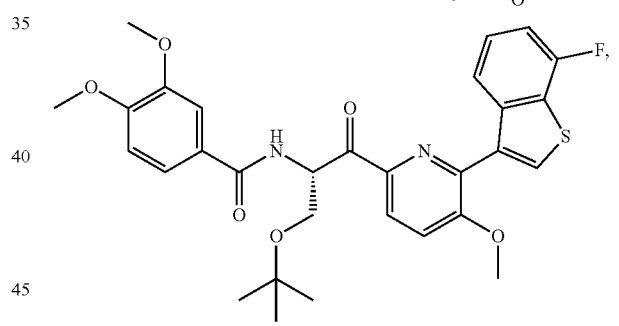
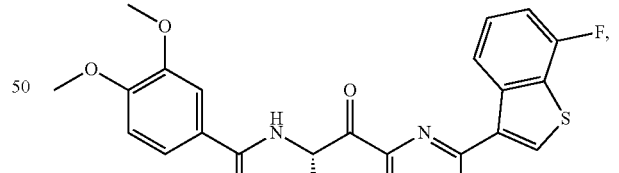
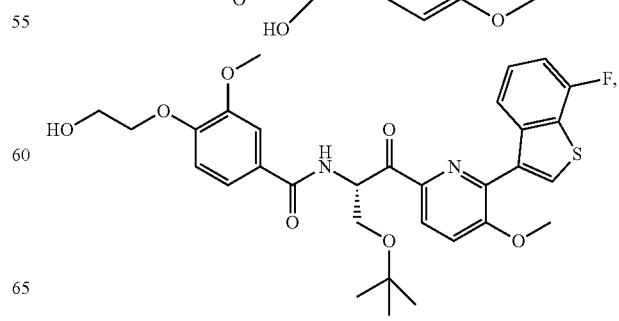

485
-continued
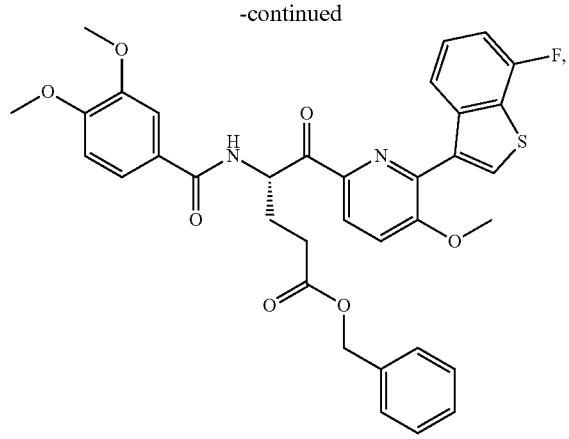
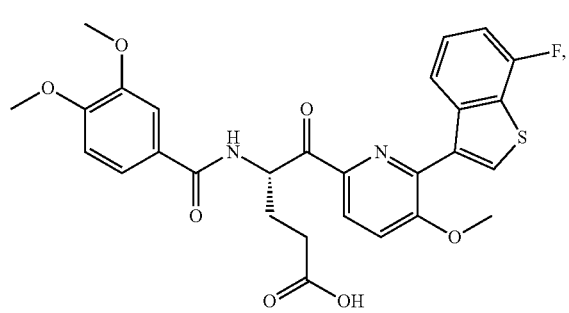
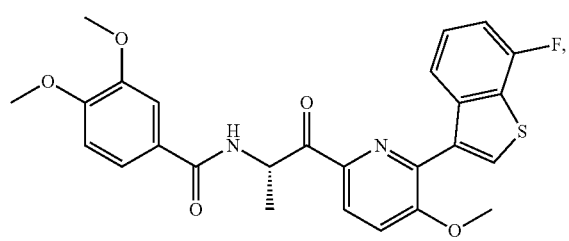
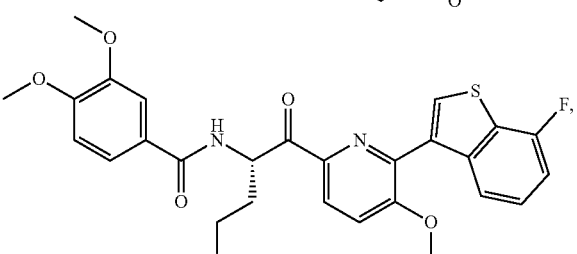
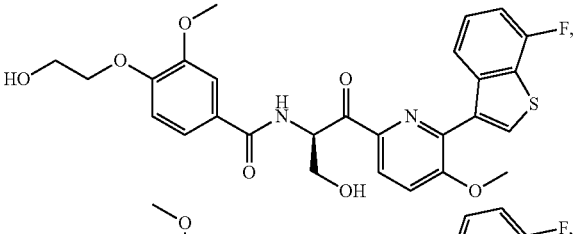
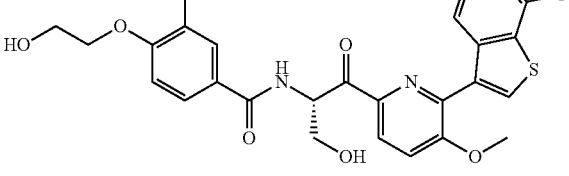
486
-continued
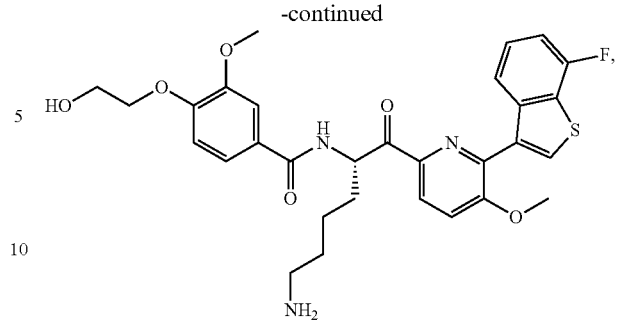
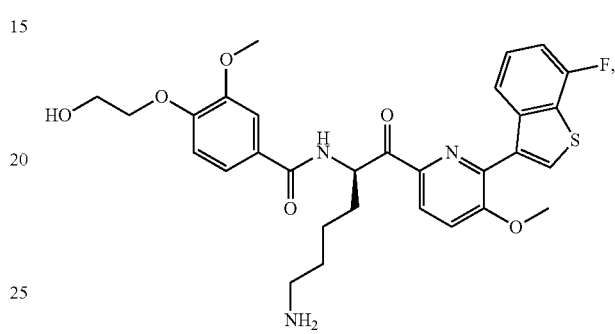
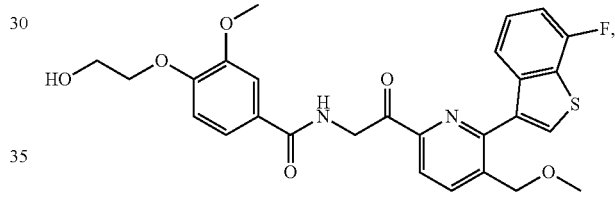
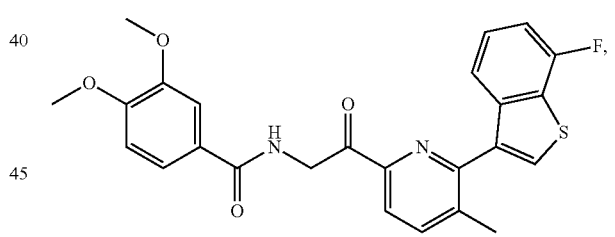
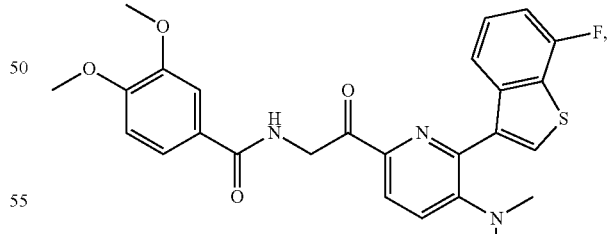
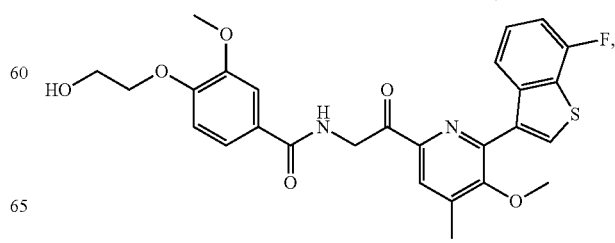

487
-continued
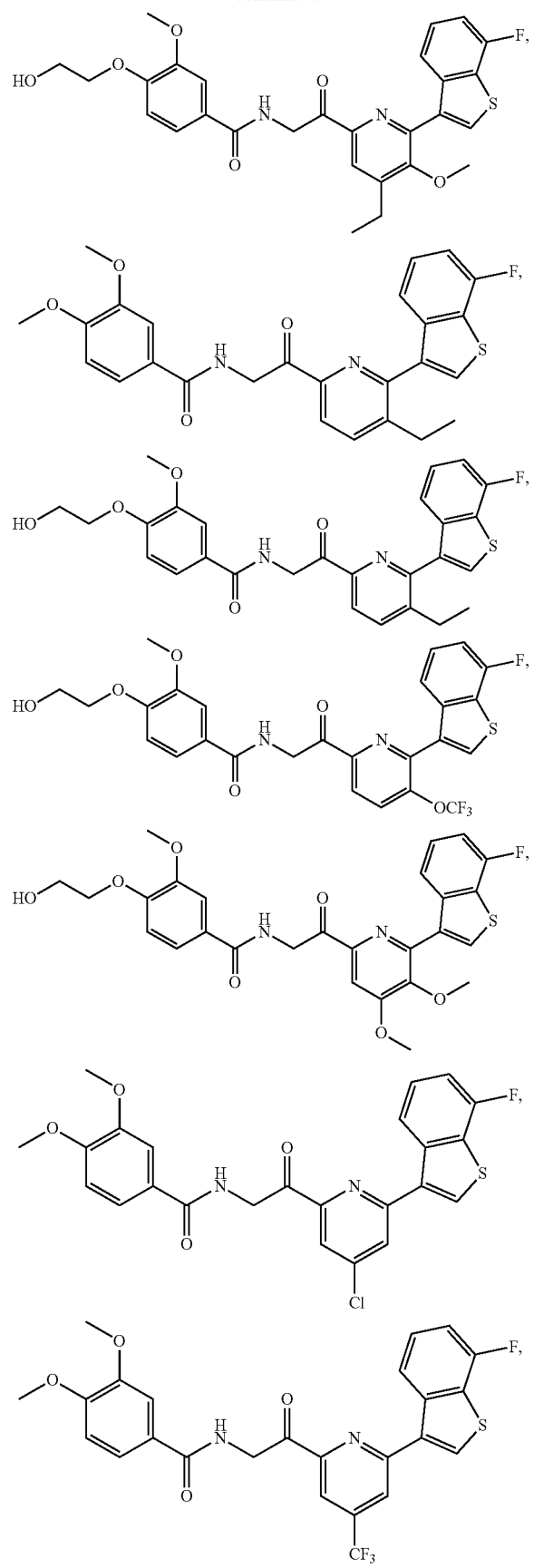
488
-continued
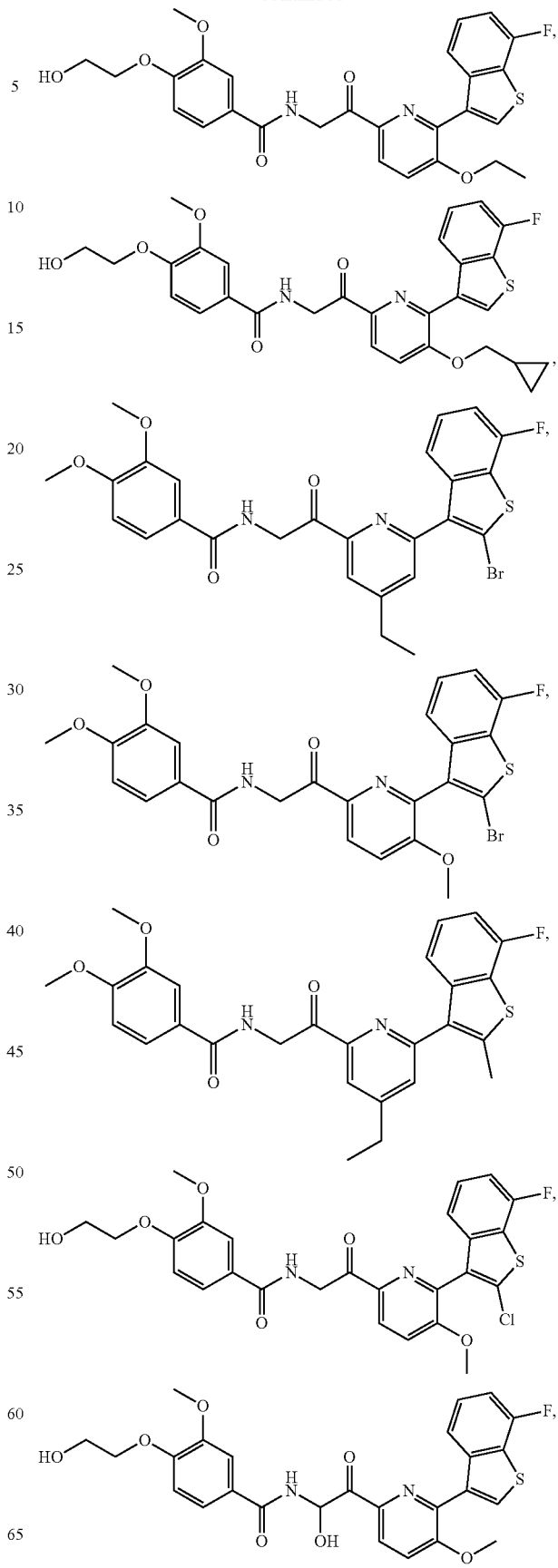

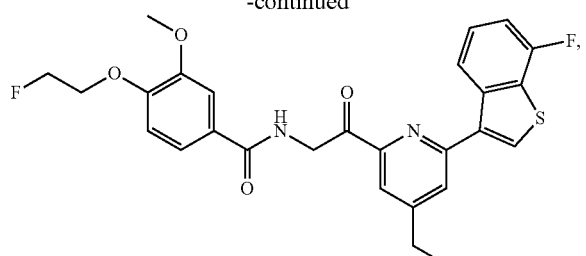

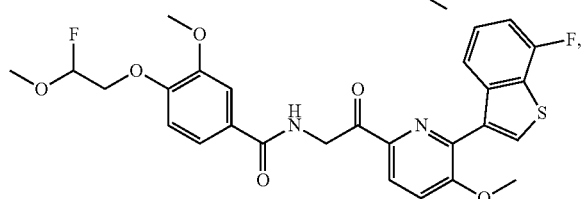

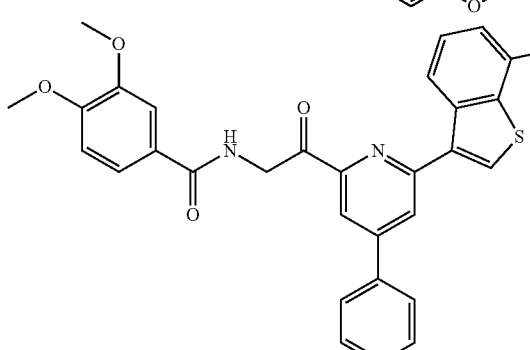

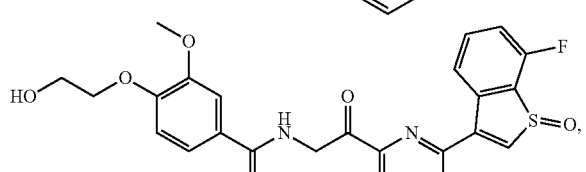

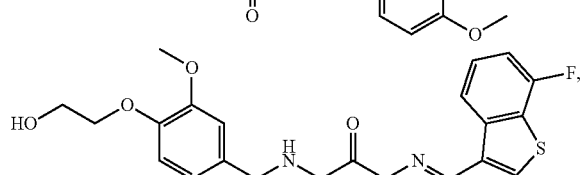

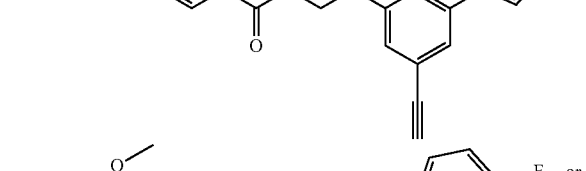

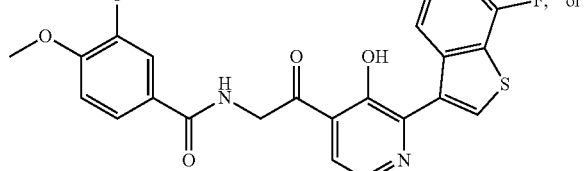

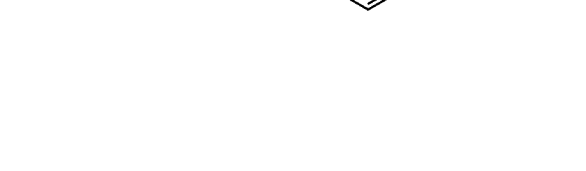

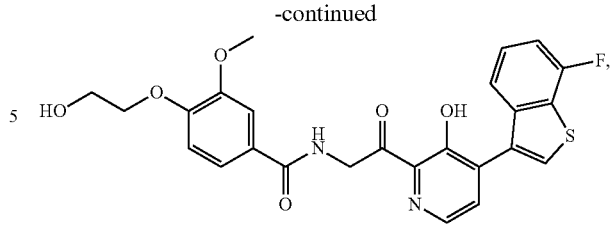

or a pharmaceutically acceptable salt of any of the foregoing.

4. The compound of claim 1, wherein B1 is selected from the group consisting of: an optionally substituted

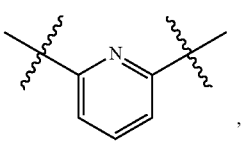 [SMILES: *c1cccc(*)n1]

an optionally substituted

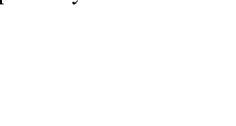

and an optionally substituted

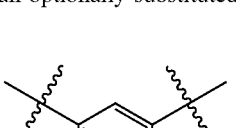

5. The compound of claim 1, wherein $R^{1b}$ is hydrogen.

6. The compound of claim 1, wherein $R^{2b}$ and $R^{2b1}$ both are hydrogen.

7. The compound of claim 1, wherein $R^{2b}$ and $R^{2b1}$ both are an optionally substituted $C_{1-4}$ alkyl.

8. The compound of claim 1, wherein $A^b$ is a di-substituted phenyl.

* * * * *